US010844363B2

(12) United States Patent
Marasco et al.

(10) Patent No.: US 10,844,363 B2
(45) Date of Patent: Nov. 24, 2020

(54) XYLOSE ISOMERASE-MODIFIED YEAST STRAINS AND METHODS FOR BIOPRODUCT PRODUCTION

(71) Applicant: CARGILL, INCORPORATED, Wayzata, MN (US)

(72) Inventors: Erin Kathleen Marasco, Excelsior, MN (US); Sara C. McFarlan, Minneapolis, MN (US); Briana Kozlowicz, Hopkins, MN (US); Chenfeng Lu, Edina, MN (US); Beth M. Mastel, Excelsior, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 61 days.

(21) Appl. No.: 15/750,353

(22) PCT Filed: Aug. 4, 2016

(86) PCT No.: PCT/US2016/045579
§ 371 (c)(1),
(2) Date: Feb. 5, 2018

(87) PCT Pub. No.: WO2017/024150
PCT Pub. Date: Feb. 9, 2017

(65) Prior Publication Data

US 2018/0223271 A1 Aug. 9, 2018

Related U.S. Application Data

(60) Provisional application No. 62/201,477, filed on Aug. 5, 2015.

(51) Int. Cl.

| | |
|---|---|
| ***C12N 9/92*** | (2006.01) |
| ***C12P 7/06*** | (2006.01) |
| ***C12N 15/81*** | (2006.01) |
| ***C12N 9/88*** | (2006.01) |
| ***C12N 9/10*** | (2006.01) |

(52) U.S. Cl.
CPC ............ *C12N 9/92* (2013.01); *C12N 9/1022* (2013.01); *C12N 9/88* (2013.01); *C12N 15/815* (2013.01); *C12P 7/06* (2013.01); *C12Y 202/01002* (2013.01); *C12Y 401/01001* (2013.01); *C12Y 503/01005* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 5,876,988 | A | 3/1999 | Selten et al. |
| 2012/0225451 | A1 | 9/2012 | Winkler et al. |
| 2014/0256048 | A1 | 9/2014 | Chen et al. |

FOREIGN PATENT DOCUMENTS

| | | | |
|---|---|---|---|
| EP | 2554668 | A1 | 2/2013 |
| JP | 2015042145 | A | 3/2015 |
| WO | 9914335 | A1 | 3/1999 |
| WO | 0071738 | A1 | 11/2000 |
| WO | 03062430 | A1 | 7/2003 |
| WO | 2004099381 | A2 | 11/2004 |
| WO | 2006009434 | A1 | 1/2006 |
| WO | 2006115455 | A1 | 11/2006 |
| WO | 2007032792 | A2 | 3/2007 |
| WO | 2007106524 | A2 | 9/2007 |
| WO | 2008041840 | A1 | 4/2008 |
| WO | 2009006135 | A2 | 1/2009 |
| WO | 2009011591 | A2 | 1/2009 |
| WO | 2009056984 | A1 | 5/2009 |
| WO | 2009109630 | A1 | 9/2009 |
| WO | 2009109631 | A1 | 9/2009 |
| WO | 2009109633 | A1 | 9/2009 |
| WO | 2009109634 | A1 | 9/2009 |
| WO | 2009112472 | A2 | 9/2009 |
| WO | 2010070549 | A1 | 6/2010 |
| WO | 2010074577 | A1 | 7/2010 |
| WO | 2011003893 | A1 | 1/2011 |
| WO | 2011131667 | A1 | 10/2011 |
| WO | 2011131674 | A1 | 10/2011 |
| WO | 2012049170 | A2 | 4/2012 |
| WO | 2012071470 | A2 | 5/2012 |
| WO | 2012142094 | A2 | 10/2012 |
| WO | 2012143513 | A2 | 10/2012 |
| WO | 2013017644 | A1 | 2/2013 |
| WO | 2013071112 | A1 | 5/2013 |
| WO | 2013081700 | A1 | 6/2013 |
| WO | 2013117631 | A1 | 8/2013 |
| WO | 2014018552 | A1 | 1/2014 |
| WO | 2014060377 | A1 | 4/2014 |
| WO | 2014098939 | A1 | 6/2014 |
| WO | 2014164392 | A1 | 10/2014 |

(Continued)

OTHER PUBLICATIONS

Dawit, Brat , et al., "Functional Expression of a Bacterial Xylose Isomerase in *Saccharomyces cerevisiae*", Applied and Environmental Microbiology, American Society for Microbiology, vol. 75 No. 8, Apr. 2009, 2304-2311.

(Continued)

*Primary Examiner* — Suzanne M Noakes

(57) ABSTRACT

The present invention relates to a genetically engineered yeast (e.g., Crabtree negative) that express a heterologous xylose isomerase. In a fermentation method the engineered yeast are capable of producing a bioproduct, such as ethanol, in a fermentation medium that includes xylose. Desirable bioproduct titers can be achieved when materials such as acetate are present in the fermentation medium.

18 Claims, 7 Drawing Sheets

Specification includes a Sequence Listing.

(56) References Cited

FOREIGN PATENT DOCUMENTS

| WO | 2014164410 A1 | 10/2014 |
|---|---|---|
| WO | 2015044101 A1 | 4/2015 |

OTHER PUBLICATIONS

Demeke MM , "Development of a D-xylose fermenting and inhibitor tolerant industrial *Saccharomyces cerevisiae* strain with high performance in lignocellulose hydrolysates using metabolic and evolutionary engineering", Biotechnology for Biofuels, 6:89, 2013. Online: http://www.biotechnologyforbiofuels.com/content/6/1/89, 2013.
Han, B.G. , et al., "Crystal structure of Xylose Isomerase from an human intestinal tract microbe Bacteroides thetaiotaomicron", Biodesign 3,, 2015, 41-47.
Kersters-Hilderson, H , et al., "Kinetic characterization of D-xylose isomerases by enzymatic assays using D-sorbitol dehydrogenase", Enzyme microb Technol vol. 9, Issue 3, Mar. 1987, pp. 145-148, Online: https://doi.org/10.1016/0141-0229(87)90067-6, Mar. 1987, 145-148.
Kuyper, M , et al., "High-level functional expression of a fungal xylose isomerase: the key to efficient ethanolic fermentation of xylose by *Saccharomyces cerevisiae*?", FEMS Yeast Research, Wiley-Blackwell Publishing Ltd, GB, NL, vol. 4 No. 1, XP002312913, Oct. 1, 2003, 69-78.
Matsushika , et al., "Ethanol production from xylose in engineered *Saccharomyces cerevisia*: current state and perspectives", Applied Microbiol Blotechnol 84:37-53, 2009, Jul. 2, 2009, 37-53.
Meaden, PG , et al., "The xylose isomerase-encoding gene (xylA) of Clostridium thermosaccharolyticum: cloning, sequencing and phylogeny of Xy1A enzymes", Gene, 141(1), Elsevier Science B.V., 1994, 97-101.
Sun-Mi, Lee , et al., "Directed Evolution of Xylose Isomerase for Improved Xylose Catabolism and Fermentation in the Yeast *Saccharomyces cerevisiae*", Applied and Environmental Microbiology, vol. 78, No. 16, Aug. 2012, 5708-5716.
Traff, K. L., et al., "Deletion of the GRE3 Aldose Reductase Gene and Its Influence on Xylose Metabolism in Recombinant Strains of *Saccharomyces cerevisiae* Expressing the xylA and XKSI Genes", Appl Environ Microbiol, vol. 67, No. 12, Dec. 2001, 5668-5674.
Van Maris, Antonius J. A. , et al., "Development of Efficient Xylose Fermentation in *Saccharomyces cerevisiae*: Xylose Isomerase as a Key Component", Adv Biochem Engin/ Biotechnol. 108:, 2007, 179-204.
Vangrysperre, W. , et al., "Single active-site histidine in D-xylose isomerase from Streptomyces violaceoruber", Biochem. J. 263, 1989, 195-199.

SEQUENCE LISTING

<160> NUMBER OF SEQ ID NOS: 100

<210> SEQ ID NO 1
<211> LENGTH: 1030
<212> TYPE: DNA
<213> ORGANISM: Issatchenkia orientalis

<400> SEQUENCE: 1

```
atatatatgc aactttacgt ggcgcagttg ttgtagaatg caaagacctg aacctcacag     60

actcaatcaa acttgtattt tcaggacatt ccaaactttt attgatgaaa ttcttgaaat    120

ctttagtttc cctcttactt gatataataa tcgatggcac attgccaata aaaatagtcc    180

gttccgcctt ttcaaactcc ttatccttta aatcaaggac ttgagccgca gttgtcttag    240

ttttcgttgg tttaccattt gcagtttctg cagactccgt agattcttcc attgttgcat    300

cttcaacgcc ctcctcatcg gaacaacctg cttcaccaac ttgagcttca tcatcagaat    360

cttcagattc ttcattctca gattcttcat ctcctgactc ttcagcttca gattctacta    420

atttagacat gtacttatct tccaatgccc catcatcatc gtcaaggtcc attttctcac    480

caactttctc tctatgttca gggtgctctt tatctgctac attctgatct gctgtaccat    540

tgtcattgtt cgaagcatca tcaccatttt ttgctgcttt cctttcgtct cttttctttt    600

gctttctttc cttcttcttg atttgaacaa tcgttctctg cttttcagca accagctttt    660

cgttatcgat cacagtaggt ttagcaaata gtccagacat tctcaactat gttttatttg    720

ctacgcttgt taccaattaa cgggttctaa aatataatag aaaaagtcca aaaaaaatct    780

tcacaaatta tcagaataat ttcaccatac acaaaaaatt acaaaaaaat acttttgtag    840

tttccttaaa gggaaaactc caactttttc ccgctttgtt ttatgatccg tacaccaaat    900

aggtgggtct caggagtaag atgaccgctt tatcaatttc ttatcagtat atgaggataa    960

tctactgtaa tggattagcc acatttttgg acacaagctt cttttcttag tttgaaatta   1020

caagtacaaa                                                          1030
```

<210> SEQ ID NO 2
<211> LENGTH: 1033
<212> TYPE: DNA
<213> ORGANISM: Issatchenkia orientalis

<400> SEQUENCE: 2

```
ataagacaag gaaaaagccc aaaaaaatga aagaaatgtt ctgaagatgc caacatttta     60

tatcttataa aactatatac caatcacttt tttgaaaact tcccgtttcg tagatttccc    120

tgttttaatg cccttgctta ccaggtcacc aactagattt tgatgatgat gatgatgatg    180

atgtggttgg tatttctggg accaatcaat accgattgtt tcccaaacag ttacgggtat    240

tgatttcggt aactttctac catacaagca ttggtctata agccacattc caacaatgaa    300

ttcctcatat gttaatgtcg aatcatcgaa catattccta tcaatgtcta gcaagttata    360
```

```
gctaacttgt tgttctcttg tgtcatcttg cacattctca gatgaacgtg aaccattcgt    420

atttgtcatt atctggttct ttggtatttc aactaaccat tcttttgatc cgttgttaac    480

tgcttttatc caacgtcttt ttcgatcatc taataccaac gaccaaatct tggataaggt    540

tgtcttatcg attttcgacc tcgtccagat ttcatagacg atcaaactgt ggatcctttc    600

gtttagtggt gtataagtgt ttacaaaatt tgataatttc aaactttcag cgtcaactag    660

cctagggtca agatcaaggt atgaggattt gtttgctgca aacacccccct cgtaacgttt   720

tttctcgtct gatgtgatca tgttcagagt ttctcgttca tggttcttcc agggcttgtt    780

ttcgttgaat ccagacttgc tgttcttatt tttcgacttt ttatcatccc tcaaagtagt    840

cctgaaaacc aactgttgtg atggtacatt tgctgactgc tgttggtaaa ttgaattact    900

agtacccatg gaattcctta gcctttgatt cggtgctgtg ttgtcaggag cagtagttgc    960

actaggcatt ggtggatcaa ctgaaatgac agaggtattc aagtcgagct tcttgatgtg   1020

gctgggtatt tgt                                                      1033
```

<210> SEQ ID NO 3
<211> LENGTH: 991
<212> TYPE: DNA
<213> ORGANISM: Issatchenkia orientalis

<400> SEQUENCE: 3

```
ctgcttgtgc aggtgcaacc gagtcgtttg ttgttgtccc ctttgagttg gtgaagatcc     60

ggttacagga taagtccaag gcgtccatgt atagcggtcc cattgatgtt ctaatgaaga    120

cagtcaaaaa tgaaggtatc ttggccttgt ataacggatt agaggcaaca ctgtggagac    180

atattgtatg gaatgccggc tattttggtg tgattttcca agttcgtgac atgttaccca    240

aggcaaagga caagacccag aaaaccatca acgatttggt gggtggtatg attggtggta    300

tcgttggtac tgccttgaac attccattcg atgttgtcaa atccagaatc caaagtgcaa    360

ccattatgga aggtcaggtc cgtaaataca attggacttg gccctctctt ggcattgtct    420

tgagggaaga aggtgtctct gcattgtata aaggattcct tccaaaagtc ctgagattgg    480

gtccaggtgg tggtattcta cttgttgtct tcacaaactg tatggacttc tttagaggcc    540

aatactatgg agacaagaaa tagtagctgg gttcttcacc atcaggttta tacaccctcc    600

acgacgtcca ttctatacta tactatgcta ttcgatgcta ttcgatgcta tcctgcccta    660

tcttatctaa tcttatctta tcttacaaaa ttatatactt tccttgtttc tttcacctcc    720

tcctttatag atcaattgat ttgataatac acttatacac attgacgtct gttgatatct    780

tcatacaaaa aaccttaaaa catagtgcaa agtcacgtgc acgccttaaa aatgcagctg    840

agcccctttc ccacttctct cccttcggat gccccacctg actattttca cttcccaatt    900

cgagcatcct cctccagtcc ccgcagactc aagagataag aaaccttaca gagactgttc    960

ccatcctcct atgctcaacg tgtcctgtat c                                  991
```

<210> SEQ ID NO 4
<211> LENGTH: 1070
<212> TYPE: DNA
<213> ORGANISM: Issatchenkia orientalis

<400> SEQUENCE: 4

```
aaatatctac gtgtttagca tttcctatat acatgactgt gtgtcctctg gttttcattt     60

cgtttggttc tcattcctct tggcagcttc actaaacaac tggtcgtgtt gttcgtcgtg    120

ttttgccttg aagaatgtat agtgcaacac aacgtcttcg atgtttctca ttgccggatc    180
```

```
tctggaaaac tctggatcga taaagaaaaa caagggcata tcaacctcct caccccttggc    240
caaccgctgc tcttcaaagc agaaacactg gatcttgttg aagtaaggcg ctacatgatc     300
gggagtcact gagtatgtgg ccatgccagt aatgtccttg tcacttatat tcttggcttt     360
gtagaaggcc aaggcagtct ctccggggac aacataaact tctctttgtt gcggtacaaa     420
cttccatggt aacgcaccac ttgtctccgc cgtaaaggat acccgcagtc ttctctctgt     480
agctactgga gttagcttgt ccctcgtgaa cctgctcttg tcggtgattg gtgtaccacc     540
ccatccagta cgttgacaaa ttgcacgata caaggggaca ctcgcatacg ataatgcaag     600
gaaaatcatc atcatggata acgaataata aatggtggtt tgcctctcat acctcttctt     660
ttctccatgg tacttatctc tcaatgcttg gaactctgcc aaagacatct ttggaagctc     720
cttccggttt gctcgtggtg atacctgatg ttctgatgac ccaccaccag gaacttcgta     780
ttttgcaata caactggcat gtacatatct cctatggagg gcaagtccgg gaatcagccc     840
aacatcccga aggggcgctt gtatactagt tctgaaaatc cgccttaaca tcaccgtaca     900
gagacacctt caccaatatg ttctccaaga ccatggggca ctagaagtta tccattgacg     960
ttcatcaacc tagtgatgtc aaatttcatc gccgtttccc aactcgcggg atttgctttt    1020
gagcatctcg tttgattcac gacaacttgt tctacattct gctgcgggcc               1070
```

<210> SEQ ID NO 5
<211> LENGTH: 900
<212> TYPE: DNA
<213> ORGANISM: Issatchenkia orientalis

<400> SEQUENCE: 5

```
ctgaagacac aaaaggggta tcactgaaat tgatcacttt tgcattgttt gggaacttat      60
tctattcaat gtctctacta ttatctgaga attcattgag aggcggggaa gaatcaaagg     120
agttttggaa ggccgaattg agttactttt taggggcaat cggaacagta ttgtttgatt     180
ttattgcaat tttacaatgg attcattatg acagccacag taatcgtacc aatcatatcc     240
aatctgtgag gttgaaagct tacaccccta aatcattaaa aagccagaca attcccaaat     300
cggtgccatt gatacattca cgtacatcgt ccatgagaga tggtacaaag atagatccca     360
tcgaaatggc ggctagcgtc aagtcaacat tgtcaccccca gaatgtacgc aaactcaatg    420
agttcacacc attgtctcct atggatttat tgctagatga acatatttca cgcagttatg     480
tttcctctac tgatacaaaa actatacctc agaagaagag acctgatagt atcaagtctg     540
tacacaggca caacgaggac ctgctaatga cattcgaaga atagaagcag tcccaattta     600
aaccgtggcc gtggtaacag ccataactgt agccacaatt ggaaattatg gatgtattgt     660
ctgatttgga cctccggggc agggacaatg gacttggcca aagagtcgaa aaaaatgttc     720
aacagacgag ataattggtc tttaattgtc tcggacatgt gatttcctta aaagtttaat     780
ttcacacccg caggtttatt tatataaaag tgtggccaca agtcttggga agatgaacat     840
cttgatattc atgtcccctc tcattttctg agactggcat aagataagta gaaagcggcc     900
```

<210> SEQ ID NO 6
<211> LENGTH: 869
<212> TYPE: DNA
<213> ORGANISM: Issatchenkia orientalis

<400> SEQUENCE: 6

```
tggagaaccg ctccccttta tatttttttt ttccacacac accttttatc ttatcgcttt      60
```

```
acattttcgg tggcaaattg attaaaaaaa gtacagaaat gctcagctcc aaatagcctt    120

gaattggggt tgcttccttt ctctgataac catttttcct ttctcaattg ctagctaaca    180

gtagcaaaac aactagccct ataccaaatg aacattcact cgtcagtatt gacatccgta    240

gtcctcttgc tcgcttcaat tacgggctcc gatgctaagg ttcattctgc cagcatccac    300

aagaatccgt tccaagacaa ttataaagat atttcctatc tagaatatgt tgactccatc    360

aagaacaagt atgttaacaa ttttgtcaag aacttcaatg caccttttgt cccatttgtt    420

gaagatgcgg tcattgagga cactcatgaa ctacccttaa ccaactatat gaatgcccaa    480

tacttcactg agattcaact tggtacccct ggccagccat tcaaggtgat tctagacact    540

gggtcttcta atttgtgggt tccttccaca aaatgtacat ctttggcatg ttatttgcac    600

tctaaatatg atcacgatgc aagttccaca tacaaacaaa atggtaccga ttctctatca    660

gatatggttc tggttccttg gaaggtttta tttcacaaga tttactaact tttggtgact    720

tggtcattcc agagcaggat ttcgctgagg caacaagtga accgggcttg gcgtttgctt    780

tcggaaaatt cgacggtatt ctaggtttag cttatgatac catctcggtg gacaaggttg    840

ttcctccaat ttacaatgcc attgacaag                                      869
```

```
<210> SEQ ID NO 7
<211> LENGTH: 1004
<212> TYPE: DNA
<213> ORGANISM: Issatchenkia orientalis

<400> SEQUENCE: 7

cataccacaa tgcggtatgc ggtgaatgga ctgctgctct cactgattgt gctaaatggc     60

tcaatggaat ggcgagaggc gcaaggtatg atgcaacata tcagaacgac actccaattg    120

gttcttgttc taacttgtac ttggctgatt attcatactt ccaacaggaa gatgttagac    180

aaacctacag aaggtatgtt gaagctcaga tggacgcata ccttcatgaa aagatgaatg    240

gatgggtttt ttggtgttgg aaaactgaaa acttgattga gtgggacttc caaaggttgg    300

ttgagttgaa tatcattcct cagccgttga actctagaga attctacaat caatgtggtt    360

attgattcat cttactttct tttgaaacaa aggaaatagg tagaaatcat aaaaccaacc    420

taaaaacatc aatcaaaaca ataatacttt ataccttaca tgccggttta cctcatttta    480

tccagcatac ttttgctttc ggggggtttg gtctaatcag atatttttgt ctgtctttac    540

tattagtatg cgttctaaaa gggaacgatt gactgtatac cttaataact ttatatttca    600

taaactagaa aaaaagacta tttactatac tcggatatgc agttgaatgg ttgacgcagt    660

tgctggagcc ttagtagacc agactaacag tacggtacga agacctgtaa aatagaacta    720

gccgtttctg tgttgactaa tctaggggaa gaaaaaaact agacagacaa ttgcatttta    780

agctgcaggg ttccctttct gtggtgaatc tccggggtga gaacaataga aatgggtttt    840

agcgattggc ctgaaattgt ctcgggcagg agatatcctt tgggcattca tgcttgcatt    900

acaagtatat aattgaaagc ttgcaaccac aacctatttt ttgcaattgg aggtcaggta    960

gaaacttttc cacaatgtat aactaaacat ttcaatcctc tcag                    1004
```

```
<210> SEQ ID NO 8
<211> LENGTH: 733
<212> TYPE: DNA
<213> ORGANISM: Issatchenkia orientalis

<400> SEQUENCE: 8

gcagtcgatg taagtacgtc tataaagccc gtaggcatca cgtaacagct atatgtgtca     60
```

```
ctcttctgta acaatcatgt atatgcattc ataggaatgg aaacgtcaaa aggaattggt    120

tgttcgccta agtaatgtaa aacgtctcgg gtattacccg ataaaagcga ggtctttttt    180

ttttcttttc agattatttg agttttctac aagaagcaga cattgcttta tcttcctgta    240

gcaatagatt cattcatacc cttggatgta ctctgtacaa gctatacatt tctctctaaa    300

taagataact ctaacgtgtt tacttggact tgaagaagac agacattagg aaggaaaaaa    360

aaaggatttt taatttcatc tcaacaaaaa atggccaaaa aaagagaatg ccccatttgt    420

ttagaagata tcacctctaa tgatccttca tatacattga caataccctg caagcatttt    480

tatcacaagt cgtgcattct ttcatggacc tcaaaatcag catctacctg tcctcagtgc    540

cgaaatgagc taacgtcatt attcacgcca gctgatcaga agactataaa gatcaaccat    600

aaagtacagg ataaactggt tgacttgatc aataatcacc catctgaacc gtcgtcgtct    660

atcatttcta caaatggact atcacatata gaaattaata cagaatcggc tttatcaaga    720

ccaaacggcc cac                                                       733
```

```
<210> SEQ ID NO 9
<211> LENGTH: 2793
<212> TYPE: DNA
<213> ORGANISM: Artificial Sequence
<220> FEATURE:
<223> OTHER INFORMATION: melibiase-loxP-URA3 integration fragment
<220> FEATURE:
<221> NAME/KEY: misc_feature
<222> LOCATION: (633)..(633)
<223> OTHER INFORMATION: n is a, c, g, or t

<400> SEQUENCE: 9

aaactatcgc tttgctacat taaaaattca catactaaag cctttgttaa acaacttttt     60

ctaaatcata agattttact ctatctagtt tttttggttg taggtgaacg taaagtacct    120

catttaattt tttttttttg cttgtgtaat tcttttcatg cttatttaaa ctagtgtaca    180

tgtatcaaat ctttgtgtaa gaagcggccg cggatcaatt cgcccttaca tatggataac    240

ttcgtataat gtatgctata cgaagttatg ctgcaacggc aacatcaatg tccacgttta    300

cacacctaca tttatatcta tatttatatt tatatttatt tatttatgct acttagcttc    360

tatagttagt taatgcactc acgatattca aaattgacac ccttcaacta ctccctacta    420

ttgtctacta ctgtctacta ctcctcttta ctatagctgc tcccaatagg ctccaccaat    480

aggctctgtc aatacatttt gcgccgccac ctttcaggtt gtgtcactcc tgaaggacca    540

tattgggtaa tcgtgcaatt tctggaagag agtgccgcga gaagtgaggc ccccactgta    600

aatcctcgag gggcatggta gtatggggca tgnaggatgg aggatggggg gggggggga    660

aaataggtag cgaaaggacc cgctatcacc ccacccggag aactcgttgc cgggaagtca    720

tatttcgaca ctccggggag tctataaaag gcgggttttg tcttttgcca gttgatgttg    780

ctgagaggac ttgtttgccg tttcttccga tttaacagta tagaatcaac cactgttaat    840

tatacacgtt atactaacac aacaaaaaca aaaacaacga caacaacaac aacaatgttt    900

gctttctact ttctcaccgc atgcaccact ttgaagggtg ttttcggagt ttctccgagt    960

tacaatggtc ttggtctcac ccccacagatg ggttgggaca gctggaatac gtttgcctgc   1020

gatgtcagtg aacagctact tctagacact gctgatagaa tttctgactt ggggctaaag   1080

gatatgggtt acaagtatgt catcctagat gactgttggt ctagcggcag ggattccgac   1140

ggtttcctcg ttgcagacaa gcacaaattt cccaacggta tgggccatgt tgcagaccac   1200
```

```
ctgcataata acagctttct tttcggtatg tattcgtctg ctggtgagta cacctgtgct   1260

gggtaccctg ggtctctggg gcgtgaggaa gaagatgctc aattctttgc aaataaccgc   1320

gttgactact tgaagtatga taattgttac aataaaggtc aatttggtac accagacgtt   1380

tcttaccacc gttacaaggc catgtcagat gctttgaata aaactggtag gcctattttc   1440

tattctctat gtaactgggg tcaggatttg acattttact ggggctctgg tatcgccaat   1500

tcttggagaa tgagcggaga tattactgct gagttcaccc gtccagatag cagatgtccc   1560

tgtgacggtg acgaatatga ttgcaagtac gccggtttcc attgttctat tatgaatatt   1620

cttaacaagg cagctccaat ggggcaaaat gcaggtgttg gtggttggaa cgatctggac   1680

aatctagagg tcggagtcgg taatttgact gacgatgagg aaaaggccca tttctctatg   1740

tgggcaatgg taaagtcccc acttatcatt ggtgccgacg tgaatcactt aaaggcatct   1800

tcgtactcga tctacagtca agcctctgtc atcgcaatta atcaagatcc aaagggtatt   1860

ccagccacaa gagtctggag atattatgtt tcagacaccg atgaatatgg acaaggtgaa   1920

attcaaatgt ggagtggtcc gcttgacaat ggtgaccaag tggttgcttt attgaatgga   1980

ggaagcgtag caagaccaat gaacacgacc ttggaagaga ttttctttga cagcaatttg   2040

ggttcaaagg aactgacatc gacttgggat atttacgact tatgggccaa cagagttgac   2100

aactctacgg cgtctgctat ccttgaacag aataaggcag ccaccggtat tctctacaat   2160

gctacagagc agtcttataa agacggtttg tctaagaatg atacaagact gtttggccag   2220

aaaattggta gtctttctcc aaatgctata cttaacacaa ctgttccagc tcatggtatc   2280

gccttctata ggttgagacc ctcggcttaa gctcaatgtt gagcaaagca ggacgagaaa   2340

aaaaaaaata atgattgtta agaagttcat gaaaaaaaaa aggaaaaata ctcaaatact   2400

tataacagag tgattaaata ataaacggca gtatacccta tcaggtattg agatagtttt   2460

atttttgtag gtatataatc tgaagccttt gaactatttt ctcgtatata tcatggagta   2520

tacattgcat tagcaacatt gcatactagt tcataacttc gtataatgta tgctatacga   2580

agttattaat taacaagggc gatttctgca gatatcggcc ggccccatgg agatccgcgg   2640

ccgcccttga caaacaaact actttattaa agcgttgaag atctattctc cagcaattaa   2700

atttgtgaag aataactggt atagagtact tcctttaaaa acatgtccgt gcaccaagaa   2760

aaaaaaaaag tttgaaaaat tgtatgtcgg ttt                                 2793
```

```
<210> SEQ ID NO 10
<211> LENGTH: 471
<212> TYPE: PRT
<213> ORGANISM: Saccharomyces cerevisiae

<400> SEQUENCE: 10

Met Phe Ala Phe Tyr Phe Leu Thr Ala Cys Thr Thr Leu Lys Gly Val
1               5                   10                  15

Phe Gly Val Ser Pro Ser Tyr Asn Gly Leu Gly Leu Thr Pro Gln Met
            20                  25                  30

Gly Trp Asp Ser Trp Asn Thr Phe Ala Cys Asp Val Ser Glu Gln Leu
        35                  40                  45

Leu Leu Asp Thr Ala Asp Arg Ile Ser Asp Leu Gly Leu Lys Asp Met
    50                  55                  60

Gly Tyr Lys Tyr Val Ile Leu Asp Asp Cys Trp Ser Ser Gly Arg Asp
65                  70                  75                  80

Ser Asp Gly Phe Leu Val Ala Asp Lys His Lys Phe Pro Asn Gly Met
                85                  90                  95
```

```
Gly His Val Ala Asp His Leu His Asn Asn Ser Phe Leu Phe Gly Met
            100                 105                 110

Tyr Ser Ser Ala Gly Glu Tyr Thr Cys Ala Gly Tyr Pro Gly Ser Leu
        115                 120                 125

Gly Arg Glu Glu Glu Asp Ala Gln Phe Phe Ala Asn Asn Arg Val Asp
    130                 135                 140

Tyr Leu Lys Tyr Asp Asn Cys Tyr Asn Lys Gly Gln Phe Gly Thr Pro
145                 150                 155                 160

Asp Val Ser Tyr His Arg Tyr Lys Ala Met Ser Asp Ala Leu Asn Lys
                165                 170                 175

Thr Gly Arg Pro Ile Phe Tyr Ser Leu Cys Asn Trp Gly Gln Asp Leu
            180                 185                 190

Thr Phe Tyr Trp Gly Ser Gly Ile Ala Asn Ser Trp Arg Met Ser Gly
        195                 200                 205

Asp Ile Thr Ala Glu Phe Thr Arg Pro Asp Ser Arg Cys Pro Cys Asp
    210                 215                 220

Gly Asp Glu Tyr Asp Cys Lys Tyr Ala Gly Phe His Cys Ser Ile Met
225                 230                 235                 240

Asn Ile Leu Asn Lys Ala Ala Pro Met Gly Gln Asn Ala Gly Val Gly
                245                 250                 255

Gly Trp Asn Asp Leu Asp Asn Leu Glu Val Gly Val Gly Asn Leu Thr
            260                 265                 270

Asp Asp Glu Glu Lys Ala His Phe Ser Met Trp Ala Met Val Lys Ser
        275                 280                 285

Pro Leu Ile Ile Gly Ala Asp Val Asn His Leu Lys Ala Ser Ser Tyr
    290                 295                 300

Ser Ile Tyr Ser Gln Ala Ser Val Ile Ala Ile Asn Gln Asp Pro Lys
305                 310                 315                 320

Gly Ile Pro Ala Thr Arg Val Trp Arg Tyr Tyr Val Ser Asp Thr Asp
                325                 330                 335

Glu Tyr Gly Gln Gly Glu Ile Gln Met Trp Ser Gly Pro Leu Asp Asn
            340                 345                 350

Gly Asp Gln Val Val Ala Leu Leu Asn Gly Gly Ser Val Ala Arg Pro
        355                 360                 365

Met Asn Thr Thr Leu Glu Glu Ile Phe Phe Asp Ser Asn Leu Gly Ser
    370                 375                 380

Lys Glu Leu Thr Ser Thr Trp Asp Ile Tyr Asp Leu Trp Ala Asn Arg
385                 390                 395                 400

Val Asp Asn Ser Thr Ala Ser Ala Ile Leu Glu Gln Asn Lys Ala Ala
                405                 410                 415

Thr Gly Ile Leu Tyr Asn Ala Thr Glu Gln Ser Tyr Lys Asp Gly Leu
            420                 425                 430

Ser Lys Asn Asp Thr Arg Leu Phe Gly Gln Lys Ile Gly Ser Leu Ser
        435                 440                 445

Pro Asn Ala Ile Leu Asn Thr Thr Val Pro Ala His Gly Ile Ala Phe
    450                 455                 460

Tyr Arg Leu Arg Pro Ser Ala
465                 470
```

<210> SEQ ID NO 11
<211> LENGTH: 145
<212> TYPE: DNA
<213> ORGANISM: Artificial Sequence
<220> FEATURE:

<223> OTHER INFORMATION: IoURA3 primer

<400> SEQUENCE: 11

```
cgacatacaa tttttcaaac tttttttttt tcttggtgca cggacatgtt tttaaaggaa     60

gtactctata ccagttattc ttcacaaatt taattgctgg agaatagatc ttcaacgctt    120

taataaagta gtttgtttgt caagg                                          145
```

<210> SEQ ID NO 12
<211> LENGTH: 199
<212> TYPE: DNA
<213> ORGANISM: Artificial Sequence
<220> FEATURE:
<223> OTHER INFORMATION: IoURA3 primer

<400> SEQUENCE: 12

```
ttcttacaca aagatttgat acatgtacac tagtttaaat aagcatgaaa agaattacac     60

aagcaaaaaa aaaaaattaa atgaggtact ttacgttcac ctacaaccaa aaaaactaga    120

tagagtaaaa tcttatgatt tagaaaaagt tgtttaacaa aggctttagt atgtgaattt    180

ttaatgtagc aaagcgata                                                 199
```

<210> SEQ ID NO 13
<211> LENGTH: 9630
<212> TYPE: DNA
<213> ORGANISM: Artificial Sequence
<220> FEATURE:
<223> OTHER INFORMATION: pVB32 plasmid
<220> FEATURE:
<221> NAME/KEY: misc_feature
<222> LOCATION: (5897)..(5897)
<223> OTHER INFORMATION: n is a, c, g, or t
<220> FEATURE:
<221> NAME/KEY: misc_feature
<222> LOCATION: (6283)..(6283)
<223> OTHER INFORMATION: n is a, c, g, or t
<220> FEATURE:
<221> NAME/KEY: misc_feature
<222> LOCATION: (6314)..(6314)
<223> OTHER INFORMATION: n is a, c, g, or t
<220> FEATURE:
<221> NAME/KEY: misc_feature
<222> LOCATION: (6343)..(6343)
<223> OTHER INFORMATION: n is a, c, g, or t
<220> FEATURE:
<221> NAME/KEY: misc_feature
<222> LOCATION: (6347)..(6347)
<223> OTHER INFORMATION: n is a, c, g, or t
<220> FEATURE:
<221> NAME/KEY: misc_feature
<222> LOCATION: (6371)..(6371)
<223> OTHER INFORMATION: n is a, c, g, or t
<220> FEATURE:
<221> NAME/KEY: misc_feature
<222> LOCATION: (6525)..(6525)
<223> OTHER INFORMATION: n is a, c, g, or t
<220> FEATURE:
<221> NAME/KEY: misc_feature
<222> LOCATION: (6543)..(6543)
<223> OTHER INFORMATION: n is a, c, g, or t
<220> FEATURE:
<221> NAME/KEY: misc_feature
<222> LOCATION: (7386)..(7386)
<223> OTHER INFORMATION: n is a, c, g, or t
<220> FEATURE:
<221> NAME/KEY: misc_feature
<222> LOCATION: (7397)..(7397)
<223> OTHER INFORMATION: n is a, c, g, or t

<400> SEQUENCE: 13

```
ctgacgcgcc ctgtagcggc gcattaagcg cggcgggtgt ggtggttacg cgcagcgtga     60
```

```
ccgctacact tgccagcgcc ctagcgcccg ctcctttcgc tttcttccct tcctttctcg    120
ccacgttcgc cggctttccc cgtcaagctc taaatcgggg gctcccttta gggttccgat    180
ttagtgcttt acggcacctc gaccccaaaa aacttgatta gggtgatggt tcacgtagtg    240
ggccatcgcc ctgatagacg gtttttcgcc ctttgacgtt ggagtccacg ttctttaata    300
gtggactctt gttccaaact ggaacaacac tcaaccctat ctcggtctat tcttttgatt    360
tataagggat tttgccgatt tcggcctatt ggttaaaaaa tgagctgatt taacaaaaat    420
ttaacgcgaa ttttaacaaa atattaacgc ttacaatttc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tggtcgagga    660
gtccatcggt tcctgtcaga tgggatactc ttgacgtgga aaattcaaac agaaaaaaaa    720
ccccaataat gaaaaataac actacgttat atccgtggta tcctctatcg tatcgtatcg    780
tagcgtatcg tagcgtaccg tatcacagta tagtctaata ttccgtatct tattgtatcc    840
tatcctattc gatcctattg tatttcagtg caccatttta atttctattg ctataatgtc    900
cttattagtt gccactgtga ggtgaccaat ggacgagggc gagccgttca gaagccgcga    960
agggtgttct tcccatgaat ttcttaagga gggcggctca gctccgagag tgaggcgaga   1020
cgtctcggtc agcgtatccc ccttcctcgg cttttacaaa tgatgcgctc ttaatagtgt   1080
gtcgttatcc ttttggcatt gacgggggag ggaaattgat tgagcgcatc catatttttg   1140
cggactgctg aggacaatgg tggtttttcc gggtggcgtg ggctacaaat gatacgatgg   1200
tttttttctt ttcggagaag gcgtataaaa aggacacgga gaacccattt attctaaaaa   1260
cagttgagct tctttaatta ttttttgata taatattcta ttattatata ttttcttccc   1320
aataaaacaa aataaaacaa aacacagcaa aacacaaaaa ggatccatgt ctaatttact   1380
tactgttcac caaaacttgc ctgcattacc agttgacgca acctccgatg aagtcagaaa   1440
gaaccttatg gatatgttta gagatagaca agctttctcc gaacatactt ggaaaatgtt   1500
attatccgtt tgtagatcct gggccgcttg gtgtaaactt aacaatagaa aatggtttcc   1560
tgctgaacca gaagacgtca gagattactt actttactta caagctagag gtttggctgt   1620
taaaactatc caacaacact taggtcaatt gaatatgtta cacagaagat ccggtttacc   1680
aagaccatcc gattccaacg cagtttccct tgttatgaga agaattagaa aagaaaatgt   1740
tgacgctggt gaaagagcta aacaagcatt agcatttgaa agaaccgatt tcgatcaagt   1800
tagatcctta atggaaaatt ccgatagatg tcaagatatt agaaacttag ctttcttagg   1860
tattgcttac aacacattat taagaatcgc tgaaattgct agaattagag ttaaagatat   1920
ttcaagaacc gatggcggta gaatgttaat ccacattggc agaacaaaaa ccttagtctc   1980
cacagcaggc gtcgaaaaag cattatcatt aggtgttact aaattagttg aacgttggat   2040
ttccgtttcc ggtgttgcag atgacccaaa caactactta ttctgtcgtg ttagaaaaaa   2100
tggtgttgcc gctccttccg ctacctcaca attatccaca agagcattag aaggcatttt   2160
tgaagctacc cacagactta tttatggtgc aaaagacgat tccggtcaaa gatatttagc   2220
ttggtctggt cattccgcta gagttggtgc cgcaagagac atggcaagag ctggtgtttc   2280
tattcctgaa attatgcaag ccggtggttg gactaatgtt aacattgtta tgaactatat   2340
cagaaactta gattccgaaa caggtgctat ggttagatta cttgaagacg gtgattaagt   2400
```

-continued

```
taattaacat ctgaatgtaa aatgaacatt aaaatgaatt actaaacttt acgtctactt   2460
tacaatctat aaactttgtt taatcatata acgaaataca ctaatacaca atcctgtacg   2520
tatgtaatac ttttatccat caaggattga gaaaaaaaag taatgattcc ctgggccatt   2580
aaaacttaga cccccaagct tggataggtc actctctatt ttcgtttctc ccttccctga   2640
tagaagggtg atatgtaatt aagaataata tataatttta taataaaaga attcggcaga   2700
tctggatcga tcccccgggc tgcatgcaac ggcaacatca atgtccacgt ttacacacct   2760
acatttatat ctatatttat atttatattt atttatttat gctacttagc ttctatagtt   2820
agttaatgca ctcacgatat tcaaaattga cacccttcaa ctactcccta ctattgtcta   2880
ctactgtcta ctactcctct ttactatagc tgctcccaat aggctccacc aataggctct   2940
gtcaatacat tttgcgccgc cacctttcag gttgtgtcac tcctgaagga ccatattggg   3000
taatcgtgca atttctggaa gagagtgccg cgagaagtga ggcccccact gtaaatcctc   3060
gagggggcat ggagtatggg gcatggagga tggaggatgg ggggggggg ggaaaatagg   3120
tagcgaaagg acccgctatc accccacccg gagaactcgt tgccgggaag tcatatttcg   3180
acactccggg gagtctataa aaggcgggtt ttgtcttttg ccagttgatg ttgctgagag   3240
gacttgtttg ccgtttcttc cgatttaaca gtatagaatc aaccactgtt aattatacac   3300
gttatactaa cacaacaaaa acaaaaacaa cgacaacaac aacaacctgc aggaaatgct   3360
tttgcaagct ttcctttcc ttttggctgg ttttgcagcc aaaatatctg catcaatgac   3420
aaacgaaact agcgatagac ctttggtcca cttcacaccc aacaagggct ggatgaatga   3480
cccaaatggg ttgtggtacg atgaaaaaga tgccaaatgg catctgtact ttcaatacaa   3540
cccaaatgac accgtatggg gtacgccatt gttttggggc catgctactt ccgatgattt   3600
gactaattgg gaagatcaac ccattgctat cgctcccaag cgtaacgatt caggtgcttt   3660
ctctggctcc atggtggttg attacaacaa cacgagtggg tttttcaatg atactattga   3720
tccaagacaa agatgcgttg cgatttggac ttataacact cctgaaagtg aagagcaata   3780
cattagctat tctcttgatg gtggttacac ttttactgaa taccaaaaga accctgtttt   3840
agctgccaac tccactcaat tcagagatcc aaaggtgttc tggtatgaac cttctcaaaa   3900
atggattatg acggctgcca aatcacaaga ctacaaaatt gaaatttact cctctgatga   3960
cttgaagtcc tggaagctag aatctgcatt tgccaatgaa ggtttcttag gctaccaata   4020
cgaatgtcca ggtttgattg aagtcccaac tgagcaagat ccttccaaat cttattgggt   4080
catgtttatt tctatcaacc caggtgcacc tgctggcggt tccttcaacc aatattttgt   4140
tggatccttc aatggtactc attttgaagc gtttgacaat caatctagag tggtagattt   4200
tggtaaggac tactatgcct tgcaaacttt cttcaacact gacccaacct acggttcagc   4260
attaggtatt gcctgggctt caaactggga gtacagtgcc tttgtcccaa ctaacccatg   4320
gagatcatcc atgtctttgg tccgcaagtt ttctttgaac actgaatatc aagctaatcc   4380
agagactgaa ttgatcaatt tgaaagccga accaatattg aacattagta atgctggtcc   4440
ctggtctcgt tttgctacta acacaactct aactaaggcc aattcttaca atgtcgattt   4500
gagcaactcg actggtaccc tagagtttga gttggtttac gctgttaaca ccacacaaac   4560
catatccaaa tccgtctttg ccgacttatc actttggttc aagggtttag aagatcctga   4620
agaatatttg agaatgggtt ttgaagtcag tgcttcttcc ttctttttgg accgtggtaa   4680
ctctaaggtc aagtttgtca aggagaaccc atatttcaca aacagaatgt ctgtcaacaa   4740
ccaaccattc aagtctgaga acgacctaag ttactataaa gtgtacggcc tactggatca   4800
```

```
aaacatcttg gaattgtact tcaacgatgg agatgtggtt tctacaaata cctacttcat   4860
gaccaccggt aacgctctag gatctgtgaa catgaccact ggtgtcgata atttgttcta   4920
cattgacaag ttccaagtaa gggaagtaaa atagcctgca ggcacgtccg acggcggccc   4980
acgggtccca ggcctcggag atccgtcccc cttttccttt gtcgatatca tgtaattagt   5040
tatgtcacgc ttacattcac gccctccccc cacatccgct ctaaccgaaa aggaaggagt   5100
tagacaacct gaagtctagg tccctattta tttttttata gttatgttag tattaagaac   5160
gttatttata tttcaaattt ttcttttttt tctgtacaga cgcgtgtacg catgtaacat   5220
tatactgaaa accttgcttg agaaggtttt gggacgctcg aaggctttaa tttgcaagct   5280
gaattcccgg gccttaccgt cgacgaattt cagcattttc atttcaaggc gatattatgt   5340
ttcactaaac tcaggacagg aatatactaa gaataactac aacatacaca caacataagc   5400
caagatggat caacttaact accaagaaca acaacaattt caaaagatcg ttgaacaaaa   5460
gcaaatggct gatttcatga ggctatgaat tcgcccttga tctgggtgta tactgcacaa   5520
cctcattgtt cgggaatttg attctcatct cacatacagg cctgtagtat tgcgccctct   5580
ccttctcctt ctccttctcc ttctccaaga gagacttctc tctcatcgcc ctcgtcatca   5640
atggctgctc gctgtattgt cgttggagca tctcccgata cttctgcaac tgtgataaac   5700
tcatctcagg tgacccatcc gattctgtat cggtgtctcc atctggggct acatctcggg   5760
ccagtctaga tttaaacttt gcagaacctt cactttgggg gatatacact agtgtctctc   5820
ccgtgactac atcaccgaca ccctcaactg taccattatt attgtcattg ttttcctcta   5880
agttctcgct ttggtcntca tccatctctc cttcgggtgc tgtatcactc ttgatgattt   5940
ctctaaccct aatacggaga ctgtgattgc ctgaaataat acccacatct ttcaacttct   6000
gatgaagtga atctccagag atgaccttca tcagcacttg cacatcaacc acatcaccct   6060
ccttttgagc atccctcatg attccataga ctacatcccg tagcgtctcc ttgttcttgt   6120
acttcttaac aacagtctcg ccacagacat ggcccctgat aatcacctcc tgtctctcct   6180
catggccatc ctggtcgcca ttgtcttcgt cgctcggctc aattgccaat gtagcaccct   6240
gtggaagatt gcttagtctg tatggaacag actcatcaac tcntttgcca ttatgcatta   6300
acttgtactt tcgnccttgg ctaagttgaa aatgtttaca tcnwtcntca agtacattgg   6360
acatgattgt ncctgcattg acatttgtcc ggtaagtcct aaacccactc gctagattca   6420
ctgtaggcat attcaatcac gttccgtttg aaaaaaagga aaccaattta ttatctccag   6480
aaatagttgg cgtcttgcat cttgtttggt cttgatcttt cgtgnttttt tttttttctg   6540
tcnttttttt tctcctctct ccaacttttt gatttttagt gtaccaaatc gcactgctta   6600
tccacattca tcataaagrg ggggggagaa gaggggcaga aaataaaagg ccatgtcacg   6660
tgcctgtgca tttatttgtg tgtgtgtcac gtgctcaaaa tgtctttttt ttacgttttt   6720
aacattttcc ctttctgtag ttgaatccat ttgcatgagt cgtacatrat gtttgctgta   6780
tttacgttaa gacactaatt caaatgacaa acagctatta ttcttagcca ttaatgcatt   6840
tttgcaaatc tttaactgga tttaactatg gctaggtraa tttgttctgg acatcattgc   6900
cttgacttgt tttagtgccg atgtccttat cacttacact cgtaacacaa cacaacagca   6960
gctaatgttg ttgtgtatcg cttgaccctt aataactgat tctttttgga tgaatgttaa   7020
gaagaaacaa acaaraaaat aaaatcaaaa caggcttctt ttgacctctt tcaagagaag   7080
gttttcttgg ttgtttcata taccaagatc tgaatatctt ctattattat acaaaccact   7140
```

```
gattatacaa atctattcat cgacagtatg arctacgaaa acacactgat aaaragagtc   7200
atttcttccc cttctttttc tttttctttt tcttcttctt cttagtatcc ccatcttcat   7260
taactccacc aagtagatcc tctacacccc ccatggccgt taaaaaatgt tcacgaaaga   7320
aatccatatc attattctta ccatccatta aactgtttag atagatggtg atcatctccc   7380
ttgcantgtc tatatcntca acgtcgagta aatgcgacgc aatggtaccc agcttttgtt   7440
ccctttagtg agggttaatt gcgcgcttgg cgtaatcatg gtcatagctg tttcctgtgt   7500
gaaattgtta tccgctcaca attccacaca acatacgagc cggaagcata aagtgtaaag   7560
cctggggtgc ctaatgagtg agctaactca cattaattgc gttgcgctca ctgcccgctt   7620
tccagtcggg aaacctgtcg tgccagctgc attaatgaat cggccaacgc gcggggagag   7680
gcggtttgcg tattgggcgc tcttccgctt cctcgctcac tgactcgctg cgctcggtcg   7740
ttcggctgcg gcgagcggta tcagctcact caaaggcggt aatacggtta tccacagaat   7800
caggggataa cgcaggaaag aacatgtgag caaaaggcca gcaaaaggcc aggaaccgta   7860
aaaaggccgc gttgctggcg tttttccata ggctccgccc ccctgacgag catcacaaaa   7920
atcgacgctc aagtcagagg tggcgaaacc cgacaggact ataaagatac caggcgtttc   7980
cccctggaag ctccctcgtg cgctctcctg ttccgaccct gccgcttacc ggatacctgt   8040
ccgcctttct cccttcggga agcgtggcgc tttctcatag ctcacgctgt aggtatctca   8100
gttcggtgta ggtcgttcgc tccaagctgg gctgtgtgca cgaacccccc gttcagcccg   8160
accgctgcgc cttatccggt aactatcgtc ttgagtccaa cccggtaaga cacgacttat   8220
cgccactggc agcagccact ggtaacagga ttagcagagc gaggtatgta ggcggtgcta   8280
cagagttctt gaagtggtgg cctaactacg gctacactag aaggacagta tttggtatct   8340
gcgctctgct gaagccagtt accttcggaa aaagagttgg tagctcttga tccggcaaac   8400
aaaccaccgc tggtagcggt ggtttttttg tttgcaagca gcagattacg cgcagaaaaa   8460
aaggatctca agaagatcct ttgatctttt ctacggggtc tgacgctcag tggaacgaaa   8520
actcacgtta agggattttg gtcatgagat tatcaaaaag gatcttcacc tagatccttt   8580
taaattaaaa atgaagtttt aaatcaatct aaagtatata tgagtaaact tggtctgaca   8640
gttaccaatg cttaatcagt gaggcaccta tctcagcgat ctgtctattt cgttcatcca   8700
tagttgcctg actccccgtc gtgtagataa ctacgatacg ggagggctta ccatctggcc   8760
ccagtgctgc aatgataccg cgagacccac gctcaccggc tccagattta tcagcaataa   8820
accagccagc cggaagggcc gagcgcagaa gtggtcctgc aactttatcc gcctccatcc   8880
agtctattaa ttgttgccgg gaagctagag taagtagttc gccagttaat agtttgcgca   8940
acgttgttgc cattgctaca ggcatcgtgg tgtcacgctc gtcgtttggt atggcttcat   9000
tcagctccgg ttcccaacga tcaaggcgag ttacatgatc ccccatgttg tgcaaaaaag   9060
cggttagctc cttcggtcct ccgatcgttg tcagaagtaa gttggccgca gtgttatcac   9120
tcatggttat ggcagcactg cataattctc ttactgtcat gccatccgta agatgctttt   9180
ctgtgactgg tgagtactca accaagtcat tctgagaata gtgtatgcgg cgaccgagtt   9240
gctcttgccc ggcgtcaata cgggataata ccgcgccaca tagcagaact ttaaaagtgc   9300
tcatcattgg aaaacgttct tcggggcgaa aactctcaag gatcttaccg ctgttgagat   9360
ccagttcgat gtaacccact cgtgcaccca actgatcttc agcatctttt actttcacca   9420
gcgtttctgg gtgagcaaaa acaggaaggc aaaatgccgc aaaaaaggga ataagggcga   9480
cacggaaatg ttgaatactc atactcttcc tttttcaata ttattgaagc atttatcagg   9540
```

```
gttattgtct catgagcgga tacatatttg aatgtattta gaaaaataaa caaatagggg   9600

ttccgcgcac atttccccga aaagtgccac                                     9630


<210> SEQ ID NO 14
<211> LENGTH: 532
<212> TYPE: PRT
<213> ORGANISM: Saccharomyces cerevisiae

<400> SEQUENCE: 14

Met Leu Leu Gln Ala Phe Leu Phe Leu Leu Ala Gly Phe Ala Ala Lys
1               5                   10                  15

Ile Ser Ala Ser Met Thr Asn Glu Thr Ser Asp Arg Pro Leu Val His
            20                  25                  30

Phe Thr Pro Asn Lys Gly Trp Met Asn Asp Pro Asn Gly Leu Trp Tyr
        35                  40                  45

Asp Glu Lys Asp Ala Lys Trp His Leu Tyr Phe Gln Tyr Asn Pro Asn
    50                  55                  60

Asp Thr Val Trp Gly Thr Pro Leu Phe Trp Gly His Ala Thr Ser Asp
65                  70                  75                  80

Asp Leu Thr Asn Trp Glu Asp Gln Pro Ile Ala Ile Ala Pro Lys Arg
                85                  90                  95

Asn Asp Ser Gly Ala Phe Ser Gly Ser Met Val Val Asp Tyr Asn Asn
            100                 105                 110

Thr Ser Gly Phe Phe Asn Asp Thr Ile Asp Pro Arg Gln Arg Cys Val
        115                 120                 125

Ala Ile Trp Thr Tyr Asn Thr Pro Glu Ser Glu Glu Gln Tyr Ile Ser
    130                 135                 140

Tyr Ser Leu Asp Gly Gly Tyr Thr Phe Thr Glu Tyr Gln Lys Asn Pro
145                 150                 155                 160

Val Leu Ala Ala Asn Ser Thr Gln Phe Arg Asp Pro Lys Val Phe Trp
                165                 170                 175

Tyr Glu Pro Ser Gln Lys Trp Ile Met Thr Ala Ala Lys Ser Gln Asp
            180                 185                 190

Tyr Lys Ile Glu Ile Tyr Ser Ser Asp Asp Leu Lys Ser Trp Lys Leu
        195                 200                 205

Glu Ser Ala Phe Ala Asn Glu Gly Phe Leu Gly Tyr Gln Tyr Glu Cys
    210                 215                 220

Pro Gly Leu Ile Glu Val Pro Thr Glu Gln Asp Pro Ser Lys Ser Tyr
225                 230                 235                 240

Trp Val Met Phe Ile Ser Ile Asn Pro Gly Ala Pro Ala Gly Gly Ser
                245                 250                 255

Phe Asn Gln Tyr Phe Val Gly Ser Phe Asn Gly Thr His Phe Glu Ala
            260                 265                 270

Phe Asp Asn Gln Ser Arg Val Val Asp Phe Gly Lys Asp Tyr Tyr Ala
        275                 280                 285

Leu Gln Thr Phe Phe Asn Thr Asp Pro Thr Tyr Gly Ser Ala Leu Gly
    290                 295                 300

Ile Ala Trp Ala Ser Asn Trp Glu Tyr Ser Ala Phe Val Pro Thr Asn
305                 310                 315                 320

Pro Trp Arg Ser Ser Met Ser Leu Val Arg Lys Phe Ser Leu Asn Thr
                325                 330                 335

Glu Tyr Gln Ala Asn Pro Glu Thr Glu Leu Ile Asn Leu Lys Ala Glu
            340                 345                 350
```

```
Pro Ile Leu Asn Ile Ser Asn Ala Gly Pro Trp Ser Arg Phe Ala Thr
        355                 360                 365

Asn Thr Thr Leu Thr Lys Ala Asn Ser Tyr Asn Val Asp Leu Ser Asn
    370                 375                 380

Ser Thr Gly Thr Leu Glu Phe Glu Leu Val Tyr Ala Val Asn Thr Thr
385                 390                 395                 400

Gln Thr Ile Ser Lys Ser Val Phe Ala Asp Leu Ser Leu Trp Phe Lys
                405                 410                 415

Gly Leu Glu Asp Pro Glu Glu Tyr Leu Arg Met Gly Phe Glu Val Ser
            420                 425                 430

Ala Ser Ser Phe Phe Leu Asp Arg Gly Asn Ser Lys Val Lys Phe Val
        435                 440                 445

Lys Glu Asn Pro Tyr Phe Thr Asn Arg Met Ser Val Asn Asn Gln Pro
    450                 455                 460

Phe Lys Ser Glu Asn Asp Leu Ser Tyr Tyr Lys Val Tyr Gly Leu Leu
465                 470                 475                 480

Asp Gln Asn Ile Leu Glu Leu Tyr Phe Asn Asp Gly Asp Val Val Ser
                485                 490                 495

Thr Asn Thr Tyr Phe Met Thr Thr Gly Asn Ala Leu Gly Ser Val Asn
            500                 505                 510

Met Thr Thr Gly Val Asp Asn Leu Phe Tyr Ile Asp Lys Phe Gln Val
        515                 520                 525

Arg Glu Val Lys
    530


<210> SEQ ID NO 15
<211> LENGTH: 343
<212> TYPE: PRT
<213> ORGANISM: Bacteriophage P1

<400> SEQUENCE: 15

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190
```

```
Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340
```

<210> SEQ ID NO 16
<211> LENGTH: 3257
<212> TYPE: DNA
<213> ORGANISM: Artificial Sequence
<220> FEATURE:
<223> OTHER INFORMATION: URA3-ODD-CYB2A integration fragment

<400> SEQUENCE: 16

```
aaacattagg acgcatacag ccgagaagcc attttactgt ttattacctg aatgtctgaa     60

ggcatttact agagcagatg ccttattgaa acatttaaag gcggttcata atatcaacgg    120

caacagttta caggatgcat acgagaatat caatagagaa ttaatccatg aaatacatga    180

attccagcga gaaaatgact tcagagttga ttttgagtct agcgggaaga aaatagcttt    240

tgatattgag aaaagagtac gcaatgaatt gatacaagat cacaataaac tgataaacaa    300

ttttaataaa ttgaaaaggc aacgtgacat atctgatgat catgatgacg aagtggaaga    360

gctaatagcc gaccattata aaatcaaaga aatcaaattt aatccctcaa tggtcattga    420

aggtacccag aaaatcaagg aatctttaat gtcgtattcc aacaaaaaag agaatgctgc    480

caaggggggg aaagttgtca acgtcgaaga cattggagat attgattcaa tgactgtaga    540

acagttagaa caaacaatac agaaacaaac agattactat gctaggctag tacgtcttag    600

gaagattctt gagcaagagc tagtcaagta taactcctcg gcgagatact attggctaaa    660

aaaacagtat ctacttaatc atctgttgct taaggaagaa gtagcaatga agaaagggtc    720

gaaataggtt gatccattag tttatttgaa ctttttcttg aatcattaga gctcgcggcc    780

gcggatccct cgaggcctta attaacatct gaatgtaaaa tgaacattaa aatgaattac    840

taaactttac gtctacttta caatctataa actttgttta atcatataac gaaatacact    900

aatacacaat cctgtacgta tgtaatactt ttatccatca aggattgaga aaaaaaagta    960

atgattccct gggccattaa aacttagacc cccaagcttg gataggtcac tctctatttt   1020

cgtttctccc ttccctgata gaagggtgat atgtaattaa gaataatata taattttata   1080

ataaaagaat tcatagcctc atgaaatcag ccatttgctt ttgttcaacg atcttttgaa   1140
```

```
attgttgttg ttcttggtag ttaagttgat ccatcttggc ttatgttgtg tgtatgttgt   1200

agttattctt agtatattcc tgtcctgagt ttagtgaaac ataatatcgc cttgaaatga   1260

aaatgctgaa attcgtcgac atacaatttt tcaaactttt ttttttcttt ggtgcacgga   1320

catgttttta aaggaagtac tctataccag ttattcttca caaatttaat tgctggagaa   1380

tagatcttca acgctttaat aaagtagttt gtttgtcaag gatggcgtca tacaaagaaa   1440

gatcagaatc acacacttcc cctgttgcta ggagactttt ctccatcatg gaggaaaaga   1500

agtctaacct ttgtgcatca ttggatatta ctgaaactga aaagcttctc tctattttgg   1560

acactattgg tccttacatc tgtctagtta aaacacacat cgatattgtt tctgatttta   1620

cgtatgaagg aactgtgttg cctttgaagg agcttgccaa gaaacataat tttatgattt   1680

ttgaagatag aaaatttgct gatattggta acactgttaa aaatcaatat aaatctggtg   1740

tcttccgtat tgccgaatgg gctgacatca ctaatgcaca tggtgtaacg ggtgcaggta   1800

ttgtttctgg cttgaaggag gcagcccaag aaacaaccag tgaacctaga ggtttgctaa   1860

tgcttgctga gttatcatca aagggttctt tagcatatgg tgaatataca gaaaaaacag   1920

tagaaattgc taaatctgat aaagagtttg tcattggttt tattgcgcaa cacgatatgg   1980

gcggtagaga agaaggtttt gactggatca ttatgactcc aggggttggt ttagatgaca   2040

aaggtgatgc acttggtcaa caatatagaa ctgttgatga agttgtaaag actggaacgg   2100

atatcataat tgttggtaga ggtttgtacg gtcaaggaag agatcctata gagcaagcta   2160

aaagatacca acaagctggt tggaatgctt atttaaacag atttaaatga ttcttacaca   2220

aagatttgat acatgtacac tagtttaaat aagcatgaaa agaattacac aagcaaaaaa   2280

aaaaaaataa atgaggtact ttacgttcac ctacaaccaa aaaaactaga tagagtaaaa   2340

tcttaagatt tagaaaaagt tgtttaacaa aggctttagt atgtgaattt ttaatgtagc   2400

aaagcgataa ctaataaaca taaacaaaag tatggttttc tttatcagtc aaatcattat   2460

cgattgattg ttccgcgtat ctgcagatag cctcatgaaa tcagccattt gcttttgttc   2520

aacgatcttt tgaaattgtt gttgttcttg gtagttaagt tgatccatct tggcttatgt   2580

tgtgtgtatg ttgtagttat tcttagtata ttcctgtcct gagtttagtg aaacataata   2640

tcgccttgaa atgaaaatgc tgaaattcgt cgacatacaa tttttcaaac tttttttttt   2700

tcttggtgca cggacatgtt tttaaaggaa gtactctata ccagttattc ttcacaaatt   2760

taattgctgg agaatagatc ttcaacgccc cgggggatct ggatccgcgg ccgccatatg   2820

ctagcaccaa cagcaacacc cacctgaaaa aaaaataata cacttgttag ggtgatgtag   2880

agaagtgatc atgagagcga gccgttattc atttactacc gtaaagttag tagctgtcta   2940

gtcaaacagc aacgaaggtg gatagtttac cctagactca gggcaaagac atctcttagg   3000

ataccgatag aacagcagcg ttgagccacc agaagttgcg cgaatttcaa cgatggcgat   3060

caacacaaac aaaaagtaga tttgcttatg taatatattc agttataggg tggaagttag   3120

tggttgaggc atacacggtg ccaattatag gagaatcccc cccaagaggt gatgtcccat   3180

gacccacaca acaggatcag cggccatgtc tcattggtag aatacaacca tcatggcggt   3240

gtcacgcatt atggttt                                                  3257
```

<210> SEQ ID NO 17
<211> LENGTH: 262
<212> TYPE: PRT
<213> ORGANISM: Issatchenkia orientalis

<400> SEQUENCE: 17

```
Met Ala Ser Tyr Lys Glu Arg Ser Glu Ser His Thr Ser Pro Val Ala
1               5                   10                  15

Arg Arg Leu Phe Ser Ile Met Glu Glu Lys Lys Ser Asn Leu Cys Ala
            20                  25                  30

Ser Leu Asp Ile Thr Glu Thr Glu Lys Leu Leu Ser Ile Leu Asp Thr
        35                  40                  45

Ile Gly Pro Tyr Ile Cys Leu Val Lys Thr His Ile Asp Ile Val Ser
    50                  55                  60

Asp Phe Thr Tyr Glu Gly Thr Val Leu Pro Leu Lys Glu Leu Ala Lys
65                  70                  75                  80

Lys His Asn Phe Met Ile Phe Glu Asp Arg Lys Phe Ala Asp Ile Gly
                85                  90                  95

Asn Thr Val Lys Asn Gln Tyr Lys Ser Gly Val Phe Arg Ile Ala Glu
            100                 105                 110

Trp Ala Asp Ile Thr Asn Ala His Gly Val Thr Gly Ala Gly Ile Val
        115                 120                 125

Ser Gly Leu Lys Glu Ala Ala Gln Glu Thr Thr Ser Glu Pro Arg Gly
    130                 135                 140

Leu Leu Met Leu Ala Glu Leu Ser Ser Lys Gly Ser Leu Ala Tyr Gly
145                 150                 155                 160

Glu Tyr Thr Glu Lys Thr Val Glu Ile Ala Lys Ser Asp Lys Glu Phe
                165                 170                 175

Val Ile Gly Phe Ile Ala Gln His Asp Met Gly Gly Arg Glu Glu Gly
            180                 185                 190

Phe Asp Trp Ile Ile Met Thr Pro Gly Val Gly Leu Asp Asp Lys Gly
        195                 200                 205

Asp Ala Leu Gly Gln Gln Tyr Arg Thr Val Asp Glu Val Val Lys Thr
    210                 215                 220

Gly Thr Asp Ile Ile Ile Val Gly Arg Gly Leu Tyr Gly Gln Gly Arg
225                 230                 235                 240

Asp Pro Ile Glu Gln Ala Lys Arg Tyr Gln Gln Ala Gly Trp Asn Ala
                245                 250                 255

Tyr Leu Asn Arg Phe Lys
            260
```

<210> SEQ ID NO 18
<211> LENGTH: 439
<212> TYPE: DNA
<213> ORGANISM: Issatchenkia orientalis

<400> SEQUENCE: 18

```
cataatgcgt gacaccgcca tgatggttgt attctaccaa tgagacatgg ccgctgatcc      60

tgttgtgtgg gtcatgggac atcacctctt ggggggatt ctcctataat tggcaccgtg     120

tatgcctcaa ccactaactt ccaccctata actgaatata ttacataagc aaatctactt    180

tttgtttgtg ttgatcgcca tcgttgaaat tcgcgcaact tctggtggct caacgctgct    240

gttctatcgg tatcctaaga gatgtctttg ccctgagtct agggtaaact atccaccttc    300

gttgctgttt gactagacag ctactaactt tacggtagta aatgaataac ggctcgctct    360

catgatcact tctctacatc accctaacaa gtgtattatt ttttttcag gtgggtgttg     420

ctgttggtgc tagcatatg                                                  439
```

<210> SEQ ID NO 19
<211> LENGTH: 770

<212> TYPE: DNA
<213> ORGANISM: Issatchenkia orientalis

<400> SEQUENCE: 19

```
gagctctaat gattcaagaa aaagttcaaa taaactaatg gatcaaccta tttcgaccct     60
ttcttcattg ctacttcttc cttaagcaac agatgattaa gtagatactg tttttttagc    120
caatagtatc tcgccgagga gttatacttg actagctctt gctcaagaat cttcctaaga    180
cgtactagcc tagcatagta atctgtttgt ttctgtattg tttgttctaa ctgttctaca    240
gtcattgaat caatatctcc aatgtcttcg acgttgacaa ctttcccccc cttggcagca    300
ttctcttttt tgttggaata cgacattaaa gattccttga ttttctgggt accttcaatg    360
accattgagg gattaaattt gatttctttg attttataat ggtcggctat tagctcttcc    420
acttcgtcat catgatcatc agatatgtca cgttgccttt tcaatttatt aaaattgttt    480
atcagtttat tgtgatcttg tatcaattca ttgcgtactc ttttctcaat atcaaaagct    540
atttcttcc cgctagactc aaaatcaact ctgaagtcat tttctcgctg gaattcatgt    600
atttcatgga ttaattctct attgatattc tcgtatgcat cctgtaaact gttgccgttg    660
atattatgaa ccgcctttaa atgtttcaat aaggcatctg ctctagtaaa tgccttcaga    720
cattcaggta ataaacagta aaatggcttc tcggctgtat gcgtcctaat               770
```

<210> SEQ ID NO 20
<211> LENGTH: 3257
<212> TYPE: DNA
<213> ORGANISM: Artificial Sequence
<220> FEATURE:
<223> OTHER INFORMATION: URA3-ODD-CYB2A integration fragment

<400> SEQUENCE: 20

```
aaaccataat gcgtgacacc gccatgatgg ttgtattcta ccaatgagac atggccgctg     60
atcctgttgt gtgggtcatg ggacatcacc tcttgggggg gattctccta taattggcac    120
cgtgtatgcc tcaaccacta acttccaccc tataactgaa tatattacat aagcaaatct    180
actttttgtt tgtgttgatc gccatcgttg aaattcgcgc aacttctggt ggctcaacgc    240
tgctgttcta tcggtatcct aagagatgtc tttgccctga gtctagggta aactatccac    300
cttcgttgct gtttgactag acagctacta actttacggt agtaaatgaa taacggctcg    360
ctctcatgat cacttctcta catcacccta acaagtgtat tatttttttt tcaggtgggt    420
gttgctgttg gtgctagcat atggcggccg cggatccctc gaggccttaa ttaacatctg    480
aatgtaaaat gaacattaaa atgaattact aaactttacg tctactttac aatctataaa    540
ctttgtttaa tcatataacg aaatacacta atacacaatc ctgtacgtat gtaatacttt    600
tatccatcaa ggattgagaa aaaaaagtaa tgattccctg ggccattaaa acttagaccc    660
ccaagcttgg ataggtcact ctctattttc gtttctccct tccctgatag aagggtgata    720
tgtaattaag aataatatat aattttataa taaaagaatt catagcctca tgaaatcagc    780
catttgcttt tgttcaacga tcttttgaaa ttgttgttgt tcttggtagt taagttgatc    840
catcttggct tatgttgtgt gtatgttgta gttattctta gtatattcct gtcctgagtt    900
tagtgaaaca taatatcgcc ttgaaatgaa aatgctgaaa ttcgtcgaca tacaattttt    960
caaacttttt ttttttcttg gtgcacggac atgtttttaa aggaagtact ctataccagt   1020
tattcttcac aaatttaatt gctggagaat agatcttcaa cgctttaata aagtagtttg   1080
tttgtcaagg atggcgtcat acaaagaaag atcagaatca cacacttccc ctgttgctag   1140
```

```
gagacttttc tccatcatgg aggaaaagaa gtctaacctt tgtgcatcat tggatattac   1200
tgaaactgaa aagcttctct ctattttgga cactattggt ccttacatct gtctagttaa   1260
aacacacatc gatattgttt ctgattttac gtatgaagga actgtgttgc ctttgaagga   1320
gcttgccaag aaacataatt ttatgatttt tgaagataga aaatttgctg atattggtaa   1380
cactgttaaa aatcaatata aatctggtgt cttccgtatt gccgaatggg ctgacatcac   1440
taatgcacat ggtgtaacgg gtgcaggtat tgtttctggc ttgaaggagg cagcccaaga   1500
aacaaccagt gaacctagag gtttgctaat gcttgctgag ttatcatcaa agggttcttt   1560
agcatatggt gaatatacag aaaaaacagt agaaattgct aaatctgata aagagtttgt   1620
cattggtttt attgcgcaac acgatatggg cggtagagaa gaaggttttg actggatcat   1680
tatgactcca ggggttggtt tagatgacaa aggtgatgca cttggtcaac aatatagaac   1740
tgttgatgaa gttgtaaaga ctggaacgga tatcataatt gttggtagag gtttgtacgg   1800
tcaaggaaga gatcctatag agcaagctaa aagataccaa caagctggtt ggaatgctta   1860
tttaaacaga tttaaatgat tcttacacaa agatttgata catgtacact agtttaaata   1920
agcatgaaaa gaattacaca agcaaaaaaa aaaaaataaa tgaggtactt tacgttcacc   1980
tacaaccaaa aaaactagat agagtaaaat cttaagattt agaaaaagtt gtttaacaaa   2040
ggctttagta tgtgaatttt taatgtagca aagcgataac taataaacat aaacaaaagt   2100
atggttttct ttatcagtca aatcattatc gattgattgt tccgcgtatc tgcagatagc   2160
ctcatgaaat cagccatttg cttttgttca acgatctttt gaaattgttg ttgttcttgg   2220
tagttaagtt gatccatctt ggcttatgtt gtgtgtatgt tgtagttatt cttagtatat   2280
tcctgtcctg agtttagtga aacataatat cgccttgaaa tgaaaatgct gaaattcgtc   2340
gacatacaat tttcaaact ttttttttt cttggtgcac ggacatgttt ttaaaggaag   2400
tactctatac cagttattct tcacaaattt aattgctgga gaatagatct tcaacgcccc   2460
gggggatctg gatccgcggc cgcgagctct aatgattcaa gaaaaagttc aaataaacta   2520
atggatcaac ctatttcgac cctttcttca ttgctacttc ttccttaagc aacagatgat   2580
taagtagata ctgttttttt agccaatagt atctcgccga ggagttatac ttgactagct   2640
cttgctcaag aatcttccta agacgtacta gcctagcata gtaatctgtt tgtttctgta   2700
ttgtttgttc taactgttct acagtcattg aatcaatatc tccaatgtct tcgacgttga   2760
caactttccc cccctggca gcattctctt ttttgttgga atacgacatt aaagattcct   2820
tgattttctg ggtaccttca atgaccattg agggattaaa tttgatttct ttgattttat   2880
aatggtcggc tattagctct tccacttcgt catcatgatc atcagatatg tcacgttgcc   2940
ttttcaattt attaaaattg tttatcagtt tattgtgatc ttgtatcaat tcattgcgta   3000
ctcttttctc aatatcaaaa gctattttct tcccgctaga ctcaaaatca actctgaagt   3060
cattttctcg ctggaattca tgtatttcat ggattaattc tctattgata ttctcgtatg   3120
catcctgtaa actgttgccg ttgatattat gaaccgcctt taaatgtttc aataaggcat   3180
ctgctctagt aaatgccttc agacattcag gtaataaaca gtaaaatggc ttctcggctg   3240
tatgcgtcct aatgttt                                                 3257
```

<210> SEQ ID NO 21
<211> LENGTH: 3682
<212> TYPE: DNA
<213> ORGANISM: Artificial Sequence
<220> FEATURE:
<223> OTHER INFORMATION: URA3-ODD-XR integration fragment

<400> SEQUENCE: 21

```
cctccagtgt tttctctct gtctctttgt ttttttttc caatctgatt tgacgtgcaa     60
ggcaaagaca tcacatgttt gagaatggca agagaagggg cgtggtagtg tataccaagc    120
cggtgtagag agtgtgattt tagagtgaat ccatccatga acacgagtag aggagatgta    180
tgagcaaatc cagggtgttt gtaatggtcc aagccgcaag gcggcgtaat ggaatgcaag    240
aaacaaggga cactaatgaa ggggtaagag gtgtctagtt gagaagtaca tartaaaaga    300
tgaatagttg agawgtacat rgtaaaagat gaatagttga gacaaatgaa ggtgtcaatg    360
ttcctgataa tgacactgca agraacaaat accgtgcagt tggaaggggg aaagagatgr    420
ccgagataag tgttgttgag gccaaaggat gttggaacct gctacaatag gagatggagc    480
ggcctataac tccggcgtgt ttgtgttgac agccctatac atcagccaat acgagagttt    540
ggcatgtcct ttaaagggtt tgctaccccc actcccgtaa tcatcgttaa aatcatcatc    600
attgaaatca ttataattaa cctcatcacc attcccacta ttatcacctt atattctcca    660
ctccagggag atgcatcgtt gtaaagggca tggctgtttg tttattttac ccgacaagcc    720
aataccaaga gcggacaaac cgcatcagaa tgcaacagaa ggttggagaa acgtgatgtc    780
attttttccg caaacggaga tctcgcacag cggtgagata taaaaggcgg agatgtggac    840
accttcttta tacaattccc ctctacttga ttgttccata ttcctaacat ctagttacaa    900
ctctgaacat cataattatt ttaaaattct caacccaact gcaattggat tgaactgcgg    960
ccgctaatta atcatagcct catgaaatca gccatttgct tttgttcaac gatcttttga   1020
aattgttgtt gttcttggta gttaagttga tccatcttgg cttatgttgt gtgtatgttg   1080
tagttattct tagtatattc ctgtcctgag tttagtgaaa cataatatcg ccttgaaatg   1140
aaaatgctga aattcgtcga catacaattt ttcaaacttt ttttttttct tggtgcacgg   1200
acatgttttt aaaggaagta ctctatacca gttattcttc acaaatttaa ttgctggaga   1260
atagatcttc aacgctttaa taaagtagtt tgtttgtcaa ggatggcgtc atacaaagaa   1320
agatcagaat cacacacttc ccctgttgct aggagacttt tctccatcat ggaggaaaag   1380
aagtctaacc tttgtgcatc attggatatt actgaaactg aaaagcttct ctctattttg   1440
gacactattg gtccttacat ctgtctagtt aaaacacaca tcgatattgt ttctgatttt   1500
acgtatgaag gaactgtgtt gcctttgaag gagcttgcca agaaacataa ttttatgatt   1560
tttgaagata gaaaatttgc tgatattggt aacactgtta aaaatcaata taaatctggt   1620
gtcttccgta ttgccgaatg ggctgacatc actaatgcac atggtgtaac gggtgcaggt   1680
attgtttctg gcttgaagga ggcagcccaa gaaacaacca gtgaacctag aggtttgcta   1740
atgcttgctg agttatcatc aaagggttct ttagcatatg gtgaatatac agaaaaaaca   1800
gtagaaattg ctaaatctga taaagagttt gtcattggtt ttattgcgca acacgatatg   1860
ggcggtagag aagaaggttt tgactggatc attatgactc caggggttgg tttagatgac   1920
aaaggtgatg cacttggtca acaatataga actgttgatg aagttgtaaa gactggaacg   1980
gatatcataa ttgttggtag aggtttgtac ggtcaaggaa gagatcctat agagcaagct   2040
aaaagatacc aacaagctgg ttggaatgct tatttaaaca gatttaaatg attcttacac   2100
aaagatttga tacatgtaca ctagtttaaa taagcatgaa aagaattaca caagcaaaaa   2160
aaaaaaaata aatgaggtac tttacgttca cctacaacca aaaaaactag atagagtaaa   2220
atcttaagat ttagaaaaag ttgtttaaca aaggctttag tatgtgaatt tttaatgtag   2280
```

```
caaagcgata actaataaac ataaacaaaa gtatggtttt ctttatcagt caaatcatta   2340

tcgattgatt gttccgcgta tctgcagata gcctcatgaa atcagccatt tgcttttgtt   2400

caacgatctt ttgaaattgt tgttgttctt ggtagttaag ttgatccatc ttggcttatg   2460

ttgtgtgtat gttgtagtta ttcttagtat attcctgtcc tgagtttagt gaaacataat   2520

atcgccttga aatgaaaatg ctgaaattcg tcgacataca atttttcaaa cttttttttt   2580

ttcttggtgc acggacatgt ttttaaagga agtactctat accagttatt cttcacaaat   2640

ttaattgctg gagaatagat cttcaacgcg gccgcgtgta aatggtgtta gtctgatcta   2700

atgacaacta attacgcact tacgactgta atgcctttat ttttctttat atttcccagc   2760

gtgttgttct ttcaaatata cgatgagtat aaattaattt tacaaagcag aaacaacagg   2820

atctttagaa acgtcactgt aaacatcgaa tcttctttga acactgaagg gaatatttct   2880

tctcgtttct tcaacaacgt ccttcttcag ttctgcataa acgatggttt cctcatggcc   2940

ggcctcaacg aggatctcac catctggatc gaccaccatg ctatggccat aagcctgata   3000

gccgccctgt gggttacgag cgggggaaca catcaacacg tagttttggt tgtcaatagc   3060

tctggcaacg gcaaactttg accagaattt aggacctgtc acggtattga atgcaccggg   3120

ataagccata ataccagcgc cacgtctggc tgcaatcatg gccaattccg ggaacctgat   3180

atcatagcaa atacctaagc cgaatctggt gtcgatttct ggaatgtcga aaactgtaac   3240

cttgttgccc ggttttaaag aatcagactc cttgaacgtg attccgcccg gaatagaaat   3300

gtcaaagagg tgcaccttac gatgcttggc aacgatttcc cccttgggat tgaaaacaag   3360

agaggtgttg tagataccgc cgtcattgtc gtcgatttcc ggaatcgaac ctccaatgat   3420

agagacattg tactttttcg cctgttcact taaaaacgtg ctagtttccc cctctgggat   3480

acgttctgca taatttgcaa attggtctac ggcatatgga gattggaaac attcaggtag   3540

aacaagaagt tgtggttttg gatcgtgttg gatcgccctc tcgatgaatt gggtcacttt   3600

ggcgagattg gccttcttgt ctccaccaca gtggaattgc agcagtgcca cttggagagt   3660

cttggagaga gtaacggcag ac                                             3682
```

<210> SEQ ID NO 22
<211> LENGTH: 956
<212> TYPE: DNA
<213> ORGANISM: Artificial Sequence
<220> FEATURE:
<223> OTHER INFORMATION: IoXR primer

<400> SEQUENCE: 22

```
cctccagtgt ttttctctct gtctctttgt ttttttttc caatctgatt tgacgtgcaa    60

ggcaaagaca tcacatgttt gagaatggca agagaagggg cgtggtagtg tataccaagc   120

cggtgtagag agtgtgattt tagagtgaat ccatccatga acacgagtag aggagatgta   180

tgagcaaatc cagggtgttt gtaatggtcc aagccgcaag gcggcgtaat ggaatgcaag   240

aaacaaggga cactaatgaa ggggtaagag gtgtctagtt gagaagtaca tartaaaaga   300

tgaatagttg agawgtacat rgtaaaagat gaatagttga gacaaatgaa ggtgtcaatg   360

ttcctgataa tgacactgca agraacaaat accgtgcagt tggaaggggg aaagagatgr   420

ccgagataag tgttgttgag gccaaaggat gttggaacct gctacaatag gagatggagc   480

ggcctataac tccggcgtgt ttgtgttgac agccctatac atcagccaat acgagagttt   540

ggcatgtcct ttaaagggtt tgctaccccc actcccgtaa tcatcgttaa aatcatcatc   600

attgaaatca ttataattaa cctcatcacc attcccacta ttatcacctt atattctcca   660
```

```
ctccagggag atgcatcgtt gtaaagggca tggctgtttg tttattttac ccgacaagcc    720

aataccaaga gcggacaaac cgcatcagaa tgcaacagaa ggttggagaa acgtgatgtc    780

attttttccg caaacggaga tctcgcacag cggtgagata taaaaggcgg agatgtggac    840

accttcttta tacaattccc ctctacttga ttgttccata ttcctaacat ctagttacaa    900

ctctgaacat cataattatt ttaaaattct caacccaact gcaattggat tgaact        956
```

<210> SEQ ID NO 23
<211> LENGTH: 1006
<212> TYPE: DNA
<213> ORGANISM: Artificial Sequence
<220> FEATURE:
<223> OTHER INFORMATION: IoXR primer

<400> SEQUENCE: 23

```
tgtaaatggt gttagtctga tctaatgaca actaattacg cacttacgac tgtaatgcct     60

ttatttttct ttatatttcc cagcgtgttg ttctttcaaa tatacgatga gtataaatta    120

attttacaaa gcagaaacaa caggatcttt agaaacgtca ctgtaaacat cgaatcttct    180

ttgaacactg aagggaatat ttcttctcgt ttcttcaaca acgtccttct tcagttctgc    240

ataaacgatg gtttcctcat ggccggcctc aacgaggatc tcaccatctg gatcgaccac    300

catgctatgg ccataagcct gatagccgcc ctgtgggtta cgagcggggg aacacatcaa    360

cacgtagttt tggttgtcaa tagctctggc aacggcaaac tttgaccaga atttaggacc    420

tgtcacggta ttgaatgcac cgggataagc cataatacca gcgccacgtc tggctgcaat    480

catggccaat tccgggaacc tgatatcata gcaaatacct aagccgaatc tggtgtcgat    540

ttctggaatg tcgaaaactg taaccttgtt gcccggtttt aaagaatcag actccttgaa    600

cgtgattccg cccggaatag aaatgtcaaa gaggtgcacc ttacgatgct tggcaacgat    660

ttccccccttg ggattgaaaa caagagaggt gttgtagata ccgccgtcat tgtcgtcgat    720

ttccggaatc gaacctccaa tgatagagac attgtacttt ttcgcctgtt cacttaaaaa    780

cgtgctagtt tccccctctg ggatacgttc tgcataattt gcaaattggt ctacggcata    840

tggagattgg aaacattcag gtagaacaag aagttgtggt tttggatcgt gttggatcgc    900

cctctcgatg aattgggtca ctttggcgag attggccttc ttgtctccac cacagtggaa    960

ttgcagcagt gccacttgga gagtcttgga gagagtaacg gcagac                   1006
```

<210> SEQ ID NO 24
<211> LENGTH: 3682
<212> TYPE: DNA
<213> ORGANISM: Artificial Sequence
<220> FEATURE:
<223> OTHER INFORMATION: URA3-ODD-XR integration fragment

<400> SEQUENCE: 24

```
cctccagtgt ttttctctct gtctctttgt ttttttttc caatctgatt tgacgtgcaa      60

ggcaaagaca tcacatgttt gagaatggca agagaagggg cgtggtagtg tataccaagc    120

cggtgtagag agtgtgattt tagagtgaat ccatccatga acacgagtag aggagatgta    180

tgagcaaatc cagggtgttt gtaatggtcc aagccgcaag gcggcgtaat ggaatgcaag    240

aaacaaggga cactaatgaa ggggtaagag gtgtctagtt gagaagtaca tartaaaaga    300

tgaatagttg agawgtacat rgtaaaagat gaatagttga gacaaatgaa ggtgtcaatg    360

ttcctgataa tgacactgca agraacaaat accgtgcagt tggaaggggg aaagagatgr    420
```

```
ccgagataag tgttgttgag gccaaaggat gttggaacct gctacaatag gagatggagc    480
ggcctataac tccggcgtgt ttgtgttgac agccctatac atcagccaat acgagagttt    540
ggcatgtcct ttaaagggtt tgctaccccc actcccgtaa tcatcgttaa aatcatcatc    600
attgaaatca ttataattaa cctcatcacc attcccacta ttatcacctt atattctcca    660
ctccagggag atgcatcgtt gtaaagggca tggctgtttg tttattttac ccgacaagcc    720
aataccaaga gcggacaaac cgcatcagaa tgcaacagaa ggttggagaa acgtgatgtc    780
atttttttccg caaacggaga tctcgcacag cggtgagata taaaaggcgg agatgtggac    840
accttcttta tacaattccc ctctacttga ttgttccata ttcctaacat ctagttacaa    900
ctctgaacat cataattatt ttaaaattct caacccaact gcaattggat tgaactgcgg    960
ccgcgttgaa gatctattct ccagcaatta aatttgtgaa gaataactgg tatagagtac   1020
ttcctttaaa aacatgtccg tgcaccaaga aaaaaaaaaa gtttgaaaaa ttgtatgtcg   1080
acgaatttca gcattttcat ttcaaggcga tattatgttt cactaaactc aggacaggaa   1140
tatactaaga ataactacaa catacacaca acataagcca agatggatca acttaactac   1200
caagaacaac aacaatttca aaagatcgtt gaacaaaagc aaatggctga tttcatgagg   1260
ctatctgcag atacgcggaa caatcaatcg ataatgattt gactgataaa gaaaaccata   1320
cttttgttta tgtttattag ttatcgcttt gctacattaa aaattcacat actaaagcct   1380
ttgttaaaca actttttcta aatcttaaga ttttactcta tctagttttt ttggttgtag   1440
gtgaacgtaa agtacctcat ttattttttt ttttttgctt gtgtaattct tttcatgctt   1500
atttaaacta gtgtacatgt atcaaatctt tgtgtaagaa tcatttaaat ctgtttaaat   1560
aagcattcca accagcttgt tggtatcttt tagcttgctc tataggatct cttccttgac   1620
cgtacaaacc tctaccaaca attatgatat ccgttccagt ctttacaact tcatcaacag   1680
ttctatattg ttgaccaagt gcatcacctt tgtcatctaa accaacccct ggagtcataa   1740
tgatccagtc aaaaccttct tctctaccgc ccatatcgtg ttgcgcaata aaaccaatga   1800
caaactcttt atcagattta gcaatttcta ctgttttttc tgtatattca ccatatgcta   1860
aagaaccctt tgatgataac tcagcaagca ttagcaaacc tctaggttca ctggttgttt   1920
cttgggctgc ctccttcaag ccagaaacaa tacctgcacc cgttacacca tgtgcattag   1980
tgatgtcagc ccattcggca atacggaaga caccagattt atattgattt ttaacagtgt   2040
taccaatatc agcaaatttt ctatcttcaa aaatcataaa attatgtttc ttggcaagct   2100
ccttcaaagg caacacagtt ccttcatacg taaaatcaga aacaatatcg atgtgtgttt   2160
taactagaca gatgtaagga ccaatagtgt ccaaaaataga gagaagcttt tcagtttcag   2220
taatatccaa tgatgcacaa aggttagact tcttttcctc catgatggag aaaagtctcc   2280
tagcaacagg ggaagtgtgt gattctgatc tttctttgta tgacgccatc cttgacaaac   2340
aaactacttt attaaagcgt tgaagatcta ttctccagca attaaatttg tgaagaataa   2400
ctggtataga gtacttcctt taaaaacatg tccgtgcacc aagaaaaaaa aaaagtttga   2460
aaaattgtat gtcgacgaat ttcagcattt tcatttcaag gcgatattat gtttcactaa   2520
actcaggaca ggaatatact aagaataact acaacataca cacaacataa gccaagatgg   2580
atcaacttaa ctaccaagaa caacaacaat ttcaaaagat cgttgaacaa aagcaaatgg   2640
ctgatttcat gaggctatga ttaattagcg gccgcgtgta aatggtgtta gtctgatcta   2700
atgacaacta attacgcact tacgactgta atgcctttat ttttctttat atttcccagc   2760
gtgttgttct ttcaaatata cgatgagtat aaattaattt tacaaagcag aaacaacagg   2820
```

```
atctttagaa acgtcactgt aaacatcgaa tcttctttga acactgaagg gaatatttct   2880

tctcgtttct tcaacaacgt ccttcttcag ttctgcataa acgatggttt cctcatggcc   2940

ggcctcaacg aggatctcac catctggatc gaccaccatg ctatggccat aagcctgata   3000

gccgccctgt gggttacgag cgggggaaca catcaacacg tagttttggt tgtcaatagc   3060

tctggcaacg gcaaactttg accagaattt aggacctgtc acggtattga atgcaccggg   3120

ataagccata ataccagcgc cacgtctggc tgcaatcatg gccaattccg ggaacctgat   3180

atcatagcaa atacctaagc cgaatctggt gtcgatttct ggaatgtcga aaactgtaac   3240

cttgttgccc ggttttaaag aatcagactc cttgaacgtg attccgcccg gaatagaaat   3300

gtcaaagagg tgcaccttac gatgcttggc aacgatttcc cccttgggat tgaaaacaag   3360

agaggtgttg tagataccgc cgtcattgtc gtcgatttcc ggaatcgaac ctccaatgat   3420

agagacattg tactttttcg cctgttcact taaaaacgtg ctagtttccc cctctgggat   3480

acgttctgca taatttgcaa attggtctac ggcatatgga gattggaaac attcaggtag   3540

aacaagaagt tgtggttttg gatcgtgttg gatcgccctc tcgatgaatt gggtcacttt   3600

ggcgagattg gccttcttgt ctccaccaca gtggaattgc agcagtgcca cttggagagt   3660

cttggagaga gtaacggcag ac                                            3682
```

<210> SEQ ID NO 25
<211> LENGTH: 6569
<212> TYPE: DNA
<213> ORGANISM: Artificial Sequence
<220> FEATURE:
<223> OTHER INFORMATION: URA3-ODD-IoXK integration fragment

<400> SEQUENCE: 25

```
ccacaaatac ccagccacat caagaagctc gacttgaata cctctgtcat ttcagttgat     60

ccaccaatgc ctagtgcaac tactgctcct gacaacacag caccgaatca aaggctaagg    120

aattccatgg gtactagtaa ttcaatttac caacagcagt cagcaaatgt accatcacaa    180

cagttggttt tcaggactac tttgagggat gataaaaagt cgaaaaataa gaacagcaag    240

tctggattca acgaaaacaa gccctggaag aaccatgaac gagaaactct gaacatgatc    300

acatcagacg agaaaaaacg ttacgagggg gtgtttgcag caaacaaatc ctcatacctt    360

gatcttgacc ctaggctagt tgacgctgaa agtttgaaat tatcaaattt tgtaaacact    420

tatacaccac taaacgaaag gatccacagt ttgatcgtct atgaaatctg gacgaggtcg    480

aaaatcgata agacaacctt atccaagatt tggtcgttgg tattagatga tcgaaaaaga    540

cgttggataa aagcagttaa caacggatca aaagaatggt tagttgaaat accaaagaac    600

cagataatga caaatacgaa tggttcacgt tcatctgaga atgtgcaaga tgacacaaga    660

gaacaacaag ttagctataa cttgctagac attgatagga atatgttcga tgattcgaca    720

ttaacatatg aggaattcat tgttggaatg tggcttatag accaatgctt gtatggtaga    780

aagttaccga aatcaatacc cgtaactgtt tgggaaacaa tcggtattga ttggtcccag    840

aaataccaac cacatcatca tcatcatcat catcaaaatc tagttggtga cctggtaagc    900

aagggcatta aaacagggaa atctacgaaa cgggaagttt tcaaaaaagt gattggtata    960

tagttttata agatataaaa tgttggcatc ttcagaacat ttctttcatt tttttgggct   1020

ttttccttgt cttatcggcg gccgcggatc cggcgcgcct ttctcgacat ttgctgcaac   1080

ggcaacatca atgtccacgt ttacacacct acatttatat ctatatttat atttatattt   1140
```

-continued

```
atttatttat gctacttagc ttctatagtt agttaatgca ctcacgatat tcaaaattga   1200
caccccttcaa ctactcccta ctattgtcta ctactgtcta ctactcctct ttactatagc   1260
tgctcccaat aggctccacc aataggctct gtcaatacat tttgcgccgc cacctttcag   1320
gttgtgtcac tcctgaagga ccatattggg taatcgtgca atttctggaa gagagtccgc   1380
gagaagtgag gcccccactg taaatcctcg agggggcatg gagtatgggg catggaggat   1440
ggaggatggg gggggggggg gggaaaatag gtagcgaaag gacccgctat caccccaccc   1500
ggagaactcg ttgccgggaa gtcatatttc gacactccgg ggagtctata aaaggcgggt   1560
tttgtctttt gccagttgat gttgctgaga ggacttgttt gccgtttctt ccgatttaac   1620
agtatagaat caaccactgt taattataca cgttatacta acacaacaaa aacaaaaaca   1680
acgacaacaa caacaacatc tagataaaat gtctttggct ctaggttttg acctctcaac   1740
acaacagctg aaaatcgtct cctgttatca ggatcttagt cttcattcaa aatactctat   1800
tgatttcgac gaattcaagg acatttacgg tatccataaa ggcgtattgt cgaatagaga   1860
tacaggtgaa gtcgttactc ctgtcaagtt gtttgtacat gccctccaga ccctcctgga   1920
ccgcatgcac aatgatgggt tcccctttga ttgcgtgaca tcaatttcag gatcgtgcca   1980
acaacatgga acgattttct gtacacgtca attcgataca ctgctctcga atttgaatcc   2040
ggcttctgat acttggcaca gcgatttgtc caatgccttc tcctacgaga atgcctccaa   2100
ttggcaagac agatcaacgg gcgaagaatt ggcggtgttt gaaaaagcat tgggatcagc   2160
agagaaactc tgtaaaatca ctggttcaaa ggcgcatttc aggttctctg gtcctcaaat   2220
gagaaggagg gccaaggagg gtggtgtcca ttgggaggag acggcccaca tatccctcat   2280
atccaatttt ctcgattcca tcttgtccgg taaggttaga ggggtggaaa ttggagaagc   2340
ttgtggtaca aacctctttg atattgagca gaacgactgg aacgatgagt tgctttcctt   2400
gatcttgatg aagaattcca atgttgacgg agttcctttg ggtgaacagc aagaggcttc   2460
tttgaaagcc cgtcaacttc taaaaacctt agttgagcct gatgattatt caacaattgc   2520
gccttacttg gccaaaaggt atggctttaa aagggactgt aaggtctggc ccattactgg   2580
cgataatttg gcaaccatca tgtccttgcc attgaaacat gacgatttgt tggtgtctat   2640
ggggaccagt acaacggtgt tgttgttgac gaaaaactac cttccaagtg tgaactatca   2700
cctctttaag catcctgttg taagggatat ctatatgggt atgttgtgct attcaaatgg   2760
tgctctggca cgtgaggaaa ttagggatga aattaacgac aagtataaaa cggtaaagtg   2820
ggataaattc aacgagattt tagacactag aaagtctccc gacaaagagg ttggaatcta   2880
tttcccccta ggcgaaatca ttcccaacgt caagccctgt aagcgtatct tcaagtattc   2940
ggcagcgaag ggctcgtgg aagtggacag agaagtcgag ctggacgacc aagtgaagct   3000
tatcattgag tcgcaggcgt tatccaatcg actccgtgta gcaccacttc taaccgatgt   3060
tgaaaccgtg aaggagaagt cggtgaccag agacattgag agtgcaagga agattgttgg   3120
tgactcggtt acaattgacc atgtcgctta cacgtttgcc gatattatca agcgtcccaa   3180
tagtgtatac tatgctggag gttcttcaca gaatgcatcg attctcaaga tttacaatga   3240
cattctagga cctaaacatg gtggctacaa ggttgaagtc ggtgatgcct gtgcgctagg   3300
cggttgtttc cgagcaatct atggatacaa cgacagcata tcatttcagg attggttgga   3360
gagcaagttt gatttccaca gacatacctc tcccattgag agggacgaaa cccatgccat   3420
ttccacgtgg gcaagttatc tcgacaaggt tgccatattg accttggcag agcagcaatt   3480
agattgttga ttaattaatt tatttgtaca taaaaaccac ataaatgtaa aagcaagaaa   3540
```

```
aaaaataact aaggagaagg atcaatatct catttataat gctcgccaaa gcagcgtacg   3600
tgaattttaa tcaagacatc aacaaatctt gcaacttggt tatatcgctt cttcacccac   3660
tcacccgctt ttctacattg ttgaacacaa atatatacag gggtatgtct caaggtcaag   3720
tgcagtttca acagagacta cctcaaggta cctcttcaga aatgcagaac ttcactcttg   3780
atcagatttt ctccgaatta aaggaattca tagcctcatg aaatcagcca tttgcttttg   3840
ttcaacgatc ttttgaaatt gttgttgttc ttggtagtta agttgatcca tcttggctta   3900
tgttgtgtgt atgttgtagt tattcttagt atattcctgt cctgagttta gtgaaacata   3960
atatcgcctt gaaatgaaaa tgctgaaatt cgtcgacata caatttttca aactttttt    4020
ttttcttggt gcacggacat gtttttaaag gaagtactct ataccagtta ttcttcacaa   4080
atttaattgc tggagaatag atcttcaacg ctttaataaa gtagtttgtt tgtcaaggat   4140
ggcgtcatac aaagaaagat cagaatcaca cacttcccct gttgctagga gacttttctc   4200
catcatggag gaaaagaagt ctaacctttg tgcatcattg gatattactg aaactgaaaa   4260
gcttctctct attttggaca ctattggtcc ttacatctgt ctagttaaaa cacacatcga   4320
tattgtttct gattttacgt atgaaggaac tgtgttgcct ttgaaggagc ttgccaagaa   4380
acataatttt atgattttg aagatagaaa atttgctgat attggtaaca ctgttaaaaa    4440
tcaatataaa tctggtgtct tccgtattgc cgaatgggct gacatcacta atgcacatgg   4500
tgtaacgggt gcaggtattg tttctggctt gaaggaggca gcccaagaaa caaccagtga   4560
acctagaggt ttgctaatgc ttgctgagtt atcatcaaag ggttctttag catatggtga   4620
atatacagaa aaaacagtag aaattgctaa atctgataaa gagtttgtca ttggttttat   4680
tgcgcaacac gatatgggcg gtagagaaga aggttttgac tggatcatta tgactccagg   4740
ggttggttta gatgacaaag gtgatgcact tggtcaacaa tatagaactg ttgatgaagt   4800
tgtaaagact ggaacggata tcataattgt tggtagaggt ttgtacggtc aaggaagaga   4860
tcctatagag caagctaaaa gataccaaca agctggttgg aatgcttatt taaacagatt   4920
taaatgattc ttacacaaag atttgataca tgtacactag tttaaataag catgaaaaga   4980
attacacaag caaaaaaaaa aaaataaatg aggtacttta cgttcaccta caaccaaaaa   5040
aactagatag agtaaaatct taagatttag aaaaagttgt ttaacaaagg ctttagtatg   5100
tgaattttta atgtagcaaa gcgataacta ataaacataa acaaaagtat ggttttcttt   5160
atcagtcaaa tcattatcga ttgattgttc cgcgtatctg cagatagcct catgaaatca   5220
gccatttgct tttgttcaac gatcttttga aattgttgtt gttcttggta gttaagttga   5280
tccatcttgg cttatgttgt gtgtatgttg tagttattct tagtatattc ctgtcctgag   5340
tttagtgaaa cataatatcg ccttgaaatg aaaatgctga aattcgtcga catacaattt   5400
ttcaaacttt tttttttct tggtgcacgg acatgttttt aaaggaagta ctctatacca    5460
gttattcttc acaaatttaa ttgctggaga atagatcttc aacgccccgg gggatctgga   5520
tccgcggccg cgtttgtact tgtaatttca aactaagaaa agaagcttgt gtccaaaaat   5580
gtggctaatc cattacagta gattatcctc atatactgat aagaaattga taaagcggtc   5640
atcttactcc tgagacccac ctatttggtg tacggatcat aaaacaaagc gggaaaaagt   5700
tggagttttc cctttaagga aactacaaaa gtattttttt gtaatttttt gtgtatggtg   5760
aaattattct gataatttgt gaagattttt tttggacttt ttctattata ttttagaacc   5820
cgttaattgg taacaagcgt agcaaataaa acatagttga gaatgtctgg actatttgct   5880
```

```
aaacctactg tgatcgataa cgaaaagctg gttgctgaaa agcagagaac gattgttcaa   5940

atcaagaaga aggaaagaaa gcaaaagaaa agagacgaaa ggaaagcagc aaaaaatggt   6000

gatgatgctt cgaacaatga caatggtaca gcagatcaga atgtagcaga taaagagcac   6060

cctgaacata gagagaaagt tggtgagaaa atggaccttg acgatgatga tggggcattg   6120

gaagataagt acatgtctaa attagtagaa tctgaagctg aagagtcagg agatgaagaa   6180

tctgagaatg aagaatctga agattctgat gatgaagctc aagttggtga agcaggttgt   6240

tccgatgagg agggcgttga agatgcaaca atggaagaat ctacggagtc tgcagaaact   6300

gcaaatggta aaccaacgaa aactaagaca actgcggctc aagtccttga tttaaaggat   6360

aaggagtttg aaaaggcgga acggactatt tttattggca atgtgccatc gattattata   6420

tcaagtaaga gggaaactaa agatttcaag aatttcatca ataaaagttt ggaatgtcct   6480

gaaaatacaa gtttgattga gtctgtgagg ttcaggtctt tgcattctac aacaactgcg   6540

ccacgtaaag ttgcatatat atccgggcc                                     6569
```

```
<210> SEQ ID NO 26
<211> LENGTH: 593
<212> TYPE: PRT
<213> ORGANISM: Issatchenkia orientalis

<400> SEQUENCE: 26

Met Ser Leu Ala Leu Gly Phe Asp Leu Ser Thr Gln Gln Leu Lys Ile
1               5                   10                  15

Val Ser Cys Tyr Gln Asp Leu Ser Leu His Ser Lys Tyr Ser Ile Asp
            20                  25                  30

Phe Asp Glu Phe Lys Asp Ile Tyr Gly Ile His Lys Gly Val Leu Ser
        35                  40                  45

Asn Arg Asp Thr Gly Glu Val Val Thr Pro Val Lys Leu Phe Val His
    50                  55                  60

Ala Leu Gln Thr Leu Leu Asp Arg Met His Asn Asp Gly Phe Pro Phe
65                  70                  75                  80

Asp Cys Val Thr Ser Ile Ser Gly Ser Cys Gln Gln His Gly Thr Ile
                85                  90                  95

Phe Cys Thr Arg Gln Phe Asp Thr Leu Leu Ser Asn Leu Asn Pro Ala
            100                 105                 110

Ser Asp Thr Trp His Ser Asp Leu Ser Asn Ala Phe Ser Tyr Glu Asn
        115                 120                 125

Ala Ser Asn Trp Gln Asp Arg Ser Thr Gly Glu Glu Leu Ala Val Phe
    130                 135                 140

Glu Lys Ala Leu Gly Ser Ala Glu Lys Leu Cys Lys Ile Thr Gly Ser
145                 150                 155                 160

Lys Ala His Phe Arg Phe Ser Gly Pro Gln Met Arg Arg Arg Ala Lys
                165                 170                 175

Glu Gly Gly Val His Trp Glu Glu Thr Ala His Ile Ser Leu Ile Ser
            180                 185                 190

Asn Phe Leu Asp Ser Ile Leu Ser Gly Lys Val Arg Gly Val Glu Ile
        195                 200                 205

Gly Glu Ala Cys Gly Thr Asn Leu Phe Asp Ile Glu Gln Asn Asp Trp
    210                 215                 220

Asn Asp Glu Leu Leu Ser Leu Ile Leu Met Lys Asn Ser Asn Val Asp
225                 230                 235                 240

Gly Val Pro Leu Gly Glu Gln Gln Glu Ala Ser Leu Lys Ala Arg Gln
                245                 250                 255
```

```
Leu Leu Lys Thr Leu Val Glu Pro Asp Asp Tyr Ser Thr Ile Ala Pro
            260                 265                 270

Tyr Leu Ala Lys Arg Tyr Gly Phe Lys Arg Asp Cys Lys Val Trp Pro
        275                 280                 285

Ile Thr Gly Asp Asn Leu Ala Thr Ile Met Ser Leu Pro Leu Lys His
    290                 295                 300

Asp Asp Leu Leu Val Ser Met Gly Thr Ser Thr Thr Val Leu Leu Leu
305                 310                 315                 320

Thr Lys Asn Tyr Leu Pro Ser Val Asn Tyr His Leu Phe Lys His Pro
                325                 330                 335

Val Val Arg Asp Ile Tyr Met Gly Met Leu Cys Tyr Ser Asn Gly Ala
            340                 345                 350

Leu Ala Arg Glu Glu Ile Arg Asp Glu Ile Asn Asp Lys Tyr Lys Thr
        355                 360                 365

Val Lys Trp Asp Lys Phe Asn Glu Ile Leu Asp Thr Arg Lys Ser Pro
    370                 375                 380

Asp Lys Glu Val Gly Ile Tyr Phe Pro Leu Gly Glu Ile Ile Pro Asn
385                 390                 395                 400

Val Lys Pro Cys Lys Arg Ile Phe Lys Tyr Ser Ala Ala Lys Gly Leu
                405                 410                 415

Val Glu Val Asp Arg Glu Val Glu Leu Asp Asp Gln Val Lys Leu Ile
            420                 425                 430

Ile Glu Ser Gln Ala Leu Ser Asn Arg Leu Arg Val Ala Pro Leu Leu
        435                 440                 445

Thr Asp Val Glu Thr Val Lys Glu Lys Ser Val Thr Arg Asp Ile Glu
    450                 455                 460

Ser Ala Arg Lys Ile Val Gly Asp Ser Val Thr Ile Asp His Val Ala
465                 470                 475                 480

Tyr Thr Phe Ala Asp Ile Ile Lys Arg Pro Asn Ser Val Tyr Tyr Ala
                485                 490                 495

Gly Gly Ser Ser Gln Asn Ala Ser Ile Leu Lys Ile Tyr Asn Asp Ile
            500                 505                 510

Leu Gly Pro Lys His Gly Gly Tyr Lys Val Glu Val Gly Asp Ala Cys
        515                 520                 525

Ala Leu Gly Gly Cys Phe Arg Ala Ile Tyr Gly Tyr Asn Asp Ser Ile
    530                 535                 540

Ser Phe Gln Asp Trp Leu Glu Ser Lys Phe Asp Phe His Arg His Thr
545                 550                 555                 560

Ser Pro Ile Glu Arg Asp Glu Thr His Ala Ile Ser Thr Trp Ala Ser
                565                 570                 575

Tyr Leu Asp Lys Val Ala Ile Leu Thr Leu Ala Glu Gln Gln Leu Asp
            580                 585                 590

Cys
```

<210> SEQ ID NO 27
<211> LENGTH: 6569
<212> TYPE: DNA
<213> ORGANISM: Artificial Sequence
<220> FEATURE:
<223> OTHER INFORMATION: URA3-ODD-PGK1-TAL1-IoGAL6 integration fragment

<400> SEQUENCE: 27

```
ccacaaatac ccagccacat caagaagctc gacttgaata cctctgtcat ttcagttgat      60

ccaccaatgc ctagtgcaac tactgctcct gacaacacag caccgaatca aaggctaagg     120
```

```
aattccatgg gtactagtaa ttcaatttac caacagcagt cagcaaatgt accatcacaa    180
cagttggttt tcaggactac tttgagggat gataaaaagt cgaaaaataa gaacagcaag    240
tctggattca acgaaaacaa gccctggaag aaccatgaac gagaaactct gaacatgatc    300
acatcagacg agaaaaaacg ttacgagggg gtgtttgcag caaacaaatc ctcatacctt    360
gatcttgacc ctaggctagt tgacgctgaa agtttgaaat tatcaaattt tgtaaacact    420
tatacaccac taaacgaaag gatccacagt ttgatcgtct atgaaatctg gacgaggtcg    480
aaaatcgata agacaacctt atccaagatt tggtcgttgg tattagatga tcgaaaaaga    540
cgttggataa aagcagttaa caacggatca aaagaatggt tagttgaaat accaaagaac    600
cagataatga caaatacgaa tggttcacgt tcatctgaga atgtgcaaga tgacacaaga    660
gaacaacaag ttagctataa cttgctagac attgatagga atatgttcga tgattcgaca    720
ttaacatatg aggaattcat tgttggaatg tggcttatag accaatgctt gtatggtaga    780
aagttaccga aatcaatacc cgtaactgtt tgggaaacaa tcggtattga ttggtcccag    840
aaataccaac cacatcatca tcatcatcat catcaaaatc tagttggtga cctggtaagc    900
aagggcatta aaacagggaa atctacgaaa cgggaagttt tcaaaaaagt gattggtata    960
tagttttata agatataaaa tgttggcatc ttcagaacat ttctttcatt tttttgggct   1020
ttttccttgt cttatcggcg gccgcggatc cagatccccc ggggcgttga agatctattc   1080
tccagcaatt aaatttgtga agaataactg gtatagagta cttcctttaa aaacatgtcc   1140
gtgcaccaag aaaaaaaaaa agtttgaaaa attgtatgtc gacgaatttc agcattttca   1200
tttcaaggcg atattatgtt tcactaaact caggacagga atatactaag aataactaca   1260
acatacacac aacataagcc aagatggatc aacttaacta ccaagaacaa caacaatttc   1320
aaaagatcgt tgaacaaaag caaatggctg atttcatgag gctatctgca gatacgcgga   1380
acaatcaatc gataatgatt tgactgataa agaaaaccat acttttgttt atgtttatta   1440
gttatcgctt tgctacatta aaaattcaca tactaaagcc tttgttaaac aacttttttct  1500
aaatcttaag attttactct atctagtttt tttggttgta ggtgaacgta aagtacctca   1560
tttatttttt tttttttgct tgtgtaattc ttttcatgct tatttaaact agtgtacatg   1620
tatcaaatct ttgtgtaaga atcatttaaa tctgtttaaa taagcattcc aaccagcttg   1680
ttggtatctt ttagcttgct ctataggatc tcttccttga ccgtacaaac ctctaccaac   1740
aattatgata tccgttccag tctttacaac ttcatcaaca gttctatatt gttgaccaag   1800
tgcatcacct ttgtcatcta aaccaacccc tggagtcata atgatccagt caaaaccttc   1860
ttctctaccg cccatatcgt gttgcgcaat aaaaccaatg acaaactctt tatcagattt   1920
agcaatttct actgtttttt ctgtatattc accatatgct aaagaaccct ttgatgataa   1980
ctcagcaagc attagcaaac ctctaggttc actggttgtt tcttgggctg cctccttcaa   2040
gccagaaaca atacctgcac ccgttacacc atgtgcatta gtgatgtcag cccattcggc   2100
aatacggaag acaccagatt tatattgatt tttaacagtg ttaccaatat cagcaaattt   2160
tctatcttca aaaatcataa aattatgttt cttggcaagc tccttcaaag gcaacacagt   2220
tccttcatac gtaaaatcag aaacaatatc gatgtgtgtt ttaactagac agatgtaagg   2280
accaatagtg tccaaaatag agagaagctt ttcagtttca gtaatatcca atgatgcaca   2340
aaggttagac ttcttttcct ccatgatgga gaaaagtctc ctagcaacag gggaagtgtg   2400
tgattctgat ctttctttgt atgacgccat ccttgacaaa caaactactt tattaaagcg   2460
```

```
ttgaagatct attctccagc aattaaattt gtgaagaata actggtatag agtacttcct   2520
ttaaaaacat gtccgtgcac caagaaaaaa aaaaagtttg aaaaattgta tgtcgacgaa   2580
tttcagcatt ttcatttcaa ggcgatatta tgtttcacta aactcaggac aggaatatac   2640
taagaataac tacaacatac acacaacata agccaagatg gatcaactta actaccaaga   2700
acaacaacaa tttcaaaaga tcgttgaaca aaagcaaatg gctgatttca tgaggctatg   2760
aattccttta attcggagaa aatctgatca agagtgaagt tctgcatttc tgaagaggta   2820
ccttgaggta gtctctgttg aaactgcact tgaccttgag acatacccct gtatatattt   2880
gtgttcaaca atgtagaaaa gcgggtgagt gggtgaagaa gcgatataac caagttgcaa   2940
gatttgttga tgtcttgatt aaaattcacg tacgctgctt tggcgagcat tataaatgag   3000
atattgatcc ttctccttag ttattttttt tcttgctttt acatttatgt ggtttttatg   3060
tacaaataaa ttaattaatc aacaatctaa ttgctgctct gccaaggtca atatggcaac   3120
cttgtcgaga taacttgccc acgtggaaat ggcatgggtt tcgtccctct caatgggaga   3180
ggtatgtctg tggaaatcaa acttgctctc caaccaatcc tgaaatgata tgctgtcgtt   3240
gtatccatag attgctcgga aacaaccgcc tagcgcacag gcatcaccga cttcaacctt   3300
gtagccacca tgtttaggtc ctagaatgtc attgtaaatc ttgagaatcg atgcattctg   3360
tgaagaacct ccagcatagt atacactatt gggacgcttg ataatatcgg caaacgtgta   3420
agcgacatgg tcaattgtaa ccgagtcacc aacaatcttc cttgcactct caatgtctct   3480
ggtcaccgac ttctccttca cggtttcaac atcggttaga agtggtgcta cacggagtcg   3540
attggataac gcctgcgact caatgataag cttcacttgg tcgtccagct cgacttctct   3600
gtccacttcc acgagcccct tcgctgccga atacttgaag atacgcttac agggcttgac   3660
gttgggaatg atttcgccta gggggaaata gattccaacc tctttgtcgg gagactttct   3720
agtgtctaaa atctcgttga atttatccca ctttaccgtt ttatacttgt cgttaatttc   3780
atccctaatt tcctcacgtg ccagagcacc atttgaatag cacaacatac ccatatagat   3840
atcccttaca acaggatgct taaagaggtg atagttcaca cttggaaggt agtttttcgt   3900
caacaacaac accgttgtac tggtccccat agacaccaac aaatcgtcat gtttcaatgg   3960
caaggacatg atggttgcca aattatcgcc agtaatgggc cagaccttac agtccctttt   4020
aaagccatac cttttggcca agtaaggcgc aattgttgaa taatcatcag gctcaactaa   4080
ggtttttaga agttgacggg ctttcaaaga agcctcttgc tgttcaccca aaggaactcc   4140
gtcaacattg gaattcttca tcaagatcaa ggaaagcaac tcatcgttcc agtcgttctg   4200
ctcaatatca aagaggtttg taccacaagc ttctccaatt tccacccctc taaccttacc   4260
ggacaagatg gaatcgagaa aattggatat gagggatatg tgggccgtct cctcccaatg   4320
gacaccaccc tccttggccc tccttctcat ttgaggacca gagaacctga aatgcgcctt   4380
tgaaccagtg attttacaga gtttctctgc tgatcccaat gctttttcaa acaccgccaa   4440
ttcttcgccc gttgatctgt cttgccaatt ggaggcattc tcgtaggaga aggcattgga   4500
caaatcgctg tgccaagtat cagaagccgg attcaaattc gagagcagtg tatcgaattg   4560
acgtgtacag aaaatcgttc catgttgttg gcacgatcct gaaattgatg tcacgcaatc   4620
aaaggggaac ccatcattgt gcatgcggtc caggagggtc tggagggcat gtacaaacaa   4680
cttgacagga gtaacgactt cacctgtatc tctattcgac aatacgcctt tatggatacc   4740
gtaaatgtcc ttgaattcgt cgaaatcaat agagtatttt gaatgaagac taagatcctg   4800
ataacaggag acgattttca gctgttgtgt tgagaggtca aaacctagag ccaaagacat   4860
```

```
tttatctaga tgttgttgtt gttgtcgttg tttttgtttt tgttgtgtta gtataacgtg   4920
tataattaac agtggttgat tctatactgt taaatcggaa gaaacggcaa acaagtcctc   4980
tcagcaacat caactggcaa aagacaaaac ccgcctttta tagactcccc ggagtgtcga   5040
aatatgactt cccggcaacg agttctccgg gtggggtgat agcgggtcct ttcgctacct   5100
atttcccccc cccccccccc catcctccat cctccatgcc ccatactcca tgccccctcg   5160
aggatttaca gtgggggcct cacttctcgc ggactctctt ccagaaattg cacgattacc   5220
caatatggtc cttcaggagt gacacaacct gaaaggtggc ggcgcaaaat gtattgacag   5280
agcctattgg tggagcctat tgggagcagc tatagtaaag aggagtagta gacagtagta   5340
gacaatagta gggagtagtt gaagggtgtc aattttgaat atcgtgagtg cattaactaa   5400
ctatagaagc taagtagcat aaataaataa atataaatat aaatatagat ataaatgtag   5460
gtgtgtaaac gtggacattg atgttgccgt tgcagcaaat gtcgagaaag gcgcgccgga   5520
tccgcggccg cgtttgtact tgtaatttca aactaagaaa agaagcttgt gtccaaaaat   5580
gtggctaatc cattacagta gattatcctc atatactgat aagaaattga taaagcggtc   5640
atcttactcc tgagacccac ctatttggtg tacggatcat aaaacaaagc gggaaaaagt   5700
tggagttttc cctttaagga aactacaaaa gtattttttt gtaatttttt gtgtatggtg   5760
aaattattct gataatttgt gaagattttt tttggacttt ttctattata ttttagaacc   5820
cgttaattgg taacaagcgt agcaaataaa acatagttga gaatgtctgg actatttgct   5880
aaacctactg tgatcgataa cgaaaagctg gttgctgaaa agcagagaac gattgttcaa   5940
atcaagaaga aggaaagaaa gcaaaagaaa agagacgaaa ggaaagcagc aaaaaaatggt  6000
gatgatgctt cgaacaatga caatggtaca gcagatcaga atgtagcaga taaagagcac   6060
cctgaacata gagagaaagt tggtgagaaa atggaccttg acgatgatga tggggcattg   6120
gaagataagt acatgtctaa attagtagaa tctgaagctg aagagtcagg agatgaagaa   6180
tctgagaatg aagaatctga agattctgat gatgaagctc aagttggtga agcaggttgt   6240
tccgatgagg agggcgttga agatgcaaca atggaagaat ctacggagtc tgcagaaact   6300
gcaaatggta aaccaacgaa aactaagaca actgcggctc aagtccttga tttaaaggat   6360
aaggagtttg aaaaggcgga acggactatt tttattggca atgtgccatc gattattata   6420
tcaagtaaga gggaaactaa agatttcaag aatttcatca ataaaagttt ggaatgtcct   6480
gaaaatacaa gtttgattga gtctgtgagg ttcaggtctt tgcattctac aacaactgcg   6540
ccacgtaaag ttgcatatat atccgggcc                                     6569
```

<210> SEQ ID NO 28
<211> LENGTH: 5908
<212> TYPE: DNA
<213> ORGANISM: Artificial Sequence
<220> FEATURE:
<223> OTHER INFORMATION: StXI-PDC-URA3-loxP-XDH integration fragment.

<400> SEQUENCE: 28

```
ctgcttgtgc aggtgcaacc gagtcgtttg ttgttgtccc ctttgagttg gtgaagatcc     60
ggttacagga taagtccaag gcgtccatgt atagcggtcc cattgatgtt ctaatgaaga    120
cagtcaaaaa tgaaggtatc ttggccttgt ataacggatt agaggcaaca ctgtggagac    180
atattgtatg gaatgccggc tattttggtg tgattttcca agttcgtgac atgttaccca    240
aggcaaagga caagacccag aaaaccatca acgatttggt gggtggtatg attggtggta    300
```

-continued

```
tcgttggtac tgccttgaac attccattcg atgttgtcaa atccagaatc caaagtgcaa    360
ccattatgga aggtcaggtc cgtaaataca attggacttg gccctctctt ggcattgtct    420
tgagggaaga aggtgtctct gcattgtata aaggattcct tccaaaagtc ctgagattgg    480
gtccaggtgg tggtattcta cttgttgtct tcacaaactg tatggacttc tttagaggcc    540
aatactatgg agacaagaaa tagtagctgg gttcttcacc atcaggttta tacaccctcc    600
acgacgtcca ttctatacta tactatgcta ttcgatgcta ttcgatgcta tcctgcccta    660
tcttatctaa tcttatctta tcttacaaaa ttatatactt tccttgtttc tttcacctcc    720
tcctttatag atcaattgat ttgataatac acttatacac attgacgtct gttgatatct    780
tcatacaaaa aaccttaaaa catagtgcaa agtcacgtgc acgccttaaa aatgcagctg    840
agccccttc ccacttctct cccttcggat gccccacctg actattttca cttcccaatt    900
cgagcatcct cctccagtcc ccgcagactc aagagataag aaaccttaca gagactgttc    960
ccatcctcct atgctcaacg tgtcctgtat ctacattgcg gccgcggatc cctcgaggag   1020
tccatcggtt cctgtcagat gggatactct tgacgtggaa aattcaaaca gaaaaaaaac   1080
cccaataatg aaaaataaca ctacgttata tccgtggtat cctctatcgt atcgtatcgt   1140
agcgtatcgt agcgtaccgt atcacagtat agtctaatat tccgtatctt attgtatcct   1200
atcctattcg atcctattgt atttcagtgc accattttaa tttctattgc tataatgtcc   1260
ttattagttg ccactgtgag gtgaccaatg gacgagggcg agccgttcag aagccgcgaa   1320
gggtgttctt cccatgaatt tcttaaggag ggcggctcag ctccgagagt gaggcgagac   1380
gtctcggtca gcgtatcccc cttcctcggc ttttacaaat gatgcgctct taatagtgtg   1440
tcgttatcct tttggcattg acgggggagg gaaattgatt gagcgcatcc atatttttgc   1500
ggactgctga ggacaatggt ggtttttccg ggtggcgtgg gctacaaatg atacgatggt   1560
ttttttcttt tcggagaagg cgtataaaaa ggacacggag aacccattta ttctaaaaac   1620
agttgagctt ctttaattat tttttgatat aatattctat tattatatat tttcttccca   1680
ataaaacaaa ataaaacaaa acacagcaaa acacaaaaat tctagaatga aggagtactt   1740
tcccgagata aaggaaatca aatatgaagg tccagagagc aaaaacgtaa tggccttcaa   1800
atactataac aaggacgagg ttattggtgg taaaccaatg agggaacact tgaaatttgc   1860
aatgtcttat tggcatactc tcaaggcaca gggattagac atgttcggtg gtgatactat   1920
ggacagagct tggaatagat atgatgatgc gttagaacaa gcaaaggcaa gagccgatgc   1980
tggttttgag tttatgcaaa agatagggat ggactatttc tgtttccacg atagggacat   2040
tatcaatgaa gccatgaccc ttaaagagac taatcgttta ctagatgaaa ttgtcgacca   2100
tttagagggt ctgatgaaaa agacaggtat aaagttgctc tggggcacga ctaatgcttt   2160
ctcacatcct aggtttctcc atggcggtgc aactgcccca aacgccgatg tttttgcata   2220
cgctgctgcc caagtgaaaa aggctatgga aattacaaaa agactgggcg gcgaaaacta   2280
tgtcctttgg ggaggtcgtg aaggatatga aacactattg aataccaaga gtgatttgga   2340
atatgacaat tttgctagat tcttacaaat ggttgttgac tataaggaaa agattgggtt   2400
tgaaggacaa ttgttaatcg aaccaaaacc taaggagcct acaaaacacc aatacgattt   2460
cgacactgct acagtcctag gatttttgcg aaaatacaac ctagataagc actacaaaat   2520
gaatattgaa gcaaatcatg caactttagc gggtcatacc ttccagcatg agttaaactt   2580
ggctagaatt aacaatgtca tgggttcgat agatgcgaat cagggtgata tgttgttggg   2640
atgggatacg gatcaatttc cgactaatat ctatgacgca gtacttgcaa tgtatgaggt   2700
```

```
gattaaaaac aacgggctgg gtaagggtgg tttgaatttt gatgctaaag tgaggagagg   2760
atcctttgaa gataaggatc tatttcttgc gtatattgct gggatggata cattcgcaaa   2820
aggacttacc atcgcttata gattatacga agataaagtt ttcgaagatt ttcaagataa   2880
acggtatgag tcatacaaaa caggaattgg gaaggatatt gttgaaggca aagttggctt   2940
tgaggaacta gcagaatacg ttgagaattt ggcagaaatc aaaaacacct ctggtagaca   3000
ggaaatgtta gaatctattt tgaatagtta catattagaa gcaaagtgat taattaacat   3060
ctgaatgtaa aatgaacatt aaaatgaatt actaaacttt acgtctactt tacaatctat   3120
aaactttgtt taatcatata acgaaataca ctaatacaca atcctgtacg tatgtaatac   3180
ttttatccat caaggattga gaaaaaaaag taatgattcc ctgggccatt aaaacttaga   3240
cccccaagct tggataggtc actctctatt ttcgtttctc ccttccctga tagaagggtg   3300
atatgtaatt aagaataata tataatttta taataaaaga attcgccctt acatatgata   3360
acttcgtata atgtatgcta tacgaagtta tcatagcctc atgaaatcag ccatttgctt   3420
ttgttcaacg atcttttgaa attgttgttg ttcttggtag ttaagttgat ccatcttggc   3480
ttatgttgtg tgtatgttgt agttattctt agtatattcc tgtcctgagt ttagtgaaac   3540
ataatatcgc cttgaaatga aaatgctgaa attcgtcgac atacaatttt tcaaactttt   3600
tttttttctt ggtgcacgga catgttttta aaggaagtac tctataccag ttattcttca   3660
caaatttaat tgctggagaa tagatcttca acgctttaat aaagtagttt gtttgtcaag   3720
gatggcgtca tacaaagaaa gatcagaatc acacacttcc cctgttgcta ggagactttt   3780
ctccatcatg gaggaaaaga agtctaacct ttgtgcatca ttggatatta ctgaaactga   3840
aaagcttctc tctattttgg acactattgg tccttacatc tgtctagtta aaacacacat   3900
cgatattgtt tctgatttta cgtatgaagg aactgtgttg cctttgaagg agcttgccaa   3960
gaaacataat tttatgattt ttgaagatag aaaatttgct gatattggta acactgttaa   4020
aaatcaatat aaatctggtg tcttccgtat tgccgaatgg gctgacatca ctaatgcaca   4080
tggtgtaacg ggtgcaggta ttgtttctgg cttgaaggag gcagcccaag aaacaaccag   4140
tgaacctaga ggtttgctaa tgcttgctga gttatcatca aagggttctt tagcatatgg   4200
tgaatataca gaaaaaacag tagaaattgc taaatctgat aaagagtttg tcattggttt   4260
tattgcgcaa cacgatatgg gcggtagaga agaaggtttt gactggatca ttatgactcc   4320
aggggttggt ttagatgaca aaggtgatgc acttggtcaa caatatagaa ctgttgatga   4380
agttgtaaag actggaacgg atatcataat tgttggtaga ggtttgtacg gtcaaggaag   4440
agatcctata gagcaagcta aaagatacca acaagctggt tggaatgctt atttaaacag   4500
atttaaatga ttcttacaca aagatttgat acatgtacac tagtttaaat aagcatgaaa   4560
agaattacac aagcaaaaaa aaaaaaataa atgaggtact ttacgttcac ctacaaccaa   4620
aaaaactaga tagagtaaaa tcttaagatt tagaaaaagt tgtttaacaa aggctttagt   4680
atgtgaattt ttaatgtagc aaagcgataa ctaataaaca taaacaaaag tatggttttc   4740
tttatcagtc aaatcattat cgattgattg ttccgcgtat ctgcagataa cttcgtataa   4800
tgtatgctat acgaagttat agatccgcgg ccgcgtgtaa atatctacgt gtttagcatt   4860
tcctatatac atgactgtgt gtcctctggt tttcatttcg tttggttctc attcctcttg   4920
gcagcttcac taaacaactg gtcgtgttgt tcgtcgtgtt ttgccttgaa gaatgtatag   4980
tgcaacacaa cgtcttcgat gtttctcatt gccggatctc tggaaaactc tggatcgata   5040
```

-continued

```
aagaaaaaca agggcatatc aacctcctca cccttggcca accgctgctc ttcaaagcag   5100

aaacactgga tcttgttgaa gtaaggcgct acatgatcgg gagtcactga gtatgtggcc   5160

atgccagtaa tgtccttgtc acttatattc ttggctttgt agaaggccaa ggcagtctct   5220

ccggggacaa cataaacttc tctttgttgc ggtacaaact tccatggtaa cgcaccactt   5280

gtctccgccg taaaggatac ccgcagtctt ctctctgtag ctactggagt tagcttgtcc   5340

ctcgtgaacc tgctcttgtc ggtgattggt gtaccacccc atccagtacg ttgacaaatt   5400

gcacgataca aggggacact cgcatacgat aatgcaagga aaatcatcat catggataac   5460

gaataataaa tggtggtttg cctctcatac ctcttctttt ctccatggta cttatctctc   5520

aatgcttgga actctgccaa agacatcttt ggaagctcct tccggtttgc tcgtggtgat   5580

acctgatgtt ctgatgaccc accaccagga acttcgtatt ttgcaataca actggcatgt   5640

acatatctcc tatggagggc aagtccggga atcagcccaa catcccgaag ggcgcttgt    5700

atactagttc tgaaaatccg ccttaacatc accgtacaga gacaccttca ccaatatgtt   5760

ctccaagacc atggggcact agaagttatc cattgacgtt catcaaccta gtgatgtcaa   5820

atttcatcgc cgtttcccaa ctcgcgggat ttgcttttga gcatctcgtt tgattcacga   5880

caacttgttc tacattctgc tgcgggcc                                       5908
```

<210> SEQ ID NO 29
<211> LENGTH: 440
<212> TYPE: PRT
<213> ORGANISM: Sebaldella termitidis ATCC 33386

<400> SEQUENCE: 29

```
Met Lys Glu Tyr Phe Pro Glu Ile Lys Glu Ile Lys Tyr Glu Gly Pro
1               5                   10                  15

Glu Ser Lys Asn Val Met Ala Phe Lys Tyr Tyr Asn Lys Asp Glu Val
            20                  25                  30

Ile Gly Gly Lys Pro Met Arg Glu His Leu Lys Phe Ala Met Ser Tyr
        35                  40                  45

Trp His Thr Leu Lys Ala Gln Gly Leu Asp Met Phe Gly Gly Asp Thr
    50                  55                  60

Met Asp Arg Ala Trp Asn Arg Tyr Asp Asp Ala Leu Glu Gln Ala Lys
65                  70                  75                  80

Ala Arg Ala Asp Ala Gly Phe Glu Phe Met Gln Lys Ile Gly Met Asp
                85                  90                  95

Tyr Phe Cys Phe His Asp Arg Asp Ile Ile Asn Glu Ala Met Thr Leu
            100                 105                 110

Lys Glu Thr Asn Arg Leu Leu Asp Glu Ile Val Asp His Leu Glu Gly
        115                 120                 125

Leu Met Lys Lys Thr Gly Ile Lys Leu Leu Trp Gly Thr Thr Asn Ala
    130                 135                 140

Phe Ser His Pro Arg Phe Leu His Gly Gly Ala Thr Ala Pro Asn Ala
145                 150                 155                 160

Asp Val Phe Ala Tyr Ala Ala Ala Gln Val Lys Lys Ala Met Glu Ile
                165                 170                 175

Thr Lys Arg Leu Gly Gly Glu Asn Tyr Val Leu Trp Gly Gly Arg Glu
            180                 185                 190

Gly Tyr Glu Thr Leu Leu Asn Thr Lys Ser Asp Leu Glu Tyr Asp Asn
        195                 200                 205

Phe Ala Arg Phe Leu Gln Met Val Val Asp Tyr Lys Glu Lys Ile Gly
    210                 215                 220
```

```
Phe Glu Gly Gln Leu Leu Ile Glu Pro Lys Pro Lys Glu Pro Thr Lys
225                 230                 235                 240

His Gln Tyr Asp Phe Asp Thr Ala Thr Val Leu Gly Phe Leu Arg Lys
                245                 250                 255

Tyr Asn Leu Asp Lys His Tyr Lys Met Asn Ile Glu Ala Asn His Ala
            260                 265                 270

Thr Leu Ala Gly His Thr Phe Gln His Glu Leu Asn Leu Ala Arg Ile
        275                 280                 285

Asn Asn Val Met Gly Ser Ile Asp Ala Asn Gln Gly Asp Met Leu Leu
    290                 295                 300

Gly Trp Asp Thr Asp Gln Phe Pro Thr Asn Ile Tyr Asp Ala Val Leu
305                 310                 315                 320

Ala Met Tyr Glu Val Ile Lys Asn Asn Gly Leu Gly Lys Gly Gly Leu
                325                 330                 335

Asn Phe Asp Ala Lys Val Arg Arg Gly Ser Phe Glu Asp Lys Asp Leu
            340                 345                 350

Phe Leu Ala Tyr Ile Ala Gly Met Asp Thr Phe Ala Lys Gly Leu Thr
        355                 360                 365

Ile Ala Tyr Arg Leu Tyr Glu Asp Lys Val Phe Glu Asp Phe Gln Asp
    370                 375                 380

Lys Arg Tyr Glu Ser Tyr Lys Thr Gly Ile Gly Lys Asp Ile Val Glu
385                 390                 395                 400

Gly Lys Val Gly Phe Glu Glu Leu Ala Glu Tyr Val Glu Asn Leu Ala
                405                 410                 415

Glu Ile Lys Asn Thr Ser Gly Arg Gln Glu Met Leu Glu Ser Ile Leu
            420                 425                 430

Asn Ser Tyr Ile Leu Glu Ala Lys
        435                 440
```

```
<210> SEQ ID NO 30
<211> LENGTH: 7345
<212> TYPE: DNA
<213> ORGANISM: Artificial Sequence
<220> FEATURE:
<223> OTHER INFORMATION: StXI-CYB2A-loxP-XDH integration fragment

<400> SEQUENCE: 30

ctgcttgtgc aggtgcaacc gagtcgtttg ttgttgtccc ctttgagttg gtgaagatcc     60

ggttacagga taagtccaag gcgtccatgt atagcggtcc cattgatgtt ctaatgaaga    120

cagtcaaaaa tgaaggtatc ttggccttgt ataacggatt agaggcaaca ctgtggagac    180

atattgtatg gaatgccggc tattttggtg tgattttcca agttcgtgac atgttaccca    240

aggcaaagga caagacccag aaaaccatca acgatttggt gggtggtatg attggtggta    300

tcgttggtac tgccttgaac attccattcg atgttgtcaa atccagaatc caaagtgcaa    360

ccattatgga aggtcaggtc cgtaaataca attggacttg gccctctctt ggcattgtct    420

tgagggaaga aggtgtctct gcattgtata aaggattcct tccaaaagtc ctgagattgg    480

gtccaggtgg tggtattcta cttgttgtct tcacaaactg tatggacttc tttagaggcc    540

aatactatgg agacaagaaa tagtagctgg gttcttcacc atcaggttta tacaccctcc    600

acgacgtcca ttctatacta tactatgcta ttcgatgcta ttcgatgcta tcctgcccta    660

tcttatctaa tcttatctta tcttacaaaa ttatatactt tccttgtttc tttcacctcc    720

tcctttatag atcaattgat ttgataatac acttatacac attgacgtct gttgatatct    780
```

```
tcatacaaaa aaccttaaaa catagtgcaa agtcacgtgc acgccttaaa aatgcagctg    840
agcccctttc ccacttctct cccttcggat gccccacctg actattttca cttcccaatt    900
cgagcatcct cctccagtcc ccgcagactc aagagataag aaaccttaca gagactgttc    960
ccatcctcct atgctcaacg tgtcctgtat ctacattgcg gccgcggatc cctcgaggag   1020
tccatcggtt cctgtcagat gggatactct tgacgtggaa aattcaaaca gaaaaaaaac   1080
cccaataatg aaaaataaca ctacgttata tccgtggtat cctctatcgt atcgtatcgt   1140
agcgtatcgt agcgtaccgt atcacagtat agtctaatat tccgtatctt attgtatcct   1200
atcctattcg atcctattgt atttcagtgc accattttaa tttctattgc tataatgtcc   1260
ttattagttg ccactgtgag gtgaccaatg gacgagggcg agccgttcag aagccgcgaa   1320
gggtgttctt cccatgaatt tcttaaggag ggcggctcag ctccgagagt gaggcgagac   1380
gtctcggtca gcgtatcccc cttcctcggc ttttacaaat gatgcgctct taatagtgtg   1440
tcgttatcct tttggcattg acgggggagg gaaattgatt gagcgcatcc atatttttgc   1500
ggactgctga ggacaatggt ggtttttccg ggtggcgtgg gctacaaatg atacgatggt   1560
tttttctttt tcggagaagg cgtataaaaa ggacacggag aacccattta ttctaaaaac   1620
agttgagctt ctttaattat tttttgatat aatattctat tattatatat tttcttccca   1680
ataaaacaaa ataaaacaaa acacagcaaa acacaaaaat tctagaatga aggagtactt   1740
tcccgagata aaggaaatca aatatgaagg tccagagagc aaaaaacgtaa tggccttcaa   1800
atactataac aaggacgagg ttattggtgg taaaccaatg agggaacact tgaaatttgc   1860
aatgtcttat tggcatactc tcaaggcaca gggattagac atgttcggtg gtgatactat   1920
ggacagagct tggaatagat atgatgatgc gttagaacaa gcaaaggcaa gagccgatgc   1980
tggttttgag tttatgcaaa agatagggat ggactatttc tgtttccacg atagggacat   2040
tatcaatgaa gccatgaccc ttaaagagac taatcgttta ctagatgaaa ttgtcgacca   2100
tttagagggt ctgatgaaaa agacaggtat aaagttgctc tggggcacga ctaatgcttt   2160
ctcacatcct aggtttctcc atggcggtgc aactgcccca aacgccgatg tttttgcata   2220
cgctgctgcc caagtgaaaa aggctatgga aattacaaaa agactgggcg gcgaaaacta   2280
tgtcctttgg ggaggtcgtg aaggatatga aacactattg aataccaaga gtgatttgga   2340
atatgacaat tttgctagat tcttacaaat ggttgttgac tataaggaaa agattgggtt   2400
tgaaggacaa ttgttaatcg aaccaaaacc taaggagcct acaaaacacc aatacgattt   2460
cgacactgct acagtcctag gatttttgcg aaaatacaac ctagataagc actacaaaat   2520
gaatattgaa gcaaatcatg caactttagc gggtcatacc ttccagcatg agttaaactt   2580
ggctagaatt aacaatgtca tgggttcgat agatgcgaat cagggtgata tgttgttggg   2640
atgggatacg gatcaatttc cgactaatat ctatgacgca gtacttgcaa tgtatgaggt   2700
gattaaaaac aacgggctgg gtaagggtgg tttgaatttt gatgctaaag tgaggagagg   2760
atcctttgaa gataaggatc tatttcttgc gtatattgct gggatggata cattcgcaaa   2820
aggacttacc atcgcttata gattatacga agataaagtt ttcgaagatt ttcaagataa   2880
acggtatgag tcatacaaaa caggaattgg gaaggatatt gttgaaggca aagttggctt   2940
tgaggaacta gcagaatacg ttgagaattt ggcagaaatc aaaaacacct ctggtagaca   3000
ggaaatgtta gaatctattt tgaatagtta catattagaa gcaaagtgat taattaacat   3060
ctgaatgtaa aatgaacatt aaaatgaatt actaaacttt acgtctactt tacaatctat   3120
aaactttgtt taatcatata acgaaataca ctaatacaca atcctgtacg tatgtaatac   3180
```

```
ttttatccat caaggattga gaaaaaaaag taatgattcc ctgggccatt aaaacttaga   3240
cccccaagct tggataggtc actctctatt ttcgtttctc ccttccctga tagaagggtg   3300
atatgtaatt aagaataata tataatttta taataaaaga attcgccctt acatatgata   3360
acttcgtata atgtatgcta tacgaagtta tgttggtggt gtgttttgtt ggaacgtaca   3420
ttagatgcat aatgcgtgac accgccatga tggttgtatt ctaccaatga gacatggccg   3480
ctgatcctgt tgtgtgggtc atgggacatc acctcttggg ggggattctc ctataattgg   3540
caccgtgtat gcctcaacca ctaacttcca ccctataact gaatatatta cataagcaaa   3600
tctacttttt gtttgtgttg atcgccatcg ttgaaattcg cgcaacttct ggtggctcaa   3660
cgctgctgtt ctatcggtat cctaagagat gtctttgccc tgagtctagg gtaaactatc   3720
caccttcgtt gctgtttgac tagacagcta ctaactttac ggtagtaaat gaataacggc   3780
tcgctctcat gatcacttct ctacatcacc ctaacaagtg tattattttt ttttcaggtg   3840
ggtgttgctg ttggtgctag ccttagtgcc ctcgttaata gttgaacaaa cactggcatt   3900
tggagtataa tgaaaaggga tcactacccc ccgcttcctg ttccgcttct cccttccgga   3960
aaaaccaccc accctttctt ttcccccact aatgtatgaa tttttccgtt cccaggggaa   4020
tggcccactt ggttctctgt taacccacac aattttgacg catcccacac accttttttt   4080
tttctacccc acactttccc ttgaaaaatc tccaatttga actggcaatt ttcacccccc   4140
accacttgca ttcattagtg agtcaatcca tcccgcggtc ggagattcgg aatccaccta   4200
ctggtaatct gtaatctata ttcccgctga ccctttataa atgaactatt gtcgtcaatt   4260
gcggtagtgc tccaacaaat tgtaaggacc ttctttaacc ttttcgattc aatccatctc   4320
cacataaacc tagttgcaca caatgttact cagatcacta aactcttctg ctcgttgtgt   4380
caaacaaaca accagaacaa aggttaggta tctcagccac gtcagtggtg caagcatggc   4440
gaaacctaca ttgaagaaca actcgagaga atccaacaaa tccagaaact atctaattgc   4500
tgctgtgaca gcattggctg tatcaacctc aattggagtt gccgtacatg tgaaggaccc   4560
cttgtataac gatgctaccg gcagtgattc tccgagaagt atatctgttg acgagtttgt   4620
caagcataat tcacaaaacg actgttggat tgcaatcaat ggcaaggttt atgatttcac   4680
tgattttatt ccaaaccatc caggtggggt acctccatta gttaatcatg ctggttatga   4740
tggtactaaa ctttatgaga aattgcatcc aaaaggtaca attgagaaat tcttgccaaa   4800
ggataagttt ctgggtgtgt tagatggtga agcgccaaaa ttggaagcag actatttggt   4860
ggacgatgat gaacaagaga gactggatta tttgaacaac ttacctcctt tgtcatctat   4920
tcagaatgtt tatgatttcg aatacttggc caagaagatt ttacctaaag atgcctgggc   4980
atattattct tgtggtgccg atgatgaaat cacaatgaga gaaaaccatt atgcttatca   5040
aagagtttat ttcagaccaa gaatttgtgt tgatgtcaag gaagttgata cttcttatga   5100
aatgttaggc actaaaacct ctgttccttt ttatgtatct gccaccgctt tggctaaatt   5160
aggccatcct gatggtgaat gctcaattgc tagaggcgct ggtaaggaag gtgtcgttca   5220
aatgatttcg accctttcct caatgtcatt agatgaaatt gccgctgcta gaatcccagg   5280
tgcaacccaa tggttccaat tatacattaa tgaggataga aatgtcgcta aaggtctggt   5340
caaacatgca gaagacttgg gtatgaaggc tatctttata actgttgatg ctccttctct   5400
aggtaacaga gaaaaggata aaagattaaa gtttgttaat gacaccgatg tcgatttggg   5460
tgattccgca gatcgaaaca gtggtgcttc aaaggcacta tcttcgttca ttgatgcttc   5520
```

-continued

```
tgtctcttgg aatgacgtca aagcggtcaa gtcgtggact aaattgcctg tcttagttaa   5580

aggtgttcaa acagttgaag acgttattga agcttacgat gctggttgtc aaggtgttgt   5640

tttgtcaaac cacggtggta ggcaactaga tactgctcct cctccaatcg aattattagc   5700

tgaaactgtt ccaactttga agagattggg taaattaaga ccagattttg aaattttaat   5760

tgacggtggt gtcaaaagag gtaccgatat tttgaaagca gtcgcaatcg gtggccaaga   5820

tgtcagagtt tcagttggta tgggtagacc tttcttatat gccaactctt gctatggtga   5880

agcaggtgtt agaaaattaa ttcaaaatct aaaggatgaa ttagaaatgg atatgagatt   5940

gttgggtgtc actaaaatgg accagctatc ttcgaaacat gtcgatacta aacgtttgat   6000

tggtagagat gcgatcaact atttgtatga taatgtatac agcccaatcg aaaccgttaa   6060

attcaacaat gaagattgat tgttggaaat atattattca taaaggcgaa aacattccct   6120

tggtatttta ttccaaattt atgatacata gacgtatttt ttatatataa agttatatta   6180

ttaatgattc aagaaaaagt tcaaataaac taatggatca accataactt cgtataatgt   6240

atgctatacg aagttataga tccgcggccg cgtgtaaata tctacgtgtt tagcatttcc   6300

tatatacatg actgtgtgtc ctctggtttt catttcgttt ggttctcatt cctcttggca   6360

gcttcactaa acaactggtc gtgttgttcg tcgtgttttg ccttgaagaa tgtatagtgc   6420

aacacaacgt cttcgatgtt tctcattgcc ggatctctgg aaaactctgg atcgataaag   6480

aaaaacaagg gcatatcaac ctcctcaccc ttggccaacc gctgctcttc aaagcagaaa   6540

cactggatct tgttgaagta aggcgctaca tgatcgggag tcactgagta tgtggccatg   6600

ccagtaatgt ccttgtcact tatattcttg gctttgtaga aggccaaggc agtctctccg   6660

gggacaacat aaacttctct ttgttgcggt acaaacttcc atggtaacgc accacttgtc   6720

tccgccgtaa aggatacccg cagtcttctc tctgtagcta ctggagttag cttgtccctc   6780

gtgaacctgc tcttgtcggt gattggtgta ccaccccatc cagtacgttg acaaattgca   6840

cgatacaagg ggacactcgc atacgataat gcaaggaaaa tcatcatcat ggataacgaa   6900

taataaatgg tggtttgcct ctcatacctc ttcttttctc catggtactt atctctcaat   6960

gcttggaact ctgccaaaga catctttgga agctccttcc ggtttgctcg tggtgatacc   7020

tgatgttctg atgacccacc accaggaact tcgtattttg caatacaact ggcatgtaca   7080

tatctcctat ggagggcaag tccgggaatc agcccaacat cccgaagggg cgcttgtata   7140

ctagttctga aaatccgcct taacatcacc gtacagagac accttcacca atatgttctc   7200

caagaccatg ggcactagat agttatccat tgacgttcat caacctagtg atgtcaaatt   7260

tcatcgccgt ttcccaactc gcgggatttg cttttgagca tctcgtttga ttcacgacaa   7320

cttgttctac attctgctgc gggcc                                         7345
```

```
<210> SEQ ID NO 31
<211> LENGTH: 578
<212> TYPE: PRT
<213> ORGANISM: Issatchenkia orientalis

<400> SEQUENCE: 31

Met Leu Leu Arg Ser Leu Asn Ser Ser Ala Arg Cys Val Lys Gln Thr
1               5                   10                  15

Thr Arg Thr Lys Val Arg Tyr Leu Ser His Val Ser Gly Ala Ser Met
            20                  25                  30

Ala Lys Pro Thr Leu Lys Asn Asn Ser Arg Glu Ser Asn Lys Ser Arg
        35                  40                  45
```

```
Asn Tyr Leu Ile Ala Ala Val Thr Ala Leu Ala Val Ser Thr Ser Ile
    50                  55                  60

Gly Val Ala Val His Val Lys Asp Pro Leu Tyr Asn Asp Ala Thr Gly
65                  70                  75                  80

Ser Asp Ser Pro Arg Ser Ile Ser Val Asp Glu Phe Val Lys His Asn
                85                  90                  95

Ser Gln Asn Asp Cys Trp Ile Ala Ile Asn Gly Lys Val Tyr Asp Phe
            100                 105                 110

Thr Asp Phe Ile Pro Asn His Pro Gly Gly Val Pro Pro Leu Val Asn
        115                 120                 125

His Ala Gly Tyr Asp Gly Thr Lys Leu Tyr Glu Lys Leu His Pro Lys
    130                 135                 140

Gly Thr Ile Glu Lys Phe Leu Pro Lys Asp Lys Phe Leu Gly Val Leu
145                 150                 155                 160

Asp Gly Glu Ala Pro Lys Leu Glu Ala Asp Tyr Leu Val Asp Asp Asp
                165                 170                 175

Glu Gln Glu Arg Leu Asp Tyr Leu Asn Asn Leu Pro Pro Leu Ser Ser
            180                 185                 190

Ile Gln Asn Val Tyr Asp Phe Glu Tyr Leu Ala Lys Lys Ile Leu Pro
        195                 200                 205

Lys Asp Ala Trp Ala Tyr Tyr Ser Cys Gly Ala Asp Asp Glu Ile Thr
    210                 215                 220

Met Arg Glu Asn His Tyr Ala Tyr Gln Arg Val Tyr Phe Arg Pro Arg
225                 230                 235                 240

Ile Cys Val Asp Val Lys Glu Val Asp Thr Ser Tyr Glu Met Leu Gly
                245                 250                 255

Thr Lys Thr Ser Val Pro Phe Tyr Val Ser Ala Thr Ala Leu Ala Lys
            260                 265                 270

Leu Gly His Pro Asp Gly Glu Cys Ser Ile Ala Arg Gly Ala Gly Lys
        275                 280                 285

Glu Gly Val Val Gln Met Ile Ser Thr Leu Ser Ser Met Ser Leu Asp
    290                 295                 300

Glu Ile Ala Ala Ala Arg Ile Pro Gly Ala Thr Gln Trp Phe Gln Leu
305                 310                 315                 320

Tyr Ile Asn Glu Asp Arg Asn Val Ala Lys Gly Leu Val Lys His Ala
                325                 330                 335

Glu Asp Leu Gly Met Lys Ala Ile Phe Ile Thr Val Asp Ala Pro Ser
            340                 345                 350

Leu Gly Asn Arg Glu Lys Asp Lys Arg Leu Lys Phe Val Asn Asp Thr
        355                 360                 365

Asp Val Asp Leu Gly Asp Ser Ala Asp Arg Asn Ser Gly Ala Ser Lys
    370                 375                 380

Ala Leu Ser Ser Phe Ile Asp Ala Ser Val Ser Trp Asn Asp Val Lys
385                 390                 395                 400

Ala Val Lys Ser Trp Thr Lys Leu Pro Val Leu Val Lys Gly Val Gln
                405                 410                 415

Thr Val Glu Asp Val Ile Glu Ala Tyr Asp Ala Gly Cys Gln Gly Val
            420                 425                 430

Val Leu Ser Asn His Gly Gly Arg Gln Leu Asp Thr Ala Pro Pro Pro
        435                 440                 445

Ile Glu Leu Leu Ala Glu Thr Val Pro Thr Leu Lys Arg Leu Gly Lys
    450                 455                 460

Leu Arg Pro Asp Phe Glu Ile Leu Ile Asp Gly Gly Val Lys Arg Gly
```

```
465                 470                 475                 480

Thr Asp Ile Leu Lys Ala Val Ala Ile Gly Gly Gln Asp Val Arg Val
                485                 490                 495

Ser Val Gly Met Gly Arg Pro Phe Leu Tyr Ala Asn Ser Cys Tyr Gly
            500                 505                 510

Glu Ala Gly Val Arg Lys Leu Ile Gln Asn Leu Lys Asp Glu Leu Glu
        515                 520                 525

Met Asp Met Arg Leu Leu Gly Val Thr Lys Met Asp Gln Leu Ser Ser
    530                 535                 540

Lys His Val Asp Thr Lys Arg Leu Ile Gly Arg Asp Ala Ile Asn Tyr
545                 550                 555                 560

Leu Tyr Asp Asn Val Tyr Ser Pro Ile Glu Thr Val Lys Phe Asn Asn
                565                 570                 575

Glu Asp
```

<210> SEQ ID NO 32
<211> LENGTH: 5908
<212> TYPE: DNA
<213> ORGANISM: Artificial Sequence
<220> FEATURE:
<223> OTHER INFORMATION: LgXI-PDC-URA3-loxP-XDH integration fragment

<400> SEQUENCE: 32

```
ctgcttgtgc aggtgcaacc gagtcgtttg ttgttgtccc ctttgagttg gtgaagatcc     60

ggttacagga taagtccaag gcgtccatgt atagcggtcc cattgatgtt ctaatgaaga    120

cagtcaaaaa tgaaggtatc ttggccttgt ataacggatt agaggcaaca ctgtggagac    180

atattgtatg gaatgccggc tattttggtg tgattttcca agttcgtgac atgttaccca    240

aggcaaagga caagacccag aaaaccatca acgatttggt gggtggtatg attggtggta    300

tcgttggtac tgccttgaac attccattcg atgttgtcaa atccagaatc caaagtgcaa    360

ccattatgga aggtcaggtc cgtaaataca attggacttg gccctctctt ggcattgtct    420

tgagggaaga aggtgtctct gcattgtata aaggattcct tccaaaagtc ctgagattgg    480

gtccaggtgg tggtattcta cttgttgtct tcacaaactg tatggacttc tttagaggcc    540

aatactatgg agacaagaaa tagtagctgg gttcttcacc atcaggttta tacaccctcc    600

acgacgtcca ttctatacta tactatgcta ttcgatgcta ttcgatgcta tcctgcccta    660

tcttatctaa tcttatctta tcttacaaaa ttatatactt tccttgtttc tttcacctcc    720

tcctttatag atcaattgat ttgataatac acttatacac attgacgtct gttgatatct    780

tcatacaaaa aaccttaaaa catagtgcaa agtcacgtgc acgccttaaa aatgcagctg    840

agcccctttc ccacttctct cccttcggat gccccacctg actattttca cttcccaatt    900

cgagcatcct cctccagtcc ccgcagactc aagagataag aaaccttaca gagactgttc    960

ccatcctcct atgctcaacg tgtcctgtat ctacattgcg gccgcggatc cctcgaggag   1020

tccatcggtt cctgtcagat gggatactct tgacgtggaa aattcaaaca gaaaaaaaac   1080

cccaataatg aaaaataaca ctacgttata tccgtggtat cctctatcgt atcgtatcgt   1140

agcgtatcgt agcgtaccgt atcacagtat agtctaatat tccgtatctt attgtatcct   1200

atcctattcg atcctattgt atttcagtgc accattttaa tttctattgc tataatgtcc   1260

ttattagttg ccactgtgag gtgaccaatg gacgagggcg agccgttcag aagccgcgaa   1320

gggtgttctt cccatgaatt tcttaaggag ggcggctcag ctccgagagt gaggcgagac   1380

gtctcggtca gcgtatcccc cttcctcggc ttttacaaat gatgcgctct taatagtgtg   1440
```

```
tcgttatcct tttggcattg acgggggagg gaaattgatt gagcgcatcc atatttttgc   1500
ggactgctga ggacaatggt ggtttttccg ggtggcgtgg gctacaaatg atacgatggt   1560
ttttttcttt tcggagaagg cgtataaaaa ggacacggag aacccattta ttctaaaaac   1620
agttgagctt ctttaattat tttttgatat aatattctat tattatatat tttcttccca   1680
ataaaacaaa ataaaacaaa acacagcaaa acacaaaaat tctagaatga aggagttttt   1740
ccccgaaatc aaagagatca aatacgaagg cgccgaatcc aaaaatgatc tagcgttcaa   1800
atactataac aaggatgaag tccttggtgg caaaactatg aaagagcatc tgaggtttgc   1860
aatgtcgtat tggcatacgt taaaagctca aggagttgat atgtttggcg gagaaactat   1920
ggatagagaa tggaacaaat atgaaaatgt tttagaaagg gcaaaagcac gggccaatgc   1980
cggattcgag ttcatgcaga aacttggatt agagtatttc tgttttcatg accgagacat   2040
aattgatgag tctatgatgt tagcggatag taacaagtta cttgacgaaa tagtagatca   2100
tattgaagag ttgatgaaaa agaccgggag aaagttactc tggggtacca cgaatgcctt   2160
ttcgcacccg agatttgttc atggtgcatc aacttctcca aacgcagatg tatttgcata   2220
tgccgctgca caagtcaaaa aggccatgga tattacaaat cgtttgggtg gtgaaaacta   2280
tgtgttgtgg ggtggtagag aaggctatga aaccttattg aacactaact ctgaacttga   2340
atacgacaat tttgctagat tcctgaagat ggtggtcgac tataaggaga agattggttt   2400
taagggccaa ctgttaatcg aaccaaagcc taaggaacca actaagcatc agtacgattt   2460
tgatactgct actgtgttag ctttcttgag aaaatacaat ttggataagt actataaagt   2520
taacattgaa gcaaatcatg ctacgctcgc gggccacaca tttcaacacg agctaaatct   2580
agctaggatc aatggtgtac ttggtagtat tgatgcgaat caaggggata tgttgcttgg   2640
ttgggataca gatcagttcc ctacaaatat ctatgacact acattagcta tgtacgaagt   2700
tgtcaaaaac aaaggattgg gttcaggggg attgaacttt gatgccaaag ttcgtagagg   2760
ttcttttgag gacaaagatc tattcttggc atatattgct ggaatggaca catttgcaaa   2820
aggtctaaag attgcatata ggttatatga ggataaggtt tttgaagatt tcattgataa   2880
gagatacgaa tcatataaga ccggtatcgg aaaagacatt atagatggga aagttgggtt   2940
cgaggaattg tccaaatatg ctgaaacatt gaccgaagtg aaaaacaata gcggtagaca   3000
agagatgttg gaatccaagc tcaatcagta catatttgaa gttaagtaat taattaacat   3060
ctgaatgtaa aatgaacatt aaaatgaatt actaaacttt acgtctactt tacaatctat   3120
aaactttgtt taatcatata acgaaataca ctaatacaca atcctgtacg tatgtaatac   3180
ttttatccat caaggattga gaaaaaaaag taatgattcc ctgggccatt aaaacttaga   3240
cccccaagct tggataggtc actctctatt ttcgtttctc ccttccctga tagaagggtg   3300
atatgtaatt aagaataata tataatttta taataaaaga attcgccctt acatatgata   3360
acttcgtata atgtatgcta tacgaagtta tcatagcctc atgaaatcag ccatttgctt   3420
ttgttcaacg atcttttgaa attgttgttg ttcttggtag ttaagttgat ccatcttggc   3480
ttatgttgtg tgtatgttgt agttattctt agtatattcc tgtcctgagt ttagtgaaac   3540
ataatatcgc cttgaaatga aaatgctgaa attcgtcgac atacaatttt tcaaactttt   3600
tttttttctt ggtgcacgga catgttttta aaggaagtac tctataccag ttattcttca   3660
caaatttaat tgctggagaa tagatcttca acgctttaat aaagtagttt gtttgtcaag   3720
gatggcgtca tacaaagaaa gatcagaatc acacacttcc cctgttgcta ggagactttt   3780
```

```
ctccatcatg gaggaaaaga agtctaacct ttgtgcatca ttggatatta ctgaaactga   3840
aaagcttctc tctattttgg acactattgg tccttacatc tgtctagtta aaacacacat   3900
cgatattgtt tctgatttta cgtatgaagg aactgtgttg cctttgaagg agcttgccaa   3960
gaaacataat tttatgattt ttgaagatag aaaatttgct gatattggta acactgttaa   4020
aaatcaatat aaatctggtg tcttccgtat tgccgaatgg gctgacatca ctaatgcaca   4080
tggtgtaacg ggtgcaggta ttgtttctgg cttgaaggag gcagcccaag aaacaaccag   4140
tgaacctaga ggtttgctaa tgcttgctga gttatcatca aagggttctt tagcatatgg   4200
tgaatataca gaaaaaacag tagaaattgc taaatctgat aaagagtttg tcattggttt   4260
tattgcgcaa cacgatatgg gcggtagaga agaaggtttt gactggatca ttatgactcc   4320
aggggttggt ttagatgaca aaggtgatgc acttggtcaa caatatagaa ctgttgatga   4380
agttgtaaag actggaacgg atatcataat tgttggtaga ggtttgtacg gtcaaggaag   4440
agatcctata gagcaagcta aaagatacca acaagctggt tggaatgctt atttaaacag   4500
atttaaatga ttcttacaca aagatttgat acatgtacac tagtttaaat aagcatgaaa   4560
agaattacac aagcaaaaaa aaaaaaataa atgaggtact ttacgttcac ctacaaccaa   4620
aaaaactaga tagagtaaaa tcttaagatt tagaaaaagt tgtttaacaa aggctttagt   4680
atgtgaattt ttaatgtagc aaagcgataa ctaataaaca taaacaaaag tatggttttc   4740
tttatcagtc aaatcattat cgattgattg ttccgcgtat ctgcagataa cttcgtataa   4800
tgtatgctat acgaagttat agatccgcgg ccgcgtgtaa atatctacgt gtttagcatt   4860
tcctatatac atgactgtgt gtcctctggt tttcatttcg tttggttctc attcctcttg   4920
gcagcttcac taaacaactg gtcgtgttgt tcgtcgtgtt ttgccttgaa gaatgtatag   4980
tgcaacacaa cgtcttcgat gtttctcatt gccggatctc tggaaaactc tggatcgata   5040
aagaaaaaca agggcatatc aacctcctca cccttggcca accgctgctc ttcaaagcag   5100
aaacactgga tcttgttgaa gtaaggcgct acatgatcgg gagtcactga gtatgtggcc   5160
atgccagtaa tgtccttgtc acttatattc ttggctttgt agaaggccaa ggcagtctct   5220
ccggggacaa cataaacttc tctttgttgc ggtacaaact tccatggtaa cgcaccactt   5280
gtctccgccg taaaggatac ccgcagtctt ctctctgtag ctactggagt tagcttgtcc   5340
ctcgtgaacc tgctcttgtc ggtgattggt gtaccacccc atccagtacg ttgacaaatt   5400
gcacgataca aggggacact cgcatacgat aatgcaagga aaatcatcat catggataac   5460
gaataataaa tggtggtttg cctctcatac ctcttctttt ctccatggta cttatctctc   5520
aatgcttgga actctgccaa agacatcttt ggaagctcct tccggtttgc tcgtggtgat   5580
acctgatgtt ctgatgaccc accaccagga acttcgtatt ttgcaataca actggcatgt   5640
acatatctcc tatggagggc aagtccggga atcagcccaa catcccgaag ggcgcttgt    5700
atactagttc tgaaaatccg ccttaacatc accgtacaga gacaccttca ccaatatgtt   5760
ctccaagacc atggggcact agaagttatc cattgacgtt catcaaccta gtgatgtcaa   5820
atttcatcgc cgtttcccaa ctcgcgggat ttgcttttga gcatctcgtt tgattcacga   5880
caacttgttc tacattctgc tgcgggcc                                      5908
```

<210> SEQ ID NO 33
<211> LENGTH: 440
<212> TYPE: PRT
<213> ORGANISM: Leptotrichia goodfellowii F0264

<400> SEQUENCE: 33

```
Met Lys Glu Phe Phe Pro Glu Ile Lys Glu Ile Lys Tyr Glu Gly Ala
1               5                   10                  15

Glu Ser Lys Asn Asp Leu Ala Phe Lys Tyr Tyr Asn Lys Asp Glu Val
            20                  25                  30

Leu Gly Gly Lys Thr Met Lys Glu His Leu Arg Phe Ala Met Ser Tyr
        35                  40                  45

Trp His Thr Leu Lys Ala Gln Gly Val Asp Met Phe Gly Gly Glu Thr
    50                  55                  60

Met Asp Arg Glu Trp Asn Lys Tyr Glu Asn Val Leu Glu Arg Ala Lys
65                  70                  75                  80

Ala Arg Ala Asn Ala Gly Phe Glu Phe Met Gln Lys Leu Gly Leu Glu
                85                  90                  95

Tyr Phe Cys Phe His Asp Arg Asp Ile Ile Asp Glu Ser Met Met Leu
            100                 105                 110

Ala Asp Ser Asn Lys Leu Leu Asp Glu Ile Val Asp His Ile Glu Glu
        115                 120                 125

Leu Met Lys Lys Thr Gly Arg Lys Leu Leu Trp Gly Thr Thr Asn Ala
    130                 135                 140

Phe Ser His Pro Arg Phe Val His Gly Ala Ser Thr Ser Pro Asn Ala
145                 150                 155                 160

Asp Val Phe Ala Tyr Ala Ala Ala Gln Val Lys Lys Ala Met Asp Ile
                165                 170                 175

Thr Asn Arg Leu Gly Gly Glu Asn Tyr Val Leu Trp Gly Gly Arg Glu
            180                 185                 190

Gly Tyr Glu Thr Leu Leu Asn Thr Asn Ser Glu Leu Glu Tyr Asp Asn
        195                 200                 205

Phe Ala Arg Phe Leu Lys Met Val Val Asp Tyr Lys Glu Lys Ile Gly
    210                 215                 220

Phe Lys Gly Gln Leu Leu Ile Glu Pro Lys Pro Lys Glu Pro Thr Lys
225                 230                 235                 240

His Gln Tyr Asp Phe Asp Thr Ala Thr Val Leu Ala Phe Leu Arg Lys
                245                 250                 255

Tyr Asn Leu Asp Lys Tyr Tyr Lys Val Asn Ile Glu Ala Asn His Ala
            260                 265                 270

Thr Leu Ala Gly His Thr Phe Gln His Glu Leu Asn Leu Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asn Ile Tyr Asp Thr Thr Leu
305                 310                 315                 320

Ala Met Tyr Glu Val Val Lys Asn Lys Gly Leu Gly Ser Gly Gly Leu
                325                 330                 335

Asn Phe Asp Ala Lys Val Arg Arg Gly Ser Phe Glu Asp Lys Asp Leu
            340                 345                 350

Phe Leu Ala Tyr Ile Ala Gly Met Asp Thr Phe Ala Lys Gly Leu Lys
        355                 360                 365

Ile Ala Tyr Arg Leu Tyr Glu Asp Lys Val Phe Glu Asp Phe Ile Asp
    370                 375                 380

Lys Arg Tyr Glu Ser Tyr Lys Thr Gly Ile Gly Lys Asp Ile Ile Asp
385                 390                 395                 400

Gly Lys Val Gly Phe Glu Glu Leu Ser Lys Tyr Ala Glu Thr Leu Thr
                405                 410                 415
```

```
Glu Val Lys Asn Asn Ser Gly Arg Gln Glu Met Leu Glu Ser Lys Leu
            420                 425                 430

Asn Gln Tyr Ile Phe Glu Val Lys
        435                 440


<210> SEQ ID NO 34
<211> LENGTH: 7345
<212> TYPE: DNA
<213> ORGANISM: Artificial Sequence
<220> FEATURE:
<223> OTHER INFORMATION: XI-PDC-IoCYB2A-loxP-XDH integration fragement

<400> SEQUENCE: 34

ctgcttgtgc aggtgcaacc gagtcgtttg ttgttgtccc ctttgagttg gtgaagatcc      60

ggttacagga taagtccaag gcgtccatgt atagcggtcc cattgatgtt ctaatgaaga     120

cagtcaaaaa tgaaggtatc ttggccttgt ataacggatt agaggcaaca ctgtggagac     180

atattgtatg gaatgccggc tattttggtg tgattttcca agttcgtgac atgttaccca     240

aggcaaagga caagacccag aaaaccatca acgatttggt gggtggtatg attggtggta     300

tcgttggtac tgccttgaac attccattcg atgttgtcaa atccagaatc caaagtgcaa     360

ccattatgga aggtcaggtc cgtaaataca attggacttg gccctctctt ggcattgtct     420

tgagggaaga aggtgtctct gcattgtata aaggattcct tccaaaagtc ctgagattgg     480

gtccaggtgg tggtattcta cttgttgtct tcacaaactg tatggacttc tttagaggcc     540

aatactatgg agacaagaaa tagtagctgg gttcttcacc atcaggttta tacaccctcc     600

acgacgtcca ttctatacta tactatgcta ttcgatgcta ttcgatgcta tcctgcccta     660

tcttatctaa tcttatctta tcttacaaaa ttatatactt tccttgtttc tttcacctcc     720

tcctttatag atcaattgat ttgataatac acttatacac attgacgtct gttgatatct     780

tcatacaaaa aaccttaaaa catagtgcaa agtcacgtgc acgccttaaa aatgcagctg     840

agcccctttc ccacttctct cccttcggat gccccacctg actattttca cttcccaatt     900

cgagcatcct cctccagtcc ccgcagactc aagagataag aaaccttaca gagactgttc     960

ccatcctcct atgctcaacg tgtcctgtat ctacattgcg gccgcggatc cctcgaggag    1020

tccatcggtt cctgtcagat gggatactct tgacgtggaa aattcaaaca gaaaaaaaac    1080

cccaataatg aaaaataaca ctacgttata tccgtggtat cctctatcgt atcgtatcgt    1140

agcgtatcgt agcgtaccgt atcacagtat agtctaatat tccgtatctt attgtatcct    1200

atcctattcg atcctattgt atttcagtgc accattttaa tttctattgc tataatgtcc    1260

ttattagttg ccactgtgag gtgaccaatg gacgagggcg agccgttcag aagccgcgaa    1320

gggtgttctt cccatgaatt tcttaaggag ggcggctcag ctccgagagt gaggcgagac    1380

gtctcggtca gcgtatcccc cttcctcggc ttttacaaat gatgcgctct taatagtgtg    1440

tcgttatcct tttggcattg acgggggagg gaaattgatt gagcgcatcc atatttttgc    1500

ggactgctga ggacaatggt ggtttttccg ggtggcgtgg gctacaaatg atacgatggt    1560

ttttttcttt tcggagaagg cgtataaaaa ggacacggag aacccattta ttctaaaaac    1620

agttgagctt ctttaattat tttttgatat aatattctat tattatatat tttcttccca    1680

ataaaacaaa ataaaacaaa acacagcaaa acacaaaaat tctagaatga aggagttttt    1740

ccccgaaatc aaagagatca aatacgaagg cgccgaatcc aaaaatgatc tagcgttcaa    1800

atactataac aaggatgaag tccttggtgg caaaactatg aaagagcatc tgaggtttgc    1860

aatgtcgtat tggcatacgt taaaagctca aggagttgat atgtttggcg gagaaactat    1920
```

```
ggatagagaa tggaacaaat atgaaaatgt tttagaaagg gcaaaagcac gggccaatgc   1980
cggattcgag ttcatgcaga aacttggatt agagtatttc tgttttcatg accgagacat   2040
aattgatgag tctatgatgt tagcggatag taacaagtta cttgacgaaa tagtagatca   2100
tattgaagag ttgatgaaaa agaccgggag aaagttactc tggggtacca cgaatgcctt   2160
ttcgcacccg agatttgttc atggtgcatc aacttctcca aacgcagatg tatttgcata   2220
tgccgctgca caagtcaaaa aggccatgga tattacaaat cgtttgggtg gtgaaaacta   2280
tgtgttgtgg ggtggtagag aaggctatga aaccttattg aacactaact ctgaacttga   2340
atacgacaat tttgctagat tcctgaagat ggtggtcgac tataaggaga agattggttt   2400
taagggccaa ctgttaatcg aaccaaagcc taaggaacca actaagcatc agtacgattt   2460
tgatactgct actgtgttag ctttcttgag aaaatacaat ttggataagt actataaagt   2520
taacattgaa gcaaatcatg ctacgctcgc gggccacaca tttcaacacg agctaaatct   2580
agctaggatc aatggtgtac ttggtagtat tgatgcgaat caaggggata tgttgcttgg   2640
ttgggataca gatcagttcc ctacaaatat ctatgacact acattagcta tgtacgaagt   2700
tgtcaaaaac aaaggattgg gttcaggggg attgaacttt gatgccaaag ttcgtagagg   2760
ttcttttgag gacaaagatc tattcttggc atatattgct ggaatggaca catttgcaaa   2820
aggtctaaag attgcatata ggttatatga ggataaggtt tttgaagatt tcattgataa   2880
gagatacgaa tcatataaga ccggtatcgg aaaagacatt atagatggga aagttgggtt   2940
cgaggaattg tccaaatatg ctgaaacatt gaccgaagtg aaaaacaata gcggtagaca   3000
agagatgttg gaatccaagc tcaatcagta catatttgaa gttaagtaat taattaacat   3060
ctgaatgtaa aatgaacatt aaaatgaatt actaaacttt acgtctactt tacaatctat   3120
aaactttgtt taatcatata acgaaataca ctaatacaca atcctgtacg tatgtaatac   3180
ttttatccat caaggattga gaaaaaaaag taatgattcc ctgggccatt aaaacttaga   3240
cccccaagct tggataggtc actctctatt ttcgtttctc ccttccctga tagaagggtg   3300
atatgtaatt aagaataata tataatttta taataaaaga attcgccctt acatatgata   3360
acttcgtata atgtatgcta tacgaagtta tgttggtggt gtgttttgtt ggaacgtaca   3420
ttagatgcat aatgcgtgac accgccatga tggttgtatt ctaccaatga gacatggccg   3480
ctgatcctgt tgtgtgggtc atgggacatc acctcttggg ggggattctc ctataattgg   3540
caccgtgtat gcctcaacca ctaacttcca ccctataact gaatatatta cataagcaaa   3600
tctacttttt gtttgtgttg atcgccatcg ttgaaattcg cgcaacttct ggtggctcaa   3660
cgctgctgtt ctatcggtat cctaagagat gtctttgccc tgagtctagg gtaaactatc   3720
caccttcgtt gctgtttgac tagacagcta ctaactttac ggtagtaaat gaataacggc   3780
tcgctctcat gatcacttct ctacatcacc ctaacaagtg tattattttt ttttcaggtg   3840
ggtgttgctg ttggtgctag ccttagtgcc ctcgttaata gttgaacaaa cactggcatt   3900
tggagtataa tgaaaaggga tcactacccc ccgcttcctg ttccgcttct cccttccgga   3960
aaaaccaccc accctttctt ttccccact aatgtatgaa tttttccgtt cccaggggaa   4020
tggcccactt ggttctctgt taacccacac aattttgacg catcccacac acctttttt    4080
tttctacccc acactttccc ttgaaaaatc tccaatttga actggcaatt ttcacccccc   4140
accacttgca ttcattagtg agtcaatcca tcccgcggtc ggagattcgg aatccaccta   4200
ctggtaatct gtaatctata ttcccgctga ccctttataa atgaactatt gtcgtcaatt   4260
```

```
gcggtagtgc tccaacaaat tgtaaggacc ttctttaacc ttttcgattc aatccatctc   4320

cacataaacc tagttgcaca caatgttact cagatcacta aactcttctg ctcgttgtgt   4380

caaacaaaca accagaacaa aggttaggta tctcagccac gtcagtggtg caagcatggc   4440

gaaacctaca ttgaagaaca actcgagaga atccaacaaa tccagaaact atctaattgc   4500

tgctgtgaca gcattggctg tatcaacctc aattggagtt gccgtacatg tgaaggaccc   4560

cttgtataac gatgctaccg gcagtgattc tccgagaagt atatctgttg acgagtttgt   4620

caagcataat tcacaaaacg actgttggat tgcaatcaat ggcaaggttt atgatttcac   4680

tgattttatt ccaaaccatc caggtggggt acctccatta gttaatcatg ctggttatga   4740

tggtactaaa ctttatgaga aattgcatcc aaaaggtaca attgagaaat tcttgccaaa   4800

ggataagttt ctgggtgtgt tagatggtga agcgccaaaa ttggaagcag actatttggt   4860

ggacgatgat gaacaagaga gactggatta tttgaacaac ttacctcctt tgtcatctat   4920

tcagaatgtt tatgatttcg aatacttggc caagaagatt ttacctaaag atgcctgggc   4980

atattattct tgtggtgccg atgatgaaat cacaatgaga gaaaaccatt atgcttatca   5040

aagagtttat ttcagaccaa gaatttgtgt tgatgtcaag gaagttgata cttcttatga   5100

aatgttaggc actaaaacct ctgttccttt ttatgtatct gccaccgctt tggctaaatt   5160

aggccatcct gatggtgaat gctcaattgc tagaggcgct ggtaaggaag gtgtcgttca   5220

aatgatttcg accctttcct caatgtcatt agatgaaatt gccgctgcta gaatcccagg   5280

tgcaacccaa tggttccaat tatacattaa tgaggataga aatgtcgcta aaggtctggt   5340

caaacatgca gaagacttgg gtatgaaggc tatctttata actgttgatg ctccttctct   5400

aggtaacaga gaaaaggata aaagattaaa gtttgttaat gacaccgatg tcgatttggg   5460

tgattccgca gatcgaaaca gtggtgcttc aaaggcacta tcttcgttca ttgatgcttc   5520

tgtctcttgg aatgacgtca aagcggtcaa gtcgtggact aaattgcctg tcttagttaa   5580

aggtgttcaa acagttgaag acgttattga agcttacgat gctggttgtc aaggtgttgt   5640

tttgtcaaac cacggtggta ggcaactaga tactgctcct cctccaatcg aattattagc   5700

tgaaactgtt ccaactttga agagattggg taaattaaga ccagattttg aaattttaat   5760

tgacggtggt gtcaaaagag gtaccgatat tttgaaagca gtcgcaatcg gtggccaaga   5820

tgtcagagtt tcagttggta tgggtagacc tttcttatat gccaactctt gctatggtga   5880

agcaggtgtt agaaaattaa ttcaaaatct aaaggatgaa ttagaaatgg atatgagatt   5940

gttgggtgtc actaaaatgg accagctatc ttcgaaacat gtcgatacta aacgtttgat   6000

tggtagagat gcgatcaact atttgtatga taatgtatac agcccaatcg aaaccgttaa   6060

attcaacaat gaagattgat tgttggaaat atattattca taaaggcgaa aacattccct   6120

tggtatttta ttccaaattt atgatacata gacgtatttt ttatatataa agttatatta   6180

ttaatgattc aagaaaaagt tcaaataaac taatggatca accataactt cgtataatgt   6240

atgctatacg aagttataga tccgcggccg cgtgtaaata tctacgtgtt tagcatttcc   6300

tatatacatg actgtgtgtc ctctggtttt catttcgttt ggttctcatt cctcttggca   6360

gcttcactaa acaactggtc gtgttgttcg tcgtgttttg ccttgaagaa tgtatagtgc   6420

aacacaacgt cttcgatgtt tctcattgcc ggatctctgg aaaactctgg atcgataaag   6480

aaaaacaagg gcatatcaac ctcctcaccc ttggccaacc gctgctcttc aaagcagaaa   6540

cactggatct tgttgaagta aggcgctaca tgatcgggag tcactgagta tgtggccatg   6600

ccagtaatgt ccttgtcact tatattcttg gctttgtaga aggccaaggc agtctctccg   6660
```

```
gggacaacat aaacttctct ttgttgcggt acaaacttcc atggtaacgc accacttgtc   6720

tccgccgtaa aggatacccg cagtcttctc tctgtagcta ctggagttag cttgtccctc   6780

gtgaacctgc tcttgtcggt gattggtgta ccacccccatc cagtacgttg acaaattgca   6840

cgatacaagg ggacactcgc atacgataat gcaaggaaaa tcatcatcat ggataacgaa   6900

taataaatgg tggtttgcct ctcatacctc ttcttttctc catggtactt atctctcaat   6960

gcttggaact ctgccaaaga catctttgga agctccttcc ggtttgctcg tggtgatacc   7020

tgatgttctg atgacccacc accaggaact tcgtattttg caatacaact ggcatgtaca   7080

tatctcctat ggagggcaag tccgggaatc agcccaacat cccgaagggg cgcttgtata   7140

ctagttctga aaatccgcct taacatcacc gtacagagac accttcacca atatgttctc   7200

caagaccatg gggcactaga agttatccat tgacgttcat caacctagtg atgtcaaatt   7260

tcatcgccgt ttcccaactc gcgggatttg cttttgagca tctcgtttga ttcacgacaa   7320

cttgttctac attctgctgc gggcc                                         7345
```

<210> SEQ ID NO 35
<211> LENGTH: 5917
<212> TYPE: DNA
<213> ORGANISM: Artificial Sequence
<220> FEATURE:
<223> OTHER INFORMATION: PaXI-PDC-URA3-loxP-XDH integration fragment

<400> SEQUENCE: 35

```
ctgcttgtgc aggtgcaacc gagtcgtttg ttgttgtccc ctttgagttg gtgaagatcc     60

ggttacagga taagtccaag gcgtccatgt atagcggtcc cattgatgtt ctaatgaaga    120

cagtcaaaaa tgaaggtatc ttggccttgt ataacggatt agaggcaaca ctgtggagac    180

atattgtatg gaatgccggc tattttggtg tgattttcca agttcgtgac atgttaccca    240

aggcaaagga caagacccag aaaaccatca acgatttggt gggtggtatg attggtggta    300

tcgttggtac tgccttgaac attccattcg atgttgtcaa atccagaatc caaagtgcaa    360

ccattatgga aggtcaggtc cgtaaataca attggacttg gccctctctt ggcattgtct    420

tgagggaaga aggtgtctct gcattgtata aaggattcct tccaaaagtc ctgagattgg    480

gtccaggtgg tggtattcta cttgttgtct tcacaaactg tatggacttc tttagaggcc    540

aatactatgg agacaagaaa tagtagctgg gttcttcacc atcaggttta tacaccctcc    600

acgacgtcca ttctatacta tactatgcta ttcgatgcta ttcgatgcta tcctgcccta    660

tcttatctaa tcttatctta tcttacaaaa ttatatactt tccttgtttc tttcacctcc    720

tcctttatag atcaattgat ttgataatac acttatacac attgacgtct gttgatatct    780

tcatacaaaa aaccttaaaa catagtgcaa agtcacgtgc acgccttaaa aatgcagctg    840

agccccttc ccacttctct cccttcggat gccccacctg actattttca cttcccaatt    900

cgagcatcct cctccagtcc ccgcagactc aagagataag aaaccttaca gagactgttc    960

ccatcctcct atgctcaacg tgtcctgtat ctacattgcg gccgcggatc cctcgaggag   1020

tccatcggtt cctgtcagat gggatactct tgacgtggaa aattcaaaca gaaaaaaaac   1080

cccaataatg aaaaataaca ctacgttata tccgtggtat cctctatcgt atcgtatcgt   1140

agcgtatcgt agcgtaccgt atcacagtat agtctaatat tccgtatctt attgtatcct   1200

atcctattcg atcctattgt atttcagtgc accattttaa tttctattgc tataatgtcc   1260

ttattagttg ccactgtgag gtgaccaatg gacgagggcg agccgttcag aagccgcgaa   1320
```

-continued

```
gggtgttctt cccatgaatt tcttaaggag ggcggctcag ctccgagagt gaggcgagac   1380
gtctcggtca gcgtatcccc cttcctcggc ttttacaaat gatgcgctct taatagtgtg   1440
tcgttatcct tttggcattg acgggggagg gaaattgatt gagcgcatcc atatttttgc   1500
ggactgctga ggacaatggt ggtttttccg ggtggcgtgg gctacaaatg atacgatggt   1560
tttttctttt tcggagaagg cgtataaaaa ggacacggag aacccattta ttctaaaaac   1620
agttgagctt ctttaattat tttttgatat aatattctat tattatatat tttcttccca   1680
ataaaacaaa ataaaacaaa acacagcaaa acacaaaaat tctagaatgg acgcagagaa   1740
aaagattgaa gagtttttcc caggaatcgg aaagattgag tttgaaggta aggaaagtaa   1800
aaacccacta gcctttcgat actatgatgc cgagaaggtt gtctatggta gaaaaatgaa   1860
ggattggttc aagttttcta tggcatattg gcacacattg tgtgctgaag caagagatcc   1920
cttcggagtc gaaactaaag acttcgaatg gaataacggt cgggatgcta tggaacgtgc   1980
taaaaaaaaa gttgatgcag gctttgaatt tatgcgtaaa gttgggattg agtacttttg   2040
ctttcatgac gttgacttgg tggacgaagc caattcattg gaggaatacg aagcaaacct   2100
aaaaactatc gtaacataca ttaaacaaaa gatgaatgaa acgggtataa ggcttctttg   2160
gggcactgca aatgttttcg gtcacaaaag atatatgaat ggtgctgcca ccaatcctaa   2220
ctttgactct gtagcctatg ccgcgaccca aatcaaaaat gcattagatg caacaattga   2280
gttgggtgga gaaaactacg tcttttgggg aggtagagaa ggctatatgt ctttactgaa   2340
caccgacatg aaaagagaaa aggagcatct cgcaatgatg ttgacaaagg ccagggatta   2400
tgctagggcc aagggtttta agggcacttt ctttatagaa cctaagccaa tggaacctac   2460
gaaacaccaa tacgattatg atgcagaaac cgtaataggt ttcttgagag cgcataacct   2520
agataaagat ttcaaactga atatcgaagt taatcatgct actttagctg gtcatacctt   2580
tgagcatgat ttacaatgtg ctgcagatgc tgggatgtta gggagcattg atgcaaatag   2640
gggggattat caaaatggtt gggacacaga tcaatttcca gtggacgtgt atgaactcac   2700
acaggcaatg cttgttattc tacagagtgg gggtttgcaa ggaggtggca caaatttcga   2760
tgcaaagact agacgtgata gtactgattt agaggacatt ttcattgctc atatagcggg   2820
tatggatgct tttgcgagag ctttagaggc agcagctgcg atcttagaag agtccccata   2880
tatcaagatg cgaaaggaaa gatatgcatc gttcgattca ggaaaaggaa aggaatttga   2940
agagggcaaa ctatctcttg aagatatgag ggcttatgct ttggcatccg gaagagaacc   3000
ggaacagatt tcaggtaaac aggagttgta cgaggccata gttaacatgt acatttgatt   3060
aattaacatc tgaatgtaaa atgaacatta aaatgaatta ctaaacttta cgtctacttt   3120
acaatctata aactttgttt aatcatataa cgaaatacac taatacacaa tcctgtacgt   3180
atgtaatact tttatccatc aaggattgag aaaaaaaagt aatgattccc tgggccatta   3240
aaacttagac ccccaagctt ggataggtca ctctctattt tcgtttctcc cttccctgat   3300
agaagggtga tatgtaatta agaataatat ataattttat aataaaagaa ttcgccctta   3360
catatgataa cttcgtataa tgtatgctat acgaagttat catagcctca tgaaatcagc   3420
catttgcttt tgttcaacga tcttttgaaa ttgttgttgt tcttggtagt taagttgatc   3480
catcttggct tatgttgtgt gtatgttgta gttattctta gtatattcct gtcctgagtt   3540
tagtgaaaca taatatcgcc ttgaaatgaa aatgctgaaa ttcgtcgaca tacaattttt   3600
caaacttttt ttttttcttg gtgcacggac atgtttttaa aggaagtact ctataccagt   3660
tattcttcac aaatttaatt gctggagaat agatcttcaa cgctttaata aagtagtttg   3720
```

```
tttgtcaagg atggcgtcat acaaagaaag atcagaatca cacacttccc ctgttgctag   3780
gagacttttc tccatcatgg aggaaaagaa gtctaacctt tgtgcatcat tggatattac   3840
tgaaactgaa aagcttctct ctattttgga cactattggt ccttacatct gtctagttaa   3900
aacacacatc gatattgttt ctgattttac gtatgaagga actgtgttgc ctttgaagga   3960
gcttgccaag aaacataatt ttatgatttt tgaagataga aaatttgctg atattggtaa   4020
cactgttaaa aatcaatata aatctggtgt cttccgtatt gccgaatggg ctgacatcac   4080
taatgcacat ggtgtaacgg gtgcaggtat tgtttctggc ttgaaggagg cagcccaaga   4140
aacaaccagt gaacctagag gtttgctaat gcttgctgag ttatcatcaa agggttcttt   4200
agcatatggt gaatatacag aaaaaacagt agaaattgct aaatctgata aagagtttgt   4260
cattggtttt attgcgcaac acgatatggg cggtagagaa gaaggttttg actggatcat   4320
tatgactcca ggggttggtt tagatgacaa aggtgatgca cttggtcaac aatatagaac   4380
tgttgatgaa gttgtaaaga ctggaacgga tatcataatt gttggtagag gtttgtacgg   4440
tcaaggaaga gatcctatag agcaagctaa aagataccaa caagctggtt ggaatgctta   4500
tttaaacaga tttaaatgat tcttacacaa agatttgata catgtacact agtttaaata   4560
agcatgaaaa gaattacaca agcaaaaaaa aaaaaataaa tgaggtactt tacgttcacc   4620
tacaaccaaa aaaactagat agagtaaaat cttaagattt agaaaaagtt gtttaacaaa   4680
ggctttagta tgtgaatttt taatgtagca aagcgataac taataaacat aaacaaaagt   4740
atggttttct ttatcagtca aatcattatc gattgattgt tccgcgtatc tgcagataac   4800
ttcgtataat gtatgctata cgaagttata gatccgcggc cgcgtgtaaa tatctacgtg   4860
tttagcattt cctatataca tgactgtgtg tcctctggtt ttcatttcgt ttggttctca   4920
ttcctcttgg cagcttcact aaacaactgg tcgtgttgtt cgtcgtgttt tgccttgaag   4980
aatgtatagt gcaacacaac gtcttcgatg tttctcattg ccggatctct ggaaaactct   5040
ggatcgataa agaaaaacaa gggcatatca acctcctcac ccttggccaa ccgctgctct   5100
tcaaagcaga aacactggat cttgttgaag taaggcgcta catgatcggg agtcactgag   5160
tatgtggcca tgccagtaat gtccttgtca cttatattct tggctttgta gaaggccaag   5220
gcagtctctc cggggacaac ataaacttct ctttgttgcg gtacaaactt ccatggtaac   5280
gcaccacttg tctccgccgt aaaggatacc cgcagtcttc tctctgtagc tactggagtt   5340
agcttgtccc tcgtgaacct gctcttgtcg gtgattggtg taccacccca tccagtacgt   5400
tgacaaattg cacgatacaa ggggacactc gcatacgata atgcaaggaa aatcatcatc   5460
atggataacg aataataaat ggtggtttgc ctctcatacc tcttctttc tccatggtac   5520
ttatctctca atgcttggaa ctctgccaaa gacatctttg gaagctcctt ccggtttgct   5580
cgtggtgata cctgatgttc tgatgaccca ccaccaggaa cttcgtattt tgcaatacaa   5640
ctggcatgta catatctcct atggagggca agtccgggaa tcagcccaac atcccgaagg   5700
ggcgcttgta tactagttct gaaaatccgc cttaacatca ccgtacagag acaccttcac   5760
caatatgttc tccaagacca tggggcacta gaagttatcc attgacgttc atcaacctag   5820
tgatgtcaaa tttcatcgcc gtttcccaac tcgcgggatt tgcttttgag catctcgttt   5880
gattcacgac aacttgttct acattctgct gcgggcc                            5917
```

<210> SEQ ID NO 36
<211> LENGTH: 443
<212> TYPE: PRT

<213> ORGANISM: Proteiniphilum acetatigenes

<400> SEQUENCE: 36

```
Met Asp Ala Glu Lys Lys Ile Glu Glu Phe Phe Pro Gly Ile Gly Lys
1               5                   10                  15

Ile Glu Phe Glu Gly Lys Glu Ser Lys Asn Pro Leu Ala Phe Arg Tyr
            20                  25                  30

Tyr Asp Ala Glu Lys Val Val Tyr Gly Arg Lys Met Lys Asp Trp Phe
        35                  40                  45

Lys Phe Ser Met Ala Tyr Trp His Thr Leu Cys Ala Glu Ala Arg Asp
    50                  55                  60

Pro Phe Gly Val Glu Thr Lys Asp Phe Glu Trp Asn Asn Gly Arg Asp
65                  70                  75                  80

Ala Met Glu Arg Ala Lys Lys Lys Val Asp Ala Gly Phe Glu Phe Met
                85                  90                  95

Arg Lys Val Gly Ile Glu Tyr Phe Cys Phe His Asp Val Asp Leu Val
            100                 105                 110

Asp Glu Ala Asn Ser Leu Glu Glu Tyr Glu Ala Asn Leu Lys Thr Ile
        115                 120                 125

Val Thr Tyr Ile Lys Gln Lys Met Asn Glu Thr Gly Ile Arg Leu Leu
    130                 135                 140

Trp Gly Thr Ala Asn Val Phe Gly His Lys Arg Tyr Met Asn Gly Ala
145                 150                 155                 160

Ala Thr Asn Pro Asn Phe Asp Ser Val Ala Tyr Ala Ala Thr Gln Ile
                165                 170                 175

Lys Asn Ala Leu Asp Ala Thr Ile Glu Leu Gly Gly Glu Asn Tyr Val
            180                 185                 190

Phe Trp Gly Gly Arg Glu Gly Tyr Met Ser Leu Leu Asn Thr Asp Met
        195                 200                 205

Lys Arg Glu Lys Glu His Leu Ala Met Met Leu Thr Lys Ala Arg Asp
    210                 215                 220

Tyr Ala Arg Ala Lys Gly Phe Lys Gly Thr Phe Phe Ile Glu Pro Lys
225                 230                 235                 240

Pro Met Glu Pro Thr Lys His Gln Tyr Asp Tyr Asp Ala Glu Thr Val
                245                 250                 255

Ile Gly Phe Leu Arg Ala His Asn Leu Asp Lys Asp Phe Lys Leu Asn
            260                 265                 270

Ile Glu Val Asn His Ala Thr Leu Ala Gly His Thr Phe Glu His Asp
        275                 280                 285

Leu Gln Cys Ala Ala Asp Ala Gly Met Leu Gly Ser Ile Asp Ala Asn
    290                 295                 300

Arg Gly Asp Tyr Gln Asn Gly Trp Asp Thr Asp Gln Phe Pro Val Asp
305                 310                 315                 320

Val Tyr Glu Leu Thr Gln Ala Met Leu Val Ile Leu Gln Ser Gly Gly
                325                 330                 335

Leu Gln Gly Gly Gly Thr Asn Phe Asp Ala Lys Thr Arg Arg Asp Ser
            340                 345                 350

Thr Asp Leu Glu Asp Ile Phe Ile Ala His Ile Ala Gly Met Asp Ala
        355                 360                 365

Phe Ala Arg Ala Leu Glu Ala Ala Ala Ala Ile Leu Glu Glu Ser Pro
    370                 375                 380

Tyr Ile Lys Met Arg Lys Glu Arg Tyr Ala Ser Phe Asp Ser Gly Lys
385                 390                 395                 400
```

```
Gly Lys Glu Phe Glu Glu Gly Lys Leu Ser Leu Glu Asp Met Arg Ala
                405                 410                 415

Tyr Ala Leu Ala Ser Gly Arg Glu Pro Glu Gln Ile Ser Gly Lys Gln
            420                 425                 430

Glu Leu Tyr Glu Ala Ile Val Asn Met Tyr Ile
        435                 440


<210> SEQ ID NO 37
<211> LENGTH: 7354
<212> TYPE: DNA
<213> ORGANISM: Artificial Sequence
<220> FEATURE:
<223> OTHER INFORMATION: PaXI-PDC-IoCYB2A-loxP-XDH

<400> SEQUENCE: 37

ctgcttgtgc aggtgcaacc gagtcgtttg ttgttgtccc ctttgagttg gtgaagatcc     60

ggttacagga taagtccaag gcgtccatgt atagcggtcc cattgatgtt ctaatgaaga    120

cagtcaaaaa tgaaggtatc ttggccttgt ataacggatt agaggcaaca ctgtggagac    180

atattgtatg gaatgccggc tattttggtg tgattttcca agttcgtgac atgttaccca    240

aggcaaagga caagacccag aaaaccatca acgatttggt gggtggtatg attggtggta    300

tcgttggtac tgccttgaac attccattcg atgttgtcaa atccagaatc caaagtgcaa    360

ccattatgga aggtcaggtc cgtaaataca attggacttg gccctctctt ggcattgtct    420

tgagggaaga aggtgtctct gcattgtata aaggattcct tccaaaagtc ctgagattgg    480

gtccaggtgg tggtattcta cttgttgtct tcacaaactg tatggacttc tttagaggcc    540

aatactatgg agacaagaaa tagtagctgg gttcttcacc atcaggttta tacaccctcc    600

acgacgtcca ttctatacta tactatgcta ttcgatgcta ttcgatgcta tcctgcccta    660

tcttatctaa tcttatctta tcttacaaaa ttatatactt tccttgtttc tttcacctcc    720

tcctttatag atcaattgat ttgataatac acttatacac attgacgtct gttgatatct    780

tcatacaaaa aaccttaaaa catagtgcaa agtcacgtgc acgccttaaa aatgcagctg    840

agccccttc ccacttctct cccttcggat gccccacctg actattttca cttcccaatt    900

cgagcatcct cctccagtcc ccgcagactc aagagataag aaaccttaca gagactgttc    960

ccatcctcct atgctcaacg tgtcctgtat ctacattgcg gccgcggatc cctcgaggag   1020

tccatcggtt cctgtcagat gggatactct tgacgtggaa aattcaaaca gaaaaaaaac   1080

cccaataatg aaaaataaca ctacgttata tccgtggtat cctctatcgt atcgtatcgt   1140

agcgtatcgt agcgtaccgt atcacagtat agtctaatat tccgtatctt attgtatcct   1200

atcctattcg atcctattgt atttcagtgc accattttaa tttctattgc tataatgtcc   1260

ttattagttg ccactgtgag gtgaccaatg gacgagggcg agccgttcag aagccgcgaa   1320

gggtgttctt cccatgaatt tcttaaggag ggcggctcag ctccgagagt gaggcgagac   1380

gtctcggtca gcgtatcccc cttcctcggc ttttacaaat gatgcgctct taatagtgtg   1440

tcgttatcct tttggcattg acgggggagg gaaattgatt gagcgcatcc atatttttgc   1500

ggactgctga ggacaatggt ggtttttccg ggtggcgtgg gctacaaatg atacgatggt   1560

ttttttcttt tcggagaagg cgtataaaaa ggacacggag aacccattta ttctaaaaac   1620

agttgagctt ctttaattat tttttgatat aatattctat tattatatat tttcttccca   1680

ataaaacaaa ataaaacaaa acacagcaaa acacaaaaat tctagaatgg acgcagagaa   1740

aaagattgaa gagtttttcc caggaatcgg aaagattgag tttgaaggta aggaaagtaa   1800
```

```
aaacccacta gcctttcgat actatgatgc cgagaaggtt gtctatggta gaaaaatgaa   1860
ggattggttc aagttttcta tggcatattg gcacacattg tgtgctgaag caagagatcc   1920
cttcggagtc gaaactaaag acttcgaatg gaataacggt cgggatgcta tggaacgtgc   1980
taaaaaaaaa gttgatgcag gctttgaatt tatgcgtaaa gttgggattg agtacttttg   2040
ctttcatgac gttgacttgg tggacgaagc caattcattg gaggaatacg aagcaaacct   2100
aaaaactatc gtaacataca ttaaacaaaa gatgaatgaa acgggtataa ggcttctttg   2160
gggcactgca aatgttttcg gtcacaaaag atatatgaat ggtgctgcca ccaatcctaa   2220
ctttgactct gtagcctatg ccgcgaccca aatcaaaaat gcattagatg caacaattga   2280
gttgggtgga gaaaactacg tcttttgggg aggtagagaa ggctatatgt ctttactgaa   2340
caccgacatg aaaagagaaa aggagcatct cgcaatgatg ttgacaaagg ccagggatta   2400
tgctagggcc aagggtttta agggcacttt ctttatagaa cctaagccaa tggaacctac   2460
gaaacaccaa tacgattatg atgcagaaac cgtaataggt ttcttgagag cgcataacct   2520
agataaagat ttcaaactga atatcgaagt taatcatgct actttagctg gtcatacctt   2580
tgagcatgat ttacaatgtg ctgcagatgc tgggatgtta gggagcattg atgcaaatag   2640
gggggattat caaaatggtt gggacacaga tcaatttcca gtggacgtgt atgaactcac   2700
acaggcaatg cttgttattc tacagagtgg gggtttgcaa ggaggtggca caaatttcga   2760
tgcaaagact agacgtgata gtactgattt agaggacatt ttcattgctc atatagcggg   2820
tatggatgct tttgcgagag ctttagaggc agcagctgcg atcttagaag agtccccata   2880
tatcaagatg cgaaaggaaa gatatgcatc gttcgattca ggaaaaggaa aggaatttga   2940
agagggcaaa ctatctcttg aagatatgag ggcttatgct ttggcatccg gaagagaacc   3000
ggaacagatt tcaggtaaac aggagttgta cgaggccata gttaacatgt acatttgatt   3060
aattaacatc tgaatgtaaa atgaacatta aaatgaatta ctaaacttta cgtctacttt   3120
acaatctata aactttgttt aatcatataa cgaaatacac taatacacaa tcctgtacgt   3180
atgtaatact tttatccatc aaggattgag aaaaaaaagt aatgattccc tgggccatta   3240
aaacttagac ccccaagctt ggataggtca ctctctattt tcgtttctcc cttccctgat   3300
agaagggtga tatgtaatta agaataatat ataattttat aataaaagaa ttcgccctta   3360
catatgataa cttcgtataa tgtatgctat acgaagttat gttggtggtg tgttttgttg   3420
gaacgtacat tagatgcata atgcgtgaca ccgccatgat ggttgtattc taccaatgag   3480
acatggccgc tgatcctgtt gtgtgggtca tgggacatca cctcttgggg gggattctcc   3540
tataattggc accgtgtatg cctcaaccac taacttccac cctataactg aatatattac   3600
ataagcaaat ctacttttg tttgtgttga tcgccatcgt tgaaattcgc gcaacttctg    3660
gtggctcaac gctgctgttc tatcggtatc ctaagagatg tctttgccct gagtctaggg   3720
taaactatcc accttcgttg ctgtttgact agacagctac taactttacg gtagtaaatg   3780
aataacggct cgctctcatg atcacttctc tacatcaccc taacaagtgt attattttt    3840
tttcaggtgg gtgttgctgt tggtgctagc cttagtgccc tcgttaatag ttgaacaaac   3900
actggcattt ggagtataat gaaaagggat cactaccccc cgcttcctgt tccgcttctc   3960
ccttccggaa aaaccaccca ccctttcttt tcccccacta atgtatgaat ttttccgttc   4020
ccaggggaat ggcccacttg gttctctgtt aacccacaca attttgacgc atcccacaca   4080
cctttttttt ttctacccca cactttccct tgaaaaatct ccaatttgaa ctggcaattt   4140
tcacccccca ccacttgcat tcattagtga gtcaatccat cccgcggtcg gagattcgga   4200
```

```
atccacctac tggtaatctg taatctatat tcccgctgac cctttataaa tgaactattg   4260
tcgtcaattg cggtagtgct ccaacaaatt gtaaggacct tctttaacct tttcgattca   4320
atccatctcc acataaacct agttgcacac aatgttactc agatcactaa actcttctgc   4380
tcgttgtgtc aaacaaacaa ccagaacaaa ggttaggtat ctcagccacg tcagtggtgc   4440
aagcatggcg aaacctacat tgaagaacaa ctcgagagaa tccaacaaat ccagaaacta   4500
tctaattgct gctgtgacag cattggctgt atcaacctca attggagttg ccgtacatgt   4560
gaaggacccc ttgtataacg atgctaccgg cagtgattct ccgagaagta tatctgttga   4620
cgagtttgtc aagcataatt cacaaaacga ctgttggatt gcaatcaatg gcaaggttta   4680
tgatttcact gattttattc caaaccatcc aggtggggta cctccattag ttaatcatgc   4740
tggttatgat ggtactaaac tttatgagaa attgcatcca aaaggtacaa ttgagaaatt   4800
cttgccaaag gataagtttc tgggtgtgtt agatggtgaa gcgccaaaat tggaagcaga   4860
ctatttggtg gacgatgatg aacaagagag actggattat ttgaacaact tacctccttt   4920
gtcatctatt cagaatgttt atgatttcga atacttggcc aagaagattt tacctaaaga   4980
tgcctgggca tattattctt gtggtgccga tgatgaaatc acaatgagag aaaaccatta   5040
tgcttatcaa agagtttatt tcagaccaag aatttgtgtt gatgtcaagg aagttgatac   5100
ttcttatgaa atgttaggca ctaaaacctc tgttcctttt tatgtatctg ccaccgcttt   5160
ggctaaatta ggccatcctg atggtgaatg ctcaattgct agaggcgctg gtaaggaagg   5220
tgtcgttcaa atgatttcga ccctttcctc aatgtcatta gatgaaattg ccgctgctag   5280
aatcccaggt gcaacccaat ggttccaatt atacattaat gaggatagaa atgtcgctaa   5340
aggtctggtc aaacatgcag aagacttggg tatgaaggct atctttataa ctgttgatgc   5400
tccttctcta ggtaacagag aaaaggataa aagattaaag tttgttaatg acaccgatgt   5460
cgatttgggt gattccgcag atcgaaacag tggtgcttca aaggcactat cttcgttcat   5520
tgatgcttct gtctcttgga atgacgtcaa agcggtcaag tcgtggacta aattgcctgt   5580
cttagttaaa ggtgttcaaa cagttgaaga cgttattgaa gcttacgatg ctggttgtca   5640
aggtgttgtt ttgtcaaacc acggtggtag gcaactagat actgctcctc ctccaatcga   5700
attattagct gaaactgttc caactttgaa gagattgggt aaattaagac cagattttga   5760
aattttaatt gacggtggtg tcaaaagagg taccgatatt ttgaaagcag tcgcaatcgg   5820
tggccaagat gtcagagttt cagttggtat gggtagacct ttcttatatg ccaactcttg   5880
ctatggtgaa gcaggtgtta gaaaattaat tcaaaatcta aaggatgaat tagaaatgga   5940
tatgagattg ttgggtgtca ctaaaatgga ccagctatct tcgaaacatg tcgatactaa   6000
acgtttgatt ggtagagatg cgatcaacta tttgtatgat aatgtataca gcccaatcga   6060
aaccgttaaa ttcaacaatg aagattgatt gttggaaata tattattcat aaaggcgaaa   6120
acattccctt ggtattttat tccaaattta tgatacatag acgtattttt tatatataaa   6180
gttatattat taatgattca agaaaaagtt caaataaact aatggatcaa ccataacttc   6240
gtataatgta tgctatacga agttatagat ccgcggccgc gtgtaaatat ctacgtgttt   6300
agcatttcct atatacatga ctgtgtgtcc tctggttttc atttcgtttg gttctcattc   6360
ctcttggcag cttcactaaa caactggtcg tgttgttcgt cgtgttttgc cttgaagaat   6420
gtatagtgca acacaacgtc ttcgatgttt ctcattgccg gatctctgga aaactctgga   6480
tcgataaaga aaaacaaggg catatcaacc tcctcaccct tggccaaccg ctgctcttca   6540
```

```
aagcagaaac actggatctt gttgaagtaa ggcgctacat gatcgggagt cactgagtat   6600

gtggccatgc cagtaatgtc cttgtcactt atattcttgg ctttgtagaa ggccaaggca   6660

gtctctccgg ggacaacata aacttctctt tgttgcggta caaacttcca tggtaacgca   6720

ccacttgtct ccgccgtaaa ggatacccgc agtcttctct ctgtagctac tggagttagc   6780

ttgtccctcg tgaacctgct cttgtcggtg attggtgtac caccccatcc agtacgttga   6840

caaattgcac gatacaaggg gacactcgca tacgataatg caaggaaaat catcatcatg   6900

gataacgaat aataaatggt ggtttgcctc tcatacctct tcttttctcc atggtactta   6960

tctctcaatg cttggaactc tgccaaagac atctttggaa gctccttccg gtttgctcgt   7020

ggtgatacct gatgttctga tgacccacca ccaggaactt cgtattttgc aatacaactg   7080

gcatgtacat atctcctatg gagggcaagt ccgggaatca gcccaacatc ccgaaggggc   7140

gcttgtatac tagttctgaa aatccgcctt aacatcaccg tacagagaca ccttcaccaa   7200

tatgttctcc aagaccatgg ggcactagaa gttatccatt gacgttcatc aacctagtga   7260

tgtcaaattt catcgccgtt tcccaactcg cgggatttgc ttttgagcat ctcgtttgat   7320

tcacgacaac ttgttctaca ttctgctgcg ggcc                               7354
```

<210> SEQ ID NO 38
<211> LENGTH: 5902
<212> TYPE: DNA
<213> ORGANISM: Artificial Sequence
<220> FEATURE:
<223> OTHER INFORMATION: PpXI-PDC-URA3-loxP-XDH integration fragment

<400> SEQUENCE: 38

```
ctgcttgtgc aggtgcaacc gagtcgtttg ttgttgtccc ctttgagttg gtgaagatcc     60

ggttacagga taagtccaag gcgtccatgt atagcggtcc cattgatgtt ctaatgaaga    120

cagtcaaaaa tgaaggtatc ttggccttgt ataacggatt agaggcaaca ctgtggagac    180

atattgtatg gaatgccggc tattttggtg tgattttcca agttcgtgac atgttaccca    240

aggcaaagga caagacccag aaaaccatca acgatttggt gggtggtatg attggtggta    300

tcgttggtac tgccttgaac attccattcg atgttgtcaa atccagaatc caaagtgcaa    360

ccattatgga aggtcaggtc cgtaaataca attggacttg gccctctctt ggcattgtct    420

tgagggaaga aggtgtctct gcattgtata aaggattcct tccaaaagtc ctgagattgg    480

gtccaggtgg tggtattcta cttgttgtct tcacaaactg tatggacttc tttagaggcc    540

aatactatgg agacaagaaa tagtagctgg gttcttcacc atcaggttta tacaccctcc    600

acgacgtcca ttctatacta tactatgcta ttcgatgcta ttcgatgcta tcctgcccta    660

tcttatctaa tcttatctta tcttacaaaa ttatatactt tccttgtttc tttcacctcc    720

tcctttatag atcaattgat ttgataatac acttatacac attgacgtct gttgatatct    780

tcatacaaaa aaccttaaaa catagtgcaa agtcacgtgc acgccttaaa aatgcagctg    840

agccccttc ccacttctct cccttcggat gccccacctg actattttca cttcccaatt    900

cgagcatcct cctccagtcc ccgcagactc aagagataag aaaccttaca gagactgttc    960

ccatcctcct atgctcaacg tgtcctgtat ctacattgcg gccgcggatc cctcgaggag   1020

tccatcggtt cctgtcagat gggatactct tgacgtggaa aattcaaaca gaaaaaaaac   1080

cccaataatg aaaaataaca ctacgttata tccgtggtat cctctatcgt atcgtatcgt   1140

agcgtatcgt agcgtaccgt atcacagtat agtctaatat tccgtatctt attgtatcct   1200

atcctattcg atcctattgt atttcagtgc accattttaa tttctattgc tataatgtcc   1260
```

```
ttattagttg ccactgtgag gtgaccaatg gacgagggcg agccgttcag aagccgcgaa   1320
gggtgttctt cccatgaatt tcttaaggag ggcggctcag ctccgagagt gaggcgagac   1380
gtctcggtca gcgtatcccc cttcctcggc ttttacaaat gatgcgctct taatagtgtg   1440
tcgttatcct tttggcattg acgggggagg gaaattgatt gagcgcatcc atatttttgc   1500
ggactgctga ggacaatggt ggtttttccg ggtggcgtgg gctacaaatg atacgatggt   1560
tttttcttt tcggagaagg cgtataaaaa ggacacggag aacccattta ttctaaaaac   1620
agttgagctt ctttaattat tttttgatat aatattctat tattatatat tttcttccca   1680
ataaaacaaa ataaaacaaa acacagcaaa acacaaaaat tctagaatgt ctaccaaggt   1740
ctactttccg agcgttgaaa agataaagtt cgaaggcaag gagtctaaaa acccactagc   1800
tttcaggtat tatgatgccg agaaggtagt ttatggtaaa accatgaaag agtggtttaa   1860
gtttagtatg gcatggtggc atacactatg tgctgaagga ggggacccat ttggtggtgg   1920
tacgcaagtt catccatggg ttggcgcagc agatgcgctt caggcagcaa aggacaaaat   1980
ggacgcagga tttgaattta tgcagaagat gggcattgag tattactgct ttcatgatat   2040
tgatctggtt agtgagggtt cttcaattga ggaatatgaa gcgaatctta aagccattgt   2100
tgcatacgca aaagagaaac aagctgcaac aggtatcaag ttaatgtggg gtacagccaa   2160
tgttttctcc cccgctagat acatgaacgg agcttctaca aatcctgatt tcaatgcagc   2220
tgctagggca atgctacaaa tcaaaaactc gatagatgca actatagaat tgggcgggaa   2280
agcctacgtg ttttggggtg ggagagaagg atatatgtcc ttactcaata caaacatgaa   2340
acgtgaaaag caacacatgg ggactatgtt gaaaatggca agagactatg ctagagcaaa   2400
aggttttaag ggtgttttct taattgaacc taaaccaatg gaacctatga agcaccaata   2460
tgatgtagac tcggaaaccg tgattggatt tttgaagcaa ttcggattag aaaacgattt   2520
caagctcaat atcgaagtca atcatgctac tttggctggt catactttcg aacacgagct   2580
gcagtgtgct gtcgatgctg gtatgttagg tgctatcgat gcaaaccggg gtgatgtcca   2640
aaatggctgg gacactgatc aatttccaat cgacattttt gaacttacac aagcgatgtt   2700
ggttgtattg cagggtggag gtatgcaagg tggcggaacc aattttgatg caaaaatcag   2760
acgaaactcc acggataaca atgatttgtt tattgcgcat gttagcgcga tggatgtcat   2820
ggccagagca ttagaggcag cagccgccat acttgaagag agtccctaca aaaagatggt   2880
gtcagaccgt tatgcttcat atgatgctgg aaaagggaaa gagttcgaag agggcaaact   2940
aacttttgaa gatgtttatg cttatgctaa ggccaatggt gaacctaagc aaatttcagg   3000
taaacaggaa ttgtatgaag ccatagtgaa tatgtacatt tgattaatta acatctgaat   3060
gtaaaatgaa cattaaaatg aattactaaa ctttacgtct actttacaat ctataaactt   3120
tgtttaatca tataacgaaa tacactaata cacaatcctg tacgtatgta atacttttat   3180
ccatcaagga ttgagaaaaa aaagtaatga ttccctgggc cattaaaact tagaccccca   3240
agcttggata ggtcactctc tattttcgtt tctcccttcc ctgatagaag ggtgatatgt   3300
aattaagaat aatatataat tttataataa aagaattcgc ccttacatat gataacttcg   3360
tataatgtat gctatacgaa gttatcatag cctcatgaaa tcagccattt gcttttgttc   3420
aacgatcttt tgaaattgtt gttgttcttg gtagttaagt tgatccatct tggcttatgt   3480
tgtgtgtatg ttgtagttat tcttagtata ttcctgtcct gagtttagtg aaacataata   3540
tcgccttgaa atgaaaatgc tgaaattcgt cgacatacaa tttttcaaac ttttttttt   3600
```

-continued

```
tcttggtgca cggacatgtt tttaaaggaa gtactctata ccagttattc ttcacaaatt   3660
taattgctgg agaatagatc ttcaacgctt taataaagta gtttgtttgt caaggatggc   3720
gtcatacaaa gaaagatcag aatcacacac ttcccctgtt gctaggagac ttttctccat   3780
catggaggaa aagaagtcta acctttgtgc atcattggat attactgaaa ctgaaaagct   3840
tctctctatt ttggacacta ttggtcctta catctgtcta gttaaaacac acatcgatat   3900
tgtttctgat tttacgtatg aaggaactgt gttgcctttg aaggagcttg ccaagaaaca   3960
taattttatg atttttgaag atagaaaatt tgctgatatt ggtaacactg ttaaaaatca   4020
atataaatct ggtgtcttcc gtattgccga atgggctgac atcactaatg cacatggtgt   4080
aacgggtgca ggtattgttt ctggcttgaa ggaggcagcc caagaaacaa ccagtgaacc   4140
tagaggtttg ctaatgcttg ctgagttatc atcaaagggt tctttagcat atggtgaata   4200
tacagaaaaa acagtagaaa ttgctaaatc tgataaagag tttgtcattg gttttattgc   4260
gcaacacgat atgggcggta gagaagaagg ttttgactgg atcattatga ctccaggggt   4320
tggtttagat gacaaaggtg atgcacttgg tcaacaatat agaactgttg atgaagttgt   4380
aaagactgga acggatatca taattgttgg tagaggtttg tacggtcaag gaagagatcc   4440
tatagagcaa gctaaaagat accaacaagc tggttggaat gcttatttaa acagatttaa   4500
atgattctta cacaaagatt tgatacatgt acactagttt aaataagcat gaaaagaatt   4560
acacaagcaa aaaaaaaaaa ataaatgagg tactttacgt tcacctacaa ccaaaaaaac   4620
tagatagagt aaaatcttaa gatttagaaa aagttgttta acaaaggctt tagtatgtga   4680
atttttaatg tagcaaagcg ataactaata aacataaaca aaagtatggt tttctttatc   4740
agtcaaatca ttatcgattg attgttccgc gtatctgcag ataacttcgt ataatgtatg   4800
ctatacgaag ttatagatcc gcggccgcgt gtaaatatct acgtgtttag catttcctat   4860
atacatgact gtgtgtcctc tggttttcat ttcgtttggt tctcattcct cttggcagct   4920
tcactaaaca actggtcgtg ttgttcgtcg tgttttgcct tgaagaatgt atagtgcaac   4980
acaacgtctt cgatgtttct cattgccgga tctctggaaa actctggatc gataaagaaa   5040
aacaagggca tatcaacctc ctcacccttg gccaaccgct gctcttcaaa gcagaaacac   5100
tggatcttgt tgaagtaagg cgctacatga tcgggagtca ctgagtatgt ggccatgcca   5160
gtaatgtcct tgtcacttat attcttggct ttgtagaagg ccaaggcagt ctctccgggg   5220
acaacataaa cttctctttg ttgcggtaca aacttccatg gtaacgcacc acttgtctcc   5280
gccgtaaagg atacccgcag tcttctctct gtagctactg gagttagctt gtccctcgtg   5340
aacctgctct tgtcggtgat tggtgtacca ccccatccag tacgttgaca aattgcacga   5400
tacaagggga cactcgcata cgataatgca aggaaaatca tcatcatgga taacgaataa   5460
taaatggtgg tttgcctctc atacctcttc ttttctccat ggtacttatc tctcaatgct   5520
tggaactctg ccaaagacat ctttggaagc tccttccggt ttgctcgtgg tgatacctga   5580
tgttctgatg acccaccacc aggaacttcg tattttgcaa tacaactggc atgtacatat   5640
ctcctatgga gggcaagtcc gggaatcagc ccaacatccc gaaggggcgc ttgtatacta   5700
gttctgaaaa tccgccttaa catcaccgta cagagacacc ttcaccaata tgttctccaa   5760
gaccatgggg cactagaagt tatccattga cgttcatcaa cctagtgatg tcaaatttca   5820
tcgccgtttc ccaactcgcg ggatttgctt ttgagcatct cgtttgattc acgacaactt   5880
gttctacatt ctgctgcggg cc                                            5902
```

<210> SEQ ID NO 39
<211> LENGTH: 438
<212> TYPE: PRT
<213> ORGANISM: Paludibacter propionicigenes WB4

<400> SEQUENCE: 39

```
Met Ser Thr Lys Val Tyr Phe Pro Ser Val Glu Lys Ile Lys Phe Glu
1               5                   10                  15

Gly Lys Glu Ser Lys Asn Pro Leu Ala Phe Arg Tyr Tyr Asp Ala Glu
            20                  25                  30

Lys Val Val Tyr Gly Lys Thr Met Lys Glu Trp Phe Lys Phe Ser Met
        35                  40                  45

Ala Trp Trp His Thr Leu Cys Ala Glu Gly Gly Asp Pro Phe Gly Gly
    50                  55                  60

Gly Thr Gln Val His Pro Trp Val Gly Ala Ala Asp Ala Leu Gln Ala
65                  70                  75                  80

Ala Lys Asp Lys Met Asp Ala Gly Phe Glu Phe Met Gln Lys Met Gly
                85                  90                  95

Ile Glu Tyr Tyr Cys Phe His Asp Ile Asp Leu Val Ser Glu Gly Ser
            100                 105                 110

Ser Ile Glu Glu Tyr Glu Ala Asn Leu Lys Ala Ile Val Ala Tyr Ala
        115                 120                 125

Lys Glu Lys Gln Ala Ala Thr Gly Ile Lys Leu Met Trp Gly Thr Ala
    130                 135                 140

Asn Val Phe Ser Pro Ala Arg Tyr Met Asn Gly Ala Ser Thr Asn Pro
145                 150                 155                 160

Asp Phe Asn Ala Ala Ala Arg Ala Met Leu Gln Ile Lys Asn Ser Ile
                165                 170                 175

Asp Ala Thr Ile Glu Leu Gly Gly Lys Ala Tyr Val Phe Trp Gly Gly
            180                 185                 190

Arg Glu Gly Tyr Met Ser Leu Leu Asn Thr Asn Met Lys Arg Glu Lys
        195                 200                 205

Gln His Met Gly Thr Met Leu Lys Met Ala Arg Asp Tyr Ala Arg Ala
    210                 215                 220

Lys Gly Phe Lys Gly Val Phe Leu Ile Glu Pro Lys Pro Met Glu Pro
225                 230                 235                 240

Met Lys His Gln Tyr Asp Val Asp Ser Glu Thr Val Ile Gly Phe Leu
                245                 250                 255

Lys Gln Phe Gly Leu Glu Asn Asp Phe Lys Leu Asn Ile Glu Val Asn
            260                 265                 270

His Ala Thr Leu Ala Gly His Thr Phe Glu His Glu Leu Gln Cys Ala
        275                 280                 285

Val Asp Ala Gly Met Leu Gly Ala Ile Asp Ala Asn Arg Gly Asp Val
    290                 295                 300

Gln Asn Gly Trp Asp Thr Asp Gln Phe Pro Ile Asp Ile Phe Glu Leu
305                 310                 315                 320

Thr Gln Ala Met Leu Val Val Leu Gln Gly Gly Gly Met Gln Gly Gly
                325                 330                 335

Gly Thr Asn Phe Asp Ala Lys Ile Arg Arg Asn Ser Thr Asp Asn Asn
            340                 345                 350

Asp Leu Phe Ile Ala His Val Ser Ala Met Asp Val Met Ala Arg Ala
        355                 360                 365

Leu Glu Ala Ala Ala Ala Ile Leu Glu Glu Ser Pro Tyr Lys Lys Met
    370                 375                 380
```

```
Val Ser Asp Arg Tyr Ala Ser Tyr Asp Ala Gly Lys Gly Lys Glu Phe
385                 390                 395                 400

Glu Glu Gly Lys Leu Thr Phe Glu Asp Val Tyr Ala Tyr Ala Lys Ala
                405                 410                 415

Asn Gly Glu Pro Lys Gln Ile Ser Gly Lys Gln Glu Leu Tyr Glu Ala
            420                 425                 430

Ile Val Asn Met Tyr Ile
        435


<210> SEQ ID NO 40
<211> LENGTH: 7339
<212> TYPE: DNA
<213> ORGANISM: Artificial Sequence
<220> FEATURE:
<223> OTHER INFORMATION: PpXI-PDC-CYB2A-loxP-XDH integration fragment

<400> SEQUENCE: 40

ctgcttgtgc aggtgcaacc gagtcgtttg ttgttgtccc ctttgagttg gtgaagatcc     60

ggttacagga taagtccaag gcgtccatgt atagcggtcc cattgatgtt ctaatgaaga    120

cagtcaaaaa tgaaggtatc ttggccttgt ataacggatt agaggcaaca ctgtggagac    180

atattgtatg gaatgccggc tattttggtg tgattttcca agttcgtgac atgttaccca    240

aggcaaagga caagacccag aaaaccatca acgatttggt gggtggtatg attggtggta    300

tcgttggtac tgccttgaac attccattcg atgttgtcaa atccagaatc caaagtgcaa    360

ccattatgga aggtcaggtc cgtaaataca attggacttg gccctctctt ggcattgtct    420

tgagggaaga aggtgtctct gcattgtata aaggattcct tccaaaagtc ctgagattgg    480

gtccaggtgg tggtattcta cttgttgtct tcacaaactg tatggacttc tttagaggcc    540

aatactatgg agacaagaaa tagtagctgg gttcttcacc atcaggttta tacaccctcc    600

acgacgtcca ttctatacta tactatgcta ttcgatgcta ttcgatgcta tcctgcccta    660

tcttatctaa tcttatctta tcttacaaaa ttatatactt tccttgtttc tttcacctcc    720

tcctttatag atcaattgat ttgataatac acttatacac attgacgtct gttgatatct    780

tcatacaaaa aaccttaaaa catagtgcaa agtcacgtgc acgccttaaa aatgcagctg    840

agccccttttc ccacttctct cccttcggat gccccacctg actattttca cttcccaatt    900

cgagcatcct cctccagtcc ccgcagactc aagagataag aaaccttaca gagactgttc    960

ccatcctcct atgctcaacg tgtcctgtat ctacattgcg gccgcggatc cctcgaggag   1020

tccatcggtt cctgtcagat gggatactct tgacgtggaa aattcaaaca gaaaaaaaac   1080

cccaataatg aaaaataaca ctacgttata tccgtggtat cctctatcgt atcgtatcgt   1140

agcgtatcgt agcgtaccgt atcacagtat agtctaatat tccgtatctt attgtatcct   1200

atcctattcg atcctattgt atttcagtgc accattttaa tttctattgc tataatgtcc   1260

ttattagttg ccactgtgag gtgaccaatg gacgagggcg agccgttcag aagccgcgaa   1320

gggtgttctt cccatgaatt tcttaaggag ggcggctcag ctccgagagt gaggcgagac   1380

gtctcggtca gcgtatcccc cttcctcggc ttttacaaat gatgcgctct taatagtgtg   1440

tcgttatcct tttggcattg acgggggagg gaaattgatt gagcgcatcc atatttttgc   1500

ggactgctga ggacaatggt ggtttttccg ggtggcgtgg gctacaaatg atacgatggt   1560

tttttctttt tcggagaagg cgtataaaaa ggacacggag aacccattta ttctaaaaac   1620

agttgagctt ctttaattat tttttgatat aatattctat tattatatat tttcttccca   1680

ataaaacaaa ataaaacaaa acacagcaaa acacaaaaat tctagaatgt ctaccaaggt   1740
```

```
ctactttccg agcgttgaaa agataaagtt cgaaggcaag gagtctaaaa acccactagc   1800
tttcaggtat tatgatgccg agaaggtagt ttatggtaaa accatgaaag agtggtttaa   1860
gtttagtatg gcatggtggc atacactatg tgctgaagga ggggacccat ttggtggtgg   1920
tacgcaagtt catccatggg ttggcgcagc agatgcgctt caggcagcaa aggacaaaat   1980
ggacgcagga tttgaattta tgcagaagat gggcattgag tattactgct ttcatgatat   2040
tgatctggtt agtgagggtt cttcaattga ggaatatgaa gcgaatctta aagccattgt   2100
tgcatacgca aaagagaaac aagctgcaac aggtatcaag ttaatgtggg gtacagccaa   2160
tgttttctcc cccgctagat acatgaacgg agcttctaca aatcctgatt tcaatgcagc   2220
tgctagggca atgctacaaa tcaaaaactc gatagatgca actatagaat tgggcgggaa   2280
agcctacgtg ttttggggtg ggagagaagg atatatgtcc ttactcaata caaacatgaa   2340
acgtgaaaag caacacatgg ggactatgtt gaaaatggca agagactatg ctagagcaaa   2400
aggttttaag ggtgttttct taattgaacc taaaccaatg gaacctatga agcaccaata   2460
tgatgtagac tcggaaaccg tgattggatt tttgaagcaa ttcggattag aaaacgattt   2520
caagctcaat atcgaagtca atcatgctac tttggctggt catactttcg aacacgagct   2580
gcagtgtgct gtcgatgctg gtatgttagg tgctatcgat gcaaaccggg gtgatgtcca   2640
aaatggctgg gacactgatc aatttccaat cgacattttt gaacttacac aagcgatgtt   2700
ggttgtattg cagggtggag gtatgcaagg tggcggaacc aattttgatg caaaaatcag   2760
acgaaactcc acggataaca atgatttgtt tattgcgcat gttagcgcga tggatgtcat   2820
ggccagagca ttagaggcag cagccgccat acttgaagag agtccctaca aaaagatggt   2880
gtcagaccgt tatgcttcat atgatgctgg aaaagggaaa gagttcgaag agggcaaact   2940
aacttttgaa gatgtttatg cttatgctaa ggccaatggt gaacctaagc aaatttcagg   3000
taaacaggaa ttgtatgaag ccatagtgaa tatgtacatt tgattaatta acatctgaat   3060
gtaaaatgaa cattaaaatg aattactaaa ctttacgtct actttacaat ctataaactt   3120
tgtttaatca tataacgaaa tacactaata cacaatcctg tacgtatgta atacttttat   3180
ccatcaagga ttgagaaaaa aaagtaatga ttccctgggc cattaaaact tagacccccca  3240
agcttggata ggtcactctc tattttcgtt tctcccttcc ctgatagaag ggtgatatgt   3300
aattaagaat aatatataat tttataataa aagaattcgc ccttacatat gataacttcg   3360
tataatgtat gctatacgaa gttatgttgg tggtgtgttt tgttggaacg tacattagat   3420
gcataatgcg tgacaccgcc atgatggttg tattctacca atgagacatg gccgctgatc   3480
ctgttgtgtg ggtcatggga catcacctct tggggggggat tctcctataa ttggcaccgt  3540
gtatgcctca accactaact tccaccctat aactgaatat attacataag caaatctact   3600
ttttgtttgt gttgatcgcc atcgttgaaa ttcgcgcaac ttctggtggc tcaacgctgc   3660
tgttctatcg gtatcctaag agatgtcttt gccctgagtc tagggtaaac tatccacctt   3720
cgttgctgtt tgactagaca gctactaact ttacggtagt aaatgaataa cggctcgctc   3780
tcatgatcac ttctctacat caccctaaca agtgtattat tttttttca ggtgggtgtt    3840
gctgttggtg ctagccttag tgccctcgtt aatagttgaa caaacactgg catttggagt   3900
ataatgaaaa gggatcacta ccccccgctt cctgttccgc ttctcccttc cggaaaaacc   3960
acccaccctt tcttttcccc cactaatgta tgaatttttc cgttcccagg ggaatggccc   4020
acttggttct ctgttaaccc acacaatttt gacgcatccc acacaccttt tttttttcta   4080
```

```
ccccacactt tcccttgaaa aatctccaat ttgaactggc aattttcacc ccccaccact   4140
tgcattcatt agtgagtcaa tccatcccgc ggtcggagat tcggaatcca cctactggta   4200
atctgtaatc tatattcccg ctgacccttt ataaatgaac tattgtcgtc aattgcggta   4260
gtgctccaac aaattgtaag gaccttcttt aacctttttcg attcaatcca tctccacata   4320
aacctagttg cacacaatgt tactcagatc actaaactct tctgctcgtt gtgtcaaaca   4380
aacaaccaga acaaaggtta ggtatctcag ccacgtcagt ggtgcaagca tggcgaaacc   4440
tacattgaag aacaactcga gagaatccaa caaatccaga aactatctaa ttgctgctgt   4500
gacagcattg gctgtatcaa cctcaattgg agttgccgta catgtgaagg acccccttgta   4560
taacgatgct accggcagtg attctccgag aagtatatct gttgacgagt ttgtcaagca   4620
taattcacaa aacgactgtt ggattgcaat caatggcaag gtttatgatt tcactgattt   4680
tattccaaac catccaggtg gggtacctcc attagttaat catgctggtt atgatggtac   4740
taaactttat gagaaattgc atccaaaagg tacaattgag aaattcttgc caaaggataa   4800
gtttctgggt gtgttagatg gtgaagcgcc aaaattggaa gcagactatt tggtggacga   4860
tgatgaacaa gagagactgg attatttgaa caacttacct cctttgtcat ctattcagaa   4920
tgtttatgat ttcgaatact tggccaagaa gattttacct aaagatgcct gggcatatta   4980
ttcttgtggt gccgatgatg aaatcacaat gagagaaaac cattatgctt atcaaagagt   5040
ttatttcaga ccaagaattt gtgttgatgt caaggaagtt gatacttctt atgaaatgtt   5100
aggcactaaa acctctgttc ctttttatgt atctgccacc gctttggcta aattaggcca   5160
tcctgatggt gaatgctcaa ttgctagagg cgctggtaag gaaggtgtcg ttcaaatgat   5220
ttcgaccctt tcctcaatgt cattagatga aattgccgct gctagaatcc caggtgcaac   5280
ccaatggttc caattataca ttaatgagga tagaaatgtc gctaaaggtc tggtcaaaca   5340
tgcagaagac ttgggtatga aggctatctt tataactgtt gatgctcctt ctctaggtaa   5400
cagagaaaag gataaaagat taaagtttgt taatgacacc gatgtcgatt tgggtgattc   5460
cgcagatcga aacagtggtg cttcaaaggc actatcttcg ttcattgatg cttctgtctc   5520
ttggaatgac gtcaaagcgg tcaagtcgtg gactaaattg cctgtcttag ttaaaggtgt   5580
tcaaacagtt gaagacgtta ttgaagctta cgatgctggt tgtcaaggtg ttgttttgtc   5640
aaaccacggt ggtaggcaac tagatactgc tcctcctcca atcgaattat tagctgaaac   5700
tgttccaact ttgaagagat tgggtaaatt aagaccagat tttgaaattt taattgacgg   5760
tggtgtcaaa agaggtaccg atattttgaa agcagtcgca atcggtggcc aagatgtcag   5820
agtttcagtt ggtatgggta gacctttctt atatgccaac tcttgctatg gtgaagcagg   5880
tgttagaaaa ttaattcaaa atctaaagga tgaattagaa atggatatga gattgttggg   5940
tgtcactaaa atggaccagc tatcttcgaa acatgtcgat actaaacgtt tgattggtag   6000
agatgcgatc aactatttgt atgataatgt atacagccca atcgaaaccg ttaaattcaa   6060
caatgaagat tgattgttgg aaatatatta ttcataaagg cgaaaacatt cccttggtat   6120
tttattccaa atttatgata catagacgta ttttttatat ataaagttat attattaatg   6180
attcaagaaa aagttcaaat aaactaatgg atcaaccata acttcgtata atgtatgcta   6240
tacgaagtta tagatccgcg gccgcgtgta aatatctacg tgtttagcat ttcctatata   6300
catgactgtg tgtcctctgg ttttcatttc gtttggttct cattcctctt ggcagcttca   6360
ctaaacaact ggtcgtgttg ttcgtcgtgt tttgccttga agaatgtata gtgcaacaca   6420
acgtcttcga tgtttctcat tgccggatct ctggaaaact ctggatcgat aaagaaaaac   6480
```

```
aagggcatat caacctcctc acccttggcc aaccgctgct cttcaaagca gaaacactgg   6540
atcttgttga agtaaggcgc tacatgatcg ggagtcactg agtatgtggc catgccagta   6600
atgtccttgt cacttatatt cttggctttg tagaaggcca aggcagtctc tccggggaca   6660
acataaactt ctctttgttg cggtacaaac ttccatggta acgcaccact tgtctccgcc   6720
gtaaaggata cccgcagtct tctctctgta gctactggag ttagcttgtc cctcgtgaac   6780
ctgctcttgt cggtgattgg tgtaccaccc catccagtac gttgacaaat tgcacgatac   6840
aaggggacac tcgcatacga taatgcaagg aaaatcatca tcatggataa cgaataataa   6900
atggtggttt gcctctcata cctcttcttt tctccatggt acttatctct caatgcttgg   6960
aactctgcca aagacatctt tggaagctcc ttccggtttg ctcgtggtga tacctgatgt   7020
tctgatgacc caccaccagg aacttcgtat tttgcaatac aactggcatg tacatatctc   7080
ctatggaggg caagtccggg aatcagccca acatcccgaa ggggcgcttg tatactagtt   7140
ctgaaaatcc gccttaacat caccgtacag agacaccttc accaatatgt tctccaagac   7200
catggggcac tagaagttat ccattgacgt tcatcaacct agtgatgtca aatttcatcg   7260
ccgtttccca actcgcggga tttgcttttg agcatctcgt ttgattcacg acaacttgtt   7320
ctacattctg ctgcgggcc                                                 7339
```

<210> SEQ ID NO 41
<211> LENGTH: 5909
<212> TYPE: DNA
<213> ORGANISM: Artificial Sequence
<220> FEATURE:
<223> OTHER INFORMATION: BtXI-PDC-URA3-loxP-XDH integration fragment

<400> SEQUENCE: 41

```
ctgcttgtgc aggtgcaacc gagtcgtttg ttgttgtccc ctttgagttg gtgaagatcc     60
ggttacagga taagtccaag gcgtccatgt atagcggtcc cattgatgtt ctaatgaaga    120
cagtcaaaaa tgaaggtatc ttggccttgt ataacggatt agaggcaaca ctgtggagac    180
atattgtatg gaatgccggc tattttggtg tgattttcca agttcgtgac atgttaccca    240
aggcaaagga caagacccag aaaaccatca acgatttggt gggtggtatg attggtggta    300
tcgttggtac tgccttgaac attccattcg atgttgtcaa atccagaatc caaagtgcaa    360
ccattatgga aggtcaggtc cgtaaataca attggacttg gccctctctt ggcattgtct    420
tgagggaaga aggtgtctct gcattgtata aaggattcct tccaaaagtc ctgagattgg    480
gtccaggtgg tggtattcta cttgttgtct tcacaaactg tatggacttc tttagaggcc    540
aatactatgg agacaagaaa tagtagctgg gttcttcacc atcaggttta tacaccctcc    600
acgacgtcca ttctatacta tactatgcta ttcgatgcta ttcgatgcta tcctgcccta    660
tcttatctaa tcttatctta tcttacaaaa ttatatactt tccttgtttc tttcacctcc    720
tcctttatag atcaattgat ttgataatac acttatacac attgacgtct gttgatatct    780
tcatacaaaa aaccttaaaa catagtgcaa agtcacgtgc acgccttaaa aatgcagctg    840
agccccttc ccacttctct cccttcggat gccccacctg actattttca cttcccaatt    900
cgagcatcct cctccagtcc ccgcagactc aagagataag aaaccttaca gagactgttc    960
ccatcctcct atgctcaacg tgtcctgtat ctacattgcg gccgcggatc cctcgaggag   1020
tccatcggtt cctgtcagat gggatactct tgacgtggaa aattcaaaca gaaaaaaaac   1080
cccaataatg aaaaataaca ctacgttata tccgtggtat cctctatcgt atcgtatcgt   1140
```

```
agcgtatcgt agcgtaccgt atcacagtat agtctaatat tccgtatctt attgtatcct   1200
atcctattcg atcctattgt atttcagtgc accattttaa tttctattgc tataatgtcc   1260
ttattagttg ccactgtgag gtgaccaatg gacgagggcg agccgttcag aagccgcgaa   1320
gggtgttctt cccatgaatt tcttaaggag ggcggctcag ctccgagagt gaggcgagac   1380
gtctcggtca gcgtatcccc cttcctcggc ttttacaaat gatgcgctct taatagtgtg   1440
tcgttatcct tttggcattg acgggggagg gaaattgatt gagcgcatcc atatttttgc   1500
ggactgctga ggacaatggt ggtttttccg ggtggcgtgg gctacaaatg atacgatggt   1560
ttttttcttt tcggagaagg cgtataaaaa ggacacggag aacccattta ttctaaaaac   1620
agttgagctt ctttaattat tttttgatat aatattctat tattatatat tttcttccca   1680
ataaaacaaa ataaaacaaa acacagcaaa acacaaaaat tctagaaaat atggctacta   1740
aagaattttt cccaggtatt gaaaagatta aatttgaagg taaagactcc aaaaatccaa   1800
tggcttttag atattacgac gcagaaaagg ttattaacgg taaaaaaatg aaggactggt   1860
tgagatttgc tatggcatgg tggcacaccc tatgtgctga aggtggtgat caattcggtg   1920
gtggtacaaa acaatttcct tggaacggta acgctgacgc tattcaagct gcaaaggaca   1980
agatggacgc cggtttcgaa tttatgcaaa agatgggtat tgaatactac tgttttcacg   2040
atgttgattt ggtctctgaa ggtgcatctg ttgaagaata tgaagctaac ttgaaggaaa   2100
tcgttgctta cgctaagcaa aagcaagctg agacaggtat taaattgttg tggggtacag   2160
caaacgtttt cggtcacgcc agatatatga atggtgctgc aactaaccca gatttcgatg   2220
ttgttgcaag agccgcagtt caaatcaaaa acgctattga cgctacaatc gaactaggtg   2280
gtgaaaacta tgtttttttgg ggtggtagag aaggttacat gtctttgttg aacactgacc   2340
aaaaaagaga aaaggaacac ttggcccaaa tgttgactat cgctagagat tacgctagag   2400
ctagaggttt taaaggtact tttttgattg aaccaaaacc aatggaacca actaagcacc   2460
aatatgacgt tgatactgaa actgttattg gtttcttgaa ggcacacggt ttggataagg   2520
attttaaggt gaatatcgaa gttaaccacg ctactttggc cggtcatact ttcgaacatg   2580
aattggctgt tgctgtggat aacggtatgt tgggttctat tgacgcaaac agaggtgact   2640
atcaaaatgg ttgggacact gatcaatttc caattgacaa ctatgaattg acacaagcaa   2700
tgatgcaaat tattagaaac ggtggtttgg gtactggtgg tactaacttc gacgctaaga   2760
ctagaagaaa ttccacagat ttggaagaca tttttatcgc tcacatcgct ggtatggacg   2820
ctatggccag agctttggaa tccgctgctg ctttgttgga cgaatcccca tacaagaaaa   2880
tgttggccga cagatacgct tctttcgacg gtggtaaggg taaggaattt gaggacggta   2940
agttgacatt ggaagatgtt gttgcttacg ctaagactaa gggtgaacca aagcaaacat   3000
ccggtaagca agaattgtac gaagctattc taaatatgta ctgttaatga ttaattaaca   3060
tctgaatgta aaatgaacat taaaatgaat tactaaactt tacgtctact ttacaatcta   3120
taaactttgt ttaatcatat aacgaaatac actaatacac aatcctgtac gtatgtaata   3180
cttttatcca tcaaggattg agaaaaaaaa gtaatgattc cctgggccat taaaacttag   3240
acccccaagc ttggataggt cactctctat tttcgtttct cccttccctg atagaagggt   3300
gatatgtaat taagaataat atataatttt ataataaaag aattcgccct tacatatgat   3360
aacttcgtat aatgtatgct atacgaagtt atcatagcct catgaaatca gccatttgct   3420
tttgttcaac gatcttttga aattgttgtt gttcttggta gttaagttga tccatcttgg   3480
cttatgttgt gtgtatgttg tagttattct tagtatattc ctgtcctgag tttagtgaaa   3540
```

```
cataatatcg ccttgaaatg aaaatgctga aattcgtcga catacaattt ttcaaacttt   3600
tttttttct tggtgcacgg acatgttttt aaaggaagta ctctatacca gttattcttc   3660
acaaatttaa ttgctggaga atagatcttc aacgctttaa taaagtagtt tgtttgtcaa   3720
ggatggcgtc atacaaagaa agatcagaat cacacacttc ccctgttgct aggagacttt   3780
tctccatcat ggaggaaaag aagtctaacc tttgtgcatc attggatatt actgaaactg   3840
aaaagcttct ctctattttg gacactattg gtccttacat ctgtctagtt aaaacacaca   3900
tcgatattgt ttctgatttt acgtatgaag gaactgtgtt gcctttgaag gagcttgcca   3960
agaaacataa ttttatgatt tttgaagata gaaaatttgc tgatattggt aacactgtta   4020
aaaatcaata taaatctggt gtcttccgta ttgccgaatg ggctgacatc actaatgcac   4080
atggtgtaac gggtgcaggt attgtttctg gcttgaagga ggcagcccaa gaaacaacca   4140
gtgaacctag aggtttgcta atgcttgctg agttatcatc aaagggttct ttagcatatg   4200
gtgaatatac agaaaaaaca gtagaaattg ctaaatctga taaagagttt gtcattggtt   4260
ttattgcgca acacgatatg ggcggtagag aagaaggttt tgactggatc attatgactc   4320
caggggttgg tttagatgac aaaggtgatg cacttggtca acaatataga actgttgatg   4380
aagttgtaaa gactggaacg gatatcataa ttgttggtag aggtttgtac ggtcaaggaa   4440
gagatcctat agagcaagct aaaagatacc aacaagctgg ttggaatgct tatttaaaca   4500
gatttaaatg attcttacac aaagatttga tacatgtaca ctagtttaaa taagcatgaa   4560
aagaattaca caagcaaaaa aaaaaaaata aatgaggtac tttacgttca cctacaacca   4620
aaaaaactag atagagtaaa atcttaagat ttagaaaaag ttgtttaaca aaggctttag   4680
tatgtgaatt tttaatgtag caaagcgata actaataaac ataaacaaaa gtatggtttt   4740
ctttatcagt caaatcatta tcgattgatt gttccgcgta tctgcagata acttcgtata   4800
atgtatgcta tacgaagtta tagatccgcg gccgcgtgta aatatctacg tgtttagcat   4860
ttcctatata catgactgtg tgtcctctgg ttttcatttc gtttggttct cattcctctt   4920
ggcagcttca ctaaacaact ggtcgtgttg ttcgtcgtgt tttgccttga agaatgtata   4980
gtgcaacaca acgtcttcga tgtttctcat tgccggatct ctggaaaact ctggatcgat   5040
aaagaaaaac aagggcatat caacctcctc acccttggcc aaccgctgct cttcaaagca   5100
gaaacactgg atcttgttga agtaaggcgc tacatgatcg ggagtcactg agtatgtggc   5160
catgccagta atgtccttgt cacttatatt cttggctttg tagaaggcca aggcagtctc   5220
tccggggaca acataaactt ctctttgttg cggtacaaac ttccatggta acgcaccact   5280
tgtctccgcc gtaaaggata cccgcagtct tctctctgta gctactggag ttagcttgtc   5340
cctcgtgaac ctgctcttgt cggtgattgg tgtaccaccc catccagtac gttgacaaat   5400
tgcacgatac aaggggacac tcgcatacga taatgcaagg aaaatcatca tcatggataa   5460
cgaataataa atggtggttt gcctctcata cctcttcttt tctccatggt acttatctct   5520
caatgcttgg aactctgcca aagacatctt tggaagctcc ttccggtttg ctcgtggtga   5580
tacctgatgt tctgatgacc caccaccagg aacttcgtat tttgcaatac aactggcatg   5640
tacatatctc ctatggaggg caagtccggg aatcagccca acatcccgaa ggggcgcttg   5700
tatactagtt ctgaaaatcc gccttaacat caccgtacag agacaccttc accaatatgt   5760
tctccaagac catggggcac tagaagttat ccattgacgt tcatcaacct agtgatgtca   5820
aatttcatcg ccgtttccca actcgcggga tttgcttttg agcatctcgt ttgattcacg   5880
```

acaacttgtt ctacattctg ctgcgggcc 5909

<210> SEQ ID NO 42
<211> LENGTH: 438
<212> TYPE: PRT
<213> ORGANISM: Bacteroides thetaiotaomicron VPI-5482

<400> SEQUENCE: 42

```
Met Ala Thr Lys Glu Phe Phe Pro Gly Ile Glu Lys Ile Lys Phe Glu
1               5                   10                  15

Gly Lys Asp Ser Lys Asn Pro Met Ala Phe Arg Tyr Tyr Asp Ala Glu
            20                  25                  30

Lys Val Ile Asn Gly Lys Lys Met Lys Asp Trp Leu Arg Phe Ala Met
        35                  40                  45

Ala Trp Trp His Thr Leu Cys Ala Glu Gly Gly Asp Gln Phe Gly Gly
    50                  55                  60

Gly Thr Lys Gln Phe Pro Trp Asn Gly Asn Ala Asp Ala Ile Gln Ala
65                  70                  75                  80

Ala Lys Asp Lys Met Asp Ala Gly Phe Glu Phe Met Gln Lys Met Gly
                85                  90                  95

Ile Glu Tyr Tyr Cys Phe His Asp Val Asp Leu Val Ser Glu Gly Ala
            100                 105                 110

Ser Val Glu Glu Tyr Glu Ala Asn Leu Lys Glu Ile Val Ala Tyr Ala
        115                 120                 125

Lys Gln Lys Gln Ala Glu Thr Gly Ile Lys Leu Leu Trp Gly Thr Ala
    130                 135                 140

Asn Val Phe Gly His Ala Arg Tyr Met Asn Gly Ala Ala Thr Asn Pro
145                 150                 155                 160

Asp Phe Asp Val Val Ala Arg Ala Ala Val Gln Ile Lys Asn Ala Ile
                165                 170                 175

Asp Ala Thr Ile Glu Leu Gly Gly Glu Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Leu Ala Gln Met Leu Thr Ile Ala Arg Asp Tyr Ala Arg Ala
    210                 215                 220

Arg Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Gly Leu Asp Lys Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Gly Met Leu Gly Ser Ile Asp Ala Asn Arg Gly Asp Tyr
    290                 295                 300

Gln Asn Gly Trp Asp Thr Asp Gln Phe Pro Ile Asp Asn Tyr Glu Leu
305                 310                 315                 320

Thr Gln Ala Met Met Gln Ile Ile Arg Asn Gly Gly Leu Gly Thr Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Ala Gly Met Asp Ala Met Ala Arg Ala
        355                 360                 365
```

```
Leu Glu Ser Ala Ala Ala Leu Leu Asp Glu Ser Pro Tyr Lys Lys Met
    370                 375                 380

Leu Ala Asp Arg Tyr Ala Ser Phe Asp Gly Gly Lys Gly Lys Glu Phe
385                 390                 395                 400

Glu Asp Gly Lys Leu Thr Leu Glu Asp Val Val Ala Tyr Ala Lys Thr
                405                 410                 415

Lys Gly Glu Pro Lys Gln Thr Ser Gly Lys Gln Glu Leu Tyr Glu Ala
            420                 425                 430

Ile Leu Asn Met Tyr Cys
        435


<210> SEQ ID NO 43
<211> LENGTH: 7346
<212> TYPE: DNA
<213> ORGANISM: Artificial Sequence
<220> FEATURE:
<223> OTHER INFORMATION: BtXI-PDC-CYB2A-loxP-XDH integration fragment

<400> SEQUENCE: 43

ctgcttgtgc aggtgcaacc gagtcgtttg ttgttgtccc ctttgagttg gtgaagatcc      60

ggttacagga taagtccaag gcgtccatgt atagcggtcc cattgatgtt ctaatgaaga     120

cagtcaaaaa tgaaggtatc ttggccttgt ataacggatt agaggcaaca ctgtggagac     180

atattgtatg gaatgccggc tattttggtg tgattttcca agttcgtgac atgttaccca     240

aggcaaagga caagacccag aaaaccatca acgatttggt gggtggtatg attggtggta     300

tcgttggtac tgccttgaac attccattcg atgttgtcaa atccagaatc caaagtgcaa     360

ccattatgga aggtcaggtc cgtaaataca attggacttg gccctctctt ggcattgtct     420

tgagggaaga aggtgtctct gcattgtata aaggattcct tccaaaagtc ctgagattgg     480

gtccaggtgg tggtattcta cttgttgtct tcacaaactg tatggacttc tttagaggcc     540

aatactatgg agacaagaaa tagtagctgg gttcttcacc atcaggttta tacaccctcc     600

acgacgtcca ttctatacta tactatgcta ttcgatgcta ttcgatgcta tcctgcccta     660

tcttatctaa tcttatctta tcttacaaaa ttatatactt tccttgtttc tttcacctcc     720

tcctttatag atcaattgat ttgataatac acttatacac attgacgtct gttgatatct     780

tcatacaaaa aaccttaaaa catagtgcaa agtcacgtgc acgccttaaa aatgcagctg     840

agcccctttc ccacttctct cccttcggat gccccacctg actattttca cttcccaatt     900

cgagcatcct cctccagtcc ccgcagactc aagagataag aaaccttaca gagactgttc     960

ccatcctcct atgctcaacg tgtcctgtat ctacattgcg gccgcggatc cctcgaggag    1020

tccatcggtt cctgtcagat gggatactct tgacgtggaa aattcaaaca gaaaaaaaac    1080

cccaataatg aaaaataaca ctacgttata tccgtggtat cctctatcgt atcgtatcgt    1140

agcgtatcgt agcgtaccgt atcacagtat agtctaatat tccgtatctt attgtatcct    1200

atcctattcg atcctattgt atttcagtgc accattttaa tttctattgc tataatgtcc    1260

ttattagttg ccactgtgag gtgaccaatg gacgagggcg agccgttcag aagccgcgaa    1320

gggtgttctt cccatgaatt tcttaaggag ggcggctcag ctccgagagt gaggcgagac    1380

gtctcggtca gcgtatcccc cttcctcggc ttttacaaat gatgcgctct taatagtgtg    1440

tcgttatcct tttggcattg acgggggagg gaaattgatt gagcgcatcc atatttttgc    1500

ggactgctga ggacaatggt ggtttttccg ggtggcgtgg gctacaaatg atacgatggt    1560

tttttctttt tcggagaagg cgtataaaaa ggacacggag aacccattta ttctaaaaac    1620
```

agttgagctt ctttaattat tttttgatat aatattctat tattatatat tttcttccca 1680
ataaaacaaa ataaaacaaa acacagcaaa acacaaaaat tctagaaaat atggctacta 1740
aagaattttt cccaggtatt gaaaagatta aatttgaagg taaagactcc aaaaatccaa 1800
tggcttttag atattacgac gcagaaaagg ttattaacgg taaaaaaatg aaggactggt 1860
tgagatttgc tatggcatgg tggcacaccc tatgtgctga aggtggtgat caattcggtg 1920
gtggtacaaa acaatttcct tggaacggta acgctgacgc tattcaagct gcaaaggaca 1980
agatggacgc cggtttcgaa tttatgcaaa agatgggtat tgaatactac tgttttcacg 2040
atgttgattt ggtctctgaa ggtgcatctg ttgaagaata tgaagctaac ttgaaggaaa 2100
tcgttgctta cgctaagcaa aagcaagctg agacaggtat taaattgttg tggggtacag 2160
caaacgtttt cggtcacgcc agatatatga atggtgctgc aactaaccca gatttcgatg 2220
ttgttgcaag agccgcagtt caaatcaaaa acgctattga cgctacaatc gaactaggtg 2280
gtgaaaacta tgtttttgg ggtggtagag aaggttacat gtctttgttg aacactgacc 2340
aaaaaagaga aaaggaacac ttggcccaaa tgttgactat cgctagagat tacgctagag 2400
ctagaggttt taaaggtact tttttgattg aaccaaaacc aatggaacca actaagcacc 2460
aatatgacgt tgatactgaa actgttattg gtttcttgaa ggcacacggt ttggataagg 2520
attttaaggt gaatatcgaa gttaaccacg ctactttggc cggtcatact ttcgaacatg 2580
aattggctgt tgctgtggat aacggtatgt tgggttctat tgacgcaaac agaggtgact 2640
atcaaaatgg ttgggacact gatcaatttc caattgacaa ctatgaattg acacaagcaa 2700
tgatgcaaat tattagaaac ggtggtttgg gtactggtgg tactaacttc gacgctaaga 2760
ctagaagaaa ttccacagat ttggaagaca tttttatcgc tcacatcgct ggtatggacg 2820
ctatggccag agctttggaa tccgctgctg ctttgttgga cgaatcccca tacaagaaaa 2880
tgttggccga cagatacgct tctttcgacg gtggtaaggg taaggaattt gaggacggta 2940
agttgacatt ggaagatgtt gttgcttacg ctaagactaa gggtgaacca aagcaaacat 3000
ccggtaagca agaattgtac gaagctattc taaatatgta ctgttaatga ttaattaaca 3060
tctgaatgta aaatgaacat taaaatgaat tactaaactt tacgtctact ttacaatcta 3120
taaactttgt ttaatcatat aacgaaatac actaatacac aatcctgtac gtatgtaata 3180
cttttatcca tcaaggattg agaaaaaaaa gtaatgattc cctgggccat taaaacttag 3240
acccccaagc ttggataggt cactctctat tttcgtttct cccttccctg atagaagggt 3300
gatatgtaat taagaataat atataatttt ataataaaag aattcgccct tacatatgat 3360
aacttcgtat aatgtatgct atacgaagtt atgttggtgg tgtgttttgt tggaacgtac 3420
attagatgca taatgcgtga caccgccatg atggttgtat tctaccaatg agacatggcc 3480
gctgatcctg ttgtgtgggt catgggacat cacctcttgg gggggattct cctataattg 3540
gcaccgtgta tgcctcaacc actaacttcc accctataac tgaatatatt acataagcaa 3600
atctactttt tgtttgtgtt gatcgccatc gttgaaattc gcgcaacttc tggtggctca 3660
acgctgctgt tctatcggta tcctaagaga tgtctttgcc ctgagtctag ggtaaactat 3720
ccaccttcgt tgctgtttga ctagacagct actaacttta cggtagtaaa tgaataacgg 3780
ctcgctctca tgatcacttc tctacatcac cctaacaagt gtattatttt tttttcaggt 3840
gggtgttgct gttggtgcta gccttagtgc cctcgttaat agttgaacaa acactggcat 3900
ttggagtata atgaaaaggg atcactaccc cccgcttcct gttccgcttc tcccttccgg 3960
aaaaaccacc caccctttct ttccccccac taatgtatga atttttccgt tcccagggga 4020

-continued atggcccact tggttctctg ttaacccaca caattttgac gcatcccaca caccttttt 4080 ttttctaccc cacactttcc cttgaaaaat ctccaatttg aactggcaat tttcaccccc 4140
caccacttgc attcattagt gagtcaatcc atcccgcggt cggagattcg gaatccacct 4200
actggtaatc tgtaatctat attcccgctg accctttata aatgaactat tgtcgtcaat 4260
tgcggtagtg ctccaacaaa ttgtaaggac cttctttaac cttttcgatt caatccatct 4320
ccacataaac ctagttgcac acaatgttac tcagatcact aaactcttct gctcgttgtg 4380
tcaaacaaac aaccagaaca aaggttaggt atctcagcca cgtcagtggt gcaagcatgg 4440
cgaaacctac attgaagaac aactcgagag aatccaacaa atccagaaac tatctaattg 4500
ctgctgtgac agcattggct gtatcaacct caattggagt tgccgtacat gtgaaggacc 4560
ccttgtataa cgatgctacc ggcagtgatt ctccgagaag tatatctgtt gacgagtttg 4620
tcaagcataa ttcacaaaac gactgttgga ttgcaatcaa tggcaaggtt tatgatttca 4680
ctgattttat tccaaaccat ccaggtgggg tacctccatt agttaatcat gctggttatg 4740
atggtactaa actttatgag aaattgcatc caaaaggtac aattgagaaa ttcttgccaa 4800
aggataagtt tctgggtgtg ttagatggtg aagcgccaaa attggaagca gactatttgg 4860
tggacgatga tgaacaagag agactggatt atttgaacaa cttacctcct ttgtcatcta 4920
ttcagaatgt ttatgatttc gaatacttgg ccaagaagat tttacctaaa gatgcctggg 4980
catattattc ttgtggtgcc gatgatgaaa tcacaatgag agaaaaccat tatgcttatc 5040
aaagagttta tttcagacca agaatttgtg ttgatgtcaa ggaagttgat acttcttatg 5100
aaatgttagg cactaaaacc tctgttcctt tttatgtatc tgccaccgct ttggctaaat 5160
taggccatcc tgatggtgaa tgctcaattg ctagaggcgc tggtaaggaa ggtgtcgttc 5220
aaatgatttc gaccctttcc tcaatgtcat tagatgaaat tgccgctgct agaatcccag 5280
gtgcaaccca atggttccaa ttatacatta atgaggatag aaatgtcgct aaaggtctgg 5340
tcaaacatgc agaagacttg ggtatgaagg ctatctttat aactgttgat gctccttctc 5400
taggtaacag agaaaaggat aaaagattaa agtttgttaa tgacaccgat gtcgatttgg 5460
gtgattccgc agatcgaaac agtggtgctt caaaggcact atcttcgttc attgatgctt 5520
ctgtctcttg gaatgacgtc aaagcggtca agtcgtggac taaattgcct gtcttagtta 5580
aaggtgttca aacagttgaa gacgttattg aagcttacga tgctggttgt caaggtgttg 5640
ttttgtcaaa ccacggtggt aggcaactag atactgctcc tcctccaatc gaattattag 5700
ctgaaactgt tccaactttg aagagattgg gtaaattaag accagatttt gaaattttaa 5760
ttgacggtgg tgtcaaaaga ggtaccgata ttttgaaagc agtcgcaatc ggtggccaag 5820
atgtcagagt ttcagttggt atgggtagac ctttcttata tgccaactct tgctatggtg 5880
aagcaggtgt tagaaaatta attcaaaatc taaaggatga attagaaatg gatatgagat 5940
tgttgggtgt cactaaaatg gaccagctat cttcgaaaca tgtcgatact aaacgtttga 6000
ttggtagaga tgcgatcaac tatttgtatg ataatgtata cagcccaatc gaaaccgtta 6060
aattcaacaa tgaagattga ttgttggaaa tatattattc ataaaggcga aaacattccc 6120
ttggtatttt attccaaatt tatgatacat agacgtattt tttatatata aagttatatt 6180
attaatgatt caagaaaaag ttcaaataaa ctaatggatc aaccataact tcgtataatg 6240
tatgctatac gaagttatag atccgcggcc gcgtgtaaat atctacgtgt ttagcatttc 6300
ctatatacat gactgtgtgt cctctggttt tcatttcgtt tggttctcat tcctcttggc 6360

```
agcttcacta aacaactggt cgtgttgttc gtcgtgtttt gccttgaaga atgtatagtg   6420
caacacaacg tcttcgatgt ttctcattgc cggatctctg gaaaactctg gatcgataaa   6480
gaaaaacaag ggcatatcaa cctcctcacc cttggccaac cgctgctctt caaagcagaa   6540
acactggatc ttgttgaagt aaggcgctac atgatcggga gtcactgagt atgtggccat   6600
gccagtaatg tccttgtcac ttatattctt ggctttgtag aaggccaagg cagtctctcc   6660
ggggacaaca taaacttctc tttgttgcgg tacaaacttc catggtaacg caccacttgt   6720
ctccgccgta aaggataccc gcagtcttct ctctgtagct actggagtta gcttgtccct   6780
cgtgaacctg ctcttgtcgg tgattggtgt accaccccat ccagtacgtt gacaaattgc   6840
acgatacaag ggacactcg catacgataa tgcaaggaaa atcatcatca tggataacga   6900
ataataaatg gtggtttgcc tctcatacct cttcttttct ccatggtact tatctctcaa   6960
tgcttggaac tctgccaaag acatctttgg aagctccttc cggtttgctc gtggtgatac   7020
ctgatgttct gatgacccac caccaggaac ttcgtatttt gcaatacaac tggcatgtac   7080
atatctccta tggagggcaa gtccgggaat cagcccaaca tcccgaaggg gcgcttgtat   7140
actagttctg aaaatccgcc ttaacatcac cgtacagaga caccttcacc aatatgttct   7200
ccaagaccat ggggcactag aagttatcca ttgacgttca tcaacctagt gatgtcaaat   7260
ttcatcgccg tttcccaact cgcgggattt gcttttgagc atctcgtttg attcacgaca   7320
acttgttcta cattctgctg cgggcc                                        7346
```

```
<210> SEQ ID NO 44
<211> LENGTH: 3821
<212> TYPE: DNA
<213> ORGANISM: Artificial Sequence
<220> FEATURE:
<223> OTHER INFORMATION: IoURA3-ODD-XDH integration fragment

<400> SEQUENCE: 44
```

```
ctgcttgtgc aggtgcaacc gagtcgtttg ttgttgtccc ctttgagttg gtgaagatcc     60
ggttacagga taagtccaag gcgtccatgt atagcggtcc cattgatgtt ctaatgaaga    120
cagtcaaaaa tgaaggtatc ttggccttgt ataacggatt agaggcaaca ctgtggagac    180
atattgtatg gaatgccggc tattttggtg tgattttcca agttcgtgac atgttaccca    240
aggcaaagga caagacccag aaaaccatca acgatttggt gggtggtatg attggtggta    300
tcgttggtac tgccttgaac attccattcg atgttgtcaa atccagaatc caaagtgcaa    360
ccattatgga aggtcaggtc cgtaaataca attggacttg gccctctctt ggcattgtct    420
tgagggaaga aggtgtctct gcattgtata aaggattcct tccaaaagtc ctgagattgg    480
gtccaggtgg tggtattcta cttgttgtct tcacaaactg tatggacttc tttagaggcc    540
aatactatgg agacaagaaa tagtagctgg gttcttcacc atcaggttta tacaccctcc    600
acgacgtcca ttctatacta tactatgcta ttcgatgcta ttcgatgcta tcctgcccta    660
tcttatctaa tcttatctta tcttacaaaa ttatatactt tccttgtttc tttcacctcc    720
tcctttatag atcaattgat ttgataatac acttatacac attgacgtct gttgatatct    780
tcatacaaaa aaccttaaaa catagtgcaa agtcacgtgc acgccttaaa aatgcagctg    840
agcccctttc ccacttctct cccttcggat gccccacctg actattttca cttcccaatt    900
cgagcatcct cctccagtcc ccgcagactc aagagataag aaaccttaca gagactgttc    960
ccatcctcct atgctcaacg tgtcctgtat ctacattgcg gccgcggatc cagatccccc   1020
ggggcgttga agatctattc tccagcaatt aaatttgtga agaataactg gtatagagta   1080
```

```
cttcctttaa aaacatgtcc gtgcaccaag aaaaaaaaaa agtttgaaaa attgtatgtc   1140
gacgaatttc agcattttca tttcaaggcg atattatgtt tcactaaact caggacagga   1200
atatactaag aataactaca acatacacac aacataagcc aagatggatc aacttaacta   1260
ccaagaacaa caacaatttc aaaagatcgt tgaacaaaag caaatggctg atttcatgag   1320
gctatctgca gatacgcgga acaatcaatc gataatgatt tgactgataa agaaaaccat   1380
acttttgttt atgtttatta gttatcgctt tgctacatta aaaattcaca tactaaagcc   1440
tttgttaaac aactttttct aaatcttaag attttactct atctagtttt tttggttgta   1500
ggtgaacgta aagtacctca tttatttttt tttttttgct tgtgtaattc ttttcatgct   1560
tatttaaact agtgtacatg tatcaaatct ttgtgtaaga atcatttaaa tctgtttaaa   1620
taagcattcc aaccagcttg ttggtatctt ttagcttgct ctataggatc tcttccttga   1680
ccgtacaaac ctctaccaac aattatgata tccgttccag tctttacaac ttcatcaaca   1740
gttctatatt gttgaccaag tgcatcacct ttgtcatcta aaccaacccc tggagtcata   1800
atgatccagt caaaaccttc ttctctaccg cccatatcgt gttgcgcaat aaaaccaatg   1860
acaaactctt tatcagattt agcaatttct actgtttttt ctgtatattc accatatgct   1920
aaagaaccct ttgatgataa ctcagcaagc attagcaaac ctctaggttc actggttgtt   1980
tcttgggctg cctccttcaa gccagaaaca atacctgcac ccgttacacc atgtgcatta   2040
gtgatgtcag cccattcggc aatacggaag acaccagatt tatattgatt tttaacagtg   2100
ttaccaatat cagcaaattt tctatcttca aaaatcataa aattatgttt cttggcaagc   2160
tccttcaaag gcaacacagt tccttcatac gtaaaatcag aaacaatatc gatgtgtgtt   2220
ttaactagac agatgtaagg accaatagtg tccaaaatag agagaagctt ttcagtttca   2280
gtaatatcca atgatgcaca aaggttagac ttcttttcct ccatgatgga gaaaagtctc   2340
ctagcaacag gggaagtgtg tgattctgat ctttctttgt atgacgccat ccttgacaaa   2400
caaactactt tattaaagcg ttgaagatct attctccagc aattaaattt gtgaagaata   2460
actggtatag agtacttcct ttaaaaacat gtccgtgcac caagaaaaaa aaaaagtttg   2520
aaaaattgta tgtcgacgaa tttcagcatt ttcatttcaa ggcgatatta tgtttcacta   2580
aactcaggac aggaatatac taagaataac tacaacatac acacaacata agccaagatg   2640
gatcaactta actaccaaga acaacaacaa tttcaaaaga tcgttgaaca aaagcaaatg   2700
gctgatttca tgaggctatg aattcgcctc gagggatccg cggccgcgtg taaatatcta   2760
cgtgtttagc atttcctata tacatgactg tgtgtcctct ggttttcatt tcgtttggtt   2820
ctcattcctc ttggcagctt cactaaacaa ctggtcgtgt tgttcgtcgt gttttgcctt   2880
gaagaatgta tagtgcaaca caacgtcttc gatgtttctc attgccggat ctctggaaaa   2940
ctctggatcg ataaagaaaa acaagggcat atcaacctcc tcacccttgg ccaaccgctg   3000
ctcttcaaag cagaaacact ggatcttgtt gaagtaaggc gctacatgat cgggagtcac   3060
tgagtatgtg gccatgccag taatgtcctt gtcacttata ttcttggctt tgtagaaggc   3120
caaggcagtc tctccgggga caacataaac ttctctttgt tgcggtacaa acttccatgg   3180
taacgcacca cttgtctccg ccgtaaagga tacccgcagt cttctctctg tagctactgg   3240
agttagcttg tccctcgtga acctgctctt gtcggtgatt ggtgtaccac cccatccagt   3300
acgttgacaa attgcacgat acaaggggac actcgcatac gataatgcaa ggaaaatcat   3360
catcatggat aacgaataat aaatggtggt ttgcctctca tacctcttct tttctccatg   3420
```

```
gtacttatct ctcaatgctt ggaactctgc caaagacatc tttggaagct ccttccggtt   3480

tgctcgtggt gatacctgat gttctgatga cccaccacca ggaacttcgt attttgcaat   3540

acaactggca tgtacatatc tcctatggag ggcaagtccg ggaatcagcc caacatcccg   3600

aaggggcgct tgtatactag ttctgaaaat ccgccttaac atcaccgtac agagacacct   3660

tcaccaatat gttctccaag accatggggc actagaagtt atccattgac gttcatcaac   3720

ctagtgatgt caaatttcat cgccgtttcc caactcgcgg gatttgcttt tgagcatctc   3780

gtttgattca cgacaacttg ttctacattc tgctgcgggc c                         3821
```

```
<210> SEQ ID NO 45
<211> LENGTH: 5908
<212> TYPE: DNA
<213> ORGANISM: Artificial Sequence
<220> FEATURE:
<223> OTHER INFORMATION: StXI-PDC-URA3-loxP-XDH integration fragment

<400> SEQUENCE: 45
```

```
ctgcttgtgc aggtgcaacc gagtcgtttg ttgttgtccc ctttgagttg gtgaagatcc     60

ggttacagga taagtccaag gcgtccatgt atagcggtcc cattgatgtt ctaatgaaga    120

cagtcaaaaa tgaaggtatc ttggccttgt ataacggatt agaggcaaca ctgtggagac    180

atattgtatg gaatgccggc tattttggtg tgattttcca agttcgtgac atgttaccca    240

aggcaaagga caagacccag aaaaccatca acgatttggt gggtggtatg attggtggta    300

tcgttggtac tgccttgaac attccattcg atgttgtcaa atccagaatc caaagtgcaa    360

ccattatgga aggtcaggtc cgtaaataca attggacttg gccctctctt ggcattgtct    420

tgagggaaga aggtgtctct gcattgtata aaggattcct tccaaaagtc ctgagattgg    480

gtccaggtgg tggtattcta cttgttgtct tcacaaactg tatggacttc tttagaggcc    540

aatactatgg agacaagaaa tagtagctgg gttcttcacc atcaggttta tacaccctcc    600

acgacgtcca ttctatacta tactatgcta ttcgatgcta ttcgatgcta tcctgcccta    660

tcttatctaa tcttatctta tcttacaaaa ttatatactt tccttgtttc tttcacctcc    720

tcctttatag atcaattgat ttgataatac acttatacac attgacgtct gttgatatct    780

tcatacaaaa aaccttaaaa catagtgcaa agtcacgtgc acgccttaaa aatgcagctg    840

agccccttc ccacttctct cccttcggat gccccacctg actattttca cttcccaatt    900

cgagcatcct cctccagtcc ccgcagactc aagagataag aaaccttaca gagactgttc    960

ccatcctcct atgctcaacg tgtcctgtat ctacattgcg gccgcggatc cctcgaggag   1020

tccatcggtt cctgtcagat gggatactct tgacgtggaa aattcaaaca gaaaaaaaac   1080

cccaataatg aaaaataaca ctacgttata tccgtggtat cctctatcgt atcgtatcgt   1140

agcgtatcgt agcgtaccgt atcacagtat agtctaatat tccgtatctt attgtatcct   1200

atcctattcg atcctattgt atttcagtgc accattttaa tttctattgc tataatgtcc   1260

ttattagttg ccactgtgag gtgaccaatg gacgagggcg agccgttcag aagccgcgaa   1320

gggtgttctt cccatgaatt tcttaaggag ggcggctcag ctccgagagt gaggcgagac   1380

gtctcggtca gcgtatcccc cttcctcggc ttttacaaat gatgcgctct taatagtgtg   1440

tcgttatcct tttggcattg acgggggagg gaaattgatt gagcgcatcc atatttttgc   1500

ggactgctga ggacaatggt ggtttttccg ggtggcgtgg gctacaaatg atacgatggt   1560

tttttcttt tcggagaagg cgtataaaaa ggacacggag aacccattta ttctaaaaac   1620

agttgagctt ctttaattat tttttgatat aatattctat tattatatat tttcttccca   1680
```

```
ataaaacaaa ataaaacaaa acacagcaaa acacaaaaat tctagaatga aagaatattt   1740
tccggaaata aaagaaataa agtatgaagg tcctgaatca aaaaatgtta tggctttcaa   1800
atattacaat aaagatgagg taataggcgg aaaaccgatg agagaacatc tgaaatttgc   1860
aatgagttac tggcatacat taaaagccca gggactggat atgttcggcg gggacacgat   1920
ggacagagca tggaacagat atgatgacgc attggaacag gcaaaagcaa gagcagatgc   1980
aggttttgaa tttatgcaga aaatagggat ggattatttc tgctttcatg acagagatat   2040
tataaatgaa gcaatgacat taaaagaaac aaacagactt cttgatgaaa tagtagatca   2100
cctagaaggt cttatgaaaa aaacaggaat aaaacttttg tggggaacaa caaatgcttt   2160
tagtcatccc agatttcttc acggaggagc aactgcacca aatgcagacg tatttgcgta   2220
tgctgcggca caggtaaaaa aggcaatgga gataacaaaa agattaggcg gggaaaatta   2280
tgttctctgg ggcggaagag agggctacga aactcttctg aatactaagt ctgatctgga   2340
atatgataac tttgccagat ttctgcagat ggtagtggat tacaaagaaa aaatagggtt   2400
tgaagggcag ctgcttatag aaccgaaacc aaaagaacct acaaagcacc agtatgattt   2460
tgatactgct acagttcttg gtttttttgag aaagtataat cttgataaac attataaaat   2520
gaatatagaa gcaaaccacg ccactcttgc cggacataca ttccagcatg aactgaacct   2580
tgcaagaata aataatgtaa tgggttccat agatgcaaat cagggagata tgcttctggg   2640
atgggataca gatcagtttc ctacaaatat atatgatgct gttctggcaa tgtatgaagt   2700
aataaaaaat aacggattgg gtaaaggtgg actgaatttt gacgcaaaag taagaagagg   2760
ctcatttgaa gacaaggatt tatttttagc ttatattgcg ggtatggaca cattcgcaaa   2820
aggattaaca atagcttaca gactttatga agataaagtt tttgaggatt ttcaggataa   2880
aagatatgaa agttacaaaa cagggatagg aaaagatata gtagaaggta aagtaggatt   2940
tgaagaactg gcggaatatg tagaaaatct tgctgaaata aaaaatactt cgggaagaca   3000
ggaaatgctg gaaagtatat tgaattcata tatattggaa gcaaaataat taattaacat   3060
ctgaatgtaa aatgaacatt aaaatgaatt actaaacttt acgtctactt tacaatctat   3120
aaactttgtt taatcatata acgaaataca ctaatacaca atcctgtacg tatgtaatac   3180
ttttatccat caaggattga gaaaaaaaag taatgattcc ctgggccatt aaaacttaga   3240
cccccaagct tggataggtc actctctatt ttcgtttctc ccttccctga tagaagggtg   3300
atatgtaatt aagaataata tataatttta taataaaaga attcgccctt acatatgata   3360
acttcgtata atgtatgcta tacgaagtta tcatagcctc atgaaatcag ccatttgctt   3420
ttgttcaacg atcttttgaa attgttgttg ttcttggtag ttaagttgat ccatcttggc   3480
ttatgttgtg tgtatgttgt agttattctt agtatattcc tgtcctgagt ttagtgaaac   3540
ataatatcgc cttgaaatga aaatgctgaa attcgtcgac atacaatttt tcaaactttt   3600
ttttttcttt ggtgcacgga catgttttta aaggaagtac tctataccag ttattcttca   3660
caaatttaat tgctggagaa tagatcttca acgctttaat aaagtagttt gtttgtcaag   3720
gatggcgtca tacaaagaaa gatcagaatc acacacttcc cctgttgcta ggagactttt   3780
ctccatcatg gaggaaaaga agtctaacct ttgtgcatca ttggatatta ctgaaactga   3840
aaagcttctc tctattttgg acactattgg tccttacatc tgtctagtta aaacacacat   3900
cgatattgtt tctgatttta cgtatgaagg aactgtgttg cctttgaagg agcttgccaa   3960
gaaacataat tttatgattt ttgaagatag aaaatttgct gatattggta acactgttaa   4020
```

```
aaatcaatat aaatctggtg tcttccgtat tgccgaatgg gctgacatca ctaatgcaca   4080
tggtgtaacg ggtgcaggta ttgtttctgg cttgaaggag gcagcccaag aaacaaccag   4140
tgaacctaga ggtttgctaa tgcttgctga gttatcatca aagggttctt tagcatatgg   4200
tgaatataca gaaaaaacag tagaaattgc taaatctgat aaagagtttg tcattggttt   4260
tattgcgcaa cacgatatgg gcggtagaga agaaggtttt gactggatca ttatgactcc   4320
aggggttggt ttagatgaca aaggtgatgc acttggtcaa caatatagaa ctgttgatga   4380
agttgtaaag actggaacgg atatcataat tgttggtaga ggtttgtacg gtcaaggaag   4440
agatcctata gagcaagcta aaagatacca acaagctggt tggaatgctt atttaaacag   4500
atttaaatga ttcttacaca aagatttgat acatgtacac tagtttaaat aagcatgaaa   4560
agaattacac aagcaaaaaa aaaaaaataa atgaggtact ttacgttcac ctacaaccaa   4620
aaaaactaga tagagtaaaa tcttaagatt tagaaaaagt tgtttaacaa aggctttagt   4680
atgtgaattt ttaatgtagc aaagcgataa ctaataaaca taaacaaaag tatggttttc   4740
tttatcagtc aaatcattat cgattgattg ttccgcgtat ctgcagataa cttcgtataa   4800
tgtatgctat acgaagttat agatccgcgg ccgcgtgtaa atatctacgt gtttagcatt   4860
tcctatatac atgactgtgt gtcctctggt tttcatttcg tttggttctc attcctcttg   4920
gcagcttcac taaacaactg gtcgtgttgt tcgtcgtgtt ttgccttgaa gaatgtatag   4980
tgcaacacaa cgtcttcgat gtttctcatt gccggatctc tggaaaactc tggatcgata   5040
aagaaaaaca agggcatatc aacctcctca cccttggcca accgctgctc ttcaaagcag   5100
aaacactgga tcttgttgaa gtaaggcgct acatgatcgg gagtcactga gtatgtggcc   5160
atgccagtaa tgtccttgtc acttatattc ttggctttgt agaaggccaa ggcagtctct   5220
ccggggacaa cataaacttc tctttgttgc ggtacaaact tccatggtaa cgcaccactt   5280
gtctccgccg taaaggatac ccgcagtctt ctctctgtag ctactggagt tagcttgtcc   5340
ctcgtgaacc tgctcttgtc ggtgattggt gtaccacccc atccagtacg ttgacaaatt   5400
gcacgataca aggggacact cgcatacgat aatgcaagga aaatcatcat catggataac   5460
gaataataaa tggtggtttg cctctcatac ctcttctttt ctccatggta cttatctctc   5520
aatgcttgga actctgccaa agacatcttt ggaagctcct tccggtttgc tcgtggtgat   5580
acctgatgtt ctgatgaccc accaccagga acttcgtatt ttgcaataca actggcatgt   5640
acatatctcc tatggagggc aagtccggga atcagcccaa catcccgaag ggcgcttgt    5700
atactagttc tgaaaatccg ccttaacatc accgtacaga gacaccttca ccaatatgtt   5760
ctccaagacc atggggcact agaagttatc cattgacgtt catcaaccta gtgatgtcaa   5820
atttcatcgc cgtttcccaa ctcgcgggat ttgcttttga gcatctcgtt tgattcacga   5880
caacttgttc tacattctgc tgcgggcc                                     5908
```

<210> SEQ ID NO 46
<211> LENGTH: 5908
<212> TYPE: DNA
<213> ORGANISM: StXI-PDC-URA3-loxP-XDH integration fragment

<400> SEQUENCE: 46

```
ctgcttgtgc aggtgcaacc gagtcgtttg ttgttgtccc ctttgagttg gtgaagatcc     60
ggttacagga taagtccaag gcgtccatgt atagcggtcc cattgatgtt ctaatgaaga    120
cagtcaaaaa tgaaggtatc ttggccttgt ataacggatt agaggcaaca ctgtggagac    180
atattgtatg gaatgccggc tattttggtg tgattttcca agttcgtgac atgttaccca    240
```

```
aggcaaagga caagacccag aaaaccatca acgatttggt gggtggtatg attggtggta    300
tcgttggtac tgccttgaac attccattcg atgttgtcaa atccagaatc caaagtgcaa    360
ccattatgga aggtcaggtc cgtaaataca attggacttg gccctctctt ggcattgtct    420
tgagggaaga aggtgtctct gcattgtata aaggattcct tccaaaagtc ctgagattgg    480
gtccaggtgg tggtattcta cttgttgtct tcacaaactg tatggacttc tttagaggcc    540
aatactatgg agacaagaaa tagtagctgg gttcttcacc atcaggttta tacaccctcc    600
acgacgtcca ttctatacta tactatgcta ttcgatgcta ttcgatgcta tcctgcccta    660
tcttatctaa tcttatctta tcttacaaaa ttatatactt tccttgtttc tttcacctcc    720
tcctttatag atcaattgat ttgataatac acttatacac attgacgtct gttgatatct    780
tcatacaaaa aaccttaaaa catagtgcaa agtcacgtgc acgccttaaa aatgcagctg    840
agcccctttc ccacttctct cccttcggat gccccacctg actattttca cttcccaatt    900
cgagcatcct cctccagtcc ccgcagactc aagagataag aaaccttaca gagactgttc    960
ccatcctcct atgctcaacg tgtcctgtat ctacattgcg gccgcggatc cctcgaggag   1020
tccatcggtt cctgtcagat gggatactct tgacgtggaa aattcaaaca gaaaaaaaac   1080
cccaataatg aaaaataaca ctacgttata tccgtggtat cctctatcgt atcgtatcgt   1140
agcgtatcgt agcgtaccgt atcacagtat agtctaatat tccgtatctt attgtatcct   1200
atcctattcg atcctattgt atttcagtgc accattttaa tttctattgc tataatgtcc   1260
ttattagttg ccactgtgag gtgaccaatg gacgagggcg agccgttcag aagccgcgaa   1320
gggtgttctt cccatgaatt tcttaaggag ggcggctcag ctccgagagt gaggcgagac   1380
gtctcggtca gcgtatcccc cttcctcggc ttttacaaat gatgcgctct taatagtgtg   1440
tcgttatcct tttggcattg acgggggagg gaaattgatt gagcgcatcc atatttttgc   1500
ggactgctga ggacaatggt ggtttttccg ggtggcgtgg gctacaaatg atacgatggt   1560
tttttctttt tcggagaagg cgtataaaaa ggacacggag aacccattta ttctaaaaac   1620
agttgagctt ctttaattat tttttgatat aatattctat tattatatat tttcttccca   1680
ataaaacaaa ataaaacaaa acacagcaaa acacaaaaat tctagaatga aggaatactt   1740
ccctgaaatc aaagagatca aatatgaagg tcctgaatcg aaaaatgtta tggcattcaa   1800
gtattacaac aaggacgagg tcataggagg aaaaccaatg agggaacatc ttaagtttgc   1860
catgtcatat tggcatacgc taaaggctca ggggttggat atgttcggtg gagatactat   1920
ggatcgtgca tggaacagat acgatgacgc tttggagcaa gcgaaagcca gagctgatgc   1980
cggcttcgag tttatgcaaa agattggcat ggactatttt tgttttcatg atcgtgacat   2040
tattaacgaa gctatgactt taaaggaaac gaataggtta ttggatgaaa ttgttgacca   2100
tcttgagggt ttgatgaaaa agactgggat caaattgttg tggggtacta caaatgcttt   2160
tagtcaccca agattcttac atggtggtgc taccgcaccg aatgccgacg tattcgcata   2220
cgcggcagct caagttaaaa aggctatgga gattaccaaa cggttgggtg gcgaaaacta   2280
cgtattatgg ggcggaagag aaggatatga aacattgcta aataccaaat ccgatttgga   2340
atatgacaat tttgcaagat ttctacaaat ggttgtcgat tacaaggaga aaattgggtt   2400
cgagggtcaa ctactcatag agccaaagcc aaaagagcct accaaacatc agtatgattt   2460
cgatactgca acagttttag gctttttgag gaagtacaat ttggacaagc attacaagat   2520
gaatatcgaa gcaaaccacg ccactttagc tggtcacaca tttcaacacg aactgaactt   2580
```

```
agcacgtatt aacaatgtca tgggttctat tgatgctaat caaggagata tgttactcgg   2640
ttgggataca gatcagtttc ccacaaatat ctacgacgct gttctagcga tgtatgaagt   2700
tatcaaaaac aatggcctcg ggaagggtgg tcttaatttt gatgcaaaag ttcgaagggg   2760
ttcatttgaa gataaggacc tatttcttgc atacatagcc ggaatggata cctttgcaaa   2820
aggtttaacc atagcatata gactgtatga ggataaagtg tttgaagatt tccaagacaa   2880
gagatatgaa agctataaga cgggtatagg caaagatatt gttgagggaa aagtcggatt   2940
cgaggaactg gctgaatatg tggaaaacct tgcagaaatc aaaaatacta gtggtagaca   3000
ggagatgctt gaatctattt tgaactccta tatattagaa gccaagtaat taattaacat   3060
ctgaatgtaa aatgaacatt aaaatgaatt actaaacttt acgtctactt tacaatctat   3120
aaactttgtt taatcatata acgaaataca ctaatacaca atcctgtacg tatgtaatac   3180
ttttatccat caaggattga gaaaaaaaag taatgattcc ctgggccatt aaaacttaga   3240
cccccaagct tggataggtc actctctatt ttcgtttctc ccttccctga tagaagggtg   3300
atatgtaatt aagaataata tataatttta taataaaaga attcgccctt acatatgata   3360
acttcgtata atgtatgcta tacgaagtta tcatagcctc atgaaatcag ccatttgctt   3420
ttgttcaacg atcttttgaa attgttgttg ttcttggtag ttaagttgat ccatcttggc   3480
ttatgttgtg tgtatgttgt agttattctt agtatattcc tgtcctgagt ttagtgaaac   3540
ataatatcgc cttgaaatga aaatgctgaa attcgtcgac atacaatttt tcaaactttt   3600
ttttttcttt ggtgcacgga catgttttta aaggaagtac tctataccag ttattcttca   3660
caaatttaat tgctggagaa tagatcttca acgctttaat aaagtagttt gtttgtcaag   3720
gatggcgtca tacaaagaaa gatcagaatc acacacttcc cctgttgcta ggagactttt   3780
ctccatcatg gaggaaaaga agtctaacct ttgtgcatca ttggatatta ctgaaactga   3840
aaagcttctc tctattttgg acactattgg tccttacatc tgtctagtta aaacacacat   3900
cgatattgtt tctgatttta cgtatgaagg aactgtgttg cctttgaagg agcttgccaa   3960
gaaacataat tttatgattt ttgaagatag aaaatttgct gatattggta acactgttaa   4020
aaatcaatat aaatctggtg tcttccgtat tgccgaatgg gctgacatca ctaatgcaca   4080
tggtgtaacg ggtgcaggta ttgtttctgg cttgaaggag gcagcccaag aaacaaccag   4140
tgaacctaga ggtttgctaa tgcttgctga gttatcatca aagggttctt tagcatatgg   4200
tgaatataca gaaaaaacag tagaaattgc taaatctgat aaagagtttg tcattggttt   4260
tattgcgcaa cacgatatgg gcggtagaga agaaggtttt gactggatca ttatgactcc   4320
aggggttggt ttagatgaca aaggtgatgc acttggtcaa caatatagaa ctgttgatga   4380
agttgtaaag actggaacgg atatcataat tgttggtaga ggtttgtacg gtcaaggaag   4440
agatcctata gagcaagcta aaagatacca acaagctggt tggaatgctt atttaaacag   4500
atttaaatga ttcttacaca aagatttgat acatgtacac tagtttaaat aagcatgaaa   4560
agaattacac aagcaaaaaa aaaaaaataa atgaggtact ttacgttcac ctacaaccaa   4620
aaaaactaga tagagtaaaa tcttaagatt tagaaaaagt tgtttaacaa aggctttagt   4680
atgtgaattt ttaatgtagc aaagcgataa ctaataaaca taaacaaaag tatggttttc   4740
tttatcagtc aaatcattat cgattgattg ttccgcgtat ctgcagataa cttcgtataa   4800
tgtatgctat acgaagttat agatccgcgg ccgcgtgtaa atatctacgt gtttagcatt   4860
tcctatatac atgactgtgt gtcctctggt tttcatttcg tttggttctc attcctcttg   4920
gcagcttcac taaacaactg gtcgtgttgt tcgtcgtgtt ttgccttgaa gaatgtatag   4980
```

```
tgcaacacaa cgtcttcgat gtttctcatt gccggatctc tggaaaactc tggatcgata   5040

aagaaaaaca agggcatatc aacctcctca cccttggcca accgctgctc ttcaaagcag   5100

aaacactgga tcttgttgaa gtaaggcgct acatgatcgg gagtcactga gtatgtggcc   5160

atgccagtaa tgtccttgtc acttatattc ttggctttgt agaaggccaa ggcagtctct   5220

ccggggacaa cataaacttc tctttgttgc ggtacaaact tccatggtaa cgcaccactt   5280

gtctccgccg taaaggatac ccgcagtctt ctctctgtag ctactggagt tagcttgtcc   5340

ctcgtgaacc tgctcttgtc ggtgattggt gtaccacccc atccagtacg ttgacaaatt   5400

gcacgataca aggggacact cgcatacgat aatgcaagga aaatcatcat catggataac   5460

gaataataaa tggtggtttg cctctcatac ctcttctttt ctccatggta cttatctctc   5520

aatgcttgga actctgccaa agacatcttt ggaagctcct tccggtttgc tcgtggtgat   5580

acctgatgtt ctgatgaccc accaccagga acttcgtatt ttgcaataca actggcatgt   5640

acatatctcc tatggagggc aagtccggga atcagcccaa catcccgaag ggcgcttgt    5700

atactagttc tgaaaatccg ccttaacatc accgtacaga gacaccttca ccaatatgtt   5760

ctccaagacc atggggcact agaagttatc cattgacgtt catcaaccta gtgatgtcaa   5820

atttcatcgc cgtttcccaa ctcgcgggat ttgcttttga gcatctcgtt tgattcacga   5880

caacttgttc tacattctgc tgcgggcc                                      5908
```

<210> SEQ ID NO 47
<211> LENGTH: 5908
<212> TYPE: DNA
<213> ORGANISM: Artificial Sequence
<220> FEATURE:
<223> OTHER INFORMATION: StXI-PDC-URA3-loxP-XDH integration fragment

<400> SEQUENCE: 47

```
ctgcttgtgc aggtgcaacc gagtcgtttg ttgttgtccc ctttgagttg gtgaagatcc     60

ggttacagga taagtccaag gcgtccatgt atagcggtcc cattgatgtt ctaatgaaga    120

cagtcaaaaa tgaaggtatc ttggccttgt ataacggatt agaggcaaca ctgtggagac    180

atattgtatg gaatgccggc tattttggtg tgattttcca agttcgtgac atgttaccca    240

aggcaaagga caagacccag aaaaccatca acgatttggt gggtggtatg attggtggta    300

tcgttggtac tgccttgaac attccattcg atgttgtcaa atccagaatc caaagtgcaa    360

ccattatgga aggtcaggtc cgtaaataca attggacttg gccctctctt ggcattgtct    420

tgagggaaga aggtgtctct gcattgtata aaggattcct tccaaaagtc ctgagattgg    480

gtccaggtgg tggtattcta cttgttgtct tcacaaactg tatggacttc tttagaggcc    540

aatactatgg agacaagaaa tagtagctgg gttcttcacc atcaggttta tacaccctcc    600

acgacgtcca ttctatacta tactatgcta ttcgatgcta ttcgatgcta tcctgcccta    660

tcttatctaa tcttatctta tcttacaaaa ttatatactt tccttgtttc tttcacctcc    720

tcctttatag atcaattgat ttgataatac acttatacac attgacgtct gttgatatct    780

tcatacaaaa aaccttaaaa catagtgcaa agtcacgtgc acgccttaaa aatgcagctg    840

agccccttc ccacttctct cccttcggat gccccacctg actattttca cttcccaatt    900

cgagcatcct cctccagtcc ccgcagactc aagagataag aaaccttaca gagactgttc    960

ccatcctcct atgctcaacg tgtcctgtat ctacattgcg gccgcggatc cctcgaggag   1020

tccatcggtt cctgtcagat gggatactct tgacgtggaa aattcaaaca gaaaaaaaac   1080
```

```
cccaataatg aaaaataaca ctacgttata tccgtggtat cctctatcgt atcgtatcgt   1140
agcgtatcgt agcgtaccgt atcacagtat agtctaatat tccgtatctt attgtatcct   1200
atcctattcg atcctattgt atttcagtgc accattttaa tttctattgc tataatgtcc   1260
ttattagttg ccactgtgag gtgaccaatg gacgagggcg agccgttcag aagccgcgaa   1320
gggtgttctt cccatgaatt tcttaaggag ggcggctcag ctccgagagt gaggcgagac   1380
gtctcggtca gcgtatcccc cttcctcggc ttttacaaat gatgcgctct taatagtgtg   1440
tcgttatcct tttggcattg acgggggagg gaaattgatt gagcgcatcc atatttttgc   1500
ggactgctga ggacaatggt ggtttttccg ggtggcgtgg gctacaaatg atacgatggt   1560
tttttctttt tcggagaagg cgtataaaaa ggacacggag aacccattta ttctaaaaac   1620
agttgagctt ctttaattat tttttgatat aatattctat tattatatat tttcttccca   1680
ataaaacaaa ataaaacaaa acacagcaaa acacaaaaat tctagaatga aggaatactt   1740
ccccgaaatc aaagagatca aatatgaagg tccagagtcc aaaaatgtca tggcattcaa   1800
gtactataac aaggatgaag tcattggtgg aaaacctatg agggagcatc taaaattcgc   1860
aatgtcttac tggcatacac ttaaagcaca gggactggat atgtttggag gcgatacgat   1920
ggatcgagcc tggaatagat acgatgatgc cctagaacaa gccaaagcta gagcagatgc   1980
tggatttgag tttatgcaaa agatcggaat ggactatttc tgttttcacg accgtgacat   2040
tatcaatgag gctatgactt tgaaggaaac gaacagattg ttagatgaaa ttgtggacca   2100
cttggaagga ttgatgaaaa agactggtat taagttactt tggggcacta caaatgcctt   2160
ttcacatccg agatttctcc atggtggcgc aacagctcca aatgctgatg tgtttgcata   2220
tgctgcggca caagtcaaaa aggctatgga aattactaag aggcttggtg gagagaatta   2280
cgtattatgg ggtggtagag aaggctatga gactttgcta aataccaagt ctgacttaga   2340
atatgacaat tttgcaagat ttttgcaaat ggttgttgac tataaggaaa agattggatt   2400
cgaaggtcaa ctattgatag aaccaaaacc taaagagcca accaaacatc aatatgactt   2460
cgacactgca acagtactgg ggttcttgag gaagtacaac ctcgataagc actataagat   2520
gaatatcgaa gctaatcatg ctacattggc cggtcataca tttcaacacg agcttaatct   2580
cgcacgtatt aacaacgtta tgggttcgat agatgcaaac cagggcgata tgttattagg   2640
ttgggatact gatcaatttc ctaccaatat ctacgatgcc gttctggcta tgtacgaagt   2700
tatcaaaaac aacggtctag ggaagggagg tttgaatttt gatgcaaaag tccggagggg   2760
aagtttcgaa gataaagatt tgtttttagc gtatattgcg ggaatggata cattcgccaa   2820
aggtttaacg atagcatata gattgtacga ggataaagtg tttgaagatt ttcaagacaa   2880
gagatatgaa tcatataaga ccgggatagg gaaagatatt gttgagggca aagttggctt   2940
tgaggaatta gcagaatacg tggaaaactt agctgagatc aaaaatacca gcggtagaca   3000
ggagatgtta gaatccatat tgaacagtta cattcttgaa gcaaagtaat taattaacat   3060
ctgaatgtaa aatgaacatt aaaatgaatt actaaacttt acgtctactt tacaatctat   3120
aaactttgtt taatcatata acgaaataca ctaatacaca atcctgtacg tatgtaatac   3180
ttttatccat caaggattga gaaaaaaaag taatgattcc ctgggccatt aaaacttaga   3240
cccccaagct tggataggtc actctctatt ttcgtttctc ccttccctga tagaagggtg   3300
atatgtaatt aagaataata tataatttta taataaaaga attcgccctt acatatgata   3360
acttcgtata atgtatgcta tacgaagtta tcatagcctc atgaaatcag ccatttgctt   3420
ttgttcaacg atcttttgaa attgttgttg ttcttggtag ttaagttgat ccatcttggc   3480
```

```
ttatgttgtg tgtatgttgt agttattctt agtatattcc tgtcctgagt ttagtgaaac   3540
ataatatcgc cttgaaatga aaatgctgaa attcgtcgac atacaatttt tcaaactttt   3600
tttttttctt ggtgcacgga catgttttta aaggaagtac tctataccag ttattcttca   3660
caaatttaat tgctggagaa tagatcttca acgctttaat aaagtagttt gtttgtcaag   3720
gatggcgtca tacaaagaaa gatcagaatc acacacttcc cctgttgcta ggagactttt   3780
ctccatcatg gaggaaaaga agtctaacct ttgtgcatca ttggatatta ctgaaactga   3840
aaagcttctc tctattttgg acactattgg tccttacatc tgtctagtta aaacacacat   3900
cgatattgtt tctgatttta cgtatgaagg aactgtgttg cctttgaagg agcttgccaa   3960
gaaacataat tttatgattt ttgaagatag aaaatttgct gatattggta acactgttaa   4020
aaatcaatat aaatctggtg tcttccgtat tgccgaatgg gctgacatca ctaatgcaca   4080
tggtgtaacg ggtgcaggta ttgtttctgg cttgaaggag gcagcccaag aaacaaccag   4140
tgaacctaga ggtttgctaa tgcttgctga gttatcatca aagggttctt tagcatatgg   4200
tgaatataca gaaaaaacag tagaaattgc taaatctgat aaagagtttg tcattggttt   4260
tattgcgcaa cacgatatgg gcggtagaga agaaggtttt gactggatca ttatgactcc   4320
aggggttggt ttagatgaca aaggtgatgc acttggtcaa caatatagaa ctgttgatga   4380
agttgtaaag actggaacgg atatcataat tgttggtaga ggtttgtacg gtcaaggaag   4440
agatcctata gagcaagcta aagataccaa acaagctggt tggaatgctt atttaaacag   4500
atttaaatga ttcttacaca aagatttgat acatgtacac tagtttaaat aagcatgaaa   4560
agaattacac aagcaaaaaa aaaaaaataa atgaggtact ttacgttcac ctacaaccaa   4620
aaaaactaga tagagtaaaa tcttaagatt tagaaaaagt tgtttaacaa aggctttagt   4680
atgtgaattt ttaatgtagc aaagcgataa ctaataaaca taaacaaaag tatggttttc   4740
tttatcagtc aaatcattat cgattgattg ttccgcgtat ctgcagataa cttcgtataa   4800
tgtatgctat acgaagttat agatccgcgg ccgcgtgtaa atatctacgt gtttagcatt   4860
tcctatatac atgactgtgt gtcctctggt tttcatttcg tttggttctc attcctcttg   4920
gcagcttcac taaacaactg gtcgtgttgt tcgtcgtgtt ttgccttgaa gaatgtatag   4980
tgcaacacaa cgtcttcgat gtttctcatt gccggatctc tggaaaactc tggatcgata   5040
aagaaaaaca agggcatatc aacctcctca cccttggcca accgctgctc ttcaaagcag   5100
aaacactgga tcttgttgaa gtaaggcgct acatgatcgg gagtcactga gtatgtggcc   5160
atgccagtaa tgtccttgtc acttatattc ttggctttgt agaaggccaa ggcagtctct   5220
ccggggacaa cataaacttc tctttgttgc ggtacaaact tccatggtaa cgcaccactt   5280
gtctccgccg taaaggatac ccgcagtctt ctctctgtag ctactggagt tagcttgtcc   5340
ctcgtgaacc tgctcttgtc ggtgattggt gtaccacccc atccagtacg ttgacaaatt   5400
gcacgataca aggggacact cgcatacgat aatgcaagga aaatcatcat catggataac   5460
gaataataaa tggtggtttg cctctcatac ctcttctttt ctccatggta cttatctctc   5520
aatgcttgga actctgccaa agacatcttt ggaagctcct tccggtttgc tcgtggtgat   5580
acctgatgtt ctgatgaccc accaccagga acttcgtatt ttgcaataca actggcatgt   5640
acatatctcc tatggagggc aagtccggga atcagcccaa catcccgaag ggcgcttgt    5700
atactagttc tgaaaatccg ccttaacatc accgtacaga gacaccttca ccaatatgtt   5760
ctccaagacc atggggcact agaagttatc cattgacgtt catcaaccta gtgatgtcaa   5820
```

atttcatcgc cgtttcccaa ctcgcgggat ttgcttttga gcatctcgtt tgattcacga 5880
caacttgttc tacattctgc tgcgggcc 5908

<210> SEQ ID NO 48
<211> LENGTH: 5908
<212> TYPE: DNA
<213> ORGANISM: Artificial Sequence
<220> FEATURE:
<223> OTHER INFORMATION: StXI-PDC-URA3-loxP-XDH integration fragment

<400> SEQUENCE: 48
ctgcttgtgc aggtgcaacc gagtcgtttg ttgttgtccc ctttgagttg gtgaagatcc 60
ggttacagga taagtccaag gcgtccatgt atagcggtcc cattgatgtt ctaatgaaga 120
cagtcaaaaa tgaaggtatc ttggccttgt ataacggatt agaggcaaca ctgtggagac 180
atattgtatg gaatgccggc tattttggtg tgattttcca agttcgtgac atgttaccca 240
aggcaaagga caagacccag aaaaccatca acgatttggt gggtggtatg attggtggta 300
tcgttggtac tgccttgaac attccattcg atgttgtcaa atccagaatc caaagtgcaa 360
ccattatgga aggtcaggtc cgtaaataca attggacttg gccctctctt ggcattgtct 420
tgagggaaga aggtgtctct gcattgtata aaggattcct tccaaaagtc ctgagattgg 480
gtccaggtgg tggtattcta cttgttgtct tcacaaactg tatggacttc tttagaggcc 540
aatactatgg agacaagaaa tagtagctgg gttcttcacc atcaggttta tacaccctcc 600
acgacgtcca ttctatacta tactatgcta ttcgatgcta ttcgatgcta tcctgcccta 660
tcttatctaa tcttatctta tcttacaaaa ttatatactt tccttgtttc tttcacctcc 720
tcctttatag atcaattgat ttgataatac acttatacac attgacgtct gttgatatct 780
tcatacaaaa aaccttaaaa catagtgcaa agtcacgtgc acgccttaaa aatgcagctg 840 agccccttc ccacttctct cccttcggat gccccacctg actattttca cttcccaatt 900
cgagcatcct cctccagtcc ccgcagactc aagagataag aaaccttaca gagactgttc 960
ccatcctcct atgctcaacg tgtcctgtat ctacattgcg gccgcggatc cctcgaggag 1020
tccatcggtt cctgtcagat gggatactct tgacgtggaa aattcaaaca gaaaaaaaac 1080
cccaataatg aaaaataaca ctacgttata tccgtggtat cctctatcgt atcgtatcgt 1140
agcgtatcgt agcgtaccgt atcacagtat agtctaatat tccgtatctt attgtatcct 1200
atcctattcg atcctattgt atttcagtgc accattttaa tttctattgc tataatgtcc 1260
ttattagttg ccactgtgag gtgaccaatg gacgagggcg agccgttcag aagccgcgaa 1320
gggtgttctt cccatgaatt tcttaaggag ggcggctcag ctccgagagt gaggcgagac 1380
gtctcggtca gcgtatcccc cttcctcggc ttttacaaat gatgcgctct taatagtgtg 1440
tcgttatcct tttggcattg acgggggagg gaaattgatt gagcgcatcc atatttttgc 1500
ggactgctga ggacaatggt ggtttttccg ggtggcgtgg gctacaaatg atacgatggt 1560
ttttttcttt tcggagaagg cgtataaaaa ggacacggag aacccattta ttctaaaaac 1620
agttgagctt ctttaattat tttttgatat aatattctat tattatatat tttcttccca 1680
ataaaacaaa ataaaacaaa acacagcaaa acacaaaaat tctagaatga aagagtattt 1740
ccctgagatt aaggaaatca aatatgaagg tccagaaagc aaaaatgtta tggcattcaa 1800
gtactacaat aaggacgagg ttattggggg caaacctatg agagaacatc ttaagtttgc 1860
aatgtcttac tggcacacgt tgaaagcaca aggtttagat atgtttggtg gagacacaat 1920
ggatagagct tggaatagat acgacgatgc attggagcaa gcgaaagccc gtgcagatgc 1980

```
gggtttcgag tttatgcaga aaattggcat ggactacttc tgtttccatg atcgtgatat   2040
tattaacgaa gctatgacac ttaaggagac aaatagatta ctagacgaaa tagttgatca   2100
tttggagggt ttgatgaaaa agactgggat caaacttcta tggggtacaa ctaatgcttt   2160
tagtcatcca agattcttac acggtggagc tacagcccca aacgctgacg tatttgcata   2220
cgccgctgcg caagtcaaaa aggctatgga gattaccaaa agattgggtg gagaaaatta   2280
tgtgctgtgg ggtggtcgag aaggttatga aacattgctc aataccaagt ccgacctgga   2340
atatgataac tttgcaaggt ttcttcaaat ggttgttgat tacaaggaga aaataggttt   2400
tgaaggccaa ttgctaattg aaccaaaacc caaggaaccg acaaaacatc aatatgattt   2460
tgatactgcc actgttttgg gtttcttgcg gaagtataac ttggataagc actataagat   2520
gaatattgaa gccaaccatg caacccttgc cggccacacc tttcaacatg aattgaatct   2580
agctaggatt aacaacgtta tgggctcaat agacgctaat cagggagata tgttattagg   2640
ttgggatacc gatcagtttc ctactaatat ctatgatgca gtgttggcta tgtatgaagt   2700
gatcaaaaac aatggtctag ggaagggtgg tctgaatttt gatgcaaaag tccgtagggg   2760
atcatttgag gacaaagatt tgttcctcgc ctacattgct ggaatggata cttttgcaaa   2820
ggggttaacg atagcttatc gattatacga ggacaaggtc tttgaagatt tccaggataa   2880
gagatatgaa tcctacaaaa ctggtatcgg aaaagatata gtagaaggaa aagttggctt   2940
tgaggaatta gcagaatatg ttgagaactt agcagaaatc aaaaatacct cagggagaca   3000
agagatgtta gaatctattc tcaactcgta tatcttggaa gcaaagtaat taattaacat   3060
ctgaatgtaa aatgaacatt aaaatgaatt actaaacttt acgtctactt tacaatctat   3120
aaactttgtt taatcatata acgaaataca ctaatacaca atcctgtacg tatgtaatac   3180
ttttatccat caaggattga gaaaaaaaag taatgattcc ctgggccatt aaaacttaga   3240
cccccaagct tggataggtc actctctatt ttcgtttctc ccttccctga tagaagggtg   3300
atatgtaatt aagaataata tataatttta taataaaaga attcgccctt acatatgata   3360
acttcgtata atgtatgcta tacgaagtta tcatagcctc atgaaatcag ccatttgctt   3420
ttgttcaacg atcttttgaa attgttgttg ttcttggtag ttaagttgat ccatcttggc   3480
ttatgttgtg tgtatgttgt agttattctt agtatattcc tgtcctgagt ttagtgaaac   3540
ataatatcgc cttgaaatga aaatgctgaa attcgtcgac atacaatttt tcaaactttt   3600
tttttttctt ggtgcacgga catgttttta aaggaagtac tctataccag ttattcttca   3660
caaatttaat tgctggagaa tagatcttca acgctttaat aaagtagttt gtttgtcaag   3720
gatggcgtca tacaaagaaa gatcagaatc acacacttcc cctgttgcta ggagactttt   3780
ctccatcatg gaggaaaaga agtctaacct ttgtgcatca ttggatatta ctgaaactga   3840
aaagcttctc tctattttgg acactattgg tccttacatc tgtctagtta aaacacacat   3900
cgatattgtt tctgatttta cgtatgaagg aactgtgttg cctttgaagg agcttgccaa   3960
gaaacataat tttatgattt ttgaagatag aaaatttgct gatattggta acactgttaa   4020
aaatcaatat aaatctggtg tcttccgtat tgccgaatgg gctgacatca ctaatgcaca   4080
tggtgtaacg ggtgcaggta ttgtttctgg cttgaaggag gcagcccaag aaacaaccag   4140
tgaacctaga ggtttgctaa tgcttgctga gttatcatca aagggttctt tagcatatgg   4200
tgaatataca gaaaaaacag tagaaattgc taaatctgat aaagagtttg tcattggttt   4260
tattgcgcaa cacgatatgg gcggtagaga agaaggtttt gactggatca ttatgactcc   4320
```

```
aggggttggt ttagatgaca aaggtgatgc acttggtcaa caatatagaa ctgttgatga   4380
agttgtaaag actggaacgg atatcataat tgttggtaga ggtttgtacg gtcaaggaag   4440
agatcctata gagcaagcta aagataccca acaagctggt tggaatgctt atttaaacag   4500
atttaaatga ttcttacaca aagatttgat acatgtacac tagtttaaat aagcatgaaa   4560
agaattacac aagcaaaaaa aaaaaaataa atgaggtact ttacgttcac ctacaaccaa   4620
aaaaactaga tagagtaaaa tcttaagatt tagaaaaagt tgtttaacaa aggctttagt   4680
atgtgaattt ttaatgtagc aaagcgataa ctaataaaca taaacaaaag tatggttttc   4740
tttatcagtc aaatcattat cgattgattg ttccgcgtat ctgcagataa cttcgtataa   4800
tgtatgctat acgaagttat agatccgcgg ccgcgtgtaa atatctacgt gtttagcatt   4860
tcctatatac atgactgtgt gtcctctggt tttcatttcg tttggttctc attcctcttg   4920
gcagcttcac taaacaactg gtcgtgttgt tcgtcgtgtt ttgccttgaa gaatgtatag   4980
tgcaacacaa cgtcttcgat gtttctcatt gccggatctc tggaaaactc tggatcgata   5040
aagaaaaaca agggcatatc aacctcctca cccttggcca accgctgctc ttcaaagcag   5100
aaacactgga tcttgttgaa gtaaggcgct acatgatcgg gagtcactga gtatgtggcc   5160
atgccagtaa tgtccttgtc acttatattc ttggctttgt agaaggccaa ggcagtctct   5220
ccggggacaa cataaacttc tctttgttgc ggtacaaact tccatggtaa cgcaccactt   5280
gtctccgccg taaaggatac ccgcagtctt ctctctgtag ctactggagt tagcttgtcc   5340
ctcgtgaacc tgctcttgtc ggtgattggt gtaccacccc atccagtacg ttgacaaatt   5400
gcacgataca aggggacact cgcatacgat aatgcaagga aaatcatcat catggataac   5460
gaataataaa tggtggtttg cctctcatac ctcttctttt ctccatggta cttatctctc   5520
aatgcttgga actctgccaa agacatcttt ggaagctcct tccggtttgc tcgtggtgat   5580
acctgatgtt ctgatgaccc accaccagga acttcgtatt ttgcaataca actggcatgt   5640
acatatctcc tatggagggc aagtccggga atcagcccaa catcccgaag ggcgcttgt    5700
atactagttc tgaaaatccg ccttaacatc accgtacaga gacaccttca ccaatatgtt   5760
ctccaagacc atggggcact agaagttatc cattgacgtt catcaaccta gtgatgtcaa   5820
atttcatcgc cgtttcccaa ctcgcgggat ttgcttttga gcatctcgtt tgattcacga   5880
caacttgttc tacattctgc tgcgggcc                                      5908
```

<210> SEQ ID NO 49
<211> LENGTH: 5908
<212> TYPE: DNA
<213> ORGANISM: Artificial Sequence
<220> FEATURE:
<223> OTHER INFORMATION: StXI-PDC-URA3-loxP-XDH integration fragment

<400> SEQUENCE: 49

```
ctgcttgtgc aggtgcaacc gagtcgtttg ttgttgtccc ctttgagttg gtgaagatcc     60
ggttacagga taagtccaag gcgtccatgt atagcggtcc cattgatgtt ctaatgaaga    120
cagtcaaaaa tgaaggtatc ttggccttgt ataacggatt agaggcaaca ctgtggagac    180
atattgtatg gaatgccggc tattttggtg tgattttcca agttcgtgac atgttaccca    240
aggcaaagga caagacccag aaaaccatca acgatttggt gggtggtatg attggtggta    300
tcgttggtac tgccttgaac attccattcg atgttgtcaa atccagaatc caaagtgcaa    360
ccattatgga aggtcaggtc cgtaaataca attggacttg gccctctctt ggcattgtct    420
tgagggaaga aggtgtctct gcattgtata aaggattcct tccaaaagtc ctgagattgg    480
```

```
gtccaggtgg tggtattcta cttgttgtct tcacaaactg tatggacttc tttagaggcc    540
aatactatgg agacaagaaa tagtagctgg gttcttcacc atcaggttta tacaccctcc    600
acgacgtcca ttctatacta tactatgcta ttcgatgcta ttcgatgcta tcctgcccta    660
tcttatctaa tcttatctta tcttacaaaa ttatatactt tccttgtttc tttcacctcc    720
tcctttatag atcaattgat ttgataatac acttatacac attgacgtct gttgatatct    780
tcatacaaaa aaccttaaaa catagtgcaa agtcacgtgc acgccttaaa aatgcagctg    840
agcccctttc ccacttctct cccttcggat gccccacctg actattttca cttcccaatt    900
cgagcatcct cctccagtcc ccgcagactc aagagataag aaaccttaca gagactgttc    960
ccatcctcct atgctcaacg tgtcctgtat ctacattgcg gccgcggatc cctcgaggag   1020
tccatcggtt cctgtcagat gggatactct tgacgtggaa aattcaaaca gaaaaaaaac   1080
cccaataatg aaaaataaca ctacgttata tccgtggtat cctctatcgt atcgtatcgt   1140
agcgtatcgt agcgtaccgt atcacagtat agtctaatat tccgtatctt attgtatcct   1200
atcctattcg atcctattgt atttcagtgc accattttaa tttctattgc tataatgtcc   1260
ttattagttg ccactgtgag gtgaccaatg gacgagggcg agccgttcag aagccgcgaa   1320
gggtgttctt cccatgaatt tcttaaggag ggcggctcag ctccgagagt gaggcgagac   1380
gtctcggtca gcgtatcccc cttcctcggc ttttacaaat gatgcgctct taatagtgtg   1440
tcgttatcct tttggcattg acgggggagg gaaattgatt gagcgcatcc atatttttgc   1500
ggactgctga ggacaatggt ggtttttccg ggtggcgtgg gctacaaatg atacgatggt   1560
tttttctttt tcggagaagg cgtataaaaa ggacacggag aacccattta ttctaaaaac   1620
agttgagctt ctttaattat tttttgatat aatattctat tattatatat tttcttccca   1680
ataaaacaaa ataaaacaaa acacagcaaa acacaaaaat tctagaatga aagagtattt   1740
tcctgaaatc aaggaaatca aatatgaagg tcccgagtcc aaaaatgtta tggcattcaa   1800
atactacaac aaggacgaag ttataggtgg caaaccaatg agagaacatt tgaaatttgc   1860
gatgtcttat tggcacacct taaaagcaca gggcctagac atgttcggcg gggatacaat   1920
ggatagagca tggaatcgat atgatgatgc attggaacaa gccaaagcta gggcagatgc   1980
tggtttcgag tttatgcaaa agattggaat ggattacttc tgttttcatg atcgtgacat   2040
cattaacgaa gcaatgactt tgaaggaaac caataggtta ttggatgaaa tagtagatca   2100
cttagaaggt cttatgaaaa agactggtat taagctgtta tggggtacaa ctaatgcctt   2160
tagtcaccca agatttcttc atgggggagc aaccgcacct aatgctgatg ttttcgctta   2220
tgctgctgcc caagtcaaaa aggctatgga aattacaaaa agactaggtg gagagaacta   2280
tgttttgtgg gggggcagag agggttatga aacacttctg aatactaagt ctgatttgga   2340
atatgacaat tttgcaagat tttgcaaat ggttgtggac tataaggaaa agatcggttt    2400
cgagggccag ctactcatag aaccaaaacc aaaggagccg acgaaacatc agtacgattt   2460
cgatacagcc actgtattgg gttttctgag gaagtataac ctcgacaaac actacaagat   2520
gaatattgaa gctaatcatg ctacactagc gggtcatacg tttcaacatg agttaaactt   2580
agcacgtatt aacaatgtca tgggcagtat agatgcaaac caaggagaca tgttgttggg   2640
ttgggacaca gatcagttcc ctactaatat ctatgatgct gtattagcta tgtacgaagt   2700
catcaaaaac aatggtttgg ggaaaggagg gttaaacttt gatgcaaaag ttcggagagg   2760
atcatttgaa gataaggatc tcttcttggc ctacattgcg ggaatggaca cttttgccaa   2820
```

-continued

```
gggtctaaca atagcatata ggttatatga ggataaggtt ttcgaggact ttcaagataa   2880
gagatacgaa tcgtacaaaa ccggtattgg caaagatatt gtggaaggaa aagtcggttt   2940
tgaggaactt gctgaatatg tggaaaacct tgcagagatc aaaaatacca gcggtagaca   3000
agagatgtta gaatcaattc taaattctta cattctcgaa gcaaagtaat taattaacat   3060
ctgaatgtaa aatgaacatt aaaatgaatt actaaacttt acgtctactt tacaatctat   3120
aaactttgtt taatcatata acgaaataca ctaatacaca atcctgtacg tatgtaatac   3180
ttttatccat caaggattga gaaaaaaaag taatgattcc ctgggccatt aaaacttaga   3240
cccccaagct tggataggtc actctctatt ttcgtttctc ccttccctga tagaagggtg   3300
atatgtaatt aagaataata tataatttta taataaaaga attcgccctt acatatgata   3360
acttcgtata atgtatgcta tacgaagtta tcatagcctc atgaaatcag ccatttgctt   3420
ttgttcaacg atcttttgaa attgttgttg ttcttggtag ttaagttgat ccatcttggc   3480
ttatgttgtg tgtatgttgt agttattctt agtatattcc tgtcctgagt ttagtgaaac   3540
ataatatcgc cttgaaatga aaatgctgaa attcgtcgac atacaatttt tcaaactttt   3600
tttttttctt ggtgcacgga catgttttta aaggaagtac tctataccag ttattcttca   3660
caaatttaat tgctggagaa tagatcttca acgctttaat aaagtagttt gtttgtcaag   3720
gatggcgtca tacaaagaaa gatcagaatc acacacttcc cctgttgcta ggagactttt   3780
ctccatcatg gaggaaaaga agtctaacct ttgtgcatca ttggatatta ctgaaactga   3840
aaagcttctc tctattttgg acactattgg tccttacatc tgtctagtta aaacacacat   3900
cgatattgtt tctgatttta cgtatgaagg aactgtgttg cctttgaagg agcttgccaa   3960
gaaacataat tttatgattt ttgaagatag aaaatttgct gatattggta acactgttaa   4020
aaatcaatat aaatctggtg tcttccgtat tgccgaatgg gctgacatca ctaatgcaca   4080
tggtgtaacg ggtgcaggta ttgtttctgg cttgaaggag gcagcccaag aaacaaccag   4140
tgaacctaga ggtttgctaa tgcttgctga gttatcatca aagggttctt tagcatatgg   4200
tgaatataca gaaaaaacag tagaaattgc taaatctgat aaagagtttg tcattggttt   4260
tattgcgcaa cacgatatgg gcggtagaga agaaggtttt gactggatca ttatgactcc   4320
aggggttggt ttagatgaca aaggtgatgc acttggtcaa caatatagaa ctgttgatga   4380
agttgtaaag actggaacgg atatcataat tgttggtaga ggtttgtacg gtcaaggaag   4440
agatcctata gagcaagcta aaagatacca acaagctggt tggaatgctt atttaaacag   4500
atttaaatga ttcttacaca aagatttgat acatgtacac tagtttaaat aagcatgaaa   4560
agaattacac aagcaaaaaa aaaaaaataa atgaggtact ttacgttcac ctacaaccaa   4620
aaaaactaga tagagtaaaa tcttaagatt tagaaaaagt tgtttaacaa aggctttagt   4680
atgtgaattt ttaatgtagc aaagcgataa ctaataaaca taaacaaaag tatggttttc   4740
tttatcagtc aaatcattat cgattgattg ttccgcgtat ctgcagataa cttcgtataa   4800
tgtatgctat acgaagttat agatccgcgg ccgcgtgtaa atatctacgt gtttagcatt   4860
tcctatatac atgactgtgt gtcctctggt tttcatttcg tttggttctc attcctcttg   4920
gcagcttcac taaacaactg gtcgtgttgt tcgtcgtgtt ttgccttgaa gaatgtatag   4980
tgcaacacaa cgtcttcgat gtttctcatt gccggatctc tggaaaactc tggatcgata   5040
aagaaaaaca agggcatatc aacctcctca cccttggcca accgctgctc ttcaaagcag   5100
aaacactgga tcttgttgaa gtaaggcgct acatgatcgg gagtcactga gtatgtggcc   5160
atgccagtaa tgtccttgtc acttatattc ttggctttgt agaaggccaa ggcagtctct   5220
```

```
ccggggacaa cataaacttc tctttgttgc ggtacaaact tccatggtaa cgcaccactt   5280

gtctccgccg taaaggatac ccgcagtctt ctctctgtag ctactggagt tagcttgtcc   5340

ctcgtgaacc tgctcttgtc ggtgattggt gtaccacccc atccagtacg ttgacaaatt   5400

gcacgataca aggggacact cgcatacgat aatgcaagga aaatcatcat catggataac   5460

gaataataaa tggtggtttg cctctcatac ctcttctttt ctccatggta cttatctctc   5520

aatgcttgga actctgccaa agacatcttt ggaagctcct tccggtttgc tcgtggtgat   5580

acctgatgtt ctgatgaccc accaccagga acttcgtatt ttgcaataca actggcatgt   5640

acatatctcc tatggagggc aagtccggga atcagcccaa catcccgaag ggcgcttgt   5700

atactagttc tgaaaatccg ccttaacatc accgtacaga gacaccttca ccaatatgtt   5760

ctccaagacc atggggcact agaagttatc cattgacgtt catcaaccta gtgatgtcaa   5820

atttcatcgc cgtttcccaa ctcgcgggat ttgcttttga gcatctcgtt tgattcacga   5880

caacttgttc tacattctgc tgcgggcc                                      5908
```

<210> SEQ ID NO 50
<211> LENGTH: 5908
<212> TYPE: DNA
<213> ORGANISM: Artificial Sequence
<220> FEATURE:
<223> OTHER INFORMATION: LgXI-PDC-URA3-loxP-XDH integration fragment

<400> SEQUENCE: 50

```
ctgcttgtgc aggtgcaacc gagtcgtttg ttgttgtccc ctttgagttg gtgaagatcc     60

ggttacagga taagtccaag gcgtccatgt atagcggtcc cattgatgtt ctaatgaaga    120

cagtcaaaaa tgaaggtatc ttggccttgt ataacggatt agaggcaaca ctgtggagac    180

atattgtatg gaatgccggc tattttggtg tgattttcca agttcgtgac atgttaccca    240

aggcaaagga caagacccag aaaaccatca acgatttggt gggtggtatg attggtggta    300

tcgttggtac tgccttgaac attccattcg atgttgtcaa atccagaatc caaagtgcaa    360

ccattatgga aggtcaggtc cgtaaataca attggacttg gccctctctt ggcattgtct    420

tgagggaaga aggtgtctct gcattgtata aaggattcct tccaaaagtc ctgagattgg    480

gtccaggtgg tggtattcta cttgttgtct tcacaaactg tatggacttc tttagaggcc    540

aatactatgg agacaagaaa tagtagctgg gttcttcacc atcaggttta tacaccctcc    600

acgacgtcca ttctatacta tactatgcta ttcgatgcta ttcgatgcta tcctgcccta    660

tcttatctaa tcttatctta tcttacaaaa ttatatactt tccttgtttc tttcacctcc    720

tcctttatag atcaattgat ttgataatac acttatacac attgacgtct gttgatatct    780

tcatacaaaa aaccttaaaa catagtgcaa agtcacgtgc acgccttaaa aatgcagctg    840

agcccctttc ccacttctct cccttcggat gccccacctg actattttca cttcccaatt    900

cgagcatcct cctccagtcc ccgcagactc aagagataag aaaccttaca gagactgttc    960

ccatcctcct atgctcaacg tgtcctgtat ctacattgcg gccgcggatc cctcgaggag   1020

tccatcggtt cctgtcagat gggatactct tgacgtggaa aattcaaaca gaaaaaaaac   1080

cccaataatg aaaaataaca ctacgttata tccgtggtat cctctatcgt atcgtatcgt   1140

agcgtatcgt agcgtaccgt atcacagtat agtctaatat tccgtatctt attgtatcct   1200

atcctattcg atcctattgt atttcagtgc accattttaa tttctattgc tataatgtcc   1260

ttattagttg ccactgtgag gtgaccaatg gacgagggcg agccgttcag aagccgcgaa   1320
```

```
gggtgttctt cccatgaatt tcttaaggag ggcggctcag ctccgagagt gaggcgagac   1380
gtctcggtca gcgtatcccc cttcctcggc ttttacaaat gatgcgctct taatagtgtg   1440
tcgttatcct tttggcattg acgggggagg gaaattgatt gagcgcatcc atatttttgc   1500
ggactgctga ggacaatggt ggtttttccg ggtggcgtgg gctacaaatg atacgatggt   1560
ttttttcttt tcggagaagg cgtataaaaa ggacacggag aacccattta ttctaaaaac   1620
agttgagctt ctttaattat tttttgatat aatattctat tattatatat tttcttccca   1680
ataaaacaaa ataaaacaaa acacagcaaa acacaaaaat tctagaatga aagagttttt   1740
tcctgaaata aaagaaataa aatatgaagg ggctgaatca aaaaatgatt tggcatttaa   1800
atactacaat aaagatgaag tattaggcgg aaaaacaatg aaagagcatt tgagatttgc   1860
aatgagttac tggcatacat tgaaagctca gggagtggac atgttcggcg gagaaacaat   1920
ggacagagag tggaataaat atgaaaatgt attggaaaga gcaaaagcaa gagcaaatgc   1980
aggatttgaa tttatgcaga aactcggttt ggaatatttc tgtttccatg acagagatat   2040
aatagatgaa agtatgatgc tcgcagacag taacaaactt cttgatgaaa tagtagatca   2100
catagaagaa cttatgaaaa aaacagggag aaaattatta tgggggacaa ctaatgcttt   2160
cagtcatccg agatttgttc atggagcttc tacttctccc aatgctgatg tatttgcgta   2220
tgctgcagct caagtaaaga aagctatgga cataactaac agattaggcg gagaaaatta   2280
cgtattatgg ggaggaagag aaggatatga aacattactg aatactaact ctgaattgga   2340
atatgataat tttgcaagat ttttgaaaat ggtagtagat tataaagaaa aaataggatt   2400
taaagggcaa cttcttatag agcctaaacc gaaagaacct acaaaacatc aatatgactt   2460
tgatactgct acagttttgg catttttaag aaaatataat cttgataaat attataaagt   2520
aaatatagag gcaaaccatg caactttagc aggacataca ttccaacatg agttaaatct   2580
ggcgagaata aacggtgttt taggctcgat agatgccaat cagggagata tgcttttagg   2640
atgggataca gatcaattcc cgacaaatat atatgatacg actttagcaa tgtatgaagt   2700
agttaaaaat aaaggactcg gttcaggagg acttaatttt gatgcaaaag taagaagagg   2760
ttcttttgag gataaagatt tattcttagc ttatatcgca ggaatggata cttttgccaa   2820
aggactcaaa atagcatata gattatatga agataaagta tttgaagatt ttattgataa   2880
aagatacgaa agctataaaa caggtatcgg aaaagatata attgatggaa aagtgggatt   2940
tgaagaactg tccaaatatg ccgaaacttt aacagaagta aaaaataatt caggtagaca   3000
ggaaatgctg gaaagtaagt tgaatcagta tatatttgag gtgaaatagt taattaacat   3060
ctgaatgtaa aatgaacatt aaaatgaatt actaaacttt acgtctactt tacaatctat   3120
aaactttgtt taatcatata acgaaataca ctaatacaca atcctgtacg tatgtaatac   3180
ttttatccat caaggattga gaaaaaaaag taatgattcc ctgggccatt aaaacttaga   3240
cccccaagct tggataggtc actctctatt ttcgtttctc ccttccctga tagaagggtg   3300
atatgtaatt aagaataata tataatttta taataaaaga attcgccctt acatatgata   3360
acttcgtata atgtatgcta tacgaagtta tcatagcctc atgaaatcag ccatttgctt   3420
ttgttcaacg atcttttgaa attgttgttg ttcttggtag ttaagttgat ccatcttggc   3480
ttatgttgtg tgtatgttgt agttattctt agtatattcc tgtcctgagt ttagtgaaac   3540
ataatatcgc cttgaaatga aaatgctgaa attcgtcgac atacaatttt tcaaactttt   3600
ttttttcttt ggtgcacgga catgttttta aaggaagtac tctataccag ttattcttca   3660
caaatttaat tgctggagaa tagatcttca acgctttaat aaagtagttt gtttgtcaag   3720
```

```
gatggcgtca tacaaagaaa gatcagaatc acacacttcc cctgttgcta ggagactttt   3780
ctccatcatg gaggaaaaga agtctaacct ttgtgcatca ttggatatta ctgaaactga   3840
aaagcttctc tctattttgg acactattgg tccttacatc tgtctagtta aaacacacat   3900
cgatattgtt tctgatttta cgtatgaagg aactgtgttg cctttgaagg agcttgccaa   3960
gaaacataat tttatgattt ttgaagatag aaaatttgct gatattggta acactgttaa   4020
aaatcaatat aaatctggtg tcttccgtat tgccgaatgg gctgacatca ctaatgcaca   4080
tggtgtaacg ggtgcaggta ttgtttctgg cttgaaggag gcagcccaag aaacaaccag   4140
tgaacctaga ggtttgctaa tgcttgctga gttatcatca aagggttctt tagcatatgg   4200
tgaatataca gaaaaaacag tagaaattgc taaatctgat aaagagtttg tcattggttt   4260
tattgcgcaa cacgatatgg gcggtagaga agaaggtttt gactggatca ttatgactcc   4320
aggggttggt ttagatgaca aaggtgatgc acttggtcaa caatatagaa ctgttgatga   4380
agttgtaaag actggaacgg atatcataat tgttggtaga ggtttgtacg gtcaaggaag   4440
agatcctata gagcaagcta aaagatacca acaagctggt tggaatgctt atttaaacag   4500
atttaaatga ttcttacaca aagatttgat acatgtacac tagtttaaat aagcatgaaa   4560
agaattacac aagcaaaaaa aaaaaaataa atgaggtact ttacgttcac ctacaaccaa   4620
aaaaactaga tagagtaaaa tcttaagatt tagaaaaagt tgtttaacaa aggctttagt   4680
atgtgaattt ttaatgtagc aaagcgataa ctaataaaca taaacaaaag tatggttttc   4740
tttatcagtc aaatcattat cgattgattg ttccgcgtat ctgcagataa cttcgtataa   4800
tgtatgctat acgaagttat agatccgcgg ccgcgtgtaa atatctacgt gtttagcatt   4860
tcctatatac atgactgtgt gtcctctggt tttcatttcg tttggttctc attcctcttg   4920
gcagcttcac taaacaactg gtcgtgttgt tcgtcgtgtt ttgccttgaa gaatgtatag   4980
tgcaacacaa cgtcttcgat gtttctcatt gccggatctc tggaaaactc tggatcgata   5040
aagaaaaaca agggcatatc aacctcctca cccttggcca accgctgctc ttcaaagcag   5100
aaacactgga tcttgttgaa gtaaggcgct acatgatcgg gagtcactga gtatgtggcc   5160
atgccagtaa tgtccttgtc acttatattc ttggctttgt agaaggccaa ggcagtctct   5220
ccggggacaa cataaacttc tctttgttgc ggtacaaact tccatggtaa cgcaccactt   5280
gtctccgccg taaaggatac ccgcagtctt ctctctgtag ctactggagt tagcttgtcc   5340
ctcgtgaacc tgctcttgtc ggtgattggt gtaccacccc atccagtacg ttgacaaatt   5400
gcacgataca aggggacact cgcatacgat aatgcaagga aaatcatcat catggataac   5460
gaataataaa tggtggtttg cctctcatac ctcttctttt ctccatggta cttatctctc   5520
aatgcttgga actctgccaa agacatcttt ggaagctcct tccggtttgc tcgtggtgat   5580
acctgatgtt ctgatgaccc accaccagga acttcgtatt ttgcaataca actggcatgt   5640
acatatctcc tatggagggc aagtccggga atcagcccaa catcccgaag ggcgcttgt    5700
atactagttc tgaaaatccg ccttaacatc accgtacaga gacaccttca ccaatatgtt   5760
ctccaagacc atggggcact agaagttatc cattgacgtt catcaaccta gtgatgtcaa   5820
atttcatcgc cgtttcccaa ctcgcgggat ttgcttttga gcatctcgtt tgattcacga   5880
caacttgttc tacattctgc tgcgggcc                                      5908
```

<210> SEQ ID NO 51
<211> LENGTH: 5908
<212> TYPE: DNA

```
<213> ORGANISM: Artificial Sequence
<220> FEATURE:
<223> OTHER INFORMATION: LgXI-PDC-URA3-loxP-XDH integration fragment

<400> SEQUENCE: 51

ctgcttgtgc aggtgcaacc gagtcgtttg ttgttgtccc ctttgagttg gtgaagatcc      60

ggttacagga taagtccaag gcgtccatgt atagcggtcc cattgatgtt ctaatgaaga     120

cagtcaaaaa tgaaggtatc ttggccttgt ataacggatt agaggcaaca ctgtggagac     180

atattgtatg gaatgccggc tattttggtg tgattttcca agttcgtgac atgttaccca     240

aggcaaagga caagacccag aaaaccatca acgatttggt gggtggtatg attggtggta     300

tcgttggtac tgccttgaac attccattcg atgttgtcaa atccagaatc caaagtgcaa     360

ccattatgga aggtcaggtc cgtaaataca attggacttg gccctctctt ggcattgtct     420

tgagggaaga aggtgtctct gcattgtata aaggattcct tccaaaagtc ctgagattgg     480

gtccaggtgg tggtattcta cttgttgtct tcacaaactg tatggacttc tttagaggcc     540

aatactatgg agacaagaaa tagtagctgg gttcttcacc atcaggttta tacaccctcc     600

acgacgtcca ttctatacta tactatgcta ttcgatgcta ttcgatgcta tcctgcccta     660

tcttatctaa tcttatctta tcttacaaaa ttatatactt tccttgtttc tttcacctcc     720

tcctttatag atcaattgat ttgataatac acttatacac attgacgtct gttgatatct     780

tcatacaaaa aaccttaaaa catagtgcaa agtcacgtgc acgccttaaa aatgcagctg     840

agccccttc ccacttctct cccttcggat gccccacctg actattttca cttcccaatt     900

cgagcatcct cctccagtcc ccgcagactc aagagataag aaaccttaca gagactgttc     960

ccatcctcct atgctcaacg tgtcctgtat ctacattgcg gccgcggatc cctcgaggag    1020

tccatcggtt cctgtcagat gggatactct tgacgtggaa aattcaaaca gaaaaaaaac    1080

cccaataatg aaaaataaca ctacgttata tccgtggtat cctctatcgt atcgtatcgt    1140

agcgtatcgt agcgtaccgt atcacagtat agtctaatat tccgtatctt attgtatcct    1200

atcctattcg atcctattgt atttcagtgc accattttaa tttctattgc tataatgtcc    1260

ttattagttg ccactgtgag gtgaccaatg gacgagggcg agccgttcag aagccgcgaa    1320

gggtgttctt cccatgaatt tcttaaggag ggcggctcag ctccgagagt gaggcgagac    1380

gtctcggtca gcgtatcccc cttcctcggc ttttacaaat gatgcgctct taatagtgtg    1440

tcgttatcct tttggcattg acgggggagg gaaattgatt gagcgcatcc atatttttgc    1500

ggactgctga ggacaatggt ggtttttccg ggtggcgtgg gctacaaatg atacgatggt    1560

tttttcttt tcggagaagg cgtataaaaa ggacacggag aacccattta ttctaaaaac    1620

agttgagctt ctttaattat tttttgatat aatattctat tattatatat tttcttccca    1680

ataaaacaaa ataaaacaaa acacagcaaa acacaaaaat tctagaatga aggagttttt    1740

ccccgaaatc aaagagatca aatacgaagg cgccgaatcc aaaaatgatc tagcgttcaa    1800

atactataac aaggatgaag tccttggtgg caaaactatg aaagagcatc tgaggtttgc    1860

aatgtcgtat tggcatacgt taaaagctca aggagttgat atgtttggcg gagaaactat    1920

ggatagagaa tggaacaaat atgaaaatgt tttagaaagg gcaaaagcac gggccaatgc    1980

cggattcgag ttcatgcaga aacttggatt agagtatttc tgttttcatg accgagacat    2040

aattgatgag tctatgatgt tagcggatag taacaagtta cttgacgaaa tagtagatca    2100

tattgaagag ttgatgaaaa agaccgggag aaagttactc tggggtacca cgaatgcctt    2160

ttcgcacccg agatttgttc atggtgcatc aacttctcca aacgcagatg tatttgcata    2220
```

```
tgccgctgca caagtcaaaa aggccatgga tattacaaat cgtttgggtg gtgaaaacta   2280
tgtgttgtgg ggtggtagag aaggctatga aaccttattg aacactaact ctgaacttga   2340
atacgacaat tttgctagat tcctgaagat ggtggtcgac tataaggaga agattggttt   2400
taagggccaa ctgttaatcg aaccaaagcc taaggaacca actaagcatc agtacgattt   2460
tgatactgct actgtgttag ctttcttgag aaaatacaat ttggataagt actataaagt   2520
taacattgaa gcaaatcatg ctacgctcgc gggccacaca tttcaacacg agctaaatct   2580
agctaggatc aatggtgtac ttggtagtat tgatgcgaat caaggggata tgttgcttgg   2640
ttgggataca gatcagttcc ctacaaatat ctatgacact acattagcta tgtacgaagt   2700
tgtcaaaaac aaaggattgg gttcaggggg attgaacttt gatgccaaag ttcgtagagg   2760
ttcttttgag gacaaagatc tattcttggc atatattgct ggaatggaca catttgcaaa   2820
aggtctaaag attgcatata ggttatatga ggataaggtt tttgaagatt tcattgataa   2880
gagatacgaa tcatataaga ccggtatcgg aaaagacatt atagatggga aagttgggtt   2940
cgaggaattg tccaaatatg ctgaaacatt gaccgaagtg aaaaacaata gcggtagaca   3000
agagatgttg gaatccaagc tcaatcagta catatttgaa gttaagtaat taattaacat   3060
ctgaatgtaa aatgaacatt aaaatgaatt actaaacttt acgtctactt tacaatctat   3120
aaactttgtt taatcatata acgaaataca ctaatacaca atcctgtacg tatgtaatac   3180
ttttatccat caaggattga gaaaaaaaag taatgattcc ctgggccatt aaaacttaga   3240
cccccaagct tggataggtc actctctatt ttcgtttctc ccttccctga tagaagggtg   3300
atatgtaatt aagaataata tataatttta taataaaaga attcgccctt acatatgata   3360
acttcgtata atgtatgcta tacgaagtta tcatagcctc atgaaatcag ccatttgctt   3420
ttgttcaacg atcttttgaa attgttgttg ttcttggtag ttaagttgat ccatcttggc   3480
ttatgttgtg tgtatgttgt agttattctt agtatattcc tgtcctgagt ttagtgaaac   3540
ataatatcgc cttgaaatga aaatgctgaa attcgtcgac atacaatttt tcaaactttt   3600
ttttttcttt ggtgcacgga catgttttta aaggaagtac tctataccag ttattcttca   3660
caaatttaat tgctggagaa tagatcttca acgctttaat aaagtagttt gtttgtcaag   3720
gatggcgtca tacaaagaaa gatcagaatc acacacttcc cctgttgcta ggagactttt   3780
ctccatcatg gaggaaaaga agtctaacct ttgtgcatca ttggatatta ctgaaactga   3840
aaagcttctc tctattttgg acactattgg tccttacatc tgtctagtta aaacacacat   3900
cgatattgtt tctgatttta cgtatgaagg aactgtgttg cctttgaagg agcttgccaa   3960
gaaacataat tttatgattt ttgaagatag aaaatttgct gatattggta acactgttaa   4020
aaatcaatat aaatctggtg tcttccgtat tgccgaatgg gctgacatca ctaatgcaca   4080
tggtgtaacg ggtgcaggta ttgtttctgg cttgaaggag gcagcccaag aaacaaccag   4140
tgaacctaga ggtttgctaa tgcttgctga gttatcatca aagggttctt tagcatatgg   4200
tgaatataca gaaaaaacag tagaaattgc taaatctgat aaagagtttg tcattggttt   4260
tattgcgcaa cacgatatgg gcggtagaga agaaggtttt gactggatca ttatgactcc   4320
aggggttggt ttagatgaca aaggtgatgc acttggtcaa caatatagaa ctgttgatga   4380
agttgtaaag actggaacgg atatcataat tgttggtaga ggtttgtacg gtcaaggaag   4440
agatcctata gagcaagcta aaagatacca acaagctggt tggaatgctt atttaaacag   4500
atttaaatga ttcttacaca aagatttgat acatgtacac tagtttaaat aagcatgaaa   4560
```

```
agaattacac aagcaaaaaa aaaaaaaataa atgaggtact ttacgttcac ctacaaccaa   4620

aaaaactaga tagagtaaaa tcttaagatt tagaaaaagt tgtttaacaa aggctttagt   4680

atgtgaattt ttaatgtagc aaagcgataa ctaataaaca taaacaaaag tatggttttc   4740

tttatcagtc aaatcattat cgattgattg ttccgcgtat ctgcagataa cttcgtataa   4800

tgtatgctat acgaagttat agatccgcgg ccgcgtgtaa atatctacgt gtttagcatt   4860

tcctatatac atgactgtgt gtcctctggt tttcatttcg tttggttctc attcctcttg   4920

gcagcttcac taaacaactg gtcgtgttgt tcgtcgtgtt ttgccttgaa gaatgtatag   4980

tgcaacacaa cgtcttcgat gtttctcatt gccggatctc tggaaaactc tggatcgata   5040

aagaaaaaca agggcatatc aacctcctca cccttggcca accgctgctc ttcaaagcag   5100

aaacactgga tcttgttgaa gtaaggcgct acatgatcgg gagtcactga gtatgtggcc   5160

atgccagtaa tgtccttgtc acttatattc ttggctttgt agaaggccaa ggcagtctct   5220

ccggggacaa cataaacttc tctttgttgc ggtacaaact tccatggtaa cgcaccactt   5280

gtctccgccg taaaggatac ccgcagtctt ctctctgtag ctactggagt tagcttgtcc   5340

ctcgtgaacc tgctcttgtc ggtgattggt gtaccacccc atccagtacg ttgacaaatt   5400

gcacgataca aggggacact cgcatacgat aatgcaagga aaatcatcat catggataac   5460

gaataataaa tggtggtttg cctctcatac ctcttctttt ctccatggta cttatctctc   5520

aatgcttgga actctgccaa agacatcttt ggaagctcct tccggtttgc tcgtggtgat   5580

acctgatgtt ctgatgaccc accaccagga acttcgtatt ttgcaataca actggcatgt   5640

acatatctcc tatggagggc aagtccggga atcagcccaa catcccgaag ggcgcttgt   5700

atactagttc tgaaaatccg ccttaacatc accgtacaga gacaccttca ccaatatgtt   5760

ctccaagacc atggggcact agaagttatc cattgacgtt catcaaccta gtgatgtcaa   5820

atttcatcgc cgtttcccaa ctcgcgggat ttgcttttga gcatctcgtt tgattcacga   5880

caacttgttc tacattctgc tgcgggcc                                     5908
```

<210> SEQ ID NO 52
<211> LENGTH: 5912
<212> TYPE: DNA
<213> ORGANISM: Artificial Sequence
<220> FEATURE:
<223> OTHER INFORMATION: LgXI-PDC-URA3-loxP-XDH integration fragment

<400> SEQUENCE: 52

```
ctgcttgtgc aggtgcaacc gagtcgtttg ttgttgtccc ctttgagttg gtgaagatcc     60

ggttacagga taagtccaag gcgtccatgt atagcggtcc cattgatgtt ctaatgaaga    120

cagtcaaaaa tgaaggtatc ttggccttgt ataacggatt agaggcaaca ctgtggagac    180

atattgtatg gaatgccggc tattttggtg tgattttcca agttcgtgac atgttaccca    240

aggcaaagga caagacccag aaaaccatca acgatttggt gggtggtatg attggtggta    300

tcgttggtac tgccttgaac attccattcg atgttgtcaa atccagaatc caaagtgcaa    360

ccattatgga aggtcaggtc cgtaaataca attggacttg gccctctctt ggcattgtct    420

tgagggaaga aggtgtctct gcattgtata aaggattcct tccaaaagtc ctgagattgg    480

gtccaggtgg tggtattcta cttgttgtct tcacaaactg tatggacttc tttagaggcc    540

aatactatgg agacaagaaa tagtagctgg gttcttcacc atcaggttta tacaccctcc    600

acgacgtcca ttctatacta tactatgcta ttcgatgcta ttcgatgcta tcctgcccta    660

tcttatctaa tcttatctta tcttacaaaa ttatatactt tccttgtttc tttcacctcc    720
```

```
tcctttatag atcaattgat ttgataatac acttatacac attgacgtct gttgatatct    780
tcatacaaaa aaccttaaaa catagtgcaa agtcacgtgc acgccttaaa aatgcagctg    840
agcccctttc ccacttctct cccttcggat gccccacctg actattttca cttcccaatt    900
cgagcatcct cctccagtcc ccgcagactc aagagataag aaaccttaca gagactgttc    960
ccatcctcct atgctcaacg tgtcctgtat ctacattgcg gccgcggatc cctcgaggag   1020
tccatcggtt cctgtcagat gggatactct tgacgtggaa aattcaaaca gaaaaaaaac   1080
cccaataatg aaaaataaca ctacgttata tccgtggtat cctctatcgt atcgtatcgt   1140
agcgtatcgt agcgtaccgt atcacagtat agtctaatat tccgtatctt attgtatcct   1200
atcctattcg atcctattgt atttcagtgc accattttaa tttctattgc tataatgtcc   1260
ttattagttg ccactgtgag gtgaccaatg gacgagggcg agccgttcag aagccgcgaa   1320
gggtgttctt cccatgaatt tcttaaggag ggcggctcag ctccgagagt gaggcgagac   1380
gtctcggtca gcgtatcccc cttcctcggc ttttacaaat gatgcgctct taatagtgtg   1440
tcgttatcct tttggcattg acgggggagg gaaattgatt gagcgcatcc atatttttgc   1500
ggactgctga ggacaatggt ggtttttccg ggtggcgtgg gctacaaatg atacgatggt   1560
tttttctttt tcggagaagg cgtataaaaa ggacacggag aacccattta ttctaaaaac   1620
agttgagctt ctttaattat tttttgatat aatattctat tattatatat tttcttccca   1680
ataaaacaaa ataaaacaaa acacagcaaa acacaaaaat tctagataaa atgaaagagt   1740
tctttcccga aatcaaggaa atcaaatatg aaggcgcaga atcgaaaaat gatttggctt   1800
tcaaatacta taacaaggat gaagtcttgg ggggaaagac tatgaaggag catctaagat   1860
tcgccatgtc atattggcat accttaaaag ctcagggtgt tgatatgttc ggtggcgaaa   1920
cgatggatag agaatggaac aaatacgaaa atgtgcttga aagggcaaaa gccagagcca   1980
atgccgggtt tgagtttatg caaaaattgg gtttagaata cttttgtttc cacgatcgag   2040
acattatcga tgagtctatg atgctagcag attctaacaa gttgctcgat gagatagtcg   2100
atcatataga ggagttgatg aaaaagaccg gaaggaaatt gttatggggt acaaccaacg   2160
cattttccca cccacgtttt gtacatggag caagcacctc accaaatgct gatgtattcg   2220
cgtatgcagc agcacaagtc aaaaaggcca tggacattac taatagacta ggaggagaaa   2280
actatgtttt atggggggt agagaaggtt acgaaactct tctaaacaca aattctgaac   2340
ttgaatatga caattttgca agatttttga agatggttgt tgactacaag gaaaagattg   2400
gttttaaggg ccaattgctt attgaaccta aaccaaaaga gcctacaaaa catcaatatg   2460
attttgacac agcaactgtt ttggcattct taaggaagta taatctggac aagtattaca   2520
aggttaacat cgaagccaat catgctactc ttgcgggtca tacattccaa cacgagttaa   2580
acttagctag gattaatggg gtattaggca gtatagatgc taatcaggga gatatgttat   2640
taggttggga caccgatcaa ttcccgacta atatctatga tacgactctg gctatgtatg   2700
aggttgtgaa aaataagggt ctgggttccg gcggtctaaa tttcgatgct aaagttcgga   2760
gaggttcatt tgaggataag gacctatttc tggcatatat cgctgggatg gatacattcg   2820
cgaagggttt gaagattgca tatcgtttgt atgaagataa ggtctttgaa gatttcatag   2880
acaaaagata tgaaagttac aaaactggaa ttggaaaaga cataattgac ggaaaagtcg   2940
gttttgagga actctcaaaa tacgcagaga cattgaccga agtgaaaaac aactctggta   3000
gacaagagat gttggaatcg aaactcaacc agtacatttt tgaagttaaa tgattaatta   3060
```

```
acatctgaat gtaaaatgaa cattaaaatg aattactaaa ctttacgtct actttacaat   3120
ctataaactt tgtttaatca tataacgaaa tacactaata cacaatcctg tacgtatgta   3180
atacttttat ccatcaagga ttgagaaaaa aaagtaatga ttccctgggc cattaaaact   3240
tagacccccca agcttggata ggtcactctc tattttcgtt tctcccttcc ctgatagaag   3300
ggtgatatgt aattaagaat aatatataat tttataataa aagaattcgc ccttacatat   3360
gataacttcg tataatgtat gctatacgaa gttatcatag cctcatgaaa tcagccattt   3420
gcttttgttc aacgatcttt tgaaattgtt gttgttcttg gtagttaagt tgatccatct   3480
tggcttatgt tgtgtgtatg ttgtagttat tcttagtata ttcctgtcct gagtttagtg   3540
aaacataata tcgccttgaa atgaaaatgc tgaaattcgt cgacatacaa tttttcaaac   3600
ttttttttt tcttggtgca cggacatgtt tttaaaggaa gtactctata ccagttattc   3660
ttcacaaatt taattgctgg agaatagatc ttcaacgctt taataaagta gtttgtttgt   3720
caaggatggc gtcatacaaa gaaagatcag aatcacacac ttcccctgtt gctaggagac   3780
ttttctccat catggaggaa aagaagtcta acctttgtgc atcattggat attactgaaa   3840
ctgaaaagct tctctctatt ttggacacta ttggtcctta catctgtcta gttaaaacac   3900
acatcgatat tgtttctgat tttacgtatg aaggaactgt gttgcctttg aaggagcttg   3960
ccaagaaaca taattttatg atttttgaag atagaaaatt tgctgatatt ggtaacactg   4020
ttaaaaatca atataaatct ggtgtcttcc gtattgccga atgggctgac atcactaatg   4080
cacatggtgt aacgggtgca ggtattgttt ctggcttgaa ggaggcagcc caagaaacaa   4140
ccagtgaacc tagaggtttg ctaatgcttg ctgagttatc atcaaagggt tctttagcat   4200
atggtgaata tacagaaaaa acagtagaaa ttgctaaatc tgataaagag tttgtcattg   4260
gttttattgc gcaacacgat atgggcggta gagaagaagg ttttgactgg atcattatga   4320
ctccaggggt tggtttagat gacaaaggtg atgcacttgg tcaacaatat agaactgttg   4380
atgaagttgt aaagactgga acggatatca taattgttgg tagaggtttg tacggtcaag   4440
gaagagatcc tatagagcaa gctaaaagat accaacaagc tggttggaat gcttatttaa   4500
acagatttaa atgattctta cacaaagatt tgatacatgt acactagttt aaataagcat   4560
gaaaagaatt acacaagcaa aaaaaaaaaa ataaatgagg tactttacgt tcacctacaa   4620
ccaaaaaaac tagatagagt aaaatcttaa gatttagaaa aagttgttta acaaaggctt   4680
tagtatgtga atttttaatg tagcaaagcg ataactaata aacataaaca aaagtatggt   4740
tttctttatc agtcaaatca ttatcgattg attgttccgc gtatctgcag ataacttcgt   4800
ataatgtatg ctatacgaag ttatagatcc gcggccgcgt gtaaatatct acgtgtttag   4860
catttcctat atacatgact gtgtgtcctc tggttttcat ttcgtttggt tctcattcct   4920
cttggcagct tcactaaaca actggtcgtg ttgttcgtcg tgttttgcct tgaagaatgt   4980
atagtgcaac acaacgtctt cgatgtttct cattgccgga tctctggaaa actctggatc   5040
gataaagaaa aacaagggca tatcaacctc ctcacccttg gccaaccgct gctcttcaaa   5100
gcagaaacac tggatcttgt tgaagtaagg cgctacatga tcgggagtca ctgagtatgt   5160
ggccatgcca gtaatgtcct tgtcacttat attcttggct ttgtagaagg ccaaggcagt   5220
ctctccgggg acaacataaa cttctctttg ttgcggtaca aacttccatg gtaacgcacc   5280
acttgtctcc gccgtaaagg atacccgcag tcttctctct gtagctactg gagttagctt   5340
gtccctcgtg aacctgctct tgtcggtgat tggtgtacca ccccatccag tacgttgaca   5400
aattgcacga tacaagggga cactcgcata cgataatgca aggaaaatca tcatcatgga   5460
```

```
taacgaataa taaatggtgg tttgcctctc atacctcttc ttttctccat ggtacttatc   5520

tctcaatgct tggaactctg ccaaagacat ctttggaagc tccttccggt ttgctcgtgg   5580

tgatacctga tgttctgatg acccaccacc aggaacttcg tattttgcaa tacaactggc   5640

atgtacatat ctcctatgga gggcaagtcc gggaatcagc ccaacatccc gaaggggcgc   5700

ttgtatacta gttctgaaaa tccgccttaa catcaccgta cagagacacc ttcaccaata   5760

tgttctccaa gaccatgggg cactagaagt tatccattga cgttcatcaa cctagtgatg   5820

tcaaatttca tcgccgtttc ccaactcgcg ggatttgctt ttgagcatct cgtttgattc   5880

acgacaactt gttctacatt ctgctgcggg cc                                 5912
```

<210> SEQ ID NO 53
<211> LENGTH: 5912
<212> TYPE: DNA
<213> ORGANISM: Artificial Sequence
<220> FEATURE:
<223> OTHER INFORMATION: LgXI-PDC-URA3-loxP-XDH integration fragment

<400> SEQUENCE: 53

```
ctgcttgtgc aggtgcaacc gagtcgtttg ttgttgtccc ctttgagttg gtgaagatcc     60

ggttacagga taagtccaag gcgtccatgt atagcggtcc cattgatgtt ctaatgaaga    120

cagtcaaaaa tgaaggtatc ttggccttgt ataacggatt agaggcaaca ctgtggagac    180

atattgtatg gaatgccggc tattttggtg tgattttcca agttcgtgac atgttaccca    240

aggcaaagga caagacccag aaaaccatca acgatttggt gggtggtatg attggtggta    300

tcgttggtac tgccttgaac attccattcg atgttgtcaa atccagaatc caaagtgcaa    360

ccattatgga aggtcaggtc cgtaaataca attggacttg gccctctctt ggcattgtct    420

tgagggaaga aggtgtctct gcattgtata aaggattcct tccaaaagtc ctgagattgg    480

gtccaggtgg tggtattcta cttgttgtct tcacaaactg tatggacttc tttagaggcc    540

aatactatgg agacaagaaa tagtagctgg gttcttcacc atcaggttta tacaccctcc    600

acgacgtcca ttctatacta tactatgcta ttcgatgcta ttcgatgcta tcctgcccta    660

tcttatctaa tcttatctta tcttacaaaa ttatatactt tccttgtttc tttcacctcc    720

tcctttatag atcaattgat ttgataatac acttatacac attgacgtct gttgatatct    780

tcatacaaaa aaccttaaaa catagtgcaa agtcacgtgc acgccttaaa aatgcagctg    840

agcccctttc ccacttctct cccttcggat gccccacctg actattttca cttcccaatt    900

cgagcatcct cctccagtcc ccgcagactc aagagataag aaaccttaca gagactgttc    960

ccatcctcct atgctcaacg tgtcctgtat ctacattgcg gccgcggatc cctcgaggag   1020

tccatcggtt cctgtcagat gggatactct tgacgtggaa aattcaaaca gaaaaaaaac   1080

cccaataatg aaaaataaca ctacgttata tccgtggtat cctctatcgt atcgtatcgt   1140

agcgtatcgt agcgtaccgt atcacagtat agtctaatat tccgtatctt attgtatcct   1200

atcctattcg atcctattgt atttcagtgc accattttaa tttctattgc tataatgtcc   1260

ttattagttg ccactgtgag gtgaccaatg gacgagggcg agccgttcag aagccgcgaa   1320

gggtgttctt cccatgaatt tcttaaggag ggcggctcag ctccgagagt gaggcgagac   1380

gtctcggtca gcgtatcccc cttcctcggc ttttacaaat gatgcgctct taatagtgtg   1440

tcgttatcct tttggcattg acgggggagg gaaattgatt gagcgcatcc atatttttgc   1500

ggactgctga ggacaatggt ggtttttccg ggtggcgtgg gctacaaatg atacgatggt   1560
```

```
tttttctttt tcggagaagg cgtataaaaa ggacacggag aacccattta ttctaaaaac   1620
agttgagctt ctttaattat tttttgatat aatattctat tattatatat tttcttccca   1680
ataaaacaaa ataaaacaaa acacagcaaa acacaaaaat tctagataaa atgaaggagt   1740
ttttcccgga aatcaaagag attaagtatg aaggagccga atcgaaaaat gacttagcct   1800
tcaagtatta caataaggac gaagttcttg gtggcaaaac tatgaaagag catttgaggt   1860
ttgccatgtc ttattggcat accttaaaag ctcaaggagt agatatgttt ggtggagaaa   1920
ccatggatag agaatggaac aaatatgaga atgtattgga gagagctaaa gccagagcaa   1980
acgctggttt tgaattcatg cagaaattgg gtttagaata cttttgtttt catgatcggg   2040
atataattga tgaatcgatg atgctggcgg atagcaataa gctattggac gaaatagtgg   2100
accatataga ggagttgatg aaaaagacag gtcgtaaact attatggggc actacgaatg   2160
cttttagtca tccaagattt gttcacggtg catctacatc accaaatgca gatgtctttg   2220
catacgcagc agcacaagtc aaaaaggcta tggatattac gaatagattg ggtggagaaa   2280
actatgtctt atggggtggt agagaaggtt acgagacttt acttaacacc aacagtgaac   2340
ttgaatatga caattttgca aggttcttga aaatggtagt ggactacaag gagaaaatag   2400
gctttaaagg acaactccta atcgaaccta aacccaagga accaactaag caccaatatg   2460
attttgatac tgcgacagtt ttagcattct tgaggaagta taatctcgat aagtactaca   2520
aagttaacat cgaagcaaac catgcaactc tggctggtca taccttccaa cacgaattga   2580
acctcgccag gattaatggg gttttaggct caatagatgc gaatcagggc gatatgctac   2640
taggttggga tacagatcaa ttccctacaa atatctatga caccactttg gctatgtatg   2700
aggttgttaa aaacaagggt ttgggctctg gaggtcttaa ctttgatgct aaagttcgac   2760
gtggttcatt cgaagataag gacttatttc tggcctacat tgctggaatg gatacgtttg   2820
caaagggatt gaaaattgca tatagactat atgaagataa ggtctttgaa gatttcattg   2880
acaaaagata cgaatcttat aagactggta ttgggaagga tatcattgat gggaaagtcg   2940
gattcgaaga gttatccaaa tatgctgaga cattaacaga agtgaaaaac aattcaggga   3000
gacaagagat gcttgaatcc aagctaaatc agtacatctt tgaagttaaa tgattaatta   3060
acatctgaat gtaaaatgaa cattaaaatg aattactaaa ctttacgtct actttacaat   3120
ctataaactt tgtttaatca tataacgaaa tacactaata cacaatcctg tacgtatgta   3180
atacttttat ccatcaagga ttgagaaaaa aaagtaatga ttccctgggc cattaaaact   3240
tagaccccca agcttggata ggtcactctc tattttcgtt tctcccttcc ctgatagaag   3300
ggtgatatgt aattaagaat aatatataat tttataataa aagaattcgc ccttacatat   3360
gataacttcg tataatgtat gctatacgaa gttatcatag cctcatgaaa tcagccattt   3420
gcttttgttc aacgatcttt tgaaattgtt gttgttcttg gtagttaagt tgatccatct   3480
tggcttatgt tgtgtgtatg ttgtagttat tcttagtata ttcctgtcct gagtttagtg   3540
aaacataata tcgccttgaa atgaaaatgc tgaaattcgt cgacatacaa tttttcaaac   3600
ttttttttt tcttggtgca cggacatgtt tttaaaggaa gtactctata ccagttattc   3660
ttcacaaatt taattgctgg agaatagatc ttcaacgctt taataaagta gtttgtttgt   3720
caaggatggc gtcatacaaa gaaagatcag aatcacacac ttcccctgtt gctaggagac   3780
ttttctccat catggaggaa aagaagtcta acctttgtgc atcattggat attactgaaa   3840
ctgaaaagct tctctctatt ttggacacta ttggtcctta catctgtcta gttaaaacac   3900
acatcgatat tgtttctgat tttacgtatg aaggaactgt gttgcctttg aaggagcttg   3960
```

```
ccaagaaaca taattttatg atttttgaag atagaaaatt tgctgatatt ggtaacactg   4020
ttaaaaatca atataaatct ggtgtcttcc gtattgccga atgggctgac atcactaatg   4080
cacatggtgt aacgggtgca ggtattgttt ctggcttgaa ggaggcagcc caagaaacaa   4140
ccagtgaacc tagaggtttg ctaatgcttg ctgagttatc atcaaagggt tctttagcat   4200
atggtgaata tacagaaaaa acagtagaaa ttgctaaatc tgataaagag tttgtcattg   4260
gttttattgc gcaacacgat atgggcggta gagaagaagg ttttgactgg atcattatga   4320
ctccaggggt tggtttagat gacaaaggtg atgcacttgg tcaacaatat agaactgttg   4380
atgaagttgt aaagactgga acggatatca taattgttgg tagaggtttg tacggtcaag   4440
gaagagatcc tatagagcaa gctaaaagat accaacaagc tggttggaat gcttatttaa   4500
acagatttaa atgattctta cacaaagatt tgatacatgt acactagttt aaataagcat   4560
gaaaagaatt acacaagcaa aaaaaaaaaa ataaatgagg tactttacgt tcacctacaa   4620
ccaaaaaaac tagatagagt aaaatcttaa gatttagaaa aagttgttta acaaaggctt   4680
tagtatgtga atttttaatg tagcaaagcg ataactaata aacataaaca aaagtatggt   4740
tttctttatc agtcaaatca ttatcgattg attgttccgc gtatctgcag ataacttcgt   4800
ataatgtatg ctatacgaag ttatagatcc gcggccgcgt gtaaatatct acgtgtttag   4860
catttcctat atacatgact gtgtgtcctc tggttttcat ttcgtttggt tctcattcct   4920
cttggcagct tcactaaaca actggtcgtg ttgttcgtcg tgttttgcct tgaagaatgt   4980
atagtgcaac acaacgtctt cgatgtttct cattgccgga tctctggaaa actctggatc   5040
gataaagaaa aacaagggca tatcaacctc ctcacccttg gccaaccgct gctcttcaaa   5100
gcagaaacac tggatcttgt tgaagtaagg cgctacatga tcgggagtca ctgagtatgt   5160
ggccatgcca gtaatgtcct tgtcacttat attcttggct ttgtagaagg ccaaggcagt   5220
ctctccgggg acaacataaa cttctctttg ttgcggtaca aacttccatg gtaacgcacc   5280
acttgtctcc gccgtaaagg atacccgcag tcttctctct gtagctactg gagttagctt   5340
gtccctcgtg aacctgctct tgtcggtgat tggtgtacca ccccatccag tacgttgaca   5400
aattgcacga tacaagggga cactcgcata cgataatgca aggaaaatca tcatcatgga   5460
taacgaataa taaatggtgg tttgcctctc atacctcttc ttttctccat ggtacttatc   5520
tctcaatgct tggaactctg ccaaagacat ctttggaagc tccttccggt ttgctcgtgg   5580
tgatacctga tgttctgatg acccaccacc aggaacttcg tattttgcaa tacaactggc   5640
atgtacatat ctcctatgga gggcaagtcc gggaatcagc ccaacatccc gaaggggcgc   5700
ttgtatacta gttctgaaaa tccgccttaa catcaccgta cagagacacc ttcaccaata   5760
tgttctccaa gaccatgggg cactagaagt tatccattga cgttcatcaa cctagtgatg   5820
tcaaatttca tcgccgtttc ccaactcgcg ggatttgctt ttgagcatct cgtttgattc   5880
acgacaactt gttctacatt ctgctgcggg cc                                 5912
```

<210> SEQ ID NO 54
<211> LENGTH: 5912
<212> TYPE: DNA
<213> ORGANISM: Artificial Sequence
<220> FEATURE:
<223> OTHER INFORMATION: LgXI-PDC-URA3-loxP-XDH integration fragment

<400> SEQUENCE: 54

```
ctgcttgtgc aggtgcaacc gagtcgtttg ttgttgtccc ctttgagttg gtgaagatcc     60
```

-continued

```
ggttacagga taagtccaag gcgtccatgt atagcggtcc cattgatgtt ctaatgaaga    120
cagtcaaaaa tgaaggtatc ttggccttgt ataacggatt agaggcaaca ctgtggagac    180
atattgtatg gaatgccggc tattttggtg tgattttcca agttcgtgac atgttaccca    240
aggcaaagga caagacccag aaaaccatca acgatttggt gggtggtatg attggtggta    300
tcgttggtac tgccttgaac attccattcg atgttgtcaa atccagaatc caaagtgcaa    360
ccattatgga aggtcaggtc cgtaaataca attggacttg gccctctctt ggcattgtct    420
tgagggaaga aggtgtctct gcattgtata aaggattcct tccaaaagtc ctgagattgg    480
gtccaggtgg tggtattcta cttgttgtct tcacaaactg tatggacttc tttagaggcc    540
aatactatgg agacaagaaa tagtagctgg gttcttcacc atcaggttta tacaccctcc    600
acgacgtcca ttctatacta tactatgcta ttcgatgcta ttcgatgcta tcctgcccta    660
tcttatctaa tcttatctta tcttacaaaa ttatatactt tccttgtttc tttcacctcc    720
tcctttatag atcaattgat ttgataatac acttatacac attgacgtct gttgatatct    780
tcatacaaaa aaccttaaaa catagtgcaa agtcacgtgc acgccttaaa aatgcagctg    840
agcccctttc ccacttctct cccttcggat gccccacctg actattttca cttcccaatt    900
cgagcatcct cctccagtcc ccgcagactc aagagataag aaaccttaca gagactgttc    960
ccatcctcct atgctcaacg tgtcctgtat ctacattgcg gccgcggatc cctcgaggag   1020
tccatcggtt cctgtcagat gggatactct tgacgtggaa aattcaaaca gaaaaaaaac   1080
cccaataatg aaaaataaca ctacgttata tccgtggtat cctctatcgt atcgtatcgt   1140
agcgtatcgt agcgtaccgt atcacagtat agtctaatat tccgtatctt attgtatcct   1200
atcctattcg atcctattgt atttcagtgc accattttaa tttctattgc tataatgtcc   1260
ttattagttg ccactgtgag gtgaccaatg gacgagggcg agccgttcag aagccgcgaa   1320
gggtgttctt cccatgaatt tcttaaggag ggcggctcag ctccgagagt gaggcgagac   1380
gtctcggtca gcgtatcccc cttcctcggc ttttacaaat gatgcgctct taatagtgtg   1440
tcgttatcct tttggcattg acgggggagg gaaattgatt gagcgcatcc atatttttgc   1500
ggactgctga ggacaatggt ggtttttccg ggtggcgtgg gctacaaatg atacgatggt   1560
tttttctttt tcggagaagg cgtataaaaa ggacacggag aacccattta ttctaaaaac   1620
agttgagctt ctttaattat tttttgatat aatattctat tattatatat tttcttccca   1680
ataaaacaaa ataaaacaaa acacagcaaa acacaaaaat tctagataaa atgaaggagt   1740
tcttcccgga aatcaaagag atcaaatatg aaggagccga gagcaaaaat gatttggcat   1800
tcaagtacta taacaaggat gaagttctag gtggaaagac catgaaggaa catttgaggt   1860
ttgccatgag ttattggcat acccttaaag cacaaggcgt tgatatgttt ggtggagaaa   1920
caatggatag agaatggaac aaatatgaaa atgttttaga aagggcgaaa gctagagcaa   1980
acgctggctt tgaattcatg cagaaattag gattagagta cttttgtttc catgatcgtg   2040
atattattga tgaatcaatg atgctagcag actctaataa gttattagat gaaattgtgg   2100
atcacatcga ggagttgatg aaaaagacag gcagaaaatt gttgtggggg acaactaatg   2160
cgttttccca tccacgtttc gtgcatggtg cttcgacctc cccaaacgct gacgtgtttg   2220
cctacgctgc tgctcaagtc aaaaaggcta tggatataac taatagattg ggtggagaaa   2280
actatgtcct ttggggagga agagaaggtt atgaaacatt attgaatacc aattcggaac   2340
tcgaatatga taactttgca agatttctga agatggttgt tgactataag gagaaaattg   2400
gttttaaggg tcaacttcta attgaaccca aaccaaaaga gcctacaaaa catcagtatg   2460
```

```
atttcgacac tgcaactgtt ttagcatttc tacgaaagta taatcttgac aagtattaca   2520
aagttaacat tgaagctaat catgcaactt tagccggtca cacatttcaa cacgagttaa   2580
acttggccag aatcaatggc gtattaggtt caatagacgc caatcaaggg gatatgttgc   2640
tgggttggga cacggatcaa tttcctacga atatctacga taccacttta gctatgtacg   2700
aagtagtgaa aaacaagggt cttggttctg gtggactcaa tttcgacgca aaagttcgga   2760
ggggaagttt tgaagataag gaccttttct tggcgtatat agcggggatg gatacatttg   2820
caaagggttt aaagattgca tataggttat atgaagataa agtatttgaa gatttcattg   2880
acaagagata cgaaagttac aaaactggta ttgggaaaga cataattgat ggcaaagttg   2940
gctttgagga attgtctaaa tatgcagaga cattgactga agtcaaaaac aattcaggga   3000
gacaagagat gctcgaatct aagctgaatc agtacatatt cgaggtcaaa tgattaatta   3060
acatctgaat gtaaaatgaa cattaaaatg aattactaaa ctttacgtct actttacaat   3120
ctataaactt tgtttaatca tataacgaaa tacactaata cacaatcctg tacgtatgta   3180
atacttttat ccatcaagga ttgagaaaaa aaagtaatga ttccctgggc cattaaaact   3240
tagaccccca agcttggata ggtcactctc tattttcgtt tctcccttcc ctgatagaag   3300
ggtgatatgt aattaagaat aatatataat tttataataa aagaattcgc ccttacatat   3360
gataacttcg tataatgtat gctatacgaa gttatcatag cctcatgaaa tcagccattt   3420
gcttttgttc aacgatcttt tgaaattgtt gttgttcttg gtagttaagt tgatccatct   3480
tggcttatgt tgtgtgtatg ttgtagttat tcttagtata ttcctgtcct gagtttagtg   3540
aaacataata tcgccttgaa atgaaaatgc tgaaattcgt cgacatacaa tttttcaaac   3600
ttttttttt tcttggtgca cggacatgtt tttaaaggaa gtactctata ccagttattc   3660
ttcacaaatt taattgctgg agaatagatc ttcaacgctt taataaagta gtttgtttgt   3720
caaggatggc gtcatacaaa gaaagatcag aatcacacac ttcccctgtt gctaggagac   3780
ttttctccat catggaggaa aagaagtcta acctttgtgc atcattggat attactgaaa   3840
ctgaaaagct tctctctatt ttggacacta ttggtcctta catctgtcta gttaaaacac   3900
acatcgatat tgtttctgat tttacgtatg aaggaactgt gttgcctttg aaggagcttg   3960
ccaagaaaca taattttatg atttttgaag atagaaaatt tgctgatatt ggtaacactg   4020
ttaaaaatca atataaatct ggtgtcttcc gtattgccga atgggctgac atcactaatg   4080
cacatggtgt aacgggtgca ggtattgttt ctggcttgaa ggaggcagcc caagaaacaa   4140
ccagtgaacc tagaggtttg ctaatgcttg ctgagttatc atcaaagggt tctttagcat   4200
atggtgaata tacagaaaaa acagtagaaa ttgctaaatc tgataaagag tttgtcattg   4260
gttttattgc gcaacacgat atgggcggta gagaagaagg ttttgactgg atcattatga   4320
ctccaggggt tggtttagat gacaaaggtg atgcacttgg tcaacaatat agaactgttg   4380
atgaagttgt aaagactgga acggatatca taattgttgg tagaggtttg tacggtcaag   4440
gaagagatcc tatagagcaa gctaaaagat accaacaagc tggttggaat gcttatttaa   4500
acagatttaa atgattctta cacaaagatt tgatacatgt acactagttt aaataagcat   4560
gaaaagaatt acacaagcaa aaaaaaaaaa ataaatgagg tactttacgt tcacctacaa   4620
ccaaaaaaac tagatagagt aaaatcttaa gatttagaaa aagttgttta acaaaggctt   4680
tagtatgtga atttttaatg tagcaaagcg ataactaata aacataaaca aaagtatggt   4740
tttctttatc agtcaaatca ttatcgattg attgttccgc gtatctgcag ataacttcgt   4800
```

```
ataatgtatg ctatacgaag ttatagatcc gcggccgcgt gtaaatatct acgtgtttag   4860

catttcctat atacatgact gtgtgtcctc tggttttcat ttcgtttggt tctcattcct   4920

cttggcagct tcactaaaca actggtcgtg ttgttcgtcg tgttttgcct tgaagaatgt   4980

atagtgcaac acaacgtctt cgatgtttct cattgccgga tctctggaaa actctggatc   5040

gataaagaaa aacaagggca tatcaacctc ctcacccttg gccaaccgct gctcttcaaa   5100

gcagaaacac tggatcttgt tgaagtaagg cgctacatga tcgggagtca ctgagtatgt   5160

ggccatgcca gtaatgtcct tgtcacttat attcttggct ttgtagaagg ccaaggcagt   5220

ctctccgggg acaacataaa cttctctttg ttgcggtaca aacttccatg gtaacgcacc   5280

acttgtctcc gccgtaaagg atacccgcag tcttctctct gtagctactg gagttagctt   5340

gtccctcgtg aacctgctct tgtcggtgat tggtgtacca ccccatccag tacgttgaca   5400

aattgcacga tacaagggga cactcgcata cgataatgca aggaaaatca tcatcatgga   5460

taacgaataa taaatggtgg tttgcctctc atacctcttc ttttctccat ggtacttatc   5520

tctcaatgct tggaactctg ccaaagacat ctttggaagc tccttccggt ttgctcgtgg   5580

tgatacctga tgttctgatg acccaccacc aggaacttcg tattttgcaa tacaactggc   5640

atgtacatat ctcctatgga gggcaagtcc gggaatcagc ccaacatccc gaaggggcgc   5700

ttgtatacta gttctgaaaa tccgccttaa catcaccgta cagagacacc ttcaccaata   5760

tgttctccaa gaccatgggg cactagaagt tatccattga cgttcatcaa cctagtgatg   5820

tcaaatttca tcgccgtttc ccaactcgcg ggatttgctt ttgagcatct cgtttgattc   5880

acgacaactt gttctacatt ctgctgcggg cc                                 5912
```

```
<210> SEQ ID NO 55
<211> LENGTH: 5912
<212> TYPE: DNA
<213> ORGANISM: Artificial Sequence
<220> FEATURE:
<223> OTHER INFORMATION: LgXI-PDC-URA3-loxP-XDH integration fragment

<400> SEQUENCE: 55

ctgcttgtgc aggtgcaacc gagtcgtttg ttgttgtccc ctttgagttg gtgaagatcc     60

ggttacagga taagtccaag gcgtccatgt atagcggtcc cattgatgtt ctaatgaaga    120

cagtcaaaaa tgaaggtatc ttggccttgt ataacggatt agaggcaaca ctgtggagac    180

atattgtatg gaatgccggc tattttggtg tgattttcca agttcgtgac atgttaccca    240

aggcaaagga caagacccag aaaaccatca acgatttggt gggtggtatg attggtggta    300

tcgttggtac tgccttgaac attccattcg atgttgtcaa atccagaatc caaagtgcaa    360

ccattatgga aggtcaggtc cgtaaataca attggacttg gccctctctt ggcattgtct    420

tgagggaaga aggtgtctct gcattgtata aaggattcct tccaaaagtc ctgagattgg    480

gtccaggtgg tggtattcta cttgttgtct tcacaaactg tatggacttc tttagaggcc    540

aatactatgg agacaagaaa tagtagctgg gttcttcacc atcaggttta tacaccctcc    600

acgacgtcca ttctatacta tactatgcta ttcgatgcta ttcgatgcta tcctgcccta    660

tcttatctaa tcttatctta tcttacaaaa ttatatactt tccttgtttc tttcacctcc    720

tcctttatag atcaattgat ttgataatac acttatacac attgacgtct gttgatatct    780

tcatacaaaa aaccttaaaa catagtgcaa agtcacgtgc acgccttaaa aatgcagctg    840

agcccctttc ccacttctct cccttcggat gccccacctg actattttca cttcccaatt    900

cgagcatcct cctccagtcc ccgcagactc aagagataag aaaccttaca gagactgttc    960
```

```
ccatcctcct atgctcaacg tgtcctgtat ctacattgcg gccgcggatc cctcgaggag   1020
tccatcggtt cctgtcagat gggatactct tgacgtggaa aattcaaaca gaaaaaaaac   1080
cccaataatg aaaaataaca ctacgttata tccgtggtat cctctatcgt atcgtatcgt   1140
agcgtatcgt agcgtaccgt atcacagtat agtctaatat tccgtatctt attgtatcct   1200
atcctattcg atcctattgt atttcagtgc accattttaa tttctattgc tataatgtcc   1260
ttattagttg ccactgtgag gtgaccaatg gacgagggcg agccgttcag aagccgcgaa   1320
gggtgttctt cccatgaatt tcttaaggag ggcggctcag ctccgagagt gaggcgagac   1380
gtctcggtca gcgtatcccc cttcctcggc ttttacaaat gatgcgctct taatagtgtg   1440
tcgttatcct tttggcattg acgggggagg gaaattgatt gagcgcatcc atatttttgc   1500
ggactgctga ggacaatggt ggtttttccg ggtggcgtgg gctacaaatg atacgatggt   1560
ttttttcttt tcggagaagg cgtataaaaa ggacacggag aacccattta ttctaaaaac   1620
agttgagctt ctttaattat tttttgatat aatattctat tattatatat tttcttccca   1680
ataaaacaaa ataaaacaaa acacagcaaa acacaaaaat tctagataaa atgaaggagt   1740
tctttcctga aatcaaagag atcaaatatg agggtgcaga aagcaaaaat gacctggctt   1800
ttaagtatta caacaaggat gaagtattgg gtggcaaaac tatgaaggaa cacttaagat   1860
ttgctatgtc gtattggcat acgttgaagg cacaaggagt tgatatgttt gggggcgaaa   1920
ccatggatag agaatggaac aaatatgaga atgttttaga aagggcaaaa gccagagcta   1980
atgcaggctt tgagtttatg caaaagttgg gccttgaata cttctgtttt catgatcgag   2040
acattattga cgagtctatg atgctagctg acagtaataa gcttttagat gagattgttg   2100
atcatattga ggagttgatg aaaaagacag gaaggaagct tttgtggggg actacaaatg   2160
cattctccca tccacgtttt gttcacggtg cctcaacatc acccaacgcc gatgtattcg   2220
cgtacgctgc ggcgcaagtt aaaaaggcca tggatattac gaatagatta ggtggagaaa   2280
actatgttct atggggtgga agagaaggat atgaaacctt acttaatact aattctgaac   2340
tagaatatga caattttgca agatttctga aaatggtcgt ggactacaaa gagaagatag   2400
gttttaaggg acaactgttg atagaaccaa aaccgaagga accaactaag catcaatatg   2460
attttgatac tgcaactgtt ttggcattct taaggaagta taacttggac aagtactaca   2520
aagttaacat tgaggctaat catgctacat tagctggtca taccttccaa cacgaactca   2580
acctcgctag aatcaatggt gtactaggtt ctatcgatgc aaaccagggc gatatgttat   2640
tgggttggga tacagatcaa tttcctacaa atatctatga tactaccctt gctatgtacg   2700
aggttgtcaa aaacaaggga ttaggaagtg gtggtctaaa ctttgatgct aaagtccgga   2760
gaggttcatt cgaagataag gacttgttct tggcatacat agccgggatg gataccttttg   2820
ccaagggttt gaaaattgca tataggctct atgaagataa agttttcgag gactttattg   2880
ataagcgtta tgaatcctac aaaacgggta ttggaaaaga cataatagat gggaaagtcg   2940
gttttgagga actttccaaa tacgctgaga cactaactga agtgaaaaac aattcaggca   3000
gacaggaaat gttagaatct aaacttaatc agtacatttt cgaagtgaaa tgattaatta   3060
acatctgaat gtaaaatgaa cattaaaatg aattactaaa ctttacgtct actttacaat   3120
ctataaactt tgtttaatca tataacgaaa tacactaata cacaatcctg tacgtatgta   3180
atacttttat ccatcaagga ttgagaaaaa aaagtaatga ttccctgggc cattaaaact   3240
tagaccccca agcttggata ggtcactctc tattttcgtt tctcccttcc ctgatagaag   3300
```

```
ggtgatatgt aattaagaat aatatataat tttataataa aagaattcgc ccttacatat   3360
gataacttcg tataatgtat gctatacgaa gttatcatag cctcatgaaa tcagccattt   3420
gcttttgttc aacgatcttt tgaaattgtt gttgttcttg gtagttaagt tgatccatct   3480
tggcttatgt tgtgtgtatg ttgtagttat tcttagtata ttcctgtcct gagtttagtg   3540
aaacataata tcgccttgaa atgaaaatgc tgaaattcgt cgacatacaa tttttcaaac   3600
ttttttttt tcttggtgca cggacatgtt tttaaaggaa gtactctata ccagttattc   3660
ttcacaaatt taattgctgg agaatagatc ttcaacgctt taataaagta gtttgtttgt   3720
caaggatggc gtcatacaaa gaaagatcag aatcacacac ttcccctgtt gctaggagac   3780
ttttctccat catggaggaa aagaagtcta acctttgtgc atcattggat attactgaaa   3840
ctgaaaagct tctctctatt ttggacacta ttggtcctta catctgtcta gttaaaacac   3900
acatcgatat tgtttctgat tttacgtatg aaggaactgt gttgcctttg aaggagcttg   3960
ccaagaaaca taattttatg atttttgaag atagaaaatt tgctgatatt ggtaacactg   4020
ttaaaaatca atataaatct ggtgtcttcc gtattgccga atgggctgac atcactaatg   4080
cacatggtgt aacgggtgca ggtattgttt ctggcttgaa ggaggcagcc caagaaacaa   4140
ccagtgaacc tagaggtttg ctaatgcttg ctgagttatc atcaaagggt tctttagcat   4200
atggtgaata tacagaaaaa acagtagaaa ttgctaaatc tgataaagag tttgtcattg   4260
gttttattgc gcaacacgat atgggcggta gagaagaagg ttttgactgg atcattatga   4320
ctccaggggt tggtttagat gacaaaggtg atgcacttgg tcaacaatat agaactgttg   4380
atgaagttgt aaagactgga acggatatca taattgttgg tagaggtttg tacggtcaag   4440
gaagagatcc tatagagcaa gctaaaagat accaacaagc tggttggaat gcttatttaa   4500
acagatttaa atgattctta cacaaagatt tgatacatgt acactagttt aaataagcat   4560
gaaaagaatt acacaagcaa aaaaaaaaaa ataaatgagg tactttacgt tcacctacaa   4620
ccaaaaaaac tagatagagt aaaatcttaa gatttagaaa aagttgttta acaaaggctt   4680
tagtatgtga atttttaatg tagcaaagcg ataactaata aacataaaca aaagtatggt   4740
tttctttatc agtcaaatca ttatcgattg attgttccgc gtatctgcag ataacttcgt   4800
ataatgtatg ctatacgaag ttatagatcc gcggccgcgt gtaaatatct acgtgtttag   4860
catttcctat atacatgact gtgtgtcctc tggttttcat ttcgtttggt tctcattcct   4920
cttggcagct tcactaaaca actggtcgtg ttgttcgtcg tgttttgcct tgaagaatgt   4980
atagtgcaac acaacgtctt cgatgtttct cattgccgga tctctggaaa actctggatc   5040
gataaagaaa aacaagggca tatcaacctc ctcacccttg gccaaccgct gctcttcaaa   5100
gcagaaacac tggatcttgt tgaagtaagg cgctacatga tcgggagtca ctgagtatgt   5160
ggccatgcca gtaatgtcct tgtcacttat attcttggct ttgtagaagg ccaaggcagt   5220
ctctccgggg acaacataaa cttctctttg ttgcggtaca aacttccatg gtaacgcacc   5280
acttgtctcc gccgtaaagg atacccgcag tcttctctct gtagctactg gagttagctt   5340
gtccctcgtg aacctgctct tgtcggtgat tggtgtacca ccccatccag tacgttgaca   5400
aattgcacga tacaagggga cactcgcata cgataatgca aggaaaatca tcatcatgga   5460
taacgaataa taaatggtgg tttgcctctc atacctcttc ttttctccat ggtacttatc   5520
tctcaatgct tggaactctg ccaaagacat ctttggaagc tccttccggt ttgctcgtgg   5580
tgatacctga tgttctgatg acccaccacc aggaacttcg tattttgcaa tacaactggc   5640
atgtacatat ctcctatgga gggcaagtcc gggaatcagc ccaacatccc gaaggggcgc   5700
```

ttgtatacta gttctgaaaa tccgccttaa catcaccgta cagagacacc ttcaccaata 5760
tgttctccaa gaccatgggg cactagaagt tatccattga cgttcatcaa cctagtgatg 5820
tcaaatttca tcgccgtttc ccaactcgcg ggatttgctt ttgagcatct cgtttgattc 5880
acgacaactt gttctacatt ctgctgcggg cc 5912

<210> SEQ ID NO 56
<211> LENGTH: 7345
<212> TYPE: DNA
<213> ORGANISM: Artificial Sequence
<220> FEATURE:
<223> OTHER INFORMATION: StXI-PDC-CYB2A-loxP-XDH integration fragment

<400> SEQUENCE: 56
cgcagcagaa tgtagaacaa gttgtcgtga atcaaacgag atgctcaaaa gcaaatcccg 60
cgagttggga aacggcgatg aaatttgaca tcactaggtt gatgaacgtc aatggataac 120
ttctagtgcc ccatggtctt ggagaacata ttggtgaagg tgtctctgta cggtgatgtt 180
aaggcggatt ttcagaacta gtatacaagc gccccttcgg gatgttgggc tgattcccgg 240
acttgccctc cataggagat atgtacatgc cagttgtatt gcaaaatacg aagttcctgg 300
tggtgggtca tcagaacatc aggtatcacc acgagcaaac cggaaggagc ttccaaagat 360
gtctttggca gagttccaag cattgagaga taagtaccat ggagaaaaga agaggtatga 420
gaggcaaacc accatttatt attcgttatc catgatgatg attttccttg cattatcgta 480
tgcgagtgtc cccttgtatc gtgcaatttg tcaacgtact ggatggggtg gtacaccaat 540
caccgacaag agcaggttca cgagggacaa gctaactcca gtagctacag agagaagact 600
gcgggtatcc tttacggcgg agacaagtgg tgcgttacca tggaagtttg taccgcaaca 660
aagagaagtt tatgttgtcc ccggagagac tgccttggcc ttctacaaag ccaagaatat 720
aagtgacaag gacattactg gcatggccac atactcagtg actcccgatc atgtagcgcc 780
ttacttcaac aagatccagt gtttctgctt tgaagagcag cggttggcca agggtgagga 840
ggttgatatg cccttgtttt tctttatcga tccagagttt tccagagatc cggcaatgag 900
aaacatcgaa gacgttgtgt tgcactatac attcttcaag gcaaaaacacg acgaacaaca 960 cgaccagttg tttagtgaag ctgccaagag gaatgagaac caaacgaaat gaaaaccaga 1020
ggacacacag tcatgtatat aggaaatgct aaacacgtag atatttacac gcggccgcgg 1080
atccctcgag gagtccatcg gttcctgtca gatgggatac tcttgacgtg gaaaattcaa 1140
acagaaaaaa aaccccaata atgaaaaata acactacgtt atatccgtgg tatcctctat 1200
cgtatcgtat cgtagcgtat cgtagcgtac cgtatcacag tatagtctaa tattccgtat 1260
cttattgtat cctatcctat tcgatcctat tgtatttcag tgcaccattt taatttctat 1320
tgctataatg tccttattag ttgccactgt gaggtgacca atggacgagg gcgagccgtt 1380
cagaagccgc gaagggtgtt cttcccatga atttcttaag gagggcggct cagctccgag 1440
agtgaggcga gacgtctcgg tcagcgtatc cccccttcctc ggcttttaca aatgatgcgc 1500
tcttaatagt gtgtcgttat ccttttggca ttgacggggg agggaaattg attgagcgca 1560
tccatatttt tgcggactgc tgaggacaat ggtggttttt ccgggtggcg tgggctacaa 1620
atgatacgat ggtttttttc ttttcggaga aggcgtataa aaaggacacg gagaacccat 1680
ttattctaaa aacagttgag cttctttaat tattttttga tataatattc tattattata 1740
tattttcttc ccaataaaac aaaataaaac aaaacacagc aaaacacaaa aattctagaa 1800

```
tgaaggaata cttccctgaa atcaaagaga tcaaatatga aggtcctgaa tcgaaaaatg   1860
ttatggcatt caagtattac aacaaggacg aggtcatagg aggaaaacca atgagggaac   1920
atcttaagtt tgccatgtca tattggcata cgctaaaggc tcaggggttg gatatgttcg   1980
gtggagatac tatggatcgt gcatggaaca gatacgatga cgctttggag caagcgaaag   2040
ccagagctga tgccggcttc gagtttatgc aaaagattgg catggactat ttttgttttc   2100
atgatcgtga cattattaac gaagctatga ctttaaagga aacgaatagg ttattggatg   2160
aaattgttga ccatcttgag ggtttgatga aaaagactgg gatcaaattg ttgtggggta   2220
ctacaaatgc ttttagtcac ccaagattct tacatggtgg tgctaccgca ccgaatgccg   2280
acgtattcgc atacgcggca gctcaagtta aaaaggctat ggagattacc aaacggttgg   2340
gtggcgaaaa ctacgtatta tggggcggaa gagaaggata tgaaacattg ctaaatacca   2400
aatccgattt ggaatatgac aattttgcaa gatttctaca aatggttgtc gattacaagg   2460
agaaaattgg gttcgagggt caactactca tagagccaaa gccaaaagag cctaccaaac   2520
atcagtatga tttcgatact gcaacagttt taggcttttt gaggaagtac aatttggaca   2580
agcattacaa gatgaatatc gaagcaaacc acgccacttt agctggtcac acatttcaac   2640
acgaactgaa cttagcacgt attaacaatg tcatgggttc tattgatgct aatcaaggag   2700
atatgttact cggttgggat acagatcagt ttcccacaaa tatctacgac gctgttctag   2760
cgatgtatga agttatcaaa aacaatggcc tcgggaaggg tggtcttaat tttgatgcaa   2820
aagttcgaag gggttcattt gaagataagg acctatttct tgcatacata gccggaatgg   2880
ataccttttgc aaaaggttta accatagcat atagactgta tgaggataaa gtgtttgaag   2940
atttccaaga caagagatat gaaagctata agacgggtat aggcaaagat attgttgagg   3000
gaaaagtcgg attcgaggaa ctggctgaat atgtggaaaa ccttgcagaa atcaaaaata   3060
ctagtggtag acaggagatg cttgaatcta ttttgaactc ctatatatta gaagccaagt   3120
aattaattaa catctgaatg taaaatgaac attaaaatga attactaaac tttacgtcta   3180
ctttacaatc tataaacttt gtttaatcat ataacgaaat acactaatac acaatcctgt   3240
acgtatgtaa tacttttatc catcaaggat tgagaaaaaa aagtaatgat tccctgggcc   3300
attaaaactt agacccccaa gcttggatag gtcactctct attttcgttt ctcccttccc   3360
tgatagaagg gtgatatgta attaagaata atatataatt ttataataaa agaattcgcc   3420
cttacatatg ataacttcgt ataatgtatg ctatacgaag ttatgttggt ggtgtgtttt   3480
gttggaacgt acattagatg cataatgcgt gacaccgcca tgatggttgt attctaccaa   3540
tgagacatgg ccgctgatcc tgttgtgtgg gtcatgggac atcacctctt ggggggggatt   3600
ctcctataat tggcaccgtg tatgcctcaa ccactaactt ccaccctata actgaatata   3660
ttacataagc aaatctactt tttgtttgtg ttgatcgcca tcgttgaaat tcgcgcaact   3720
tctggtggct caacgctgct gttctatcgg tatcctaaga gatgtctttg ccctgagtct   3780
agggtaaact atccaccttc gttgctgttt gactagacag ctactaactt tacggtagta   3840
aatgaataac ggctcgctct catgatcact tctctacatc accctaacaa gtgtattatt   3900
tttttttcag gtgggtgttg ctgttggtgc tagccttagt gccctcgtta atagttgaac   3960
aaacactggc atttggagta taatgaaaag ggatcactac cccccgcttc ctgttccgct   4020
tctcccttcc ggaaaaacca cccacccttt cttttccccc actaatgtat gaatttttcc   4080
gttcccaggg gaatggccca cttggttctc tgttaaccca cacaattttg acgcatccca   4140
cacacctttt ttttttctac cccacacttt cccttgaaaa atctccaatt tgaactggca   4200
```

```
atttttcaccc cccaccactt gcattcatta gtgagtcaat ccatcccgcg gtcggagatt   4260
cggaatccac ctactggtaa tctgtaatct atattcccgc tgaccctttta taaatgaact   4320
attgtcgtca attgcggtag tgctccaaca aattgtaagg accttcttta accttttcga   4380
ttcaatccat ctccacataa acctagttgc acacaatgtt actcagatca ctaaactctt   4440
ctgctcgttg tgtcaaacaa acaaccagaa caaaggttag gtatctcagc cacgtcagtg   4500
gtgcaagcat ggcgaaacct acattgaaga acaactcgag agaatccaac aaatccagaa   4560
actatctaat tgctgctgtg acagcattgg ctgtatcaac ctcaattgga gttgccgtac   4620
atgtgaagga ccccttgtat aacgatgcta ccggcagtga ttctccgaga agtatatctg   4680
ttgacgagtt tgtcaagcat aattcacaaa acgactgttg gattgcaatc aatggcaagg   4740
tttatgattt cactgatttt attccaaacc atccaggtgg ggtacctcca ttagttaatc   4800
atgctggtta tgatggtact aaactttatg agaaattgca tccaaaaggt acaattgaga   4860
aattcttgcc aaaggataag tttctgggtg tgttagatgg tgaagcgcca aaattggaag   4920
cagactattt ggtggacgat gatgaacaag agagactgga ttatttgaac aacttacctc   4980
ctttgtcatc tattcagaat gtttatgatt tcgaatactt ggccaagaag attttaccta   5040
aagatgcctg ggcatattat tcttgtggtg ccgatgatga aatcacaatg agagaaaacc   5100
attatgctta tcaaagagtt tatttcagac caagaatttg tgttgatgtc aaggaagttg   5160
atacttctta tgaaatgtta ggcactaaaa cctctgttcc tttttatgta tctgccaccg   5220
ctttggctaa attaggccat cctgatggtg aatgctcaat tgctagaggc gctggtaagg   5280
aaggtgtcgt tcaaatgatt tcgacccttt cctcaatgtc attagatgaa attgccgctg   5340
ctagaatccc aggtgcaacc caatggttcc aattatacat taatgaggat agaaatgtcg   5400
ctaaaggtct ggtcaaacat gcagaagact tgggtatgaa ggctatcttt ataactgttg   5460
atgctccttc tctaggtaac agagaaaagg ataaaagatt aaagtttgtt aatgacaccg   5520
atgtcgattt gggtgattcc gcagatcgaa acagtggtgc ttcaaaggca ctatcttcgt   5580
tcattgatgc ttctgtctct tggaatgacg tcaaagcggt caagtcgtgg actaaattgc   5640
ctgtcttagt taaaggtgtt caaacagttg aagacgttat tgaagcttac gatgctggtt   5700
gtcaaggtgt tgttttgtca aaccacggtg gtaggcaact agatactgct cctcctccaa   5760
tcgaattatt agctgaaact gttccaactt tgaagagatt gggtaaatta agaccagatt   5820
ttgaaatttt aattgacggt ggtgtcaaaa gaggtaccga tattttgaaa gcagtcgcaa   5880
tcggtggcca agatgtcaga gtttcagttg gtatgggtag acctttctta tatgccaact   5940
cttgctatgg tgaagcaggt gttagaaaat taattcaaaa tctaaaggat gaattagaaa   6000
tggatatgag attgttgggt gtcactaaaa tggaccagct atcttcgaaa catgtcgata   6060
ctaaacgttt gattggtaga gatgcgatca actatttgta tgataatgta tacagcccaa   6120
tcgaaaccgt taaattcaac aatgaagatt gattgttgga aatatattat tcataaaggc   6180
gaaaacattc ccttggtatt ttattccaaa tttatgatac atagacgtat tttttatata   6240
taaagttata ttattaatga ttcaagaaaa agttcaaata aactaatgga tcaaccataa   6300
cttcgtataa tgtatgctat acgaagttat agatccgcgg ccgcaatgta gatacaggac   6360
acgttgagca taggaggatg ggaacagtct ctgtaaggtt tcttatctct tgagtctgcg   6420
gggactggag gaggatgctc gaattgggaa gtgaaaatag tcaggtgggg catccgaagg   6480
gagagaagtg ggaaaggggc tcagctgcat ttttaaggcg tgcacgtgac tttgcactat   6540
```

```
gttttaaggt tttttgtatg aagatatcaa cagacgtcaa tgtgtataag tgtattatca   6600

aatcaattga tctataaagg aggaggtgaa agaaacaagg aaagtatata attttgtaag   6660

ataagataag attagataag atagggcagg atagcatcga atagcatcga atagcatagt   6720

atagtataga atggacgtcg tggagggtgt ataaacctga tggtgaagaa cccagctact   6780

atttcttgtc tccatagtat tggcctctaa agaagtccat acagtttgtg aagacaacaa   6840

gtagaatacc accacctgga cccaatctca ggacttttgg aaggaatcct ttatacaatg   6900

cagagacacc ttcttccctc aagacaatgc caagagaggg ccaagtccaa ttgtatttac   6960

ggacctgacc ttccataatg gttgcacttt ggattctgga tttgacaaca tcgaatggaa   7020

tgttcaaggc agtaccaacg ataccaccaa tcataccacc caccaaatcg ttgatggttt   7080

tctgggtctt gtcctttgcc ttgggtaaca tgtcacgaac ttggaaaatc acaccaaaat   7140

agccggcatt ccatacaata tgtctccaca gtgttgcctc taatccgtta tacaaggcca   7200

agataccttc atttttgact gtcttcatta gaacatcaat gggaccgcta tacatggacg   7260

ccttggactt atcctgtaac cggatcttca ccaactcaaa ggggacaaca acaaacgact   7320

cggttgcacc tgcacaagca gagct                                          7345
```

<210> SEQ ID NO 57
<211> LENGTH: 7345
<212> TYPE: DNA
<213> ORGANISM: Artificial Sequence
<220> FEATURE:
<223> OTHER INFORMATION: StXI-PDC-CYB2A-loxP-XDH integration fragment

<400> SEQUENCE: 57

```
cgcagcagaa tgtagaacaa gttgtcgtga atcaaacgag atgctcaaaa gcaaatcccg     60

cgagttggga aacggcgatg aaatttgaca tcactaggtt gatgaacgtc aatggataac    120

ttctagtgcc ccatggtctt ggagaacata ttggtgaagg tgtctctgta cggtgatgtt    180

aaggcggatt ttcagaacta gtatacaagc gccccttcgg gatgttgggc tgattcccgg    240

acttgccctc cataggagat atgtacatgc cagttgtatt gcaaaatacg aagttcctgg    300

tggtgggtca tcagaacatc aggtatcacc acgagcaaac cggaaggagc ttccaaagat    360

gtctttggca gagttccaag cattgagaga taagtaccat ggagaaaaga agaggtatga    420

gaggcaaacc accatttatt attcgttatc catgatgatg attttccttg cattatcgta    480

tgcgagtgtc cccttgtatc gtgcaatttg tcaacgtact ggatggggtg gtacaccaat    540

caccgacaag agcaggttca cgagggacaa gctaactcca gtagctacag agagaagact    600

gcgggtatcc tttacggcgg agacaagtgg tgcgttacca tggaagtttg taccgcaaca    660

aagagaagtt tatgttgtcc ccggagagac tgccttggcc ttctacaaag ccaagaatat    720

aagtgacaag gacattactg gcatggccac atactcagtg actcccgatc atgtagcgcc    780

ttacttcaac aagatccagt gtttctgctt tgaagagcag cggttggcca agggtgagga    840

ggttgatatg cccttgtttt tctttatcga tccagagttt tccagagatc cggcaatgag    900

aaacatcgaa gacgttgtgt tgcactatac attcttcaag gcaaaacacg acgaacaaca    960

cgaccagttg tttagtgaag ctgccaagag gaatgagaac caaacgaaat gaaaaccaga   1020

ggacacacag tcatgtatat aggaaatgct aaacacgtag atatttacac gcggccgcgg   1080

atccctcgag gagtccatcg gttcctgtca gatgggatac tcttgacgtg gaaaattcaa   1140

acagaaaaaa aaccccaata atgaaaaata acactacgtt atatccgtgg tatcctctat   1200

cgtatcgtat cgtagcgtat cgtagcgtac cgtatcacag tatagtctaa tattccgtat   1260
```

```
cttattgtat cctatcctat tcgatcctat tgtatttcag tgcaccattt taatttctat   1320
tgctataatg tccttattag ttgccactgt gaggtgacca atggacgagg gcgagccgtt   1380
cagaagccgc gaagggtgtt cttcccatga atttcttaag gagggcggct cagctccgag   1440
agtgaggcga gacgtctcgg tcagcgtatc cccttcctc ggcttttaca aatgatgcgc    1500
tcttaatagt gtgtcgttat ccttttggca ttgacggggg agggaaattg attgagcgca   1560
tccatatttt tgcggactgc tgaggacaat ggtggttttt ccgggtggcg tgggctacaa   1620
atgatacgat ggtttttttc ttttcggaga aggcgtataa aaaggacacg gagaacccat   1680
ttattctaaa aacagttgag cttctttaat tattttttga tataatattc tattattata   1740
tattttcttc ccaataaaac aaaataaaac aaaacacagc aaaacacaaa aattctagaa   1800
tgaaagagta tttccctgag attaaggaaa tcaaatatga aggtccagaa agcaaaaatg   1860
ttatggcatt caagtactac aataaggacg aggttattgg gggcaaacct atgagagaac   1920
atcttaagtt tgcaatgtct tactggcaca cgttgaaagc acaaggttta gatatgtttg   1980
gtggagacac aatggataga gcttggaata gatacgacga tgcattggag caagcgaaag   2040
cccgtgcaga tgcgggtttc gagtttatgc agaaaattgg catggactac ttctgtttcc   2100
atgatcgtga tattattaac gaagctatga cacttaagga gacaaataga ttactagacg   2160
aaatagttga tcatttggag ggtttgatga aaaagactgg gatcaaactt ctatggggta   2220
caactaatgc ttttagtcat ccaagattct tacacggtgg agctacagcc ccaaacgctg   2280
acgtatttgc atacgccgct gcgcaagtca aaaaggctat ggagattacc aaaagattgg   2340
gtggagaaaa ttatgtgctg tggggtggtc gagaaggtta tgaaacattg ctcaatacca   2400
agtccgacct ggaatatgat aactttgcaa ggtttcttca aatggttgtt gattacaagg   2460
agaaaatagg ttttgaaggc caattgctaa ttgaaccaaa acccaaggaa ccgacaaaac   2520
atcaatatga ttttgatact gccactgttt tgggtttctt gcggaagtat aacttggata   2580
agcactataa gatgaatatt gaagccaacc atgcaaccct tgccggccac acctttcaac   2640
atgaattgaa tctagctagg attaacaacg ttatgggctc aatagacgct aatcagggag   2700
atatgttatt aggttgggat accgatcagt ttcctactaa tatctatgat gcagtgttgg   2760
ctatgtatga agtgatcaaa aacaatggtc tagggaaggg tggtctgaat tttgatgcaa   2820
aagtccgtag ggatcatttt gaggacaaag atttgttcct cgcctacatt gctggaatgg   2880
atacttttgc aaaggggtta acgatagctt atcgattata cgaggacaag gtctttgaag   2940
atttccagga taagagatat gaatcctaca aaactggtat cggaaaagat atagtagaag   3000
gaaaagttgg ctttgaggaa ttagcagaat atgttgagaa cttagcagaa atcaaaaata   3060
cctcagggag acaagagatg ttagaatcta ttctcaactc gtatatcttg gaagcaaagt   3120
aattaattaa catctgaatg taaaatgaac attaaaatga attactaaac tttacgtcta   3180
ctttacaatc tataaacttt gtttaatcat ataacgaaat acactaatac acaatcctgt   3240
acgtatgtaa tacttttatc catcaaggat tgagaaaaaa aagtaatgat tccctgggcc   3300
attaaaactt agacccccaa gcttggatag gtcactctct attttcgttt ctcccttccc   3360
tgatagaagg gtgatatgta attaagaata atatataatt ttataataaa agaattcgcc   3420
cttacatatg ataacttcgt ataatgtatg ctatacgaag ttatgttggt ggtgtgtttt   3480
gttggaacgt acattagatg cataatgcgt gacaccgcca tgatggttgt attctaccaa   3540
tgagacatgg ccgctgatcc tgttgtgtgg gtcatgggac atcacctctt ggggggggatt  3600
```

```
ctcctataat tggcaccgtg tatgcctcaa ccactaactt ccaccctata actgaatata   3660
ttacataagc aaatctactt tttgtttgtg ttgatcgcca tcgttgaaat tcgcgcaact   3720
tctggtggct caacgctgct gttctatcgg tatcctaaga gatgtctttg ccctgagtct   3780
agggtaaact atccaccttc gttgctgttt gactagacag ctactaactt tacggtagta   3840
aatgaataac ggctcgctct catgatcact tctctacatc accctaacaa gtgtattatt   3900
ttttttcag gtgggtgttg ctgttggtgc tagccttagt gccctcgtta atagttgaac   3960
aaacactggc atttggagta taatgaaaag ggatcactac cccccgcttc ctgttccgct   4020
tctcccttcc ggaaaaacca cccacccttt cttttccccc actaatgtat gaatttttcc   4080
gttcccaggg gaatggccca cttggttctc tgttaaccca cacaattttg acgcatccca   4140
cacacctttt ttttttctac cccacacttt cccttgaaaa atctccaatt tgaactggca   4200
attttcaccc cccaccactt gcattcatta gtgagtcaat ccatcccgcg gtcggagatt   4260
cggaatccac ctactggtaa tctgtaatct atattcccgc tgaccctta taaatgaact   4320
attgtcgtca attgcggtag tgctccaaca aattgtaagg accttcttta accttttcga   4380
ttcaatccat ctccacataa acctagttgc acacaatgtt actcagatca ctaaactctt   4440
ctgctcgttg tgtcaaacaa acaaccagaa caaaggttag gtatctcagc cacgtcagtg   4500
gtgcaagcat ggcgaaacct acattgaaga acaactcgag agaatccaac aaatccagaa   4560
actatctaat tgctgctgtg acagcattgg ctgtatcaac ctcaattgga gttgccgtac   4620
atgtgaagga ccccttgtat aacgatgcta ccggcagtga ttctccgaga agtatatctg   4680
ttgacgagtt tgtcaagcat aattcacaaa acgactgttg gattgcaatc aatggcaagg   4740
tttatgattt cactgatttt attccaaacc atccaggtgg ggtacctcca ttagttaatc   4800
atgctggtta tgatggtact aaactttatg agaaattgca tccaaaaggt acaattgaga   4860
aattcttgcc aaaggataag tttctgggtg tgttagatgg tgaagcgcca aaattggaag   4920
cagactattt ggtggacgat gatgaacaag agagactgga ttatttgaac aacttacctc   4980
ctttgtcatc tattcagaat gtttatgatt tcgaatactt ggccaagaag attttaccta   5040
aagatgcctg ggcatattat tcttgtggtg ccgatgatga aatcacaatg agagaaaacc   5100
attatgctta tcaaagagtt tatttcagac caagaatttg tgttgatgtc aaggaagttg   5160
atacttctta tgaaatgtta ggcactaaaa cctctgttcc tttttatgta tctgccaccg   5220
ctttggctaa attaggccat cctgatggtg aatgctcaat tgctagaggc gctggtaagg   5280
aaggtgtcgt tcaaatgatt tcgacccttt cctcaatgtc attagatgaa attgccgctg   5340
ctagaatccc aggtgcaacc caatggttcc aattatacat taatgaggat agaaatgtcg   5400
ctaaaggtct ggtcaaacat gcagaagact tgggtatgaa ggctatcttt ataactgttg   5460
atgctccttc tctaggtaac agagaaaagg ataaaagatt aaagtttgtt aatgacaccg   5520
atgtcgattt gggtgattcc gcagatcgaa acagtggtgc ttcaaaggca ctatcttcgt   5580
tcattgatgc ttctgtctct tggaatgacg tcaaagcggt caagtcgtgg actaaattgc   5640
ctgtcttagt taaaggtgtt caaacagttg aagacgttat tgaagcttac gatgctggtt   5700
gtcaaggtgt tgttttgtca aaccacggtg gtaggcaact agatactgct cctcctccaa   5760
tcgaattatt agctgaaact gttccaactt tgaagagatt gggtaaatta agaccagatt   5820
ttgaaatttt aattgacggt ggtgtcaaaa gaggtaccga tattttgaaa gcagtcgcaa   5880
tcggtggcca agatgtcaga gtttcagttg gtatgggtag acctttctta tatgccaact   5940
cttgctatgg tgaagcaggt gttagaaaat taattcaaaa tctaaaggat gaattagaaa   6000
```

tggatatgag attgttgggt gtcactaaaa tggaccagct atcttcgaaa catgtcgata 6060
ctaaacgttt gattggtaga gatgcgatca actatttgta tgataatgta tacagcccaa 6120
tcgaaaccgt taaattcaac aatgaagatt gattgttgga aatatattat tcataaaggc 6180
gaaaacattc ccttggtatt ttattccaaa tttatgatac atagacgtat tttttatata 6240
taaagttata ttattaatga ttcaagaaaa agttcaaata aactaatgga tcaaccataa 6300
cttcgtataa tgtatgctat acgaagttat agatccgcgg ccgcaatgta gatacaggac 6360
acgttgagca taggaggatg ggaacagtct ctgtaaggtt tcttatctct tgagtctgcg 6420
gggactggag gaggatgctc gaattgggaa gtgaaaatag tcaggtgggg catccgaagg 6480
gagagaagtg ggaaaggggc tcagctgcat ttttaaggcg tgcacgtgac tttgcactat 6540
gttttaaggt tttttgtatg aagatatcaa cagacgtcaa tgtgtataag tgtattatca 6600
aatcaattga tctataaagg aggaggtgaa agaaacaagg aaagtatata attttgtaag 6660
ataagataag attagataag atagggcagg atagcatcga atagcatcga atagcatagt 6720
atagtataga atggacgtcg tggagggtgt ataaacctga tggtgaagaa cccagctact 6780
atttcttgtc tccatagtat tggcctctaa agaagtccat acagtttgtg aagacaacaa 6840
gtagaatacc accacctgga cccaatctca ggacttttgg aaggaatcct ttatacaatg 6900
cagagacacc ttcttccctc aagacaatgc caagagaggg ccaagtccaa ttgtatttac 6960
ggacctgacc ttccataatg gttgcacttt ggattctgga tttgacaaca tcgaatggaa 7020
tgttcaaggc agtaccaacg ataccaccaa tcataccacc caccaaatcg ttgatggttt 7080
tctgggtctt gtcctttgcc ttgggtaaca tgtcacgaac ttggaaaatc acaccaaaat 7140
agccggcatt ccatacaata tgtctccaca gtgttgcctc taatccgtta tacaaggcca 7200
agataccttc atttttgact gtcttcatta gaacatcaat gggaccgcta tacatggacg 7260
ccttggactt atcctgtaac cggatcttca ccaactcaaa ggggacaaca acaaacgact 7320
cggttgcacc tgcacaagca gagct 7345

<210> SEQ ID NO 58
<211> LENGTH: 7349
<212> TYPE: DNA
<213> ORGANISM: Artificial Sequence
<220> FEATURE:
<223> OTHER INFORMATION: LgXI-PDC-CYB2A-loxP-XDH integration fragment

<400> SEQUENCE: 58
cgcagcagaa tgtagaacaa gttgtcgtga atcaaacgag atgctcaaaa gcaaatcccg 60
cgagttggga aacggcgatg aaatttgaca tcactaggtt gatgaacgtc aatggataac 120
ttctagtgcc ccatggtctt ggagaacata ttggtgaagg tgtctctgta cggtgatgtt 180
aaggcggatt ttcagaacta gtatacaagc gccccttcgg gatgttgggc tgattcccgg 240
acttgccctc cataggagat atgtacatgc cagttgtatt gcaaaatacg aagttcctgg 300
tggtgggtca tcagaacatc aggtatcacc acgagcaaac cggaaggagc ttccaaagat 360
gtctttggca gagttccaag cattgagaga taagtaccat ggagaaaaga agaggtatga 420
gaggcaaacc accatttatt attcgttatc catgatgatg attttccttg cattatcgta 480
tgcgagtgtc cccttgtatc gtgcaatttg tcaacgtact ggatggggtg gtacaccaat 540
caccgacaag agcaggttca cgagggacaa gctaactcca gtagctacag agagaagact 600
gcgggtatcc tttacggcgg agacaagtgg tgcgttacca tggaagtttg taccgcaaca 660

```
aagagaagtt tatgttgtcc ccggagagac tgccttggcc ttctacaaag ccaagaatat    720
aagtgacaag gacattactg gcatggccac atactcagtg actcccgatc atgtagcgcc    780
ttacttcaac aagatccagt gtttctgctt tgaagagcag cggttggcca agggtgagga    840
ggttgatatg cccttgtttt tctttatcga tccagagttt tccagagatc cggcaatgag    900
aaacatcgaa gacgttgtgt tgcactatac attcttcaag gcaaaacacg acgaacaaca    960
cgaccagttg tttagtgaag ctgccaagag gaatgagaac caaacgaaat gaaaaccaga   1020
ggacacacag tcatgtatat aggaaatgct aaacacgtag atatttacac gcggccgcgg   1080
atccctcgag gagtccatcg gttcctgtca gatgggatac tcttgacgtg gaaaattcaa   1140
acagaaaaaa aaccccaata atgaaaaata acactacgtt atatccgtgg tatcctctat   1200
cgtatcgtat cgtagcgtat cgtagcgtac cgtatcacag tatagtctaa tattccgtat   1260
cttattgtat cctatcctat tcgatcctat tgtatttcag tgcaccattt taatttctat   1320
tgctataatg tccttattag ttgccactgt gaggtgacca atggacgagg gcgagccgtt   1380
cagaagccgc gaagggtgtt cttcccatga atttcttaag gagggcggct cagctccgag   1440
agtgaggcga gacgtctcgg tcagcgtatc ccccttcctc ggcttttaca aatgatgcgc   1500
tcttaatagt gtgtcgttat ccttttggca ttgacggggg agggaaattg attgagcgca   1560
tccatatttt tgcggactgc tgaggacaat ggtggttttt ccgggtggcg tgggctacaa   1620
atgatacgat ggtttttttc ttttcggaga aggcgtataa aaaggacacg gagaacccat   1680
ttattctaaa aacagttgag cttctttaat tattttttga tataatattc tattattata   1740
tattttcttc ccaataaaac aaaataaaac aaaacacagc aaaacacaaa aattctagat   1800
aaaatgaaag agttctttcc cgaaatcaag gaaatcaaat atgaaggcgc agaatcgaaa   1860
aatgatttgg ctttcaaata ctataacaag gatgaagtct tggggggaaa gactatgaag   1920
gagcatctaa gattcgccat gtcatattgg cataccttaa aagctcaggg tgttgatatg   1980
ttcggtggcg aaacgatgga tagagaatgg aacaaatacg aaaatgtgct tgaaagggca   2040
aaagccagag ccaatgccgg gtttgagttt atgcaaaaat tgggtttaga atacttttgt   2100
ttccacgatc gagacattat cgatgagtct atgatgctag cagattctaa caagttgctc   2160
gatgagatag tcgatcatat agaggagttg atgaaaaaga ccggaaggaa attgttatgg   2220
ggtacaacca acgcattttc ccacccacgt tttgtacatg gagcaagcac ctcaccaaat   2280
gctgatgtat tcgcgtatgc agcagcacaa gtcaaaaagg ccatggacat tactaataga   2340
ctaggaggag aaaactatgt tttatggggg ggtagagaag gttacgaaac tcttctaaac   2400
acaaattctg aacttgaata tgacaatttt gcaagatttt tgaagatggt tgttgactac   2460
aaggaaaaga ttggttttaa gggccaattg cttattgaac ctaaaccaaa agagcctaca   2520
aaacatcaat atgattttga cacagcaact gttttggcat tcttaaggaa gtataatctg   2580
gacaagtatt acaaggttaa catcgaagcc aatcatgcta ctcttgcggg tcatacattc   2640
caacacgagt taaacttagc taggattaat ggggtattag gcagtataga tgctaatcag   2700
ggagatatgt tattaggttg ggacaccgat caattcccga ctaatatcta tgatacgact   2760
ctggctatgt atgaggttgt gaaaaataag ggtctgggtt ccggcggtct aaatttcgat   2820
gctaaagttc ggagaggttc atttgaggat aaggacctat ttctggcata tatcgctggg   2880
atggatacat tcgcgaaggg tttgaagatt gcatatcgtt tgtatgaaga taaggtcttt   2940
gaagatttca tagacaaaag atatgaaagt tacaaaactg gaattggaaa agacataatt   3000
gacggaaaag tcggttttga ggaactctca aaatacgcag agacattgac cgaagtgaaa   3060
```

```
aacaactctg gtagacaaga gatgttggaa tcgaaactca accagtacat ttttgaagtt   3120
aaatgattaa ttaacatctg aatgtaaaat gaacattaaa atgaattact aaactttacg   3180
tctactttac aatctataaa ctttgtttaa tcatataacg aaatacacta atacacaatc   3240
ctgtacgtat gtaatacttt tatccatcaa ggattgagaa aaaaaagtaa tgattccctg   3300
ggccattaaa acttagaccc ccaagcttgg ataggtcact ctctattttc gtttctccct   3360
tccctgatag aagggtgata tgtaattaag aataatatat aattttataa taaaagaatt   3420
cgcccttaca tatgataact tcgtataatg tatgctatac gaagttatgt tggtggtgtg   3480
ttttgttgga acgtacatta gatgcataat gcgtgacacc gccatgatgg ttgtattcta   3540
ccaatgagac atggccgctg atcctgttgt gtgggtcatg ggacatcacc tcttgggggg   3600
gattctccta taattggcac cgtgtatgcc tcaaccacta acttccaccc tataactgaa   3660
tatattacat aagcaaatct actttttgtt tgtgttgatc gccatcgttg aaattcgcgc   3720
aacttctggt ggctcaacgc tgctgttcta tcggtatcct aagagatgtc tttgccctga   3780
gtctagggta aactatccac cttcgttgct gtttgactag acagctacta actttacggt   3840
agtaaatgaa taacggctcg ctctcatgat cacttctcta catcacccta acaagtgtat   3900
tatttttttt tcaggtgggt gttgctgttg gtgctagcct tagtgccctc gttaatagtt   3960
gaacaaacac tggcatttgg agtataatga aaagggatca ctaccccccg cttcctgttc   4020
cgcttctccc ttccggaaaa accacccacc ctttcttttc ccccactaat gtatgaattt   4080
ttccgttccc aggggaatgg cccacttggt tctctgttaa cccacacaat tttgacgcat   4140
cccacacacc tttttttttt ctaccccaca ctttcccttg aaaaatctcc aatttgaact   4200
ggcaattttc acccccccacc acttgcattc attagtgagt caatccatcc cgcggtcgga   4260
gattcggaat ccacctactg gtaatctgta atctatattc ccgctgaccc tttataaatg   4320
aactattgtc gtcaattgcg gtagtgctcc aacaaattgt aaggaccttc tttaaccttt   4380
tcgattcaat ccatctccac ataaacctag ttgcacacaa tgttactcag atcactaaac   4440
tcttctgctc gttgtgtcaa acaaacaacc agaacaaagg ttaggtatct cagccacgtc   4500
agtggtgcaa gcatggcgaa acctacattg aagaacaact cgagagaatc caacaaatcc   4560
agaaactatc taattgctgc tgtgacagca ttggctgtat caacctcaat tggagttgcc   4620
gtacatgtga aggacccctt gtataacgat gctaccggca gtgattctcc gagaagtata   4680
tctgttgacg agtttgtcaa gcataattca caaaacgact gttggattgc aatcaatggc   4740
aaggtttatg atttcactga ttttattcca aaccatccag gtggggtacc tccattagtt   4800
aatcatgctg gttatgatgg tactaaactt tatgagaaat tgcatccaaa aggtacaatt   4860
gagaaattct tgccaaagga taagtttctg ggtgtgttag atggtgaagc gccaaaattg   4920
gaagcagact atttggtgga cgatgatgaa caagagagac tggattattt gaacaactta   4980
cctcctttgt catctattca gaatgtttat gatttcgaat acttggccaa gaagatttta   5040
cctaaagatg cctgggcata ttattcttgt ggtgccgatg atgaaatcac aatgagagaa   5100
aaccattatg cttatcaaag agtttatttc agaccaagaa tttgtgttga tgtcaaggaa   5160
gttgatactt cttatgaaat gttaggcact aaaacctctg ttcctttttta tgtatctgcc   5220
accgctttgg ctaaattagg ccatcctgat ggtgaatgct caattgctag aggcgctggt   5280
aaggaaggtg tcgttcaaat gatttcgacc ctttcctcaa tgtcattaga tgaaattgcc   5340
gctgctagaa tcccaggtgc aacccaatgg ttccaattat acattaatga ggatagaaat   5400
```

```
gtcgctaaag gtctggtcaa acatgcagaa gacttgggta tgaaggctat ctttataact   5460
gttgatgctc cttctctagg taacagagaa aaggataaaa gattaaagtt tgttaatgac   5520
accgatgtcg atttgggtga ttccgcagat cgaaacagtg gtgcttcaaa ggcactatct   5580
tcgttcattg atgcttctgt ctcttggaat gacgtcaaag cggtcaagtc gtggactaaa   5640
ttgcctgtct tagttaaagg tgttcaaaca gttgaagacg ttattgaagc ttacgatgct   5700
ggttgtcaag gtgttgtttt gtcaaaccac ggtggtaggc aactagatac tgctcctcct   5760
ccaatcgaat tattagctga aactgttcca actttgaaga gattgggtaa attaagacca   5820
gattttgaaa ttttaattga cggtggtgtc aaaagaggta ccgatatttt gaaagcagtc   5880
gcaatcggtg gccaagatgt cagagtttca gttggtatgg gtagaccttt cttatatgcc   5940
aactcttgct atggtgaagc aggtgttaga aaattaattc aaaatctaaa ggatgaatta   6000
gaaatggata tgagattgtt gggtgtcact aaaatggacc agctatcttc gaaacatgtc   6060
gatactaaac gtttgattgg tagagatgcg atcaactatt tgtatgataa tgtatacagc   6120
ccaatcgaaa ccgttaaatt caacaatgaa gattgattgt tggaaatata ttattcataa   6180
aggcgaaaac attcccttgg tattttattc caaatttatg atacatagac gtattttttta  6240
tatataaagt tatattatta atgattcaag aaaaagttca aataaactaa tggatcaacc   6300
ataacttcgt ataatgtatg ctatacgaag ttatagatcc gcggccgcaa tgtagataca   6360
ggacacgttg agcataggag gatgggaaca gtctctgtaa ggtttcttat ctcttgagtc   6420
tgcggggact ggaggaggat gctcgaattg ggaagtgaaa atagtcaggt ggggcatccg   6480
aagggagaga agtgggaaag ggctcagct gcatttttaa ggcgtgcacg tgactttgca    6540
ctatgtttta aggtttttg tatgaagata tcaacagacg tcaatgtgta taagtgtatt    6600
atcaaatcaa ttgatctata aaggaggagg tgaaagaaac aaggaaagta tataattttg   6660
taagataaga taagattaga taagataggg caggatagca tcgaatagca tcgaatagca   6720
tagtatagta tagaatggac gtcgtggagg gtgtataaac ctgatggtga agaacccagc   6780
tactatttct tgtctccata gtattggcct ctaaagaagt ccatacagtt tgtgaagaca   6840
acaagtagaa taccaccacc tggacccaat ctcaggactt ttggaaggaa tcctttatac   6900
aatgcagaga caccttcttc cctcaagaca atgccaagag agggccaagt ccaattgtat   6960
ttacggacct gaccttccat aatggttgca ctttggattc tggatttgac aacatcgaat   7020
ggaatgttca aggcagtacc aacgatacca ccaatcatac cacccaccaa atcgttgatg   7080
gttttctggg tcttgtcctt tgccttgggt aacatgtcac gaacttggaa aatcacacca   7140
aaatagccgg cattccatac aatatgtctc cacagtgttg cctctaatcc gttatacaag   7200
gccaagatac cttcattttt gactgtcttc attagaacat caatgggacc gctatacatg   7260
gacgccttgg acttatcctg taaccggatc ttcaccaact caaaggggac aacaacaaac   7320
gactcggttg cacctgcaca agcagagct                                      7349
```

<210> SEQ ID NO 59
<211> LENGTH: 6905
<212> TYPE: DNA
<213> ORGANISM: Artificial Sequence
<220> FEATURE:
<223> OTHER INFORMATION: ScTK-TDH3-TKL-URA3-AR4 integration fragment

<400> SEQUENCE: 59

```
cgtgggccgt ttggtcttga taaagccgat tctgtattaa tttctatatg tgatagtcca     60
tttgtagaaa tgatagacga cgacggttca gatgggtgat tattgatcaa gtcaaccagt    120
```

```
ttatcctgta ctttatggtt gatctttata gtcttctgat cagctggcgt gaataatgac    180
gttagctcat ttcggcactg aggacaggta gatgctgatt ttgaggtcca tgaaagaatg    240
cacgacttgt gataaaaatg cttgcagggt attgtcaatg tatatgaagg atcattagag    300
gtgatatctt ctaaacaaat ggggcattct ctttttttgg ccatttttttg ttgagatgaa    360
attaaaaatc cttttttttt ccttcctaat gtctgtcttc ttcaagtcca agtaaacacg    420
ttagagttat cttatttaga gagaaatgta tagcttgtac agagtacatc caagggtatg    480
aatgaatcta ttgctacagg aagataaagc aatgtctgct tcttgtagaa aactcaaata    540
atctgaaaag aaaaaaaaaa gacctcgctt ttatcgggta atacccgaga cgttttacat    600
tacttaggcg aacaaccaat tccttttgac gtttccattc ctatgaatgc atatacatga    660
ttgttacaga agagtgacac atatagctgt tacgtgatgc ctacgggctt tatagacgta    720
cttacatcga ctgcggccgc ggatccctcg agagcaattt gaggaaggaa taggagaagg    780
agaagcaatt tctaggaaag agcaaggtgt gcaacagcat gctctgaatg atattttcag    840
caatagttca gttgaagaac ctgttggcgt atctacatca cttcctacaa acaacaccac    900
gaattgcgtc cgtggtgacg caactacgaa tggcattgtc aatgccaatg ccagtgcaca    960
tacacgtgca agtcccaccg gttccctgcc cggctatggt agagacaaga aggacgatac   1020
cggcatcgac atcaacagtt tcaacagcaa tgcgtttggc gtcgacgcgt cgatggggct   1080
gccgtatttg gatttggacg ggctagattt cgatatggat atggatatgg atatggatat   1140
ggagatgaat ttgaatttag atttgggtct tgatttgggg ttggaattaa aaggggataa   1200
caatgagggt tttcctgttg atttaaacaa tggacgtggg aggtgattga tttaacctga   1260
tccaaaaggg gtatgtctat tttttagagt gtgtctttgt gtcaaattat ggtagaatgt   1320
gtaaagtagt ataaactttc ctctcaaatg acgaggttta aaacaccccc cgggtgagcc   1380
gagccgagaa tggggcaatt gttcaatgtg aaatagaagt atcgagtgag aaacttgggt   1440
gttggccagc caagggggaa ggaaaatggc gcgaatgctc aggtgagatt gttttggaat   1500
tgggtgaagc gaggaaatga gcgacccgga ggttgtgact ttagtggcgg aggaggacgg   1560
aggaaaagcc aagagggaag tgtatataag gggagcaatt tgccaccagg atagaattgg   1620
atgagttata attctactgt atttattgta taatttattt ctccttttat atcaaacaca   1680
ttacaaaaca cacaaaacac acaaacaaac acatctagat aaaatgactc aattcactga   1740
cattgataag ctagccgtct ccaccataag aattttggct gtggacaccg tatccaaggc   1800
caactcaggt cacccaggtg ctccattggg tatggcacca gctgcacacg ttctatggag   1860
tcaaatgcgc atgaacccaa ccaacccaga ctggatcaac agagatagat ttgtcttgtc   1920
taacggtcac gcggtcgctt tgttgtattc tatgctacat ttgactggtt acgatctgtc   1980
tattgaagac ttgaaacagt tcagacagtt gggttccaga acaccaggtc atcctgaatt   2040
tgagttgcca ggtgttgaag ttactaccgg tccattaggt caaggtatct ccaacgctgt   2100
tggtatggcc atggctcaag ctaacctggc tgccacttac aacaagccgg gctttacctt   2160
gtctgacaac tacacctatg ttttcttggg tgacggttgt ttgcaagaag gtatttcttc   2220
agaagcttcc tccttggctg gtcatttgaa attgggtaac ttgattgcca tctacgatga   2280
caacaagatc actatcgatg gtgctaccag tatctcattc gatgaagatg ttgctaagag   2340
atacgaagcc tacggttggg aagttttgta cgtagaaaat ggtaacgaag atctagccgg   2400
tattgccaag gctattgctc aagctaagtt atccaaggac aaaccaactt tgatcaaaat   2460
```

-continued

```
gaccacaacc attggttacg gttccttgca tgccggctct cactctgtgc acggtgcccc   2520

attgaaagca gatgatgtta aacaactaaa gagcaaattc ggtttcaacc cagacaagtc   2580

ctttgttgtt ccacaagaag tttacgacca ctaccaaaag acaattttaa agccaggtgt   2640

cgaagccaac aacaagtgga acaagttgtt cagcgaatac caaaagaaat tcccagaatt   2700

aggtgctgaa ttggctagaa gattgagcgg ccaactaccc gcaaattggg aatctaagtt   2760

gccaacttac accgccaagg actctgccgt ggccactaga aaattatcag aaactgttct   2820

tgaggatgtt tacaatcaat tgccagagtt gattggtggt tctgccgatt taacaccttc   2880

taacttgacc agatggaagg aagcccttga cttccaacct ccttcttccg gttcaggtaa   2940

ctactctggt agatacatta ggtacggtat tagagaacac gctatgggtg ccataatgaa   3000

cggtatttca gctttcggtg ccaactacaa accatacggt ggtactttct tgaacttcgt   3060

ttcttatgct gctggtgccg ttagattgtc cgctttgtct ggccacccag ttatttgggt   3120

tgctacacat gactctatcg gtgtcggtga agatggtcca acacatcaac ctattgaaac   3180

tttagcacac ttcagatccc taccaaacat tcaagtttgg agaccagctg atggtaacga   3240

agtttctgcc gcctacaaga actctttaga atccaagcat actccaagta tcattgcttt   3300

gtccagacaa aacttgccac aattggaagg tagctctatt gaaagcgctt ctaagggtgg   3360

ttacgtacta caagatgttg ctaacccaga tattatttta gtggctactg gttccgaagt   3420

gtctttgagt gttgaagctg ctaagacttt ggccgcaaag aacatcaagg ctcgtgttgt   3480

ttctctacca gatttcttca cttttgacaa acaaccccta gaatacagac tatcagtctt   3540

accagacaac gttccaatca tgtctgttga agttttggct accacatgtt ggggcaaata   3600

cgctcatcaa tccttcggta ttgacagatt tggtgcctcc ggtaaggcac cagaagtctt   3660

caagttcttc ggtttcaccc cagaaggtgt tgctgaaagg gctcaaaaga ccattgcatt   3720

ctataagggt gacaagctaa tttctccttt gaaaaaagct ttctaaattc tgatcgtaga   3780

tcatcagatt tgatatgata ttatttgtga aaaaatgaaa taaaacttta tacaacttaa   3840

atacaacttt ttttataaac gattaagcaa aaaaatagtt tcaaactttt aacaatattc   3900

caaacactca gtccttttcc ttcttatatt ataggtgtac gtattataga aaaatttcaa   3960

tgattacttt ttctttcttt ttccttgtac cagcacatgg ccgagcttga atgttaaacc   4020

cttcgagaga atcacaccat tcaagtataa agccaataaa gaatataact cctaaaaggc   4080

taattgaaac cctgtgattt ttgataagcg atagaaaact gagaagggaa agttaacacg   4140

aaaatgacaa ttgaaaaacc aaaaatatcg gaattcatag cctcatgaaa tcagccattt   4200

gcttttgttc aacgatcttt tgaaattgtt gttgttcttg gtagttaagt tgatccatct   4260

tggcttatgt tgtgtgtatg ttgtagttat tcttagtata ttcctgtcct gagtttagtg   4320

aaacataata tcgccttgaa atgaaaatgc tgaaattcgt cgacatacaa tttttcaaac   4380

ttttttttt tcttggtgca cggacatgtt tttaaaggaa gtactctata ccagttattc   4440

ttcacaaatt taattgctgg agaatagatc ttcaacgctt taataaagta gtttgtttgt   4500

caaggatggc gtcatacaaa gaaagatcag aatcacacac ttcccctgtt gctaggagac   4560

ttttctccat catggaggaa aagaagtcta acctttgtgc atcattggat attactgaaa   4620

ctgaaaagct tctctctatt ttggacacta ttggtcctta catctgtcta gttaaaacac   4680

acatcgatat tgtttctgat tttacgtatg aaggaactgt gttgcctttg aaggagcttg   4740

ccaagaaaca taattttatg atttttgaag atagaaaatt tgctgatatt ggtaacactg   4800

ttaaaaatca atataaatct ggtgtcttcc gtattgccga atgggctgac atcactaatg   4860
```

```
cacatggtgt aacgggtgca ggtattgttt ctggcttgaa ggaggcagcc caagaaacaa   4920

ccagtgaacc tagaggtttg ctaatgcttg ctgagttatc atcaaagggt tctttagcat   4980

atggtgaata tacagaaaaa acagtagaaa ttgctaaatc tgataaagag tttgtcattg   5040

gttttattgc gcaacacgat atgggcggta gagaagaagg ttttgactgg atcattatga   5100

ctccaggggt tggtttagat gacaaaggtg atgcacttgg tcaacaatat agaactgttg   5160

atgaagttgt aaagactgga acggatatca taattgttgg tagaggtttg tacggtcaag   5220

gaagagatcc tatagagcaa gctaaaagat accaacaagc tggttggaat gcttatttaa   5280

acagatttaa atgattctta cacaaagatt tgatacatgt acactagttt aaataagcat   5340

gaaaagaatt acacaagcaa aaaaaaaaaa ataaatgagg tactttacgt tcacctacaa   5400

ccaaaaaaac tagatagagt aaaatcttaa gatttagaaa aagttgttta acaaaggctt   5460

tagtatgtga atttttaatg tagcaaagcg ataactaata aacataaaca aaagtatggt   5520

tttctttatc agtcaaatca ttatcgattg attgttccgc gtatctgcag atagcctcat   5580

gaaatcagcc atttgctttt gttcaacgat cttttgaaat tgttgttgtt cttggtagtt   5640

aagttgatcc atcttggctt atgttgtgtg tatgttgtag ttattcttag tatattcctg   5700

tcctgagttt agtgaaacat aatatcgcct tgaaatgaaa atgctgaaat tcgtcgacat   5760

acaatttttc aaactttttt tttttcttgg tgcacggaca tgtttttaaa ggaagtactc   5820

tataccagtt attcttcaca aatttaattg ctggagaata gatcttcaac gccccggggg   5880

atctggatcc gcggccgctg agaggattga aatgtttagt tatacattgt ggaaaagttt   5940

ctacctgacc tccaattgca aaaaataggt tgtggttgca agctttcaat tatatacttg   6000

taatgcaagc atgaatgccc aaaggatatc tcctgcccga gacaatttca ggccaatcgc   6060

taaaacccat ttctattgtt ctcaccccgg agattcacca cagaaaggga accctgcagc   6120

ttaaaatgca attgtctgtc tagttttttt cttcccctag attagtcaac acagaaacgg   6180

ctagttctat tttacaggtc ttcgtaccgt actgttagtc tggtctacta aggctccagc   6240

aactgcgtca accattcaac tgcatatccg agtatagtaa atagtctttt tttctagttt   6300

atgaaatata aagttattaa ggtatacagt caatcgttcc cttttagaac gcatactaat   6360

agtaaagaca gacaaaaata tctgattaga ccaaaccccc cgaaagcaaa agtatgctgg   6420

ataaaatgag gtaaaccggc atgtaaggta taaagtatta ttgttttgat tgatgttttt   6480

aggttggttt tatgatttct acctatttcc tttgtttcaa aagaaagtaa gatgaatcaa   6540

taaccacatt gattgtagaa ttctctagag ttcaacggct gaggaatgat attcaactca   6600

accaaccttt ggaagtccca ctcaatcaag ttttcagttt tccaacacca aaaaacccat   6660

ccattcatct tttcatgaag gtatgcgtcc atctgagctt caacatacct tctgtaggtt   6720

tgtctaacat cttcctgttg gaagtatgaa taatcagcca agtacaagtt agaacaagaa   6780

ccaattggag tgtcgttctg atatgttgca tcataccttg cgcctctcgc cattccattg   6840

agccatttag cacaatcagt gagagcagca gtccattcac cgcataccgc attgtggtat   6900

gggcc                                                               6905
```

<210> SEQ ID NO 60
<211> LENGTH: 6905
<212> TYPE: DNA
<213> ORGANISM: Artificial Sequence
<220> FEATURE:
<223> OTHER INFORMATION: ScTK-TDH3-TKL-URA3-AR4 integration fragment

<400> SEQUENCE: 60

```
cataccacaa tgcggtatgc ggtgaatgga ctgctgctct cactgattgt gctaaatggc     60
tcaatggaat ggcgagaggc gcaaggtatg atgcaacata tcagaacgac actccaattg    120
gttcttgttc taacttgtac ttggctgatt attcatactt ccaacaggaa gatgttagac    180
aaacctacag aaggtatgtt gaagctcaga tggacgcata ccttcatgaa aagatgaatg    240
gatgggtttt ttggtgttgg aaaactgaaa acttgattga gtgggacttc caaaggttgg    300
ttgagttgaa tatcattcct cagccgttga actctagaga attctacaat caatgtggtt    360
attgattcat cttactttct tttgaaacaa aggaaatagg tagaaatcat aaaaccaacc    420
taaaaacatc aatcaaaaca ataatacttt ataccttaca tgccggttta cctcatttta    480
tccagcatac ttttgctttc ggggggtttg gtctaatcag atatttttgt ctgtctttac    540
tattagtatg cgttctaaaa gggaacgatt gactgtatac cttaataact ttatatttca    600
taaactagaa aaaaagacta tttactatac tcggatatgc agttgaatgg ttgacgcagt    660
tgctggagcc ttagtagacc agactaacag tacggtacga agacctgtaa aatagaacta    720
gccgtttctg tgttgactaa tctaggggaa gaaaaaaact agacagacaa ttgcatttta    780
agctgcaggg ttccctttct gtggtgaatc tccggggtga gaacaataga aatgggtttt    840
agcgattggc ctgaaattgt ctcgggcagg agatatcctt tgggcattca tgcttgcatt    900
acaagtatat aattgaaagc ttgcaaccac aacctatttt ttgcaattgg aggtcaggta    960
gaaacttttc cacaatgtat aactaaacat ttcaatcctc tcagcggccg cggatccctc   1020
gagagcaatt tgaggaagga ataggagaag gagaagcaat ttctaggaaa gagcaaggtg   1080
tgcaacagca tgctctgaat gatattttca gcaatagttc agttgaagaa cctgttggcg   1140
tatctacatc acttcctaca aacaacacca cgaattgcgt ccgtggtgac gcaactacga   1200
atggcattgt caatgccaat gccagtgcac atacacgtgc aagtcccacc ggttccctgc   1260
ccggctatgg tagagacaag aaggacgata ccggcatcga catcaacagt ttcaacagca   1320
atgcgtttgg cgtcgacgcg tcgatggggc tgccgtattt ggatttggac gggctagatt   1380
tcgatatgga tatggatatg gatatggata tggagatgaa tttgaattta gatttgggtc   1440
ttgatttggg gttggaatta aaaggggata acaatgaggg ttttcctgtt gatttaaaca   1500
atggacgtgg gaggtgattg atttaacctg atccaaaagg ggtatgtcta ttttttagag   1560
tgtgtctttg tgtcaaatta tggtagaatg tgtaaagtag tataaacttt cctctcaaat   1620
gacgaggttt aaaacacccc ccgggtgagc cgagccgaga atggggcaat tgttcaatgt   1680
gaaatagaag tatcgagtga gaaacttggg tgttggccag ccaaggggga aggaaaatgg   1740
cgcgaatgct caggtgagat tgttttggaa ttgggtgaag cgaggaaatg agcgacccgg   1800
aggttgtgac tttagtggcg gaggaggacg gaggaaaagc caagagggaa gtgtatataa   1860
ggggagcaat ttgccaccag gatagaattg gatgagttat aattctactg tatttattgt   1920
ataatttatt tctcctttta tatcaaacac attacaaaac acacaaaaca cacaaacaaa   1980
cacatctaga taaaatgact caattcactg acattgataa gctagccgtc tccaccataa   2040
gaattttggc tgtggacacc gtatccaagg ccaactcagg tcacccaggt gctccattgg   2100
gtatggcacc agctgcacac gttctatgga gtcaaatgcg catgaaccca accaacccag   2160
actggatcaa cagagataga tttgtcttgt ctaacggtca cgcggtcgct ttgttgtatt   2220
ctatgctaca tttgactggt tacgatctgt ctattgaaga cttgaaacag ttcagacagt   2280
tgggttccag aacaccaggt catcctgaat ttgagttgcc aggtgttgaa gttactaccg   2340
```

```
gtccattagg tcaaggtatc tccaacgctg ttggtatggc catggctcaa gctaacctgg   2400
ctgccactta caacaagccg ggctttacct tgtctgacaa ctacacctat gttttcttgg   2460
gtgacggttg tttgcaagaa ggtatttctt cagaagcttc ctccttggct ggtcatttga   2520
aattgggtaa cttgattgcc atctacgatg acaacaagat cactatcgat ggtgctacca   2580
gtatctcatt cgatgaagat gttgctaaga gatacgaagc ctacggttgg gaagttttgt   2640
acgtagaaaa tggtaacgaa gatctagccg gtattgccaa ggctattgct caagctaagt   2700
tatccaagga caaaccaact ttgatcaaaa tgaccacaac cattggttac ggttccttgc   2760
atgccggctc tcactctgtg cacggtgccc cattgaaagc agatgatgtt aaacaactaa   2820
agagcaaatt cggtttcaac ccagacaagt cctttgttgt tccacaagaa gtttacgacc   2880
actaccaaaa gacaatttta aagccaggtg tcgaagccaa caacaagtgg aacaagttgt   2940
tcagcgaata ccaaaagaaa ttcccagaat taggtgctga attggctaga agattgagcg   3000
gccaactacc cgcaaattgg gaatctaagt tgccaactta caccgccaag gactctgccg   3060
tggccactag aaaattatca gaaactgttc ttgaggatgt ttacaatcaa ttgccagagt   3120
tgattggtgg ttctgccgat ttaacacctt ctaacttgac cagatggaag gaagcccttg   3180
acttccaacc tccttcttcc ggttcaggta actactctgg tagatacatt aggtacggta   3240
ttagagaaca cgctatgggt gccataatga acggtatttc agctttcggt gccaactaca   3300
aaccatacgg tggtactttc ttgaacttcg tttcttatgc tgctggtgcc gttagattgt   3360
ccgctttgtc tggccaccca gttatttggg ttgctacaca tgactctatc ggtgtcggtg   3420
aagatggtcc aacacatcaa cctattgaaa ctttagcaca cttcagatcc ctaccaaaca   3480
ttcaagtttg gagaccagct gatggtaacg aagtttctgc cgcctacaag aactctttag   3540
aatccaagca tactccaagt atcattgctt tgtccagaca aaacttgcca caattggaag   3600
gtagctctat tgaaagcgct tctaagggtg gttacgtact acaagatgtt gctaacccag   3660
atattatttt agtggctact ggttccgaag tgtctttgag tgttgaagct gctaagactt   3720
tggccgcaaa gaacatcaag gctcgtgttg tttctctacc agatttcttc acttttgaca   3780
aacaaccccct agaatacaga ctatcagtct taccagacaa cgttccaatc atgtctgttg   3840
aagttttggc taccacatgt tggggcaaat acgctcatca atccttcggt attgacagat   3900
ttggtgcctc cggtaaggca ccagaagtct tcaagttctt cggtttcacc ccagaaggtg   3960
ttgctgaaag ggctcaaaag accattgcat tctataaggg tgacaagcta atttctcctt   4020
tgaaaaaagc tttctaaatt ctgatcgtag atcatcagat ttgatatgat attatttgtg   4080
aaaaaatgaa ataaaacttt atacaactta aatacaactt tttttataaa cgattaagca   4140
aaaaaatagt ttcaaacttt taacaatatt ccaaacactc agtccttttc cttcttatat   4200
tataggtgta cgtattatag aaaaatttca atgattactt tttctttctt tttccttgta   4260
ccagcacatg gccgagcttg aatgttaaac ccttcgagag aatcacacca ttcaagtata   4320
aagccaataa agaatataac tcctaaaagg ctaattgaaa ccctgtgatt tttgataagc   4380
gatagaaaac tgagaaggga aagttaacac gaaaatgaca attgaaaaac caaaaatatc   4440
ggaattcata gcctcatgaa atcagccatt tgcttttgtt caacgatctt ttgaaattgt   4500
tgttgttctt ggtagttaag ttgatccatc ttggcttatg ttgtgtgtat gttgtagtta   4560
ttcttagtat attcctgtcc tgagtttagt gaaacataat atcgccttga aatgaaaatg   4620
ctgaaattcg tcgacataca atttttcaaa cttttttttt ttcttggtgc acggacatgt   4680
```

```
ttttaaagga agtactctat accagttatt cttcacaaat ttaattgctg gagaatagat   4740
cttcaacgct ttaataaagt agtttgtttg tcaaggatgg cgtcatacaa agaaagatca   4800
gaatcacaca cttcccctgt tgctaggaga cttttctcca tcatggagga aaagaagtct   4860
aacctttgtg catcattgga tattactgaa actgaaaagc ttctctctat tttggacact   4920
attggtcctt acatctgtct agttaaaaca cacatcgata ttgtttctga ttttacgtat   4980
gaaggaactg tgttgccttt gaaggagctt gccaagaaac ataattttat gatttttgaa   5040
gatagaaaat ttgctgatat tggtaacact gttaaaaatc aatataaatc tggtgtcttc   5100
cgtattgccg aatgggctga catcactaat gcacatggtg taacgggtgc aggtattgtt   5160
tctggcttga aggaggcagc ccaagaaaca accagtgaac ctagaggttt gctaatgctt   5220
gctgagttat catcaaaggg ttctttagca tatggtgaat atacagaaaa aacagtagaa   5280
attgctaaat ctgataaaga gtttgtcatt ggttttattg cgcaacacga tatgggcggt   5340
agagaagaag gttttgactg gatcattatg actccagggg ttggtttaga tgacaaaggt   5400
gatgcacttg gtcaacaata tagaactgtt gatgaagttg taaagactgg aacggatatc   5460
ataattgttg gtagaggttt gtacggtcaa ggaagagatc ctatagagca agctaaaaga   5520
taccaacaag ctggttggaa tgcttattta aacagattta aatgattctt acacaaagat   5580
ttgatacatg tacactagtt taaataagca tgaaaagaat tacacaagca aaaaaaaaaa   5640
aataaatgag gtactttacg ttcacctaca accaaaaaaa ctagatagag taaaatctta   5700
agatttagaa aaagttgttt aacaaaggct ttagtatgtg aatttttaat gtagcaaagc   5760
gataactaat aaacataaac aaaagtatgg ttttctttat cagtcaaatc attatcgatt   5820
gattgttccg cgtatctgca gatagcctca tgaaatcagc catttgcttt tgttcaacga   5880
tcttttgaaa ttgttgttgt tcttggtagt taagttgatc catcttggct tatgttgtgt   5940
gtatgttgta gttattctta gtatattcct gtcctgagtt tagtgaaaca taatatcgcc   6000
ttgaaatgaa aatgctgaaa ttcgtcgaca tacaattttt caaacttttt ttttttcttg   6060
gtgcacggac atgtttttaa aggaagtact ctataccagt tattcttcac aaatttaatt   6120
gctggagaat agatcttcaa cgccccgggg gatctggatc cgcggccgca gtcgatgtaa   6180
gtacgtctat aaagcccgta ggcatcacgt aacagctata tgtgtcactc ttctgtaaca   6240
atcatgtata tgcattcata ggaatggaaa cgtcaaaagg aattggttgt tcgcctaagt   6300
aatgtaaaac gtctcgggta ttacccgata aaagcgaggt cttttttttt tcttttcaga   6360
ttatttgagt tttctacaag aagcagacat tgctttatct tcctgtagca atagattcat   6420
tcataccctt ggatgtactc tgtacaagct atacatttct ctctaaataa gataactcta   6480
acgtgtttac ttggacttga agaagacaga cattaggaag gaaaaaaaaa ggatttttaa   6540
tttcatctca acaaaaaatg gccaaaaaaa gagaatgccc catttgttta gaagatatca   6600
cctctaatga tccttcatat acattgacaa taccctgcaa gcatttttat cacaagtcgt   6660
gcattctttc atggacctca aaatcagcat ctacctgtcc tcagtgccga aatgagctaa   6720
cgtcattatt cacgccagct gatcagaaga ctataaagat caaccataaa gtacaggata   6780
aactggttga cttgatcaat aatcacccat ctgaaccgtc gtcgtctatc atttctacaa   6840
atggactatc acatatagaa attaatacag aatcggcttt atcaagacca aacggcccac   6900
gagct                                                               6905
```

<210> SEQ ID NO 61
<211> LENGTH: 680

```
<212> TYPE: PRT
<213> ORGANISM: Saccharomyces cerevisiae

<400> SEQUENCE: 61

Met Thr Gln Phe Thr Asp Ile Asp Lys Leu Ala Val Ser Thr Ile Arg
1               5                   10                  15

Ile Leu Ala Val Asp Thr Val Ser Lys Ala Asn Ser Gly His Pro Gly
            20                  25                  30

Ala Pro Leu Gly Met Ala Pro Ala Ala His Val Leu Trp Ser Gln Met
        35                  40                  45

Arg Met Asn Pro Thr Asn Pro Asp Trp Ile Asn Arg Asp Arg Phe Val
    50                  55                  60

Leu Ser Asn Gly His Ala Val Ala Leu Leu Tyr Ser Met Leu His Leu
65                  70                  75                  80

Thr Gly Tyr Asp Leu Ser Ile Glu Asp Leu Lys Gln Phe Arg Gln Leu
                85                  90                  95

Gly Ser Arg Thr Pro Gly His Pro Glu Phe Glu Leu Pro Gly Val Glu
            100                 105                 110

Val Thr Thr Gly Pro Leu Gly Gln Gly Ile Ser Asn Ala Val Gly Met
        115                 120                 125

Ala Met Ala Gln Ala Asn Leu Ala Ala Thr Tyr Asn Lys Pro Gly Phe
    130                 135                 140

Thr Leu Ser Asp Asn Tyr Thr Tyr Val Phe Leu Gly Asp Gly Cys Leu
145                 150                 155                 160

Gln Glu Gly Ile Ser Ser Glu Ala Ser Ser Leu Ala Gly His Leu Lys
                165                 170                 175

Leu Gly Asn Leu Ile Ala Ile Tyr Asp Asp Asn Lys Ile Thr Ile Asp
            180                 185                 190

Gly Ala Thr Ser Ile Ser Phe Asp Glu Asp Val Ala Lys Arg Tyr Glu
        195                 200                 205

Ala Tyr Gly Trp Glu Val Leu Tyr Val Glu Asn Gly Asn Glu Asp Leu
    210                 215                 220

Ala Gly Ile Ala Lys Ala Ile Ala Gln Ala Lys Leu Ser Lys Asp Lys
225                 230                 235                 240

Pro Thr Leu Ile Lys Met Thr Thr Thr Ile Gly Tyr Gly Ser Leu His
                245                 250                 255

Ala Gly Ser His Ser Val His Gly Ala Pro Leu Lys Ala Asp Asp Val
            260                 265                 270

Lys Gln Leu Lys Ser Lys Phe Gly Phe Asn Pro Asp Lys Ser Phe Val
        275                 280                 285

Val Pro Gln Glu Val Tyr Asp His Tyr Gln Lys Thr Ile Leu Lys Pro
    290                 295                 300

Gly Val Glu Ala Asn Asn Lys Trp Asn Lys Leu Phe Ser Glu Tyr Gln
305                 310                 315                 320

Lys Lys Phe Pro Glu Leu Gly Ala Glu Leu Ala Arg Arg Leu Ser Gly
                325                 330                 335

Gln Leu Pro Ala Asn Trp Glu Ser Lys Leu Pro Thr Tyr Thr Ala Lys
            340                 345                 350

Asp Ser Ala Val Ala Thr Arg Lys Leu Ser Glu Thr Val Leu Glu Asp
        355                 360                 365

Val Tyr Asn Gln Leu Pro Glu Leu Ile Gly Gly Ser Ala Asp Leu Thr
    370                 375                 380

Pro Ser Asn Leu Thr Arg Trp Lys Glu Ala Leu Asp Phe Gln Pro Pro
385                 390                 395                 400
```

```
Ser Ser Gly Ser Gly Asn Tyr Ser Gly Arg Tyr Ile Arg Tyr Gly Ile
                405                 410                 415

Arg Glu His Ala Met Gly Ala Ile Met Asn Gly Ile Ser Ala Phe Gly
            420                 425                 430

Ala Asn Tyr Lys Pro Tyr Gly Gly Thr Phe Leu Asn Phe Val Ser Tyr
        435                 440                 445

Ala Ala Gly Ala Val Arg Leu Ser Ala Leu Ser Gly His Pro Val Ile
    450                 455                 460

Trp Val Ala Thr His Asp Ser Ile Gly Val Gly Glu Asp Gly Pro Thr
465                 470                 475                 480

His Gln Pro Ile Glu Thr Leu Ala His Phe Arg Ser Leu Pro Asn Ile
                485                 490                 495

Gln Val Trp Arg Pro Ala Asp Gly Asn Glu Val Ser Ala Ala Tyr Lys
            500                 505                 510

Asn Ser Leu Glu Ser Lys His Thr Pro Ser Ile Ile Ala Leu Ser Arg
        515                 520                 525

Gln Asn Leu Pro Gln Leu Glu Gly Ser Ser Ile Glu Ser Ala Ser Lys
    530                 535                 540

Gly Gly Tyr Val Leu Gln Asp Val Ala Asn Pro Asp Ile Ile Leu Val
545                 550                 555                 560

Ala Thr Gly Ser Glu Val Ser Leu Ser Val Glu Ala Ala Lys Thr Leu
                565                 570                 575

Ala Ala Lys Asn Ile Lys Ala Arg Val Val Ser Leu Pro Asp Phe Phe
            580                 585                 590

Thr Phe Asp Lys Gln Pro Leu Glu Tyr Arg Leu Ser Val Leu Pro Asp
        595                 600                 605

Asn Val Pro Ile Met Ser Val Glu Val Leu Ala Thr Thr Cys Trp Gly
    610                 615                 620

Lys Tyr Ala His Gln Ser Phe Gly Ile Asp Arg Phe Gly Ala Ser Gly
625                 630                 635                 640

Lys Ala Pro Glu Val Phe Lys Phe Phe Gly Phe Thr Pro Glu Gly Val
                645                 650                 655

Ala Glu Arg Ala Gln Lys Thr Ile Ala Phe Tyr Lys Gly Asp Lys Leu
            660                 665                 670

Ile Ser Pro Leu Lys Lys Ala Phe
        675                 680
```

<210> SEQ ID NO 62
<211> LENGTH: 3688
<212> TYPE: DNA
<213> ORGANISM: Artificial Sequence
<220> FEATURE:
<223> OTHER INFORMATION: IoURA3-XR integration fragment

<400> SEQUENCE: 62

```
ccctccagtg ttttctctc tgtctctttg ttttttttt ccaatctgat ttgacgtgca     60

aggcaaagac atcacatgtt tgagaatggc aagagaaggg gcgtggtagt gtataccaag    120

ccggtgtaga gagtgtgatt ttagagtgaa tccatccatg aacacgagta gaggagatgt    180

atgagcaaat ccagggtgtt tgtaatggtc caagccgcaa ggcggcgtaa tggaatgcaa    240

gaaacaaggg acactaatga aggggtaaga ggtgtctagt tgagaagtac atartaaaag    300

atgaatagtt gagawgtaca trgtaaaaga tgaatagttg agacaaatga aggtgtcaat    360

gttcctgata atgacactgc aagraacaaa taccgtgcag ttggaagggg gaaagagatg    420
```

-continued

```
rccgagataa gtgttgttga ggccaaagga tgttggaacc tgctacaata ggagatggag    480

cggcctataa ctccggcgtg tttgtgttga cagccctata catcagccaa tacgagagtt    540

tggcatgtcc tttaaagggt ttgctacccc cactcccgta atcatcgtta aaatcatcat    600

cattgaaatc attataatta acctcatcac cattcccact attatcacct tatattctcc    660

actccaggga gatgcatcgt tgtaaagggc atggctgttt gtttatttta cccgacaagc    720

caataccaag agcggacaaa ccgcatcaga atgcaacaga aggttggaga aacgtgatgt    780

catttttcc gcaaacggag atctcgcaca gcggtgagat ataaaaggcg gagatgtgga    840

caccttcttt atacaattcc cctctacttg attgttccat attcctaaca tctagttaca    900

actctgaaca tcataattat tttaaaattc tcaacccaac tgcaattgga ttgaactgcg    960

gccgctaatt aatcatagcc tcatgaaatc agccatttgc ttttgttcaa cgatcttttg   1020

aaattgttgt tgttcttggt agttaagttg atccatcttg gcttatgttg tgtgtatgtt   1080

gtagttattc ttagtatatt cctgtcctga gtttagtgaa acataatatc gccttgaaat   1140

gaaaatgctg aaattcgtcg acatacaatt tttcaaactt tttttttttc ttggtgcacg   1200

gacatgtttt taaaggaagt actctatacc agttattctt cacaaattta attgctggag   1260

aatagatctt caacgcttta ataaagtagt ttgtttgtca aggatggcgt catacaaaga   1320

aagatcagaa tcacacactt cccctgttgc taggagactt ttctccatca tggaggaaaa   1380

gaagtctaac ctttgtgcat cattggatat tactgaaact gaaaagcttc tctctatttt   1440

ggacactatt ggtccttaca tctgtctagt taaaacacac atcgatattg tttctgattt   1500

tacgtatgaa ggaactgtgt tgcctttgaa ggagcttgcc aagaaacata attttatgat   1560

ttttgaagat agaaaatttg ctgatattgg taacactgtt aaaaatcaat ataaatctgg   1620

tgtcttccgt attgccgaat gggctgacat cactaatgca catggtgtaa cgggtgcagg   1680

tattgtttct ggcttgaagg aggcagccca agaaacaacc agtgaaccta gaggtttgct   1740

aatgcttgct gagttatcat caaagggttc tttagcatat ggtgaatata cagaaaaaac   1800

agtagaaatt gctaaatctg ataaagagtt tgtcattggt tttattgcgc aacacgatat   1860

gggcggtaga gaagaaggtt ttgactggat cattatgact ccaggggttg gtttagatga   1920

caaaggtgat gcacttggtc aacaatatag aactgttgat gaagttgtaa agactggaac   1980

ggatatcata attgttggta gaggtttgta cggtcaagga agagatccta tagagcaagc   2040

taaaagatac caacaagctg gttggaatgc ttatttaaac agatttaaat gattcttaca   2100

caaagatttg atacatgtac actagtttaa ataagcatga aaagaattac acaagcaaaa   2160

aaaaaaaaat aaatgaggta ctttacgttc acctacaacc aaaaaaacta gatagagtaa   2220

aatcttaaga tttagaaaaa gttgtttaac aaaggcttta gtatgtgaat ttttaatgta   2280

gcaaagcgat aactaataaa cataaacaaa agtatggttt tctttatcag tcaaatcatt   2340

atcgattgat tgttccgcgt atctgcagat agcctcatga aatcagccat ttgcttttgt   2400

tcaacgatct tttgaaattg ttgttgttct tggtagttaa gttgatccat cttggcttat   2460

gttgtgtgta tgttgtagtt attcttagta tattcctgtc ctgagtttag tgaaacataa   2520

tatcgccttg aaatgaaaat gctgaaattc gtcgacatac aatttttcaa actttttttt   2580

tttcttggtg cacggacatg tttttaaagg aagtactcta taccagttat tcttcacaaa   2640

tttaattgct ggagaataga tcttcaacgc ggccgcgtgt aaatggtgtt agtctgatct   2700

aatgacaact aattacgcac ttacgactgt aatgccttta tttttcttta tatttcccag   2760

cgtgttgttc tttcaaatat acgatgagta taaattaatt ttacaaagca gaaacaacag   2820
```

```
gatctttaga aacgtcactg taaacatcga atcttctttg aacactgaag ggaatatttc   2880

ttctcgtttc ttcaacaacg tccttcttca gttctgcata aacgatggtt tcctcatggc   2940

cggcctcaac gaggatctca ccatctggat cgaccaccat gctatggcca taagcctgat   3000

agccgccctg tgggttacga gcgggggaac acatcaacac gtagttttgg ttgtcaatag   3060

ctctggcaac ggcaaacttt gaccagaatt taggacctgt cacggtattg aatgcaccgg   3120

gataagccat aataccagcg ccacgtctgg ctgcaatcat ggccaattcc gggaacctga   3180

tatcatagca aatacctaag ccgaatctgg tgtcgatttc tggaatgtcg aaaactgtaa   3240

ccttgttgcc cggttttaaa gaatcagact ccttgaacgt gattccgccc ggaatagaaa   3300

tgtcaaagag gtgcacctta cgatgcttgg caacgatttc ccccttggga ttgaaaacaa   3360

gagaggtgtt gtagataccg ccgtcattgt cgtcgatttc cggaatcgaa cctccaatga   3420

tagagacatt gtactttttc gcctgttcac ttaaaaacgt gctagtttcc ccctctggga   3480

tacgttctgc ataatttgca aattggtcta cggcatatgg agattggaaa cattcaggta   3540

gaacaagaag ttgtggtttt ggatcgtgtt ggatcgccct ctcgatgaat tgggtcactt   3600

tggcgagatt ggccttcttg tctccaccac agtggaattg cagcagtgcc acttggagag   3660

tcttggagag agtaacggca gacgggcc                                      3688
```

<210> SEQ ID NO 63
<211> LENGTH: 3688
<212> TYPE: DNA
<213> ORGANISM: Artificial Sequence
<220> FEATURE:
<223> OTHER INFORMATION: IoURA3-XR integration fragment

<400> SEQUENCE: 63

```
ccctccagtg tttttctctc tgtctctttg tttttttttt ccaatctgat ttgacgtgca     60

aggcaaagac atcacatgtt tgagaatggc aagagaaggg gcgtggtagt gtataccaag    120

ccggtgtaga gagtgtgatt ttagagtgaa tccatccatg aacacgagta gaggagatgt    180

atgagcaaat ccagggtgtt tgtaatggtc caagccgcaa ggcggcgtaa tggaatgcaa    240

gaaacaaggg acactaatga aggggtaaga ggtgtctagt tgagaagtac atartaaaag    300

atgaatagtt gagawgtaca trgtaaaaga tgaatagttg agacaaatga aggtgtcaat    360

gttcctgata atgacactgc aagraacaaa taccgtgcag ttggaagggg gaaagagatg    420

rccgagataa gtgttgttga ggccaaagga tgttggaacc tgctacaata ggagatggag    480

cggcctataa ctccggcgtg tttgtgttga cagccctata catcagccaa tacgagagtt    540

tggcatgtcc tttaaagggt ttgctacccc cactcccgta atcatcgtta aaatcatcat    600

cattgaaatc attataatta acctcatcac cattcccact attatcacct tatattctcc    660

actccaggga gatgcatcgt tgtaaagggc atggctgttt gtttatttta cccgacaagc    720

caataccaag agcggacaaa ccgcatcaga atgcaacaga aggttggaga aacgtgatgt    780

catttttttcc gcaaacggag atctcgcaca gcggtgagat ataaaaggcg gagatgtgga    840

caccttcttt atacaattcc cctctacttg attgttccat attcctaaca tctagttaca    900

actctgaaca tcataattat tttaaaattc tcaacccaac tgcaattgga ttgaactgcg    960

gccgctaatt aatcatagcc tcatgaaatc agccatttgc ttttgttcaa cgatcttttg   1020

aaattgttgt tgttcttggt agttaagttg atccatcttg gcttatgttg tgtgtatgtt   1080

gtagttattc ttagtatatt cctgtcctga gtttagtgaa acataatatc gccttgaaat   1140
```

-continued

```
gaaaatgctg aaattcgtcg acatacaatt tttcaaactt ttttttttc ttggtgcacg   1200
gacatgtttt taaaggaagt actctatacc agttattctt cacaaattta attgctggag   1260
aatagatctt caacgcttta ataaagtagt ttgtttgtca aggatggcgt catacaaaga   1320
aagatcagaa tcacacactt cccctgttgc taggagactt ttctccatca tggaggaaaa   1380
gaagtctaac ctttgtgcat cattggatat tactgaaact gaaaagcttc tctctatttt   1440
ggacactatt ggtccttaca tctgtctagt taaaacacac atcgatattg tttctgattt   1500
tacgtatgaa ggaactgtgt tgcctttgaa ggagcttgcc aagaaacata attttatgat   1560
ttttgaagat agaaaatttg ctgatattgg taacactgtt aaaaatcaat ataaatctgg   1620
tgtcttccgt attgccgaat gggctgacat cactaatgca catggtgtaa cgggtgcagg   1680
tattgtttct ggcttgaagg aggcagccca agaaacaacc agtgaaccta gaggtttgct   1740
aatgcttgct gagttatcat caaagggttc tttagcatat ggtgaatata cagaaaaaac   1800
agtagaaatt gctaaatctg ataaagagtt tgtcattggt tttattgcgc aacacgatat   1860
gggcggtaga gaagaaggtt ttgactggat cattatgact ccaggggttg gtttagatga   1920
caaaggtgat gcacttggtc aacaatatag aactgttgat gaagttgtaa agactggaac   1980
ggatatcata attgttggta gaggtttgta cggtcaagga agagatccta tagagcaagc   2040
taaaagatac caacaagctg gttggaatgc ttatttaaac agatttaaat gattcttaca   2100
caaagatttg atacatgtac actagtttaa ataagcatga aagaattac acaagcaaaa   2160
aaaaaaaaat aaatgaggta ctttacgttc acctacaacc aaaaaaacta gatagagtaa   2220
aatcttaaga tttagaaaaa gttgtttaac aaaggcttta gtatgtgaat ttttaatgta   2280
gcaaagcgat aactaataaa cataaacaaa agtatggttt tctttatcag tcaaatcatt   2340
atcgattgat tgttccgcgt atctgcagat agcctcatga aatcagccat ttgcttttgt   2400
tcaacgatct tttgaaattg ttgttgttct tggtagttaa gttgatccat cttggcttat   2460
gttgtgtgta tgttgtagtt attcttagta tattcctgtc ctgagtttag tgaaacataa   2520
tatcgccttg aaatgaaaat gctgaaattc gtcgacatac aatttttcaa actttttttt   2580
tttcttggtg cacggacatg tttttaaagg aagtactcta taccagttat tcttcacaaa   2640
tttaattgct ggagaataga tcttcaacgc ggccgcgtgt aaatggtgtt agtctgatct   2700
aatgacaact aattacgcac ttacgactgt aatgccttta tttttcttta tatttcccag   2760
cgtgttgttc tttcaaatat acgatgagta taaattaatt ttacaaagca gaaacaacag   2820
gatctttaga aacgtcactg taaacatcga atcttcttgg aacactgaag ggaatatttc   2880
ttctcgtttc ttcaacaacg tccttcttca gttctgcata aacgatggtt tcctcatggc   2940
cggcctcaac gaggatctca ccatctggat cgaccaccat gctatggcca taagcctgat   3000
agccgccctg tgggttacga gcgggggaac acatcaacac gtagttttgg ttgtcaatag   3060
ctctggcaac ggcaaacttt gaccagaatt taggacctgt cacggtattg aatgcaccgg   3120
gataagccat aataccagcg ccacgtctgg ctgcaatcat ggccaattcc gggaacctga   3180
tatcatagca aatacctaag ccgaatctgg tgtcgatttc tggaatgtcg aaaactgtaa   3240
ccttgttgcc cggttttaaa gaatcagact ccttgaacgt gattccgccc ggaatagaaa   3300
tgtcaaagag gtgcacctta cgatgcttgg caacgatttc cccttggga ttgaaaacaa   3360
gagaggtgtt gtagataccg ccgtcattgt cgtcgatttc cggaatcgaa cctccaatga   3420
tagagacatt gtactttttc gcctgttcac ttaaaaacgt gctagtttcc ccctctggga   3480
tacgttctgc ataatttgca aattggtcta cggcatatgg agattggaaa cattcaggta   3540
```

```
gaacaagaag ttgtggtttt ggatcgtgtt ggatcgccct ctcgatgaat tgggtcactt   3600
tggcgagatt ggccttcttg tctccaccac agtggaattg cagcagtgcc acttggagag   3660
tcttggagag agtaacggca gacgggcc                                      3688

<210> SEQ ID NO 64
<211> LENGTH: 6085
<212> TYPE: DNA
<213> ORGANISM: Artificial Sequence
<220> FEATURE:
<223> OTHER INFORMATION: IoURA3-KmXT-IoAXR2 integration fragment

<400> SEQUENCE: 64

ctgaagacac aaaaggggta tcactgaaat tgatcacttt tgcattgttt gggaacttat     60
tctattcaat gtctctacta ttatctgaga attcattgag aggcggggaa gaatcaaagg    120
agttttggaa ggccgaattg agttactttt taggggcaat cggaacagta ttgtttgatt    180
ttattgcaat tttacaatgg attcattatg acagccacag taatcgtacc aatcatatcc    240
aatctgtgag gttgaaagct tacaccccta aatcattaaa aagccagaca attcccaaat    300
cggtgccatt gatacattca cgtacatcgt ccatgagaga tggtacaaag atagatccca    360
tcgaaatggc ggctagcgtc aagtcaacat tgtcacccca gaatgtacgc aaactcaatg    420
agttcacacc attgtctcct atggatttat tgctagatga acatatttca cgcagttatg    480
tttcctctac tgatacaaaa actatacctc agaagaagag acctgatagt atcaagtctg    540
tacacaggca caacgaggac ctgctaatga cattcgaaga atagaagcag tcccaattta    600
aaccgtggcc gtggtaacag ccataactgt agccacaatt ggaaattatg gatgtattgt    660
ctgatttgga cctccggggc agggacaatg gacttggcca aagagtcgaa aaaaatgttc    720
aacagacgag ataattggtc tttaattgtc tcggacatgt gatttcctta aaagtttaat    780
ttcacacccg caggtttatt tatataaaag tgtggccaca agtcttggga agatgaacat    840
cttgatattc atgtcccctc tcattttctg agactggcat aagataagta gaaagcggcc    900
gcggatccct cgaggagtcc atcggttcct gtcagatggg atactcttga cgtggaaaat    960
tcaaacagaa aaaaaacccc aataatgaaa aataacacta cgttatatcc gtggtatcct   1020
ctatcgtatc gtatcgtagc gtatcgtagc gtaccgtatc acagtatagt ctaatattcc   1080
gtatcttatt gtatcctatc ctattcgatc ctattgtatt tcagtgcacc attttaattt   1140
ctattgctat aatgtcctta ttagttgcca ctgtgaggtg accaatggac gagggcgagc   1200
cgttcagaag ccgcgaaggg tgttcttccc atgaatttct taaggagggc ggctcagctc   1260
cgagagtgag gcgagacgtc tcggtcagcg tatcccccctt cctcggcttt tacaaatgat   1320
gcgctcttaa tagtgtgtcg ttatcctttt ggcattgacg ggggagggaa attgattgag   1380
cgcatccata tttttgcgga ctgctgagga caatggtggt ttttccgggt ggcgtgggct   1440
acaaatgata cgatggtttt tttcttttcg gagaaggcgt ataaaaagga cacggagaac   1500
ccatttattc taaaaacagt tgagcttctt taattatttt ttgatataat attctattat   1560
tatatatttt cttcccaata aaacaaaata aaacaaaaca cagcaaaaca caaaaaattct  1620
agataaaatg tccgaagctg ctggtttaca aacgggcaca gctgctcaaa gcactcctgt   1680
agacaccaag tcttttgaga gttctcaagt ttcgactcca accaacgttg gctcgaagga   1740
tgagttgaag gtcgatgaga ccaacactga ggttgagctt ccaaagaaac ctgcttccgc   1800
ttacatcact gtctccattc tatgtttaat ggttgccttt ggtggtttcg ttttcggttg   1860
```

-continued

```
ggataccggt accatttctg gttttgttaa ccaaactgat ttcgtgagaa gattcggttc   1920
tactcatgcc gatggtactc actatttgtc taacgctaga actggtatga ttgtttccat   1980
tttcaacatt ggttgtgcat ttggtggtat ctttttgtcc aaggtcggtg acgtttacgg   2040
tcgtcgtatt ggtctaatgg ctgttgttct agtttacgtt gttggtattg ttatccaaat   2100
cgcttcttct gacaaatggt accaatactt catcggtaga attgtttccg gtttgggtgt   2160
cggtggtatc gctgtcttgt ccccaatgtt gatttctgaa actgctccaa agcaattgag   2220
aggtactttg gtgtcttgtt accaattgat gattaccttc ggtatcttct tgggttactg   2280
taccaactac ggtaccaaga ctcactccga ctctgtccaa tggagagtcc cattgggtct   2340
atgtttcttg tgggccattt tcatgatcgg tggtatgttg ttcgttcctg aatccccaag   2400
atacttgatt gaaaaggaca gaattgaaga agctaaggct tccatcgcca agtctaacaa   2460
ggtttccatc gaagacccag ctgtccaagc tgaaactgat ttgttgattg ccggtgttga   2520
agctgaaaga ctagctggtt ctgcttcttt caaggagttg ttctccacca agaccaaggt   2580
tttccaacgt ttggtcatgg gtattatgat ccaatctttc caacaattga ccggtaacaa   2640
ctacttcttc tactacggta ctagtatctt caagtccgtc ggtatgaccg attctttcga   2700
aacttctatt gtcttgggta ttgttaactt cgcttccact ttcttgggta tctacattgt   2760
tggtagattt ggccgtcgtc aatgtttgct atggggtgct gctctaatga cctgttgtat   2820
ggttgtcttt gcatccgtcg gtgttaccaa gttgtggcca aagggtccaa acggtggtgt   2880
ttcttctaag ggtgctggtg actgtatgat tgtcttcacc tgtttctaca ttctatgttt   2940
cgctaccacc tgggctccaa ttgcttacgt cgttgttgct gaatcttacc cattgagagt   3000
caagtccaag tgtatgggtg tcgctaccgc ttctaactgg gtctggggtt tcttgattgg   3060
tttcttcact ccattcatta cttctgacat ccacttctac tacggttacg tcttcatggg   3120
ctgtttggtt gccatgttct tctacgtctt cttctttgtc ccagaaacca agggtctaac   3180
tttggaagaa gtcgatgaaa tgtggttaga aggtgtcttg ccatggaagt ccgaatcatg   3240
ggtcccatct tccagaagag gtgctgacta caacgccgat gacttgcaac acgatgacaa   3300
gccatggtac aaggctatga tgaaataatt aattaacatc tgaatgtaaa atgaacatta   3360
aaatgaatta ctaaacttta cgtctacttt acaatctata aactttgttt aatcatataa   3420
cgaaatacac taatacacaa tcctgtacgt atgtaatact tttatccatc aaggattgag   3480
aaaaaaaagt aatgattccc tgggccatta aaacttagac cccaagcttg ggataggtca   3540
ctctctattt tcgtttctcc cttccctgat agaagggtga tatgtaatta agaataatat   3600
ataattttat aataaaagaa ttcgccctta catatgataa cttcgtataa tgtatgctat   3660
acgaagttat catagcctca tgaaatcagc catttgcttt tgttcaacga tcttttgaaa   3720
ttgttgttgt tcttggtagt taagttgatc catcttggct tatgttgtgt gtatgttgta   3780
gttattctta gtatattcct gtcctgagtt tagtgaaaca taatatcgcc ttgaaatgaa   3840
aatgctgaaa ttcgtcgaca tacaattttt caaacttttt tttttcttgg gtgcacggac   3900
atgtttttaa aggaagtact ctataccagt tattcttcac aaatttaatt gctggagaat   3960
agatcttcaa cgctttaata aagtagtttg tttgtcaagg atggcgtcat acaaagaaag   4020
atcagaatca cacacttccc ctgttgctag gagacttttc tccatcatgg aggaaaagaa   4080
gtctaacctt tgtgcatcat tggatattac tgaaactgaa aagcttctct ctattttgga   4140
cactattggt ccttacatct gtctagttaa aacacacatc gatattgttt ctgattttac   4200
gtatgaagga actgtgttgc ctttgaagga gcttgccaag aaacataatt ttatgatttt   4260
```

```
tgaagataga aaatttgctg atattggtaa cactgttaaa aatcaatata aatctggtgt   4320

cttccgtatt gccgaatggg ctgacatcac taatgcacat ggtgtaacgg gtgcaggtat   4380

tgtttctggc ttgaaggagg cagcccaaga aacaaccagt gaacctagag gtttgctaat   4440

gcttgctgag ttatcatcaa agggttcttt agcatatggt gaatatacag aaaaaacagt   4500

agaaattgct aaatctgata aagagtttgt cattggtttt attgcgcaac acgatatggg   4560

cggtagagaa gaaggttttg actggatcat tatgactcca ggggttggtt tagatgacaa   4620

aggtgatgca cttggtcaac aatatagaac tgttgatgaa gttgtaaaga ctggaacgga   4680

tatcataatt gttggtagag gtttgtacgg tcaaggaaga gatcctatag agcaagctaa   4740

aagataccaa caagctggtt ggaatgctta tttaaacaga tttaaatgat tcttacacaa   4800

agatttgata catgtacact agtttaaata agcatgaaaa gaattacaca agcaaaaaaa   4860

aaaaaataaa tgaggtactt tacgttcacc tacaaccaaa aaaactagat agagtaaaat   4920

cttaagattt agaaaaagtt gtttaacaaa ggctttagta tgtgaatttt taatgtagca   4980

aagcgataac taataaacat aaacaaaagt atggttttct ttatcagtca aatcattatc   5040

gattgattgt tccgcgtatc tgcagataac ttcgtataat gtatgctata cgaagttata   5100

gatccgcggc cgcaaggcgg tgtaacatac cagtcagtaa atctatccct actagctttt   5160

tttttctata tatttacaca aaccaacagc tacatgtttc aatacataaa catggagaac   5220

cgctcccctt tatatttttt ttttccacac acacctttta tcttatcgct ttacattttc   5280

ggtggcaaat tgattaaaaa aagtacagaa atgctcagct ccaaatagcc ttgaattggg   5340

gttgcttcct ttctctgata accatttttc ctttctcaat tgctagctaa cagtagcaaa   5400

acaactagcc ctataccaaa tgaacattca ctcgtcagta ttgacatccg tagtcctctt   5460

gctcgcttca attacgggct ccgatgctaa ggttcattct gccagcatcc acaagaatcc   5520

gttccaagac aattataaag atatttccta tctagaatat gttgactcca tcaagaacaa   5580

gtatgttaac aattttgtca agaacttcaa tgcacctttt gtcccatttg ttgaagatgc   5640

ggtcattgag gacactcatg aactaccctt aaccaactat atgaatgccc aatacttcac   5700

tgagattcaa cttggtaccc ctggccagcc attcaaggtg attctagaca ctgggtcttc   5760

taatttgtgg gttccttcca caaaatgtac atctttggca tgttatttgc actctaaata   5820

tgatcacgat gcaagttcca catacaaaca aaatggtacc gattctctat cagatatggt   5880

tctggttcct tggaaggttt tatttcacaa gatttactaa cttttggtga cttggtcatt   5940

ccagagcagg atttcgctga ggcaacaagt gaaccgggct tggcgtttgc tttcggaaaa   6000

ttcgacggta ttctaggttt agcttatgat accatctcgg tggacaaggt tgttcctcca   6060

atttacaatg ccattgacaa gggcc                                         6085
```

```
<210> SEQ ID NO 65
<211> LENGTH: 2540
<212> TYPE: DNA
<213> ORGANISM: Artificial Sequence
<220> FEATURE:
<223> OTHER INFORMATION: ScM-IoPGK-IoAXR2 integration fragment
<220> FEATURE:
<221> NAME/KEY: misc_feature
<222> LOCATION: (492)..(492)
<223> OTHER INFORMATION: n is a, c, g, or t

<400> SEQUENCE: 65

tgaagacgac aaaaggggta tcactgaaat tgatcacttt tgcattgttt gggaacttat     60
```

```
tctattcaat cctggaattc gcccttacat atggataact tcgtataatg tatgctatac    120
gaagttatgc tgcaacggca acatcaatgt ccacgtttac acacctacat ttatatctat    180
atttatattt atatttattt atttatgcta cttagcttct atagttagtt aatgcactca    240
cgatattcaa aattgacacc cttcaactac tccctactat tgtctactac tgtctactac    300
tcctctttac tatagctgct cccaataggc tccaccaata ggctctgtca atacattttg    360
cgccgccacc tttcaggttg tgtcactcct gaaggaccat attgggtaat cgtgcaattt    420
ctggaagaga gtgccgcgag aagtgaggcc cccactgtaa atcctcgagg gggcatggag    480
tatggggcat gnaggatgga ggatgggggg gggggggaa aataggtagc gaaaggaccc    540
gctatcaccc cacccggaga actcgttgcc gggaagtcat atttcgacac tccggggagt    600
ctataaaagg cgggttttgt cttttgccag ttgatgttgc tgagaggact tgtttgccgt    660
ttcttccgat ttaacagtat agaatcaacc actgttaatt atacacgtta tactaacaca    720
acaaaaacaa aaacaacgac aacaacaaca acaatgtttg ctttctactt tctcaccgca    780
tgcaccactt tgaagggtgt tttcggagtt tctccgagtt acaatggtct tggtctcacc    840
ccacagatgg gttgggacag ctggaatacg tttgcctgcg atgtcagtga acagctactt    900
ctagacactg ctgatagaat ttctgacttg ggctaaagg atatgggtta caagtatgtc    960
atcctagatg actgttggtc tagcggcagg gattccgacg gtttcctcgt tgcagacaag   1020
cacaaatttc ccaacggtat gggccatgtt gcagaccacc tgcataataa cagctttctt   1080
ttcggtatgt attcgtctgc tggtgagtac acctgtgctg ggtaccctgg gtctctgggg   1140
cgtgaggaag aagatgctca attctttgca aataaccgcg ttgactactt gaagtatgat   1200
aattgttaca ataaaggtca atttggtaca ccagacgttt cttaccaccg ttacaaggcc   1260
atgtcagatg ctttgaataa aactggtagg cctattttct attctctatg taactggggt   1320
caggatttga cattttactg gggctctggt atcgccaatt cttggagaat gagcggagat   1380
attactgctg agttcacccg tccagatagc agatgtccct gtgacggtga cgaatatgat   1440
tgcaagtacg ccggtttcca ttgttctatt atgaatattc ttaacaaggc agctccaatg   1500
gggcaaaatg caggtgttgg tggttggaac gatctggaca atctagaggt cggagtcggt   1560
aatttgactg acgatgagga aaaggcccat ttctctatgt gggcaatggt aaagtcccca   1620
cttatcattg gtgccgacgt gaatcactta aaggcatctt cgtactcgat ctacagtcaa   1680
gcctctgtca tcgcaattaa tcaagatcca aagggtattc cagccacaag agtctggaga   1740
tattatgttt cagacaccga tgaatatgga caaggtgaaa ttcaaatgtg gagtggtccg   1800
cttgacaatg gtgaccaagt ggttgcttta ttgaatggag gaagcgtagc aagaccaatg   1860
aacacgacct tggaagagat ttctctttgac agcaatttgg gttcaaagga actgacatcg   1920
acttgggata tttacgactt atgggccaac agagttgaca actctacggc gtctgctatc   1980
cttgaacaga ataaggcagc caccggtatt ctctacaatg ctacagagca gtcttataaa   2040
gacggtttgt ctaagaatga tacaagactg tttggccaga aaattggtag tctttctcca   2100
aatgctatac ttaacacaac tgttccagct catggtatcg ccttctatag gttgagaccc   2160
tcggcttaag ctcaatgttg agcaaagcag gacgagaaaa aaaaaaataa tgattgttaa   2220
gaagttcatg aaaaaaaaaa ggaaaaatac tcaaatactt ataacagagt gattaaataa   2280
taaacggcag tataccctat caggtattga gatagtttta tttttgtagg tatataatct   2340
gaagcctttg aactattttc tcgtatatat catggagtat acattgcatt agcaacattg   2400
catactagtt cataacttcg tataatgtat gctatacgaa gttattaatt aacaagggcg   2460
```

```
aattctgcag taggtttagc ttatgatacc atctcggtgg acaaggttgt tcctccaatt   2520

tacaatgcca ttgacaaggg                                               2540


<210> SEQ ID NO 66
<211> LENGTH: 6215
<212> TYPE: DNA
<213> ORGANISM: Artificial Sequence
<220> FEATURE:
<223> OTHER INFORMATION: StXI-IoENO1-PDC-TDH3-TEF2-URA3-loxP-AXR2
      integration fragment

<400> SEQUENCE: 66

ctgaagacac aaaaggggta tcactgaaat tgatcacttt tgcattgttt gggaacttat     60

tctattcaat gtctctacta ttatctgaga attcattgag aggcggggaa gaatcaaagg    120

agttttggaa ggccgaattg agttactttt taggggcaat cggaacagta ttgtttgatt    180

ttattgcaat tttacaatgg attcattatg acagccacag taatcgtacc aatcatatcc    240

aatctgtgag gttgaaagct tacacccccta aatcattaaa aagccagaca attcccaaat    300

cggtgccatt gatacattca cgtacatcgt ccatgagaga tggtacaaag atagatccca    360

tcgaaatggc ggctagcgtc aagtcaacat tgtcacccca gaatgtacgc aaactcaatg    420

agttcacacc attgtctcct atggatttat tgctagatga acatatttca cgcagttatg    480

tttcctctac tgatacaaaa actatacctc agaagaagag acctgatagt atcaagtctg    540

tacacaggca caacgaggac ctgctaatga cattcgaaga atagaagcag tcccaattta    600

aaccgtggcc gtggtaacag ccataactgt agccacaatt ggaaattatg gatgtattgt    660

ctgatttgga cctccggggc agggacaatg gacttggcca aagagtcgaa aaaaatgttc    720

aacagacgag ataattggtc tttaattgtc tcggacatgt gatttcctta aaagtttaat    780

ttcacacccg caggtttatt tatataaaag tgtggccaca agtcttggga agatgaacat    840

cttgatattc atgtcccctc tcattttctg agactggcat aagataagta gaaagcggcc    900

gcgttgttga tgctgcgcac ctgtggttgc ccaacatggt tgtatatcgt gtaaccacac    960

caacacatgt gcagcacatg tgtttaaaag agtgtcatgg aggtggatca tgatggaagt   1020

ggactttacc acttgggaac tgtctccact cccgggaaga aaagacccgg cgtatcacgc   1080

ggttgcctca atggggcaat ttggaaggag aaatataggg aaaatcacgt cgctctcgga   1140

cggggaagag ttccagacta tgaggggggg gggtggtata taaagacagg agatgtccac   1200

ccccagagag aggaagaagt tggaacttta gaagagagag ataactttcc ccagtgtcca   1260

tcaatacaca accaaacaca aactctatat ttacacatat aaccccctcc aaccaaaagg   1320

ctagaatgaa ggagtacttt cccgagataa aggaaatcaa atatgaaggt ccagagagca   1380

aaaacgtaat ggccttcaaa tactataaca aggacgaggt tattggtggt aaaccaatga   1440

gggaacactt gaaatttgca atgtcttatt ggcatactct caaggcacag ggattagaca   1500

tgttcggtgg tgatactatg gacagagctt ggaatagata tgatgatgcg ttagaacaag   1560

caaaggcaag agccgatgct ggttttgagt ttatgcaaaa gatagggatg gactatttct   1620

gtttccacga tagggacatt atcaatgaag ccatgaccct taaagagact aatcgtttac   1680

tagatgaaat tgtcgaccat ttagagggtc tgatgaaaaa gacaggtata aagttgctct   1740

ggggcacgac taatgctttc tcacatccta ggtttctcca tggcggtgca actgccccaa   1800

acgccgatgt ttttgcatac gctgctgccc aagtgaaaaa ggctatggaa attacaaaaa   1860

gactgggcgg cgaaaactat gtcctttggg gaggtcgtga aggatatgaa acactattga   1920
```

```
ataccaagag tgatttggaa tatgacaatt ttgctagatt cttacaaatg gttgttgact   1980
ataaggaaaa gattgggttt gaaggacaat tgttaatcga accaaaacct aaggagccta   2040
caaaacacca atacgatttc gacactgcta cagtcctagg atttttgcga aaatacaacc   2100
tagataagca ctacaaaatg aatattgaag caaatcatgc aactttagcg ggtcatacct   2160
tccagcatga gttaaacttg gctagaatta acaatgtcat gggttcgata gatgcgaatc   2220
agggtgatat gttgttggga tgggatacgg atcaatttcc gactaatatc tatgacgcag   2280
tacttgcaat gtatgaggtg attaaaaaca acgggctggg taagggtggt ttgaattttg   2340
atgctaaagt gaggagagga tcctttgaag ataaggatct atttcttgcg tatattgctg   2400
ggatggatac attcgcaaaa ggacttacca tcgcttatag attatacgaa gataaagttt   2460
tcgaagattt tcaagataaa cggtatgagt catacaaaac aggaattggg aaggatattg   2520
ttgaaggcaa agttggcttt gaggaactag cagaatacgt tgagaatttg gcagaaatca   2580
aaaacacctc tggtagacag gaaatgttag aatctatttt gaatagttac atattagaag   2640
caaagtgatt aatcgtaaat ctaactaatg cttttactaa atatctagta caatttttac   2700
agtccctacg tttataaatg aatttaatga aaaaaaaata ttttgtaacg atgtgtttat   2760
taagttgcgc tcttccgata atcccggact ttggttaatt tctcaatggg ttttttttc    2820
aaaaccattg ttgtagtgta acagacttta acaaaaggac atcactctac agggcagctt   2880
taaaatccct cagtgtaatt gttcttcatt cataacgtgg cagtcaagga ctcgaggagt   2940
ccatcggttc ctgtcagatg ggatactctt gacgtggaaa attcaaacag aaaaaaaacc   3000
ccaataatga aaaataacac tacgttatat ccgtggtatc ctctatcgta tcgtatcgta   3060
gcgtatcgta gcgtaccgta tcacagtata gtctaatatt ccgtatctta ttgtatccta   3120
tcctattcga tcctattgta tttcagtgca ccattttaat ttctattgct ataatgtcct   3180
tattagttgc cactgtgagg tgaccaatgg acgagggcga gccgttcaga agccgcgaag   3240
ggtgttcttc ccatgaattt cttaaggagg gcggctcagc tccgagagtg aggcgagacg   3300
tctcggtcag cgtatccccc ttcctcggct tttacaaatg atgcgctctt aatagtgtgt   3360
cgttatcctt ttggcattga cgggggaggg aaattgattg agcgcatcca tatttttgcg   3420
gactgctgag gacaatggtg gtttttccgg gtggcgtggg ctacaaatga tacgatggtt   3480
tttttctttt cggagaaggc gtataaaaag gacacggaga acccatttat tctaaaaaca   3540
gttgagcttc tttaattatt ttttgatata atattctatt attatatatt ttcttcccaa   3600
taaaacaaaa taaaacaaaa cacagcaaaa cacaaaaatt ctagaatgaa ggaatacttc   3660
cccgaaatca aagagatcaa atatgaaggt ccagagtcca aaaatgtcat ggcattcaag   3720
tactataaca aggatgaagt cattggtgga aaacctatga gggagcatct aaaattcgca   3780
atgtcttact ggcatacact taaagcacag ggactggata tgtttggagg cgatacgatg   3840
gatcgagcct ggaatagata cgatgatgcc ctagaacaag ccaaagctag agcagatgct   3900
ggatttgagt ttatgcaaaa gatcggaatg gactatttct gttttcacga ccgtgacatt   3960
atcaatgagg ctatgacttt gaaggaaacg aacagattgt tagatgaaat tgtggaccac   4020
ttggaaggat tgatgaaaaa gactggtatt aagttacttt ggggcactac aaatgccttt   4080
tcacatccga gatttctcca tggtggcgca acagctccaa atgctgatgt gtttgcatat   4140
gctgcggcac aagtcaaaaa ggctatggaa attactaaga ggcttggtgg agagaattac   4200
gtattatggg gtggtagaga aggctatgag actttgctaa ataccaagtc tgacttagaa   4260
```

```
tatgacaatt ttgcaagatt tttgcaaatg gttgttgact ataaggaaaa gattggattc   4320

gaaggtcaac tattgataga accaaaacct aaagagccaa ccaaacatca atatgacttc   4380

gacactgcaa cagtactggg gttcttgagg aagtacaacc tcgataagca ctataagatg   4440

aatatcgaag ctaatcatgc tacattggcc ggtcatacat ttcaacacga gcttaatctc   4500

gcacgtatta acaacgttat gggttcgata gatgcaaacc agggcgatat gttattaggt   4560

tgggatactg atcaatttcc taccaatatc tacgatgccg ttctggctat gtacgaagtt   4620

atcaaaaaca acggtctagg gaagggaggt ttgaattttg atgcaaaagt ccggaggggga   4680

agtttcgaag ataaagattt gtttttagcg tatattgcgg gaatggatac attcgccaaa   4740

ggtttaacga tagcatatag attgtacgag gataaagtgt ttgaagattt tcaagacaag   4800

agatatgaat catataagac cgggataggg aaagatattg ttgagggcaa agttggcttt   4860

gaggaattag cagaatacgt ggaaaactta gctgagatca aaaataccag cggtagacag   4920

gagatgttag aatccatatt gaacagttac attcttgaag caaagtaatt aattaacatc   4980

tgaatgtaaa atgaacatta aaatgaatta ctaaacttta cgtctacttt acaatctata   5040

aactttgttt aatcatataa cgaaatacac taatacacaa tcctgtacgt atgtaatact   5100

tttatccatc aaggattgag aaaaaaaagt aatgattccc tgggccatta aaacttagac   5160

ccccaagctt ggataggtca ctctctattt tcgtttctcc cttccctgat agaagggtga   5220

tatgtaatta agaataatat ataattttat aataaaagaa ttcgccctta catatgataa   5280

cttcgtataa tgtatgctat acgaagttat catagcctca tgaaatcagc catttgcttt   5340

tgttcaacga tcttttgaaa ttgttgttgt tcttggtagt taagttgatc catcttggct   5400

tatgttgtgt gtatgttgta gttattctta gtatattcct gtcctgagtt tagtgaaaca   5460

taatatcgcc ttgaaatgaa aatgctgaaa ttcgtcgaca tacaattttt caaacttttt   5520

ttttttcttg gtgcacggac atgtttttaa aggaagtact ctataccagt tattcttcac   5580

aaatttaatt gctggagaat agatcttcaa cgctttaata aagtagtttg tttgtcaagg   5640

atggcgtcat acaaagaaag atcagaatca cacacttccc ctgttgctag gagacttttc   5700

tccatcatgg aggaaaagaa gtctaacctt tgtgcatcat tggatattac tgaaactgaa   5760

aagcttctct ctattttgga cactattggt ccttacatct gtctagttaa aacacacatc   5820

gatattgttt ctgattttac gtatgaagga actgtgttgc ctttgaagga gcttgccaag   5880

aaacataatt ttatgatttt tgaagataga aaatttgctg atattggtaa cactgttaaa   5940

aatcaatata aatctggtgt cttccgtatt gccgaatggg ctgacatcac taatgcacat   6000

ggtgtaacgg gtgcaggtat tgtttctggc ttgaaggagg cagcccaaga aacaaccagt   6060

gaacctagag gtttgctaat gcttgctgag ttatcatcaa agggttcttt agcatatggt   6120

gaatatacag aaaaaacagt agaaattgct aaatctgata aagagtttgt cattggtttt   6180

attgcgcaac acgatatggg cggtagagaa gggcc                              6215


<210> SEQ ID NO 67
<211> LENGTH: 5988
<212> TYPE: DNA
<213> ORGANISM: Artificial Sequence
<220> FEATURE:
<223> OTHER INFORMATION: StXI-IoENO1-PDC-TDH3-TEF2-URA3-loxP-AXR2
      integration fragment

<400> SEQUENCE: 67

ccacatggtg taacgggtgc aggtattgtt tctggcttga aggaggcagc ccaagaaaca     60
```

```
accagtgaac ctagaggttt gctaatgctt gctgagttat catcaaaggg ttctttagca    120
tatggtgaat atacagaaaa aacagtagaa attgctaaat ctgataaaga gtttgtcatt    180
ggttttattg cgcaacacga tatgggcggt agagaagaag gttttgactg gatcattatg    240
actccagggg ttggtttaga tgacaaaggt gatgcacttg gtcaacaata tagaactgtt    300
gatgaagttg taaagactgg aacggatatc ataattgttg gtagaggttt gtacggtcaa    360
ggaagagatc ctatagagca agctaaaaga taccaacaag ctggttggaa tgcttattta    420
aacagattta aatgattctt acacaaagat ttgatacatg tacactagtt taaataagca    480
tgaaaagaat tacacaagca aaaaaaaaaa aataaatgag gtactttacg ttcacctaca    540
accaaaaaaa ctagatagag taaaatctta agatttagaa aaagttgttt aacaaaggct    600
ttagtatgtg aatttttaat gtagcaaagc gataactaat aaacataaac aaaagtatgg    660
ttttctttat cagtcaaatc attatcgatt gattgttccg cgtatctgca gataacttcg    720
tataatgtat gctatacgaa gttatagatc gcggccgcta acctgatcca aaaggggtat    780
gtctattttt tagagtgtgt ctttgtgtca aattatggta gaatgtgtaa agtagtataa    840
actttcctct caaatgacga ggtttaaaac acccccccggg tgagccgagc cgagaatggg    900
gcaattgttc aatgtgaaat agaagtatcg agtgagaaac ttgggtgttg gccagccaag    960
ggggaaggaa aatggcgcga atgctcaggt gagattgttt tggaattggg tgaagcgagg   1020
aaatgagcga cccggaggtt gtgactttag tggcggagga ggacggagga aaagccaaga   1080
gggaagtgta tataagggga gcaatttgcc accaggatag aattggatga gttataattc   1140
tactgtattt attgtataat ttatttctcc ttttatatca aacacattac aaaacacaca   1200
aaacacacaa acaaacacaa ttacaaaaag ctagcatgaa ggaatacttc cctgaaatca   1260
aagagatcaa atatgaaggt cctgaatcga aaaatgttat ggcattcaag tattacaaca   1320
aggacgaggt cataggagga aaaccaatga gggaacatct taagtttgcc atgtcatatt   1380
ggcatacgct aaaggctcag gggttggata tgttcggtgg agatactatg gatcgtgcat   1440
ggaacagata cgatgacgct ttggagcaag cgaaagccag agctgatgcc ggcttcgagt   1500
ttatgcaaaa gattggcatg gactattttt gttttcatga tcgtgacatt attaacgaag   1560
ctatgacttt aaaggaaacg aataggttat tggatgaaat tgttgaccat cttgagggtt   1620
tgatgaaaaa gactgggatc aaattgttgt ggggtactac aaatgctttt agtcacccaa   1680
gattcttaca tggtggtgct accgcaccga atgccgacgt attcgcatac gcggcagctc   1740
aagttaaaaa ggctatggag attaccaaac ggttgggtgg cgaaaactac gtattatggg   1800
gcggaagaga aggatatgaa acattgctaa ataccaaatc cgatttggaa tatgacaatt   1860
ttgcaagatt tctacaaatg gttgtcgatt acaaggagaa aattgggttc gagggtcaac   1920
tactcataga gccaaagcca aaagagccta ccaaacatca gtatgatttc gatactgcaa   1980
cagttttagg ctttttgagg aagtacaatt tggacaagca ttacaagatg aatatcgaag   2040
caaaccacgc cactttagct ggtcacacat ttcaacacga actgaactta gcacgtatta   2100
acaatgtcat gggttctatt gatgctaatc aaggagatat gttactcggt tgggatacag   2160
atcagtttcc cacaaatatc tacgacgctg ttctagcgat gtatgaagtt atcaaaaaca   2220
atggcctcgg gaagggtggt cttaattttg atgcaaaagt tcgaaggggt tcatttgaag   2280
ataaggacct atttcttgca tacatagccg gaatggatac ctttgcaaaa ggtttaacca   2340
tagcatatag actgtatgag gataaagtgt ttgaagattt ccaagacaag agatatgaaa   2400
gctataagac gggtataggc aaagatattg ttgagggaaa agtcggattc gaggaactgg   2460
```

```
ctgaatatgt ggaaaacctt gcagaaatca aaaatactag tggtagacag gagatgcttg   2520
aatctatttt gaactcctat atattagaag ccaagtaacg atcgtaagcg gcgaatctct   2580
ggctcatggg ggatatcctc tttgtttggc tttttttcc cattctctgt tttgattatc   2640
taatgactca ttgggaggat tttctcactt caagcttttt tttcttgcac tctttcataa   2700
ctccagctct ctctaactga ggctacaatg ccttttaacg aacttatgag acgtttctaa   2760
attatatagg tatatgccaa tatataatta cacataaaaa taaatataaa taaaatataa   2820
aaataaaaat aaacatcgaa aaagaagatg tgaaattgcg aagactagaa agcacaaacg   2880
agcggtctat atcggcgact cgaggctcta caagcctcat atgggttcaa tgggtctgca   2940
atgaccgcat acggacttgg acaattacct tctattgaat ttctgagaag agatacatct   3000
gaccagcaat gtaagcagac aatcccaatt ctgtaaacaa cctctttgtc cataattccc   3060
catcagaaga gtgaaaaatg ccctcaaaac gcatgcgcca ctcccacctc tcagctgcac   3120
tgcgccacct ctgagggtcc tttcaggggt cgactacccc ggacacctcg cagaggagcg   3180
acgtcacgta cttttaaaat ggcagagacg cgcagtttct tgaagaaagg ataaaaatga   3240
aatggtgcgg aaatgcgaaa atgatgaaaa attttcttgg tggcgaggaa attgagtgca   3300
ataattggca cgaggttgtt gccacccgag tgtgagtata tatcctagtt tctgcacttt   3360
tcttcttctt ttccttgcgt tttcttttca actttttta ctttttcctt caacagacaa   3420
atctaactta tatatcacat ctagaatgaa agagtatttc cctgagatta aggaaatcaa   3480
atatgaaggt ccagaaagca aaaatgttat ggcattcaag tactacaata aggacgaggt   3540
tattgggggc aaacctatga gagaacatct taagtttgca atgtcttact ggcacacgtt   3600
gaaagcacaa ggtttagata tgtttggtgg agacacaatg gatagagctt ggaatagata   3660
cgacgatgca ttggagcaag cgaaagcccg tgcagatgcg ggtttcgagt ttatgcagaa   3720
aattggcatg gactacttct gtttccatga tcgtgatatt attaacgaag ctatgacact   3780
taaggagaca aatagattac tagacgaaat agttgatcat ttggagggtt tgatgaaaaa   3840
gactgggatc aaacttctat ggggtacaac taatgctttt agtcatccaa gattcttaca   3900
cggtggagct acagccccaa acgctgacgt atttgcatac gccgctgcgc aagtcaaaaa   3960
ggctatggag attaccaaaa gattgggtgg agaaaattat gtgctgtggg gtggtcgaga   4020
aggttatgaa acattgctca ataccaagtc cgacctggaa tatgataact ttgcaaggtt   4080
tcttcaaatg gttgttgatt acaaggagaa aataggtttt gaaggccaat tgctaattga   4140
accaaaaccc aaggaaccga caaaacatca atatgatttt gatactgcca ctgttttggg   4200
tttcttgcgg aagtataact tggataagca ctataagatg aatattgaag ccaaccatgc   4260
aacccttgcc ggccacacct ttcaacatga attgaatcta gctaggatta acaacgttat   4320
gggctcaata gacgctaatc agggagatat gttattaggt tgggataccg atcagtttcc   4380
tactaatatc tatgatgcag tgttggctat gtatgaagtg atcaaaaaca atggtctagg   4440
gaagggtggt ctgaattttg atgcaaaagt ccgtagggga tcatttgagg acaaagattt   4500
gttcctcgcc tacattgctg gaatggatac ttttgcaaag gggttaacga tagcttatcg   4560
attatacgag gacaaggtct ttgaagattt ccaggataag agatatgaat cctacaaaac   4620
tggtatcgga aaagatatag tagaaggaaa agttggcttt gaggaattag cagaatatgt   4680
tgagaactta gcagaaatca aaaatacctc agggagacaa gagatgttag aatctattct   4740
caactcgtat atcttggaag caaagtaatt aattaagtat agccatatag tttaattcct   4800
```

```
ttatactttt tataactatt tcttacacta attattatta tcaattattt attgtagaac   4860

ttgactcttg cgtcgatcac catgacaggg ctatcttaac aaggggtaat tttgttgat    4920

ggagtcaagt agcattccga cgggaagtgt cgatgcctct gaacgaaatc ttccgattag   4980

ctctgcaaag aagtggaaat tgtcagcgca gaattcaagg cggtgtaaca taccagtcag   5040

taaatctatc cctactagct tttttttct atatatttac acaaaccaac agctacatgt    5100

ttcaatacat aaacatggag aaccgctccc ctttatattt ttttttcca cacacacctt    5160

ttatcttatc gctttacatt ttcggtggca aattgattaa aaaaagtaca gaaatgctca   5220

gctccaaata gccttgaatt ggggttgctt cctttctctg ataaccattt ttcctttctc   5280

aattgctagc taacagtagc aaaacaacta gccctatacc aaatgaacat tcactcgtca   5340

gtattgacat ccgtagtcct cttgctcgct tcaattacgg gctccgatgc taaggttcat   5400

tctgccagca tccacaagaa tccgttccaa gacaattata aagatatttc ctatctagaa   5460

tatgttgact ccatcaagaa caagtatgtt aacaatttg tcaagaactt caatgcacct    5520

tttgtcccat ttgttgaaga tgcggtcatt gaggacactc atgaactacc cttaaccaac   5580

tatatgaatg cccaatactt cactgagatt caacttggta cccctggcca gccattcaag   5640

gtgattctag acactgggtc ttctaatttg tgggttcctt ccacaaaatg tacatctttg   5700

gcatgttatt tgcactctaa atatgatcac gatgcaagtt ccacatacaa acaaaatggt   5760

accgattctc tatcagatat ggttctggtt ccttggaagg ttttatttca caagatttac   5820

taacttttgg tgacttggtc attccagagc aggatttcgc tgaggcaaca agtgaaccgg   5880

gcttggcgtt tgctttcgga aaattcgacg gtattctagg tttagcttat gataccatct   5940

cggtggacaa ggttgttcct ccaatttaca atgccattga caagggcc                5988
```

<210> SEQ ID NO 68
<211> LENGTH: 6349
<212> TYPE: DNA
<213> ORGANISM: Artificial Sequence
<220> FEATURE:
<223> OTHER INFORMATION: StXI-IoENO1-PDC-TDH3-TEF2-MEL5-loxP-AXR2 integration fragment

<400> SEQUENCE: 68

```
ctgctgagtt cacccgtcca gatagcagat gtccctgtga cggtgacgaa tatgattgca     60

agtacgccgg tttccattgt tctattatga atattcttaa caaggcagct ccaatggggc    120

aaaatgcagg tgttggtggt tggaacgatc tggacaatct agaggtcgga gtcggtaatt    180

tgactgacga tgaggaaaag gcccatttct ctatgtgggc aatggtaaag tccccactta    240

tcattggtgc cgacgtgaat cacttaaagg catcttcgta ctcgatctac agtcaagcct    300

ctgtcatcgc aattaatcaa gatccaaagg gtattccagc cacaagagtc tggagatatt    360

atgtttcaga caccgatgaa tatggacaag gtgaaattca aatgtggagt ggtccgcttg    420

acaatggtga ccaagtggtt gctttattga atggaggaag cgtagcaaga ccaatgaaca    480

cgaccttgga agagattttc tttgacagca atttgggttc aaaggaactg acatcgactt    540

gggatattta cgacttatgg gccaacagag ttgacaactc tacggcgtct gctatccttg    600

aacagaataa ggcagccacc ggtattctct acaatgctac agagcagtct tataaagacg    660

gtttgtctaa gaatgataca agactgtttg gccagaaaat tggtagtctt tctccaaatg    720

ctatacttaa cacaactgtt ccagctcatg gtatcgcctt ctataggttg agaccctcgg    780

cttaagctca atgttgagca aagcaggacg agaaaaaaaa aaataatgat tgttaagaag    840
```

```
ttcatgaaaa aaaaaaggaa aaatactcaa atacttataa cagagtgatt aaataataaa    900
cggcagtata ccctatcagg tattgagata gttttatttt tgtaggtata taatctgaag    960
cctttgaact attttctcgt atatatcatg gagtatacat tgcattagca acattgcata   1020
ctagttcata acttcgtata atgtatgcta tacgaagtta ttaattaaca agggcgattt   1080
ctgcagatat cggccggccc catggagatc cgcggccgct aacctgatcc aaaaggggta   1140
tgtctatttt ttagagtgtg tctttgtgtc aaattatggt agaatgtgta aagtagtata   1200
aactttcctc tcaaatgacg aggtttaaaa caccccccgg gtgagccgag ccgagaatgg   1260
ggcaattgtt caatgtgaaa tagaagtatc gagtgagaaa cttgggtgtt ggccagccaa   1320
gggggaagga aaatggcgcg aatgctcagg tgagattgtt ttggaattgg gtgaagcgag   1380
gaaatgagcg acccggaggt tgtgacttta gtggcggagg aggacggagg aaaagccaag   1440
agggaagtgt atataagggg agcaatttgc caccaggata gaattggatg agttataatt   1500
ctactgtatt tattgtataa tttatttctc cttttatatc aaacacatta caaaacacac   1560
aaaacacaca aacaaacaca attacaaaaa gctagcatga aggaatactt ccctgaaatc   1620
aaagagatca aatatgaagg tcctgaatcg aaaaatgtta tggcattcaa gtattacaac   1680
aaggacgagg tcataggagg aaaaccaatg agggaacatc ttaagtttgc catgtcatat   1740
tggcatacgc taaaggctca ggggttggat atgttcggtg gagatactat ggatcgtgca   1800
tggaacagat acgatgacgc tttggagcaa gcgaaagcca gagctgatgc cggcttcgag   1860
tttatgcaaa agattggcat ggactatttt tgttttcatg atcgtgacat tattaacgaa   1920
gctatgactt taaaggaaac gaataggtta ttggatgaaa ttgttgacca tcttgagggt   1980
ttgatgaaaa agactgggat caaattgttg tggggtacta caaatgcttt tagtcaccca   2040
agattcttac atggtggtgc taccgcaccg aatgccgacg tattcgcata cgcggcagct   2100
caagttaaaa aggctatgga gattaccaaa cggttgggtg gcgaaaacta cgtattatgg   2160
ggcggaagag aaggatatga aacattgcta aataccaaat ccgatttgga atatgacaat   2220
tttgcaagat ttctacaaat ggttgtcgat tacaaggaga aaattgggtt cgagggtcaa   2280
ctactcatag agccaaagcc aaaagagcct accaaacatc agtatgattt cgatactgca   2340
acagttttag gctttttgag gaagtacaat ttggacaagc attacaagat gaatatcgaa   2400
gcaaaccacg ccactttagc tggtcacaca tttcaacacg aactgaactt agcacgtatt   2460
aacaatgtca tgggttctat tgatgctaat caaggagata tgttactcgg ttgggataca   2520
gatcagtttc ccacaaatat ctacgacgct gttctagcga tgtatgaagt tatcaaaaac   2580
aatggcctcg ggaagggtgg tcttaatttt gatgcaaaag ttcgaagggg ttcatttgaa   2640
gataaggacc tatttcttgc atacatagcc ggaatggata cctttgcaaa aggtttaacc   2700
atagcatata gactgtatga ggataaagtg tttgaagatt tccaagacaa gagatatgaa   2760
agctataaga cgggtatagg caaagatatt gttgagggaa aagtcggatt cgaggaactg   2820
gctgaatatg tggaaaacct tgcagaaatc aaaaatacta gtggtagaca ggagatgctt   2880
gaatctattt tgaactccta tatattagaa gccaagtaac gatcgtaagc ggcgaatctc   2940
tggctcatgg gggatatcct ctttgtttgg cttttttttc ccattctctg ttttgattat   3000
ctaatgactc attgggagga ttttctcact tcaagctttt ttttcttgca ctctttcata   3060
actccagctc tctctaactg aggctacaat gccttttaac gaacttatga gacgtttcta   3120
aattatatag gtatatgcca atatataatt acacataaaa ataaatataa ataaaatata   3180
aaaataaaaa taaacatcga aaaagaagat gtgaaattgc gaagactaga aagcacaaac   3240
```

```
gagcggtcta tatcggcgac tcgaggctct acaagcctca tatgggttca atgggtctgc   3300
aatgaccgca tacggacttg gacaattacc ttctattgaa tttctgagaa gagatacatc   3360
tgaccagcaa tgtaagcaga caatcccaat tctgtaaaca acctctttgt ccataattcc   3420
ccatcagaag agtgaaaaat gccctcaaaa cgcatgcgcc actcccacct ctcagctgca   3480
ctgcgccacc tctgagggtc ctttcagggg tcgactaccc cggacacctc gcagaggagc   3540
gacgtcacgt acttttaaaa tggcagagac gcgcagtttc ttgaagaaag gataaaaatg   3600
aaatggtgcg gaaatgcgaa aatgatgaaa aattttcttg gtggcgagga aattgagtgc   3660
aataattggc acgaggttgt tgccacccga gtgtgagtat atatcctagt ttctgcactt   3720
ttcttcttct tttccttgcg ttttcttttc aacttttttt actttttcct tcaacagaca   3780
aatctaactt atatatcaca tctagaatga aagagtattt ccctgagatt aaggaaatca   3840
aatatgaagg tccagaaagc aaaaatgtta tggcattcaa gtactacaat aaggacgagg   3900
ttattggggg caaacctatg agagaacatc ttaagtttgc aatgtcttac tggcacacgt   3960
tgaaagcaca aggtttagat atgtttggtg gagacacaat ggatagagct tggaatagat   4020
acgacgatgc attggagcaa gcgaaagccc gtgcagatgc gggtttcgag tttatgcaga   4080
aaattggcat ggactacttc tgtttccatg atcgtgatat tattaacgaa gctatgacac   4140
ttaaggagac aaatagatta ctagacgaaa tagttgatca tttggagggt ttgatgaaaa   4200
agactgggat caaacttcta tggggtacaa ctaatgcttt tagtcatcca agattcttac   4260
acggtggagc tacagcccca aacgctgacg tatttgcata cgccgctgcg caagtcaaaa   4320
aggctatgga gattaccaaa agattgggtg gagaaaatta tgtgctgtgg ggtggtcgag   4380
aaggttatga aacattgctc aataccaagt ccgacctgga atatgataac tttgcaaggt   4440
ttcttcaaat ggttgttgat tacaaggaga aaataggttt tgaaggccaa ttgctaattg   4500
aaccaaaacc caaggaaccg acaaaacatc aatatgattt tgatactgcc actgttttgg   4560
gtttcttgcg gaagtataac ttggataagc actataagat gaatattgaa gccaaccatg   4620
caacccttgc cggccacacc tttcaacatg aattgaatct agctaggatt aacaacgtta   4680
tgggctcaat agacgctaat cagggagata tgttattagg ttgggatacc gatcagtttc   4740
ctactaatat ctatgatgca gtgttggcta tgtatgaagt gatcaaaaac aatggtctag   4800
ggaagggtgg tctgaatttt gatgcaaaag tccgtagggg atcatttgag gacaaagatt   4860
tgttcctcgc ctacattgct ggaatggata cttttgcaaa ggggttaacg atagcttatc   4920
gattatacga ggacaaggtc tttgaagatt tccaggataa gagatatgaa tcctacaaaa   4980
ctggtatcgg aaaagatata gtagaaggaa aagttggctt tgaggaatta gcagaatatg   5040
ttgagaactt agcagaaatc aaaaatacct cagggagaca agagatgtta gaatctattc   5100
tcaactcgta tatcttggaa gcaaagtaat taattaagta tagccatata gtttaattcc   5160
tttatacttt ttataactat ttcttacact aattattatt atcaattatt tattgtagaa   5220
cttgactctt gcgtcgatca ccatgacagg gctatcttaa caaggggtaa tttttgttga   5280
tggagtcaag tagcattccg acgggaagtg tcgatgcctc tgaacgaaat cttccgatta   5340
gctctgcaaa gaagtggaaa ttgtcagcgc agaattcaag gcggtgtaac ataccagtca   5400
gtaaatctat ccctactagc tttttttttc tatatattta cacaaaccaa cagctacatg   5460
tttcaataca taaacatgga gaaccgctcc cctttatatt tttttttccc acacacacct   5520
tttatcttat cgctttacat tttcggtggc aaattgatta aaaaaagtac agaaatgctc   5580
```

```
agctccaaat agccttgaat tggggttgct tcctttctct gataaccatt tttcctttct   5640

caattgctag ctaacagtag caaaacaact agccctatac caaatgaaca ttcactcgtc   5700

agtattgaca tccgtagtcc tcttgctcgc ttcaattacg ggctccgatg ctaaggttca   5760

ttctgccagc atccacaaga atccgttcca agacaattat aaagatattt cctatctaga   5820

atatgttgac tccatcaaga acaagtatgt taacaatttt gtcaagaact tcaatgcacc   5880

ttttgtccca tttgttgaag atgcggtcat tgaggacact catgaactac ccttaaccaa   5940

ctatatgaat gcccaatact tcactgagat tcaacttggt acccctggcc agccattcaa   6000

ggtgattcta gacactgggt cttctaattt gtgggttcct tccacaaaat gtacatcttt   6060

ggcatgttat ttgcactcta aatatgatca cgatgcaagt tccacataca aacaaaatgg   6120

taccgattct ctatcagata tggttctggt tccttggaag gttttatttc acaagattta   6180

ctaacttttg gtgacttggt cattccagag caggatttcg ctgaggcaac aagtgaaccg   6240

ggcttggcgt ttgctttcgg aaaattcgac ggtattctag gtttagctta tgataccatc   6300

tcggtggaca aggttgttcc tccaatttac aatgccattg acaagggcc             6349
```

<210> SEQ ID NO 69
<211> LENGTH: 6753
<212> TYPE: DNA
<213> ORGANISM: Artificial Sequence
<220> FEATURE:
<223> OTHER INFORMATION: StXI-IoENO1-PDC-TDH3-TEF2-MEL5-loxP-AXR2 integration fragment
<220> FEATURE:
<221> NAME/KEY: misc_feature
<222> LOCATION: (5675)..(5675)
<223> OTHER INFORMATION: n is a, c, g, or t

<400> SEQUENCE: 69

```
ctgaagacac aaaaggggta tcactgaaat tgatcacttt tgcattgttt gggaacttat     60

tctattcaat gtctctacta ttatctgaga attcattgag aggcggggaa gaatcaaagg    120

agttttggaa ggccgaattg agttactttt taggggcaat cggaacagta ttgtttgatt    180

ttattgcaat tttacaatgg attcattatg acagccacag taatcgtacc aatcatatcc    240

aatctgtgag gttgaaagct tacacccccta aatcattaaa aagccagaca attcccaaat    300

cggtgccatt gatacattca cgtacatcgt ccatgagaga tggtacaaag atagatccca    360

tcgaaatggc ggctagcgtc aagtcaacat tgtcacccca gaatgtacgc aaactcaatg    420

agttcacacc attgtctcct atggatttat tgctagatga acatatttca cgcagttatg    480

tttcctctac tgatacaaaa actatacctc agaagaagag acctgatagt atcaagtctg    540

tacacaggca caacgaggac ctgctaatga cattcgaaga atagaagcag tcccaattta    600

aaccgtggcc gtggtaacag ccataactgt agccacaatt ggaaattatg gatgtattgt    660

ctgatttgga cctccggggc agggacaatg gacttggcca aagagtcgaa aaaaatgttc    720

aacagacgag ataattggtc tttaattgtc tcggacatgt gatttcctta aaagtttaat    780

ttcacacccg caggtttatt tatataaaag tgtggccaca agtcttggga agatgaacat    840

cttgatattc atgtcccctc tcattttctg agactggcat aagataagta gaaagcggcc    900

gcgttgttga tgctgcgcac ctgtggttgc ccaacatggt tgtatatcgt gtaaccacac    960

caacacatgt gcagcacatg tgtttaaaag agtgtcatgg aggtggatca tgatggaagt   1020

ggactttacc acttgggaac tgtctccact cccgggaaga aaagacccgg cgtatcacgc   1080

ggttgcctca atggggcaat ttggaaggag aaatataggg aaaatcacgt cgctctcgga   1140
```

```
cggggaagag ttccagacta tgaggggggg gggtggtata taaagacagg agatgtccac   1200
ccccagagag aggaagaagt tggaacttta gaagagagag ataactttcc ccagtgtcca   1260
tcaatacaca accaaacaca aactctatat ttacacatat aaccccctcc aaccaaaagg   1320
ctagaatgaa ggagtacttt cccgagataa aggaaatcaa atatgaaggt ccagagagca   1380
aaaacgtaat ggccttcaaa tactataaca aggacgaggt tattggtggt aaaccaatga   1440
gggaacactt gaaatttgca atgtcttatt ggcatactct caaggcacag ggattagaca   1500
tgttcggtgg tgatactatg gacagagctt ggaatagata tgatgatgcg ttagaacaag   1560
caaaggcaag agccgatgct ggttttgagt ttatgcaaaa gatagggatg gactatttct   1620
gtttccacga tagggacatt atcaatgaag ccatgaccct taaagagact aatcgtttac   1680
tagatgaaat tgtcgaccat ttagagggtc tgatgaaaaa gacaggtata aagttgctct   1740
ggggcacgac taatgctttc tcacatccta ggtttctcca tggcggtgca actgccccaa   1800
acgccgatgt tttgcatac gctgctgccc aagtgaaaaa ggctatggaa attacaaaaa   1860
gactgggcgg cgaaaactat gtcctttggg gaggtcgtga aggatatgaa acactattga   1920
ataccaagag tgatttggaa tatgacaatt ttgctagatt cttacaaatg gttgttgact   1980
ataaggaaaa gattgggttt gaaggacaat tgttaatcga accaaaacct aaggagccta   2040
caaaacacca atacgatttc gacactgcta cagtcctagg atttttgcga aaatacaacc   2100
tagataagca ctacaaaatg aatattgaag caaatcatgc aactttagcg ggtcatacct   2160
tccagcatga gttaaacttg gctagaatta acaatgtcat gggttcgata gatgcgaatc   2220
agggtgatat gttgttggga tgggatacgg atcaatttcc gactaatatc tatgacgcag   2280
tacttgcaat gtatgaggtg attaaaaaca acgggctggg taagggtggt ttgaattttg   2340
atgctaaagt gaggagagga tcctttgaag ataaggatct atttcttgcg tatattgctg   2400
ggatggatac attcgcaaaa ggacttacca tcgcttatag attatacgaa gataaagttt   2460
tcgaagattt tcaagataaa cggtatgagt catacaaaac aggaattggg aaggatattg   2520
ttgaaggcaa agttggcttt gaggaactag cagaatacgt tgagaatttg gcagaaatca   2580
aaaacacctc tggtagacag gaaatgttag aatctatttt gaatagttac atattagaag   2640
caaagtgatt aatcgtaaat ctaactaatg cttttactaa atatctagta caatttttac   2700
agtccctacg tttataaatg aatttaatga aaaaaaaata ttttgtaacg atgtgtttat   2760
taagttgcgc tcttccgata atcccggact ttggttaatt tctcaatggg ttttttttc   2820
aaaaccattg ttgtagtgta acagacttta acaaaaggac atcactctac agggcagctt   2880
taaaatccct cagtgtaatt gttcttcatt cataacgtgg cagtcaagga ctcgaggagt   2940
ccatcggttc ctgtcagatg ggatactctt gacgtggaaa attcaaacag aaaaaaaacc   3000
ccaataatga aaaataacac tacgttatat ccgtggtatc ctctatcgta tcgtatcgta   3060
gcgtatcgta gcgtaccgta tcacagtata gtctaatatt ccgtatctta ttgtatccta   3120
tcctattcga tcctattgta tttcagtgca ccattttaat ttctattgct ataatgtcct   3180
tattagttgc cactgtgagg tgaccaatgg acgagggcga gccgttcaga agccgcgaag   3240
ggtgttcttc ccatgaattt cttaaggagg gcggctcagc tccgagagtg aggcgagacg   3300
tctcggtcag cgtatccccc ttcctcggct tttacaaatg atgcgctctt aatagtgtgt   3360
cgttatcctt ttggcattga cgggggaggg aaattgattg agcgcatcca tatttttgcg   3420
gactgctgag gacaatggtg gtttttccgg gtggcgtggg ctacaaatga tacgatggtt   3480
tttttctttt cggagaaggc gtataaaaag gacacggaga acccatttat tctaaaaaca   3540
```

```
gttgagcttc tttaattatt ttttgatata atattctatt attatatatt ttcttcccaa   3600
taaaacaaaa taaaacaaaa cacagcaaaa cacaaaaatt ctagaatgaa ggaatacttc   3660
cccgaaatca aagagatcaa atatgaaggt ccagagtcca aaaatgtcat ggcattcaag   3720
tactataaca aggatgaagt cattggtgga aaacctatga gggagcatct aaaattcgca   3780
atgtcttact ggcatacact taaagcacag ggactggata tgtttggagg cgatacgatg   3840
gatcgagcct ggaatagata cgatgatgcc ctagaacaag ccaaagctag agcagatgct   3900
ggatttgagt ttatgcaaaa gatcggaatg gactatttct gttttcacga ccgtgacatt   3960
atcaatgagg ctatgacttt gaaggaaacg aacagattgt tagatgaaat tgtggaccac   4020
ttggaaggat tgatgaaaaa gactggtatt aagttacttt ggggcactac aaatgccttt   4080
tcacatccga gatttctcca tggtggcgca acagctccaa atgctgatgt gtttgcatat   4140
gctgcggcac aagtcaaaaa ggctatggaa attactaaga ggcttggtgg agagaattac   4200
gtattatggg gtggtagaga aggctatgag actttgctaa ataccaagtc tgacttagaa   4260
tatgacaatt ttgcaagatt tttgcaaatg gttgttgact ataaggaaaa gattggattc   4320
gaaggtcaac tattgataga accaaaacct aaagagccaa ccaaacatca atatgacttc   4380
gacactgcaa cagtactggg gttcttgagg aagtacaacc tcgataagca ctataagatg   4440
aatatcgaag ctaatcatgc tacattggcc ggtcatacat ttcaacacga gcttaatctc   4500
gcacgtatta acaacgttat gggttcgata gatgcaaacc agggcgatat gttattaggt   4560
tgggatactg atcaatttcc taccaatatc tacgatgccg ttctggctat gtacgaagtt   4620
atcaaaaaca acggtctagg gaagggaggt ttgaattttg atgcaaaagt ccggagggga   4680
agtttcgaag ataaagattt gtttttagcg tatattgcgg gaatggatac attcgccaaa   4740
ggtttaacga tagcatatag attgtacgag gataaagtgt ttgaagattt tcaagacaag   4800
agatatgaat catataagac cgggatatagg aaagatattg ttgagggcaa agttggcttt   4860
gaggaattag cagaatacgt ggaaaactta gctgagatca aaaataccag cggtagacag   4920
gagatgttag aatccatatt gaacagttac attcttgaag caaagtaatt aattaacatc   4980
tgaatgtaaa atgaacatta aaatgaatta ctaaacttta cgtctacttt acaatctata   5040
aactttgttt aatcatataa cgaaatacac taatacacaa tcctgtacgt atgtaatact   5100
tttatccatc aaggattgag aaaaaaaagt aatgattccc tgggccatta aaacttagac   5160
ccccaagctt ggataggtca ctctctattt tcgtttctcc cttccctgat agaagggtga   5220
tatgtaatta agaataatat ataattttat aataaaagaa ttcgccctta catatggata   5280
acttcgtata atgtatgcta tacgaagtta tgctgcaacg gcaacatcaa tgtccacgtt   5340
tacacaccta catttatatc tatatttata tttatattta tttatttatg ctacttagct   5400
tctatagtta gttaatgcac tcacgatatt caaaattgac acccttcaac tactccctac   5460
tattgtctac tactgtctac tactcctctt tactatagct gctcccaata ggctccacca   5520
ataggctctg tcaatacatt ttgcgccgcc acctttcagg ttgtgtcact cctgaaggac   5580
catattgggt aatcgtgcaa tttctggaag agagtgccgc gagaagtgag gcccccactg   5640
taaatcctcg agggggcatg gagtatgggg catgnaggat ggaggatggg gggggggggg   5700
gaaaataggt agcgaaagga cccgctatca ccccacccgg agaactcgtt gccgggaagt   5760
catatttcga cactccgggg agtctataaa aggcgggttt tgtcttttgc cagttgatgt   5820
tgctgagagg acttgtttgc cgtttcttcc gatttaacag tatagaatca accactgtta   5880
```

```
attatacacg ttatactaac acaacaaaaa caaaaacaac gacaacaaca acaacaatgt   5940

ttgctttcta ctttctcacc gcatgcacca ctttgaaggg tgttttcgga gtttctccga   6000

gttacaatgg tcttggtctc accccacaga tgggttggga cagctggaat acgtttgcct   6060

gcgatgtcag tgaacagcta cttctagaca ctgctgatag aatttctgac ttggggctaa   6120

aggatatggg ttacaagtat gtcatcctag atgactgttg gtctagcggc agggattccg   6180

acggtttcct cgttgcagac aagcacaaat ttcccaacgg tatgggccat gttgcagacc   6240

acctgcataa taacagcttt cttttcggta tgtattcgtc tgctggtgag tacacctgtg   6300

ctgggtaccc tgggtctctg gggcgtgagg aagaagatgc tcaattcttt gcaaataacc   6360

gcgttgacta cttgaagtat gataattgtt acaataaagg tcaatttggt acaccagacg   6420

tttcttacca ccgttacaag gccatgtcag atgctttgaa taaaactggt aggcctattt   6480

tctattctct atgtaactgg ggtcaggatt tgacatttta ctggggctct ggtatcgcca   6540

attcttggag aatgagcgga gatattactg ctgagttcac ccgtccagat agcagatgtc   6600

cctgtgacgg tgacgaatat gattgcaagt acgccggttt ccattgttct attatgaata   6660

ttcttaacaa ggcagctcca atggggcaaa atgcaggtgt tggtggttgg aacgatctgg   6720

acaatctaga ggtcggagtc ggtaatttgg gcc                                 6753
```

```
<210> SEQ ID NO 70
<211> LENGTH: 6278
<212> TYPE: DNA
<213> ORGANISM: Artificial Sequence
<220> FEATURE:
<223> OTHER INFORMATION: StXI-IoENO1-PDC-TDH3-TEF2-URA3-loxP-XR
      integration fragment

<400> SEQUENCE: 70
```

```
ccctccagtg tttttctctc tgtctctttg tttttttttt ccaatctgat ttgacgtgca     60

aggcaaagac atcacatgtt tgagaatggc aagagaaggg gcgtggtagt gtataccaag    120

ccggtgtaga gagtgtgatt ttagagtgaa tccatccatg aacacgagta gaggagatgt    180

atgagcaaat ccagggtgtt tgtaatggtc caagccgcaa ggcggcgtaa tggaatgcaa    240

gaaacaaggg acactaatga aggggtaaga ggtgtctagt tgagaagtac atartaaaag    300

atgaatagtt gagawgtaca trgtaaaaga tgaatagttg agacaaatga aggtgtcaat    360

gttcctgata atgacactgc aagraacaaa taccgtgcag ttggaagggg gaaagagatg    420

rccgagataa gtgttgttga ggccaaagga tgttggaacc tgctacaata ggagatggag    480

cggcctataa ctccggcgtg tttgtgttga cagccctata catcagccaa tacgagagtt    540

tggcatgtcc tttaaagggt ttgctacccc cactcccgta atcatcgtta aaatcatcat    600

cattgaaatc attataatta acctcatcac cattcccact attatcacct tatattctcc    660

actccaggga gatgcatcgt tgtaaagggc atggctgttt gtttatttta cccgacaagc    720

caataccaag agcggacaaa ccgcatcaga atgcaacaga aggttggaga aacgtgatgt    780

catttttcc gcaaacggag atctcgcaca gcggtgagat ataaaaggcg gagatgtgga    840

caccttcttt atacaattcc cctctacttg attgttccat attcctaaca tctagttaca    900

actctgaaca tcataattat tttaaaattc tcaacccaac tgcaattgga ttgaactgcg    960

gccgcgttgt tgatgctgcg cacctgtggt tgcccaacat ggttgtatat cgtgtaacca   1020

caccaacaca tgtgcagcac atgtgtttaa aagagtgtca tggaggtgga tcatgatgga   1080

agtggacttt accacttggg aactgtctcc actcccggga agaaaagacc cggcgtatca   1140
```

```
cgcggttgcc tcaatggggc aatttggaag gagaaatata gggaaaatca cgtcgctctc   1200

ggacggggaa gagttccaga ctatgagggg ggggggtggt atataaagac aggagatgtc   1260

cacccccaga gagaggaaga agttggaact ttagaagaga gagataactt tccccagtgt   1320

ccatcaatac acaaccaaac acaaactcta tatttacaca tataaccccc tccaaccaaa   1380

aggctagaat gaaggagtac tttcccgaga taaaggaaat caaatatgaa ggtccagaga   1440

gcaaaaacgt aatggccttc aaatactata acaaggacga ggttattggt ggtaaaccaa   1500

tgagggaaca cttgaaattt gcaatgtctt attggcatac tctcaaggca cagggattag   1560

acatgttcgg tggtgatact atggacagag cttggaatag atatgatgat gcgttagaac   1620

aagcaaaggc aagagccgat gctggttttg agtttatgca aaagataggg atggactatt   1680

tctgtttcca cgatagggac attatcaatg aagccatgac ccttaaagag actaatcgtt   1740

tactagatga aattgtcgac catttagagg gtctgatgaa aaagacaggt ataaagttgc   1800

tctggggcac gactaatgct ttctcacatc ctaggtttct ccatggcggt gcaactgccc   1860

caaacgccga tgtttttgca tacgctgctg cccaagtgaa aaaggctatg gaaattacaa   1920

aaagactggg cggcgaaaac tatgtccttt ggggaggtcg tgaaggatat gaaacactat   1980

tgaataccaa gagtgatttg gaatatgaca attttgctag attcttacaa atggttgttg   2040

actataagga aaagattggg tttgaaggac aattgttaat cgaaccaaaa cctaaggagc   2100

ctacaaaaca ccaatacgat ttcgacactg ctacagtcct aggatttttg cgaaaataca   2160

acctagataa gcactacaaa atgaatattg aagcaaatca tgcaacttta gcgggtcata   2220

ccttccagca tgagttaaac ttggctagaa ttaacaatgt catgggttcg atagatgcga   2280

atcagggtga tatgttgttg ggatgggata cggatcaatt tccgactaat atctatgacg   2340

cagtacttgc aatgtatgag gtgattaaaa acaacgggct gggtaagggt ggtttgaatt   2400

ttgatgctaa agtgaggaga ggatcccttg aagataagga tctatttctt gcgtatattg   2460

ctgggatgga tacattcgca aaaggactta ccatcgctta tagattatac gaagataaag   2520

ttttcgaaga ttttcaagat aaacggtatg agtcatacaa aacaggaatt gggaaggata   2580

ttgttgaagg caaagttggc tttgaggaac tagcagaata cgttgagaat ttggcagaaa   2640

tcaaaaacac ctctggtaga caggaaatgt tagaatctat tttgaatagt tacatattag   2700

aagcaaagtg attaatcgta aatctaacta atgcttttac taaatatcta gtacaatttt   2760

tacagtccct acgtttataa atgaatttaa tgaaaaaaaa atattttgta acgatgtgtt   2820

tattaagttg cgctcttccg ataatcccgg actttggtta atttctcaat gggttttttt   2880

ttcaaaacca ttgttgtagt gtaacagact ttaacaaaag gacatcactc tacagggcag   2940

ctttaaaatc cctcagtgta attgttcttc attcataacg tggcagtcaa ggactcgagg   3000

agtccatcgg ttcctgtcag atgggatact cttgacgtgg aaaattcaaa cagaaaaaaa   3060

accccaataa tgaaaaataa cactacgtta tatccgtggt atcctctatc gtatcgtatc   3120

gtagcgtatc gtagcgtacc gtatcacagt atagtctaat attccgtatc ttattgtatc   3180

ctatcctatt cgatcctatt gtatttcagt gcaccatttt aatttctatt gctataatgt   3240

ccttattagt tgccactgtg aggtgaccaa tggacgaggg cgagccgttc agaagccgcg   3300

aagggtgttc ttcccatgaa tttcttaagg agggcggctc agctccgaga gtgaggcgag   3360

acgtctcggt cagcgtatcc cccttcctcg gcttttacaa atgatgcgct cttaatagtg   3420

tgtcgttatc cttttggcat tgacggggga gggaaattga ttgagcgcat ccatattttt   3480

gcggactgct gaggacaatg gtggtttttc cgggtggcgt gggctacaaa tgatacgatg   3540
```

```
gtttttttct tttcggagaa ggcgtataaa aaggacacgg agaacccatt tattctaaaa   3600
acagttgagc ttctttaatt attttttgat ataatattct attattatat attttcttcc   3660
caataaaaca aaataaaaca aaacacagca aaacacaaaa attctagaat gaaggaatac   3720
ttccccgaaa tcaaagagat caaatatgaa ggtccagagt ccaaaaatgt catggcattc   3780
aagtactata acaaggatga agtcattggt ggaaaaccta tgagggagca tctaaaattc   3840
gcaatgtctt actggcatac acttaaagca cagggactgg atatgtttgg aggcgatacg   3900
atggatcgag cctggaatag atacgatgat gccctagaac aagccaaagc tagagcagat   3960
gctggatttg agtttatgca aaagatcgga atggactatt tctgttttca cgaccgtgac   4020
attatcaatg aggctatgac tttgaaggaa acgaacagat tgttagatga aattgtggac   4080
cacttggaag gattgatgaa aaagactggt attaagttac tttggggcac tacaaatgcc   4140
ttttcacatc cgagatttct ccatggtggc gcaacagctc caaatgctga tgtgtttgca   4200
tatgctgcgg cacaagtcaa aaaggctatg gaaattacta agaggcttgg tggagagaat   4260
tacgtattat ggggtggtag agaaggctat gagactttgc taaataccaa gtctgactta   4320
gaatatgaca attttgcaag atttttgcaa atggttgttg actataagga aaagattgga   4380
ttcgaaggtc aactattgat agaaccaaaa cctaaagagc caaccaaaca tcaatatgac   4440
ttcgacactg caacagtact ggggttcttg aggaagtaca acctcgataa gcactataag   4500
atgaatatcg aagctaatca tgctacattg gccggtcata catttcaaca cgagcttaat   4560
ctcgcacgta ttaacaacgt tatgggttcg atagatgcaa accagggcga tatgttatta   4620
ggttgggata ctgatcaatt tcctaccaat atctacgatg ccgttctggc tatgtacgaa   4680
gttatcaaaa acaacggtct agggaaggga ggtttgaatt ttgatgcaaa agtccggagg   4740
ggaagtttcg aagataaaga tttgttttta gcgtatattg cgggaatgga tacattcgcc   4800
aaaggtttaa cgatagcata tagattgtac gaggataaag tgtttgaaga ttttcaagac   4860
aagagatatg aatcatataa gaccgggata gggaaagata ttgttgaggg caaagttggc   4920
tttgaggaat tagcagaata cgtggaaaac ttagctgaga tcaaaaatac cagcggtaga   4980
caggagatgt tagaatccat attgaacagt tacattcttg aagcaaagta attaattaac   5040
atctgaatgt aaaatgaaca ttaaaatgaa ttactaaact ttacgtctac tttacaatct   5100
ataaactttg tttaatcata taacgaaata cactaataca caatcctgta cgtatgtaat   5160
acttttatcc atcaaggatt gagaaaaaaa agtaatgatt ccctgggcca ttaaaactta   5220
gacccccaag cttggatagg tcactctcta ttttcgtttc tcccttccct gatagaaggg   5280
tgatatgtaa ttaagaataa tatataattt tataataaaa gaattcgccc ttacatatga   5340
taacttcgta taatgtatgc tatacgaagt tatcatagcc tcatgaaatc agccatttgc   5400
ttttgttcaa cgatcttttg aaattgttgt tgttcttggt agttaagttg atccatcttg   5460
gcttatgttg tgtgtatgtt gtagttattc ttagtatatt cctgtcctga gtttagtgaa   5520
acataatatc gccttgaaat gaaaatgctg aaattcgtcg acatacaatt tttcaaactt   5580
tttttttttc ttggtgcacg gacatgtttt taaaggaagt actctatacc agttattctt   5640
cacaaattta attgctggag aatagatctt caacgcttta ataaagtagt ttgtttgtca   5700
aggatggcgt catacaaaga aagatcagaa tcacacactt cccctgttgc taggagactt   5760
ttctccatca tggaggaaaa gaagtctaac ctttgtgcat cattggatat tactgaaact   5820
gaaaagcttc tctctatttt ggacactatt ggtccttaca tctgtctagt taaaacacac   5880
```

```
atcgatattg tttctgattt tacgtatgaa ggaactgtgt tgcctttgaa ggagcttgcc   5940

aagaaacata attttatgat ttttgaagat agaaaatttg ctgatattgg taacactgtt   6000

aaaaatcaat ataaatctgg tgtcttccgt attgccgaat gggctgacat cactaatgca   6060

catggtgtaa cgggtgcagg tattgtttct ggcttgaagg aggcagccca agaaacaacc   6120

agtgaaccta gaggtttgct aatgcttgct gagttatcat caaagggttc tttagcatat   6180

ggtgaatata cagaaaaaac agtagaaatt gctaaatctg ataaagagtt tgtcattggt   6240

tttattgcgc aacacgatat gggcggtaga gaagggcc                           6278
```

<210> SEQ ID NO 71
<211> LENGTH: 6028
<212> TYPE: DNA
<213> ORGANISM: Artificial Sequence
<220> FEATURE:
<223> OTHER INFORMATION: StXI-IoENO1-PDC-TDH3-TEF2-URA3-loxP-XR integration fragment

<400> SEQUENCE: 71

```
ccacatggtg taacgggtgc aggtattgtt tctggcttga aggaggcagc ccaagaaaca     60

accagtgaac ctagaggttt gctaatgctt gctgagttat catcaaaggg ttctttagca    120

tatggtgaat atacagaaaa aacagtagaa attgctaaat ctgataaaga gtttgtcatt    180

ggttttattg cgcaacacga tatgggcggt agagaagaag gttttgactg gatcattatg    240

actccagggg ttggtttaga tgacaaaggt gatgcacttg gtcaacaata tagaactgtt    300

gatgaagttg taaagactgg aacggatatc ataattgttg gtagaggttt gtacggtcaa    360

ggaagagatc ctatagagca agctaaaaga taccaacaag ctggttggaa tgcttattta    420

aacagattta aatgattctt acacaaagat ttgatacatg tacactagtt taaataagca    480

tgaaaagaat tacacaagca aaaaaaaaaa aataaatgag gtactttacg ttcacctaca    540

accaaaaaaa ctagatagag taaaatctta agatttagaa aaagttgttt aacaaaggct    600

ttagtatgtg aatttttaat gtagcaaagc gataactaat aaacataaac aaaagtatgg    660

ttttctttat cagtcaaatc attatcgatt gattgttccg cgtatctgca gataacttcg    720

tataatgtat gctatacgaa gttatagatc gcggccgcta acctgatcca aaaggggtat    780

gtctattttt tagagtgtgt ctttgtgtca aattatggta gaatgtgtaa agtagtataa    840

actttcctct caaatgacga ggtttaaaac accccccggg tgagccgagc cgagaatggg    900

gcaattgttc aatgtgaaat agaagtatcg agtgagaaac ttgggtgttg gccagccaag    960

ggggaaggaa aatggcgcga atgctcaggt gagattgttt tggaattggg tgaagcgagg   1020

aaatgagcga cccggaggtt gtgactttag tggcggagga ggacggagga aaagccaaga   1080

gggaagtgta tataagggga gcaatttgcc accaggatag aattggatga gttataattc   1140

tactgtattt attgtataat ttatttctcc ttttatatca aacacattac aaaacacaca   1200

aaacacacaa acaaacacaa ttacaaaaag ctagcatgaa ggaatacttc cctgaaatca   1260

aagagatcaa atatgaaggt cctgaatcga aaaatgttat ggcattcaag tattacaaca   1320

aggacgaggt cataggagga aaaccaatga gggaacatct taagtttgcc atgtcatatt   1380

ggcatacgct aaaggctcag ggttggata tgttcggtgg agatactatg gatcgtgcat   1440

ggaacagata cgatgacgct ttggagcaag cgaaagccag agctgatgcc ggcttcgagt   1500

ttatgcaaaa gattggcatg gactattttt gttttcatga tcgtgacatt attaacgaag   1560

ctatgacttt aaaggaaacg aataggttat tggatgaaat tgttgaccat cttgagggtt   1620
```

```
tgatgaaaaa gactgggatc aaattgttgt ggggtactac aaatgctttt agtcacccaa   1680

gattcttaca tggtggtgct accgcaccga atgccgacgt attcgcatac gcggcagctc   1740

aagttaaaaa ggctatggag attaccaaac ggttgggtgg cgaaaactac gtattatggg   1800

gcggaagaga aggatatgaa acattgctaa ataccaaatc cgatttggaa tatgacaatt   1860

ttgcaagatt tctacaaatg gttgtcgatt acaaggagaa aattgggttc gagggtcaac   1920

tactcataga gccaaagcca aaagagccta ccaaacatca gtatgatttc gatactgcaa   1980

cagttttagg ctttttgagg aagtacaatt tggacaagca ttacaagatg aatatcgaag   2040

caaaccacgc cactttagct ggtcacacat ttcaacacga actgaactta gcacgtatta   2100

acaatgtcat gggttctatt gatgctaatc aaggagatat gttactcggt tgggatacag   2160

atcagtttcc cacaaatatc tacgacgctg ttctagcgat gtatgaagtt atcaaaaaca   2220

atggcctcgg gaagggtggt cttaattttg atgcaaaagt tcgaaggggt tcatttgaag   2280

ataaggacct atttcttgca tacatagccg gaatggatac ctttgcaaaa ggtttaacca   2340

tagcatatag actgtatgag gataaagtgt ttgaagattt ccaagacaag agatatgaaa   2400

gctataagac gggtataggc aaagatattg ttgagggaaa agtcggattc gaggaactgg   2460

ctgaatatgt ggaaaacctt gcagaaatca aaaatactag tggtagacag gagatgcttg   2520

aatctatttt gaactcctat atattagaag ccaagtaacg atcgtaagcg gcgaatctct   2580

ggctcatggg ggatatcctc tttgtttggc tttttttttcc cattctctgt tttgattatc   2640

taatgactca ttgggaggat tttctcactt caagcttttt tttcttgcac tctttcataa   2700

ctccagctct ctctaactga ggctacaatg ccttttaacg aacttatgag acgtttctaa   2760

attatatagg tatatgccaa tatataatta cacataaaaa taaatataaa taaaatataa   2820

aaataaaaat aaacatcgaa aaagaagatg tgaaattgcg aagactagaa agcacaaacg   2880

agcggtctat atcggcgact cgaggctcta caagcctcat atgggttcaa tgggtctgca   2940

atgaccgcat acggacttgg acaattacct tctattgaat ttctgagaag agatacatct   3000

gaccagcaat gtaagcagac aatcccaatt ctgtaaacaa cctctttgtc cataattccc   3060

catcagaaga gtgaaaaatg ccctcaaaac gcatgcgcca ctcccacctc tcagctgcac   3120

tgcgccacct ctgagggtcc tttcaggggt cgactacccc ggacacctcg cagaggagcg   3180

acgtcacgta cttttaaaat ggcagagacg cgcagtttct tgaagaaagg ataaaaatga   3240

aatggtgcgg aaatgcgaaa atgatgaaaa attttcttgg tggcgaggaa attgagtgca   3300

ataattggca cgaggttgtt gccacccgag tgtgagtata tatcctagtt tctgcacttt   3360

tcttcttctt ttccttgcgt tttcttttca actttttttta ctttttcctt caacagacaa   3420

atctaactta tatatcacat ctagaatgaa agagtatttc cctgagatta aggaaatcaa   3480

atatgaaggt ccagaaagca aaaatgttat ggcattcaag tactacaata aggacgaggt   3540

tattgggggc aaacctatga gagaacatct taagtttgca atgtcttact ggcacacgtt   3600

gaaagcacaa ggtttagata tgtttggtgg agacacaatg gatagagctt ggaatagata   3660

cgacgatgca ttggagcaag cgaaagcccg tgcagatgcg ggtttcgagt ttatgcagaa   3720

aattggcatg gactacttct gtttccatga tcgtgatatt attaacgaag ctatgacact   3780

taaggagaca aatagattac tagacgaaat agttgatcat ttggagggtt tgatgaaaaa   3840

gactgggatc aaacttctat ggggtacaac taatgctttt agtcatccaa gattcttaca   3900

cggtggagct acagccccaa acgctgacgt atttgcatac gccgctgcgc aagtcaaaaa   3960

ggctatggag attaccaaaa gattgggtgg agaaaattat gtgctgtggg gtggtcgaga   4020
```

```
aggttatgaa acattgctca ataccaagtc cgacctggaa tatgataact ttgcaaggtt   4080
tcttcaaatg gttgttgatt acaaggagaa aataggtttt gaaggccaat tgctaattga   4140
accaaaaccc aaggaaccga caaaacatca atatgatttt gatactgcca ctgttttggg   4200
tttcttgcgg aagtataact tggataagca ctataagatg aatattgaag ccaaccatgc   4260
aacccttgcc ggccacacct ttcaacatga attgaatcta gctaggatta acaacgttat   4320
gggctcaata gacgctaatc agggagatat gttattaggt tgggataccg atcagtttcc   4380
tactaatatc tatgatgcag tgttggctat gtatgaagtg atcaaaaaca atggtctagg   4440
gaagggtggt ctgaattttg atgcaaaagt ccgtagggga tcatttgagg acaaagattt   4500
gttcctcgcc tacattgctg gaatggatac ttttgcaaag ggttaacga tagcttatcg    4560
attatacgag gacaaggtct ttgaagattt ccaggataag agatatgaat cctacaaaac   4620
tggtatcgga aaagatatag tagaaggaaa agttggcttt gaggaattag cagaatatgt   4680
tgagaactta gcagaaatca aaaatacctc agggagacaa gagatgttag aatctattct   4740
caactcgtat atcttggaag caaagtaatt aattaagtat agccatatag tttaattcct   4800
ttatactttt tataactatt tcttacacta attattatta tcaattattt attgtagaac   4860
ttgactcttg cgtcgatcac catgacaggg ctatcttaac aaggggtaat ttttgttgat   4920
ggagtcaagt agcattccga cgggaagtgt cgatgcctct gaacgaaatc ttccgattag   4980
ctctgcaaag aagtggaaat tgtcagcgca gaattcgtgt aaatggtgtt agtctgatct   5040
aatgacaact aattacgcac ttacgactgt aatgccttta tttttcttta tatttcccag   5100
cgtgttgttc tttcaaatat acgatgagta taaattaatt ttacaaagca gaaacaacag   5160
gatctttaga aacgtcactg taaacatcga atcttctttg aacactgaag ggaatatttc   5220
ttctcgtttc ttcaacaacg tccttcttca gttctgcata aacgatggtt tcctcatggc   5280
cggcctcaac gaggatctca ccatctggat cgaccaccat gctatggcca taagcctgat   5340
agccgccctg tgggttacga gcgggggaac acatcaacac gtagttttgg ttgtcaatag   5400
ctctggcaac ggcaaacttt gaccagaatt taggacctgt cacggtattg aatgcaccgg   5460
gataagccat aataccagcg ccacgtctgg ctgcaatcat ggccaattcc gggaacctga   5520
tatcatagca aatacctaag ccgaatctgg tgtcgatttc tggaatgtcg aaaactgtaa   5580
ccttgttgcc cggttttaaa gaatcagact ccttgaacgt gattccgccc ggaatagaaa   5640
tgtcaaagag gtgcacctta cgatgcttgg caacgatttc ccccttggga ttgaaaacaa   5700
gagaggtgtt gtagataccg ccgtcattgt cgtcgatttc cggaatcgaa cctccaatga   5760
tagagacatt gtactttttc gcctgttcac ttaaaaacgt gctagtttcc ccctctggga   5820
tacgttctgc ataatttgca aattggtcta cggcatatgg agattggaaa cattcaggta   5880
gaacaagaag ttgtggtttt ggatcgtgtt ggatcgccct ctcgatgaat tgggtcactt   5940
tggcgagatt ggccttcttg tctccaccac agtggaattg cagcagtgcc acttggagag   6000
tcttggagag agtaacggca gacgggcc                                      6028
```

<210> SEQ ID NO 72
<211> LENGTH: 6816
<212> TYPE: DNA
<213> ORGANISM: Artificial Sequence
<220> FEATURE:
<223> OTHER INFORMATION: StXI-IoENO1-PDC-TDH3-TEF2-MEL5-loxP-XR integration fragment
<220> FEATURE:
<221> NAME/KEY: misc_feature
<222> LOCATION: (5738)..(5738)
<223> OTHER INFORMATION: n is a, c, g, or t

<400> SEQUENCE: 72
ccctccagtg tttttctctc tgtctctttg tttttttttt ccaatctgat ttgacgtgca 60
aggcaaagac atcacatgtt tgagaatggc aagagaaggg gcgtggtagt gtataccaag 120
ccggtgtaga gagtgtgatt ttagagtgaa tccatccatg aacacgagta gaggagatgt 180
atgagcaaat ccagggtgtt tgtaatggtc caagccgcaa ggcggcgtaa tggaatgcaa 240
gaaacaaggg acactaatga aggggtaaga ggtgtctagt tgagaagtac atartaaaag 300
atgaatagtt gagawgtaca trgtaaaaga tgaatagttg agacaaatga aggtgtcaat 360
gttcctgata atgacactgc aagraacaaa taccgtgcag ttggaagggg gaaagagatg 420
rccgagataa gtgttgttga ggccaaagga tgttggaacc tgctacaata ggagatggag 480
cggcctataa ctccggcgtg tttgtgttga cagccctata catcagccaa tacgagagtt 540
tggcatgtcc tttaaagggt ttgctacccc cactcccgta atcatcgtta aaatcatcat 600
cattgaaatc attataatta acctcatcac cattcccact attatcacct tatattctcc 660
actccaggga gatgcatcgt tgtaaagggc atggctgttt gtttatttta cccgacaagc 720
caataccaag agcggacaaa ccgcatcaga atgcaacaga aggttggaga aacgtgatgt 780 catttttttcc gcaaacggag atctcgcaca gcggtgagat ataaaaggcg gagatgtgga 840
caccttcttt atacaattcc cctctacttg attgttccat attcctaaca tctagttaca 900
actctgaaca tcataattat tttaaaattc tcaacccaac tgcaattgga ttgaactgcg 960
gccgcgttgt tgatgctgcg cacctgtggt tgcccaacat ggttgtatat cgtgtaacca 1020
caccaacaca tgtgcagcac atgtgtttaa aagagtgtca tggaggtgga tcatgatgga 1080
agtggacttt accacttggg aactgtctcc actcccggga agaaaagacc cggcgtatca 1140
cgcggttgcc tcaatggggc aatttggaag gagaaatata gggaaaatca cgtcgctctc 1200
ggacggggaa gagttccaga ctatgagggg ggggggtggt atataaagac aggagatgtc 1260 caccccccaga gagaggaaga agttggaact ttagaagaga gagataactt tccccagtgt 1320
ccatcaatac acaaccaaac acaaactcta tatttacaca tataaccccc tccaaccaaa 1380
aggctagaat gaaggagtac tttcccgaga taaaggaaat caaatatgaa ggtccagaga 1440
gcaaaaacgt aatggccttc aaatactata acaaggacga ggttattggt ggtaaaccaa 1500
tgagggaaca cttgaaattt gcaatgtctt attggcatac tctcaaggca cagggattag 1560
acatgttcgg tggtgatact atggacagag cttggaatag atatgatgat gcgttagaac 1620
aagcaaaggc aagagccgat gctggttttg agtttatgca aaagataggg atggactatt 1680
tctgtttcca cgatagggac attatcaatg aagccatgac ccttaaagag actaatcgtt 1740
tactagatga aattgtcgac catttagagg gtctgatgaa aaagacaggt ataaagttgc 1800
tctggggcac gactaatgct ttctcacatc ctaggtttct ccatggcggt gcaactgccc 1860
caaacgccga tgtttttgca tacgctgctg cccaagtgaa aaaggctatg gaaattacaa 1920
aaagactggg cggcgaaaac tatgtccttt ggggaggtcg tgaaggatat gaaacactat 1980
tgaataccaa gagtgatttg gaatatgaca attttgctag attcttacaa atggttgttg 2040
actataagga aaagattggg tttgaaggac aattgttaat cgaaccaaaa cctaaggagc 2100
ctacaaaaca ccaatacgat ttcgacactg ctacagtcct aggatttttg cgaaaataca 2160
acctagataa gcactacaaa atgaatattg aagcaaatca tgcaacttta gcgggtcata 2220

```
ccttccagca tgagttaaac ttggctagaa ttaacaatgt catgggttcg atagatgcga   2280
atcagggtga tatgttgttg ggatgggata cggatcaatt tccgactaat atctatgacg   2340
cagtacttgc aatgtatgag gtgattaaaa acaacgggct gggtaagggt ggtttgaatt   2400
ttgatgctaa agtgaggaga ggatcctttg aagataagga tctatttctt gcgtatattg   2460
ctgggatgga tacattcgca aaaggactta ccatcgctta tagattatac gaagataaag   2520
ttttcgaaga ttttcaagat aaacggtatg agtcatacaa aacaggaatt gggaaggata   2580
ttgttgaagg caaagttggc tttgaggaac tagcagaata cgttgagaat ttggcagaaa   2640
tcaaaaacac ctctggtaga caggaaatgt tagaatctat tttgaatagt tacatattag   2700
aagcaaagtg attaatcgta aatctaacta atgcttttac taaatatcta gtacaatttt   2760
tacagtccct acgtttataa atgaatttaa tgaaaaaaaa atattttgta acgatgtgtt   2820
tattaagttg cgctcttccg ataatcccgg actttggtta atttctcaat gggttttttt   2880
ttcaaaacca ttgttgtagt gtaacagact ttaacaaaag gacatcactc tacagggcag   2940
ctttaaaatc cctcagtgta attgttcttc attcataacg tggcagtcaa ggactcgagg   3000
agtccatcgg ttcctgtcag atgggatact cttgacgtgg aaaattcaaa cagaaaaaaa   3060
accccaataa tgaaaaataa cactacgtta tatccgtggt atcctctatc gtatcgtatc   3120
gtagcgtatc gtagcgtacc gtatcacagt atagtctaat attccgtatc ttattgtatc   3180
ctatcctatt cgatcctatt gtatttcagt gcaccatttt aatttctatt gctataatgt   3240
ccttattagt tgccactgtg aggtgaccaa tggacgaggg cgagccgttc agaagccgcg   3300
aagggtgttc ttcccatgaa tttcttaagg agggcggctc agctccgaga gtgaggcgag   3360
acgtctcggt cagcgtatcc cccttcctcg gcttttacaa atgatgcgct cttaatagtg   3420
tgtcgttatc cttttggcat tgacgggga gggaaattga ttgagcgcat ccatattttt   3480
gcggactgct gaggacaatg gtggtttttc cgggtggcgt gggctacaaa tgatacgatg   3540
gtttttttct tttcggagaa ggcgtataaa aaggacacgg agaacccatt tattctaaaa   3600
acagttgagc ttctttaatt attttttgat ataatattct attattatat attttcttcc   3660
caataaaaca aaataaaaca aaacacagca aaacacaaaa attctagaat gaaggaatac   3720
ttccccgaaa tcaaagagat caaatatgaa ggtccagagt ccaaaaatgt catggcattc   3780
aagtactata acaaggatga agtcattggt ggaaaaccta tgagggagca tctaaaattc   3840
gcaatgtctt actggcatac acttaaagca cagggactgg atatgtttgg aggcgatacg   3900
atggatcgag cctggaatag atacgatgat gccctagaac aagccaaagc tagagcagat   3960
gctggatttg agtttatgca aaagatcgga atggactatt tctgttttca cgaccgtgac   4020
attatcaatg aggctatgac tttgaaggaa acgaacagat tgttagatga aattgtggac   4080
cacttggaag gattgatgaa aaagactggt attaagttac tttggggcac tacaaatgcc   4140
ttttcacatc cgagatttct ccatggtggc gcaacagctc caaatgctga tgtgtttgca   4200
tatgctgcgg cacaagtcaa aaaggctatg gaaattacta agaggcttgg tggagagaat   4260
tacgtattat ggggtggtag agaaggctat gagactttgc taaataccaa gtctgactta   4320
gaatatgaca attttgcaag atttttgcaa atggttgttg actataagga aaagattgga   4380
ttcgaaggtc aactattgat agaaccaaaa cctaaagagc caaccaaaca tcaatatgac   4440
ttcgacactg caacagtact ggggttcttg aggaagtaca acctcgataa gcactataag   4500
atgaatatcg aagctaatca tgctacattg gccggtcata catttcaaca cgagcttaat   4560
ctcgcacgta ttaacaacgt tatgggttcg atagatgcaa accagggcga tatgttatta   4620
```

```
ggttgggata ctgatcaatt tcctaccaat atctacgatg ccgttctggc tatgtacgaa   4680
gttatcaaaa acaacggtct agggaaggga ggtttgaatt ttgatgcaaa agtccggagg   4740
ggaagtttcg aagataaaga tttgttttta gcgtatattg cgggaatgga tacattcgcc   4800
aaaggtttaa cgatagcata tagattgtac gaggataaag tgtttgaaga ttttcaagac   4860
aagagatatg aatcatataa gaccgggata gggaaagata ttgttgaggg caaagttggc   4920
tttgaggaat tagcagaata cgtggaaaac ttagctgaga tcaaaaatac cagcggtaga   4980
caggagatgt tagaatccat attgaacagt tacattcttg aagcaaagta attaattaac   5040
atctgaatgt aaaatgaaca ttaaaatgaa ttactaaact ttacgtctac tttacaatct   5100
ataaactttg tttaatcata taacgaaata cactaataca caatcctgta cgtatgtaat   5160
acttttatcc atcaaggatt gagaaaaaaa agtaatgatt ccctgggcca ttaaaactta   5220
gacccccaag cttggatagg tcactctcta ttttcgtttc tcccttccct gatagaaggg   5280
tgatatgtaa ttaagaataa tatataattt tataataaaa gaattcgccc ttacatatgg   5340
ataacttcgt ataatgtatg ctatacgaag ttatgctgca acggcaacat caatgtccac   5400
gtttacacac ctacatttat atctatattt atatttatat ttatttattt atgctactta   5460
gcttctatag ttagttaatg cactcacgat attcaaaatt gacacccttc aactactccc   5520
tactattgtc tactactgtc tactactcct ctttactata gctgctccca ataggctcca   5580
ccaataggct ctgtcaatac attttgcgcc gccacctttc aggttgtgtc actcctgaag   5640
gaccatattg ggtaatcgtg caatttctgg aagagagtgc cgcgagaagt gaggccccca   5700
ctgtaaatcc tcgagggggc atggagtatg gggcatgnag gatggaggat gggggggggg   5760
ggggaaaata ggtagcgaaa ggacccgcta tcaccccacc cggagaactc gttgccggga   5820
agtcatattt cgacactccg gggagtctat aaaaggcggg ttttgtcttt tgccagttga   5880
tgttgctgag aggacttgtt tgccgtttct tccgatttaa cagtatagaa tcaaccactg   5940
ttaattatac acgttatact aacacaacaa aaacaaaaac aacgacaaca acaacaacaa   6000
tgtttgcttt ctactttctc accgcatgca ccactttgaa gggtgttttc ggagtttctc   6060
cgagttacaa tggtcttggt ctcaccccac agatgggttg ggacagctgg aatacgtttg   6120
cctgcgatgt cagtgaacag ctacttctag acactgctga tagaatttct gacttggggc   6180
taaaggatat gggttacaag tatgtcatcc tagatgactg ttggtctagc ggcagggatt   6240
ccgacggttt cctcgttgca gacaagcaca aatttcccaa cggtatgggc catgttgcag   6300
accacctgca taataacagc tttcttttcg gtatgtattc gtctgctggt gagtacacct   6360
gtgctgggta ccctgggtct ctggggcgtg aggaagaaga tgctcaattc tttgcaaata   6420
accgcgttga ctacttgaag tatgataatt gttacaataa aggtcaattt ggtacaccag   6480
acgtttctta ccaccgttac aaggccatgt cagatgcttt gaataaaact ggtaggccta   6540
ttttctattc tctatgtaac tggggtcagg atttgacatt ttactggggc tctggtatcg   6600
ccaattcttg gagaatgagc ggagatatta ctgctgagtt cacccgtcca gatagcagat   6660
gtccctgtga cggtgacgaa tatgattgca agtacgccgg tttccattgt tctattatga   6720
atattcttaa caaggcagct ccaatggggc aaaatgcagg tgttggtggt tggaacgatc   6780
tggacaatct agaggtcgga gtcggtaatt tgggcc                             6816
```

<210> SEQ ID NO 73
<211> LENGTH: 6410
<212> TYPE: DNA

<213> ORGANISM: Artificial Sequence
<220> FEATURE:
<223> OTHER INFORMATION: StXI-IoENO1-PDC-TDH3-TEF2-MEL5-loxP-XR
integration fragment

<400> SEQUENCE: 73

```
ctgctgagtt cacccgtcca gatagcagat gtccctgtga cggtgacgaa tatgattgca     60
agtacgccgg tttccattgt tctattatga atattcttaa caaggcagct ccaatggggc    120
aaaatgcagg tgttggtggt tggaacgatc tggacaatct agaggtcgga gtcggtaatt    180
tgactgacga tgaggaaaag gcccatttct ctatgtgggc aatggtaaag tccccactta    240
tcattggtgc cgacgtgaat cacttaaagg catcttcgta ctcgatctac agtcaagcct    300
ctgtcatcgc aattaatcaa gatccaaagg gtattccagc cacaagagtc tggagatatt    360
atgtttcaga caccgatgaa tatggacaag gtgaaattca aatgtggagt ggtccgcttg    420
acaatggtga ccaagtggtt gctttattga atggaggaag cgtagcaaga ccaatgaaca    480
cgaccttgga agagattttc tttgacagca atttgggttc aaaggaactg acatcgactt    540
gggatattta cgacttatgg gccaacagag ttgacaactc tacggcgtct gctatccttg    600
aacagaataa ggcagccacc ggtattctct acaatgctac agagcagtct tataaagacg    660
gtttgtctaa gaatgataca agactgtttg gccagaaaat tggtagtctt tctccaaatg    720
ctatacttaa cacaactgtt ccagctcatg gtatcgcctt ctataggttg agaccctcgg    780
cttaagctca atgttgagca aagcaggacg agaaaaaaaa aaataatgat tgttaagaag    840
ttcatgaaaa aaaaaaggaa aaatactcaa atacttataa cagagtgatt aaataataaa    900
cggcagtata ccctatcagg tattgagata gttttatttt tgtaggtata taatctgaag    960
cctttgaact attttctcgt atatatcatg gagtatacat tgcattagca acattgcata   1020
ctagttcata acttcgtata atgtatgcta tacgaagtta ttaattaaca agggcgattt   1080
ctgcagatat cggccggccc catggagatc cgcggccgct aacctgatcc aaaaggggta   1140
tgtctatttt ttagagtgtg tctttgtgtc aaattatggt agaatgtgta aagtagtata   1200
aactttcctc tcaaatgacg aggtttaaaa caccccccgg gtgagccgag ccgagaatgg   1260
ggcaattgtt caatgtgaaa tagaagtatc gagtgagaaa cttgggtgtt ggccagccaa   1320
gggggaagga aaatggcgcg aatgctcagg tgagattgtt ttggaattgg gtgaagcgag   1380
gaaatgagcg acccggaggt tgtgacttta gtggcggagg aggacggagg aaaagccaag   1440
agggaagtgt atataagggg agcaatttgc caccaggata gaattggatg agttataatt   1500
ctactgtatt tattgtataa tttatttctc cttttatatc aaacacatta caaaacacac   1560
aaaacacaca aacaaacaca attacaaaaa gctagcatga aggaatactt ccctgaaatc   1620
aaagagatca aatatgaagg tcctgaatcg aaaaatgtta tggcattcaa gtattacaac   1680
aaggacgagg tcataggagg aaaaccaatg agggaacatc ttaagtttgc catgtcatat   1740
tggcatacgc taaaggctca ggggttggat atgttcggtg gagatactat ggatcgtgca   1800
tggaacagat acgatgacgc tttggagcaa gcgaaagcca gagctgatgc cggcttcgag   1860
tttatgcaaa agattggcat ggactatttt tgttttcatg atcgtgacat tattaacgaa   1920
gctatgactt taaaggaaac gaataggtta ttggatgaaa ttgttgacca tcttgagggt   1980
ttgatgaaaa agactgggat caaattgttg tggggtacta caaatgcttt tagtcaccca   2040
agattcttac atggtggtgc taccgcaccg aatgccgacg tattcgcata cgcggcagct   2100
caagttaaaa aggctatgga gattaccaaa cggttgggtg gcgaaaacta cgtattatgg   2160
```

```
ggcggaagag aaggatatga aacattgcta aataccaaat ccgatttgga atatgacaat   2220
tttgcaagat ttctacaaat ggttgtcgat tacaaggaga aaattgggtt cgagggtcaa   2280
ctactcatag agccaaagcc aaaagagcct accaaacatc agtatgattt cgatactgca   2340
acagttttag gctttttgag gaagtacaat ttggacaagc attacaagat gaatatcgaa   2400
gcaaaccacg ccactttagc tggtcacaca tttcaacacg aactgaactt agcacgtatt   2460
aacaatgtca tgggttctat tgatgctaat caaggagata tgttactcgg ttgggataca   2520
gatcagtttc ccacaaatat ctacgacgct gttctagcga tgtatgaagt tatcaaaaac   2580
aatggcctcg ggaagggtgg tcttaatttt gatgcaaaag ttcgaagggg ttcatttgaa   2640
gataaggacc tatttcttgc atacatagcc ggaatggata cctttgcaaa aggtttaacc   2700
atagcatata gactgtatga ggataaagtg tttgaagatt tccaagacaa gagatatgaa   2760
agctataaga cgggtatagg caaagatatt gttgagggaa aagtcggatt cgaggaactg   2820
gctgaatatg tggaaaacct tgcagaaatc aaaaatacta gtggtagaca ggagatgctt   2880
gaatctattt tgaactccta tatattagaa gccaagtaac gatcgtaagc ggcgaatctc   2940
tggctcatgg gggatatcct ctttgtttgg ctttttttc ccattctctg ttttgattat   3000
ctaatgactc attgggagga ttttctcact tcaagctttt ttttcttgca ctctttcata   3060
actccagctc tctctaactg aggctacaat gccttttaac gaacttatga gacgtttcta   3120
aattatatag gtatatgcca atatataatt acacataaaa ataaatataa ataaaatata   3180
aaaataaaaa taaacatcga aaaagaagat gtgaaattgc gaagactaga aagcacaaac   3240
gagcggtcta tatcggcgac tcgagtgtgc ccgtggtatc ttgctcgctc tacaagcctc   3300
atatgggttc aatgggtctg caatgaccgc atacggactt ggacaattac cttctattga   3360
atttctgaga agagatacat ctgaccagca atgtaagcag acaatcccaa ttctgtaaac   3420
aacctctttg tccataattc cccatcagaa gagtgaaaaa tgccctcaaa acgcatgcgc   3480
cactcccacc tctcagctgc actgcgccac ctctgagggt cctttcaggg gtcgactacc   3540
ccggacacct cgcagaggag cgacgtcacg tacttttaaa atggcagaga cgcgcagttt   3600
cttgaagaaa ggataaaaat gaaatggtgc ggaaatgcga aaatgatgaa aaattttctt   3660
ggtggcgagg aaattgagtg caataattgg cacgaggttg ttgccacccg agtgtgagta   3720
tatatcctag tttctgcact tttcttcttc ttttccttgc gtttttcttt caactttttt   3780
tactttttcc ttcaacagac aaatctaact tatatatcac atctagaatg aaagagtatt   3840
tccctgagat taaggaaatc aaatatgaag gtccagaaag caaaaatgtt atggcattca   3900
agtactacaa taaggacgag gttattgggg gcaaacctat gagagaacat cttaagtttg   3960
caatgtctta ctggcacacg ttgaaagcac aaggtttaga tatgtttggt ggagacacaa   4020
tggatagagc ttggaataga tacgacgatg cattggagca agcgaaagcc cgtgcagatg   4080
cgggtttcga gtttatgcag aaaattggca tggactactt ctgtttccat gatcgtgata   4140
ttattaacga agctatgaca cttaaggaga caaatagatt actagacgaa atagttgatc   4200
atttggaggg tttgatgaaa aagactggga tcaaacttct atggggtaca actaatgctt   4260
ttagtcatcc aagattctta cacggtggag ctacagcccc aaacgctgac gtatttgcat   4320
acgccgctgc gcaagtcaaa aaggctatgg agattaccaa aagattgggt ggagaaaatt   4380
atgtgctgtg gggtggtcga gaaggttatg aaacattgct caataccaag tccgacctgg   4440
aatatgataa ctttgcaagg tttcttcaaa tggttgttga ttacaaggag aaaataggtt   4500
ttgaaggcca attgctaatt gaaccaaaac ccaaggaacc gacaaaacat caatatgatt   4560
```

```
ttgatactgc cactgttttg ggtttcttgc ggaagtataa cttggataag cactataaga   4620

tgaatattga agccaaccat gcaacccttg ccggccacac ctttcaacat gaattgaatc   4680

tagctaggat taacaacgtt atgggctcaa tagacgctaa tcagggagat atgttattag   4740

gttgggatac cgatcagttt cctactaata tctatgatgc agtgttggct atgtatgaag   4800

tgatcaaaaa caatggtcta gggaagggtg gtctgaattt tgatgcaaaa gtccgtaggg   4860

gatcatttga ggacaaagat ttgttcctcg cctacattgc tggaatggat acttttgcaa   4920

aggggttaac gatagcttat cgattatacg aggacaaggt ctttgaagat ttccaggata   4980

agagatatga atcctacaaa actggtatcg gaaaagatat agtagaagga aaagttggct   5040

ttgaggaatt agcagaatat gttgagaact tagcagaaat caaaaatacc tcagggagac   5100

aagagatgtt agaatctatt ctcaactcgt atatcttgga agcaaagtaa ttaattaagt   5160

atagccatat agtttaattc ctttatactt tttataacta tttcttacac taattattat   5220

tatcaattat ttattgtaga acttgactct tgcgtcgatc accatgacag ggctatctta   5280

acaaggggta atttttgttg atggagtcaa gtagcattcc gacgggaagt gtcgatgcct   5340

ctgaacgaaa tcttccgatt agctctgcaa agaagtggaa attgtcagcg cagaattcgt   5400

gtaaatggtg ttagtctgat ctaatgacaa ctaattacgc acttacgact gtaatgcctt   5460

tatttttctt tatatttccc agcgtgttgt tctttcaaat atacgatgag tataaattaa   5520

ttttacaaag cagaaacaac aggatcttta gaaacgtcac tgtaaacatc gaatcttctt   5580

tgaacactga agggaatatt tcttctcgtt tcttcaacaa cgtccttctt cagttctgca   5640

taaacgatgg tttcctcatg gccggcctca acgaggatct caccatctgg atcgaccacc   5700

atgctatggc cataagcctg atagccgccc tgtgggttac gagcggggga acacatcaac   5760

acgtagtttt ggttgtcaat agctctggca acggcaaact ttgaccagaa tttaggacct   5820

gtcacggtat tgaatgcacc gggataagcc ataataccag cgccacgtct ggctgcaatc   5880

atggccaatt ccgggaacct gatatcatag caaataccta agccgaatct ggtgtcgatt   5940

tctggaatgt cgaaaactgt aaccttgttg cccggtttta aagaatcaga ctccttgaac   6000

gtgattccgc ccggaataga aatgtcaaag aggtgcacct tacgatgctt ggcaacgatt   6060

tccccccttgg gattgaaaac aagagaggtg ttgtagatac cgccgtcatt gtcgtcgatt   6120

tccggaatcg aacctccaat gatagagaca ttgtactttt tcgcctgttc acttaaaaac   6180

gtgctagttt ccccctctgg gatacgttct gcataatttg caaattggtc tacggcatat   6240

ggagattgga aacattcagg tagaacaaga agttgtggtt ttggatcgtg ttggatcgcc   6300

ctctcgatga attgggtcac tttggcgaga ttggccttct tgtctccacc acagtggaat   6360

tgcagcagtg ccacttggag agtcttggag agagtaacgg cagacgggcc              6410
```

<210> SEQ ID NO 74
<211> LENGTH: 3889
<212> TYPE: DNA
<213> ORGANISM: Artificial Sequence
<220> FEATURE:
<223> OTHER INFORMATION: IoURA3-IoGPD

<400> SEQUENCE: 74

```
cggatttggt tggttcatag ctcttcttta gcgttgattg tagcctctgt tgcagaaaag     60

accttgtttt caagaaactg gttggtctga gtgttctgac accaatggtt atatttctag    120

ttgcaaacat gttggaataa tggtagtaat gttgatgctg gcagtgacag tagtgctagt    180
```

```
tcttgttctt gttctcgttc tcgttctcgt tctctttttt gtgctgtagc tgttactgta    240
ttggctactc tatataatat gcttgcaaag gaaaggaaat ctatgcaaac cactctctcc    300
tgcacaaacg ctagttcctt tgtcagggtt gaatgtagcc actctacgaa tgcgattcct    360
cttcccctct ctttcgcgtt gagcatattc aaaattgtga gaggtggcaa ggaaaaccat    420
acgattttcg gggtgcacgg atgcacagtg gacgtaagat ctgctctatt taagatacta    480
aagaaagtgg cagcgggaag accatcatgg aggacaacgt acatggacga ttccctgcta    540
gaaacaatga catgcaaacc cgtgcagtag gtagaagcag atttgctgag acagccatgc    600
caagtggaat tgttgtttaa ctctagtaga tattattgtt atagaaaaga tttatatata    660
agatccatgg aggggggagg gaggtaagag aaatacgaaa aagaatgtgt aatgaatctt    720
aatgtagaca agtggaaatg cagctaaagg gggtcaaagg gaatgtgata atgcaaggtt    780
aggtttaaca agaatgggtt ggcggactcg tcaatggaga gtacaatgcc aaagttctcc    840
ctgaggttat tgcggccgcg gatccagatc ccccggggcg ttgaagatct attctccagc    900
aattaaattt gtgaagaata actggtatag agtacttcct ttaaaaacat gtccgtgcac    960
caagaaaaaa aaaaagtttg aaaaattgta tgtcgacgaa tttcagcatt ttcatttcaa   1020
ggcgatatta tgtttcacta aactcaggac aggaatatac taagaataac tacaacatac   1080
acacaacata agccaagatg gatcaactta actaccaaga acaacaacaa tttcaaaaga   1140
tcgttgaaca aaagcaaatg gctgatttca tgaggctatc tgcagatacg cggaacaatc   1200
aatcgataat gatttgactg ataaagaaaa ccatactttt gtttatgttt attagttatc   1260
gctttgctac attaaaaatt cacatactaa agcctttgtt aaacaacttt ttctaaatct   1320
taagatttta ctctatctag ttttttggt tgtaggtgaa cgtaaagtac ctcatttatt    1380
ttttttttt tgcttgtgta attcttttca tgcttattta aactagtgta catgtatcaa    1440
atctttgtgt aagaatcatt taaatctgtt taaataagca ttccaaccag cttgttggta   1500
tcttttagct tgctctatag gatctcttcc ttgaccgtac aaacctctac caacaattat   1560
gatatccgtt ccagtcttta caacttcatc aacagttcta tattgttgac caagtgcatc   1620
acctttgtca tctaaaccaa cccctggagt cataatgatc cagtcaaaac cttcttctct   1680
accgcccata tcgtgttgcg caataaaacc aatgacaaac tctttatcag atttagcaat   1740
ttctactgtt ttttctgtat attcaccata tgctaaagaa ccctttgatg ataactcagc   1800
aagcattagc aaacctctag gttcactggt tgtttcttgg gctgcctcct tcaagccaga   1860
aacaatacct gcacccgtta caccatgtgc attagtgatg tcagcccatt cggcaatacg   1920
gaagacacca gatttatatt gatttttaac agtgttacca atatcagcaa attttctatc   1980
ttcaaaaatc ataaaattat gtttcttggc aagctccttc aaaggcaaca cagttccttc   2040
atacgtaaaa tcagaaacaa tatcgatgtg tgttttaact agacagatgt aaggaccaat   2100
agtgtccaaa atagagagaa gcttttcagt ttcagtaata tccaatgatg cacaaaggtt   2160
agacttcttt tcctccatga tggagaaaag tctcctagca acaggggaag tgtgtgattc   2220
tgatctttct ttgtatgacg ccatccttga caaacaaact actttattaa agcgttgaag   2280
atctattctc cagcaattaa atttgtgaag aataactggt atagagtact tcctttaaaa   2340
acatgtccgt gcaccaagaa aaaaaaaaag tttgaaaaat tgtatgtcga cgaatttcag   2400
cattttcatt tcaaggcgat attatgtttc actaaactca ggacaggaat atactaagaa   2460
taactacaac atacacacaa cataagccaa gatggatcaa cttaactacc aagaacaaca   2520
acaatttcaa aagatcgttg aacaaaagca aatggctgat ttcatgaggc tatgaattct   2580
```

```
tttattataa aattatatat tattcttaat tacatatcac ccttctatca gggaagggag   2640
aaacgaaaat agagagtgac ctatccaagc ttggggggtct aagttttaat ggcccaggga   2700
atcattactt ttttttctca atccttgatg gataaaagta ttacatacgt acaggattgt   2760
gtattagtgt atttcgttat atgattaaac aaagtttata gattgtaaag tagacgtaaa   2820
gtttagtaat tcattttaat gttcatttta cattcagatg ttaattaagg cctcgaggga   2880
tccgcggccg caaataaatt taaaataaac gatatcaaaa ttcaaagggt tcaaagtggg   2940
aattccttga tttatataca cctttgccaa ccgcttgtta cttgataagg aaaagataga   3000
tttctaaagt gcaggaaaag aaacgccact acgtcatgaa acaaaagaaa tgaaacactc   3060
tgcaaaaggg aaaaccaatg acgccttcaa aacgtactga ctttccgcct ccttttctgc   3120
cttttttttt tctccctcaa tttgccaatt cccctttccg ctaattttac atcacctttt   3180
tgtttgtttc ccttttcggc caagttttcc atttcttttt tcggctgagc ccttctttgg   3240
cgtcgacgta atttctcggc atgtggccaa tgtatattga cagtagatga agtagacgtt   3300
cttagtaact gttagggtga gattgccacc ccccccttcct tcttttacta tctgtaatac   3360
catcaccata gcaatagttt aaccatgttg gagctggaaa tacaacgtct atagagggaa   3420
gtcatcatat tacgccattt tacggaccag ggacaccctg tagtgtgttt cctctcttgt   3480
agaggtaggt tttcaaatgg actctggcgt cgatttccag caagtcattc ccgtggttca   3540
ccatttctac tttttgcgct acctctcttg acacagaaat gaatgatgac gtgtaaatta   3600
cccgtccgag acctggactc cggagaaact gtattaatta cgcgccaaac aagacaggtg   3660
tcggataaac gtgcatgtac agactgcgag ccgaaaacgg aagggggggaa agaaaacagt   3720
ggagtcccat tgttgttccg gaaatggaaa acgggaactg gcggaaaaga aacgaaacaa   3780
aacaaaagaa aaagaggaaa aaaaagaaaa aaaaaagaaa aagacactgc acgtgattgc   3840
tggtgtgtgc tgcgtaaccg cggcacttta tttcgtaaat gaaggggcc              3889
```

<210> SEQ ID NO 75
<211> LENGTH: 1004
<212> TYPE: DNA
<213> ORGANISM: Artificial Sequence
<220> FEATURE:
<223> OTHER INFORMATION: IoGPD primer

<400> SEQUENCE: 75

```
ggccgcaaat aaatttaaaa taaacgatat caaaattcaa agggttcaaa gtgggaattc     60
cttgatttat atacaccttt gccaaccgct tgttacttga taaggaaaag atagatttct    120
aaagtgcagg aaaagaaacg ccactacgtc atgaaacaaa agaaatgaaa cactctgcaa    180
aagggaaaac caatgacgcc ttcaaaacgt actgactttc cgcctccttt tctgcctttt    240
tttttctcc ctcaatttgc caattcccct ttccgctaat tttacatcac ctttttgttt    300
gtttcccttt tcggccaagt tttccatttc tttttcggc tgagcccttc tttggcgtcg    360
acgtaatttc tcggcatgtg gccaatgtat attgacagta gatgaagtag acgttcttag    420
taactgttag ggtgagattg ccaccccccc ttccttcttt tactatctgt aataccatca    480
ccatagcaat agtttaacca tgttggagct ggaaatacaa cgtctataga gggaagtcat    540
catattacgc cattttacgg accagggaca ccctgtagtg tgtttcctct cttgtagagg    600
taggttttca aatggactct ggcgtcgatt tccagcaagt cattcccgtg gttcaccatt    660
tctacttttt gcgctacctc tcttgacaca gaaatgaatg atgacgtgta aattacccgt    720
```

```
ccgagacctg gactccggag aaactgtatt aattacgcgc caaacaagac aggtgtcgga    780

taaacgtgca tgtacagact gcgagccgaa aacggaaggg gggaaagaaa acagtggagt    840

cccattgttg ttccggaaat ggaaaacggg aactggcgga aaagaaacga aacaaaacaa    900

aagaaaaaga ggaaaaaaaa gaaaaaaaaa agaaaaagac actgcacgtg attgctggtg    960

tgtgctgcgt aaccgcggca ctttatttcg taaatgaagg ggcc                    1004
```

```
<210> SEQ ID NO 76
<211> LENGTH: 853
<212> TYPE: DNA
<213> ORGANISM: Artificial Sequence
<220> FEATURE:
<223> OTHER INFORMATION: IoGPD primer

<400> SEQUENCE: 76

cggatttggt tggttcatag ctcttcttta gcgttgattg tagcctctgt tgcagaaaag     60

accttgtttt caagaaactg gttggtctga gtgttctgac accaatggtt atatttctag    120

ttgcaaacat gttggaataa tggtagtaat gttgatgctg gcagtgacag tagtgctagt    180

tcttgttctt gttctcgttc tcgttctcgt tctctttttt gtgctgtagc tgttactgta    240

ttggctactc tatataatat gcttgcaaag gaaaggaaat ctatgcaaac cactctctcc    300

tgcacaaacg ctagttcctt tgtcagggtt gaatgtagcc actctacgaa tgcgattcct    360

cttcccctct ctttcgcgtt gagcatattc aaaattgtga gaggtggcaa ggaaaaccat    420

acgattttcg ggtgcacgg atgcacagtg gacgtaagat ctgctctatt taagatacta    480

aagaaagtgg cagcgggaag accatcatgg aggacaacgt acatggacga ttccctgcta    540

gaaacaatga catgcaaacc cgtgcagtag gtagaagcag atttgctgag acagccatgc    600

caagtggaat tgttgtttaa ctctagtaga tattattgtt atagaaaaga tttatatata    660

agatccatgg aggggggagg gaggtaagag aaatacgaaa aagaatgtgt aatgaatctt    720

aatgtagaca agtggaaatg cagctaaagg gggtcaaagg gaatgtgata atgcaaggtt    780

aggtttaaca agaatgggtt ggcggactcg tcaatggaga gtacaatgcc aaagttctcc    840

ctgaggttat tgc                                                       853
```

```
<210> SEQ ID NO 77
<211> LENGTH: 3889
<212> TYPE: DNA
<213> ORGANISM: Artificial Sequence
<220> FEATURE:
<223> OTHER INFORMATION: IoURA3-XR integration fragment

<400> SEQUENCE: 77

cggatttggt tggttcatag ctcttcttta gcgttgattg tagcctctgt tgcagaaaag     60

accttgtttt caagaaactg gttggtctga gtgttctgac accaatggtt atatttctag    120

ttgcaaacat gttggaataa tggtagtaat gttgatgctg gcagtgacag tagtgctagt    180

tcttgttctt gttctcgttc tcgttctcgt tctctttttt gtgctgtagc tgttactgta    240

ttggctactc tatataatat gcttgcaaag gaaaggaaat ctatgcaaac cactctctcc    300

tgcacaaacg ctagttcctt tgtcagggtt gaatgtagcc actctacgaa tgcgattcct    360

cttcccctct ctttcgcgtt gagcatattc aaaattgtga gaggtggcaa ggaaaaccat    420

acgattttcg ggtgcacgg atgcacagtg gacgtaagat ctgctctatt taagatacta    480

aagaaagtgg cagcgggaag accatcatgg aggacaacgt acatggacga ttccctgcta    540

gaaacaatga catgcaaacc cgtgcagtag gtagaagcag atttgctgag acagccatgc    600
```

```
caagtggaat tgttgtttaa ctctagtaga tattattgtt atagaaaaga tttatatata    660
agatccatgg aggggggagg gaggtaagag aaatacgaaa aagaatgtgt aatgaatctt    720
aatgtagaca agtggaaatg cagctaaagg gggtcaaagg gaatgtgata atgcaaggtt    780
aggtttaaca agaatgggtt ggcggactcg tcaatggaga gtacaatgcc aaagttctcc    840
ctgaggttat tgcggccgcg gatccctcga ggccttaatt aacatctgaa tgtaaaatga    900
acattaaaat gaattactaa actttacgtc tactttacaa tctataaact ttgtttaatc    960
atataacgaa atacactaat acacaatcct gtacgtatgt aatactttta tccatcaagg   1020
attgagaaaa aaaagtaatg attccctggg ccattaaaac ttagaccccc aagcttggat   1080
aggtcactct ctattttcgt ttctcccttc cctgatagaa gggtgatatg taattaagaa   1140
taatatataa ttttataata aaagaattca tagcctcatg aaatcagcca tttgcttttg   1200
ttcaacgatc ttttgaaatt gttgttgttc ttggtagtta agttgatcca tcttggctta   1260
tgttgtgtgt atgttgtagt tattcttagt atattcctgt cctgagttta gtgaaacata   1320
atatcgcctt gaaatgaaaa tgctgaaatt cgtcgacata caatttttca aacttttttt   1380
ttttcttggt gcacggacat gtttttaaag gaagtactct ataccagtta ttcttcacaa   1440
atttaattgc tggagaatag atcttcaacg ctttaataaa gtagtttgtt tgtcaaggat   1500
ggcgtcatac aaagaaagat cagaatcaca cacttcccct gttgctagga gacttttctc   1560
catcatggag gaaaagaagt ctaacctttg tgcatcattg gatattactg aaactgaaaa   1620
gcttctctct attttggaca ctattggtcc ttacatctgt ctagttaaaa cacacatcga   1680
tattgtttct gattttacgt atgaaggaac tgtgttgcct ttgaaggagc ttgccaagaa   1740
acataatttt atgatttttg aagatagaaa atttgctgat attggtaaca ctgttaaaaa   1800
tcaatataaa tctggtgtct tccgtattgc cgaatgggct gacatcacta atgcacatgg   1860
tgtaacgggt gcaggtattg tttctggctt gaaggaggca gcccaagaaa caaccagtga   1920
acctagaggt ttgctaatgc ttgctgagtt atcatcaaag ggttctttag catatggtga   1980
atatacagaa aaaacagtag aaattgctaa atctgataaa gagtttgtca ttggttttat   2040
tgcgcaacac gatatgggcg gtagagaaga aggttttgac tggatcatta tgactccagg   2100
ggttggttta gatgacaaag gtgatgcact tggtcaacaa tatagaactg ttgatgaagt   2160
tgtaaagact ggaacggata tcataattgt tggtagaggt ttgtacggtc aaggaagaga   2220
tcctatagag caagctaaaa gataccaaca agctggttgg aatgcttatt taaacagatt   2280
taaatgattc ttacacaaag atttgataca tgtacactag tttaaataag catgaaaaga   2340
attacacaag caaaaaaaaa aaaataaatg aggtacttta cgttcaccta caaccaaaaa   2400
aactagatag agtaaaatct taagatttag aaaaagttgt ttaacaaagg ctttagtatg   2460
tgaattttta atgtagcaaa gcgataacta ataaacataa acaaaagtat ggttttcttt   2520
atcagtcaaa tcattatcga ttgattgttc cgcgtatctg cagatagcct catgaaatca   2580
gccatttgct tttgttcaac gatcttttga aattgttgtt gttcttggta gttaagttga   2640
tccatcttgg cttatgttgt gtgtatgttg tagttattct tagtatattc ctgtcctgag   2700
tttagtgaaa cataatatcg ccttgaaatg aaaatgctga aattcgtcga catacaattt   2760
ttcaaacttt tttttttct tggtgcacgg acatgttttt aaaggaagta ctctatacca   2820
gttattcttc acaaatttaa ttgctggaga atagatcttc aacgccccgg gggatctgga   2880
tccgcggccg caaataaatt taaaataaac gatatcaaaa ttcaaagggt tcaaagtggg   2940
```

```
aattccttga tttatataca cctttgccaa ccgcttgtta cttgataagg aaaagataga   3000

tttctaaagt gcaggaaaag aaacgccact acgtcatgaa acaaaagaaa tgaaacactc   3060

tgcaaaaggg aaaaccaatg acgccttcaa aacgtactga ctttccgcct ccttttctgc   3120

cttttttttt tctccctcaa tttgccaatt cccctttccg ctaattttac atcacctttt   3180

tgtttgtttc ccttttcggc caagttttcc atttcttttt tcggctgagc ccttctttgg   3240

cgtcgacgta atttctcggc atgtggccaa tgtatattga cagtagatga agtagacgtt   3300

cttagtaact gttagggtga gattgccacc ccccccttcct tcttttacta tctgtaatac   3360

catcaccata gcaatagttt aaccatgttg gagctggaaa tacaacgtct atagagggaa   3420

gtcatcatat tacgccattt tacggaccag ggacaccctg tagtgtgttt cctctcttgt   3480

agaggtaggt tttcaaatgg actctggcgt cgatttccag caagtcattc ccgtggttca   3540

ccatttctac tttttgcgct acctctcttg acacagaaat gaatgatgac gtgtaaatta   3600

cccgtccgag acctggactc cggagaaact gtattaatta cgcgccaaac aagacaggtg   3660

tcggataaac gtgcatgtac agactgcgag ccgaaaacgg aagggggggaa agaaaacagt   3720

ggagtcccat tgttgttccg gaaatggaaa acgggaactg gcggaaaaga aacgaaacaa   3780

aacaaaagaa aaagaggaaa aaaaagaaaa aaaaaagaaa aagacactgc acgtgattgc   3840

tggtgtgtgc tgcgtaaccg cggcacttta tttcgtaaat gaaggggcc                3889
```

<210> SEQ ID NO 78
<211> LENGTH: 6045
<212> TYPE: DNA
<213> ORGANISM: Artificial Sequence
<220> FEATURE:
<223> OTHER INFORMATION: SmGPD-IoPDC-URA3-IoADH integration fragment

<400> SEQUENCE: 78

```
ctaagtagtg gtgttggtga actcaagatg gactctttag gtaattatat tcttgaatag     60

ttgtgtaaag cgaatatgca aatagatttg ttttataatt atgcatctct ttgaaagagg    120

tttagaggca aagttcttgc atacaatatt gtgattgttt taatgtcatt cttgattttc    180

ataaagagat taaaaaaaaa aaaaaaaaac ttataaaatt gagtagaacc atttatatat    240

aagacaaaga ttgtctgtat tagtcctcaa cacactaaac cttacatact tagggtaaat    300

ttgctaatag agtgatatgt tcatgagaac tccaacgaca acacaaccac ctatttgcac    360

aacaaacacc attgtcgcac gctgcgcgcc ctagaagtag aaagaaaggg aaatgacatt    420

aagagaatca taccccgtgc ccgtaacgcc gaaaaaatca caccccgtcc cccacacctt    480

aaaacctcaa ccgcttaaca ccgccacacc ctttctcttt ataaacgccg tttgcattac    540

tcattcttct tataaaccgc accccccaaa acgcggaata gcttcaaccc cccaatcaga    600

tatgagtttc ccgggaaacc cgcttttccc gacagcccca caaggggttg gtctataaaa    660

gaggacgttt tccccgtcat cgagattgaa gattcttaca ggcccattta ttcaaattgg    720

agttgattct tcttgtcttt actttctttc tctcttttc ttccttttt aatattatct    780

tttgtcaagc ctggttccct aagttgaact ctcttttctt gtgatcctcc tatatagata    840

cgccttgcca aatgcggccg cggatccctc gaggagtcca tcggttcctg tcagatggga    900

tactcttgac gtggaaaatt caaacagaaa aaaaacccca ataatgaaaa ataacactac    960

gttatatccg tggtatcctc tatcgtatcg tatcgtagcg tatcgtagcg taccgtatca   1020

cagtatagtc taatattccg tatcttattg tatcctatcc tattcgatcc tattgtattt   1080

cagtgcacca ttttaatttc tattgctata atgtccttat tagttgccac tgtgaggtga   1140
```

```
ccaatggacg agggcgagcc gttcagaagc cgcgaagggt gttcttccca tgaatttctt   1200
aaggagggcg gctcagctcc gagagtgagg cgagacgtct cggtcagcgt atccccccttc  1260
ctcggctttt acaaatgatg cgctcttaat agtgtgtcgt tatccttttg gcattgacgg   1320
gggagggaaa ttgattgagc gcatccatat ttttgcggac tgctgaggac aatggtggtt   1380
tttccgggtg gcgtgggcta caaatgatac gatggttttt ttcttttcgg agaaggcgta   1440
taaaaaggac acggagaacc catttattct aaaaacagtt gagcttcttt aattattttt   1500
tgatataata ttctattatt atatattttc ttcccaataa aacaaaataa aacaaaacac   1560
agcaaaacac aaaaattcta gcatgactaa gcaatacaaa aactatgtta atggtgaatg   1620
gaagttgtct gaaaacgaga tcaaaatcta tgaaccagca tccggtgcag agttaggctc   1680
tgtccctgct atgtccaccg aagaggttga ctatgtttat gcttctgcca aaaaggcaca   1740
accagcttgg agatcacttt cctacattga aagagctgca tacttgcaca aagttgctga   1800
cattttgatg agagataagg aaaagattgg tgctgttttg tctaaggaag ttgctaaggg   1860
ttacaagtcc gcagtttccg aagttgtccg tactgcagaa atcattaact atgctgcaga   1920
ggaaggtttg agaatggaag gtgaagtctt agaaggcggt tcctttgaag cagcttccaa   1980
gaaaaagatt gccgttgtca gaagagaacc agttggttta gttttagcaa tttccccatt   2040
caattaccct gttaacttgg ctggttcaaa gatcgcccca gcattgatcg caggcaatgt   2100
cattgctttc aagccaccta cccaaggttc tatttctggt ttgttattgg ccgaggcttt   2160
tgctgaagct ggtttaccag ccggtgtttt caataccatt actggtagag gttctgaaat   2220
cggtgactac attgttgagc accaggcagt taacttcatc aatttcaccg gttcaactgg   2280
tattggtgaa cgtattggca agatggctgg tatgcgtcca atcatgttgg aacttggtgg   2340
taaagattct gcaattgttt tagaagatgc agatttggaa cttacagcca aaaacatcat   2400
cgctggtgca ttcggttact ccggtcaaag atgtacagct gtcaagagag tcttggtcat   2460
ggaatcagtt gcagatgaat tagttgaaaa gatcagagag aaagttttag ctttaaccat   2520
tggtaaccca gaagatgacg ctgacattac ccctttgatt gataccaaat ctgctgacta   2580
tgtcgagggt ttgattaacg atgcaaatga taagggtgca gcagcattaa ccgaaatcaa   2640
gagagaaggc aatttgattt gtccaatcct tttgataaa gttaccactg atatgagatt    2700
ggcatgggag gaaccattcg gtccagtttt accaatcatt agagtcacat ccgttgagga   2760
ggctattgaa atctctaaca agtctgaata tggcttacag gcctcaatct ttactaatga   2820
ttttcctaga gctttcggta ttgctgaaca attagaagtc ggtacagtcc atatcaacaa   2880
caagacacaa agaggtactg acaacttccc attccttggt gccaaaaagt ccggtgctgg   2940
tattcaaggt gttaagtact ctattgaagc tatgactact gttaagtctg ttgtttttga   3000
cattaagtaa ttaattaaca tctgaatgta aaatgaacat taaaatgaat tactaaactt   3060
tacgtctact ttacaatcta taaactttgt ttaatcatat aacgaaatac actaatacac   3120
aatcctgtac gtatgtaata cttttatcca tcaaggattg agaaaaaaaa gtaatgattc   3180
cctgggccat taaaacttag acccccaagc ttggataggt cactctctat tttcgtttct   3240
cccttccctg atagaagggt gatatgtaat taagaataat atataatttt ataataaaag   3300
aattcatagc ctcatgaaat cagccatttg cttttgttca acgatctttt gaaattgttg   3360
ttgttcttgg tagttaagtt gatccatctt ggcttatgtt gtgtgtatgt tgtagttatt   3420
cttagtatat tcctgtcctg agtttagtga aacataatat cgccttgaaa tgaaaatgct   3480
```

```
gaaattcgtc gacatacaat tttcaaact ttttttttt cttggtgcac ggacatgttt   3540
ttaaaggaag tactctatac cagttattct tcacaaattt aattgctgga gaatagatct   3600
tcaacgcttt aataaagtag tttgtttgtc aaggatggcg tcatacaaag aaagatcaga   3660
atcacacact tcccctgttg ctaggagact tttctccatc atggaggaaa agaagtctaa   3720
cctttgtgca tcattggata ttactgaaac tgaaaagctt ctctctattt tggacactat   3780
tggtccttac atctgtctag ttaaaacaca catcgatatt gtttctgatt ttacgtatga   3840
aggaactgtg ttgcctttga aggagcttgc caagaaacat aattttatga tttttgaaga   3900
tagaaaattt gctgatattg gtaacactgt taaaaatcaa tataaatctg gtgtcttccg   3960
tattgccgaa tgggctgaca tcactaatgc acatggtgta acgggtgcag gtattgtttc   4020
tggcttgaag gaggcagccc aagaaacaac cagtgaacct agaggtttgc taatgcttgc   4080
tgagttatca tcaaagggtt ctttagcata tggtgaatat acagaaaaaa cagtagaaat   4140
tgctaaatct gataaagagt ttgtcattgg ttttattgcg caacacgata tgggcggtag   4200
agaagaaggt tttgactgga tcattatgac tccaggggtt ggtttagatg acaaaggtga   4260
tgcacttggt caacaatata gaactgttga tgaagttgta aagactggaa cggatatcat   4320
aattgttggt agaggtttgt acggtcaagg aagagatcct atagagcaag ctaaaagata   4380
ccaacaagct ggttggaatg cttatttaaa cagatttaaa tgattcttac acaaagattt   4440
gatacatgta cactagttta aataagcatg aaaagaatta cacaagcaaa aaaaaaaaaa   4500
taaatgaggt actttacgtt cacctacaac caaaaaaact agatagagta aaatcttaag   4560
atttagaaaa agttgtttaa caaaggcttt agtatgtgaa tttttaatgt agcaaagcga   4620
taactaataa acataaacaa aagtatggtt ttctttatca gtcaaatcat tatcgattga   4680
ttgttccgcg tatctgcaga tagcctcatg aaatcagcca tttgcttttg ttcaacgatc   4740
ttttgaaatt gttgttgttc ttggtagtta agttgatcca tcttggctta tgttgtgtgt   4800
atgttgtagt tattcttagt atattcctgt cctgagttta gtgaaacata atatcgcctt   4860
gaaatgaaaa tgctgaaatt cgtcgacata caatttttca aacttttttt ttttcttggt   4920
gcacggacat gtttttaaag gaagtactct ataccagtta ttcttcacaa atttaattgc   4980
tggagaatag atcttcaacg ccccggggtt taaacccgcg gagcaggccg gccccatgga   5040
gatccgcggc cgctaccata atgtatgcgt tgagcctctt gcaccttctt tattaggaaa   5100
tcagttgaaa aatttccgga ttgtctttat tattggccca ttttttttg gtcacacctt   5160
tatttttgta cacttctcgg gcaaagcaaa aactatagta ccggataggc ctttataaaa   5220
ctccagtgtg tatgatttta gttggtgtgc catctacacg ttctcttagt ttctttatca   5280
tgtcacagaa agcaagcatg caaaccctta caaaaaataa caacatacaa atgcctaaac   5340
aactggacta taatgatggt gagtcagtta cgaaaagagc aagtgggtta atacgatttc   5400
gtaagggaca gtctgaggaa gactacaatt ttcaaaagga gcagttctgg tccacgggtc   5460
ctttagtaca gaatcacaca tttgtgactg aatttgttga aaagtttatt gaaaacacaa   5520
ttagtgaaga ttattcaatc acagatagat cgaaaataga acgtgaaaca atcatacacg   5580
gattggagaa gctgtatttt caaagggaat atgagcgatg tctaaaagat gttcaactat   5640
tgaaggacaa tatcgataag ttcaatccta atttggatct taatgaaaag aatttataat   5700
gagctgaatt atatttcttg gatgtgcatc aaaaagatcc atgagagtaa cgaaaagaaa   5760
ctgggggaaa tctaataatt tacaatttca atatacactt ctatatcctt taatgtaatg   5820
gctttataaa taaacacgaa cttctacagc accgacgttt ctttttctta ccagctcctc   5880
```

```
ttcttcttct tcttcttctt cttcttcttc ttcttcttct tcttcttctt cttcttcttc   5940

ttctttctta ccatcattgc cattttcctt ttttcttatt tgctcttgat cctctgtttt   6000

ttcaatttgg acaaactcat ctaatacacc aacactttta gggcc                   6045


<210> SEQ ID NO 79
<211> LENGTH: 475
<212> TYPE: PRT
<213> ORGANISM: Streptococcus mutans

<400> SEQUENCE: 79

Met Thr Lys Gln Tyr Lys Asn Tyr Val Asn Gly Glu Trp Lys Leu Ser
1               5                   10                  15

Glu Asn Glu Ile Lys Ile Tyr Glu Pro Ala Ser Gly Ala Glu Leu Gly
            20                  25                  30

Ser Val Pro Ala Met Ser Thr Glu Glu Val Asp Tyr Val Tyr Ala Ser
        35                  40                  45

Ala Lys Lys Ala Gln Pro Ala Trp Arg Ser Leu Ser Tyr Ile Glu Arg
    50                  55                  60

Ala Ala Tyr Leu His Lys Val Ala Asp Ile Leu Met Arg Asp Lys Glu
65                  70                  75                  80

Lys Ile Gly Ala Val Leu Ser Lys Glu Val Ala Lys Gly Tyr Lys Ser
                85                  90                  95

Ala Val Ser Glu Val Val Arg Thr Ala Glu Ile Ile Asn Tyr Ala Ala
            100                 105                 110

Glu Glu Gly Leu Arg Met Glu Gly Glu Val Leu Glu Gly Gly Ser Phe
        115                 120                 125

Glu Ala Ala Ser Lys Lys Lys Ile Ala Val Val Arg Arg Glu Pro Val
    130                 135                 140

Gly Leu Val Leu Ala Ile Ser Pro Phe Asn Tyr Pro Val Asn Leu Ala
145                 150                 155                 160

Gly Ser Lys Ile Ala Pro Ala Leu Ile Ala Gly Asn Val Ile Ala Phe
                165                 170                 175

Lys Pro Pro Thr Gln Gly Ser Ile Ser Gly Leu Leu Leu Ala Glu Ala
            180                 185                 190

Phe Ala Glu Ala Gly Leu Pro Ala Gly Val Phe Asn Thr Ile Thr Gly
        195                 200                 205

Arg Gly Ser Glu Ile Gly Asp Tyr Ile Val Glu His Gln Ala Val Asn
    210                 215                 220

Phe Ile Asn Phe Thr Gly Ser Thr Gly Ile Gly Glu Arg Ile Gly Lys
225                 230                 235                 240

Met Ala Gly Met Arg Pro Ile Met Leu Glu Leu Gly Gly Lys Asp Ser
                245                 250                 255

Ala Ile Val Leu Glu Asp Ala Asp Leu Glu Leu Thr Ala Lys Asn Ile
            260                 265                 270

Ile Ala Gly Ala Phe Gly Tyr Ser Gly Gln Arg Cys Thr Ala Val Lys
        275                 280                 285

Arg Val Leu Val Met Glu Ser Val Ala Asp Glu Leu Val Glu Lys Ile
    290                 295                 300

Arg Glu Lys Val Leu Ala Leu Thr Ile Gly Asn Pro Glu Asp Asp Ala
305                 310                 315                 320

Asp Ile Thr Pro Leu Ile Asp Thr Lys Ser Ala Asp Tyr Val Glu Gly
                325                 330                 335

Leu Ile Asn Asp Ala Asn Asp Lys Gly Ala Ala Ala Leu Thr Glu Ile
```

```
            340                 345                 350

Lys Arg Glu Gly Asn Leu Ile Cys Pro Ile Leu Phe Asp Lys Val Thr
        355                 360                 365

Thr Asp Met Arg Leu Ala Trp Glu Glu Pro Phe Gly Pro Val Leu Pro
    370                 375                 380

Ile Ile Arg Val Thr Ser Val Glu Glu Ala Ile Glu Ile Ser Asn Lys
385                 390                 395                 400

Ser Glu Tyr Gly Leu Gln Ala Ser Ile Phe Thr Asn Asp Phe Pro Arg
                405                 410                 415

Ala Phe Gly Ile Ala Glu Gln Leu Glu Val Gly Thr Val His Ile Asn
            420                 425                 430

Asn Lys Thr Gln Arg Gly Thr Asp Asn Phe Pro Phe Leu Gly Ala Lys
        435                 440                 445

Lys Ser Gly Ala Gly Ile Gln Gly Val Lys Tyr Ser Ile Glu Ala Met
    450                 455                 460

Thr Thr Val Lys Ser Val Val Phe Asp Ile Lys
465                 470                 475


<210> SEQ ID NO 80
<211> LENGTH: 857
<212> TYPE: DNA
<213> ORGANISM: Artificial Sequence
<220> FEATURE:
<223> OTHER INFORMATION: IoADH primer

<400> SEQUENCE: 80

agctctaagt agtggtgttg gtgaactcaa gatggactct ttaggtaatt atattcttga      60

atagttgtgt aaagcgaata tgcaaataga tttgttttat aattatgcat ctctttgaaa     120

gaggtttaga ggcaaagttc ttgcatacaa tattgtgatt gttttaatgt cattcttgat     180

tttcataaag agattaaaaa aaaaaaaaaa aaacttataa aattgagtag aaccatttat     240

atataagaca aagattgtct gtattagtcc tcaacacact aaaccttaca tacttagggt     300

aaatttgcta atagagtgat atgttcatga gaactccaac gacaacacaa ccacctattt     360

gcacaacaaa caccattgtc gcacgctgcg cgccctagaa gtagaaagaa agggaaatga     420

cattaagaga atcatacccc gtgcccgtaa cgccgaaaaa atcacacccc gtcccccaca     480

ccttaaaacc tcaaccgctt aacaccgcca caccctttct ctttataaac gccgtttgca     540

ttactcattc ttcttataaa ccgcaccccc caaaacgcgg aatagcttca accccccaat     600

cagatatgag tttcccggga aacccgcttt tcccgacagc cccacaaggg gttggtctat     660

aaaagaggac gttttccccg tcatcgagat tgaagattct tacaggccca tttattcaaa     720

ttggagttga ttcttcttgt ctttactttc tttctctctt tttcttcctt ttttaatatt     780

atcttttgtc aagcctggtt ccctaagttg aactctcttt tcttgtgatc ctcctatata     840

gatacgcctt gccaaat                                                    857


<210> SEQ ID NO 81
<211> LENGTH: 988
<212> TYPE: DNA
<213> ORGANISM: Artificial Sequence
<220> FEATURE:
<223> OTHER INFORMATION: IoADH primer

<400> SEQUENCE: 81

taccataatg tatgcgttga gcctcttgca ccttctttat taggaaatca gttgaaaaat      60

ttccggattg tctttattat tggcccattt ttttttggtc acacctttat ttttgtacac     120
```

```
ttctcgggca aagcaaaaac tatagtaccg gataggcctt tataaaactc cagtgtgtat    180

gattttagtt ggtgtgccat ctacacgttc tcttagtttc tttatcatgt cacagaaagc    240

aagcatgcaa acccttacaa aaaataacaa catacaaatg cctaaacaac tggactataa    300

tgatggtgag tcagttacga aaagagcaag tgggttaata cgatttcgta agggacagtc    360

tgaggaagac tacaattttc aaaaggagca gttctggtcc acgggtcctt tagtacagaa    420

tcacacattt gtgactgaat ttgttgaaaa gtttattgaa aacacaatta gtgaagatta    480

ttcaatcaca gatagatcga aaatagaacg tgaaacaatc atacacggat tggagaagct    540

gtattttcaa agggaatatg agcgatgtct aaaagatgtt caactattga aggacaatat    600

cgataagttc aatcctaatt tggatcttaa tgaaaagaat ttataatgag ctgaattata    660

tttcttggat gtgcatcaaa aagatccatg agagtaacga aaagaaactg gggaaatct     720

aataatttac aatttcaata tacacttcta tatcctttaa tgtaatggct ttataaataa    780

acacgaactt ctacagcacc gacgtttctt tttcttacca gctcctcttc ttcttcttct    840

tcttcttctt cttcttcttc ttcttcttct tcttcttctt cttcttcttc tttcttacca    900

tcattgccat tttccttttt tcttatttgc tcttgatcct ctgtttttc aatttggaca     960

aactcatcta atacaccaac acttttag                                       988
```

```
<210> SEQ ID NO 82
<211> LENGTH: 6045
<212> TYPE: DNA
<213> ORGANISM: Artificial Sequence
<220> FEATURE:
<223> OTHER INFORMATION: SmGPD-IoPDC-URA3-IoADH integration fragment

<400> SEQUENCE: 82
```

```
ctaagtagtg gtgttggtga actcaagatg gactctttag gtaattatat tcttgaatag     60

ttgtgtaaag cgaatatgca aatagatttg ttttataatt atgcatctct ttgaaagagg    120

tttagaggca aagttcttgc atacaatatt gtgattgttt taatgtcatt cttgattttc    180

ataaagagat taaaaaaaaa aaaaaaaaac ttataaaatt gagtagaacc atttatatat    240

aagacaaaga ttgtctgtat tagtcctcaa cacactaaac cttacatact tagggtaaat    300

ttgctaatag agtgatatgt tcatgagaac tccaacgaca acacaaccac ctatttgcac    360

aacaaacacc attgtcgcac gctgcgcgcc ctagaagtag aaagaaaggg aaatgacatt    420

aagagaatca taccccgtgc ccgtaacgcc gaaaaaatca caccccgtcc cccacacctt    480

aaaacctcaa ccgcttaaca ccgccacacc ctttctcttt ataaacgccg tttgcattac    540

tcattcttct tataaaccgc accccccaaa acgcggaata gcttcaaccc cccaatcaga    600

tatgagtttc ccgggaaacc cgcttttccc gacagcccca caaggggttg gtctataaaa    660

gaggacgttt tccccgtcat cgagattgaa gattcttaca ggcccattta ttcaaattgg    720

agttgattct tcttgtcttt actttctttc tctcttttc ttccttttt aatattatct      780

tttgtcaagc ctggttccct aagttgaact ctcttttctt gtgatcctcc tatatagata    840

cgccttgcca aatgcggccg cggatctcca tggggccggc ctgctccgcg ggtttaaacc    900

ccggggcgtt gaagatctat tctccagcaa ttaaatttgt gaagaataac tggtatagag    960

tacttccttt aaaaacatgt ccgtgcacca agaaaaaaaa aaagtttgaa aaattgtatg   1020

tcgacgaatt tcagcatttt catttcaagg cgatattatg tttcactaaa ctcaggacag   1080

gaatatacta agaataacta caacatacac acaacataag ccaagatgga tcaacttaac   1140
```

```
taccaagaac aacaacaatt tcaaaagatc gttgaacaaa agcaaatggc tgatttcatg   1200
aggctatctg cagatacgcg gaacaatcaa tcgataatga tttgactgat aaagaaaacc   1260
atacttttgt ttatgtttat tagttatcgc tttgctacat taaaaattca catactaaag   1320
cctttgttaa acaacttttt ctaaatctta agattttact ctatctagtt tttttggttg   1380
taggtgaacg taaagtacct catttatttt tttttttttg cttgtgtaat tcttttcatg   1440
cttatttaaa ctagtgtaca tgtatcaaat ctttgtgtaa gaatcattta aatctgttta   1500
aataagcatt ccaaccagct tgttggtatc ttttagcttg ctctatagga tctcttcctt   1560
gaccgtacaa acctctacca acaattatga tatccgttcc agtctttaca acttcatcaa   1620
cagttctata ttgttgacca agtgcatcac ctttgtcatc taaaccaacc cctggagtca   1680
taatgatcca gtcaaaacct tcttctctac cgcccatatc gtgttgcgca ataaaaccaa   1740
tgacaaactc tttatcagat ttagcaattt ctactgtttt ttctgtatat tcaccatatg   1800
ctaaagaacc ctttgatgat aactcagcaa gcattagcaa acctctaggt tcactggttg   1860
tttcttgggc tgcctccttc aagccagaaa caatacctgc acccgttaca ccatgtgcat   1920
tagtgatgtc agcccattcg gcaatacgga agacaccaga tttatattga tttttaacag   1980
tgttaccaat atcagcaaat tttctatctt caaaaatcat aaaattatgt ttcttggcaa   2040
gctccttcaa aggcaacaca gttccttcat acgtaaaatc agaaacaata tcgatgtgtg   2100
ttttaactag acagatgtaa ggaccaatag tgtccaaaat agagagaagc ttttcagttt   2160
cagtaatatc caatgatgca caaaggttag acttcttttc ctccatgatg gagaaaagtc   2220
tcctagcaac aggggaagtg tgtgattctg atctttcttt gtatgacgcc atccttgaca   2280
aacaaactac tttattaaag cgttgaagat ctattctcca gcaattaaat ttgtgaagaa   2340
taactggtat agagtacttc ctttaaaaac atgtccgtgc accaagaaaa aaaaaaagtt   2400
tgaaaaattg tatgtcgacg aatttcagca ttttcatttc aaggcgatat tatgtttcac   2460
taaactcagg acaggaatat actaagaata actacaacat acacacaaca taagccaaga   2520
tggatcaact taactaccaa gaacaacaac aatttcaaaa gatcgttgaa caaaagcaaa   2580
tggctgattt catgaggcta tgaattcttt tattataaaa ttatatatta ttcttaatta   2640
catatcaccc ttctatcagg gaagggagaa acgaaaatag agagtgacct atccaagctt   2700
gggggtctaa gttttaatgg cccagggaat cattactttt ttttctcaat ccttgatgga   2760
taaaagtatt acatacgtac aggattgtgt attagtgtat ttcgttatat gattaaacaa   2820
agtttataga ttgtaaagta gacgtaaagt ttagtaattc attttaatgt tcattttaca   2880
ttcagatgtt aattaattac ttaatgtcaa aaacaacaga cttaacagta gtcatagctt   2940
caatagagta cttaacacct tgaataccag caccggactt tttggcacca aggaatggga   3000
agttgtcagt acctctttgt gtcttgttgt tgatatggac tgtaccgact tctaattgtt   3060
cagcaatacc gaaagctcta ggaaaatcat tagtaaagat tgaggcctgt aagccatatt   3120
cagacttgtt agagatttca atagcctcct caacggatgt gactctaatg attggtaaaa   3180
ctggaccgaa tggttcctcc catgccaatc tcatatcagt ggtaacttta tcaaaaagga   3240
ttggacaaat caaattgcct tctctcttga tttcggttaa tgctgctgca cccttatcat   3300
ttgcatcgtt aatcaaaccc tcgacatagt cagcagattt ggtatcaatc aaaggggtaa   3360
tgtcagcgtc atcttctggg ttaccaatgg ttaaagctaa aactttctct ctgatctttt   3420
caactaattc atctgcaact gattccatga ccaagactct cttgacagct gtacatcttt   3480
gaccggagta accgaatgca ccagcgatga tgtttttggc tgtaagttcc aaatctgcat   3540
```

```
cttctaaaac aattgcagaa tctttaccac caagttccaa catgattgga cgcataccag   3600
ccatcttgcc aatacgttca ccaataccag ttgaaccggt gaaattgatg aagttaactg   3660
cctggtgctc aacaatgtag tcaccgattt cagaacctct accagtaatg gtattgaaaa   3720
caccggctgg taaaccagct tcagcaaaag cctcggccaa taacaaacca gaaatagaac   3780
cttgggtagg tggcttgaaa gcaatgacat tgcctgcgat caatgctggg gcgatctttg   3840
aaccagccaa gttaacaggg taattgaatg gggaaattgc taaaactaaa ccaactggtt   3900
ctcttctgac aacggcaatc tttttcttgg aagctgcttc aaaggaaccg ccttctaaga   3960
cttcaccttc cattctcaaa ccttcctctg cagcatagtt aatgatttct gcagtacgga   4020
caacttcgga aactgcggac ttgtaaccct tagcaacttc cttagacaaa acagcaccaa   4080
tcttttcctt atctctcatc aaaatgtcag caactttgtg caagtatgca gctctttcaa   4140
tgtaggaaag tgatctccaa gctggttgtg cctttttggc agaagcataa acatagtcaa   4200
cctcttcggt ggacatagca gggacagagc ctaactctgc accggatgct ggttcataga   4260
ttttgatctc gttttcagac aacttccatt caccattaac atagtttttg tattgcttag   4320
tcatgctaga atttttgtgt tttgctgtgt tttgttttat tttgttttat tgggaagaaa   4380
atatataata atagaatatt atatcaaaaa ataattaaag aagctcaact gtttttagaa   4440
taaatgggtt ctccgtgtcc tttttatacg ccttctccga aaagaaaaaa accatcgtat   4500
catttgtagc ccacgccacc cggaaaaacc accattgtcc tcagcagtcc gcaaaaatat   4560
ggatgcgctc aatcaatttc cctcccccgt caatgccaaa aggataacga cacactatta   4620
agagcgcatc atttgtaaaa gccgaggaag gggatacgc  tgaccgagac gtctcgcctc   4680
actctcggag ctgagccgcc ctccttaaga aattcatggg aagaacaccc ttcgcggctt   4740
ctgaacggct cgccctcgtc cattggtcac ctcacagtgg caactaataa ggacattata   4800
gcaatagaaa ttaaaatggt gcactgaaat acaataggat cgaataggat aggatacaat   4860
aagatacgga atattagact atactgtgat acggtacgct acgatacgct acgatacgat   4920
acgatagagg ataccacgga tataacgtag tgttattttt cattattggg gttttttttc   4980
tgtttgaatt ttccacgtca agagtatccc atctgacagg aaccgatgga ctcctcgagg   5040
gatccgcggc cgctaccata atgtatgcgt tgagcctctt gcaccttctt tattaggaaa   5100
tcagttgaaa aatttccgga ttgtctttat tattggccca tttttttttg gtcacacctt   5160
tatttttgta cacttctcgg gcaaagcaaa aactatagta ccggataggc ctttataaaa   5220
ctccagtgtg tatgatttta gttggtgtgc catctacacg ttctcttagt ttctttatca   5280
tgtcacagaa agcaagcatg caaaccctta caaaaaataa caacatacaa atgcctaaac   5340
aactggacta taatgatggt gagtcagtta cgaaaagagc aagtgggtta atacgatttc   5400
gtaagggaca gtctgaggaa gactacaatt ttcaaaagga gcagttctgg tccacgggtc   5460
ctttagtaca gaatcacaca tttgtgactg aatttgttga aaagtttatt gaaaacacaa   5520
ttagtgaaga ttattcaatc acagatagat cgaaaataga acgtgaaaca atcatacacg   5580
gattggagaa gctgtatttt caaagggaat atgagcgatg tctaaaagat gttcaactat   5640
tgaaggacaa tatcgataag ttcaatccta atttggatct taatgaaaag aatttataat   5700
gagctgaatt atatttcttg gatgtgcatc aaaaagatcc atgagagtaa cgaaaagaaa   5760
ctgggggaaa tctaataatt tacaatttca atatacactt ctatatcctt taatgtaatg   5820
gctttataaa taaacacgaa cttctacagc accgacgttt ctttttctta ccagctcctc   5880
```

```
ttcttcttct tcttcttctt cttcttcttc ttcttcttct tcttcttctt cttcttcttc   5940

ttctttctta ccatcattgc cattttcctt ttttcttatt tgctcttgat cctctgtttt   6000

ttcaatttgg acaaactcat ctaatacacc aacactttta gggcc                   6045


<210> SEQ ID NO 83
<211> LENGTH: 6215
<212> TYPE: DNA
<213> ORGANISM: Artificial Sequence
<220> FEATURE:
<223> OTHER INFORMATION: StXI-IoENO1-PDC-TDH3-TEF2-URA3-loxP-IoAXR2
      integration fragment

<400> SEQUENCE: 83

ctgaagacac aaaaggggta tcactgaaat tgatcacttt tgcattgttt gggaacttat     60

tctattcaat gtctctacta ttatctgaga attcattgag aggcggggaa gaatcaaagg    120

agttttggaa ggccgaattg agttactttt taggggcaat cggaacagta ttgtttgatt    180

ttattgcaat tttacaatgg attcattatg acagccacag taatcgtacc aatcatatcc    240

aatctgtgag gttgaaagct tacaccccta aatcattaaa aagccagaca attcccaaat    300

cggtgccatt gatacattca cgtacatcgt ccatgagaga tggtacaaag atagatccca    360

tcgaaatggc ggctagcgtc aagtcaacat tgtcacccca gaatgtacgc aaactcaatg    420

agttcacacc attgtctcct atggatttat tgctagatga acatatttca cgcagttatg    480

tttcctctac tgatacaaaa actatacctc agaagaagag acctgatagt atcaagtctg    540

tacacaggca caacgaggac ctgctaatga cattcgaaga atagaagcag tcccaattta    600

aaccgtggcc gtggtaacag ccataactgt agccacaatt ggaaattatg gatgtattgt    660

ctgatttgga cctccggggc agggacaatg gacttggcca aagagtcgaa aaaaatgttc    720

aacagacgag ataattggtc tttaattgtc tcggacatgt gatttcctta aaagtttaat    780

ttcacacccg caggtttatt tatataaaag tgtggccaca agtcttggga agatgaacat    840

cttgatattc atgtcccctc tcattttctg agactggcat aagataagta gaaagcggcc    900

gcgttgttga tgctgcgcac ctgtggttgc ccaacatggt tgtatatcgt gtaaccacac    960

caacacatgt gcagcacatg tgtttaaaag agtgtcatgg aggtggatca tgatggaagt   1020

ggactttacc acttgggaac tgtctccact cccgggaaga aaagacccgg cgtatcacgc   1080

ggttgcctca atggggcaat ttggaaggag aaatataggg aaaatcacgt cgctctcgga   1140

cggggaagag ttccagacta tgaggggggg gggtggtata taaagacagg agatgtccac   1200

ccccagagag aggaagaagt tggaacttta gaagagagag ataactttcc ccagtgtcca   1260

tcaatacaca accaaacaca aactctatat ttacacatat aaccccctcc aaccaaaagg   1320

ctagaatgaa ggagtacttt cccgagataa aggaaatcaa atatgaaggt ccagagagca   1380

aaaacgtaat ggccttcaaa tactataaca aggacgaggt tattggtggt aaaccaatga   1440

gggaacactt gaaatttgca atgtcttatt ggcatactct caaggcacag ggattagaca   1500

tgttcggtgg tgatactatg gacagagctt ggaatagata tgatgatgcg ttagaacaag   1560

caaaggcaag agccgatgct ggttttgagt ttatgcaaaa gatagggatg gactatttct   1620

gtttccacga tagggacatt atcaatgaag ccatgaccct taaagagact aatcgtttac   1680

tagatgaaat tgtcgaccat ttagagggtc tgatgaaaaa gacaggtata aagttgctct   1740

ggggcacgac taatgctttc tcacatccta ggtttctcca tggcggtgca actgccccaa   1800

acgccgatgt ttttgcatac gctgctgccc aagtgaaaaa ggctatggaa attacaaaaa   1860
```

gactgggcgg cgaaaactat gtcctttggg gaggtcgtga aggatatgaa acactattga 1920
ataccaagag tgatttggaa tatgacaatt ttgctagatt cttacaaatg gttgttgact 1980
ataaggaaaa gattgggttt gaaggacaat tgttaatcga accaaaacct aaggagccta 2040
caaaacacca atacgatttc gacactgcta cagtcctagg atttttgcga aaatacaacc 2100
tagataagca ctacaaaatg aatattgaag caaatcatgc aactttagcg ggtcatacct 2160
tccagcatga gttaaacttg gctagaatta acaatgtcat gggttcgata gatgcgaatc 2220
agggtgatat gttgttggga tgggatacgg atcaatttcc gactaatatc tatgacgcag 2280
tacttgcaat gtatgaggtg attaaaaaca acgggctggg taagggtggt ttgaattttg 2340
atgctaaagt gaggagagga tcctttgaag ataaggatct atttcttgcg tatattgctg 2400
ggatggatac attcgcaaaa ggacttacca tcgcttatag attatacgaa gataaagttt 2460
tcgaagattt tcaagataaa cggtatgagt catacaaaac aggaattggg aaggatattg 2520
ttgaaggcaa agttggcttt gaggaactag cagaatacgt tgagaatttg gcagaaatca 2580
aaaacacctc tggtagacag gaaatgttag aatctatttt gaatagttac atattagaag 2640
caaagtgatt aatcgtaaat ctaactaatg cttttactaa atatctagta caatttttac 2700
agtccctacg tttataaatg aatttaatga aaaaaaaata ttttgtaacg atgtgtttat 2760
taagttgcgc tcttccgata atcccggact ttggttaatt tctcaatggg tttttttttc 2820
aaaaccattg ttgtagtgta acagacttta acaaaaggac atcactctac agggcagctt 2880
taaaatccct cagtgtaatt gttcttcatt cataacgtgg cagtcaagga ctcgaggagt 2940
ccatcggttc ctgtcagatg ggatactctt gacgtggaaa attcaaacag aaaaaaaacc 3000
ccaataatga aaaataacac tacgttatat ccgtggtatc ctctatcgta tcgtatcgta 3060
gcgtatcgta gcgtaccgta tcacagtata gtctaatatt ccgtatctta ttgtatccta 3120
tcctattcga tcctattgta tttcagtgca ccattttaat ttctattgct ataatgtcct 3180
tattagttgc cactgtgagg tgaccaatgg acgagggcga gccgttcaga agccgcgaag 3240
ggtgttcttc ccatgaattt cttaaggagg gcggctcagc tccgagagtg aggcgagacg 3300
tctcggtcag cgtatccccc ttcctcggct tttacaaatg atgcgctctt aatagtgtgt 3360
cgttatcctt ttggcattga cgggggaggg aaattgattg agcgcatcca tatttttgcg 3420
gactgctgag gacaatggtg gtttttccgg gtggcgtggg ctacaaatga tacgatggtt 3480
tttttctttt cggagaaggc gtataaaaag gacacggaga acccatttat tctaaaaaca 3540
gttgagcttc tttaattatt ttttgatata atattctatt attatatatt ttcttcccaa 3600
taaaacaaaa taaaacaaaa cacagcaaaa cacaaaaatt ctagaatgaa ggagtacttt 3660
cccgagataa aggaaatcaa atatgaaggt ccagagagca aaaacgtaat ggccttcaaa 3720
tactataaca aggacgaggt tattggtggt aaaccaatga gggaacactt gaaatttgca 3780
atgtcttatt ggcatactct caaggcacag ggattagaca tgttcggtgg tgatactatg 3840
gacagagctt ggaatagata tgatgatgcg ttagaacaag caaaggcaag agccgatgct 3900
ggttttgagt ttatgcaaaa gatagggatg gactatttct gtttccacga tagggacatt 3960
atcaatgaag ccatgaccct taaagagact aatcgtttac tagatgaaat tgtcgaccat 4020
ttagagggtc tgatgaaaaa gacaggtata aagttgctct ggggcacgac taatgctttc 4080
tcacatccta ggtttctcca tggcggtgca actgccccaa acgccgatgt ttttgcatac 4140
gctgctgccc aagtgaaaaa ggctatggaa attacaaaaa gactgggcgg cgaaaactat 4200
gtcctttggg gaggtcgtga aggatatgaa acactattga ataccaagag tgatttggaa 4260

```
tatgacaatt ttgctagatt cttacaaatg gttgttgact ataaggaaaa gattgggttt   4320
gaaggacaat tgttaatcga accaaaacct aaggagccta caaaacacca atacgatttc   4380
gacactgcta cagtcctagg atttttgcga aaatacaacc tagataagca ctacaaaatg   4440
aatattgaag caaatcatgc aactttagcg ggtcatacct tccagcatga gttaaacttg   4500
gctagaatta acaatgtcat gggttcgata gatgcgaatc agggtgatat gttgttggga   4560
tgggatacgg atcaatttcc gactaatatc tatgacgcag tacttgcaat gtatgaggtg   4620
attaaaaaca acgggctggg taagggtggt ttgaattttg atgctaaagt gaggagagga   4680
tcctttgaag ataaggatct atttcttgcg tatattgctg ggatggatac attcgcaaaa   4740
ggacttacca tcgcttatag attatacgaa gataaagttt tcgaagattt tcaagataaa   4800
cggtatgagt catacaaaac aggaattggg aaggatattg ttgaaggcaa agttggcttt   4860
gaggaactag cagaatacgt tgagaatttg gcagaaatca aaaacacctc tggtagacag   4920
gaaatgttag aatctatttt gaatagttac atattagaag caaagtgatt aattaacatc   4980
tgaatgtaaa atgaacatta aaatgaatta ctaaacttta cgtctacttt acaatctata   5040
aactttgttt aatcatataa cgaaatacac taatacacaa tcctgtacgt atgtaatact   5100
tttatccatc aaggattgag aaaaaaaagt aatgattccc tgggccatta aaacttagac   5160
ccccaagctt ggataggtca ctctctattt tcgtttctcc cttccctgat agaagggtga   5220
tatgtaatta agaataatat ataattttat aataaaagaa ttcgccctta catatgataa   5280
cttcgtataa tgtatgctat acgaagttat catagcctca tgaaatcagc catttgcttt   5340
tgttcaacga tcttttgaaa ttgttgttgt tcttggtagt taagttgatc catcttggct   5400
tatgttgtgt gtatgttgta gttattctta gtatattcct gtcctgagtt tagtgaaaca   5460
taatatcgcc ttgaaatgaa aatgctgaaa ttcgtcgaca tacaattttt caaacttttt   5520
tttttcttg gtgcacggac atgtttttaa aggaagtact ctataccagt tattcttcac   5580
aaatttaatt gctggagaat agatcttcaa cgctttaata aagtagtttg tttgtcaagg   5640
atggcgtcat acaaagaaag atcagaatca cacacttccc ctgttgctag gagacttttc   5700
tccatcatgg aggaaaagaa gtctaacctt tgtgcatcat tggatattac tgaaactgaa   5760
aagcttctct ctattttgga cactattggt ccttacatct gtctagttaa aacacacatc   5820
gatattgttt ctgattttac gtatgaagga actgtgttgc ctttgaagga gcttgccaag   5880
aaacataatt ttatgatttt tgaagataga aaatttgctg atattggtaa cactgttaaa   5940
aatcaatata aatctggtgt cttccgtatt gccgaatggg ctgacatcac taatgcacat   6000
ggtgtaacgg gtgcaggtat tgtttctggc ttgaaggagg cagcccaaga aacaaccagt   6060
gaacctagag gtttgctaat gcttgctgag ttatcatcaa agggttcttt agcatatggt   6120
gaatatacag aaaaaacagt agaaattgct aaatctgata aagagtttgt cattggtttt   6180
attgcgcaac acgatatggg cggtagagaa gggcc                              6215
```

<210> SEQ ID NO 84
<211> LENGTH: 5989
<212> TYPE: DNA
<213> ORGANISM: Artificial Sequence
<220> FEATURE:
<223> OTHER INFORMATION: StXI-IoENO1-PDC-TDH3-TEF2-URA3-loxP-IoAXR2 integration fragment

<400> SEQUENCE: 84

```
ccacatggtg taacgggtgc aggtattgtt tctggcttga aggaggcagc ccaagaaaca     60
```

```
accagtgaac ctagaggttt gctaatgctt gctgagttat catcaaaggg ttctttagca    120
tatggtgaat atacagaaaa aacagtagaa attgctaaat ctgataaaga gtttgtcatt    180
ggttttattg cgcaacacga tatgggcggt agagaagaag gttttgactg gatcattatg    240
actccagggg ttggtttaga tgacaaaggt gatgcacttg gtcaacaata tagaactgtt    300
gatgaagttg taaagactgg aacggatatc ataattgttg gtagaggttt gtacggtcaa    360
ggaagagatc ctatagagca agctaaaaga taccaacaag ctggttggaa tgcttattta    420
aacagattta aatgattctt acacaaagat ttgatacatg tacactagtt taaataagca    480
tgaaaagaat tacacaagca aaaaaaaaaa aataaatgag gtactttacg ttcacctaca    540
accaaaaaaa ctagatagag taaaatctta agatttagaa aaagttgttt aacaaaggct    600
ttagtatgtg aatttttaat gtagcaaagc gataactaat aaacataaac aaaagtatgg    660
ttttctttat cagtcaaatc attatcgatt gattgttccg cgtatctgca gataacttcg    720
tataatgtat gctatacgaa gttatagatc gcggccgcta acctgatcca aaaggggtat    780
gtctattttt tagagtgtgt ctttgtgtca aattatggta gaatgtgtaa agtagtataa    840
actttcctct caaatgacga ggtttaaaac accccccggg tgagccgagc cgagaatggg    900
gcaattgttc aatgtgaaat agaagtatcg agtgagaaac ttgggtgttg gccagccaag    960
ggggaaggaa aatggcgcga atgctcaggt gagattgttt tggaattggg tgaagcgagg   1020
aaatgagcga cccggaggtt gtgactttag tggcggagga ggacggagga aaagccaaga   1080
gggaagtgta tataagggga gcaatttgcc accaggatag aattggatga gttataattc   1140
tactgtattt attgtataat ttatttctcc ttttatatca aacacattac aaaacacaca   1200
aaacacacaa acaaacacaa ttacaaaaag ctagaatgaa ggagtacttt cccgagataa   1260
aggaaatcaa atatgaaggt ccagagagca aaaacgtaat ggccttcaaa tactataaca   1320
aggacgaggt tattggtggt aaaccaatga gggaacactt gaaatttgca atgtcttatt   1380
ggcatactct caaggcacag ggattagaca tgttcggtgg tgatactatg gacagagctt   1440
ggaatagata tgatgatgcg ttagaacaag caaaggcaag agccgatgct ggttttgagt   1500
ttatgcaaaa gatagggatg gactatttct gtttccacga tagggacatt atcaatgaag   1560
ccatgaccct taaagagact aatcgtttac tagatgaaat tgtcgaccat ttagagggtc   1620
tgatgaaaaa gacaggtata aagttgctct ggggcacgac taatgctttc tcacatccta   1680
ggtttctcca tggcggtgca actgccccaa acgccgatgt ttttgcatac gctgctgccc   1740
aagtgaaaaa ggctatggaa attacaaaaa gactgggcgg cgaaaactat gtcctttggg   1800
gaggtcgtga aggatatgaa acactattga ataccaagag tgatttggaa tatgacaatt   1860
ttgctagatt cttacaaatg gttgttgact ataaggaaaa gattgggttt gaaggacaat   1920
tgttaatcga accaaaacct aaggagccta caaaacacca atacgatttc gacactgcta   1980
cagtcctagg atttttgcga aaatacaacc tagataagca ctacaaaatg aatattgaag   2040
caaatcatgc aactttagcg ggtcatacct tccagcatga gttaaacttg gctagaatta   2100
acaatgtcat gggttcgata gatgcgaatc agggtgatat gttgttggga tgggatacgg   2160
atcaatttcc gactaatatc tatgacgcag tacttgcaat gtatgaggtg attaaaaaca   2220
acgggctggg taagggtggt ttgaattttg atgctaaagt gaggagagga tcctttgaag   2280
ataaggatct atttcttgcg tatattgctg ggatggatac attcgcaaaa ggacttacca   2340
tcgcttatag attatacgaa gataaagttt tcgaagattt tcaagataaa cggtatgagt   2400
```

```
catacaaaac aggaattggg aaggatattg ttgaaggcaa agttggcttt gaggaactag   2460
cagaatacgt tgagaatttg gcagaaatca aaaacacctc tggtagacag gaaatgttag   2520
aatctatttt gaatagttac atattagaag caaagtgatt aatcgtaagc ggcgaatctc   2580
tggctcatgg gggatatcct ctttgtttgg cttttttttc ccattctctg ttttgattat   2640
ctaatgactc attgggagga ttttctcact tcaagctttt ttttcttgca ctctttcata   2700
actccagctc tctctaactg aggctacaat gccttttaac gaacttatga gacgtttcta   2760
aattatatag gtatatgcca atatataatt acacataaaa ataaatataa ataaaatata   2820
aaaataaaaa taaacatcga aaaagaagat gtgaaattgc gaagactaga aagcacaaac   2880
gagcggtcta tatcggcgac tcgaggctct acaagcctca tatgggttca atgggtctgc   2940
aatgaccgca tacggacttg gacaattacc ttctattgaa tttctgagaa gagatacatc   3000
tgaccagcaa tgtaagcaga caatcccaat tctgtaaaca acctctttgt ccataattcc   3060
ccatcagaag agtgaaaaat gccctcaaaa cgcatgcgcc actcccacct ctcagctgca   3120
ctgcgccacc tctgagggtc ctttcagggg tcgactaccc cggacacctc gcagaggagc   3180
gacgtcacgt acttttaaaa tggcagagac gcgcagtttc ttgaagaaag gataaaaatg   3240
aaatggtgcg gaaatgcgaa aatgatgaaa aattttcttg gtggcgagga aattgagtgc   3300
aataattggc acgaggttgt tgccacccga gtgtgagtat atatcctagt ttctgcactt   3360
ttcttcttct tttccttgcg ttttcttttc aacttttttt actttttcct tcaacagaca   3420
aatctaactt atatatcaca tctagaatga aggagtactt tcccgagata aaggaaatca   3480
aatatgaagg tccagagagc aaaaacgtaa tggccttcaa atactataac aaggacgagg   3540
ttattggtgg taaaccaatg agggaacact tgaaatttgc aatgtcttat tggcatactc   3600
tcaaggcaca gggattagac atgttcggtg gtgatactat ggacagagct tggaatagat   3660
atgatgatgc gttagaacaa gcaaaggcaa gagccgatgc tggttttgag tttatgcaaa   3720
agatagggat ggactatttc tgtttccacg atagggacat tatcaatgaa gccatgaccc   3780
ttaaagagac taatcgttta ctagatgaaa ttgtcgacca tttagagggt ctgatgaaaa   3840
agacaggtat aaagttgctc tggggcacga ctaatgcttt ctcacatcct aggtttctcc   3900
atggcggtgc aactgcccca aacgccgatg tttttgcata cgctgctgcc caagtgaaaa   3960
aggctatgga aattacaaaa agactgggcg gcgaaaacta tgtcctttgg ggaggtcgtg   4020
aaggatatga aacactattg aataccaaga gtgatttgga atatgacaat tttgctagat   4080
tcttacaaat ggttgttgac tataaggaaa agattgggtt tgaaggacaa ttgttaatcg   4140
aaccaaaacc taaggagcct acaaaacacc aatacgattt cgacactgct acagtcctag   4200
gatttttgcg aaaatacaac ctagataagc actacaaaat gaatattgaa gcaaatcatg   4260
caactttagc gggtcatacc ttccagcatg agttaaactt ggctagaatt aacaatgtca   4320
tgggttcgat agatgcgaat cagggtgata tgttgttggg atgggatacg gatcaatttc   4380
cgactaatat ctatgacgca gtacttgcaa tgtatgaggt gattaaaaac aacgggctgg   4440
gtaagggtgg tttgaatttt gatgctaaag tgaggagagg atcctttgaa gataaggatc   4500
tatttcttgc gtatattgct gggatggata cattcgcaaa aggacttacc atcgcttata   4560
gattatacga agataaagtt ttcgaagatt ttcaagataa acggtatgag tcatacaaaa   4620
caggaattgg gaaggatatt gttgaaggca aagttggctt tgaggaacta gcagaatacg   4680
ttgagaattt ggcagaaatc aaaaacacct ctggtagaca ggaaatgtta gaatctattt   4740
tgaatagtta catattagaa gcaaagtgat taattaagta tagccatata gtttaattcc   4800
```

```
tttatacttt ttataactat ttcttacact aattattatt atcaattatt tattgtagaa   4860
cttgactctt gcgtcgatca ccatgacagg gctatcttaa caaggggtaa tttttgttga   4920
tggagtcaag tagcattccg acgggaagtg tcgatgcctc tgaacgaaat cttccgatta   4980
gctctgcaaa gaagtggaaa ttgtcagcgc agaattcaag gcggtgtaac ataccagtca   5040
gtaaatctat ccctactagc ttttttttttc tatatattta cacaaaccaa cagctacatg   5100
tttcaataca taaacatgga gaaccgctcc cctttatatt tttttttcc acacacacct   5160
tttatcttat cgctttacat tttcggtggc aaattgatta aaaaaagtac agaaatgctc   5220
agctccaaat agccttgaat tggggttgct tcctttctct gataaccatt tttcctttct   5280
caattgctag ctaacagtag caaaacaact agccctatac caaatgaaca ttcactcgtc   5340
agtattgaca tccgtagtcc tcttgctcgc ttcaattacg ggctccgatg ctaaggttca   5400
ttctgccagc atccacaaga atccgttcca agacaattat aaagatattt cctatctaga   5460
atatgttgac tccatcaaga acaagtatgt taacaatttt gtcaagaact tcaatgcacc   5520
ttttgtccca tttgttgaag atgcggtcat tgaggacact catgaactac ccttaaccaa   5580
ctatatgaat gcccaatact tcactgagat tcaacttggt acccctggcc agccattcaa   5640
ggtgattcta gacactgggt cttctaattt gtgggttcct tccacaaaat gtacatcttt   5700
ggcatgttat ttgcactcta aatatgatca cgatgcaagt tccacataca aacaaaatgg   5760
taccgattct ctatcagata tggttctggt tccttggaag gttttatttc acaagattta   5820
ctaacttttg gtgacttggt cattccagag caggatttcg ctgaggcaac aagtgaaccg   5880
ggcttggcgt ttgctttcgg aaaattcgac ggtattctag gtttagctta tgataccatc   5940
tcggtggaca aggttgttcc tccaatttac aatgccattg acaagggcc              5989
```

<210> SEQ ID NO 85
<211> LENGTH: 6389
<212> TYPE: DNA
<213> ORGANISM: Artificial Sequence
<220> FEATURE:
<223> OTHER INFORMATION: StXI-IoENO1-PDC-TDH3-TEF2-MEL5-loxP-XR
integration fragment

<400> SEQUENCE: 85

```
ctgctgagtt cacccgtcca gatagcagat gtccctgtga cggtgacgaa tatgattgca     60
agtacgccgg tttccattgt tctattatga atattcttaa caaggcagct ccaatggggc    120
aaaatgcagg tgttggtggt tggaacgatc tggacaatct agaggtcgga gtcggtaatt    180
tgactgacga tgaggaaaag gcccatttct ctatgtgggc aatggtaaag tccccactta    240
tcattggtgc cgacgtgaat cacttaaagg catcttcgta ctcgatctac agtcaagcct    300
ctgtcatcgc aattaatcaa gatccaaagg gtattccagc cacaagagtc tggagatatt    360
atgtttcaga caccgatgaa tatggacaag gtgaaattca aatgtggagt ggtccgcttg    420
acaatggtga ccaagtggtt gctttattga atggaggaag cgtagcaaga ccaatgaaca    480
cgaccttgga agagattttc tttgacagca atttgggttc aaaggaactg acatcgactt    540
gggatattta cgacttatgg gccaacagag ttgacaactc tacggcgtct gctatccttg    600
aacagaataa ggcagccacc ggtattctct acaatgctac agagcagtct tataaagacg    660
gtttgtctaa gaatgataca agactgtttg gccagaaaat tggtagtctt tctccaaatg    720
ctatacttaa cacaactgtt ccagctcatg gtatcgcctt ctataggttg agaccctcgg    780
cttaagctca atgttgagca aagcaggacg agaaaaaaaa aaataatgat tgttaagaag    840
```

```
ttcatgaaaa aaaaaaggaa aaatactcaa atacttataa cagagtgatt aaataataaa    900
cggcagtata ccctatcagg tattgagata gttttatttt tgtaggtata taatctgaag    960
cctttgaact attttctcgt atatatcatg gagtatacat tgcattagca acattgcata   1020
ctagttcata acttcgtata atgtatgcta tacgaagtta ttaattaaca agggcgattt   1080
ctgcagatat cggccggccc catggagatc cgcggccgct aacctgatcc aaaaggggta   1140
tgtctatttt ttagagtgtg tctttgtgtc aaattatggt agaatgtgta aagtagtata   1200
aactttcctc tcaaatgacg aggtttaaaa caccccccgg gtgagccgag ccgagaatgg   1260
ggcaattgtt caatgtgaaa tagaagtatc gagtgagaaa cttgggtgtt ggccagccaa   1320
gggggaagga aaatggcgcg aatgctcagg tgagattgtt ttggaattgg gtgaagcgag   1380
gaaatgagcg acccggaggt tgtgacttta gtggcggagg aggacggagg aaaagccaag   1440
agggaagtgt atataagggg agcaatttgc caccaggata gaattggatg agttataatt   1500
ctactgtatt tattgtataa tttatttctc cttttatatc aaacacatta caaaacacac   1560
aaaacacaca aacaaacaca attacaaaaa gctagcatga aggaatactt ccctgaaatc   1620
aaagagatca aatatgaagg tcctgaatcg aaaaatgtta tggcattcaa gtattacaac   1680
aaggacgagg tcataggagg aaaaccaatg agggaacatc ttaagtttgc catgtcatat   1740
tggcatacgc taaaggctca ggggttggat atgttcggtg gagatactat ggatcgtgca   1800
tggaacagat acgatgacgc tttggagcaa gcgaaagcca gagctgatgc cggcttcgag   1860
tttatgcaaa agattggcat ggactatttt tgttttcatg atcgtgacat tattaacgaa   1920
gctatgactt taaaggaaac gaataggtta ttggatgaaa ttgttgacca tcttgagggt   1980
ttgatgaaaa agactgggat caaattgttg tggggtacta caaatgcttt tagtcaccca   2040
agattcttac atggtggtgc taccgcaccg aatgccgacg tattcgcata cgcggcagct   2100
caagttaaaa aggctatgga gattaccaaa cggttgggtg gcgaaaacta cgtattatgg   2160
ggcggaagag aaggatatga aacattgcta aataccaaat ccgatttgga atatgacaat   2220
tttgcaagat ttctacaaat ggttgtcgat tacaaggaga aaattgggtt cgagggtcaa   2280
ctactcatag agccaaagcc aaaagagcct accaaacatc agtatgattt cgatactgca   2340
acagttttag gctttttgag gaagtacaat ttggacaagc attacaagat gaatatcgaa   2400
gcaaaccacg ccactttagc tggtcacaca tttcaacacg aactgaactt agcacgtatt   2460
aacaatgtca tgggttctat tgatgctaat caaggagata tgttactcgg ttgggataca   2520
gatcagtttc ccacaaatat ctacgacgct gttctagcga tgtatgaagt tatcaaaaac   2580
aatggcctcg ggaagggtgg tcttaatttt gatgcaaaag ttcgaagggg ttcatttgaa   2640
gataaggacc tatttcttgc atacatagcc ggaatggata cctttgcaaa aggtttaacc   2700
atagcatata gactgtatga ggataaagtg tttgaagatt tccaagacaa gagatatgaa   2760
agctataaga cgggtatagg caaagatatt gttgagggaa aagtcggatt cgaggaactg   2820
gctgaatatg tggaaaacct tgcagaaatc aaaaatacta gtggtagaca ggagatgctt   2880
gaatctattt tgaactccta tatattagaa gccaagtaac gatcgtaagc ggcgaatctc   2940
tggctcatgg gggatatcct ctttgtttgg cttttttttc ccattctctg ttttgattat   3000
ctaatgactc attgggagga ttttctcact tcaagctttt ttttcttgca ctctttcata   3060
actccagctc tctctaactg aggctacaat gccttttaac gaacttatga gacgtttcta   3120
aattatatag gtatatgcca atatataatt acacataaaa ataaatataa ataaaatata   3180
```

```
aaaataaaaa taaacatcga aaaagaagat gtgaaattgc gaagactaga aagcacaaac   3240
gagcggtcta tatcggcgac tcgaggctct acaagcctca tatgggttca atgggtctgc   3300
aatgaccgca tacggacttg gacaattacc ttctattgaa tttctgagaa gagatacatc   3360
tgaccagcaa tgtaagcaga caatcccaat tctgtaaaca acctctttgt ccataattcc   3420
ccatcagaag agtgaaaaat gccctcaaaa cgcatgcgcc actcccacct ctcagctgca   3480
ctgcgccacc tctgagggtc ctttcagggg tcgactaccc cggacacctc gcagaggagc   3540
gacgtcacgt acttttaaaa tggcagagac gcgcagtttc ttgaagaaag gataaaaatg   3600
aaatggtgcg gaaatgcgaa aatgatgaaa aattttcttg gtggcgagga aattgagtgc   3660
aataattggc acgaggttgt tgccacccga gtgtgagtat atatcctagt ttctgcactt   3720
ttcttcttct tttccttgcg ttttcttttc aacttttttt actttttcct tcaacagaca   3780
aatctaactt atatatcaca tctagaatga aagagtattt ccctgagatt aaggaaatca   3840
aatatgaagg tccagaaagc aaaaatgtta tggcattcaa gtactacaat aaggacgagg   3900
ttattggggg caaacctatg agagaacatc ttaagtttgc aatgtcttac tggcacacgt   3960
tgaaagcaca aggtttagat atgtttggtg gagacacaat ggatagagct tggaatagat   4020
acgacgatgc attggagcaa gcgaaagccc gtgcagatgc gggtttcgag tttatgcaga   4080
aaattggcat ggactacttc tgtttccatg atcgtgatat tattaacgaa gctatgacac   4140
ttaaggagac aaatagatta ctagacgaaa tagttgatca tttggagggt ttgatgaaaa   4200
agactgggat caaacttcta tggggtacaa ctaatgcttt tagtcatcca agattcttac   4260
acggtggagc tacagcccca aacgctgacg tatttgcata cgccgctgcg caagtcaaaa   4320
aggctatgga gattaccaaa agattgggtg gagaaaatta tgtgctgtgg ggtggtcgag   4380
aaggttatga aacattgctc aataccaagt ccgacctgga atatgataac tttgcaaggt   4440
ttcttcaaat ggttgttgat tacaaggaga aaataggttt tgaaggccaa ttgctaattg   4500
aaccaaaacc caaggaaccg acaaaacatc aatatgattt tgatactgcc actgttttgg   4560
gtttcttgcg gaagtataac ttggataagc actataagat gaatattgaa gccaaccatg   4620
caacccttgc cggccacacc tttcaacatg aattgaatct agctaggatt aacaacgtta   4680
tgggctcaat agacgctaat cagggagata tgttattagg ttgggatacc gatcagtttc   4740
ctactaatat ctatgatgca gtgttggcta tgtatgaagt gatcaaaaac aatggtctag   4800
ggaagggtgg tctgaatttt gatgcaaaag tccgtagggg atcatttgag gacaaagatt   4860
tgttcctcgc ctacattgct ggaatggata cttttgcaaa ggggttaacg atagcttatc   4920
gattatacga ggacaaggtc tttgaagatt tccaggataa gagatatgaa tcctacaaaa   4980
ctggtatcgg aaaagatata gtagaaggaa aagttggctt tgaggaatta gcagaatatg   5040
ttgagaactt agcagaaatc aaaaatacct cagggagaca agagatgtta gaatctattc   5100
tcaactcgta tatcttggaa gcaaagtaat taattaagta tagccatata gtttaattcc   5160
tttatacttt ttataactat ttcttacact aattattatt atcaattatt tattgtagaa   5220
cttgactctt gcgtcgatca ccatgacagg gctatcttaa caaggggtaa tttttgttga   5280
tggagtcaag tagcattccg acgggaagtg tcgatgcctc tgaacgaaat cttccgatta   5340
gctctgcaaa gaagtggaaa ttgtcagcgc agaattcgtg taaatggtgt tagtctgatc   5400
taatgacaac taattacgca cttacgactg taatgccttt atttttcttt atatttccca   5460
gcgtgttgtt ctttcaaata tacgatgagt ataaattaat tttacaaagc agaaacaaca   5520
ggatctttag aaacgtcact gtaaacatcg aatcttcttt gaacactgaa gggaatattt   5580
```

```
cttctcgttt cttcaacaac gtccttcttc agttctgcat aaacgatggt ttcctcatgg   5640

ccggcctcaa cgaggatctc accatctgga tcgaccacca tgctatggcc ataagcctga   5700

tagccgccct gtgggttacg agcgggggaa cacatcaaca cgtagttttg gttgtcaata   5760

gctctggcaa cggcaaactt tgaccagaat ttaggacctg tcacggtatt gaatgcaccg   5820

ggataagcca taataccagc gccacgtctg gctgcaatca tggccaattc cgggaacctg   5880

atatcatagc aaatacctaa gccgaatctg gtgtcgattt ctggaatgtc gaaaactgta   5940

accttgttgc ccggttttaa agaatcagac tccttgaacg tgattccgcc cggaatagaa   6000

atgtcaaaga ggtgcacctt acgatgcttg gcaacgattt ccccccttggg attgaaaaca   6060

agagaggtgt tgtagatacc gccgtcattg tcgtcgattt ccggaatcga acctccaatg   6120

atagagacat tgtacttttt cgcctgttca cttaaaaacg tgctagtttc cccctctggg   6180

atacgttctg cataatttgc aaattggtct acggcatatg gagattggaa acattcaggt   6240

agaacaagaa gttgtggttt tggatcgtgt tggatcgccc tctcgatgaa ttgggtcact   6300

ttggcgagat tggccttctt gtctccacca cagtggaatt gcagcagtgc cacttggaga   6360

gtcttggaga gagtaacggc agacgggcc                                    6389
```

```
<210> SEQ ID NO 86
<211> LENGTH: 6816
<212> TYPE: DNA
<213> ORGANISM: Artificial Sequence
<220> FEATURE:
<223> OTHER INFORMATION: StXI-IoENO1-PDC-TDH3-TEF2-MEL5-loxP-XR
      integration fragment
<220> FEATURE:
<221> NAME/KEY: misc_feature
<222> LOCATION: (5738)..(5738)
<223> OTHER INFORMATION: n is a, c, g, or t

<400> SEQUENCE: 86
```

```
ccctccagtg tttttctctc tgtctctttg ttttttttt ccaatctgat ttgacgtgca      60

aggcaaagac atcacatgtt tgagaatggc aagagaaggg gcgtggtagt gtataccaag    120

ccggtgtaga gagtgtgatt ttagagtgaa tccatccatg aacacgagta gaggagatgt    180

atgagcaaat ccagggtgtt tgtaatggtc caagccgcaa ggcggcgtaa tggaatgcaa    240

gaaacaaggg acactaatga aggggtaaga ggtgtctagt tgagaagtac atartaaaag    300

atgaatagtt gagawgtaca trgtaaaaga tgaatagttg agacaaatga aggtgtcaat    360

gttcctgata atgacactgc aagraacaaa taccgtgcag ttggaagggg gaaagagatg    420

rccgagataa gtgttgttga ggccaaagga tgttggaacc tgctacaata ggagatggag    480

cggcctataa ctccggcgtg tttgtgttga cagccctata catcagccaa tacgagagtt    540

tggcatgtcc tttaaagggt ttgctacccc cactcccgta atcatcgtta aaatcatcat    600

cattgaaatc attataatta acctcatcac cattcccact attatcacct tatattctcc    660

actccaggga gatgcatcgt tgtaaagggc atggctgttt gtttatttta cccgacaagc    720

caataccaag agcggacaaa ccgcatcaga atgcaacaga aggttggaga aacgtgatgt    780

catttttcc gcaaacggag atctcgcaca gcggtgagat ataaaaggcg gagatgtgga    840

caccttcttt atacaattcc cctctacttg attgttccat attcctaaca tctagttaca    900

actctgaaca tcataattat tttaaaattc tcaacccaac tgcaattgga ttgaactgcg    960

gccgcgttgt tgatgctgcg cacctgtggt tgcccaacat ggttgtatat cgtgtaacca   1020

caccaacaca tgtgcagcac atgtgtttaa aagagtgtca tggaggtgga tcatgatgga   1080
```

```
agtggacttt accacttggg aactgtctcc actcccggga agaaaagacc cggcgtatca   1140
cgcggttgcc tcaatggggc aatttggaag gagaaatata gggaaaatca cgtcgctctc   1200
ggacggggaa gagttccaga ctatgagggg gggggtggt atataaagac aggagatgtc    1260
cacccccaga gagaggaaga agttggaact ttagaagaga gagataactt tccccagtgt   1320
ccatcaatac acaaccaaac acaaactcta tatttacaca tataaccccc tccaaccaaa   1380
aggctagaat gaaggagtac tttcccgaga taaaggaaat caaatatgaa ggtccagaga   1440
gcaaaaacgt aatggccttc aaatactata acaaggacga ggttattggt ggtaaaccaa   1500
tgagggaaca cttgaaattt gcaatgtctt attggcatac tctcaaggca cagggattag   1560
acatgttcgg tggtgatact atggacagag cttggaatag atatgatgat gcgttagaac   1620
aagcaaaggc aagagccgat gctggttttg agtttatgca aaagataggg atggactatt   1680
tctgtttcca cgatagggac attatcaatg aagccatgac ccttaaagag actaatcgtt   1740
tactagatga aattgtcgac catttagagg gtctgatgaa aaagacaggt ataaagttgc   1800
tctggggcac gactaatgct ttctcacatc ctaggtttct ccatggcggt gcaactgccc   1860
caaacgccga tgtttttgca tacgctgctg cccaagtgaa aaaggctatg gaaattacaa   1920
aaagactggg cggcgaaaac tatgtccttt ggggaggtcg tgaaggatat gaaacactat   1980
tgaataccaa gagtgatttg gaatatgaca attttgctag attcttacaa atggttgttg   2040
actataagga aaagattggg tttgaaggac aattgttaat cgaaccaaaa cctaaggagc   2100
ctacaaaaca ccaatacgat ttcgacactg ctacagtcct aggatttttg cgaaaataca   2160
acctagataa gcactacaaa atgaatattg aagcaaatca tgcaacttta gcgggtcata   2220
ccttccagca tgagttaaac ttggctagaa ttaacaatgt catgggttcg atagatgcga   2280
atcagggtga tatgttgttg ggatgggata cggatcaatt tccgactaat atctatgacg   2340
cagtacttgc aatgtatgag gtgattaaaa acaacgggct gggtaagggt ggtttgaatt   2400
ttgatgctaa agtgaggaga ggatcctttg aagataagga tctatttctt gcgtatattg   2460
ctgggatgga tacattcgca aaaggactta ccatcgctta tagattatac gaagataaag   2520
ttttcgaaga ttttcaagat aaacggtatg agtcatacaa aacaggaatt gggaaggata   2580
ttgttgaagg caaagttggc tttgaggaac tagcagaata cgttgagaat ttggcagaaa   2640
tcaaaaacac ctctggtaga caggaaatgt tagaatctat tttgaatagt tacatattag   2700
aagcaaagtg attaatcgta aatctaacta atgcttttac taaatatcta gtacaatttt   2760
tacagtccct acgtttataa atgaatttaa tgaaaaaaaa atattttgta acgatgtgtt   2820
tattaagttg cgctcttccg ataatcccgg actttggtta atttctcaat gggttttttt   2880
ttcaaaacca ttgttgtagt gtaacagact ttaacaaaag gacatcactc tacagggcag   2940
ctttaaaatc cctcagtgta attgttcttc attcataacg tggcagtcaa ggactcgagg   3000
agtccatcgg ttcctgtcag atgggatact cttgacgtgg aaaattcaaa cagaaaaaaa   3060
accccaataa tgaaaaataa cactacgtta tatccgtggt atcctctatc gtatcgtatc   3120
gtagcgtatc gtagcgtacc gtatcacagt atagtctaat attccgtatc ttattgtatc   3180
ctatcctatt cgatcctatt gtatttcagt gcaccatttt aatttctatt gctataatgt   3240
ccttattagt tgccactgtg aggtgaccaa tggacgaggg cgagccgttc agaagccgcg   3300
aagggtgttc ttcccatgaa tttcttaagg agggcggctc agctccgaga gtgaggcgag   3360
acgtctcggt cagcgtatcc cccttcctcg gcttttacaa atgatgcgct cttaatagtg   3420
```

```
tgtcgttatc cttttggcat tgacggggga gggaaattga ttgagcgcat ccatattttt   3480
gcggactgct gaggacaatg gtggtttttc cgggtggcgt gggctacaaa tgatacgatg   3540
gtttttttct tttcggagaa ggcgtataaa aaggacacgg agaacccatt tattctaaaa   3600
acagttgagc ttctttaatt attttttgat ataatattct attattatat attttcttcc   3660
caataaaaca aaataaaaca aaacacagca aaacacaaaa attctagaat gaaggaatac   3720
ttccccgaaa tcaaagagat caaatatgaa ggtccagagt ccaaaaatgt catggcattc   3780
aagtactata acaaggatga agtcattggt ggaaaaccta tgagggagca tctaaaattc   3840
gcaatgtctt actggcatac acttaaagca cagggactgg atatgtttgg aggcgatacg   3900
atggatcgag cctggaatag atacgatgat gccctagaac aagccaaagc tagagcagat   3960
gctggatttg agtttatgca aaagatcgga atggactatt tctgttttca cgaccgtgac   4020
attatcaatg aggctatgac tttgaaggaa acgaacagat tgttagatga aattgtggac   4080
cacttggaag gattgatgaa aaagactggt attaagttac tttggggcac tacaaatgcc   4140
ttttcacatc cgagatttct ccatggtggc gcaacagctc caaatgctga tgtgtttgca   4200
tatgctgcgg cacaagtcaa aaaggctatg gaaattacta agaggcttgg tggagagaat   4260
tacgtattat ggggtggtag agaaggctat gagactttgc taaataccaa gtctgactta   4320
gaatatgaca attttgcaag atttttgcaa atggttgttg actataagga aaagattgga   4380
ttcgaaggtc aactattgat agaaccaaaa cctaaagagc caaccaaaca tcaatatgac   4440
ttcgacactg caacagtact ggggttcttg aggaagtaca acctcgataa gcactataag   4500
atgaatatcg aagctaatca tgctacattg gccggtcata catttcaaca cgagcttaat   4560
ctcgcacgta ttaacaacgt tatgggttcg atagatgcaa accagggcga tatgttatta   4620
ggttgggata ctgatcaatt tcctaccaat atctacgatg ccgttctggc tatgtacgaa   4680
gttatcaaaa acaacggtct agggaaggga ggtttgaatt ttgatgcaaa agtccggagg   4740
ggaagtttcg aagataaaga tttgttttta gcgtatattg cgggaatgga tacattcgcc   4800
aaaggtttaa cgatagcata tagattgtac gaggataaag tgtttgaaga ttttcaagac   4860
aagagatatg aatcatataa gaccgggata gggaaagata ttgttgaggg caaagttggc   4920
tttgaggaat tagcagaata cgtggaaaac ttagctgaga tcaaaaatac cagcggtaga   4980
caggagatgt tagaatccat attgaacagt tacattcttg aagcaaagta attaattaac   5040
atctgaatgt aaaatgaaca ttaaaatgaa ttactaaact ttacgtctac tttacaatct   5100
ataaactttg tttaatcata taacgaaata cactaataca caatcctgta cgtatgtaat   5160
acttttatcc atcaaggatt gagaaaaaaa agtaatgatt ccctgggcca ttaaaactta   5220
gacccccaag cttggatagg tcactctcta ttttcgtttc tcccttccct gatagaaggg   5280
tgatatgtaa ttaagaataa tatataattt tataataaaa gaattcgccc ttacatatgg   5340
ataacttcgt ataatgtatg ctatacgaag ttatgctgca acggcaacat caatgtccac   5400
gtttacacac ctacatttat atctatattt atatttatat ttatttattt atgctactta   5460
gcttctatag ttagttaatg cactcacgat attcaaaatt gacacccttc aactactccc   5520
tactattgtc tactactgtc tactactcct ctttactata gctgctccca ataggctcca   5580
ccaataggct ctgtcaatac attttgcgcc gccacctttc aggttgtgtc actcctgaag   5640
gaccatattg ggtaatcgtg caatttctgg aagagagtgc cgcgagaagt gaggccccca   5700
ctgtaaatcc tcgagggggc atggagtatg gggcatgnag gatggaggat gggggggggg   5760
ggggaaaata ggtagcgaaa ggacccgcta tcaccccacc cggagaactc gttgccggga   5820
```

```
agtcatattt cgacactccg gggagtctat aaaaggcggg ttttgtcttt tgccagttga   5880
tgttgctgag aggacttgtt tgccgtttct tccgatttaa cagtatagaa tcaaccactg   5940
ttaattatac acgttatact aacacaacaa aaacaaaaac aacgacaaca acaacaacaa   6000
tgtttgcttt ctactttctc accgcatgca ccactttgaa gggtgttttc ggagtttctc   6060
cgagttacaa tggtcttggt ctcaccccac agatgggttg ggacagctgg aatacgtttg   6120
cctgcgatgt cagtgaacag ctacttctag acactgctga tagaatttct gacttggggc   6180
taaaggatat gggttacaag tatgtcatcc tagatgactg ttggtctagc ggcagggatt   6240
ccgacggttt cctcgttgca gacaagcaca aatttcccaa cggtatgggc catgttgcag   6300
accacctgca taataacagc tttcttttcg gtatgtattc gtctgctggt gagtacacct   6360
gtgctgggta ccctgggtct ctggggcgtg aggaagaaga tgctcaattc tttgcaaata   6420
accgcgttga ctacttgaag tatgataatt gttacaataa aggtcaattt ggtacaccag   6480
acgtttctta ccaccgttac aaggccatgt cagatgcttt gaataaaact ggtaggccta   6540
ttttctattc tctatgtaac tggggtcagg atttgacatt ttactggggc tctggtatcg   6600
ccaattcttg gagaatgagc ggagatatta ctgctgagtt cacccgtcca gatagcagat   6660
gtccctgtga cggtgacgaa tatgattgca agtacgccgg tttccattgt tctattatga   6720
atattcttaa caaggcagct ccaatggggc aaaatgcagg tgttggtggt tggaacgatc   6780
tggacaatct agaggtcgga gtcggtaatt tgggcc                              6816
```

<210> SEQ ID NO 87
<211> LENGTH: 1323
<212> TYPE: DNA
<213> ORGANISM: Sebaldella termitidis

<400> SEQUENCE: 87

```
atgaaagaat attttccgga aataaaagaa ataaagtatg aaggtcctga atcaaaaaat     60
gttatggctt tcaaatatta caataaagat gaggtaatag gcggaaaacc gatgagagaa    120
catctgaaat ttgcaatgag ttactggcat acattaaaag cccagggact ggatatgttc    180
ggcggggaca cgatggacag agcatggaac agatatgatg acgcattgga acaggcaaaa    240
gcaagagcag atgcaggttt tgaatttatg cagaaaatag ggatggatta tttctgcttt    300
catgacagag atattataaa tgaagcaatg acattaaaag aaacaaacag acttcttgat    360
gaaatagtag atcatctaga aggtcttatg aaaaaaacag gaataaaact tttgtgggga    420
acaacaaatg cttttagtca tcccagattt cttcacggag gagcaactgc accaaatgca    480
gacgtatttg cgtatgctgc ggcacaggta aaaaaggcaa tggagataac aaaaagatta    540
ggcggggaaa attatgttct ctggggcgga agagagggct acgaaactct tctgaatact    600
aagtctgatc tggaatatga taactttgcc agatttctgc agatggtagt ggattacaaa    660
gaaaaaatag ggtttgaagg gcagctgctt atagaaccga aaccaaaaga acctacaaag    720
caccagtatg attttgatac tgctacagtt cttggttttt tgagaaagta taatcttgat    780
aaacattata aaatgaatat agaagcaaac cacgccactc ttgccggaca tacattccag    840
catgaactga accttgcaag aataaataat gtaatgggtt ccatagatgc aaatcaggga    900
gatatgcttc tgggatggga tacagatcag tttcctacaa atatatatga tgctgttctg    960
gcaatgtatg aagtaataaa aaataacgga ttgggtaaag gtggactgaa ttttgacgca   1020
aaagtaagaa gaggctcatt tgaagacaag gatttatttt tagcttatat tgcgggtatg   1080
```

gacacattcg caaaaggatt aacaatagct tacagacttt atgaagataa agtttttgag 1140
gattttcagg ataaaagata tgaaagttac aaaacaggga taggaaaaga tatagtagaa 1200
ggtaaagtag gatttgaaga actggcggaa tatgtagaaa atcttgctga aataaaaaat 1260
acttcgggaa gacaggaaat gctggaaagt atattgaatt catatatatt ggaagcaaaa 1320
taa 1323

<210> SEQ ID NO 88
<211> LENGTH: 1323
<212> TYPE: DNA
<213> ORGANISM: Artificial Sequence
<220> FEATURE:
<223> OTHER INFORMATION: St XI codon optimized variant

<400> SEQUENCE: 88
atgaaggagt actttcccga gataaaggaa atcaaatatg aaggtccaga gagcaaaaac 60
gtaatggcct tcaaatacta taacaaggac gaggttattg gtggtaaacc aatgagggaa 120
cacttgaaat ttgcaatgtc ttattggcat actctcaagg cacagggatt agacatgttc 180
ggtggtgata ctatggacag agcttggaat agatatgatg atgcgttaga acaagcaaag 240
gcaagagccg atgctggttt tgagtttatg caaaagatag ggatggacta tttctgtttc 300
cacgataggg acattatcaa tgaagccatg acccttaaag agactaatcg tttactagat 360
gaaattgtcg accatttaga gggtctgatg aaaaagacag gtataaagtt gctctggggc 420
acgactaatg ctttctcaca tcctaggttt ctccatggcg gtgcaactgc cccaaacgcc 480
gatgtttttg catacgctgc tgcccaagtg aaaaaggcta tggaaattac aaaaagactg 540
ggcggcgaaa actatgtcct ttggggaggt cgtgaaggat atgaaacact attgaatacc 600
aagagtgatt tggaatatga caattttgct agattcttac aaatggttgt tgactataag 660
gaaaagattg ggtttgaagg acaattgtta atcgaaccaa aacctaagga gcctacaaaa 720
caccaatacg atttcgacac tgctacagtc ctaggatttt tgcgaaaata caacctagat 780
aagcactaca aaatgaatat tgaagcaaat catgcaactt tagcgggtca taccttccag 840
catgagttaa acttggctag aattaacaat gtcatgggtt cgatagatgc gaatcagggt 900
gatatgttgt tgggatggga tacggatcaa tttccgacta atatctatga cgcagtactt 960
gcaatgtatg aggtgattaa aaacaacggg ctgggtaagg gtggtttgaa ttttgatgct 1020
aaagtgagga gaggatcctt tgaagataag gatctatttc ttgcgtatat tgctgggatg 1080
gatacattcg caaaaggact taccatcgct tatagattat acgaagataa agttttcgaa 1140
gattttcaag ataaacggta tgagtcatac aaaacaggaa ttgggaagga tattgttgaa 1200
ggcaaagttg gctttgagga actagcagaa tacgttgaga atttggcaga aatcaaaaac 1260
acctctggta gacaggaaat gttagaatct attttgaata gttacatatt agaagcaaag 1320
tga 1323

<210> SEQ ID NO 89
<211> LENGTH: 1323
<212> TYPE: DNA
<213> ORGANISM: Artificial Sequence
<220> FEATURE:
<223> OTHER INFORMATION: St XI codon optimized variant

<400> SEQUENCE: 89
atgaaggaat acttccctga aatcaaagag atcaaatatg aaggtcctga atcgaaaaat 60
gttatggcat tcaagtatta caacaaggac gaggtcatag gaggaaaacc aatgagggaa 120

```
catcttaagt ttgccatgtc atattggcat acgctaaagg ctcaggggtt ggatatgttc    180

ggtggagata ctatggatcg tgcatggaac agatacgatg acgctttgga gcaagcgaaa    240

gccagagctg atgccggctt cgagtttatg caaaagattg gcatggacta tttttgtttt    300

catgatcgtg acattattaa cgaagctatg actttaaagg aaacgaatag gttattggat    360

gaaattgttg accatcttga gggtttgatg aaaaagactg ggatcaaatt gttgtggggt    420

actacaaatg cttttagtca cccaagattc ttacatggtg gtgctaccgc accgaatgcc    480

gacgtattcg catacgcggc agctcaagtt aaaaaggcta tggagattac caaacggttg    540

ggtggcgaaa actacgtatt atggggcgga agagaaggat atgaaacatt gctaaatacc    600

aaatccgatt tggaatatga caattttgca agatttctac aaatggttgt cgattacaag    660

gagaaaattg ggttcgaggg tcaactactc atagagccaa agccaaaaga gcctaccaaa    720

catcagtatg atttcgatac tgcaacagtt ttaggctttt tgaggaagta caatttggac    780

aagcattaca agatgaatat cgaagcaaac cacgccactt tagctggtca cacatttcaa    840

cacgaactga acttagcacg tattaacaat gtcatgggtt ctattgatgc taatcaagga    900

gatatgttac tcggttggga tacagatcag tttcccacaa atatctacga cgctgttcta    960

gcgatgtatg aagttatcaa aaacaatggc ctcgggaagg gtggtcttaa ttttgatgca   1020

aaagttcgaa ggggttcatt tgaagataag gacctatttc ttgcatacat agccggaatg   1080

gataccttt g caaaaggttt aaccatagca tatagactgt atgaggataa agtgtttgaa   1140

gatttccaag acaagagata tgaaagctat aagacgggta taggcaaaga tattgttgag   1200

ggaaaagtcg gattcgagga actggctgaa tatgtggaaa accttgcaga aatcaaaaat   1260

actagtggta gacaggagat gcttgaatct attttgaact cctatatatt agaagccaag   1320

taa                                                                 1323
```

<210> SEQ ID NO 90
<211> LENGTH: 1323
<212> TYPE: DNA
<213> ORGANISM: Artificial Sequence
<220> FEATURE:
<223> OTHER INFORMATION: St XI codon optimized variant

<400> SEQUENCE: 90

```
atgaaggaat acttccccga aatcaaagag atcaaatatg aaggtccaga gtccaaaaat     60

gtcatggcat tcaagtacta taacaaggat gaagtcattg gtggaaaacc tatgagggag    120

catctaaaat tcgcaatgtc ttactggcat acacttaaag cacagggact ggatatgttt    180

ggaggcgata cgatggatcg agcctggaat agatacgatg atgccctaga acaagccaaa    240

gctagagcag atgctggatt tgagtttatg caaaagatcg gaatggacta tttctgtttt    300

cacgaccgtg acattatcaa tgaggctatg actttgaagg aaacgaacag attgttagat    360

gaaattgtgg accacttgga aggattgatg aaaaagactg gtattaagtt actttggggc    420

actacaaatg ccttttcaca tccgagattt ctccatggtg gcgcaacagc tccaaatgct    480

gatgtgtttg catatgctgc ggcacaagtc aaaaaggcta tggaaattac taagaggctt    540

ggtggagaga attacgtatt atggggtggt agagaaggct atgagacttt gctaaatacc    600

aagtctgact tagaatatga caattttgca agatttttgc aaatggttgt tgactataag    660

gaaaagattg gattcgaagg tcaactattg atagaaccaa aacctaaaga gccaaccaaa    720

catcaatatg acttcgacac tgcaacagta ctggggttct tgaggaagta caacctcgat    780
```

```
aagcactata agatgaatat cgaagctaat catgctacat tggccggtca tacatttcaa    840

cacgagctta atctcgcacg tattaacaac gttatgggtt cgatagatgc aaaccagggc    900

gatatgttat taggttggga tactgatcaa tttcctacca atatctacga tgccgttctg    960

gctatgtacg aagttatcaa aaacaacggt ctagggaagg gaggtttgaa ttttgatgca   1020

aaagtccgga ggggaagttt cgaagataaa gatttgtttt tagcgtatat tgcgggaatg   1080

gatacattcg ccaaaggttt aacgatagca tatagattgt acgaggataa agtgtttgaa   1140

gattttcaag acaagagata tgaatcatat aagaccggga tagggaaaga tattgttgag   1200

ggcaaagttg gctttgagga attagcagaa tacgtggaaa acttagctga gatcaaaaat   1260

accagcggta gacaggagat gttagaatcc atattgaaca gttacattct tgaagcaaag   1320

taa                                                                 1323
```

<210> SEQ ID NO 91
<211> LENGTH: 1323
<212> TYPE: DNA
<213> ORGANISM: Artificial Sequence
<220> FEATURE:
<223> OTHER INFORMATION: St XI codon optimized variant

<400> SEQUENCE: 91

```
atgaaagagt atttccctga gattaaggaa atcaaatatg aaggtccaga aagcaaaaat     60

gttatggcat tcaagtacta caataaggac gaggttattg ggggcaaacc tatgagagaa    120

catcttaagt ttgcaatgtc ttactggcac acgttgaaag cacaaggttt agatatgttt    180

ggtggagaca caatggatag agcttggaat agatacgacg atgcattgga gcaagcgaaa    240

gcccgtgcag atgcgggttt cgagtttatg cagaaaattg gcatggacta cttctgtttc    300

catgatcgtg atattattaa cgaagctatg acacttaagg agacaaatag attactagac    360

gaaatagttg atcatttgga gggtttgatg aaaaagactg ggatcaaact tctatggggt    420

acaactaatg cttttagtca tccaagattc ttacacggtg gagctacagc cccaaacgct    480

gacgtatttg catacgccgc tgcgcaagtc aaaaaggcta tggagattac caaaagattg    540

ggtggagaaa attatgtgct gtggggtggt cgagaaggtt atgaaacatt gctcaatacc    600

aagtccgacc tggaatatga taactttgca aggtttcttc aaatggttgt tgattacaag    660

gagaaaatag gttttgaagg ccaattgcta attgaaccaa aacccaagga accgacaaaa    720

catcaatatg attttgatac tgccactgtt ttgggtttct tgcggaagta taacttggat    780

aagcactata agatgaatat tgaagccaac catgcaaccc ttgccggcca cacctttcaa    840

catgaattga atctagctag gattaacaac gttatgggct caatagacgc taatcaggga    900

gatatgttat taggttggga taccgatcag tttcctacta atatctatga tgcagtgttg    960

gctatgtatg aagtgatcaa aaacaatggt ctagggaagg gtggtctgaa ttttgatgca   1020

aaagtccgta ggggatcatt tgaggacaaa gatttgttcc tcgcctacat tgctggaatg   1080

gatacttttg caaaggggtt aacgatagct tatcgattat acgaggacaa ggtctttgaa   1140

gatttccagg ataagagata tgaatcctac aaaactggta tcggaaaaga tatagtagaa   1200

ggaaaagttg gctttgagga attagcagaa tatgttgaga acttagcaga aatcaaaaat   1260

acctcaggga gacaagagat gttagaatct attctcaact cgtatatctt ggaagcaaag   1320

taa                                                                 1323
```

<210> SEQ ID NO 92
<211> LENGTH: 1323

<212> TYPE: DNA
<213> ORGANISM: Artificial Sequence
<220> FEATURE:
<223> OTHER INFORMATION: St XI codon optimized variant

<400> SEQUENCE: 92

```
atgaaagagt attttcctga aatcaaggaa atcaaatatg aaggtcccga gtccaaaaat      60

gttatggcat tcaaatacta caacaaggac gaagttatag gtggcaaacc aatgagagaa     120

catttgaaat ttgcgatgtc ttattggcac accttaaaag cacagggcct agacatgttc     180

ggcggggata caatggatag agcatggaat cgatatgatg atgcattgga acaagccaaa     240

gctagggcag atgctggttt cgagtttatg caaaagattg gaatggatta cttctgtttt     300

catgatcgtg acatcattaa cgaagcaatg actttgaagg aaaccaatag gttattggat     360

gaaatagtag atcacttaga aggtcttatg aaaaagactg gtattaagct gttatggggt     420

acaactaatg cctttagtca cccaagattt cttcatgggg gagcaaccgc acctaatgct     480

gatgttttcg cttatgctgc tgcccaagtc aaaaaggcta tggaaattac aaaaagacta     540

ggtggagaga actatgtttt gtggggggc agagagggtt atgaaacact tctgaatact      600

aagtctgatt tggaatatga caattttgca agatttttgc aaatggttgt ggactataag     660

gaaaagatcg gtttcgaggg ccagctactc atagaaccaa aaccaaagga gccgacgaaa     720

catcagtacg atttcgatac agccactgta ttgggttttc tgaggaagta taacctcgac     780

aaacactaca agatgaatat tgaagctaat catgctacac tagcgggtca tacgtttcaa     840

catgagttaa acttagcacg tattaacaat gtcatgggca gtatagatgc aaaccaagga     900

gacatgttgt tgggttggga cacagatcag ttccctacta atatctatga tgctgtatta     960

gctatgtacg aagtcatcaa aaacaatggt ttggggaaag gagggttaaa ctttgatgca    1020

aaagttcgga gaggatcatt tgaagataag gatctcttct tggcctacat tgcgggaatg    1080

gacacttttg ccaagggtct aacaatagca tataggttat atgaggataa ggtttttcgag   1140

gactttcaag ataagagata cgaatcgtac aaaaccggta ttggcaaaga tattgtggaa    1200

ggaaaagtcg gttttgagga acttgctgaa tatgtggaaa accttgcaga gatcaaaaat    1260

accagcggta gacaagagat gttagaatca attctaaatt cttacattct cgaagcaaag    1320

taa                                                                  1323
```

<210> SEQ ID NO 93
<211> LENGTH: 1323
<212> TYPE: DNA
<213> ORGANISM: Leptotrichia goodfellowii

<400> SEQUENCE: 93

```
atgaaagagt tttttcctga aataaaagaa ataaaatatg aaggggctga atcaaaaaat      60

gatttggcat ttaaatacta caataaagat gaagtattag gcggaaaaac aatgaaagag     120

catttgagat ttgcaatgag ttactggcat acattgaaag ctcagggagt ggacatgttc     180

ggcggagaaa caatggacag agagtggaat aaatatgaaa atgtattgga aagagcaaaa     240

gcaagagcaa atgcaggatt tgaatttatg cagaaactcg gtttggaata tttctgtttc     300

catgacagag atataataga tgaaagtatg atgctcgcag acagtaacaa acttcttgat     360

gaaatagtag atcacataga agaacttatg aaaaaaacag ggagaaaatt attatggggg     420

acaactaatg ctttcagtca tccgagattt gttcatggag cttctacttc tcccaatgct     480

gatgtatttg cgtatgctgc agctcaagta aagaaagcta tggacataac taacagatta     540
```

```
ggcggagaaa attacgtatt atggggagga agagaaggat atgaaacatt actgaatact    600
aactctgaat tggaatatga taattttgca agatttttga aaatggtagt agattataaa    660
gaaaaaatag gatttaaagg gcaacttctt atagagccta aaccgaaaga acctacaaaa    720
catcaatatg actttgatac tgctacagtt ttggcatttt taagaaaata taatcttgat    780
aaatattata aagtaaatat agaggcaaac catgcaactt tagcaggaca tacattccaa    840
catgagttaa atctggcgag aataaacggt gttttaggct cgatagatgc caatcaggga    900
gatatgcttt taggatggga tacagatcaa ttcccgacaa atatatatga tacgacttta    960
gcaatgtatg aagtagttaa aaataaagga ctcggttcag gaggacttaa ttttgatgca   1020
aaagtaagaa gaggttcttt tgaggataaa gatttattct tagcttatat cgcaggaatg   1080
gatacttttg ccaaaggact caaaatagca tatagattat atgaagataa agtatttgaa   1140
gattttattg ataaaagata cgaaagctat aaaacaggta tcggaaaaga tataattgat   1200
ggaaaagtgg gatttgaaga actgtccaaa tatgccgaaa ctttaacaga agtaaaaaat   1260
aattcaggta gacaggaaat gctggaaagt aagttgaatc agtatatatt tgaggtgaaa   1320
tag                                                                  1323
```

<210> SEQ ID NO 94
<211> LENGTH: 1323
<212> TYPE: DNA
<213> ORGANISM: Artificial Sequence
<220> FEATURE:
<223> OTHER INFORMATION: Lg XI codon optimized variant

<400> SEQUENCE: 94

```
atgaaggagt tttccccga aatcaaagag atcaaatacg aaggcgccga atccaaaaat       60
gatctagcgt tcaaatacta taacaaggat gaagtccttg gtggcaaaac tatgaaagag    120
catctgaggt ttgcaatgtc gtattggcat acgttaaaag ctcaaggagt tgatatgttt    180
ggcggagaaa ctatggatag agaatggaac aaatatgaaa atgttttaga aagggcaaaa    240
gcacgggcca atgccggatt cgagttcatg cagaaacttg gattagagta tttctgtttt    300
catgaccgag acataattga tgagtctatg atgttagcgg atagtaacaa gttacttgac    360
gaaatagtag atcatattga agagttgatg aaaaagaccg ggagaaagtt actctggggt    420
accacgaatg ccttttcgca cccgagattt gttcatggtg catcaacttc tccaaacgca    480
gatgtatttg catatgccgc tgcacaagtc aaaaaggcca tggatattac aaatcgtttg    540
ggtggtgaaa actatgtgtt gtggggtggt agagaaggct atgaaacctt attgaacact    600
aactctgaac ttgaatacga caattttgct agattcctga agatggtggt cgactataag    660
gagaagattg gttttaaggg ccaactgtta atcgaaccaa agcctaagga accaactaag    720
catcagtacg attttgatac tgctactgtg ttagctttct tgagaaaata caatttggat    780
aagtactata aagttaacat tgaagcaaat catgctacgc tcgcgggcca cacatttcaa    840
cacgagctaa atctagctag gatcaatggt gtacttggta gtattgatgc gaatcaaggg    900
gatatgttgc ttggttggga tacagatcag ttccctacaa atatctatga cactacatta    960
gctatgtacg aagttgtcaa aaacaaagga ttgggttcag gggattgaa ctttgatgcc   1020
aaagttcgta gaggttcttt tgaggacaaa gatctattct tggcatatat tgctggaatg   1080
gacacatttg caaaaggtct aaagattgca tataggttat atgaggataa ggtttttgaa   1140
gatttcattg ataagagata cgaatcatat aagaccggta tcggaaaaga cattatagat   1200
gggaaagttg ggttcgagga attgtccaaa tatgctgaaa cattgaccga agtgaaaaac   1260
```

aatagcggta gacaagagat gttggaatcc aagctcaatc agtacatatt tgaagttaag 1320
taa 1323

<210> SEQ ID NO 95
<211> LENGTH: 1331
<212> TYPE: DNA
<213> ORGANISM: Artificial Sequence
<220> FEATURE:
<223> OTHER INFORMATION: Lg XI codon optimized variant

<400> SEQUENCE: 95
atgaaagagt tctttcccga aatcaaggaa atcaaatatg aaggcgcaga atcgaaaaat 60
gatttggctt tcaaatacta taacaaggat gaagtcttgg ggggaaagac tatgaaggag 120
catctaagat tcgccatgtc atattggcat accttaaaag ctcagggtgt tgatatgttc 180
ggtggcgaaa cgatggatag agaatggaac aaatacgaaa atgtgcttga aagggcaaaa 240
gccagagcca atgccgggtt tgagtttatg caaaaattgg gtttagaata cttttgtttc 300
cacgatcgag acattatcga tgagtctatg atgctagcag attctaacaa gttgctcgat 360
gagatagtcg atcatataga ggagttgatg aaaaagaccg gaaggaaatt gttatggggt 420
acaaccaacg cattttccca cccacgtttt gtacatggag caagcacctc accaaatgct 480
gatgtattcg cgtatgcagc agcacaagtc aaaaaggcca tggacattac taatagacta 540
ggaggagaaa actatgtttt atggggggt agagaaggtt acgaaactct tctaaacaca 600
aattctgaac ttgaatatga caattttgca agatttttga agatggttgt tgactacaag 660
gaaaagattg gttttaaggg ccaattgctt attgaaccta aaccaaaaga gcctacaaaa 720
catcaatatg attttgacac agcaactgtt ttggcattct taaggaagta taatctggac 780
aagtattaca aggttaacat cgaagccaat catgctactc ttgcgggtca tacattccaa 840
cacgagttaa acttagctag gattaatggg gtattaggca gtatagatgc taatcaggga 900
gatatgttat taggttggga caccgatcaa ttcccgacta atatctatga tacgactctg 960
gctatgtatg aggttgtgaa aaataagggt ctgggttccg gcggtctaaa tttcgatgct 1020
aaagttcgga gaggttcatt tgaggataag gacctatttc tggcatatat cgctgggatg 1080
gatacattcg cgaagggttt gaagattgca tatcgtttgt atgaagataa ggtctttgaa 1140
gatttcatag acaaaagata tgaaagttac aaaactggaa ttggaaaaga cataattgac 1200
ggaaaagtcg gttttgagga actctcaaaa tacgcagaga cattgaccga agtgaaaaac 1260
aactctggta gacaagagat gttggaatcg aaactcaacc agtacatttt tgaagttaaa 1320
tgattaatta a 1331

<210> SEQ ID NO 96
<211> LENGTH: 1331
<212> TYPE: DNA
<213> ORGANISM: Artificial Sequence
<220> FEATURE:
<223> OTHER INFORMATION: Lg XI codon optimized variant

<400> SEQUENCE: 96
atgaaggagt tttcccgga aatcaaagag attaagtatg aaggagccga atcgaaaaat 60
gacttagcct tcaagtatta caataaggac gaagttcttg gtggcaaaac tatgaaagag 120
catttgaggt ttgccatgtc ttattggcat accttaaaag ctcaaggagt agatatgttt 180
ggtggagaaa ccatggatag agaatggaac aaatatgaga atgtattgga gagagctaaa 240

```
gccagagcaa acgctggttt tgaattcatg cagaaattgg gtttagaata cttttgtttt    300
catgatcggg atataattga tgaatcgatg atgctggcgg atagcaataa gctattggac    360
gaaatagtgg accatataga ggagttgatg aaaaagacag gtcgtaaact attatggggc    420
actacgaatg cttttagtca tccaagattt gttcacggtg catctacatc accaaatgca    480
gatgtctttg catacgcagc agcacaagtc aaaaaggcta tggatattac gaatagattg    540
ggtggagaaa actatgtctt atggggtggt agagaaggtt acgagacttt acttaacacc    600
aacagtgaac ttgaatatga caattttgca aggttcttga aatggtagt ggactacaag     660
gagaaaatag gctttaaagg acaactccta atcgaaccta aacccaagga accaactaag    720
caccaatatg attttgatac tgcgacagtt ttagcattct tgaggaagta taatctcgat    780
aagtactaca aagttaacat cgaagcaaac catgcaactc tggctggtca taccttccaa    840
cacgaattga acctcgccag gattaatggg gttttaggct caatagatgc gaatcagggc    900
gatatgctac taggttggga tacagatcaa ttccctacaa atatctatga caccactttg    960
gctatgtatg aggttgttaa aaacaagggt ttgggctctg gaggtcttaa ctttgatgct   1020
aaagttcgac gtggttcatt cgaagataag gacttatttc tggcctacat tgctggaatg   1080
gatacgtttg caaagggatt gaaaattgca tatagactat atgaagataa ggtctttgaa   1140
gatttcattg acaaaagata cgaatcttat aagactggta ttgggaagga tatcattgat   1200
gggaaagtcg gattcgaaga gttatccaaa tatgctgaga cattaacaga agtgaaaaac   1260
aattcaggga gacaagagat gcttgaatcc aagctaaatc agtacatctt tgaagttaaa   1320
tgattaatta a                                                        1331
```

<210> SEQ ID NO 97
<211> LENGTH: 1331
<212> TYPE: DNA
<213> ORGANISM: Artificial Sequence
<220> FEATURE:
<223> OTHER INFORMATION: Lg XI codon optimized variant

<400> SEQUENCE: 97

```
atgaaggagt tcttcccgga aatcaaagag atcaaatatg aaggagccga gagcaaaaat     60
gatttggcat tcaagtacta taacaaggat gaagttctag gtggaaagac catgaaggaa    120
catttgaggt ttgccatgag ttattggcat acccttaaag cacaaggcgt tgatatgttt    180
ggtggagaaa caatggatag agaatggaac aaatatgaaa atgttttaga aagggcgaaa    240
gctagagcaa acgctggctt tgaattcatg cagaaattag gattagagta cttttgtttc    300
catgatcgtg atattattga tgaatcaatg atgctagcag actctaataa gttattagat    360
gaaattgtgg atcacatcga ggagttgatg aaaaagacag gcagaaaatt gttgtggggg    420
acaactaatg cgttttccca tccacgtttc gtgcatggtg cttcgacctc cccaaacgct    480
gacgtgtttg cctacgctgc tgctcaagtc aaaaaggcta tggatataac taatagattg    540
ggtggagaaa actatgtcct ttggggagga agagaaggtt atgaaacatt attgaatacc    600
aattcggaac tcgaatatga taactttgca agatttctga agatggttgt tgactataag    660
gagaaaattg gttttaaggg tcaacttcta attgaaccca aaccaaaaga gcctacaaaa    720
catcagtatg atttcgacac tgcaactgtt ttagcatttc tacgaaagta taatcttgac    780
aagtattaca aagttaacat tgaagctaat catgcaactt tagccggtca cacatttcaa    840
cacgagttaa acttggccag aatcaatggc gtattaggtt caatagacgc caatcaaggg    900
gatatgttgc tgggttggga cacggatcaa tttcctacga atatctacga taccacttta    960
```

```
gctatgtacg aagtagtgaa aaacaagggt cttggttctg gtggactcaa tttcgacgca   1020

aaagttcgga ggggaagttt tgaagataag gaccttttct tggcgtatat agcggggatg   1080

gatacatttg caaagggttt aaagattgca tataggttat atgaagataa agtatttgaa   1140

gatttcattg acaagagata cgaaagttac aaaactggta ttgggaaaga cataattgat   1200

ggcaaagttg gctttgagga attgtctaaa tatgcagaga cattgactga agtcaaaaac   1260

aattcaggga gacaagagat gctcgaatct aagctgaatc agtacatatt cgaggtcaaa   1320

tgattaatta a                                                        1331
```

<210> SEQ ID NO 98
<211> LENGTH: 1331
<212> TYPE: DNA
<213> ORGANISM: Artificial Sequence
<220> FEATURE:
<223> OTHER INFORMATION: Lg XI codon optimized variant

<400> SEQUENCE: 98

```
atgaaggagt tctttcctga aatcaaagag atcaaatatg agggtgcaga aagcaaaaat     60

gacctggctt ttaagtatta caacaaggat gaagtattgg gtggcaaaac tatgaaggaa    120

cacttaagat ttgctatgtc gtattggcat acgttgaagg cacaaggagt tgatatgttt    180

gggggcgaaa ccatggatag agaatggaac aaatatgaga atgttttaga aagggcaaaa    240

gccagagcta atgcaggctt tgagtttatg caaaagttgg gccttgaata cttctgtttt    300

catgatcgag acattattga cgagtctatg atgctagctg acagtaataa gcttttagat    360

gagattgttg atcatattga ggagttgatg aaaaagacag gaaggaagct tttgtggggg    420

actacaaatg cattctccca tccacgtttt gttcacggtg cctcaacatc acccaacgcc    480

gatgtattcg cgtacgctgc ggcgcaagtt aaaaaggcca tggatattac gaatagatta    540

ggtggagaaa actatgttct atggggtgga agagaaggat atgaaacctt acttaatact    600

aattctgaac tagaatatga caattttgca agatttctga aaatggtcgt ggactacaaa    660

gagaagatag gttttaaggg acaactgttg atagaaccaa aaccgaagga accaactaag    720

catcaatatg attttgatac tgcaactgtt ttggcattct taaggaagta taacttggac    780

aagtactaca aagttaacat tgaggctaat catgctacat tagctggtca taccttccaa    840

cacgaactca acctcgctag aatcaatggt gtactaggtt ctatcgatgc aaaccagggc    900

gatatgttat tgggttggga tacagatcaa tttcctacaa atatctatga tactaccctt    960

gctatgtacg aggttgtcaa aaacaaggga ttaggaagtg gtggtctaaa ctttgatgct   1020

aaagtccgga gaggttcatt cgaagataag gacttgttct tggcatacat agccgggatg   1080

gataccttg ccaagggttt gaaaattgca tataggctct atgaagataa agttttcgag    1140

gactttattg ataagcgtta tgaatcctac aaaacgggta ttggaaaaga cataatagat   1200

gggaaagtcg gttttgagga actttccaaa tacgctgaga cactaactga agtgaaaaac   1260

aattcaggca gacaggaaat gttagaatct aaacttaatc agtacatttt cgaagtgaaa   1320

tgattaatta a                                                        1331
```

<210> SEQ ID NO 99
<211> LENGTH: 1131
<212> TYPE: DNA
<213> ORGANISM: Issatchenkia orientalis

<400> SEQUENCE: 99

```
atgtttgcat caaccttcag aagtcaagct gtaagagctg caagatttac tagattccaa     60

tccacttttg ccattcctga gaagcaaatg ggtgttatct ttgaaactca tggtggtcct    120

ttacaataca aggaaattcc agttccaaaa ccaaaaccaa ctgaaatttt aatcaatgtt    180

aaatactctg gtgtctgcca taccgattta cacgcatgga aaggtgactg gccattacca    240

gcaaagttac ccctagttgg tggtcacgaa ggtgcgggca ttgttgttgc gaaaggttct    300

gcagttacca actttgagat tggcgattat gctggtatta agtggttaaa cggttcatgt    360

atgtcatgtg aattctgtga acaaggtgat gaatctaact gtgaacatgc cgatttgagt    420

ggttatactc atgatggttc tttccaacaa tatgccactg ctgacgctat tcaagctgca    480

aagatcccaa agggtaccga cttatctgaa gttgcgccaa ttttatgtgc tggtgttact    540

gtctataaag ctttgaaaac tgctgattta agagcaggtc aatgggttgc gatttctggt    600

gccgctggtg gtctaggttc tcttgctgtc caatatgcaa aggcaatggg tctaagagtt    660

ttaggtatcg atggtggtga aggtaaaaag gaactttttg aacaatgtgg tggtgatgtg    720

tttatcgatt tcaccagata cccaagagat gcacctgaaa agatggttgc tgatattaag    780

gctgcaacta acggtttggg tccacacggt gttatcaatg tctctgtctc cccagctgct    840

atctctcaat catgtgacta tgttagagca actggtaagg ttgtccttgt cggtatgcca    900

tctggtgctg tctgtaagtc tgatgtcttc actcatgttg ttaaatcctt acaaattaaa    960

ggttcttatg ttggtaacag agcagatacc agagaagctt tggaattctt taatgaaggt   1020

aaggtcagat ctccaatcaa ggttgtccca ttatctactt tacctgaaat ttacgaattg   1080

atggagcaag gtaagatttt aggtagatac gttgttgata cttctaaata a            1131
```

<210> SEQ ID NO 100
<211> LENGTH: 1134
<212> TYPE: DNA
<213> ORGANISM: Issatchenkia orientalis

<400> SEQUENCE: 100

```
atgttatcca agaccatcac tgctgcattg aggggcaata caactcgtac tgcattcaga     60

atcaatgcca ttagaagttt agcgatccca gctattccag agacacaaaa gggtgttatc    120

ttttatgaga acggaggtga actattttac aaggacattc cagttccaaa gccaaagcca    180

aatgagattt tggtgaatgt caagtattct ggtgtttgtc ataccgattt acacgcatgg    240

aaaggtgact ggcctttggc gaccaagttg ccattggttg gtggacatga aggtgccgga    300

gttgttgttg ctaaggggga caatgtcacc aactttgaaa ttggcgatta tgccggtatc    360

aagtggttga atggttcatg tatggggtgt gaattttgcc aacaaggtgc agagccaaac    420

tgtccacagg ccgacttgag tggttacacc catgacgggt cctttcaaca atatgccact    480

gccgatgctg ttcaggcagc caagattcct cagggcactg atttggctca agttgcgcca    540

attttatgtg caggtattac tgtctataag gctttaaaga ctgcagaatt aagaccaggt    600

caatgggttg ccatttctgg tgctgctgga ggtttaggtt ctcttgctgt tcaatatgcc    660

aaggccatgg gtttgagagt tttgggtatt gatggtggtg aggagaaggg caagtttgca    720

aagtctcttg gagctgaagt tttcattgat ttcaccaaat ccaaggacat tgtcaaggat    780

atccaagagg ccaccaatgg tggtccacat ggtgtcatta atgtttctgt ttctccagct    840

gctatttctc aaagtaccca gtatgtcaga accttgggta aggttgtcct tgttggatta    900

ccagcgcatg ctgtatgcga gtcttcggtt ttcgaccatg ttgtcaagtc gattcaaatt    960

agaggctctt atgttggtaa cagggaagat actagtgagg ctattgattt tttcaccagg   1020
```

-continued

```
ggtttagtga agtcaccaat taagattgtt ggtttgagtg agttgccaaa gatctatgaa   1080

ttgatggagc aaggtaagat tttaggcaga tatgttgttg acacttcgaa atga         1134
```

XYLOSE ISOMERASE-MODIFIED YEAST STRAINS AND METHODS FOR BIOPRODUCT PRODUCTION

CROSS-REFERENCE TO RELATED APPLICATIONS

This application is a national phase application of international application PCT/US2016/045579, filed Aug. 4, 2016, and entitled XYLOSE ISOMERASE-MODIFIED YEAST STRAINS AND METHODS FOR BIOPRODUCT PRODUCTION, which claims the benefit of U.S. Provisional Patent Application Ser. No. 62/201,477, filed on Aug. 5, 2015, entitled XYLOSE ISOMERASE-MODIFIED YEAST STRAINS AND METHODS FOR BIOPRODUCT PRODUCTION, both of which applications are hereby incorporated by reference herein in their entirety.

SEQUENCE LISTING

The entire contents of the ASCII text file entitled "N00288_ST25.txt," created on Feb. 5, 2018, and having a size of 520 kilobytes is incorporated herein by reference in its entirety.

FIELD OF THE INVENTION

The current invention relates to genetically modified yeast having a heterologous xylose isomerase gene, and fermentations methods using xylose for producing a bioproduct, such as ethanol.

BACKGROUND

Ethanol production by fermentation is a well know industrial process. However increasing ethanol yields can be technically difficult. There are various factors that make it challenging for microorganisms to grow in fermentation conditions designed for increased ethanol production. For example, the fermentation media may have higher substrate concentrations to promote ethanol production, but these conditions can have a negative impact on cell growth. Also, increased ethanol concentration and accumulation of undesirable byproducts can also be detrimental to cell health.

In addition to the genetic profile of the fermentation microorganism, the components of the fermentation media can have a significant impact on ethanol production. In fermentation processes, a carbohydrate or carbohydrate mixture is present in the media. Starch is a material that can be used as an energy source in a fermentation process, and it is available from a wide variety of plant sources such as corn, wheat, rice, barley, and the like. However, there is great demand for these types of plant sources in the food industry.

Lignocellulosics can provide an alternative source of carbohydrates for a fermentation process, and therefore can reduce the reliance on starch-generating plant sources. Components of lignocellulosics include cellulose, hemicellulose, and lignin, and the amount of these components can vary from one plant species to another. In a fermentation medium, cellulose and/or hemicellulose can be subjected to hydrolysis, such as acid hydrolysis, enzymatic hydrolysis, or combinations thereof to provide monomeric sugars for consumption by the organism. The hydrolysis products can include D-xylose, which can be consumed by the yeast and, converted into a five carbon phosphate intermediate, and then introduced into the pentose phosphate pathway to provide intermediates for the production of a bioproduct.

As compared to starch-based materials, the use of lignocellulosic materials for fermentation by yeast has generally been less preferred, due to issues such as decreased product yield and productivity when lignocellulosic substrates are used. Various molecular techniques have been attempted in yeast to improve consumption of lignocellulosic degradation products, but these approaches have yielded varying degrees of success.

SUMMARY OF THE INVENTION

The invention relates to fermentation methods using a fermentation media that includes xylose, engineered yeast expressing a heterologous xylose isomerase, methods for bioproduct production using the engineered yeast, and bioproduct compositions obtained from the fermentation methods of the invention.

In one embodiment, the invention provides a fermentation method that includes steps of (a) providing a fermentation medium comprising a carbohydrate composition comprising xylose; and (b) fermenting the fermentation media using a genetically engineered yeast, which is preferably Crabtree negative, the yeast comprising a heterologous nucleic acid encoding a xylose isomerase having an amino acid sequence having 70% or greater identity to SEQ ID NO:29 (St XI) or SEQ ID NO:33 (Lg XI), wherein the engineered yeast produce at least 10 g/L of a bioproduct in a fermented medium. The engineered yeast may further include a heterologous nucleic acid encoding a transaldolase, and one or more heterologous genetic modification(s) selected from the group consisting of (a) a nucleic acid encoding a xylulokinase, (b) attenuation or elimination of xylose reductase expression, and (c) a nucleic acid encoding a transaldolase.

In another embodiment the invention provides a genetically engineered yeast, preferably Crabtree negative, comprising an heterologous nucleic acid encoding a xylose isomerase having an amino acid sequence having 70% or greater identity to SEQ ID NO:29 (St XI) or SEQ ID NO:33 (Lg XI).

The engineered yeast strain expresses the heterologous xylose isomerase and is able to produce high levels of a bioproduct, such as ethanol, in a fermentation medium. Further, use of the engineered yeast of the disclosure is advantageous when the concentrations of acetic acid are about 20 g/L or greater in the fermentation medium.

Accordingly, in another embodiment, the invention also provides a method for reducing glycerol production by an engineered yeast in a fermentation process, comprising fermenting a liquid media comprising xylose, using an engineered yeast comprising an heterologous nucleic acid encoding a xylose isomerase having an amino acid sequence having 70% or greater identity to SEQ ID NO:29 (St XI) or SEQ ID NO:33 (Lg XI). Further, in another embodiment, the invention also provides a method for fermenting an engineered yeast in a fermentation process, comprising fermenting a liquid media comprising a xylose and an acetate concentration of 20 g/L or greater using an engineered yeast comprising an heterologous nucleic acid encoding a xylose isomerase having an amino acid sequence having 70% or greater identity to SEQ ID NO:29 (St XI) or SEQ ID NO:33 (Lg XI).

Figure 1A:
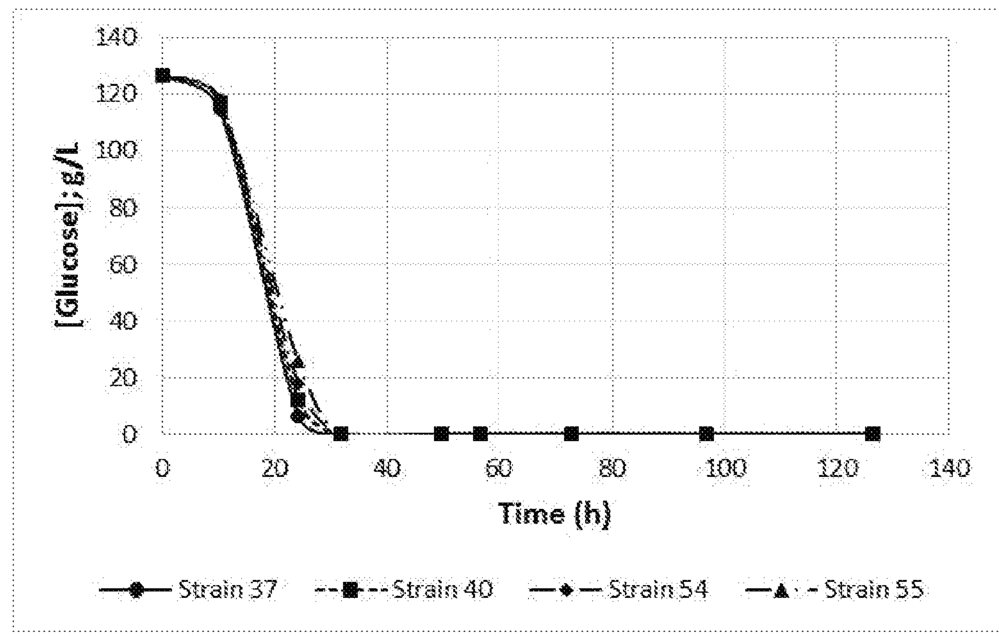
FIGS. 1A-1D are graphs showing metabolite concentrations in mixed sugar acetate medium shake flask experiments of Example 11. The solid lines with circles (●)
Figure 1B:
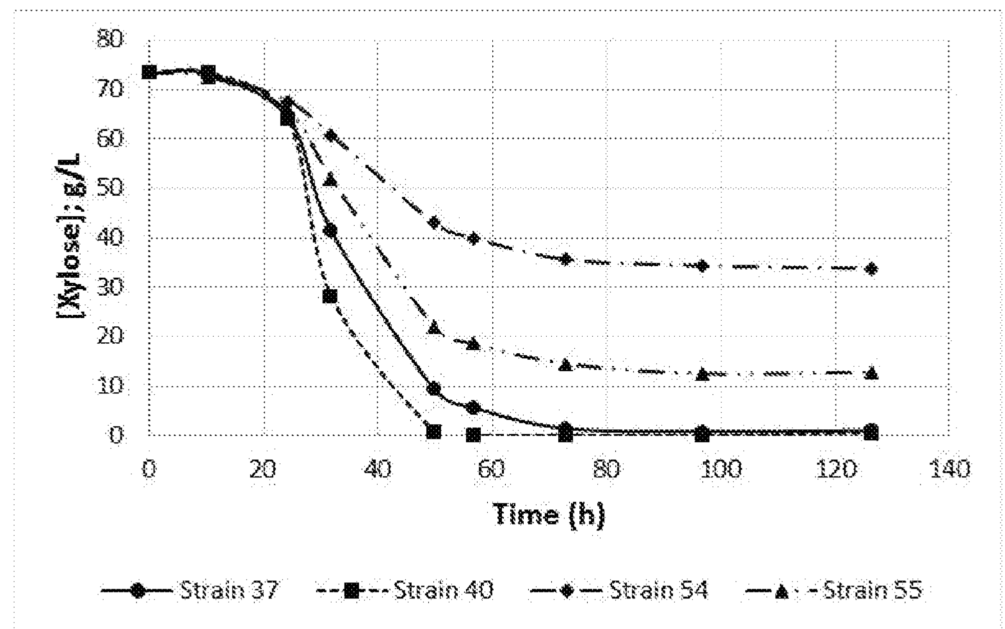
Figure 1C:
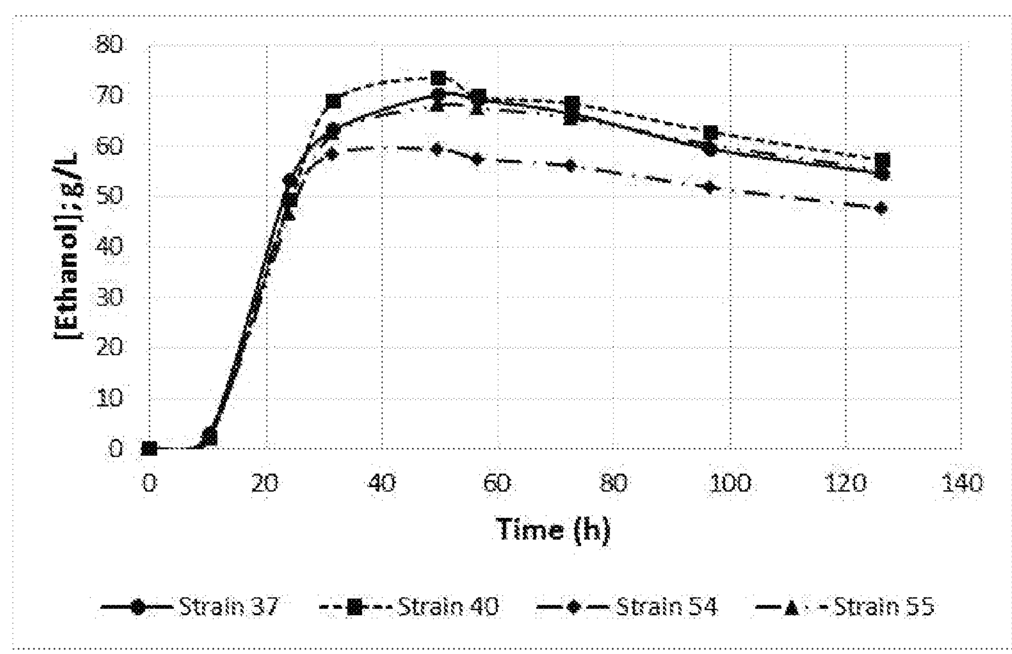
Figure 1D:
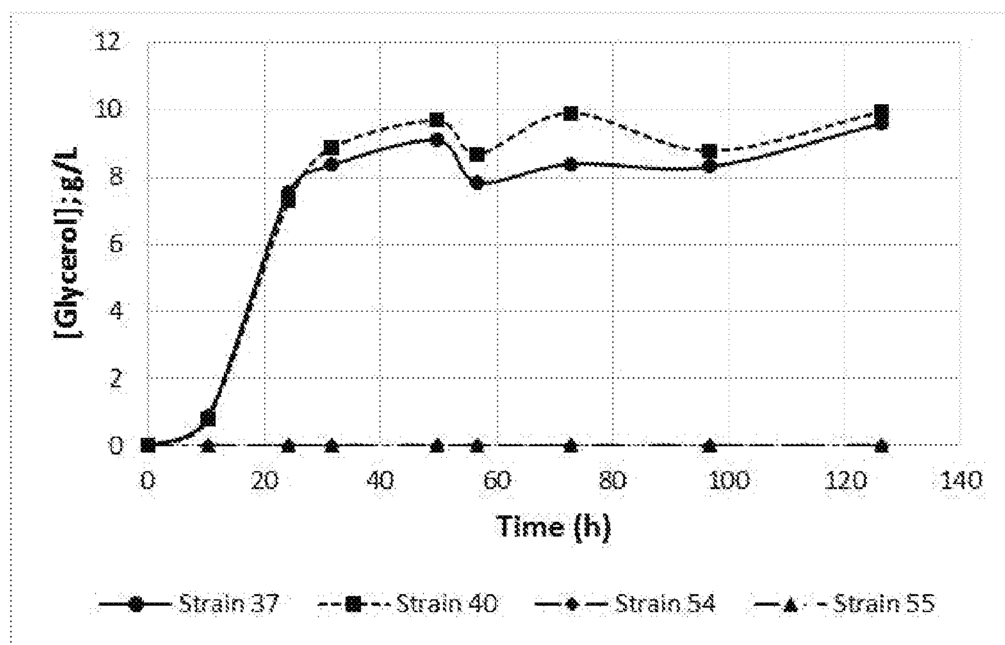
Figure 2A:
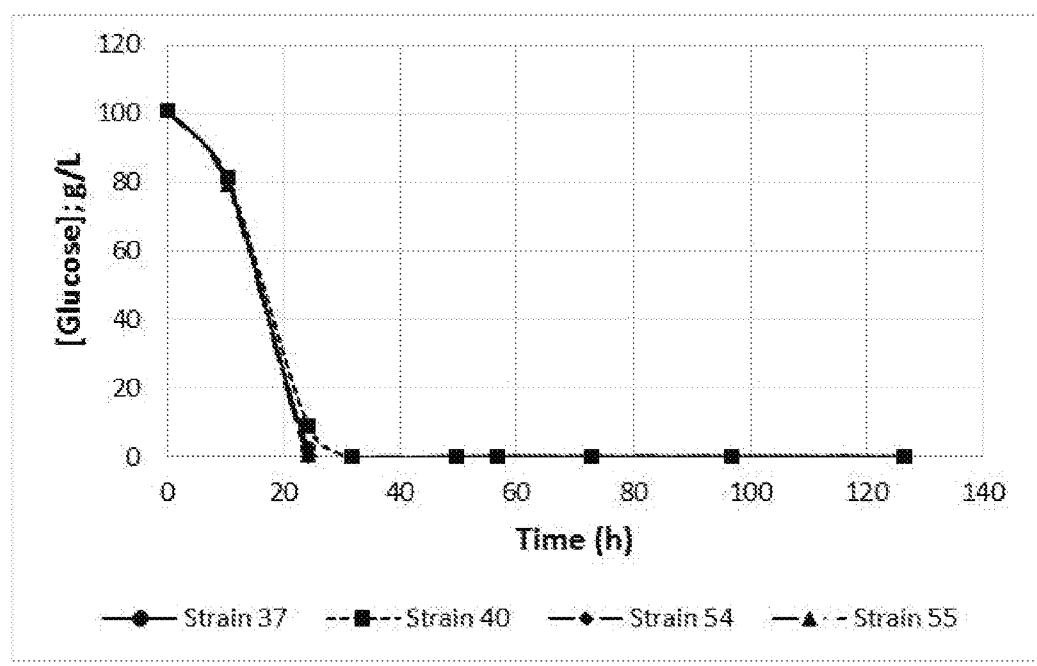
Figure 2B:
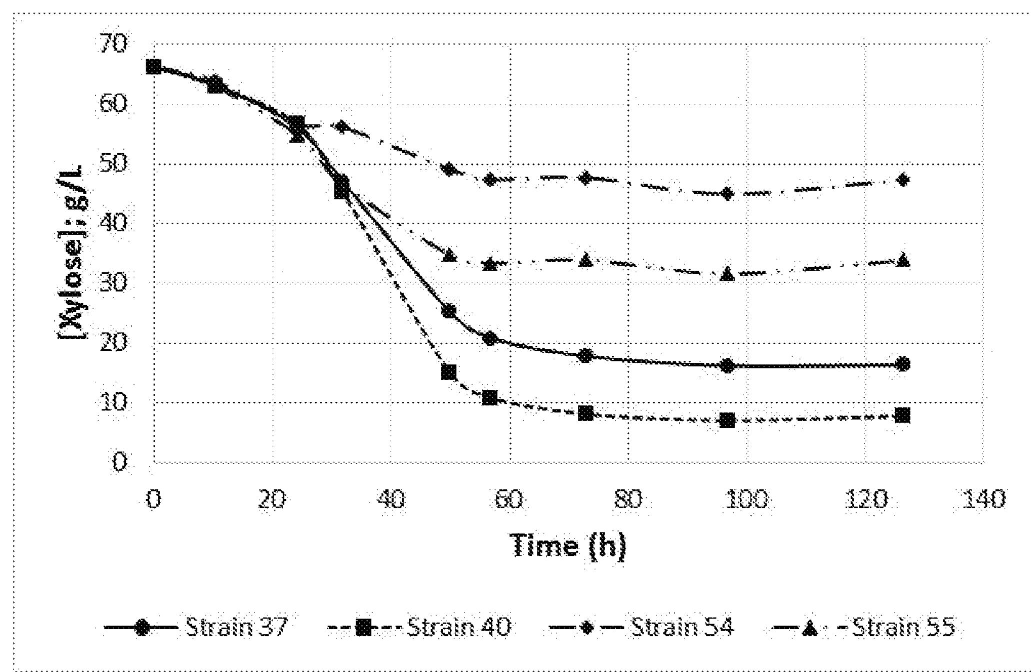
Figure 2C:
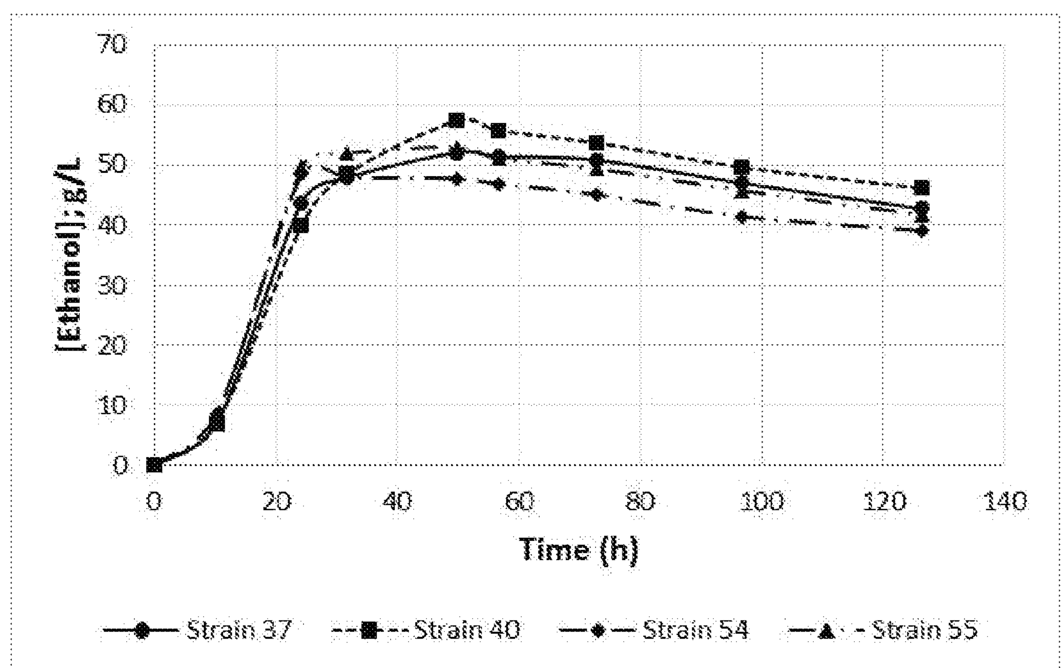
Figure 2D:
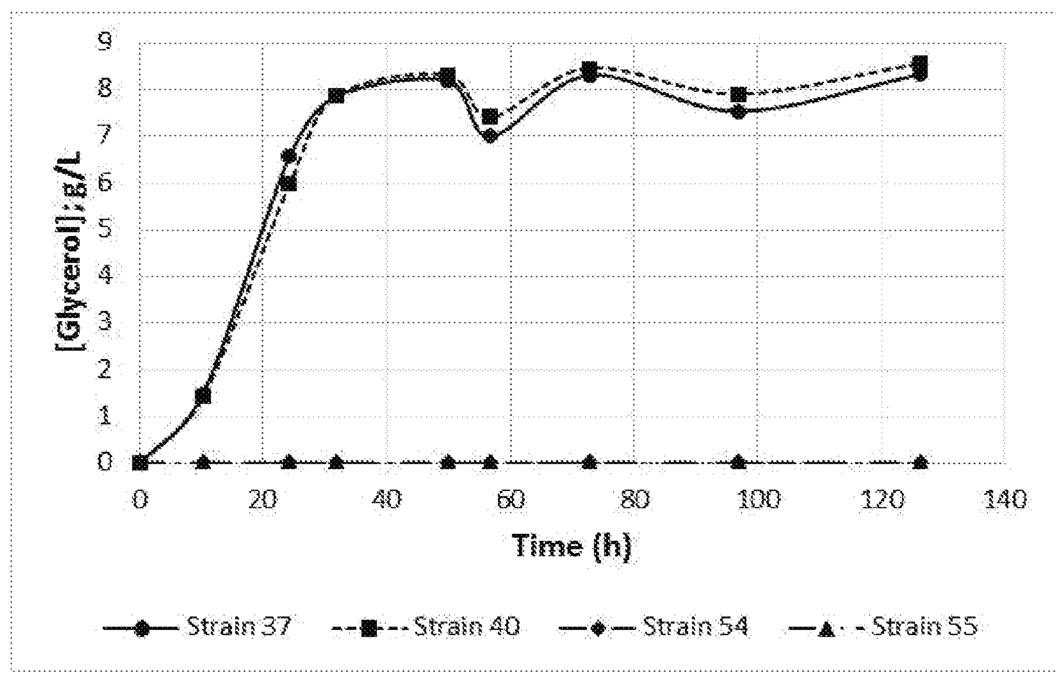
Figure 3A:
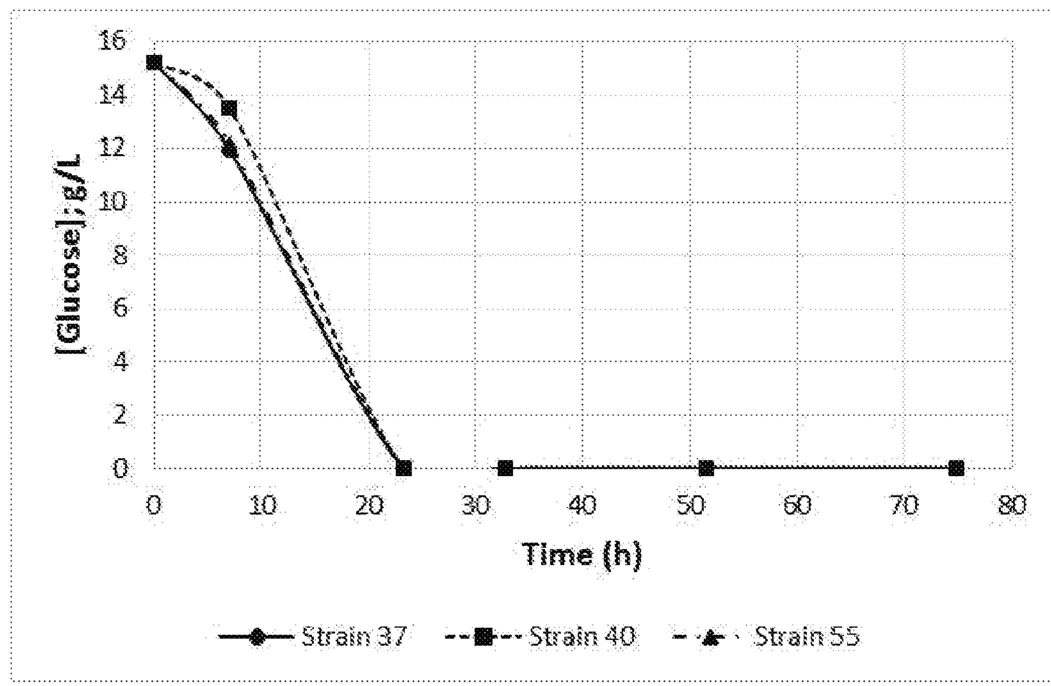
Figure 3B:
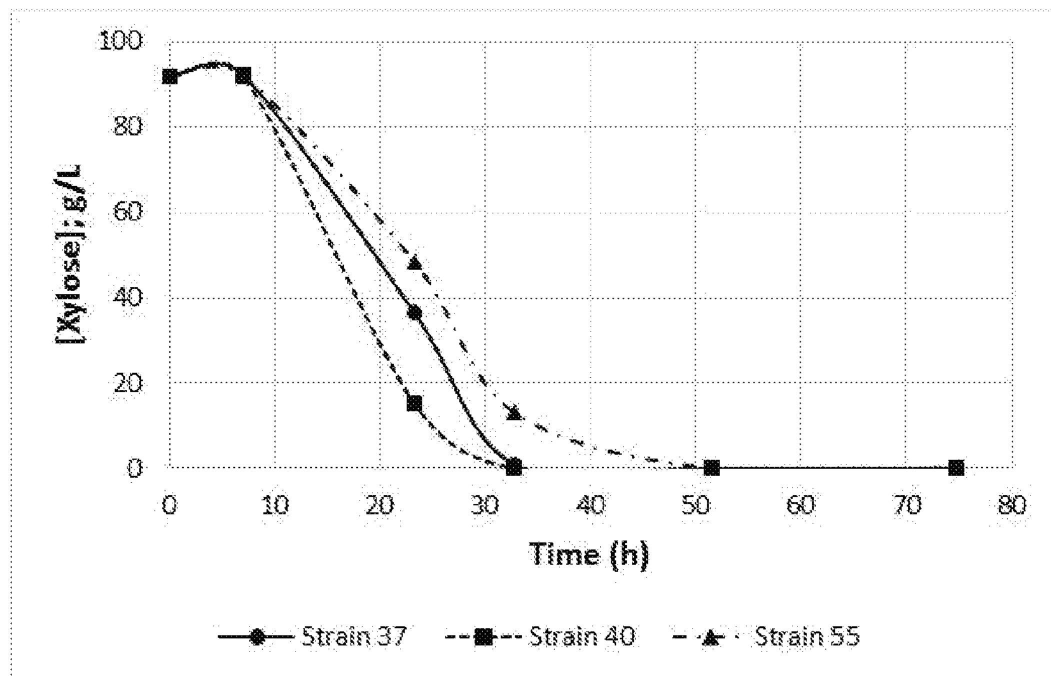
Figure 3C:
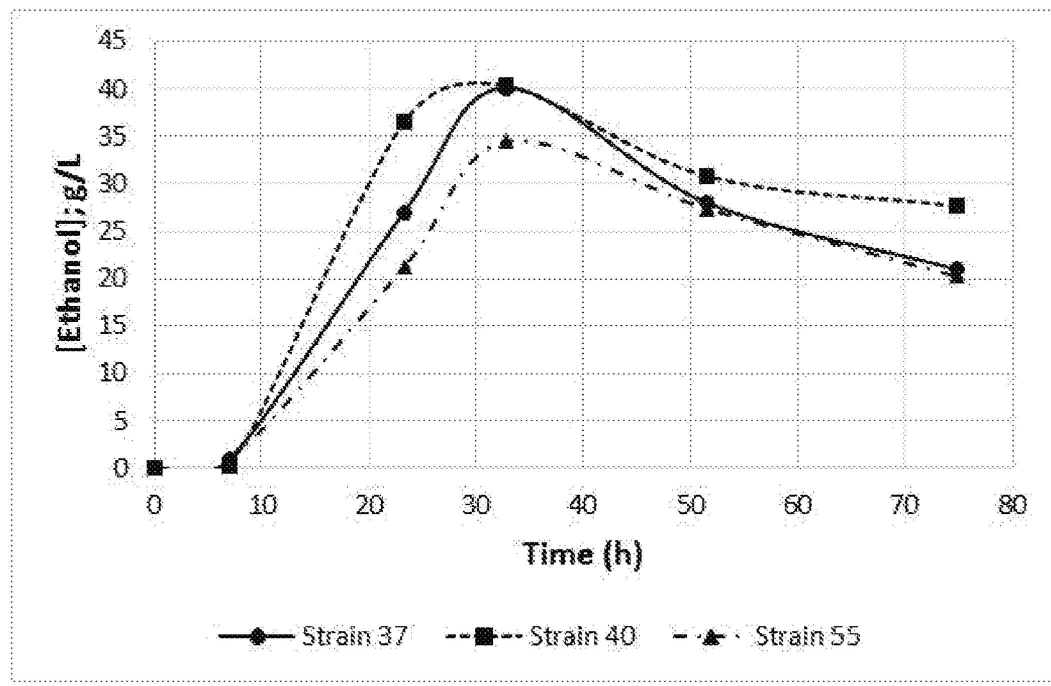
Figure 3D:
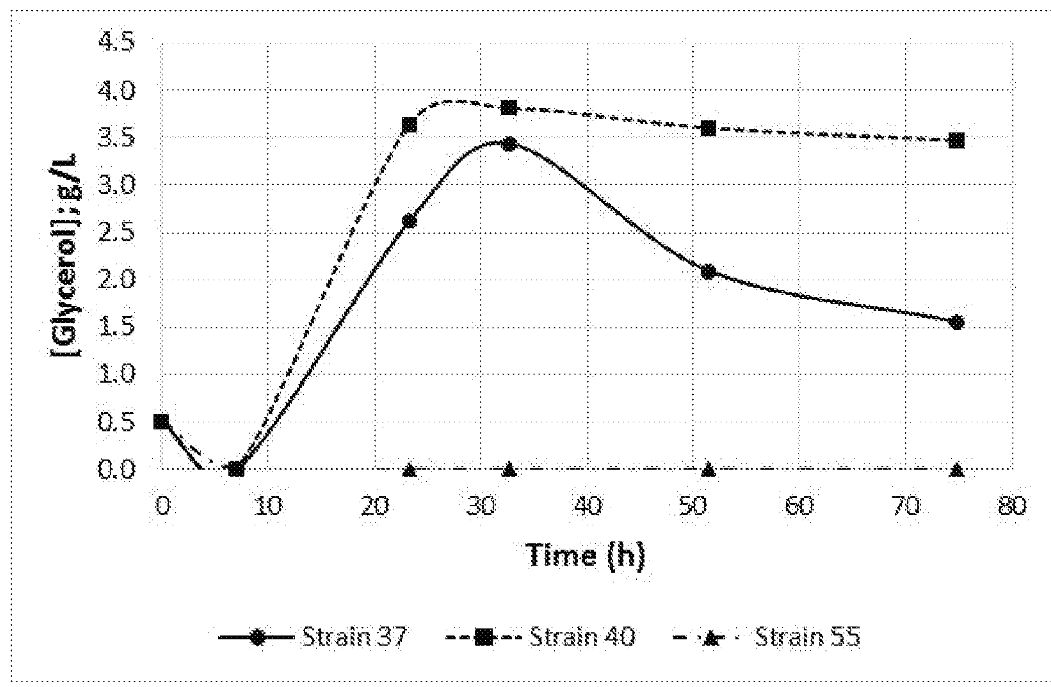

represent the data for strain 37, the short dashed lines with squares (■) represent the data for strain 40, the dot-dashed lines with diamonds (♦) represent the data for strain 54, and the dot-dashed lines with triangles (▲) represent the data for strain 55.

FIGS. 2A-2D are graphs showing metabolite concentrations in NREL corn stover hydrolysate shake flask experiments of Example 11. The solid lines with circles (●) represent the data for strain 37, the short dashed lines with squares (■) represent the data for strain 40, the dot-dashed lines with diamonds (♦) represent the data for strain 54, and the dot-dashed lines with triangles (▲) represent the data for strain.

FIGS. 3A-3D are graphs showing metabolite concentrations for strains 37, 40, and 55 of Example 12 xylose defined medium shake flasks experiments. The solid lines with circles (●) represent the data for strain 37, the dashed lines with squares (■) represent the data for strain 40, and the dot-dash lines with triangles (▲) represent the data for strain 55.

Figure 4:
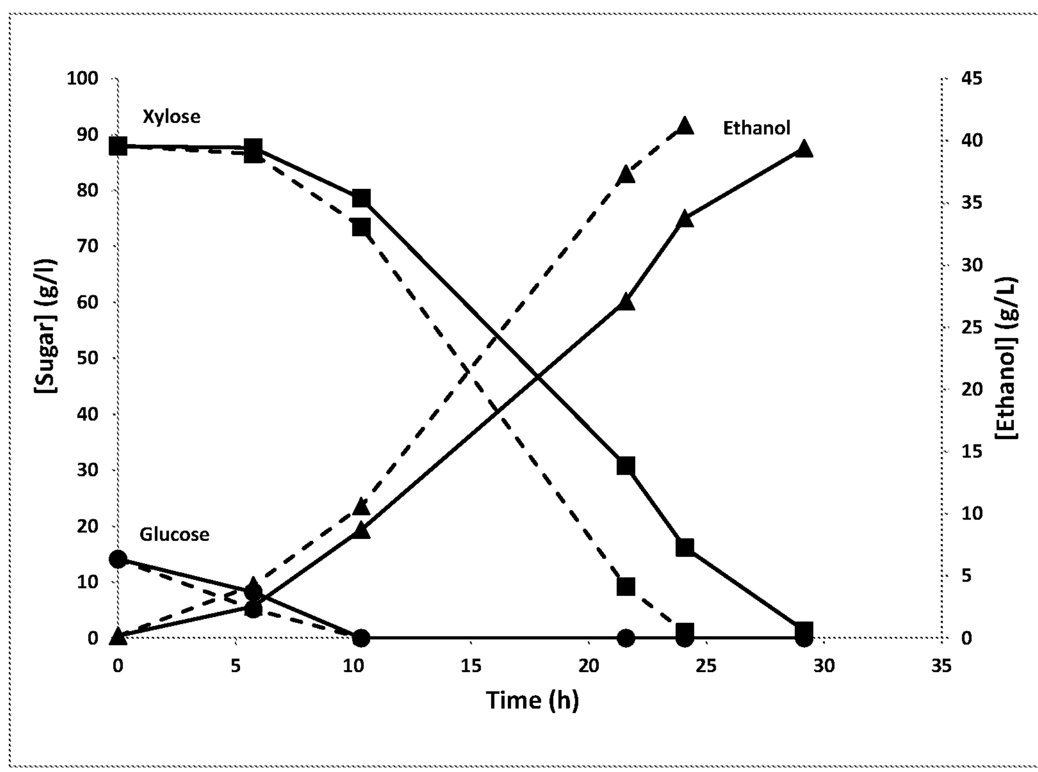

FIG. 4 is a graph showing the concentration and conversion of xylose in batch fermentors with yeast strains 37 and 40 containing 8 and 16 copies, respectively, of *Sebaldella termitidis* xylose isomerase codon variants. The solid lines represent the results for strain 37 and the dashed lines represent the results for strain 40; [Glucose] ●; [Xylose] ■; [Ethanol] ▲.

Figure 5:
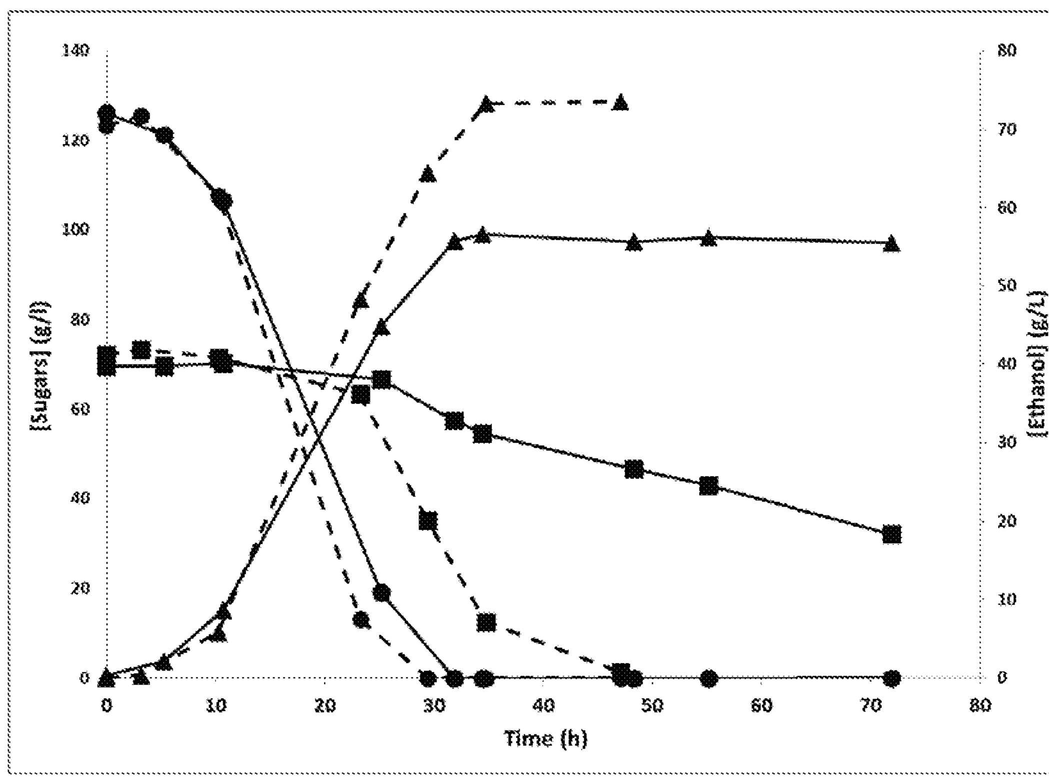

FIG. 5 is a graph showing the concentration and conversion of xylose to ethanol in batch fermentors with yeast strains 36 and 40 containing 4 copies and 16 copies, respectively, of *Sebaldella termitidis* XI codon variants. The solid lines represent the results for strain 36 and the dashed lines represent the results for strain 40; [Glucose] ●; [Xylose] ■; [Ethanol] ▲

DETAILED DESCRIPTION

The embodiments of the present invention described below are not intended to be exhaustive or to limit the invention to the precise forms disclosed in the following detailed description. Rather a purpose of the embodiments chosen and described is so that the appreciation and understanding by others skilled in the art of the principles and practices of the present invention can be facilitated.

Embodiments of the invention relate to engineered yeast strains expressing an heterologous xylose isomerase, fermentation methods that use the engineered yeast with a fermentation medium that includes xylose, fermentation medium, and compositions and bioproducts obtained from the fermentation methods.

Expression of the heterologous xylose isomerase in the engineered yeast can promote consumption of D-xylose present in the fermentation medium. D-Xylose is converted into a five carbon phosphate intermediate which is then introduced into the pentose phosphate pathway. This can result in increased flux of five carbon sugars and increased production of bioproducts in the cell that are generated through this pathway. In particular, the xylose isomerase enzyme can cause the conversion of D-xylose to D-xylulose. D-Xylulose is then converted to xylulose-5-phosphate (Xu5P) by ATP:D-xylulose 5-phosphotransferase (also known as xylulokinase, phosphorylating) and D-xylulokinase. Increased xylulose-5-phosphate formation can provide a precursor pool for the formation of pathway intermediate compounds such as D-ribulose-5-phosphate, fructose-6-phosphate, erythrose-4-phosphate, sedoheptulose-7-phosphate, and glyceraldehyde-3-phosphate. The pathway intermediate compounds can be used for the formation of a bioproduct, such as an amino acid, an organic acid, a hydroxyl-organic acid, an alcohol, a polyol, a fatty acid, a fatty acid methyl ester, a monoacyl glyceride, a diacyl glyceride, or a triacyl glyceride.

Increased flux of intermediates via expression of the xylose isomerase and the pentose phosphate pathway can be further used for bioproduct production using a pathway that is native to the yeast that is engineered (i.e., an "endogenous pathway") or for bioproduct production using a pathway that is not native to the yeast that is engineered (i.e., an "exogenous pathway").

In addition to the heterologous xylose isomerase, the engineered yeast can express one or more other enzymes to promote production of a desired bioproduct. For example, the yeast can be further engineered to increase the expression of one or more endogenous genes that increases the flux of intermediate compound(s) through an endogenous pathway to a desired bioproduct. Alternatively, further to the heterologous xylose isomerase, the yeast can be modified to cause the expression of one or more heterologous gene(s) that forms a new bioproduct pathway (a heterologous pathway) in the cells. Therefore, the engineered yeast can include two or more exogenous nucleic acids that result in expression of enzymes that are not native to the yeast and promote a desired bioproduct formation.

Nucleic acids that are templates for the expression of these enzymes are also embodiments of the invention, as well as constructs including these nucleic acids.

The term "heterologous" (e.g., "non-native") refers to a change that is different than a native state. Heterologous can refer to a molecule or activity that is from a source that is different than the referenced molecule or organism, and it also can refer to a molecule or activity that is changed from the native molecule or activity. Accordingly, a gene or protein that is heterologous to a referenced organism is a gene or protein not found in that organism, or a gene or protein that is found in the referenced organism but that has some change that is not found in the organism. For example, a heterologous gene can be a gene endogenous ("native to") or exogenous ("not native to") to the host organism which has a modification to the coding region, regulatory elements, or position in the host organism genome, wherein the gene is useful for producing a desired fermentation product. Examples include an endogenous gene having a promoter or terminator that has been modified, an endogenous gene in which the location of the gene's coding region in the genome has been changed from its native location, and/or an endogenous gene in which the copy number of the gene has been modified (e.g., increased) from its native number.

A "heterologous xylose isomerase" can be a xylose isomerase polypeptide that is different in its amino acid sequence from a xylose isomerase polypeptide native to the host organism. Heterologous xylose isomerases therefore include sequence modifications to endogenous xylose isomerases, and also exogenous xylose isomerases with wild type sequences or sequences that are modified from the wild type. As an example, a xylose isomerase gene that is native to a fungal species, but is present at a genome location that is different than the native location is also "heterologous". As another example, a xylose isomerase gene that is native to a fungal species but is flanked by one or more regulatory elements (e.g. promoter or terminator) whose nucleic acid sequences differ from the sequences of the native regulatory elements is "heterologous" and further, such regulatory elements are also "heterologous".

The term "exogenous" as used herein, means that a molecule, such as a nucleic acid, or an activity, such as an enzyme activity, that is non-native to the host cell. Exogenous therefore refers to something coming from other than the referenced organism, such as from a genus or species different from the referenced organism. An exogenous gene or activity can be introduced into the host organism, such as by well-known techniques and can be maintained external to the hosts chromosomal material (e.g., maintained on a non-integrating vector), or can be integrated into the host's chromosome, such as by a recombination event. An exogenous nucleic acid can encode an enzyme, or portion thereof, that is heterologous to the host organism. For example, a nucleic acid encoding *Sebaldella termitidis* xylose isomerase that is introduced into the yeast host *Issatchenkia orientalis* is an exogenous nucleic acid. Conversely, the term "endogenous" as used herein refers to something that is found within the cell (i.e., that is native to the cell).

Xylose isomerases (E.C. 5.3.1.5) are isomerase enzymes that fall into the family of intramolecular oxidoreductases that interconvert aldoses and ketoses. Xylose isomerases may also go by other names such as D-xylose ketoisomerase or D-xylose ketol-isomerase. In particular, the xylose isomerase enzyme can cause the conversion of D-xylose (also known as D-xylopyranose) to D-xylulose. Functionally, it is understood that a xylose isomerase will bind the closed form of D-xylose and catalyze ring opening of the sugar to generate an open-chain conformation with isomerization proceeding by a hydride-shift mechanism. The isomerization may be coordinated to one of the metal sites of the enzyme. Different xylose isomerases can utilize different divalent cations, such as magnesium, manganese, and cobalt. Some studies have shown the N-terminal portion of the xylose isomerase includes the catalytic site (e.g., see Vangrysperre, W., et al. Biochem. J. 263:195-199; 1989).

Xylose isomerases have been identified in prokaryotic and eukaryotic organisms.

In some embodiments of the disclosure, the engineered yeast include an heterologous nucleic acid encoding a xylose isomerase which can be from any organism (e.g., prokaryotic or eukaryotic species) and a heterologous nucleic acid encoding a transaldolase. In other embodiments of the disclosure, the engineered yeast include an heterologous nucleic acid encoding a xylose isomerase with an amino acid sequence having 70% or greater identity to SEQ ID NO:29 (St XI) or SEQ ID NO:33 (Lg XI), where one or more other heterologous genetic modifications are not required, but such modifications could optionally be further engineered in the yeast if desired.

Exemplary fungal xylose isomerases that can be included in an engineered yeast include, but are not limited to, xylose isomerases such as, *Piromyces* sp. E2 xylA (AJ249909) and *Cyllamyces aberensis* XI (see SEQ ID NOs. 58 and 151 of WO2004/099381).

Exemplary bacterial xylose isomerases that can be included in an engineered yeast include, but are not limited to, xylose isomerases such as *Clostridium phytofermentans* xylA (A9KN98), *Thermus thermophilus* xylA (P26997), *Bacteroides thetaiotaomicron* xylA (Q8A9M2), and *Prevotella ruminicola* TC2-24 xylose isomerase (KC847096). The functionality of prokaryotic xylose isomerases has been established in eukaryotic organisms. For example, various bacterial xylose isomerases have been reported to be active in the yeast *Saccharomyces cerevisiae* (e.g., see Brat, D., et al., Appl Environ Microbiol. 75: 2304-2311, 2009; and Kuyper, et al. FEMS Yeast Res. 4:69-78, 2003).

In a preferred embodiment, the engineered yeast express a xylose isomerase that has at least 70% or greater identity to xylose isomerase from *Sebaldella termitidis* (strain ATCC 33386) xylA according to SEQ ID NO:29 (St XI). Preferably, xylose isomerase has at least 75%, 80%, 85%, 90%, 91%, 92%, 93%, 94%, 95%, 96%, 97%, 98%, or 99% or greater identity to SEQ ID NO:29 (St XI). In one embodiment, the disclosure provides sequence identifier numbers having an amino acid sequence that has 85% or greater identity SEQ ID NO; 29. In some embodiments, the xylose isomerase has 100% identity to SEQ ID NO:29. *Sebaldella termitidis* ATCC 33386 xylA (accession D1ANS7) is a 440 amino acid polypeptide having certain residues implicated in active site function (xylose isomerase activity) and divalent metal binding. For example residues 101H, 104D and 234K are implicated in active site function, and residues 232E, 268E, 271H, 296D, 307D, 309E, and 339D are implicated in metal binding (see Han, B.-G., et al., Bio Design 3:41-47, 2015)

Regarding metal binding, Han, B-G., et al. (Crystal structure of a class 2 D-xylose isomerase from the human intestinal tract microbe *Bacteroides thetaiotaomicron*, Bio-Design 3:41-47, 2015) investigated the structure of a xylose isomerase (XI) of *Bacteroides thetaiotaomicron*, which like the XI from *Sebaldella termitidis*, belongs to the class 2 XIs. It was found that structures around the metal and substrate binding site were also almost identical regardless of the XI classes, suggesting common enzymological properties between class 1 and class 2 XIs.

In another preferred embodiment, the engineered yeast expresses a xylose isomerase that has at least 70% or greater identity to xylose isomerase from *Leptotrichia goodfellowii* xylA according to SEQ ID NO:33 (Lg XI). Preferably, xylose isomerase has at least 75%, 80%, 85%, 90%, 91%, 92%, 93%, 94%, 95%, 96%, 97%, 98%, or 99% or greater identity to SEQ ID NO:33 (Lg XI). In one embodiment, the disclosure provides SEQ ID NO:102 having a amino acid sequence that has 85% or greater identity SEQ ID NO:33. In some embodiments, the xylose isomerase has 100% identity to SEQ ID NO:33. *Leptotrichia goodfellowii* xylA is another 440 amino acid polypeptide having certain residues implicated in active site function (xylose isomerase activity) and divalent metal ion binding. For example residues 101H, 104D and 234K are implicated in active site function, and residues 232E, 268E, 271H, 296D, 307D, 309E, and 339D are implicated in metal binding.

For embodiments using a nucleic acid encoding a xylose isomerase polypeptide with less than 100% identify to SEQ ID NO:29 (St XI) or SEQ ID NO:33 (Lg XI), the difference in identity may be due to one or more amino acid substitutions in one or more region(s) of the polypeptide, for example, in regions outside of those understood to be important for active site function and metal binding and/or outside of conserved regions based on alignment with one or more other xylose isomerase(s).

If one or more amino acid substitutions, deletions, or additions are made to SEQ ID NO:29 (St XI) or SEQ ID NO:33 (Lg XI), they are preferably made in one or more regions of the polypeptide not important for xylose isomerase activity, or at locations that have a lower degree of identity between SEQ ID NO:29 (St XI) or SEQ ID NO:33 (Lg XI) and other xylose isomerases.

In some embodiments, the xylose isomerase has one or more amino acid substitutions, deletions, or additions which cause the sequence to vary from a native xylose isomerase sequence while retaining certain sequence features. That is, if the xylose isomerase is modified, it is modified at one or more amino acid locations outside of regions that are conserved and/or important for enzymatic functioning of the protein. For example, the xylose isomerase comprises (I) one or more of the sequences selected from (a)-(i): (a) VXW[GP]GREG[YSTA]: residues 186-194 of SEQ ID NO: 29 (b) [LIVM]EPKPX[EQ]P: residues 231-238 of SEQ ID NO: 29 or 33 (c) residues at positions 101H, 104D, 234K, 339D of SEQ ID NO: 29 or 33; (d) residue 232E of SEQ ID NO: 29 or 33; (e) the amino acid E at position 268 of SEQ ID NO: 29 or 33; (f) the amino acid H at position 271 of SEQ ID NO: 29 or 33; (g) the amino acid D at position 296 of SEQ ID NO: 29 or 33; (h) the amino acid D at position 307 of SEQ ID NO: 29 or 33; (i) the amino acid E at position 309 of SEQ ID NO: 29 or 33; and (II) one or more amino acid substitutions, deletions, or additions outside of (a)-(i). For example, optionally the XI amino acid sequence may also comprise the following changes: E14D and E114G (see, e.g., Lee et al. AEM, 78:5708-5716, 2012), while retaining the conserved residues as in (a)-(i).

Polypeptide sequence identity regions between St XI and Lg XI, as well as between St XI and/or Lg XI and other XIs, can be understood using sequence alignment tools as described herein.

Xylose isomerase polypeptides of the disclosure can also have deletions to one or more regions of the native xylose isomerase polypeptide, wherein the deletions do not affect the polypeptides' isomerase activity. The deletions can be based on known information regarding the structure and function of native xylose isomerases, including information regarding regions that are conserved and/or important for enzymatic functioning of the protein, for example such as the sequences (a)-(i) as described herein The determination of "corresponding" amino acids from two or more xylose isomerases can be determined by alignments of all or portions of their amino acid sequences. Sequence alignment and generation of sequence identity include global alignments and local alignments, which typically use computational approaches. In order to provide global alignment, global optimization forcing sequence alignment spanning the entire length of all query sequences is used. By comparison, in local alignment, shorter regions of similarity within long sequences are identified.

As used herein, an "equivalent position" means a position that is common to the two sequences (e.g., a St XI or Lg XI and a different XI sequence having the desired substitution (s)) that is based on a best alignment of the amino acid sequences of one xylose isomerases or as alignment of the three-dimensional structures. Thus either sequence alignment or structural alignment, or both, may be used to determine equivalence.

In some modes of practice, the BLAST algorithm is used to compare and determine sequence similarity or identity. In addition, the presence or significance of gaps in the sequence which can be assigned a weight or score can be determined. These algorithms can also be used for determining nucleotide sequence similarity or identity. Parameters for to determine relatedness are computed based on art known methods for calculating statistical similarity and the significance of the match determined. Gene products that are related are expected to have a high similarity, such as greater than 50% sequence identity. Exemplary parameters for determining relatedness of two or more sequences using the BLAST algorithm can be as follows.

In some modes of practice, an alignment is performed using BLAST (National Center for Biological Information (NCBI) Basic Local Alignment Search Tool) version 2.2.29 software with default parameters. A sequence having an identity score of XX % (for example, 80%) with regard to a reference sequence using the BLAST version 2.2.29 algorithm with default parameters is considered to be at least XX % identical or, equivalently, have XX % sequence identity to the reference sequence.

A global alignment can be used to align sequences with significant identity to, for example, SEQ ID NO:29 (St XI) or SEQ ID NO:33 (Lg XI) in order to determine which corresponding amino acid position(s) in the target sequence (e.g., a xylose isomerases ortholog) can be substituted with the one or more of the amino acid if a xylose isomerases variant is used.

In some embodiments, the engineered yeast can include two or more copies of heterologous nucleic acids that encodes a xylose isomerase polypeptide, such as a xylose isomerase with an amino acid sequence having 70% or greater identity to SEQ ID NO:29 (St XI) or SEQ ID NO:33 (Lg XI), that is heterologous to the yeast cell. In some embodiments, all copies of the genes encode a xylose isomerase that has a specific amino acid sequence, such as SEQ ID NO:29 (St XI) or SEQ ID NO:33 (Lg XI).

The multiple nucleic acid sequences that encode the xylose isomerase having a specific amino acid sequence may be identical to each other, or may differ from one another. If the multiple nucleic acid sequences are different from one another but still code for the same XI polypeptide, the differences, for example, can be based on the degeneracy of codons in the coding region of the nucleic acid sequences. In other words, these nucleic sequences may not be 100% identical to each other but still encode a common xylose isomerase polypeptide. That is, the difference in nucleic acid sequences between the versions of the xylose isomerase genes are a result of changes in the second and/or third nucleotide in at least one codon triplet in the encoding nucleic acid sequence. Preferably, the differences in the nucleic acid sequences are based on differences in multiple codons in the sequences. In this regard, when referring to nucleic acid sequences, the term "copies" is intended to refer to those nucleic acid sequences that are not identical but encode a common xylose isomerase polypeptide.

Exemplary nucleic acid sequences encoding the St XI polypeptide include the wild type sequence SEQ ID NO:87, as well as codon optimized sequences and codon variants of SEQ ID NO:87, including one or more of SEQ ID NO:88 to SEQ ID NO:92. The engineered yeast can include two or more copies of any of SEQ ID NO:87 to SEQ ID NO:92, or combinations thereof. For example, the engineered yeast can include (a) SEQ ID NO:89 and SEQ ID NO:91; (b) SEQ ID NO:89 and SEQ ID NO:92; (c) SEQ ID NO:91 and SEQ ID NO:92; (d) SEQ ID NO:89, SEQ ID NO:91, and SEQ ID NO:92; or (e) two or more copies of SEQ ID NO:89, SEQ ID NO:91, and/or SEQ ID NO:92 in any of (a)-(d).

Exemplary nucleic acid sequences encoding the Lg XI polypeptide include the wild type sequence SEQ ID NO:93, as well as codon optimized sequences and codon variants of SEQ ID NO:93, including one or more of SEQ ID NO:94 to SEQ ID NO:98. The engineered yeast can include two or more copies of any of SEQ ID NO:93 to SEQ ID NO:98, or combinations thereof.

For example, the engineered yeast can include (a) SEQ ID NO:95 and SEQ ID NO:96; (b) SEQ ID NO:95 and SEQ ID NO:97; (c) SEQ ID NO:95 and SEQ ID NO:98; (d) SEQ ID NO:96 and SEQ ID NO:97; (e) SEQ ID NO:96 and SEQ ID NO:98; (f) SEQ ID NO:97 and SEQ ID NO:98; (g) SEQ ID NO:95, SEQ ID NO:96, and SEQ ID NO:97; (h) SEQ ID NO:95, SEQ ID NO:96, and SEQ ID NO:98; (i) SEQ ID NO:96, SEQ ID NO:97, and SEQ ID NO:98; (j) SEQ ID NO:95, SEQ ID NO:96, SEQ ID NO:97, and SEQ ID NO:98; or (k) two or more copies of SEQ ID NO:95, SEQ ID NO:96, SEQ ID NO:97, and SEQ ID NO:98 in any of (a)-(k).

The disclosure also provides engineered yeast having a combination (i) one or more nucleic acid sequences encoding the St XI polypeptide, and (ii) one or more nucleic acid sequences encoding the Lg XI polypeptide. For example, the provides engineered yeast having a combination (i) one or more nucleic acid sequences selected from SEQ ID NO:87 to SEQ ID NO:92, and (ii) one or more nucleic acid the sequences selected from SEQ ID NO:93 to SEQ ID NO:98. For example, the engineered yeast can include (a) SEQ ID NO:89 and SEQ ID NO:94; (b) SEQ ID NO: 89 and SEQ ID NO:95; (c) SEQ ID NO: 89 and SEQ ID NO:96; (d) SEQ ID NO: 89 and SEQ ID NO:97; (e) SEQ ID NO: 89 and SEQ ID NO:98; (f) SEQ ID NO:91 and SEQ ID NO:94; (g) SEQ ID NO:91 and SEQ ID NO:95; (h) SEQ ID NO:91 and SEQ ID NO:96; (i) SEQ ID NO:91 and SEQ ID NO:97; (j) SEQ ID NO:91 and SEQ ID NO:98; (k) or two or more copies of SEQ ID NO:89 and/or SEQ ID NO:91, and or two or more copies of SEQ ID NO:94 to SEQ ID NO:98.

The engineered yeast can be described in terms of the copy number of the nucleic acids that encode a xylose isomerase polypeptide or polypeptides. For example, the engineered yeast can have a xylose isomerase nucleic acid copy number of two or more, such as a copy number in the range of two to twenty four. However, one of skill could engineer the yeast with more than twenty four copies of the xylose isomerase nucleic acid using techniques known in the art. For example, the engineered yeast can have a xylose isomerase nucleic acid copy number of two or more, such as a copy number in the range of two to twenty four, two to sixteen, or four to sixteen. For example, the engineered yeast can have a nucleic acid copy number of two, three, four, five, six, seven, eight, nine, ten, eleven, twelve, thirteen, fourteen, fifteen, or sixteen, seventeen, eighteen, nineteen, twenty, twenty one, twenty two, twenty three, or twenty four xylose isomerase nucleic acids that are the same as one another, or different from one another, and which can encode the same xylose isomerase polypeptide or different xylose isomerase polypeptides.

If the yeast is engineered to include multiple copies of the xylose isomerase gene, the copies can be placed in a tandem orientation at a nucleic acid site in the cell, such as integrated into a desired locus of a yeast chromosome as tandem repeats. Copies can also be placed in at multiple nucleic acid sites in the cell, such as integrated into multiple loci of a yeast chromosome(s).

In multiple copy embodiments, the differences in nucleic acid sequences can be expressed as the percent difference in the number of nucleic acids between two different xylose isomerase nucleic acid sequences. For example, for two specific xylose isomerase nucleotide sequences, $XI_1$ and $XI_2$, which are aligned according to methods described herein, and each sequence having 1323 nucleotides and encoding a common xylose isomerase polypeptide, whose nucleotide sequences differ at 239 residues, the percent nucleotide sequence difference would be approximately 18% (or conversely, the percent identity would be 82%). In some embodiments, if multiple, different, heterologous nucleic acid sequences are used to encode a xylose isomerase polypeptide, the nucleic acid sequences differ from each other by at least 10%. When comparing each pairing of different nucleotide sequences to each other, the differences can optionally be expressed as a range. For example, the range can be approximately an amount of the smallest difference to an amount of the largest difference between any two xylose isomerase nucleotide sequences. Therefore, in some embodiments, the first, second, third, and fourth heterologous nucleic acids encoding a XI polypeptide (s) can differ from each other by an amount in the range of about 5% to about 30%, about 10% to about 30%, about 15% to about 27%, or about 17% to about 25%.

Exemplary nucleic acid sequences encoding the St XI polypeptide that have differences in nucleic acid sequence include, for example, SEQ ID NO:87 to SEQ ID NO:92, and those sequence having at least 70% nucleic acid identity to any of SEQ ID NO:87 to SEQ ID NO:92. Exemplary nucleic acid sequences encoding the Lg XI polypeptide that have differences in nucleic acid sequence include, for example, SEQ ID NO:93 to SEQ ID NO:98, and those sequence having at least 70% nucleic acid identity to any of SEQ ID NO:93 to SEQ ID NO:98.

In other embodiments, the engineered yeast can include two or more copies of heterologous nucleic acids that encode xylose isomerase polypeptides with different amino acid sequences. In these embodiments at least two heterologous nucleic acids have different sequences and therefore encode different xylose isomerase polypeptides. The heterologous nucleic acids can encode xylose isomerase polypeptides having a certain amino acid sequence identity to each other, such as about 50% or greater, about 60% or greater, about 70% or greater, about 80% or greater, about 85% or greater, about 90% or greater, or about 95% or greater identity to each other. Exemplary identity ranges are about 50% to about 99%, about 60% to about 99%, about 70% to about 99%, about 80% to about 99%, about 85% to about 99%, or about 90% to about 99%. Other exemplary identity ranges are about 75% to about 95%, about 78% to about 92%, about 80% to about 90%, or about 82% to about 88%, about 85% to about 99%, or about 90% to about 99%.

In some embodiments, the difference can be described relative to a reference polypeptide sequence. For example, the engineered yeast can include two or more copies of heterologous nucleic acids that encode xylose isomerase polypeptides with different sequences that have about 50% or greater, about 60% or greater, about 70% or greater, about 80% or greater, about 85% or greater, about 90% or greater, or about 95% or greater identity to SEQ ID NO:29 (St XI) or SEQ ID NO:33 (Lg XI). Exemplary identity ranges are about 50% to about 99%, about 60% to about 99%, about 70% to about 99%, about 80% to about 99%, about 85% to about 99%, or about 90% to about 99%. Other exemplary identity ranges are about 75% to about 95%, about 78% to about 92%, about 80% to about 90%, or about 82% to about 88%. For example, the engineered yeast can include a first nucleic acid sequence that encodes SEQ ID NO:29 (St XI) (100% identity), and a second nucleic acid sequence that encodes a xylose isomerase polypeptide that has less than 100% identity to SEQ ID NO:29 (St XI). The engineered yeast can optionally include third, fourth, fifth, sixth, etc. nucleic acid sequences that encodes a xylose isomerase polypeptide(s) that has less than 100% identity to SEQ ID NO:29 (St XI), which can be the same or different than the xylose isomerase polypeptide encoded by the second nucleic acid.

If multiple heterologous nucleic acid sequences encode two or more xylose isomerase polypeptides that are different from one another, then the two or more xylose isomerase polypeptides can also have substitutions, such as described herein. A xylose isomerase polypeptide with substitutions can have about 50% or greater, about 60% or greater, about 70% or greater, about 80% or greater, about 85% or greater, about 90% or greater, or about 95% or greater identity to SEQ ID NO:29 (St XI) or SEQ ID NO:33 (Lg XI). That is, the heterologous nucleic acid sequences, which have different sequences, can encode xylose isomerases that also have distinct sequences but that are close enough in identity to function similarly, having xylose isomerase activity.

In other embodiments, the xylose isomerase sequence optionally comprises additional sequence that is not present in the native xylose isomerase polypeptide. The additional sequence can provide functionality to the xylose isomerase that is not present in the native polypeptide. Additional functionalities include, for example, protease sites or binding sites for other proteins or materials.

An example of an additional sequence that may not be present in a native xylose isomerase polypeptide, but that can be added, is a tag sequence. A tag sequence can be located at the C-terminus, the N-terminus, or both, of the xylose isomerase sequence, and such proteins can be annotated as follows: [XI]-[$T_C$], etc., wherein "$T_C$" denotes one or more amino acids that provide the C-terminal tag sequence, or [$T_N$]-[XI], etc., wherein "$T_N$" denotes one or more amino acids that provide the N-terminal tag sequence. Exemplary peptide tags include up to 5, 10, 15, or 20 amino acids. The peptide tag can be useful for any one or more of a variety of purposes. For example, the tag can allow purification of the enzyme from the media by the ability of a tag-binding member to specifically interact with the tag. The tag can also allow detection or identification of the protein using a tag-binding member with a detectable label. Exemplary short peptide tags are poly-Arg, FLAG, poly-His, c-myc, S, and Strep II. (See, for example, Terpe, K. (2003) Appl. Microbiol. Biotechnol. 60:523-533).

Nucleic acids sequence(s) encoding the xylose isomerase St XI polypeptide include the wild type sequence SEQ ID NO:87, as well as codon optimized sequences and codon variants of SEQ ID NO:87, such as SEQ ID NO:88, SEQ ID NO:89, SEQ ID NO:90, SEQ ID NO:91, and SEQ ID NO:92, or nucleic acids sequence(s) encoding the xylose isomerase Lg XI polypeptide include the wild type sequence SEQ ID NO:93, as well as codon optimized sequences and codon variants of SEQ ID NO:93, such as SEQ ID NO:94, SEQ ID NO:95, SEQ ID NO:96, SEQ ID NO:97, and SEQ ID NO:98, as well as any regulatory sequence (e.g., terminator, promoter, etc.) and vector sequence (e.g., including a selection marker, integration marker, replication sequence, etc.) can, in some modes of practice, be prepared using known molecular techniques. General guidance for methods for preparing DNA constructs (e.g., for the DNA constructs including the gene encoding SEQ ID NO:29 (St XI) or SEQ ID NO:33 (Lg XI) can be found in Sambrook et al. Molecular Cloning, A Laboratory Manual, Cold Spring Harbor Laboratory Press, Cold Spring Harbor, N.Y., 1989; and Ausubel et al. Current Protocols in Molecular Biology, Greene Publishing and Wiley-Interscience, New York, N.Y., 1993.

PCR techniques can be used for preparing or modifying a xylose isomerase nucleic acid sequence, such as to introduce one or more mutations in the xylose isomerase nucleic acid sequence to provide a variant. PCR techniques are described in, for example, Higuchi, (1990) in PCR Protocols, pp. 177-183, Academic Press; Ito et al (1991) Gene 102:67-70; Bernhard et al (1994) Bioconjugate Chem. 5:126-132; and Vallette et al. (1989) Nuc. Acids Res. 17:723-733. The techniques may optionally include site-directed (or oligonucleotide-mediated) mutagenesis, PCR mutagenesis, and cassette mutagenesis of an earlier prepared DNA encoding a xylose isomerase polypeptide.

Alternatively, nucleic acid molecules can be generated by custom gene synthesis providers such as DNA2.0 (Menlo Park, Calif.) or GeneArt (Life Technologies, Thermo Fisher Scientific).

An expression vector can be constructed to include the xylose isomerase nucleic acid sequence operably linked to expression control sequences functional in the host organism. Expression vectors applicable for use in the host organisms include, for example, plasmids, episomes and artificial chromosomes. The vectors can include selection sequences or markers operable for stable integration into a host chromosome. Additionally, the vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art.

In some embodiments, a nucleic acid encoding an XI or any other polypeptide that is introduced into a host yeast can be codon optimized. A nucleic acid template that is used for expression of the xylose isomerase can be the native DNA sequence that codes for the xylose isomerase, or the template can be a codon-optimized version that is optimized for expression in a desired host cell. In this regard, a specific codon optimization scheme may be used. The use of preferred codons in the host organism may result in increased activity, for example as caused by improved expression of the gene. For example, codon optimized DNA constructs encoding SEQ ID NO:29 (St XI) or SEQ ID NO:33 (Lg XI), or a polypeptide that has about 90% or greater, about 95% or greater, about 97% or greater sequence identity to these sequences can be prepared and inserted into a desired host cell.

Databases that provide information on desired codon uses in particular host organisms are known in the art. In some embodiments, the xylose isomerase nucleic acid is codon optimized for expression in a Crabtree negative yeast. For example, in an embodiment, the xylose isomerase nucleic acid is codon optimized for expression in a yeast of the *I. orientalis/P. fermentans* clade.

According to one embodiment of the disclosure, a DNA construct comprising a xylose isomerase gene is operably linked to a promoter sequence, wherein the promoter sequence is functional in a host cell of choice. In some embodiments, the promoter shows transcriptional activity in a yeast host cell and may be derived from genes encoding proteins either homologous or heterologous to the host cell. In some embodiments the promoter sequence is a strong promoter selected from translational elongation factor promoter (pTEF), pyruvate decarboxylase (PDC) promoter, glyceraldehyde-3-phosphate dehydrogenase promoter (pGPD/TDH3), and enolase (ENO) promoter. Other promoters that can be used to drive expression include the cytochrome c promoter (pCYC), and the phosphoglycerate kinase promoter (PGK). Optionally, an additional factor that controls expression such as an enhancer or the like may also be included on the vector.

The expression vector including the xylose isomerase gene can also include any promoter and terminator sequence functional in the host cell. For example, the promoter sequence and the terminator sequence can be endogenous to the host cell, or the promoter sequence and the terminator sequence can be from an organism exogenous to the host cell, but yet still functional in the host cell.

The DNA construct may be introduced into a host cell using a vector. The vector may be any vector which when introduced into a host cell is stably maintained. In some embodiments, the vector is integrated into the host cell genome and is replicated. Vectors include cloning vectors, expression vectors, shuttle vectors, plasmids, phage particles, cassettes and the like. In some embodiments, the vector is an expression vector that comprises regulatory sequences operably linked to the xylose isomerase coding sequence.

The DNA construct comprising the xylose isomerase gene can further include a selectable marker, thereby facilitating the selection in a host cell. For example, the selectable marker can be for transformed yeast. Examples of yeast selectable marker include markers commonly used for selecting for transformed yeast cells. Auxotrophic markers can be used using a gene that controls an auxotrophy, meaning that the gene enables yeast to produce a nutrient required for the growth of the yeast. Examples of yeast genes that control auxotrophies include leucine auxotrophy (LEU2), histidine auxotrophy (HIS3), uracil auxotrophy (URA3, URA5), and tryptophan auxotrophy (TRP1). MEL5, which encodes an alpha-galactosidase (melibiase) in yeast, can be used as a dominant selection marker to select for transformants of alpha-galactosidase negative yeast strains. Genetic modification of the yeast with one or more selective markers can allow the yeast to utilize certain substrates.

The DNA construct may be one which is integrated into the genome and replicated together with the chromosome(s) into which it has been integrated. For example, a yeast cell may be transformed with the DNA construct encoding the xylose isomerase, and integrating the DNA construct, in one or more copies, in the host chromosome(s). This integration is generally considered to be an advantage, as the DNA sequence is more likely to be stably maintained. Integration of the DNA constructs into the host chromosome may be performed according to conventional methods, such as by homologous recombination or random integration.

In one mode of practice, one or more DNA construct(s) comprising the xylose isomerase genes is integrated at a genetic locus, wherein the integration does not have a significant adverse effect on the health of the cell. For example, the integration can be at a locus of the genome that is not known to have any polypeptide coding sequence, or at a locus of the genome that has a gene that is not essential for function under desired growth conditions, such as under fermentation conditions using a lignocellulosic or a lignocellulosic-derived product as the energy source. In *Saccharomyces cerevisiae*, a large amount of information is available about the essentiality of open reading frames (ORFs) in its genome. See, for example, www-sequence.stanford.edu/group/yeast_deletion_project/deletions3. This information can be used to as guidance for understanding the essentiality of corresponding genes in other yeast strains, such as Crabtree negative yeasts like *Issatchenkia orientalis*, and engineering such strains accordingly. Given information known in the art, one of skill can choose one or more non-essential genes as targets for integrations of the one or more DNA construct(s) comprising the xylose isomerase genes. Whether or not a gene is "essential" can be determined in growth conditions using rich media with glucose.

In some embodiments, in addition to the xylose isomerase modification, the engineered yeast includes one or more additional genetic modifications. The one or more additional genetic modifications can affect other aspects of the xylose consumption and processing, including, but not limited to D-xylose formation in the fermentation media, D-xylose uptake in the engineered yeast, the pentose phosphate pathway, other enzymes that act on xylulose-5-phosphate and downstream metabolites, and improvement of tolerance to inhibitory compounds present in lignocellulosic hydrolysates.

In some embodiments the engineered yeast includes one or more genetic modifications, further to the xylose isomerase modification, that promote xylose consumption, processing, or formation of a bioproduct using xylose as a precursor. Such modifications may cause enzyme activity to be introduced into the cell, cause an increased amount of enzyme in the cell, and/or cause an increase in enzyme activity. For example, expression of an heterologous nucleic acid in a host that otherwise in a wild-type form does not have the nucleic acid can be referred to as expression that is introduced. If an enzyme is expressed in an amount greater than the amount of enzyme is expressed in the native host, the gene expression can be referred to as upregulated. Introduced or upregulated expression can be caused by a modification that is not present in the native host. If an enzyme, such as one in an altered form, exhibits activity greater than the activity of the enzyme in native form, the enzyme activity can be referred to as enhanced.

One or more types of genetic modifications can be used to cause introduced or upregulated expression, or enhanced activity. For example, the enhanced activity can be caused by the addition of or modifications to regulatory elements (promoters, terminators, etc.) that upregulate expression of the desired gene(s). The enhanced activity can also be caused by an increase in copy numbers of the desired gene(s). The enhanced activity can also be caused by one or more genetic modifications to nucleic acid sequences or proteins that may otherwise function to repress expression of the gene whose activity is desired to be enhanced.

As an example, upregulating the expression of a gene to provide a greater amount of enzyme in the cell can be performed by placing a gene under the control of a heterologous promoter that drives a greater level of expression than when the gene is driven by its native promoter. A gene under the control of a heterologous promoter can be a gene that is native to the host cell (i.e., an endogenous gene), or a gene that is non-native (i.e., exogenous) to the host.

The yeast cell can have a heterologous genetic modification causing the desired enzyme to have enhanced activity in the engineered yeast. The heterologous modification can be the introduction of an exogenous gene into the yeast, or the modification of an endogenous gene and/or its surrounding genetic elements, such as expression regulatory elements. The heterologous modification can include one or more of the following: the use of a promoter that is different than the native promoter of the desired gene; the use of a terminator that is different than the native terminator of the desired gene; the introduction of the gene at a location in the genome that is different than its native location; the introduction of multiple copies of the desired gene.

The modifications can include changes to regulatory elements that either upregulate or down regulate expression of genes; increase in gene copy numbers, and deletions or mutations that eliminate expression, reduce expression, or increase expression or activity of a gene or gene product.

One optional additional genetic modification affects xylulokinase (XK) expression or activity. Xylulokinases (EC 2.7.1.17) are enzymes that use ATP for catalyzes the chemical reaction of D-xylulose to D-xylulose 5-phosphate. For example, the yeast can include an exogenous XK (i.e., a XK that is not native to the yeast), such as exogenous XKs with wild-type or altered sequences that are different than the wild type.

Exemplary eukaryotic xylulokinases (which can be an exogenous XK depending on the host yeast) include, but are not limited to, *Arabidopsis thaliana* XK-2 (Q949W8), *Saccharomyces cerevisiae* XKS1 (P42826), *Schizosaccharomyces pombe* xksI, (Q9C0U6), *Aspergillus niger* xkiA (Q8X167), *Candida albicans* XKS1, (Q59P16), and *Kluyveromyces marxianus* xk (F6JVF3). Expression of an exogenous XK gene can be controlled by a heterologous promoter, terminator, or both. For example, the XK can be over expressed using a strong promoter. Regulatory sequences can be chosen to provide XK activity in an amount that is greater than the amount of XK activity occurring naturally in the cell. Further, an exogenous XK can be placed at one or more desired locations in the genome, which may also provide desired expression. One or more copies (e.g., two, three, four, five, etc.) of an exogenous XK can be engineered in the cell.

XK activity can also be altered in the cell by changing the one or more features of the endogenous XK gene such as to provide: a heterologous promoter, a heterologous terminator, a different genomic location for the endogenous XK gene, or multiple copies of the endogenous XK gene. The one or more changes can be result in increased expression of the endogenous XK gene, and thereby increased endogenous XK activity Another optional additional genetic modification affects transaldolase (TAL) expression or activity. Transaldolases (EC 2.2.1.2) are enzymes of the non-oxidative phase of the pentose phosphate pathway the promote the conversion of sedoheptulose 7-phosphate and D-glyceraldehyde 3-phosphate to D-erythrose 4-phosphate and D-fructose 6-phosphate. For example, the yeast can include an exogenous TAL (i.e., a TAL that is not native to the yeast), such as exogenous TALs with wild-type or altered sequences that are different than the wild type.

Exemplary eukaryotic transaldolases (which can be an exogenous TAL depending on the host yeast) include, but are not limited to, *Arabidopsis thaliana* TAL (Q9LYR4), *Saccharomyces cerevisiae* TAL1 (P15019), *Schizosaccharomyces pombe* tall, (O42700), *Aspergillus niger* TAL (A2QMZ4), *Candida albicans* TAL1 (Q5A017), and *Kluyveromyces lactis* TAL1 (P34214). Expression of an exogenous TAL gene can be controlled by a heterologous promoter, terminator, or both. For example, the TAL gene can be over expressed using a strong promoter. Regulatory sequences can be chosen to provide TAL activity in an amount that is greater than the amount of TAL activity occurring naturally in the cell. Further, an exogenous TAL can be placed at one or more desired locations in the genome, which may also provide desired expression. One or more copies (e.g., two, three, four, five, etc.) of an exogenous TAL can be engineered in the cell.

TAL activity can also be altered in the cell by changing the one or more features of the endogenous TAL gene such as to provide: a heterologous promoter, a heterologous terminator, a different genomic location for the endogenous TAL gene, or multiple copies of the endogenous TAL gene. The one or more changes can be result in increased expression of the endogenous TAL gene, and thereby increased endogenous TAL activity.

Another optional additional genetic modification affects transketolase (TKL) expression or activity. Transketolases (EC 2.2.1.2) are enzymes of the pentose phosphate pathway. These enzymes catalyze the transfer of a two-carbon ketol group from a ketose donor to an aldose acceptor using thiamine pyrophosphate cofactor, for example, converting sedoheptulose 7-phosphate and D-glyceraldehyde 3-phosphate to D-ribose 5-phosphate and D-xylulose 5-phosphate.

For example, the yeast can include an exogenous TKL (i.e., a TKL that is not native to the yeast), such as exogenous TKLs with wild-type or altered sequences that are different than the wild type. Exemplary eukaryotic transaldolases include, but are not limited to *Arabidopsis thaliana* TKL-1 (Q8RWV0), *Saccharomyces cerevisiae* TKL1 (P23254), *Schizosaccharomyces pombe* TKL, (Q9URM2), *Aspergillus niger* TKL (A2R395), *Candida albicans* TKT1 (O94039), and *Kluyveromyces lactis* TKL1 (Q12630).

Expression of an exogenous TKL gene can be controlled by a heterologous promoter, terminator, or both. For example, the TKL can be over expressed using a strong promoter. Regulatory sequences can be chosen to provide TKL activity in an amount that is greater than the amount of TKL activity occurring naturally in the cell. Further, an exogenous TKL can be placed at one or more desired locations in the genome, which may also provide desired expression. One or more copies (e.g., two, three, four, five, etc.) of an exogenous TKL can be engineered in the cell.

TKL activity can also be altered in the cell by changing the one or more features of the endogenous TKL gene such as to provide: a heterologous promoter, a heterologous terminator, a different genomic location for the endogenous TKL gene, or multiple copies of the endogenous TKL gene. The one or more changes can be result in increased expression of the endogenous TKL gene, and thereby increased endogenous TKL activity.

Another optional additional genetic modification affects ribulose phosphate 3-epimerase (RPE) (also known as phosphopentose epimerase) expression or activity. RPEs (EC 5.1.3.1) are metalloproteins that catalyze the interconversion between D-ribulose 5-phosphate and D-xylulose 5-phosphate.

For example, the yeast can include an exogenous RPE (i.e., a RPE that is not native to the yeast), such as exogenous RPEs with wild-type or altered sequences that are different than the wild type. Exemplary eukaryotic RPEs include, but are not limited to, *Arabidopsis thaliana* RPE (Q9SAU2), *Saccharomyces cerevisiae* RPE1 (P46969), *Schizosaccharomyces pombe* RPE (O14105), *Aspergillus niger* RPE (A2QTW0), *Candida albicans* RPE1 (Q5AFG0), and *Kluyveromyces lactis* RPE (Q6CN60).

Expression of an exogenous RPE gene can be controlled by a heterologous promoter, terminator, or both. For example, the RPE can be over expressed using a strong promoter. Regulatory sequences can be chosen to provide RPE activity in an amount that is greater than the amount of RPE activity occurring naturally in the cell. Further, an exogenous RPE can be placed at one or more desired locations in the genome, which may also provide desired expression. One or more copies (e.g., two, three, four, five, etc.) of an exogenous RPE can be engineered in the cell.

RPE activity can also be altered in the cell by changing the one or more features of the endogenous RPE gene such as to provide: a heterologous promoter, a heterologous terminator, a different genomic location for the endogenous RPE gene, or multiple copies of the endogenous RPE gene. The one or more changes can be result in increased expression of the endogenous RPE gene, and thereby increased endogenous RPE activity.

Another optional additional genetic modification affects ribose 5-phosphate isomerase (RKI/RPI) expression or activity. Ribose-5-phosphate isomerases (EC 5.3.1.6) are enzymes that catalyze the conversion between ribose-5-phosphate (R5P) and ribulose-5-phosphate (Ru5P).

For example, the yeast can include an exogenous RKI/RPI (i.e., a RKI/RPI that is not native to the yeast), such as exogenous RKIs/RPIs with wild-type or altered sequences that are different than the wild type. Exemplary eukaryotic RKI/RPIs include, but are not limited to, *Arabidopsis thaliana* RPI1 (Q9C998), *Saccharomyces cerevisiae* RKI1 (Q12189), *Schizosaccharomyces pombe* rki1 (Q9UTL3), *Aspergillus niger* RPI (G3Y280), *Candida albicans* RKI1 (Q5AJ92), and *Kluyveromyces lactis* RKI1 (Q6CTD5).

Expression of an exogenous RKI/RPI gene can be controlled by a heterologous promoter, terminator, or both. For example, the RKI/RPI can be over expressed using a strong promoter. Regulatory sequences can be chosen to provide RKI/RPI activity in an amount that is greater than the amount of RKI/RPI activity occurring naturally in the cell. Further, an exogenous RKI/RPI can be placed at one or more desired locations in the genome, which may also provide desired expression. One or more copies (e.g., two, three, four, five, etc.) of an exogenous RKI/RPI can be engineered in the cell.

RKI/RPI activity can also be altered in the cell by changing the one or more features of the endogenous RKI/RPI gene such as to provide: a heterologous promoter, a heterologous terminator, a different genomic location for the endogenous RKI/RPI gene, or multiple copies of the endogenous RKI/RPI gene. The one or more changes can be result in increased expression of the endogenous RKI/RPI gene, and thereby increased endogenous RKI/RPI activity.

Another optional additional genetic modification affects a xylose transporter expression or activity. For example, the yeast can include an exogenous a xylose transporter (i.e., a xylose transporter that is not native to the yeast), such as exogenous a xylose transporters with wild-type or altered sequences that are different than the wild type. Exemplary xylose transporters include, but are not limited to *Aspergillus nidulans* xtrD (AN0250), *Candida intermedia* Gxf1 (Q2MDH1), and *Kluyveromyces marxianus* KHT105.

Expression of an exogenous xylose transporter gene can be controlled by a heterologous promoter, terminator, or both. For example, the xylose transporter can be over expressed using a strong promoter. Regulatory sequences can be chosen to provide xylose transporter activity in an amount that is greater than the amount of xylose transporter activity occurring naturally in the cell. Further, an exogenous xylose transporter can be placed at one or more desired locations in the genome, which may also provide desired expression. One or more copies (e.g., two, three, four, five, etc.) of an exogenous xylose transporter can be engineered in the cell.

Xylose transporter activity can also be altered in the cell by changing the one or more features of the endogenous xylose transporter gene such as to provide: a heterologous promoter, a heterologous terminator, a different genomic location for the endogenous xylose transporter gene, or multiple copies of the endogenous xylose transporter gene. The one or more changes can be result in increased expression of the endogenous xylose transporter gene, and thereby increased endogenous xylose transporter activity.

Another optional additional genetic modification affects one or more genes affecting arabinose consumption (e.g., araA, araB, and araD) expression or activity. For example, the yeast can include an exogenous arabinose consumption gene (i.e., that is not native to the yeast), including those that are exogenous arabinose consumption genes with wild-type or altered sequences that are different than the wild type. The arabinose consumption genes can be obtained from organisms such as *Bacteroides thetaiotaomicron* and *Leuconostoc citreum.*

Expression of an exogenous arabinose consumption gene can be controlled by a heterologous promoter, terminator, or both. For example, the arabinose consumption gene can be over expressed using a strong promoter. Regulatory sequences can be chosen to provide arabinose consumption activity in an amount that is greater than the amount of arabinose consumption activity occurring naturally in the cell. Further, an exogenous arabinose consumption gene can be placed at one or more desired locations in the genome, which may also provide desired expression. One or more copies (e.g., two, three, four, five, etc.) of an arabinose consumption gene can be engineered in the cell.

Arabinose consumption activity can also be altered in the cell by changing the one or more features of the endogenous arabinose transporter gene such as to provide: a heterologous promoter, a heterologous terminator, a different genomic location for the endogenous arabinose transporter gene, or multiple copies of the endogenous arabinose transporter gene. The one or more changes can be result in increased expression of the endogenous arabinose transporter gene, and thereby increased endogenous arabinose transporter activity.

Other optional modifications include changes to regulatory elements that down regulate expression of genes; and deletions or mutations that eliminate expression, or reduce expression of a gene or gene product. Attenuate means weakening, reducing or diminishing the activity or amount of an enzyme or protein, such as compared to the activity of the naturally occurring. The attenuation of enzyme activity can reflect complete disruption if the attenuation causes the activity or amount to fall below a critical level required for a given pathway to function. When an enzyme is eliminated or its activity is eliminated, this means the enzyme or its activity is not present in the cell. Expression of an enzyme can be eliminated when the nucleic acid that normally encodes the enzyme or protein, is not transcribed.

Another optional additional genetic modification affects an aldose reductase, such as xylose reductase (XR), expression or activity. For example, XR gene can be deleted or mutated to eliminate or reduce its activity. Alternatively, the nucleic acid-encoding sequence can be de-optimized so the host cell does not efficiently express the gene, or the gene regulatory elements can be modified, such as by using a weak promoter and/or terminator.

Other aldose reductases are present in yeast and these can also be targeted for genetic modification. For example, another additional genetic modification affects aldose reductase (AXR2 or AXR3) expression or activity. For example, AXR2 or AXR3 can be deleted or mutated to eliminate or reduce its activity.

Another optional additional genetic modification affects xylitol dehydrogenase (XDH) expression or activity. For example, XDH can be deleted or mutated to eliminate or reduce its activity. Alternatively, a host strain may be chosen that has low XDH activity. For example, in some yeasts (e.g. some *S. cerevisiae*), the native XDH activity can be low enough to provide a desired lower level of activity.

Another optional additional genetic modification affects a glycerol-3-phosphate dehydrogenase (GPD) expression or activity. For example, a GPD gene can be deleted or mutated to eliminated or reduce its activity. Alternatively, the nucleic acid-encoding sequence can be de-optimized so the host cell does not efficiently express the GPD gene, or the gene regulatory elements can be modified, such as by using a weak promoter and/or terminator. Depending on the yeast host organism, more than one GPD gene may be present. If there are one than one GPD gene present, those GPD genes (e.g., GPD1, GPD2) can be altered to eliminate or reduce its expression or activity.

Optionally, for strains that have eliminated or reduced GPD expression or activity, a non-phosphorylating glyceraldehyde-3-phosphate dehydrogenase (GAPN) gene can be introduced, e.g., exogenously, into the cell. GAPN catalyzes the irreversible reaction of glyceraldehyde-3-phosphate to 3-phosphoglycerate by the reduction of NADP to NADPH. Exemplary exogenous GAPN genes are gapN from *Streptococcus mutans* serotype c (strain ATCC 700610/UA159) (Q59931), and gapN from *Bacillus anthracis* (Q81UL6).

Another optional additional genetic modification affects an alcohol dehydrogenase (ADH) expression or activity. For example, ADH gene can be deleted or mutated to eliminate or reduce its activity. Alternatively, the nucleic acid-encoding sequence can be de-optimized so the host cell does not efficiently express the gene, or the gene regulatory elements can be modified, such as by using a weak promoter and/or terminator.

In some embodiments, the activity of an alcohol dehydrogenase with at least 80%, at least 85%, at least 90%, or at least 95% identity SEQ ID NO:99 (ADH9091) or SEQ ID NO:100 (ADH1202) can be reduced or eliminated by genetic modification.

In another embodiment, the activity of a NADP-dependent alcohol dehydrogenase, such as ADH6 (*S. cerevisiae* Q04894) can be reduced or eliminated by genetic modification.

Other optional additional genetic modifications can affect the transport of acetate. For example, the yeast cell can be modified to introduce or increase the expression or activity of an acetate transporter, such as ADY2 (*S. cerevisiae* P25613). As another option, a bacterial autotransporter (AT) such as the *Escherichia coli* (aatA) autotransporter gene is introduced into the yeast. As yet another option, the expression or activity of a gene such as FPS1 (*S. cerevisiae* P23900), which is involved in uptake of acetic acid and also the passive diffusion of glycerol, is reduced or eliminated.

Another optional additional genetic modification affects an pyruvate decarboxylase expression or activity. The pyruvate decarboxylase (PDC) enzymes class carries out the non-oxidative decarboxylation of pyruvate to acetaldehyde. Fermentative organisms such as *Saccharomyces cerevisiae* express several PDC isozymes (e.g., PDC1, PDC5, PDC6), and *Issatchenkia orientalis* (and other Crabtree-negative yeasts), also express a PDC. In some embodiments, a PDC gene can be deleted or mutated to eliminate or reduce its activity. Alternatively, the nucleic acid-encoding sequence can be de-optimized so the host cell does not efficiently express the gene, or the gene regulatory elements can be modified, such as by using a weak promoter and/or terminator.

Another optional additional genetic modification affects a heat shock protein (HSP) or chaperonin. HSP genes are cytoprotective genes that can act during periods of thermal and other environmental stresses. Chaperonins are protein remodelers capable of shielding, folding, or unfolding substrates in a context-dependent manner. One or more genetic alterations can be made in the yeast to affect HSP or chaperonin expression or activity. For example, a heterologous gene construct encoding an exogenous or endogenous HSP or chaperonin can be expressed in the host yeast. Optionally the HSP or chaperonin can be functional in the cytosol. Optionally, a mitochrondrial targeting sequence is removed from the gene encoding the heterologous HSP or chaperonin. Optionally, the protein may by a member of the HSP60 or HSP70 families of proteins. Optionally, the mitochondrial targeting sequence that is removed can be identified be using predication algorithms (for example, see MITOPROT: Prediction of mitochondrial targeting sequences from Institute of Human Genetics, Helmholtz Center Munich; ihg.gsf.de/ihg/mitoprot.html)

Optionally, the yeast can include one or more further genetic modifications which improve fermentation performance on a substrate containing a lignocellulosic hydrolysate. Fermentation can be improved by heterologous expression of one or more of the following genes: acetyl-coA synthetase (e.g., ACS1, shown to improve acetic acid tolerance in *S. cerevisiae*), aldehyde dehydrogenase (e.g., ALD1 shown to degrade undesirable aldehydes present in hydrolysates, such a furfurals), carnitine acetyl-CoA transferase (e.g., CAT2, shown to improve acetic acid tolerance in *S. cerevisiae*), carnitine acetyltransferase (e.g., YAT1, YAT2, shown to improve acetic acid tolerance in *S. cerevisiae*), and citrate synthase (e.g., CIT1 shown to increase cell growth and ethanol production in *E. coli*, and reduce the need for complex nutrients). Expression of any of these genes can be controlled by a heterologous promoter, terminator, or both. Further, one or more copies of any of these genes can be engineered in the cell.

Other optional additional genetic modifications include increased activity of a heat shock transcription factor, such as HSF-1 (*S. cerevisiae* P10961), transformation with a heterologous invertase, and increased activity of PUT4. Another genetic modification is deletion of pho13, which encodes haloacid dehalogenase typeIIA phosphatase that improves xylose utilization when XI expression is high in *Saccharomyces cerevisiae* (Lee et al, Biotechnology for Biofuels, 7:122, 2014).

Various host cells can be transformed with a nucleic acid including the xylose isomerase gene. In some embodiments the nucleic acid including the xylose isomerase gene is present in a bacterial cell. The bacterial cell can be used, for example, for propagation of the nucleic acid sequence or for production of quantities of the polypeptide.

In other aspects, the host cell is a eukaryotic cell, such as a fungal or yeast cell.

In preferred aspects, the host cell is a Crabtree negative yeast. The "Crabtree effect," concerns the inhibition of synthesis of respiratory enzymes. The Crabtree effect is defined as the occurrence of fermentative metabolism under aerobic conditions as a result of the inhibition of oxygen consumption by a microorganism when cultured at high specific growth rates (long-term effect) or in the presence of high concentrations of glucose (short-term effect). Organisms with the Crabtree negative phenotype do not exhibit this effect, and are thus able to consume oxygen even in the presence of high concentrations of glucose or at high growth rates. Whether an organism is Crabtree positive or Crabtree negative can be determined by comparing the ratio of fermented glucose to respirated glucose during cultivation under aerobic conditions, with a ratio of greater than 1 indicative of a Crabtree positive organism (e.g., see De Deken, R. H. (1965) J. gen. Microbiol., 44:149-156). *S. cerevisiae* is an example of a yeast that exhibits the Crabtree effect, and is therefore Crabtree positive. "Crabtree negative" yeasts, on the other hand, do not show a Crabtree effect.

In one embodiment, the Crabtree-negative yeast is selected from a genera group of *Kluyveromyces, Pichia, Issatchenkia, Hansenula*, and *Candida*. Preferably the Crabtree-negative yeast is selected from a genera group of *Kluyveromyces*, *Pichia*, and *Issatchenkia*. Examples of Crabtree-negative yeasts include *Kluyveromyces lactis*, *Kluyveromyces marxianus*, *Pichia anomala*, *Pichia stipitis*, *Hansenula anomala*, *Candida utilis* and *Kluyveromyces waltii*.

In an embodiment, the genetically modified microorganism is a yeast of the *I. orientalis/P. fermentans* clade. The *I. orientalis/P. fermentans* clade is the most terminal clade that contains at least the species *I. orientalis*, *Pichia galeiformis*, *Pichia* sp. YB-4149 (NRRL designation), *Candida ethanolica*, *Pichia deserticola*, *P. membranifaciens*, and *P. fermentans*. Members of the *I. orientalis/P. fermentans* clade are identified by analysis of the variable D1/D2 domain of the 26S ribosomal DNA of yeast species, using the method described by Kurtzman and Robnett in "Identification and Phylogeny of Ascomycetous Yeasts from Analysis of Nuclear Large Subunit (26S) Ribosomal DNA Partial Sequences," *Antonie van Leeuwenhoek* 73:331-371, 1998, incorporated herein by reference (see especially p. 349). Analysis of the variable D1/D2 domain of the 26S ribosomal DNA from hundreds of ascomycetes has revealed that the *I. orientalis/P. fermentans* clade contains very closely related species. Members of the *I. orientalis/P. fermentans* clade exhibit greater similarity in the variable D1/D2 domain of the 26S ribosomal DNA to other members of the clade than to yeast species outside of the clade. Therefore, other members of the *I. orientalis/P. fermentans* clade can be identified by comparison of the D1/D2 domains of their respective ribosomal DNA and comparing to that of other members of the clade and closely related species outside of the clade, using Kurtzman and Robnett's methods.

In certain embodiments, the genetically modified yeast cells provided herein belong to the genus *Issatchenkia*, and in certain of these embodiments the yeast cells are *I. orientalis*. An alternative name for *I. orientalis* is *Pichia kudriavzevii*. The anamorph (asexual form) of *I. orientalis* is known as *C. krusei*. Numerous additional synonyms for the species *I. orientalis* have been listed elsewhere (Kurtzman and Fell, The Yeasts, a Taxonomic Study. Section 35. *Issatchenkia Kudryavtsev*, pp 222-223 (1998)).

In some aspects the host cell has tolerance to a higher amount of a bioderived product, such as ethanol, in the fermentation media. In some embodiments, the host cell is an "industrial yeast" which refers to any yeasts used conventionally in ethanol fermentation. Examples include sake yeasts, shochu yeasts, wine yeasts, beer yeasts, baker's yeasts, and the like. Sake yeasts demonstrate high ethanol fermentability and high ethanol resistance and genetic stability. Typically, an industrial yeast has high ethanol resistance and preferably is viable at ethanol concentrations of 10% or greater.

In some embodiments, the host cell is *S. cerevisiae*. Some *S. cerevisiae* have high tolerance to ethanol. Various strains of ethanol tolerant yeast are commercially available, such as RED STAR® and ETHANOL RED® yeast (Fermentis/Lesaffre, USA), FALI (Fleischmann's Yeast, USA), SUPERSTART and THERMOSACC® yeast (Ethanol Technology, Wis., USA), BIOFERM AFT and XR (NABC—North American Bioproducts Corporation, GA, USA), GERT STRAND (Gert Strand AB, Sweden), and FERMIOL (DSM Specialties).

Most yeast strains are prototrophic and do not have an auxotrophic marker suitable for selecting for a transformant. If the host cell does not have the genetic background that would otherwise facilitate retention of the xylose isomerase gene (alone or with other heterologous genes) within the cell upon transformation, the host cell can be engineered to introduce one or more genetic mutation(s) to establish use of a marker gene in association with and to maintain the exogenous gene in the cell.

A marker for a different auxotrophy can be provided by disrupting the gene that controls the auxotrophy. In one mode of practice, a strain of yeast is engineered to disrupt copies of one or more genes that control auxotrophies, such as LEU2, HIS3, URA3, URA5, and TRP1. In the case of providing uracil auxotrophy, for example, a normal URA3 gene of a yeast strain can be replaced with an $URA3^{-}$ fragment obtained from a uracil auxotrophic mutant (for example, a *Saccharomyces cerevisiae* MT-8 strain) to disrupt the normal URA3 gene. In the case of a URA3 gene-disrupted strain, the presence/absence of a marker can be easily identified or selected by taking advantage of the fact that a URA3 gene-disrupted strain is able to grow in a medium containing 5-fluoroorotic acid (5-FOA) while a normal URA3 strain (wild-type yeast or usual industrial yeast) is not able to grow. In the case of a LYS2 gene-disrupted strain, the presence/absence of a marker can be easily identified or selected by taking advantage of the fact that a LYS2 gene-disrupted strain is able to grow in a medium containing α-aminoadipic acid while a normal LYS2 strain (wild-type yeast or usual industrial yeast) is not able to grow. Methods for disrupting an auxotrophy-controlling gene and for selectively separating auxotrophy-controlling gene mutants may be used depending on the auxotrophy employed. Alternatively, one can employ dominant selection markers, such as the amdS from *Aspergillus nidulans* (U.S. Pat. No. 5,876,988), which allows for growth on acetamide as the sole nitrogen source; or ARO4-OFP, which allows for growth in the presence of fluoro-phenylalanine (Fukuda et. al.). Additionally markers may enable use of a substrate, such as melibiose. An example of such a marker is the melibiase (alpha-galactosidase) gene from *S. cerevisiae* (MEL5). These markers can be used repeatedly using the recyclable cre-loxP system, using counter-selection techniques such as growth of a normal URA3 strain in the presence of 5-FOA, or alternatively can be used to create auxotrophic strains that allow additional markers to be utilized.

After the host cell has been engineered to provide a desired genetic background for introduction of the xylose isomerase gene (alone or with other heterologous genes), the gene construct is introduced into a cell to allow for expression. Methods for introducing a gene construct into a host cell include transformation, transduction, transfection, co-transfection, electroporation. In particular, yeast transformation can be carried out using the lithium acetate method, the protoplast method, and the like. The gene construct to be introduced may be incorporated into a chromosome in the form of a plasmid, or by insertion into the gene of a host, or through homologous recombination with the gene of a host. The transformed yeast into which the gene construct has been introduced can be selected with a selectable marker (for example, an auxotrophic marker as mentioned above). Further confirmation can be made by measuring the activity of the expressed protein.

The transformation of exogenous nucleic acid sequences including the xylose isomerase gene (alone or with other heterologous genes) can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The engineered yeast strains expressing a heterologous xylose isomerase, such as SEQ ID NO:29 (St XI) or SEQ ID NO:33 (Lg XI), along with one or more additional genetic modifications, such as a heterologous nucleic acid encoding a transaldolase, can be used in a fermentation process to make a product. The fermentation product (also referred to herein as "bioproduct") can be any product that can be prepared by consumption of carbohydrates from a composition that includes xylose, in a fermentation process.

In embodiments, the fermentation product is selected from the group consisting of amino acids, organic acids, hydroxyl-organic acids, alcohols, polyols, fatty acids, fatty acids such as methyl esters, monoacyl glycerides, diacyl glycerides, triacyl glycerides, and mixtures thereof.

Other exemplary bioproducts that are organic acids or amino acids include lactic acid, citric acid, malonic acid, hydroxy butyric acid, adipic acid, lysine, keto-glutaric acid, glutaric acid, 3-hydroxy-proprionic acid, succinic acid, malic acid, fumaric acid, itaconic acid, muconic acid, methacrylic acid, and acetic acid and derivatives thereof and salts thereof.

In some modes of practice, the xylose isomerase modified yeast strain can be further modified to include a heterologous lactate dehydrogenase (LDH) gene for enhancing the production of lactic acid. Heterologous LDH genes transformed into yeast strains are described in, for example, WO 99/14335, WO 00/71738, and WO 02/42471.

"Inoculation," as understood in the art, is the point in time wherein a microorganism capable of producing a fermentation product is introduced into the fermentation media.

"End of fermentation" is the point in time where the fermentation is stopped to harvest the fermentation product. The end of fermentation can coincide with one or more of the following events: exhaustion of the desired fraction of carbon source supplied, cessation of carbon source consumption, or cessation of fermentation product formation.

"Cell dry weight at inoculation" refers to the concentration of dry cell mass present in the fermentation medium at inoculation, as measured in a fermentation sample. For fed-batch fermentations, the initial cell dry weight is calculated based on the final volume of fermentation media. Measurement of dry cell weight is a method known to those skilled in the art. Cell dry weight at inoculation is commonly expressed in units of g/L.

"Cell dry weight at end of fermentation" refers to the concentration of dry cell mass present in the fermentation medium at end of fermentation, as measured in a fermentation sample. Cell dry weight at end of fermentation is commonly expressed in units of g/L.

"Final titer" shall be defined as the concentration of a substance in the fermentation broth at the end of fermentation. The final titer is commonly expressed in units of grams/liter (g/L).

"Initial titer" refers to the concentration of a substance present at inoculation. The initial titer is commonly expressed in units of grams/liter (g/L).

"Batch time" refers to the amount of time that has elapsed between the inoculation and the end of fermentation. The batch time is commonly expressed in units of hours (h).

"Production rate" refers to the final titer of fermentation product at end of fermentation divided by the batch time. The production rate is commonly expressed in units of grams per liter per hour (g/L/h).

One skilled in the art will recognize that the unit designation "x/y/z" is equivalent to and represents a shorthand version of the units $xy^{-1}z^{-1}$ or x/(y*z). For example g/L/h is equivalent to $gL^{-1}$ $h^{-1}$ or g/(L*h).

The "specific production rate" refers to the production rate divided by the cell dry weight at the end of fermentation.

The "consumption rate of a substrate", such as xylose, is defined using the following equation:

$$\frac{\text{total substrate consumed}}{\text{batch time} \times \text{volume at end of fermentation}}$$

That is, the substrate consumed divided by the product of batch time and the fermentation volume at the end of fermentation. The "consumption rate of a substrate" is commonly expressed in grams per liter per hour (g/L/h). The "total substrate consumed" is defined as the "total substrate added" minus the "residual substrate". It is expressed in units of grams (g).

The "total substrate added" is the mass of substrate present in the fermentation medium at the time of inoculation in addition to the mass of any additional substrate added or formed (for example, the formation of xylose due to hydrolysis of xylan) prior to the end of fermentation. The "total substrate added" is commonly expressed in units of grams (g).

The "residual substrate" is the mass of substrate present in the broth at the end of fermentation. The "residual substrate" is commonly expressed in units of grams (g). In this way, one can calculate a "xylose consumption rate" or "consumption rate of xylose". Other exemplary consumption rates can include "glucose consumption rate" or "sugar consumption rate".

As used herein, "product yield" for fermentation product is defined as a ratio of two quantities: a) mass of product produced in the course of the batch (numerator) b) the mass of the fermentable carbon source added to the batch (denominator). A lignocellulosic feedstock may include carbon source(s) that are not fermentable by the engineered yeast, and therefore the feedstock can include fermentable carbon source(s) and non-fermentable carbon source(s). The product yield as a percentage is commonly expressed in units of gram per gram (g/g) times 100. The product yield is calculated as a ratio of masses (g).

The mass of fermentation product should account for the mass of fermentation product present in the fermentation medium at the end of the batch, as well as the mass of any fermentation product harvested during the course of the batch, less the mass of fermentation product present at the start of batch, and further less the mass of any fermentation product added during the course of the batch. The mass of fermentable carbon source added to the batch should include the mass of all fermentable carbon source(s) present in the fermenter at the start of the batch in addition to the mass of any fermentable carbon source(s) added or formed (for example, the formation of xylose due to hydrolysis of xylan) during the course of the batch less the mass of fermentable carbon source(s) present in the fermenter at the end of fermentation.

Fermentation using a host cell expressing the heterologous xylose isomerase, such as SEQ ID NO:29 (St XI) or SEQ ID NO:33 (Lg XI), can be performed in the presence of carbohydrate composition that include xylose, or that includes xylose source. The carbohydrate composition can be used to form the fermentation medium for the engineered yeast. The carbohydrate composition can be formed from a polysaccharide-containing plant material, referring to a polysaccharide-containing plant material derivable from any plant or plant part, such as tubers, roots, stems, leaves, and seeds.

Part or all of the carbohydrate composition that includes xylose can be obtained from cellulosic biomass. Examples of cellulosic biomass include agricultural materials, such as corn stover and sugarcane bagasse, forestry materials such as sawdust, and mill wastes, some municipal solid waste, such as waste paper, and herbaceous and woody materials, such as switchgrass and poplar trees. Optionally, the carbohydrate composition can be formed from a cellulosic biomass and a starch-containing biomass.

Lignocellulosics can provide a source of xylose. Components of lignocellulosics include cellulose, hemicellulose, and lignin, and the amount of these components can vary from one plant species to another. Cellulose is a linear polymer of β-(1→4)-linked D-glucopyranose.

Hemicellulose is polysaccharide that is found in abundance in the plant cell wall. Hemicellulose includes short branched chain heteropolysaccharides of mixed hexosans and penosans. Classification of hemicelluloses is according to the main sugar residue in the backbone. Classes include xylans, mannans, and glucans. There are also subclasses of hemicellulose which include glucuronoxylans, arabinoxylans, linear mannans, glucomannans, galactomannans, galactoglucomannans, h-glucans, and xyloglucans.

Xylans and mannans are classes of hemicelluloses in greatest abundance. A common hemicellulose is xylan, a xylose polymer. Xylans include those polysaccharides that have a β-(1→4)-D-xylopyranose backbone with various side chains. The specific type of xylan is dictated by the composition and linkages of its side chains. The rate of degradation of xylan by endoxylanase enzymes can be enhanced by removal of side chains.

Mannans are linear polymers of β-(1→4)-linked mannopyranosyl residues and have structural and degradation properties similar to cellulose. β-Glucan and xyloglucan are also structurally similar to cellulose and are based on a β-linked glucose backbone. ρ-Glucan includes mixtures of β-(1→4), β-(1→4), and β-(1→6)-linked glucose residues. Xyloglucan is a straight β-(1→4) glucopyranose polymer including some α-(1→6)-linked xylose residues.

In some modes of practice, a fermentation composition that includes hemicellulose and/or cellulose can be affected by one or more compounds, such as acids or enzymes, that cause the formation of monomeric sugars that can be consumed by the engineered yeast and converted into one or more bioproducts. In some modes of practice, cellulose and/or hemicellulose is subjected to hydrolysis, such as acid hydrolysis, enzymatic hydrolysis, or combinations thereof. The process may include pretreatment steps of pressurizing the lignocellulosics for feeding to pretreatment reactors. The lignocellulosic material may be kept at high at high solids concentrations to efficiently use of any steam applied to the materials to promote hydrolysis. In some modes of practice, the lignocellulosic material is treated with a strong acid, such as sulfuric acid. An exemplary concentration is an amount in the range of about 0.5 to about 1% (w/v), an exemplary treatment time is in the range of about 10 to about 20 minutes, and an exemplary temperature is in the range of about 140° C. to about 190° C. The hydrolyzed lignocellulosic material can be cooled after treatment and treated to remove inhibitors, such as by base addition or column (e.g., ion exchange) treatment.

For example, the acid hydrolysis of hemicellulose proceeds in a manner similar to that for cellulose, where the acid catalyzes the cleavage of long hemicellulose chains to form shorter chain oligomers and then to sugar monomers. The amorphous nature of hemicellulose makes it susceptible to degradation in conditions that are not as harsh as conditions used for cellulose degradation.

Enzyme treatment for the hydrolysis of the lignocellulosic materials can be used as an alternative acid treatment, or can be used as a supplement to, or in combination with, the acid treatment. Enzyme treatment can involve the addition of one or more lignocellulosic-degrading enzyme(s), to the lignocellulosic material. Alternatively, lignocellulosic material is placed in a medium with a microorganism that produces a lignocellulosic-degrading enzyme(s). The microorganism may be one that is different from the xylose isomerase-modified yeast of the disclosure. For example, various cellulolytic fungi can be used to treat the lignocellulosic materials, such as a fungi from the group of hyphomycetes, ascomycetes, and basidiomycetes. As yet another option, the xylose isomerase-modified yeast can be further engineered to produce a lignocellulosic-degrading enzyme(s).

Various types of lignocellulosic-degrading enzymes can be used. For example, endoglucanases, such as "endo-1→4-β-glucanases" or 1,4-β-D-glucan 4-glucanohydrolases (EC 3.2.1.4), which act randomly on soluble and insoluble 1,4-β-glucan substrates, can be used to treat lignocellulosic materials. Exoglucanases, such as "exo-1,4-β-D-glucanases" include both the 1,4-β-D-glucan glucohydrolases (EC 3.2.1.74), which liberate D-glucose from 1,4-β-D-glucans and hydrolyze D-cellobiose, and 1,4-β-D-glucan cellobiohydrolases (EC 3.2.1.91), which liberate D-cellobiose from 1,4-β-glucans, can be used to treat lignocellulosic materials. Beta-D-Glucosidase, such as "β-D-glucosidases" or β-D-glucoside glucohydrolases (EC 3.2.1.21) act to release D-glucose units from cellobiose and soluble cellodextrins, as well as various glycosides.

Hemicellulases are produced by various bacteria and fungi, as well as by several plants. Common commercial hemicellulase preparations are from engineered *Trichoderma* or *Aspergillus* strains. Many microbial hemicellulases are active in a pH range of between 4 and 6 and at temperatures below 70° C. Xylanases, which are stable and function efficiently at high temperatures, have been isolated especially from thermophilic bacteria. Several xylanase genes, encoding proteins active at temperatures from 75° C. up to 95° C. (pH 6-8), have been isolated.

Endoxylanases (1,4-β-D-xylan xylanohydrolases, EC 3.2.1.8) randomly cleave the main chain 1,4-β-D-xylosidic linkages and can have specificity to the linkage type, sugar type, and presence or absence of nearby substituents. An endoxylanase that cleaves β-(1,4) linkages will usually have no effect on β-(1,3) linkages. In addition, an endoxylanase that cleaves main-chain linkages near an O-2-linked arabinose will have no effect on an open-chain xylan. Although there are such specific examples of endo-acting hemicellulose hydrolases requiring side chains for maximal activity, the majority of the endo-acting hemicellulose hydrolases tend to be more active on debranched or partially debranched hemicellulose, especially in the case of xylanases.

Endomannanases (1,4-β-D-mannan mannanohydrolase, EC 3.2.1.78) catalyze the random hydrolysis of β-D-1,4 mannopyranosyl linkages within the main chain of mannans and various polysaccharides consisting mainly of mannose, such as glucomannans, galactomannans, and galactoglucomannans. Mannanases are generally larger proteins than xylanases (Mr 30-90 kDa) and have acidic isoelectric points.

Enzymes for further hydrolysis of the short oligomeric compounds produced by endo-enzymes from hemicelluloses are β-xylosidase (1,4-β-D-xyloside xylohydrolase EC 3.2.1.37), β-mannosidase (1,4-β-D-mannoside mannohydrolase, EC 3.1.1.25), and β-glucosidase (EC 3.2.1.21). β-Xylosidases and β-mannosidase catalyze the hydrolysis of xylo- and manno-oligosaccharides, respectively, by removing successive xylose or mannose residues from the nonreducing termini. Exoglycanases are generally larger proteins than endoglycanases, with molecular weights above 100 kDa and they are often built up by two or more subunits.

The side groups connected to xylan and glucomannan main chains are removed by α-glucuronidase (EC 3.2.1.139), α-arabinosidase (α-L-arabinofuranoside arabinofuranohydrolase, EC 3.2.1.55), and α-D-galactosidase (α-D-galactoside galactohydrolase, EC 3.2.1.22). Acetyl and hydroxycinnamic acid substituents bound to hemicellulose are removed by acetyl xylan esterases (3.1.1.72) and other esterases.

A fermentation composition can include one or more enzymes in addition to any enzymes that are used for hydrolysis of the lignocellulosic material. Exemplary enzymes that are useful for digestion of non-lignocellulosic material include those that are used for digesting starch materials, proteins, and fats. For example, additional enzymes include alpha-amylases, beta-amylases, peptidases (proteases, proteinases, endopeptidases, exopeptidases), pullulanases, isoamylases, acetolactate decarboxylases, cyclodextrin glycotransferases, lipases, phytases, laccases, oxidases, esterases, cutinases, and granular starch hydrolyzing enzymes.

In some embodiments the fermentation method can be explained with reference to an amount of xylose present in the fermentation medium for use by the engineered yeast. Xylose can be added to or formed in the fermentation medium, or both. For example, in some modes of practice an amount of lignocellulosic material is added to a fermentation medium and then it is hydrolyzed to provide a desired amount of xylose. Using known degradation techniques, such as described herein and including chemical or enzymatic hydrolysis, the lignocellulosic material can be hydrolyzed to provide a desired amount of xylose in the medium. Such hydrolysis can take place before the fermentation process is started, or before and during the fermentation process.

In other modes of practice, xylose is generated in a composition by hydrolysis of a lignocellulosic material to generate a desired amount of xylose. The composition can optionally be refined, such as by enriching the amount of xylose in the composition, and then the composition can be added to a fermentation medium to provide xylose at a desired concentration.

In some modes of practice, the fermentation method can include a concentration of xylose (e.g., generated by hydrolysis lignocellulosic feedstock, or addition of a xylose-containing composition to the fermentation medium) of over a certain amount in the fermentation medium, under a certain amount in the fermentation medium, or within a certain range in the in the fermentation medium. For example, in some embodiments, the fermentation medium has an amount of xylose of at least about 15 g/L, at least about 25 g/L, at least about 35 g/L, at least about 50 g/L, at least about 60 g/L, at least about 70 g/L, at least about 80 g/L, at least about 90 g/L, or at least about 100 g/L, in the fermentation medium during at least one fermentation time point.

In other embodiments, the fermentation medium has an amount of xylose of not greater than about 300 g/L, not greater than about 275 g/L, not greater than about 250 g/L, not greater than about 225 g/L, not greater than about 200 g/L, not greater than about 175 g/L, or not greater than about 150 g/L in the fermentation medium during at least one fermentation time point.

In other embodiments, the fermentation medium has an amount of xylose in the range of about 15 g/L to about 300 g/L, about 25 g/L to about 225 g/L, about 35 g/L to about 150 g/L, about 50 g/L to about 150 g/L, or about 50 g/L to about 100 g/L, or about 100 g/L to about 150 g/L during at least one fermentation time point.

The amount of xylose in the fermentation medium may also be defined with regards to the total amount of fermentable carbohydrates in the medium. Fermentable carbohydrates include those of monomeric sugars, as well as polymers that can be hydrolyzed in the medium during the course of fermentation. The amount of xylose can be expressed as a weight percentage (wt/wt) of the fermentable carbohydrates. In some modes of practice, the amount of xylose is about 15% (wt) or greater, about 25% (wt) or greater, about 35% (wt) or greater, about 45% (wt) or greater, about 55% (wt) or greater, about 65% (wt) or greater, about 75% (wt) or greater, about 85% (wt) or greater, or about 95% (wt) or greater of the total fermentable carbohydrates in the carbohydrate composition in the fermentation during at least one fermentation time point. Other carbohydrates that may be in the fermentation media are ones that do not use the xylose pathway, such as glucose.

In some modes of practice, the amount of xylose is in the range of about 15% (wt) to about 98% (wt), about 25% (wt) to about 98% (wt), about 35% (wt) to about 98% (wt), about 50% (wt) to about 98% (wt), about 60% (wt) to about 98% (wt), about 70% (wt) to about 98% (wt), about 80% (wt) to about 98% (wt), or about 90% (wt) to about 98% (wt), of the total fermentable carbohydrates in the carbohydrate composition in the fermentation during at least one fermentation time point. Other carbohydrates that may be in the fermentation media are ones that do not use the xylose pathway, such as glucose.

The amount of xylose in the fermentation medium may also be defined with regards to the amount of glucose, if present, in the medium. If glucose is present in the fermentation medium xylose can be present in an amount greater than glucose, as measured by weight. More specifically, in the fermentation medium xylose can present in an amount of at least about two times, at least about three times, at least about four times, at least about five times, at least about six times, at least about seven times, at least about eight times, at least about nine times, or at least about ten times, greater than glucose.

The amount of xylose can be expressed as a weight percentage (wt/wt) of the fermentable carbohydrates. In some modes of practice, the amount of xylose is about 15% (wt) or greater, about 25% (wt) or greater, about 35% (wt) or greater, about 45% (wt) or greater, about 55% (wt) or greater, about 65% (wt) or greater, about 75% (wt) or greater, about 85% (wt) or greater, or about 95% (wt) or greater of the total fermentable carbohydrates in the carbohydrate composition in the fermentation. Other carbohydrates that may be in the fermentation media are ones that do not use the xylose pathway, such as glucose.

Also, growth of the engineered yeast can be performed with aeration, and with agitation. Aeration conditions can have an effect on the amount of oxygen dissolved in the medium, and therefore the oxygen available to the engineered yeast. The amount of oxygen uptake by the engineered yeast can be controlled by the rate at which oxygen is supplied the formation of small oxygen bubbles in the medium, which can be achieved through agitation and/or sparging. The fermentation method can include introducing an oxygen containing fluid into the fermentation medium. In some modes of practice, the during fermenting there is an oxygen uptake rate (OUR) in the range of 0.3 mmoles $L^{-1}$ $hr^{-1}$ to 20 mmoles $L^{-1}$ $hr^{-1}$ and the dissolved oxygen is less than 1% of atmospheric air saturation.

Optionally, in addition to the lignocellulosic material, a starch and/or sugar-containing plant material can be used as fermentation feedstock. The starch and/or sugar-containing plant material can be one obtained from cereal, such as barley, wheat, maize, rye, sorghum, millet, barley, potatoes, cassava, or rice, and any combination thereof. The starch- and/or sugar comprising plant material can be processed, such as by methods such as milling, malting, or partially malting. In some embodiments, the starch material is from corn flour, milled corn endosperm, sorghum flour, soybean flour, wheat flour, biomass derived starch, barley flour, and combinations thereof.

For example, a fermentation feedstock can include a partially hydrolyzed starch in addition to the lignocellulosic material. The partially hydrolyzed starch can include high molecular weight dextrins and high molecular weight maltodextrins. Exemplary partially hydrolyzed starch products have a dextrose equivalent ("DE") in the range of about 5 to about 95 or more preferably about 45 to about 65, is used in the fermentation media. DE is the reducing sugars content expressed as dextrose percentage on dry matter. For example, dextrose-free pure starch has a DE of zero, while pure dextrose has a DE of 100.

Partially hydrolyzed starches and preparation thereof are well known in the art. Partially hydrolyzed starches can be prepared by heating the starch with an acid such as hydrochloric or sulfuric acid at a high temperature and then neutralizing the hydrolysis mixture with a suitable base such as sodium carbonate. Alternatively, partially hydrolyzed starches can be prepared by an enzymatic process, such as by adding alpha-amylase to a starch preparation. An alpha amylase can cause the endohydrolysis of (1→4)-alpha-D-glucosidic linkages in polysaccharides containing three or more (1→4)-alpha-linked D-glucose units. For example, a partially hydrolyzed corn starch by enzymatic treatment is a liquefied corn starch that has been taken through liquefaction and treated with an alpha-amylase. A partially hydrolyzed starch product can be used that has amounts of starch and starch degradation products within desired ranges.

The fermentation broth includes water and preferably includes nutrients, such as a nitrogen source (such as proteins), vitamins and salts. A buffering agent can also be present in the fermentation media. Other components may also be present in the fermentation broth after a period of fermentation, such as fermentation products which can accumulate as the fermentation progresses, and other metabolites. Optionally, the fermentation broth can be buffered with a base such as calcium hydroxide or calcium carbonate, ammonia or ammonium hydroxide, sodium hydroxide, or potassium hydroxide in order to maintain a pH at which the organism functions well.

In some embodiments, in addition to the lignocellulosic feedstock, the fermentation medium can be supplemented with one or more materials to provide a desired medium for yeast growth. For example, the fermentation medium can include yeast extract in an amount of about 0.01% (wt) or greater, about 0.05% (wt) or greater, or about 0.1% (wt) or greater, such as in the range of about 0.01% (wt) to about 1% (wt), or about 0.05% (wt) to about 0.5% (wt). Another material that can be present in the fermentation medium is acetate. For example, the fermentation medium can include acetate in an amount of about 1 g/L or greater, about 5 g/L or greater, such as in the range of about 1 g/L to about 20 g/L, or about 5 g/L to about 15 g/L.

Fermentation can be carried out in industrial capacity fermenters in order to achieve commercial scale economic benefits and control. In embodiments, the process is carried out in fermentation broth quantities of at least 25,000 gallons, at least 50,000 gallons, at least 75,000 gallons, at least 100,000 gallons, at least 125,000 gallons, at least 150,000 gallons, at least 175,000 gallons, or even at least 200,000 gallons. Preferably fermentation is carried out as a continuous process or a fed-batch process on a large scale.

The fermentation is carried out under conditions so that fermentation and desired production of a bioproduct can occur. Although conditions can vary depending on the particular organism and desired fermentation product, typical conditions include a temperature of about 20° C. or greater, and more typically in the range of about 30° C. to about 50° C., about 30° C. to about 45° C., or about 30° C. to about 40° C. During fermentation the reaction mixture can be mixed or agitated. In some modes of practice, the mixing or agitation can occur by the mechanical action of sparging gas to the fermentation broth. Alternatively direct mechanical agitation such as by an impellor or by other means can be used during fermentation.

The pH of the fermentation media can be adjusted to provide optimal conditions for xylose isomerase activity, cell growth, and fermentation activity to provide a desired product, such as ethanol. For example, pH of the solution can be adjusted to in the range of 3 to 7. In one mode of practice, the pH of the fermentation media is in the range of 4 to 6.5. During fermentation the medium can be monitored for pH, and acid or base can be added as needed to maintain the medium at a desired pH range.

In some modes of practice, the fermentation is carried out as a single batch until completion. In other modes of practice, the fermentation is carried out as a fed batch fermentation process. In this mode of practice, a first portion of a total amount of feedstock including the lignocellulosic material and/or hydrolysate thereof, to be fermented is added to the fermentation media. Additional feedstock including the lignocellulosic material and/or hydrolysate thereof is added in one or more portions to provide more carbohydrate for the fermentation. The addition of the feedstock material can be regulated. Optionally the amount of xylose present in the medium can be monitored to provide efficient fermentation.

In some modes of practice, a portion of the final fermentation broth is retained in the fermenter or recycled back into the fermenter to serve as inoculum for a subsequent batch fermentation.

In some modes of practice the fermentation process is carried out to provide a rate of xylose consumption of at least of about 1.0 g/L/hr, at least of about 1.25 g/L/hr, at least of about 1.5 g/L/hr, at least of about 1.75 g/L/hr, at least of about 2.0 g/L/hr, at least of about 2.25 g/L/hr, at least of about 2.5 g/L/hr, at least of about 2.75 g/L/hr, at least of about 3.0 g/L/hr, at least of about 3.25 g/L/hr, or at least of about 3.5 g/L/hr. Exemplary rates of xylose consumption are in the range of about 1.0 g/L/hr to about 10.0 g/L/hr, about 1.5 g/L/hr to about 10.0 g/L/hr, about 2.0 g/L/hr to about 10.0 g/L/hr, about 2.5 g/L/hr to about 10.0 g/L/hr, or about 3.0 g/L/hr to about 10.0 g/L/hr. In embodiments these rates of xylose consumption may be observed when xylose is in an amount of at least 15 g/L in the fermentation medium, and more preferably in an amount in the range of about 35 g/L to about 150 g/L, about 50 g/L to about 150 g/L, or about 50 g/L to about 100 g/L, or about 100 g/L to about 150 g/L in the fermentation medium. In embodiments these rates of xylose consumption may be observed when fermentation is carried out for a period of about 10, 15, or 20 hours or greater, such as up to 60, 70, or 80 hours. For example, fermentation is carried out for a period in the range of about 10 to about 80 hours, or about 15 to about 70 hours, or preferably about 20 to about 80 hours.

In some embodiments, the disclosure provides a method for producing ethanol by fermentation, wherein the ethanol is present in the fermentation media at a concentration of 10 g/L or greater. In the method, a liquid media comprising a lignocellulosic material and a yeast species with a heterologous xylose isomerase is fermented. Fermentation can provide an ethanol concentration of about 10 g/L or greater in the liquid media, about 15 g/L or greater in the liquid media, about 20 g/L or greater in the liquid media, about 25 g/L or greater in the liquid media, about 30 g/L or greater in the liquid media, such as in the range of about 10 g/L to about 130 g/L, in the range of about 15 g/L to about 120 g/L, in the range of about 20 g/L to about 110 g/L, in the range of about 25 g/L to about 100 g/L, or in the range of about 30 g/L to about 90 g/L. In embodiments these rates of ethanol production may be observed when xylose is in an amount of at least 15 g/L in the fermentation medium, and more preferably in an amount in the range of about 35 g/L to about 150 g/L, about 50 g/L to about 150 g/L, or about 100 g/L to about 150 g/L in the fermentation medium. In embodiments these rates of ethanol production may be observed when fermentation is carried out for a period of about 10, 15, or 20 hours or greater, such as up to 60, 70, or 80 hours. For example, fermentation is carried out for a period in the range of about 10 to about 80 hours, or about 15 to about 70 hours, or preferably about 20 to about 80 hours.

During fermentation, the medium can be monitored for the production of a desired bioproduct, such as ethanol. Fermentation can be stopped at a point where the bioproduct reaches a maximum or desired amount. For example, in some embodiments, fermentation is stopped at a point of about 40 hours, about 50 hours, about 60 hours, about 70 hours, or about 80 hours, from the start of fermentation.

The fermentation product may be first treated with one or more agents a treatment system. The treated fermentation product can then be sent to a distillation system. In the distillation system, the fermentation product can be distilled and dehydrated into ethanol. In some embodiments, the components removed from the fermentation media include water, soluble components, oil and unfermented solids. Some of these components can be used for other purposed, such as for an animal feed product. Other co-products, can be recovered from the stillage.

Backset is the remaining fermentation broth following the removal of a bioproduct, such as alcohol, during the distillation process. Scrubber water is the liquid collected from a scrubber. Definitions of common terms of the disclosure can be found in *The Alcohol Textbook*, $4^{th}$ Edition. 1995.

The present disclosure also provides a method for the production of a food, feed, or beverage product, such as an alcoholic or non-alcoholic beverage, such as a cereal- or malt-based beverage like beer or whiskey, such as wine, cider, vinegar, rice wine, soya sauce, or juice, said method comprising the step of treating a starch and/or sugar containing plant material with a composition as described herein. The invention also relates to a fermented beverage produced by a method using the xylose isomerase.

In some modes of practice, the fermentation product can be recovered from the fermentation broth. The manner of accomplishing this will depend on the particular product. However, in some modes of practice, the organism is separated from the liquid phase, typically via a filtration step or centrifugation step, and the product recovered via, for example, distillation, extraction, crystallization, membrane separation, osmosis, reverse osmosis, or other suitable technique.

Methods

Methods for the production of competent yeast cells using standard lithium acetate methods suitable for chemical transformation with linear DNA are known in the art, such as described herein. See for example, Gietz et al. (1992), Nucleic Acids Res. 20:1425.

Methods for the selection of suitable sites in a yeast genome for gene integration are known in the art. Examples of suitable sites for integration of exogenous genes such as those that enable xylose utilization in *Issatchenkia orientalis*, include, but are not limited to, the following loci: locus GAL6, which is flanked by SEQ ID NO: 1 and SEQ ID NO: 2; locus XDH, which is flanked by SEQ ID NO: 3 and SEQ ID NO: 4; locus AXR2, which is flanked by SEQ ID NO: 5 and SEQ ID NO: 6, and locus AR4, which is flanked by SEQ ID NO:7 and SEQ ID NO: 8. Verfication of correct integrations at these loci can be carried out using oligonucleotide primers and PCR techniques known in the art, such as described herein.

Example 1: Construction of Strain D (ΔURA3, ΔCYB2A Base Strain)

An *Issatchenkia orientalis* host strain is generated by evolving *I. orientalis* strain ATCC PTA-6658 (Strain A) in a low dilution, low pH, glucose-limited chemostat with externally added lactic acid in the feed medium. Single colonies are isolated from the chemostat and screened for improved growth rate in the presence of free lactic acid. An isolate showing improvement in the screen is designated as Strain B. Both alleles of the URA3 gene and the CYB2A gene are deleted from Strain B to generate the ΔURA3, ΔCYB2A base strain, Strain D as described below.

Strain B is transformed with SEQ ID NO: 9. SEQ ID NO: 9 contains: i) an expression cassette for the selectable marker gene melibiase (alpha-D-galactosidase) from *S. cerevisiae*, encoding the amino acid sequence of SEQ ID NO: 10, that is flanked by loxP sequences and ii) flanking DNA for targeted chromosomal integration into the *I. orientalis* (Io) URA3 locus. Transformants are selected on Yeast Nitrogen Base (YNB) with amino acids and ammonium sulfate (BD #239210) plates containing 2% melibiose as the sole carbon source and 32 μg/ml 5-Bromo-4-chloro-3-indolyl a-D-galactopyranoside (x-alpha-gal), which provides a colorimetric indication of the presence of the ScMEL5 marker gene. The resulting transformants are streaked for single colony isolation on YPD (BD #24820) plates containing 32 μg/ml x-alpha-gal. The correct integration of SEQ ID NO: 9 into the selected blue colonies is verified by PCR using primers designed for the flanking regions of the IoURA3 gene (SEQ ID NO: 11 and SEQ ID NO: 12). A PCR verified isolate is transformed with SEQ ID: 13 to loop out the ScMEL5 marker. SEQ ID NO: 13 contains: i) an expression cassette for the selectable marker gene invertase from *S. cerevisiae*, encoding the amino acid sequence of SEQ ID NO: 14, and ii) an expression cassette for CRE recombinase gene, encoding the amino acid sequence of SEQ ID NO: 15, to recycle the selectable markers ScMEL5. Transformants are selected on YNB plates containing 2% sucrose as the sole carbon source and 32 μg/ml x-alpha-gal. The resulting transformants are streaked for single colony isolation on YPD containing 32 μg/ml x-alpha-gal. Loss of ScMEL5 and IoURA3 from selected white colonies is verified by PCR. To loop out the second URA3 allele, a PCR verified isolate is transformed with the SEQ ID NO: 9 as described above. Transformants are selected on YNB plates containing 2% melibiose as the sole carbon source, 50 μg/mL uracil and 32 μg/ml x-alpha-gal. The resulting transformants are streaked for single colony isolation on YPD containing 32 μg/ml x-alpha-gal. Correct integration of SEQ ID NO: 9 into the selected blue colonies is verified by PCR. The ScMEL5 marker is deleted from a PCR verified isolate by transformation with SEQ ID NO: 13 as described above. Transformants are selected on YNB plates containing 2% sucrose as the sole carbon source, 50 μg/mL uracil, and 32 μg/ml x-alpha-gal. The resulting transformants are streaked for single colony isolation on YPD containing 32 μg/ml x-alpha-gal. Loss of both the markers ScMEL5 and IoURA3 at both alleles from the selected white colonies is verified by PCR. A PCR verified isolate is designated Strain C.

Strain C is transformed with SEQ ID NO: 16. SEQ ID NO: 16 contains: i) an expression cassette for the selectable marker URA3 from *I. orientalis* (consisting of the *I. orientalis* promoter, coding sequence and terminator), encoding the amino acid sequence for SEQ ID NO: 17 (orotidine 5'-diphosphate decarboxylase), that is flanked by a direct repeat of the *I. orientalis* URA3 promoter for marker loop out and ii) flanking DNA for targeted chromosomal integration into locus CYB2A. CYB2 refers to a gene that encodes an L-lactate ferricytochrome-c oxidoreductase. In the yeast *Issatchenkia orientalis*, there are two such genes. CYB2A refers to the gene that resides at the locus flanked by SEQ ID NO: 18 and SEQ ID NO: 19.

Transformants are selected on SCD-URA plates containing glucose as the sole carbon source. The resulting transformants are streaked for single colony isolation on SCD-URA plates. The correct integration of SEQ ID NO: 16 into the selected colonies is verified by PCR using primers designed for the flanking regions of the IoCYB2A gene (SEQ ID NO: 18 and SEQ ID NO: 19). A PCR verified isolate is plated on SCD medium plates containing 1-2 g/L 5-fluorooritic acid (5-FOA) to loop out the URA3 marker. Isolates are single colony purified by growth on YPD plates and are screened by PCR to confirm the loss of the marker (leaving a scar containing only the URA3 promoter). To loop out the second CYB2A allele, a PCR verified isolate is transformed with SEQ ID NO: 20. SEQ ID NO: 20 contains: i) an expression cassette for the selectable marker URA3 from *I. orientalis* (consisting of the *I. orientalis* promoter, coding sequence and terminator), encoding the amino acid sequence for SEQ ID NO: 17 (orotidine 5'-diphosphate decarboxylase), that is flanked by a direct repeat of the *I. orientalis* URA3 promoter for marker loop out and ii) flanking DNA for targeted chromosomal integration into locus CYB2A. SEQ ID NO: 16 and SEQ ID NO: 20 differ in the orientation of the URA3 expression cassettes with respect to the IoCYB2A flanking sequences. Transformants are selected on SCD-URA plates. The resulting transformants are streaked for single colony isolation on SCD-URA. The correct integration of SEQ ID NO: 20 into the selected colonies is verified by PCR. A PCR verified isolate is plated on SCD medium plates containing 1-2 g/L 5-FOA to loop out the URA3 marker. Isolates are single colony purified by growth on YPD plates and are screened by PCR to confirm the loss of the marker (leaving a scar containing only the URA3 promoter). A PCR verified isolate is designated strain D.

TABLE 1-1

| SCD Medium Plates | |
|---|---|
| Difco ™ Yeast Nitrogen Base without amino acids (BD #291940) | 6.7 g |
| Glucose | 20 g |
| Agar | 20 g |
| SC Amino Acid Mixture (MP Biomedicals #4400-022) | 2 g |
| Distilled $H_2O$ | to 1 L |

TABLE 1-2

| SCD-URA Plates | |
|---|---|
| Difco ™ Yeast Nitrogen Base without amino acids (BD #291940) | 6.7 g |
| Glucose | 20 g |
| Agar | 20 g |
| SC-Ura Mixture (MP Biomedicals #4410-622) | 2 g |
| Distilled $H_2O$ | to 1 L |

Example 2: Construction of Strain 1

Strain D is transformed with SEQ ID NO: 21. SEQ ID NO: 21 contains the following elements: i) an expression cassette for the selectable marker URA3 from *I. orientalis* (consisting of the *I. orientalis* promoter, coding sequence and terminator), encoding the amino acid sequence for SEQ ID NO: 17 (orotidine 5'-diphosphate decarboxylase), that is flanked by a direct repeat of the *I. orientalis* URA3 promoter for marker loop out and ii) flanking DNA for targeted chromosomal integration into the integration locus XR. Transformants are selected on SCD-URA plates containing glucose as the sole carbon source. The resulting transformants are streaked for single colony isolation on SCD-URA plates. Correct integration of SEQ ID NO: 21 into the selected colonies is verified by PCR using primers designed to the IoXR flanking sequences, SEQ ID NO: 22 and SEQ ID NO: 23. A PCR verified isolate is plated on SCD medium containing 1-2 g/L 5-fluorooritic acid (5-FOA) to loop out the URA3 marker. Colonies are streaked for single colony isolation on YPD plates. The correct loop out of the marker (leaving a scar containing only the URA3 promoter) in selected colonies is verified by PCR. The deletion of the second XR allele is performed by transformation of the ΔIoXR heterozygote strain with SEQ ID NO: 24. SEQ ID NO: 24 contains the following elements: i) an expression cassette for the selectable marker URA3 from *I. orientalis* (consisting of the *I. orientalis* promoter, coding sequence and terminator), encoding the amino acid sequence for SEQ ID NO: 17 (orotidine 5'-diphosphate decarboxylase), that is flanked by a direct repeat of the *I. orientalis* URA3 promoter for marker loop out; and ii) flanking DNA for targeted chromosomal integration into integration locus XR. SEQ ID NO: 21 and SEQ ID NO: 24 differ in the orientation of the URA3 expression cassettes with respect to the IoXR flanking sequences. Transformants are selected on SCD-URA plates containing glucose as the sole carbon source. The resulting transformants are streaked for single colony isolation on SCD-URA plates. Correct integration of SEQ ID NO: 24 into the selected colonies is verified by PCR. The URA3 marker is looped out as described above. Colonies are streaked for single colony isolation on YPD plates. After single colony isolation, the correct loop out of the IoURA3 marker (leaving a scar containing only the URA3 promoter) is verified by PCR. A PCR verified isolate is designated strain E.

Strain E is transformed with SEQ ID NO: 25. SEQ ID NO: 25 contains the following elements: i) an expression cassette for the selectable marker URA3 from *I. orientalis* (consisting of the *I. orientalis* promoter, coding sequence and terminator), encoding the amino acid sequence for SEQ ID NO: 17 (orotidine 5'-diphosphate decarboxylase), that is flanked by a direct repeat of the *I. orientalis* URA3 promoter for marker loop out; ii) an expression cassette for the *I. orientalis* xylulokinase gene (IoXK) encoding the amino acid sequence SEQ ID NO: 26 flanked by *I. orientalis* PGK1 (3-phosphoglycerate kinase gene) promoter and *I. orientalis* TAL1 (transaldolase gene) terminator sequences; and iii) flanking DNA for targeted chromosomal integration into integration locus IoGAL6. Transformants are selected on SCD-URA plates containing glucose as the sole carbon source. The resulting transformants are streaked for single colony isolation on SCD-URA plates. Correct integration of SEQ ID NO: 25 into the selected colonies is verified by PCR. A PCR verified isolate is plated on SCD medium containing 1-2 g/L 5-fluoroorotic acid (5-FOA) plates to loop out the URA3 marker. Colonies are streaked for single colony isolation on YPD plates. The correct loop out of the IoURA3 marker (leaving a scar with only the URA3 promoter) is verified by PCR in selected colonies. The integration of a second XK gene is performed by transformation of the IoXK heterozygote strain with SEQ ID NO: 27. SEQ ID NO: 27 contains the following elements: i) an expression cassette for the selectable marker URA3 from *I. orientalis* (consisting of the *I. orientalis* promoter, coding sequence and terminator), encoding the amino acid sequence for SEQ ID NO: 17 (orotidine 5'-diphosphate decarboxylase), that is flanked by a direct repeat of the *I. orientalis* URA3 promoter for marker loop out; ii) an expression cassette for the *I. orientalis* xylulokinase gene (IoXK) encoding the amino acid sequence SEQ ID NO: 26 flanked by *I. orientalis* PGK1 (3-phosphoglycerate kinase gene) promoter and *I. orientalis* TAL1 (transaldolase gene) terminator sequences; and iii) flanking DNA for targeted chromosomal integration into integration locus IoGAL6. SEQ ID NO: 25 and SEQ ID NO: 27 differ in the orientation of both the expression cassettes with respect to the IoGAL6 flanking sequences. The correct integration of SEQ ID NO: 25 and SEQ ID NO: 27 into both alleles of integration locus IoGAL6 of selected colonies is verified by PCR. After the integration of the second XK gene, the IoURA3 marker gene is deleted as described above. Colonies are streaked for single colony isolation on YPD plates. After single colony isolation, the correct loop out of the IoURA3 marker (leaving a scar containing only the URA3 promoter) is verified by PCR. PCR verified isolates are designated as Strain 1.

Example 3: Construction of Strains 2 Through 6 Containing Different Xylose Isomerase Genes at the XDH Locus Strain 1 is transformed with SEQ ID NO: 28 containing the following elements: i) an expression cassette for a xylose isomerase (XI) gene from *Sebaldella termitidis* encoding the amino acid sequence SEQ ID NO: 29 flanked by *I. orientalis* pyruvate decarboxylase gene (PDC) promoter and terminator sequences; ii) an expression cassette containing the promoter, coding sequence and terminator for the selectable marker gene URA3 from *I. orientalis*, encoding the amino acid sequence SEQ ID NO: 17, flanked by loxP sequences; and iii) flanking DNA for targeted chromosomal integration into integration locus XDH. Transformants are selected on SCD-URA plates and then are streaked for single colony isolation on SCD-URA plates. After single colony isolation, the correct integration of SEQ ID NO: 28 is verified by PCR using primers designed to the flanking regions of the *I. orientalis* locus XDH (SEQ ID NO: 3 and SEQ ID NO: 4). The integration of a second xylose isomerase gene is performed by transformation of a PCR verified XI heterozygote strain with SEQ ID NO: 30. SEQ ID NO: 30 contains the following elements: i) an expression cassette for a xylose isomerase gene from *Sebaldella termitidis* encoding the amino acid sequence SEQ ID NO: 29 flanked by *I. orientalis* PDC promoter and terminator sequences; ii) an expression cassette containing the promoter, coding sequence and terminator for the selectable marker gene CYB2A from *I. orientalis*, encoding the amino acid sequence SEQ ID NO: 31 flanked by loxP sequences; and iii) flanking DNA for targeted chromosomal integration into integration locus XDH. Transformants are selected on YNB plates containing 2% lactic acid as sole carbon source. The resulting transformants are streaked for single colony isolation on YNB plates containing 2% lactic acid as sole carbon source. After single colony selection, the correct integration of SEQ ID NO: 30 into the integration locus XDH is verified by PCR using primers designed to the flanking regions of the *I. orientalis* locus XDH (SEQ ID NO: 3 and SEQ ID NO: 4). PCR verified isolates are designated as Strain 2.

Strain 1 is transformed with SEQ ID NO: 32 containing the following elements: i) an expression cassette for a xylose isomerase gene from *Leptotrichia goodfellowii* encoding the amino acid sequence SEQ ID NO: 33 flanked by *I. orientalis* pyruvate decarboxylase (PDC) promoter and terminator sequences; ii) an expression cassette containing the promoter, coding sequence and terminator for the selectable marker gene URA3 from *I. orientalis*, encoding the amino acid sequence SEQ ID NO: 17, flanked by loxP sequences; and iii) flanking DNA for targeted chromosomal integration into integration locus XDH. Transformants are selected on SCD-URA plates and then are streaked for single colony isolation on SCD-URA plates. After single colony isolation, the correct integration of SEQ ID NO: 32 is verified by PCR using primers designed to the flanking regions of the *I. orientalis* locus XDH (SEQ ID NO: 3 and SEQ ID NO: 4). The integration of a second xylose isomerase gene is performed by transformation of a PCR verified XI heterozygote strain with SEQ ID NO: 34. SEQ ID NO: 34 contains the following elements: i) an expression cassette for a xylose isomerase gene encoding the amino acid sequence SEQ ID NO: 33 flanked by *I. orientalis* PDC promoter and terminator sequences; ii) an expression cassette containing the promoter, coding sequence and terminator for the selectable marker gene CYB2A from *I. orientalis* (IoCYB2A), encoding the amino acid sequence SEQ ID NO: 31 flanked by loxP sequences; and iii) flanking DNA for targeted chromosomal integration into integration locus XDH. Transformants are selected on YNB plates containing 2% lactic acid as sole carbon source. The resulting transformants are streaked for single colony isolation on YNB plates containing 2% lactic acid as sole carbon source. After single colony selection, the correct integration of SEQ ID NO: 34 into the integration locus XDH is verified by PCR using primers designed to the flanking regions of the *I. orientalis* locus XDH (SEQ ID NO: 3 and SEQ ID NO: 4). PCR verified isolates are designated as Strain 3.

Strain 1 is transformed with SEQ ID NO: 35 containing the following elements: i) an expression cassette for a xylose isomerase (XI) gene from *Proteiniphilum acetatigenes* encoding the amino acid sequence SEQ ID NO: 36 flanked by *I. orientalis* pyruvate decarboxylase (PDC) promoter and terminator sequences; ii) an expression cassette containing the promoter, coding sequence and terminator for the selectable marker gene URA3 from *I. orientalis*, encoding the amino acid sequence SEQ ID NO: 17, flanked by loxP sequences; and iii) flanking DNA for targeted chromosomal integration into integration locus XDH. Transformants are selected on SCD-URA plates and then are streaked for single colony isolation on SCD-URA plates. After single colony isolation, the correct integration of SEQ ID NO: 35 is verified by PCR using primers designed to the flanking regions of the *I. orientalis* locus XDH (SEQ ID NO: 3 and SEQ ID NO: 4). The integration of a second xylose isomerase gene is performed by transformation of a PCR verified XI heterozygote strain with SEQ ID NO: 37. SEQ ID NO: 37 contains the following elements: i) an expression cassette for a xylose isomerase gene from *Proteiniphilum acetatigenes* encoding the amino acid sequence SEQ ID NO: 36 flanked by *I. orientalis* PDC promoter and terminator sequences; ii) an expression cassette containing the promoter, coding sequence and terminator for the selectable marker gene CYB2A from *I. orientalis*, encoding the amino acid sequence SEQ ID NO: 31 flanked by loxP sequences; and iii) flanking DNA for targeted chromosomal integration into integration locus XDH. Transformants are selected on YNB plates containing 2% lactic acid as sole carbon source. The resulting transformants are streaked for single colony isolation on YNB plates containing 2% lactic acid as sole carbon source. After single colony selection, the correct integration of SEQ ID NO: 37 into the integration locus XDH is verified by PCR using primers designed to the flanking regions of the *I. orientalis* locus XDH (SEQ ID NO: 3 and SEQ ID NO: 4). PCR verified isolates are designated as Strain 4.

Strain 1 is transformed with SEQ ID NO: 38 containing the following elements: i) an expression cassette for a xylose isomerase (XI) gene from *Paludibacter propionicigenes* WB4 encoding the amino acid sequence SEQ ID NO: 39 flanked by *I. orientalis* pyruvate decarboxylase (PDC) promoter and terminator sequences; ii) an expression cassette containing the promoter, coding sequence and terminator for the selectable marker gene URA3 from *I. orientalis*, encoding the amino acid sequence SEQ ID NO: 17, flanked by loxP sequences; and iii) flanking DNA for targeted chromosomal integration into integration locus XDH. Transformants are selected on SCD-URA plates and then are streaked for single colony isolation on SCD-URA plates. After single colony isolation, the correct integration of SEQ ID NO: 38 is verified by PCR using primers designed to the flanking regions of the *I. orientalis* locus XDH (SEQ ID NO: 3 and SEQ ID NO: 4). The integration of a second xylose isomerase gene is performed by transformation of a PCR verified XI heterozygote strain with SEQ ID NO: 40. SEQ ID NO: 40 cassette contains the following elements: i) an expression cassette for a xylose isomerase gene from *Paludibacter propionicigenes* WB4 encoding the amino acid sequence SEQ ID NO: 39 flanked by *I. orientalis* PDC promoter and terminator sequences; ii) an expression cassette containing the promoter, coding sequence and terminator for the selectable marker gene CYB2A from *I. orientalis*, encoding the amino acid sequence SEQ ID NO: 31 flanked by loxP sequences; and iii) flanking DNA for targeted chromosomal integration into integration locus XDH. Transformants are selected on YNB plates containing 2% lactic acid as sole carbon source. Resulting transformants are streaked for single colony isolation on YNB plates containing 2% lactic acid as sole carbon source. After single colony selection, the correct integration of SEQ ID NO: 40 into the integration locus XDH is verified by PCR using primers designed to the flanking regions of the *I. orientalis* locus XDH (SEQ ID NO: 3 and SEQ ID NO: 4). PCR verified isolates are designated as Strain 5

Strain 1 is transformed with SEQ ID NO: 41 containing the following elements: i) an expression cassette for a xylose isomerase (XI) gene from *Bacteroides thetaiotaomicron* encoding the amino acid sequence SEQ ID NO: 42 flanked by *I. orientalis* pyruvate decarboxylase (PDC) promoter and terminator sequences; ii) an expression cassette containing the promoter, coding sequence and terminator for the selectable marker gene URA3 from *I. orientalis*, encoding the amino acid sequence SEQ ID NO: 17, flanked by loxP sequences; and iii) flanking DNA for targeted chromosomal integration into integration locus XDH. Transformants are selected on SCD-URA plates and then are streaked for single colony isolation on SCD-URA plates. After single colony isolation, the correct integration of SEQ ID NO: 41 is verified by PCR using primers designed to the flanking regions of the *I. orientalis* locus XDH (SEQ ID NO: 3 and SEQ ID NO: 4). The integration of a second xylose isomerase gene is performed by transformation of a PCR verified XI heterozygote strain with SEQ ID NO: 43). SEQ ID NO: 43 contains the following elements: i) an expression cassette for a xylose isomerase gene from *Bacteroides thetaiotaomicron* encoding the amino acid sequence SEQ ID NO: 42 flanked by *I. orientalis* PDC promoter and terminator sequences; ii) an expression cassette containing the promoter, coding sequence and terminator for the selectable marker gene CYB2A from *I. orientalis* (IoCYB2A), encoding the amino acid sequence SEQ ID NO: 31 flanked by loxP sequences; and iii) flanking DNA for targeted chromosomal integration into integration locus XDH. Transformants are selected on YNB plates containing 2% lactic acid as sole carbon source. Resulting transformants are streaked for single colony isolation on YNB plates containing 2% lactic acid as sole carbon source. After single colony selection, the correct integration of SEQ ID NO: 43 into the integration locus XDH is verified by PCR using primers designed to the flanking regions of the *I. orientalis* locus XDH (SEQ ID NO: 3 and SEQ ID NO: 4). PCR verified isolates are designated as Strain 6.

Example 4: Construction of Strain 7 (ΔXDH Control Strain)

A ΔXDH control strain is generated from strain 1 (yBK676; 14828) by deletion of one XDH gene to produce strain 7. Strain 1 is transformed with SEQ ID NO: 44 containing the following elements: i) an expression cassette for the selectable marker URA3 from *I. orientalis* (consisting of the *I. orientalis* promoter, coding sequence and terminator), encoding the amino acid sequence for SEQ ID NO: 17 (orotidine 5'-diphosphate decarboxylase), that is flanked by a direct repeat of the *I. orientalis* URA3 promoter for marker loop out; and ii) flanking DNA for targeted chromosomal integration into integration locus XDH. Transformants are selected on SCD-URA plates and are then streaked for single colony isolation on the same plates. The correct integration of SEQ ID NO: 44 of selected colonies is verified by PCR using primers designed to the XDH locus flanking regions, SEQ ID NO: 3 and SEQ ID NO: 4. PCR verified isolates are designated as Strain 7.

TABLE 4-1

Strains described in Examples 1-4

| Strain | Description | Parent |
|---|---|---|
| Strain A | Wild Type | N/A |
| Strain B | Chemostat evolved wild type | Strain A |
| Strain C | ΔURA3 | Strain B |
| Strain D | ΔURA3, ΔCYB2A | Strain C |
| Strain E | ΔURA3, ΔCYB2A, ΔXR | Strain D |
| 1 | ΔURA3, ΔCYB2A, ΔXR, ΔGAL6, +2xIoXK | Strain E |
| 2 | ΔURA3, ΔCYB2A, ΔXR, ΔGAL6, +2xIoXK, +2xStXI, 1xCYB2A, 1xURA3 | 1 |
| 3 | ΔURA3, ΔCYB2A, ΔXR, ΔGAL6, +2xIoXK, +2xLgXI, 1xCYB2A, 1xURA3 | 1 |
| 4 | ΔURA3, ΔCYB2A, ΔXR, ΔGAL6, +2xIoXK, +2xPaXI, 1xCYB2A, 1xURA3 | 1 |
| 5 | ΔURA3, ΔCYB2A, ΔXR, ΔGAL6, +2xIoXK, +2xPpXI, 1xCYB2A, 1xURA3 | 1 |
| 6 | ΔURA3, ΔCYB2A, ΔXR, ΔGAL6, +2xIoXK, +2xBtXI, 1xCYB2A, 1xURA3 | 1 |
| 7 | ΔURA3, ΔCYB2A, ΔXR, ΔGAL6, +2xIoXK, 1xURA3 | 1 |

Example 5: Construction of Strains 8-12 Containing Codon Variants of the Xylose Isomerase Gene from *Sebaldella termitidis* at the XDH Locus Strain 1 is transformed with SEQ ID NO: 45 containing the following elements: i) an expression cassette for a xylose isomerase gene from *Sebaldella termitidis* encoding the amino acid sequence SEQ ID NO: 29 flanked by *I. orientalis* pyruvate decarboxylase (PDC) promoter and terminator sequences; ii) an expression cassette consisting of a promoter, coding sequence and terminator for the selectable marker gene URA3 from *I. orientalis*, encoding the amino acid sequence SEQ ID NO: 17, flanked by loxP sequences; and iii) flanking DNA for targeted chromosomal integration into integration locus XDH. Transformants are selected on SCD-URA plates and then are streaked for single colony isolation on SCD-URA plates. After single colony isolation, the correct integration of SEQ ID NO: 45 verified by PCR using primers designed to flanking regions of the *I. orientalis* XDH locus (SEQ ID NO: 3 and SEQ ID NO: 4). PCR verified isolates are designated as Strain 8.

Strain is transformed with SEQ ID NO: 46 containing the following elements: i) an expression cassette for a codon variant of the xylose isomerase gene from *Sebaldella termitidis* encoding the amino acid sequence SEQ ID NO: 29 flanked by *I. orientalis* pyruvate decarboxylase (PDC) promoter and terminator sequences; ii) an expression cassette consisting of a promoter, coding sequence and terminator for the selectable marker gene URA3 from *I. orientalis*, encoding the amino acid sequence SEQ ID NO: 17, flanked by loxP sequences; and iii) flanking DNA for targeted chromosomal integration into integration locus XDH. Transformants are selected on SCD-URA plates and then are streaked for single colony isolation on SCD-URA plates. After single colony isolation, the correct integration of SEQ ID NO: 46 is verified by PCR using primers designed to flanking regions of the *I. orientalis* XDH locus (SEQ ID NO: 3 and SEQ ID NO: 4). PCR verified isolates are designated as Strain 9.

Strain 1 is transformed with SEQ ID NO: 47 containing the following elements: i) an expression cassette for a codon variant of the xylose isomerase gene from *Sebaldella termitidis* encoding the amino acid sequence SEQ ID NO: 29 flanked by *I. orientalis* pyruvate decarboxylase (PDC) promoter and terminator sequences; ii) an expression cassette consisting of a promoter, coding sequence and terminator for the selectable marker gene URA3 from *I. orientalis*, encoding the amino acid sequence SEQ ID NO: 17, flanked by loxP sequences; and iii) flanking DNA for targeted chromosomal integration into integration locus XDH. Transformants are selected on SCD-URA plates and then are streaked for single colony isolation on SCD-URA plates. After single colony isolation, the correct integration of SEQ ID NO: 47 cassette is verified by PCR using primers designed to flanking regions of the *I. orientalis* XDH locus (SEQ ID NO: 3 and SEQ ID NO: 4). PCR verified isolates are designated as Strain 10.

Strain 1 is transformed with SEQ ID NO: 48 containing the following elements: i) an expression cassette for a xylose isomerase gene from *Sebaldella termitidis* encoding the amino acid sequence SEQ ID NO: 29 flanked by *I. orientalis* pyruvate decarboxylase (PDC) promoter and terminator sequences; ii) an expression cassette consisting of a promoter, coding sequence and terminator for the selectable marker gene URA3 from *I. orientalis*, encoding the amino acid sequence SEQ ID NO: 17, flanked by loxP sequences; and iii) flanking DNA for targeted chromosomal integration into integration locus XDH. Transformants are selected on SCD-URA plates and then are streaked for single colony isolation on SCD-URA plates. After single colony isolation, the correct integration of SEQ ID NO: 48 is verified by PCR using primers designed to flanking regions of the *I. orientalis* XDH locus (SEQ ID NO: 3 and SEQ ID NO: 4). PCR verified isolates are designated as Strain 11.

Strain 1 is transformed with SEQ ID NO: 49 containing the following elements: i) an expression cassette for a xylose isomerase gene from *Sebaldella termitidis* encoding the amino acid sequence SEQ ID NO: 29 flanked by *I. orientalis* pyruvate decarboxylase (PDC) promoter and terminator sequences; ii) an expression cassette consisting of a promoter, coding sequence and terminator for the selectable marker gene URA3 from *I. orientalis*, encoding the amino acid sequence SEQ ID NO: 17, flanked by loxP sequences; and iii) flanking DNA for targeted chromosomal integration into integration locus XDH. Transformants are selected on SCD-URA plates and then are streaked for single colony isolation on SCD-URA plates. After single colony isolation, the correct integration of SEQ ID NO: 49 is verified by PCR using primers designed to flanking regions of the *I. orientalis* XDH locus (SEQ ID NO: 3 and SEQ ID NO: 4). PCR verified isolates are designated as Strain.

Example 6: Construction of Strains 13-18 Containing Codon Variants of the Xylose Isomerase Gene from *Leptotrichia goodfellowii* at the XDH Locus Strain 1 is transformed with SEQ ID NO: 50 containing the following elements: i) an expression cassette for a xylose isomerase gene from *Leptotrichia goodfellowii* encoding the amino acid sequence SEQ ID NO: 33 flanked by *I. orientalis* pyruvate decarboxylase (PDC) promoter and terminator sequences; ii) an expression cassette for the selectable marker gene URA3 from *I. orientalis* (consisting of the *I. orientalis* promoter, coding sequence and terminator), encoding the amino acid sequence SEQ ID NO: 17, flanked by loxP sequences; and iii) flanking DNA for targeted chromosomal integration into integration locus XDH. Transformants are selected on SCD-URA plates and then are streaked for single colony isolation on SCD-URA plates. After single colony isolation, the correct integration of SEQ ID NO: 50 is verified by PCR using primers designed to the XDH locus flanking regions, SEQ ID NO: 3 and SEQ ID NO: 4. PCR verified isolates are designated as Strain 13.

Strain 1 is transformed with SEQ ID NO: 51 containing the following elements: i) an expression cassette for a xylose isomerase gene from *Leptotrichia goodfellowii* encoding the amino acid sequence SEQ ID NO: 33 flanked by *I. orientalis* pyruvate decarboxylase (PDC) promoter and terminator sequences; ii) an expression cassette for the selectable marker gene URA3 from *I. orientalis* (consisting of the *I. orientalis* promoter, coding sequence and terminator), encoding the amino acid sequence SEQ ID NO: 17, flanked by loxP sequences; and iii) flanking DNA for targeted chromosomal integration into integration locus XDH. Transformants are selected on SCD-URA plates and then are streaked for single colony isolation on SCD-URA plates. After single colony isolation, the correct integration of SEQ ID NO: 51 is verified by PCR using primers designed to the XDH locus flanking regions, SEQ ID NO: 3 and SEQ ID NO: 4. PCR verified isolates are designated as Strain 14.

Strain 1 is transformed with SEQ ID NO: 52 containing the following elements: i) an expression cassette for a xylose isomerase gene from *Leptotrichia goodfellowii* encoding the amino acid sequence SEQ ID NO: 33 flanked by *I. orientalis* pyruvate decarboxylase (PDC) promoter and terminator sequences; ii) an expression cassette for the selectable marker gene URA3 from *I. orientalis* (consisting of the *I. orientalis* promoter, coding sequence and terminator), encoding the amino acid sequence SEQ ID NO: 17, flanked by loxP sequences; and iii) flanking DNA for targeted chromosomal integration into integration locus XDH. Transformants are selected on SCD-URA plates and then are streaked for single colony isolation on SCD-URA plates. After single colony isolation, the correct integration of SEQ ID NO: 52 is verified by PCR using primers designed to the XDH locus flanking regions, SEQ ID NO: 3 and SEQ ID NO: 4. PCR verified isolates are designated as Strain 15.

Strain 1 is transformed with SEQ ID NO: 53 containing the following elements: i) an expression cassette for a codon variant of the xylose isomerase gene from *Leptotrichia goodfellowii* encoding the amino acid sequence SEQ ID NO: 33 flanked by *I. orientalis* pyruvate decarboxylase (PDC) promoter and terminator sequences; ii) an expression cassette for the selectable marker gene URA3 from *I. orientalis* (consisting of the *I. orientalis* promoter, coding sequence and terminator), encoding the amino acid sequence SEQ ID NO: 17, flanked by loxP sequences; and iii) flanking DNA for targeted chromosomal integration into integration locus XDH. Transformants are selected on SCD-URA plates and then are streaked for single colony isolation on SCD-URA plates. After single colony isolation, the correct integration of SEQ ID NO: 53 is verified by PCR using primers designed to the XDH locus flanking regions, SEQ ID NO: 3 and SEQ ID NO: 4. PCR verified isolates are designated as Strain 16.

Strain 1 is transformed with SEQ ID NO: 54 containing the following elements: i) an expression cassette for a codon variant of the xylose isomerase gene from *Leptotrichia goodfellowii* encoding the amino acid sequence SEQ ID NO: 33 flanked by *I. orientalis* pyruvate decarboxylase (PDC) promoter and terminator sequences; ii) an expression cassette for the selectable marker gene URA3 from *I. orientalis* (consisting of the *I. orientalis* promoter, coding sequence and terminator), encoding the amino acid sequence SEQ ID NO: 17, flanked by loxP sequences; and iii) flanking DNA for targeted chromosomal integration into integration locus XDH. Transformants are selected on SCD-URA plates and then are streaked for single colony isolation on SCD-URA plates. After single colony isolation, the correct integration of SEQ ID NO: 54 is verified by PCR using primers designed to the XDH locus flanking regions, SEQ ID NO: 3 and SEQ ID NO: 4. PCR verified isolates are designated as Strain 17.

Strain 1 is transformed with SEQ ID NO: 55 containing the following elements: i) an expression cassette for a xylose isomerase gene from *Leptotrichia goodfellowii* encoding the amino acid sequence SEQ ID NO: 33 flanked by *I. orientalis* pyruvate decarboxylase (PDC) promoter and terminator sequences; ii) an expression cassette for the selectable marker gene URA3 from *I. orientalis* (consisting of the *I. orientalis* promoter, coding sequence and terminator), encoding the amino acid sequence SEQ ID NO: 17, flanked by loxP sequences; and iii) flanking DNA for targeted chromosomal integration into integration locus XDH. Transformants are selected on SCD-URA plates and then are streaked for single colony isolation on SCD-URA plates. After single colony isolation, the correct integration of SEQ ID NO: 55 is verified by PCR using primers designed to the XDH locus flanking regions, SEQ ID NO: 3 and SEQ ID NO: 4. PCR verified isolates are designated as Strain 18.

Example 7: Construction of Strains 19-24 Containing Codon Variants of the Xylose Isomerase Gene from *Sebaldella termitidis* or *Leptotrichia goodfellowii* at the XDH Locus Strain 9 is transformed with SEQ ID NO: 56. SEQ ID NO: 56 contains the following elements: i) an expression cassette for a xylose isomerase gene from *Sebaldella termitidis* encoding the amino acid sequence SEQ ID NO: 29 flanked by *I. orientalis* PDC promoter and terminator sequences; ii) an expression cassette for the selectable marker gene CYB2A (consisting of the *I. orientalis* promoter, coding sequence and terminator), encoding the amino acid sequence SEQ ID NO: 31 flanked by loxP sequences; and iii) flanking DNA for targeted chromosomal integration into integration locus XDH. Transformants are selected on YNB plates containing 2% lactic acid as sole carbon source. The resulting transformants are streaked for single colony isolation on YNB plates containing 2% lactic acid as sole carbon source. After single colony selection, the correct integration of SEQ ID NO: 56 into the integration locus XDH is verified by PCR using primers designed to the XDH locus flanking regions, SEQ ID NO: 3 and SEQ ID NO: 4. In addition, the integrity of the first copy of the gene is confirmed by PCR as described in Example 5. PCR verified isolates for both alleles are designated as Strain 19.

Strain 11 is transformed with SEQ ID NO: 57. SEQ ID NO: 57 contains the following elements: i) an expression cassette for a xylose isomerase gene from *Sebaldella termitidis* encoding the amino acid sequence SEQ ID NO: 29 flanked by *I. orientalis* PDC promoter and terminator sequences; ii) an expression cassette for the selectable marker gene CYB2A (consisting of the *I. orientalis* promoter, coding sequence and terminator), encoding the amino acid sequence SEQ ID NO: 31 flanked by loxP sequences; and iii) flanking DNA for targeted chromosomal integration into integration locus XDH. Transformants are selected on YNB plates containing 2% lactic acid as sole carbon source.

The resulting transformants are streaked for single colony isolation on YNB plates containing 2% lactic acid as sole carbon source. After single colony selection, the correct integration of SEQ ID NO: 57 into the integration locus XDH is verified by PCR using primers designed to the XDH locus flanking regions, SEQ ID NO: 3 and SEQ ID NO: 4. In addition, the integrity of the first copy of the gene is confirmed by PCR as described in Example 5. PCR verified isolates are designated as Strain 20.

Strain 15 is transformed with SEQ ID NO: 58. SEQ ID NO: 58 contains the following elements: i) an expression cassette for a xylose isomerase gene from *Leptotrichia goodfellowii* encoding the amino acid sequence SEQ ID NO: 33 flanked by *I. orientalis* PDC promoter and terminator sequences; ii) an expression cassette for the selectable marker gene CYB2A (consisting of the *I. orientalis* promoter, coding sequence and terminator), encoding the amino acid sequence SEQ ID NO: 31 flanked by loxP sequences; and iii) flanking DNA for targeted chromosomal integration into integration locus XDH. Transformants are selected on SC-URA plates containing 2% lactic acid as sole carbon source. The resulting transformants are streaked for single colony isolation on SC-URA plates containing 2% lactic acid as sole carbon source. After single colony selection, the correct integration of SEQ ID NO: 58 into the integration locus XDH is verified by PCR using primers designed to the XDH locus flanking regions, SEQ ID NO: 3 and SEQ ID NO: 4. In addition, the integrity of the first transformation is confirmed by PCR. PCR verified isolates for both alleles are designated as Strain 21.

Strain 16 is transformed with SEQ ID NO: 58. SEQ ID NO: 58 contains the following elements: i) an expression cassette for a xylose isomerase gene from *Leptotrichia goodfellowii* encoding the amino acid sequence SEQ ID NO: 33 flanked by *I. orientalis* PDC promoter and terminator sequences; ii) an expression cassette for the selectable marker gene CYB2A (consisting of the *I. orientalis* promoter, coding sequence and terminator), encoding the amino acid sequence SEQ ID NO: 31 flanked by loxP sequences; and iii) flanking DNA for targeted chromosomal integration into integration locus XDH. Transformants are selected on SC-URA plates containing 2% lactic acid as sole carbon source. The resulting transformants are streaked for single colony isolation on SC-URA plates containing 2% lactic acid as sole carbon source. After single colony selection, the correct integration of SEQ ID NO: 58 into the integration locus XDH is verified by PCR using primers designed to the XDH locus flanking regions, SEQ ID NO: 3 and SEQ ID NO: 4. In addition, the integrity of the first transformation is confirmed by PCR. PCR verified isolates for both alleles are designated as Strain 22.

Strain 17 is transformed with SEQ ID NO: 58. SEQ ID NO: 58 contains the following elements: i) an expression cassette for a xylose isomerase gene from *Leptotrichia goodfellowii* encoding the amino acid sequence SEQ ID NO: 33 flanked by *I. orientalis* PDC promoter and terminator sequences; ii) an expression cassette for the selectable marker gene CYB2A (consisting of the *I. orientalis* promoter, coding sequence and terminator), encoding the amino acid sequence SEQ ID NO: 31 flanked by loxP sequences; and iii) flanking DNA for targeted chromosomal integration into integration locus XDH. Transformants are selected on SC-URA plates containing 2% lactic acid as sole carbon source. The resulting transformants are streaked for single colony isolation on SC-URA plates containing 2% lactic acid as sole carbon source. After single colony selection, the correct integration of SEQ ID NO: 58 into the integration locus XDH is verified by PCR using primers designed to the XDH locus flanking regions, SEQ ID NO: 3 and SEQ ID NO: 4. In addition, the integrity of the first copy of the gene is confirmed by PCR. PCR verified isolates for both alleles are designated as Strain 23.

Strain 18 is transformed with SEQ ID NO: 58. SEQ ID NO: 58 contains the following elements: i) an expression cassette for a xylose isomerase gene from *Leptotrichia goodfellowii* encoding the amino acid sequence SEQ ID NO: 33 flanked by *I. orientalis* PDC promoter and terminator sequences; ii) an expression cassette for the selectable marker gene CYB2A (consisting of the *I. orientalis* promoter, coding sequence and terminator), encoding the amino acid sequence SEQ ID NO: 31 flanked by loxP sequences; and iii) flanking DNA for targeted chromosomal integration into integration locus XDH. Transformants are selected on SC-URA plates containing 2% lactic acid as sole carbon source. The resulting transformants are streaked for single colony isolation on SC-URA plates containing 2% lactic acid as sole carbon source. After single colony selection, the correct integration of SEQ ID NO: 58 into the integration locus XDH is verified by PCR using primers designed to the XDH locus flanking regions, SEQ ID NO: 3 and SEQ ID NO: 4. In addition, the integrity of the first copy of the gene is confirmed by PCR. PCR verified isolates for both alleles are designated as Strain 24.

TABLE 7-1

Strains described in Examples 6 and 7

| Strains | Description | Parent |
| --- | --- | --- |
| 8 through 12 | ΔURA3, ΔCYB2A, ΔXR, ΔGAL6, ΔXDH, +2xIoXK, +1xStXI, 1xURA3 | 1 |
| 13 through 18 | ΔURA3, ΔCYB2A, ΔXR, ΔGAL6, ΔXDH, +2xIoXK, +1xLgXI, 1xURA3 | 1 |
| 19 | ΔURA3, ΔCYB2A, ΔXR, ΔGAL6, ΔXDH, +2xIoXK, +2xStXI, 1xCYB2A, 1xURA3 | 9 |
| 20 | ΔURA3, ΔCYB2A, ΔXR, ΔGAL6, ΔXDH, +2xIoXK, +2xStXI, 1xCYB2A, 1xURA3 | 11 |
| 21 | ΔURA3, ΔCYB2A, ΔXR, ΔGAL6, ΔXDH, +2xIoXK, +2xLgX+, 1xCYB2A, 1xURA3 | 15 |
| 22 | ΔURA3, ΔCYB2A, ΔXR, ΔGAL6, ΔXDH, +2xIoXK,, +2xLgXI, 1xCYB2A, 1xURA3 | 16 |
| 23 | ΔURA3, ΔCYB2A, ΔXR, ΔGAL6, ΔXDH, +2xIoXK, +2xLgXI, 1xCYB2A, 1xURA3 | 17 |
| 24 | ΔURA3, ΔCYB2A, ΔXR, ΔGAL6, ΔXDH, +2xIoXK, +2xLgXI, 1xCYB2A, 1xURA3 | 18 |

Example 8: Construction of Strains 25-26 Containing a Codon Variant of the Xylose Isomerase Gene from *Sebaldella termitidis* and a Codon Variant of the Xylose Isomerase Gene from *Leptotrichia goodfellowii* at the XDH Locus Strain 15 is transformed with SEQ ID NO: 57. SEQ ID NO: 57 contains the following elements: i) an expression cassette for a xylose isomerase gene from *Sebaldella termitidis* encoding the amino acid sequence SEQ ID NO: 29 flanked by *I. orientalis* PDC promoter and terminator sequences; ii) an expression cassette for the selectable marker gene CYB2A from *I. orientalis* CYB2A (consisting of the *I. orientalis* promoter, coding sequence and terminator), encoding the amino acid sequence SEQ ID NO: 31, flanked by loxP sequences; and iii) flanking DNA for targeted chromosomal integration into integration locus XDH. Transformants are selected on SC-URA plates containing 2% lactic acid as sole carbon source. The resulting transformants are streaked for single colony isolation on SC-URA plates containing 2% lactic acid as sole carbon source. After single colony selection, the correct integration of SEQ ID NO: 57 into the integration locus XDH is verified by PCR. In addition, the integrity of the *Leptotrichia goodfellowii* xylose isomerase gene is confirmed by PCR using primers designed to the XDH locus flanking regions, SEQ ID NO: 3 and SEQ ID NO: 4. PCR verified isolates for both alleles are designated as Strain 25.

Strain 18 (yCPE483) is transformed with SEQ ID NO: 57. SEQ ID NO: 57 contains the following elements: i) an expression cassette for a xylose isomerase gene from *Sebaldella termitidis* encoding the amino acid sequence SEQ ID NO:29 flanked by *I. orientalis* PDC promoter and terminator sequences; ii) an expression cassette for the selectable marker gene CYB2A from *I. orientalis* (consisting of the *I. orientalis* promoter, coding sequence and terminator), encoding the amino acid sequence SEQ ID NO: 31 flanked by loxP sequences; and iii) flanking DNA for targeted chromosomal integration into integration locus XDH. Transformants are selected on SC-URA plates containing 2% lactic acid as sole carbon source. The resulting transformants are streaked for single colony isolation on SC-URA plates containing 2% lactic acid as sole carbon source. After single colony selection, the correct integration of SEQ ID NO: 57 into the integration locus XDH is verified by PCR. In addition, the integrity of the *Leptotrichia goodfellowii* xylose isomerase gene is confirmed by PCR using primers designed to the XDH locus flanking regions, SEQ ID NO: 3 and SEQ ID NO: 4. PCR verified isolates for both alleles are designated as Strain 26.

TABLE 8-1

Xylose enabled strains with DNA variants of the xylose isomerase gene from *Sebaldella termitidis* and *Leptotrichia goodfellowii*

| Strains | Description | Parent |
|---|---|---|
| 25 | ΔURA3, ΔCYB2A, ΔXR, ΔGAL6, ΔXDH, +2xIoXK, +1xStXI, +1xLgXI, 1xCYB2A, 1xURA3 | 15 |
| 26 | ΔURA3, ΔCYB2A, ΔXR, ΔGAL6, ΔXDH, +2xIoXK, +1xStXI, +1xLgXI, 1xCYB2A, 1xURA3 | 18 |

Example 9: Construction of Ethanol Producing Strains Containing Multiple Codon Variants of the Xylose Isomerase Gene from *Sebaldella termitidis*

The transketolase (TKL) genes of *Issatchenkia orientalis* strain 12215 (described in patent application US20140038253 A1) at the AR4 integration locus are replaced with the *S. cerevisiae* TKL gene by sequential transformation with 1) SEQ ID NO: 59 and 2) SEQ ID NO: 60. Each contain the following elements: i) an expression cassette for the transketolase from *Saccharomyces cerevisiae* encoding the amino acid SEQ ID NO: 61 flanked by *I. orientalis* TDH3 promoter and the *S. cerevisiae* TKL terminator; ii) an expression cassette for the selectable marker URA3 from *I. orientalis* consisting of the promoter, coding sequence and terminator, encoding the amino acid sequence SEQ ID NO: 17, that is flanked by a direct repeat of the *I. orientalis* URA3 promoter for marker loop out; and iii) flanking DNA for targeted chromosomal integration into locus AR4. The expression cassettes are in the opposite orientation with respect to the AR4 flanking regions in SEQ ID NO: 59 and SEQ ID NO: 60. The URA3 marker is recycled before and after the first transformation as described in previous examples by growth on SCD medium plates containing 1-2 g/L 5-FOA. The correct integrations of SEQ ID NO: 59 and SEQ ID NO: 60 are verified by PCR using primers designed to the IoAR4 locus, SEQ ID NO: 7 and SEQ ID NO: 8. A PCR verified isolate is called 27.

Strain 27 is plated on DM-1 defined medium (pH 5.1) with 20 g/L arabinose as the carbon source. Individual fast growing isolates are streaked three times on SCD-URA plates and then plated on defined medium (DM-1, pH 5.1) with 20 g/L arabinose a second time to confirm faster growth. A fast growing isolate is called strain 28. The defined medium (DM-1) is adapted from Verduyn, et. al, 1992, Yeast 8, 501-517. The medium recipe is described in Table 9-1.

A slurry of strain 28 cells is subjected to mutagenesis with 2% ethane methylsulfonate (EMS) for 1 h at 37° C., is washed several times to remove the EMS, and then is recovered in YP5D medium (YP5D medium contains 100 g/L glucose instead of the standard 20 g/L glucose of YPD). After recovery the cells are plated on selective media (DM-1 medium with 20 g/L xylose, 3 g/L yeast extract, 5 g/L acetic acid, pH 5.4) and the plates are incubated anaerobically at 37° C. for several days. Isolates are picked and grown on non-selective YPD plates overnight. Growth of individual isolates on the solid selective medium for several days followed by non-selective medium is repeated twice with a final plating on SCD-URA medium to confirm the retention of the URA3 selectable marker. Isolates are characterized for xylose consumption in defined liquid medium (DM-1 containing 50 g/L glucose, 55 g/L xylose, 10 g/L arabinose, and 5 g/L acetate, pH 5.0) at 37° C. and 250 rpm for several days. The isolate with the most improved xylose consumption rate is called strain 29.

Strain 29 is evolved by growth in a chemostat containing DM-1 medium with 1.5 g/L glucose, 3 g/L xylose, 6 g/L arabinose, 1 g/L galactose and 0.5 g/L acetate at pH 5.0, an OTR of ~25 mM/h and a dilution rate of 0.4/h. Single colonies are isolated from the system at several time points and characterized by growth in DM-1(u) defined liquid medium, pH 5.0, containing 20 g/L xylose, 80 g/L glucose, 10 g/L acetate at 37° C. and 100 rpm. The defined medium (DM-1(u)) is adapted from Verduyn, et. al, 1992, Yeast 8, 501-517. The media recipes are described in Tables 9-2 and 9-3. An isolate with improved xylose utilization and ethanol production is called strain 30.

Strain 30 is evolved by growth in a chemostat containing DM-1 medium with 20 g/L xylose and 10 g/L acetate at pH 5.0, an OTR of ~15 mM/h and a dilution rate of 0.13/h. Single colonies are isolated from the system at several time points and characterized by growth, sugar utilization, and ethanol production in DMU defined medium, pH 5.8, containing 20 g/L glucose, 80 g/L xylose and 10 g/L acetate at 37° C. and 125 rpm. The DMU defined medium is adapted from Verduyn, et. al, 1992, Yeast 8, 501-517. The media recipes are described in Tables 9-2 and 9-4. An isolate with improved xylose utilization and ethanol production is called strain 31.

The URA3 marker of strain 31 is looped out by plating on SCD medium containing 1-2 g/L 5-fluoroouritic acid (5-FOA). Colonies are streaked for single colony isolation on YPD plates. The correct loop out of the IoURA3 marker (leaving a scar containing only the URA3 promoter) in selected colonies is verified by PCR using primers designed to the IoAR4 locus, SEQ ID NO: 7 and SEQ ID NO: 8. A PCR verified isolate is called 32.

The PCR verified ΔURA3 strain 32 is transformed with SEQ ID NO: 62 containing the following elements: i) an expression cassette for the selectable marker URA3 from *I. orientalis* consisting of a promoter, coding sequence and terminator, encoding the amino acid sequence SEQ ID NO: 17, that is flanked by a direct repeat of the *I. orientalis* URA3 promoter for marker loop out; and ii) flanking DNA for targeted chromosomal integration into integration locus XR. Transformants are selected on SCD-URA plates and then are streaked for single colony isolation on SCD-URA plates. After single colony isolation, the correct integration of SEQ ID NO: 62 is verified by PCR using primers designed to the IoXR locus, SEQ ID NO: 22 and SEQ ID NO: 23. The URA3 marker is removed by growth on SCD medium plates containing 1-2 g/L 5-FOA. Isolates are single colony purified and screened by PCR to confirm the loss of the URA3 marker (leaving a scar containing only the URA3 promoter). A PCR verified isolate is transformed with SEQ ID NO: 63. SEQ ID NO: 63 contains the following elements: i) an expression cassette for the selectable marker URA3 from *I. orientalis* (consisting of a promoter, coding sequence and terminator) encoding the amino acid sequence SEQ ID NO: 17, that is flanked by a direct repeat of the *I. orientalis* URA3 promoter for marker loop out; and ii) flanking DNA for targeted chromosomal integration into integration locus IoXR. The two expression cassettes of SEQ ID NO: 62 and SEQ ID NO: 63 are in the opposite orientation with respect to the XR flanking regions. Transformants are selected on SCD-URA plates and then are streaked for single colony isolation on SCD-URA plates. After single colony isolation, the correct integration of SEQ ID NO: 63 is verified by PCR using primers designed to the IoXR locus, SEQ ID NO: 22 and SEQ ID NO: 23. The URA3 marker is removed by growth on SCD medium plates containing 1-2 g/L 5-FOA. Isolates are single colony purified and screened by PCR to confirm the loss of the URA3 marker (leaving a scar containing only the URA3 promoter). A PCR verified isolate is called 33.

The PCR verified ΔURA3 strain 33 is transformed with SEQ ID NO: 64 containing the following elements: i) an expression cassette for the selectable marker URA3 from *I. orientalis* (consisting of a promoter, coding sequence and terminator), encoding the amino acid sequence SEQ ID NO: 17, ii) an expression cassette consisting of a promoter, coding sequence and terminator for the *K. marxianus* xylose transporter gene KHT105 described in US patent application 20140038253; and iii) flanking DNA for targeted chromosomal integration into integration locus IoAXR2). The two expression cassettes are flanked by loxP sequences. Transformants are selected on SCD-URA plates and then are streaked for single colony isolation on SCD-URA plates. After single colony isolation, the correct integration of SEQ ID NO: 64 is verified by PCR using primers designed to the IoAXR2 locus, SEQ ID NO: 5 and SEQ ID NO: 6. A PCR verified isolate is transformed with SEQ ID NO: 65 containing the following elements: i) an expression cassette consisting of the promoter, coding sequence and terminator for the selectable marker gene melibiase from *S. cerevisiae* (SEQ ID NO: 10) under the control of the *Issatchenkia orientalis* phosphoglycerate kinase promoter and ii) flanking DNA for targeted chromosomal integration into locus IoAXR2. The expression cassette of element is flanked by loxP sequences.

Transformants are selected on Yeast Nitrogen Base (YNB) with amino acids and ammonium sulfate (BD #239210) plates containing 2% melibiose as the sole carbon source and 32 μg/ml 5-Bromo-4-chloro-3-indolyl a-D-galactopyranoside (x-alpha-gal) which provides a colorimetric indication of the presence of the ScMEL5 marker gene. The resulting transformants are streaked for single colony isolation on YPD (BD #24820) plates containing 32 μg/ml x-alpha-gal. The correct integration of SEQ ID NO: 65 into the isolated blue colonies is verified by PCR using primers designed for the flanking regions of the IoAXR2 gene (SEQ ID NO: 5 and SEQ ID NO: 6). A PCR verified isolate is called 34.

A PCR verified isolate of strain 34 is transformed with SEQ ID: 13 to loop out the URA3 and ScMEL5 markers. SEQ ID NO: 13 contains: i) an expression cassette for the selectable marker gene invertase from *S. cerevisiae* (SEQ ID NO: 14) consisting of a promoter, coding sequence and terminator; and ii) an expression cassette consisting of a promoter, coding sequence and terminator for CRE recombinase gene (Cre), encoding the amino acid sequence SEQ ID NO: 15. Transformants are selected on YNB plates containing 2% sucrose as the sole carbon source and 32 μg/ml x-alpha-gal. Selected transformants are streaked SCD medium plates containing 1-2 g/L 5-FOA as described previously. Isolates from the 5-FOA plates are streaked for single colony isolation on YPD plates containing 32 μg/ml x-alpha-gal. Loss of ScMEL5 and IoURA3 in selected isolates is verified by PCR using primers designed to the flanking regions of the IoAXR2 gene (SEQ ID NO: 5 and SEQ ID NO: 6). A PCR verified isolate is called 35.

Strain 35 is transformed simultaneously with SEQ ID NO: 66: and SEQ ID NO: 67. Recombination of the two pieces during transformation results in integration of the following elements: i) four expression cassettes (each containing a promoter, a gene, and a terminator) for a xylose isomerase gene from *Sebaldella termitidis* encoding the amino acid sequence SEQ ID NO: 29 flanked by the *I. orientalis* ENO1 (phosphopyruvate hydratase), PDC (pyruvate decarboxylase), TDH3 (glyceraldehyde-3-phosphate dehydrogenase), or TEF2 (translation elongation factor) promoter and terminator sequences, respectively; ii) an expression cassette for the selectable marker gene URA3 from *I. orientalis* consisting of a promoter, coding sequence and terminator, encoding the amino acid sequence SEQ ID NO: 17, flanked by loxP sequences; and iii) flanking DNA for targeted chromosomal integration into integration locus AXR2. Transformants are selected on SCD-URA plates and then are streaked for single colony isolation on SCD-URA plates. After single colony isolation, the correct integration of the expression cassettes is verified by PCR using primers designed to the flanking regions of the IoAXR2 gene (SEQ ID NO: 5 and SEQ ID NO: 6. A PCR verified isolate is designated as Strain 36.

Strain 36 is transformed simultaneously with SEQ ID NO: 68 and SEQ ID NO: 69. Recombination of the two pieces during transformation results in integration of the following elements: i) four expression cassettes for a xylose isomerase gene from *Sebaldella termitidis* encoding the amino acid sequence SEQ ID NO: 29 flanked by ENO1, PDC, TDH3, and TEF2 promoter and terminator sequences, respectively; ii) an expression cassette consisting of a promoter, coding sequence and terminator for the selectable marker gene MEL5 from *Saccharomyces cerevisiae*, encoding the amino acid sequence SEQ ID NO: 10, flanked by loxP sequences; and iii) flanking DNA for targeted chromosomal integration into locus AXR2. Transformants are selected on Yeast Nitrogen Base (YNB) with amino acids and ammonium sulfate (BD #239210) plates containing 2% melibiose as the sole carbon source and 32 μg/ml 5-Bromo-4-chloro-3-indolyl a-D-galactopyranoside (x-alpha-gal) which provides a colorimetric indication of the presence of the ScMEL5 marker gene. Colonies are streaked for single colony isolation on YPD (BD #24820) plates containing 32 μg/ml x-alpha-gal. After single colony isolation, the correct integration of the two plasmids is verified by PCR using primers designed to the flanking regions of the IoAXR2 gene (SEQ ID NO: 5 and SEQ ID NO: 6). A PCR verified isolate is designated as Strain 37.

A PCR verified isolate of strain 37 is transformed with SEQ ID: 13 to loop out the URA3 and ScMEL5 markers. SEQ ID NO: 13 contains: i) an expression cassette consisting of a promoter, coding sequence and terminator for the selectable marker gene invertase from *S. cerevisiae* (SEQ ID NO: 14); and ii) an expression cassette consisting of a promoter, coding sequence and terminator for CRE recombinase gene (Cre), encoding the amino acid sequence SEQ ID NO: 15. Transformants are selected on YNB plates containing 2% sucrose as the sole carbon source and 32 μg/ml x-alpha-gal. Selected transformants are streaked SCD medium plates containing 1-2 g/L 5-FOA as described previously. Isolates from the 5-FOA plates are streaked for single colony isolation on YPD plates containing 32 μg/ml x-alpha-gal. Loss of ScMEL5 and IoURA3 in selected isolates is verified by PCR using designed to the flanking regions of the IoAXR2 gene (SEQ ID NO: 5 and SEQ ID NO: 6). A PCR verified isolate is called 38

Strain 38 is transformed simultaneously with SEQ ID NO: 70 and SEQ ID NO: 71. Recombination of the two pieces during transformation results in integration of the following elements: i) four expression cassettes (each containing a promoter, a gene, and a terminator) for a xylose isomerase gene from *Sebaldella termitidis* encoding the amino acid sequence SEQ ID NO: 29 flanked by ENO1, PDC, TDH3, or TEF2 promoter and terminator sequences, respectively; ii) an expression cassette consisting of a promoter, coding sequence and terminator for the selectable marker gene URA3 from *I. orientalis*, encoding the amino acid sequence SEQ ID NO: 17, flanked by loxP sequences; and iii) flanking DNA for targeted chromosomal integration into integration locus XR. Transformants are selected on SCD-URA plates and then are streaked for single colony isolation on SCD-URA plates. After single colony isolation, the correct integration of the expression cassettes is verified by PCR using primers designed to the flanking regions of the IoXR gene (SEQ ID NO: 22 and SEQ ID NO: 23). A PCR verified isolate is designated as Strain 39.

Strain 39 is transformed simultaneously with SEQ ID NO: 72 and SEQ ID NO: 73. Recombination of the two pieces during transformation results in integration of the following elements: i) four expression cassettes for a xylose isomerase gene from *Sebaldella termitidis* encoding the amino acid sequence SEQ ID NO: 29 flanked by ENO1, PDC, TDH3, or TEF2 promoter and terminator sequences, respectively; ii) an expression cassette, consisting of a promoter, coding sequence and terminator, for the selectable marker gene MEL5 from *Saccharomyces cerevisiae* (MEL5), encoding the amino acid sequence SEQ ID NO: 10, flanked by loxP sequences; and iii) flanking DNA for targeted chromosomal integration into locus XR. Transformants are selected on Yeast Nitrogen Base (YNB) with amino acids and ammonium sulfate (BD #239210) plates containing 2% melibiose as the sole carbon source and 32 μg/ml x-alpha-gal which provides a colorimetric indication of the presence of the ScMEL5 marker gene. Colonies are streaked for single colony isolation on YPD (BD #24820) plates containing 32 μg/ml x-alpha-gal. After single colony isolation, the correct integration of the two plasmids is verified by PCR using primers designed to the flanking regions of the IoXR gene (SEQ ID NO: 22 and SEQ ID NO: 23). A PCR verified isolate is designated as Strain 40.

TABLE 9-1

Description of Example 9 strains containing multiple codon variants of the xylose isomerase gene from *Sebaldella termitidis*

| Strains | Description | StXI gene sequences | Progenitor |
|---|---|---|---|
| 27 | 2x ScTKL replacement | | 12215 |
| 28 | DM arabinose growth selection | | 27 |
| 29 | Xylose/acetate anaerobic growth selection | | 28 |
| 30 | Chemostat evolution | | 29 |
| 31 | Chemostat evolution | | 30 |
| 35 | Deletion of XI genes from XR and XRAXR2 loci | | 32 |
| 36 | 4x StXI genes added at first AXR2 allele (total of 4 StXI genes) | SEQ ID NO: 88, 89, 90, 91 | 35 |
| 37 | 4x StXI added at second AXR2 allele (total of 8 StXI genes) | SEQ ID NO: 88, 89, 90, 91 | 36 |
| 39 | 4x SiXI added at first XR allele (total of 12 StXI genes) | SEQ ID NO: 88, 89, 90, 91 | 37 |
| 40 | 4x StXI added at second XR allele (total of 16 StXI genes) | SEQ ID NO: 88, 89, 90, 91 | 39 |

TABLE 9-2

DM-1 Defined Medium for chemostat evolution for generating strain 30 and 31

| Pre-sterilization: | |
|---|---|
| DI water | Fill to 0.8 L |
| Carbon Source(s) | variable g/L |
| MES (0.1M) | 19.5 g/L |
| 25X DM-1 Salts Solution (Table 9-5) | 40.0 ml/L |
| Post-sterilization (add aseptically): | |
| 1000X DM-1 Vitamin Solution (Table 9-7) | 1.0 mL/L |
| 1000X DM Trace Elements Solution (Table 9-9) | 1.0 mL/L |

Adjust final volume to 1 L

TABLE 9-3

DM-1(u) Defined Medium for shake flask characterization of strain 30

| Pre-sterilization: | |
|---|---|
| DI water | Fill to 0.8 L |
| Carbon Source(s) | variable g/L |
| MES (0.1M) | 19.5 g/L |
| 25X DMU Salts Solution (Table 9-6) | 40.0 ml/L |
| Post-sterilization (add aseptically): | |
| 1000X DM-1 Vitamin Solution (Table 9-7) | 1.0 mL/L |
| 1000X DM Trace Elements Solution (Table 9-9) | 1.0 mL/L |

Adjust final volume to 1 L

TABLE 9-4

DMU Defined Medium for shake flask characterization of strain 31

| Pre-sterilization: | |
|---|---|
| DI water | Fill to 0.8 L |
| Carbon source(s) | variable g/L |
| MES (0.1M) | 19.5 g/L |
| 25X DMU Salts Solution (Table 9-6) | 40.0 mL/L |
| Post-sterilization (add aseptically): | |
| 1000X DM3 Vitamin Solution (Table 9-8) | 1.0 mL/L |
| 1000X DM Trace Elements Solution (Table 9-9) | 1.0 mL/L |

Adjust final volume to 1 L

TABLE 9-5

| 25X DM-1 Salts Solution | |
|---|---|
| Ammonium sulfate | 125.0 g/L |
| Potassium phosphate monobasic | 75.0 g/L |
| Magnesium sulphate heptahydrate | 12.5 g/L |
| Demineralized water | To 1000 mL |

TABLE 9-6

| 25X DMU Salts Solution | |
|---|---|
| Urea | 56.75 g/L |
| Potassium phosphate monobasic | 75.0 g/L |
| Magnesium sulphate heptahydrate | 12.5 g/L |
| Demineralized water | To 1000 mL |

TABLE 9-7

| 1000X DM-1 Vitamin Solution | |
|---|---|
| Biotin (D−) | 0.05 g/L |
| Calcium D(+) pantothenate | 1.0 g/L |
| Nicotinic acid | 5.0 g/L |
| Myo-inositol (for microbiology) | 25.0 g/L |
| Thiamine hydrochloride | 1.0 g/L |
| Pyridoxine hydrochloride | 1.0 g/L |
| p-Aminobenzoic acid | 0.20 g/L |
| Demineralized water | To 1000 mL |

Dissolve biotin in 10 ml 0.1M NaOH solution. Quickly add this biotin solution to 750 ml of demineralized water and adjust the pH to 6.5 with 1M HCl. Dissolve all components one by one in the latter solution while continuously maintaining the pH at 6.5. When all components have been added adjust the volume to 1000 ml, pH 6.5. Filter the solution through a 0.2 micron filter to sterilize. Perform for the solution of Table 9-8 as well.

TABLE 9-8

| 1000X DM3 Vitamin Solution | |
|---|---|
| Biotin (D−) | 0.5 g/L |
| Calcium D(+) pantothenate | 1.0 g/L |
| Nicotinic acid | 5.0 g/L |
| Myo-inositol (for microbiology) | 25.0 g/L |
| Thiamine hydrochloride | 1.0 g/L |
| Pyridoxine hydrochloride | 1.0 g/L |
| p-Aminobenzoic acid | 0.20 g/L |
| Demineralized water | To 1000 mL |

TABLE 9-9

| 1000X DM Trace Elements Solution | |
|---|---|
| EDTA (Titriplex III ®) | 15.00 g/L |
| Zinc sulphate heptahydrate | 4.50 g/L |
| Manganese chloride tetrahydrate | 1.20 g/L |
| Cobalt(II) chloride hexahydrate | 0.30 g/L |
| Copper(II) sulphate pentahydrate | 0.30 g/L |
| Di-sodium molybdenum dihydrate | 0.40 g/L |
| Calcium chloride dihydrate | 4.50 g/L |
| Iron sulphate heptahydrate | 3.00 g/L |
| Boric acid | 1.00 g/L |
| Potassium iodide | 0.10 g/L |
| Demineralized water | To 1000 mL |

Dissolve the EDTA and $ZnSO_4 \cdot 7H_2O$ in 750 ml of demineralized water and adjust the pH to 6.0 with NaOH. While maintaining the pH at 6.0 dissolve the components one by one. After all the components are added, adjust the pH to 4.0 with 1M HCl and the volume to 1 liter. Filter through a 0.2 micron filter to sterilize.

Example 10: Construction of Ethanol Producing Strains Containing Multiple Codon Variants of the Xylose Isomerase Gene from *Sebaldella termitidis* that Produce No Detectable Glycerol The PCR verified ΔURA3 strain 32 described in Example 9 is transformed with SEQ ID NO: 74 containing the following elements: i) an expression cassette for the selectable marker URA3 from *I. orientalis* (consisting of the *I. orientalis* promoter, coding sequence and terminator), encoding the amino acid sequence SEQ ID NO: 17, that is flanked by a direct repeat of the *I. orientalis* URA3 promoter for marker loop out; and iii) flanking DNA for targeted chromosomal integration into the integration locus IoGPD (encoding glyceraldehyde-3-phosphate dehydrogenase). Transformants are selected on SCD-URA plates and then are streaked for single colony isolation on SCD-URA plates. After single colony isolation, the correct integration of SEQ ID NO: 74 is verified by PCR using primers designed to the flanking regions of the IoGPD locus, SEQ ID NO: 75 and SEQ ID NO: 76. A PCR confirmed strain is called 41. The URA3 marker of strain 41 is removed by growth on SCD medium plates containing 1-2 g/L 5-FOA). Isolates are single colony purified by growth on YPD plates and are screened by PCR to confirm the loss of the URA3 marker (leaving a scar containing only the URA3 promoter). A PCR verified isolate, strain 42, is transformed with SEQ ID NO: 77. SEQ ID NO: 77 contains the following elements: i) an expression cassette for the selectable marker URA3 from *I. orientalis* (consisting of the *I. orientalis* promoter, coding sequence and terminator), encoding the amino acid sequence SEQ ID NO: 17 that is flanked by a direct repeat region for marker loop out; and iii) flanking DNA for targeted chromosomal integration into integration locus XR. The URA3 cassettes in SEQ ID NO: 74 and SEQ ID NO: 77 are in the opposite orientation with respect to the GPD flanking regions. Transformants are selected on SCD-URA plates and then are streaked for single colony isolation on SCD-URA plates. After single colony isolation, the correct integration of SEQ ID NO: 77 is verified by PCR using primers designed to the flanking regions of the IoGPD locus, SEQ ID NO: 75 and SEQ ID NO: 76. A PCR verified isolate is called 43.

The URA3 marker of strain 43 is looped out by plating on SCD medium containing 1-2 g/L 5-fluoroоritic acid (5-FOA). Isolates are single colony purified by growth on YPD plates and are screened by PCR to confirm the loss of the URA3 marker (leaving a scar containing only the URA3 promoter). The correct loop out of the IoURA3 marker in selected colonies is verified by PCR using primers designed to the flanking regions of the IoGPD locus, SEQ ID NO: 75 and SEQ ID NO: 76. A PCR verified isolate is called 44.

The PCR verified ΔURA3 strain 44 is transformed with SEQ ID NO: 78 containing the following elements: i) an expression cassette for a codon optimized version of the non-phosphorylating glyceraldehyde-3-phosphate dehydrogenase gene from *Streptococcus mutans* encoding the amino acid sequence SEQ ID NO: 79 flanked by *I. orientalis* pyruvate decarboxylase (PDC) promoter and terminator sequences; ii) an expression cassette for the selectable marker gene URA3 from *I. orientalis* (consisting of the promoter, coding sequence and terminator), encoding the amino acid sequence SEQ ID NO: 17, flanked by direct repeat URA3 promoter regions for marker loop out; and iii) flanking DNA for targeted chromosomal integration into integration locus IoADH9091. ADH9091 refers to a gene that encodes a non-specific alcohol dehydrogenase. Transformants are selected on SCD-URA plates and then are streaked for single colony isolation on SCD-URA plates. After single colony isolation, the correct integration of SEQ ID NO: 78 is verified by PCR using primers designed to the IoADH9091 locus, SEQ ID NO: 80 and SEQ ID NO: 81. A PCR verified isolate is called strain 45.

The URA3 marker is removed from strain 45 by growth on SCD medium plates containing 1-2 g/L 5-FOA. Isolates are single colony purified by growth on YPD plates and are screened by PCR using primers designed to the flanking regions of the IoGPD locus, SEQ ID NO: 75 and SEQ ID NO: 76, to confirm the loss of the URA3 marker (leaving a scar containing only the URA3 promoter).

A PCR verified isolate (strain 46), is transformed with SEQ ID NO: 82. SEQ ID NO: 82 contains the following elements: i) an expression cassette for a codon optimized version of the non-phosphorylating glyceraldehyde-3-phosphate dehydrogenase gene from *Streptococcus mutans* encoding the amino acid sequence SEQ ID NO: 79 flanked by *I. orientalis* pyruvate decarboxylase (PDC) promoter and terminator sequences; ii) an expression cassette for the selectable marker gene URA3 from *I. orientalis* (consisting of the promoter, coding region and terminator), encoding the amino acid sequence SEQ ID NO: 17, that is flanked by a direct repeat of the *I. orientalis* URA3 promoter for marker loop out; and iii) flanking DNA for targeted chromosomal integration into integration locus IoADH9091. Both expression cassettes of SEQ ID NO: 78 and SEQ ID NO: 82 are in the opposite orientation with respect to the IoADH9091 flanking regions. Transformants are selected on SCD-URA plates and then are streaked for single colony isolation on SCD-URA plates. After single colony isolation, the correct integration of SEQ ID NO: 82 is verified by PCR using primers designed to the ADH9091 locus, SEQ ID NO: 80 and SEQ ID NO: 81. A PCR verified isolate is called strain 47.

The URA3 marker of strain 47 is looped out by plating on SCD medium containing 1-2 g/L 5-fluoroorotic acid (5-FOA). Isolates are single colony purified by growth on YPD plates and are screened by PCR using primers designed to the ADH9091 locus, SEQ ID NO: 80 and SEQ ID NO: 81, to confirm the loss of the URA3 marker (leaving a scar containing only the URA3 promoter). A PCR verified isolate is called 48.

The PCR verified ΔURA3 strain 48 is transformed with SEQ ID NO: 62 containing the following elements: i) an expression cassette for the selectable marker URA3 from *I. orientalis* (consisting of a promoter, coding sequence and terminator), encoding the amino acid sequence SEQ ID NO: 17, that is flanked by a direct repeat of the *I. orientalis* URA3 promoter for marker loop out; and ii) flanking DNA for targeted chromosomal integration into integration locus XR. Transformants are selected on SCD-URA plates and then are streaked for single colony isolation on SCD-URA plates. After single colony isolation, the correct integration of SEQ ID NO: 62 is verified by PCR using primers designed to the IoXR locus, SEQ ID NO: 22 and SEQ ID NO: 23. A PCR verified isolate is called strain 49.

The URA3 marker is removed from strain 49 by growth on SCD medium plates containing 1-2 g/L 5-FOA. Isolates are single colony purified by growth on YPD plates and are screened by PCR using primers designed to the flanking regions of IoXR locus, SEQ ID NO: 22 and SEQ ID NO: 23, to confirm the loss of the URA3 marker (leaving a scar containing only the URA3 promoter). A PCR verified ΔURA3 isolate is transformed with SEQ ID NO: 63. SEQ ID NO: 63 contains the following elements: i) an expression cassette for the selectable marker URA3 from *I. orientalis*, encoding the amino acid sequence SEQ ID NO: 17, that is flanked by a direct repeat of the *I. orientalis* URA3 promoter for marker loop out; and ii) flanking DNA for targeted chromosomal integration into integration locus XR. The *I. orientalis* URA3 expression cassettes of SEQ ID NO: 62 and SEQ ID NO: 63 are in the opposite orientation with respect to the XR flanking regions. Transformants are selected on SCD-URA plates and then are streaked for single colony isolation on SCD-URA plates. After single colony isolation, the correct integration of SEQ ID NO: 63 is verified by PCR using primers designed to the IoXR locus, SEQ ID NO: 22 and SEQ ID NO: 23. A PCR verified isolate is called strain 50.

The URA3 marker of strain 50 is looped out by plating on SCD medium containing 1-2 g/L 5-fluorooritic acid (5-FOA). Isolates are single colony purified by growth on YPD plates and are screened by PCR to confirm the loss of the *I. orientalis* URA3 marker (leaving a scar containing only the URA3 promoter) using primers designed to the IoXR locus, SEQ ID NO: 22 and SEQ ID NO: 23. A PCR verified ΔURA strain is transformed simultaneously with SEQ ID NO: 83 and SEQ ID NO: 84. Recombination of the two pieces during transformation results in integration of the following elements: i) four expression cassettes (each containing a promoter, a gene, and a terminator) for a xylose isomerase gene from *Sebaldella termitidis* encoding the amino acid sequence SEQ ID NO: 29 flanked by the *I. orientalis* ENOL (phosphopyruvate hydratase), PDC (pyruvate decarboxylase), TDH3 (glyceraldehyde-3-phosphate dehydrogenase), or TEF2 (translation elongation factor) promoter and terminator sequences, respectively; ii) an expression cassette for the selectable marker gene URA3 from *I. orientalis* (consisting of a promoter, coding sequence and terminator), encoding the amino acid sequence SEQ ID NO: 17, flanked by loxP sequences; and iii) flanking DNA for targeted chromosomal integration into integration locus IoAXR2. Transformants are selected on SCD-URA plates and then are streaked for single colony isolation on SCD-URA plates. After single colony isolation, the correct integration of the expression cassettes is verified by PCR using primers designed to the IoAXR2 locus, SEQ ID NO: 5 AXR2 5' flank and SEQ ID NO: 6 AXR2 3' flank. A PCR verified isolate is designated as Strain 51.

A PCR verified isolate of strain 51 is transformed with SEQ ID: 13 to loop out the URA3 marker. SEQ ID NO: 13 contains: i) an expression cassette consisting of a promoter, coding sequence and terminator for the selectable marker gene invertase from *S. cerevisiae* (SEQ ID NO: 14); and ii) an expression cassette consisting of a promoter, coding sequence and terminator for CRE recombinase gen (Cre), encoding the amino acid sequence SEQ ID NO: 15. Transformants are selected on YNB plates containing 2% sucrose as the sole carbon source and 32 μg/ml x-alpha-gal. Selected transformants are streaked on SCD medium plates containing 1-2 g/L FOA as described previously. Isolates from the 5-FOA plates are streaked for single colony isolation on YPD plates containing 32 μg/ml x-alpha-gal. Loss of the URA3 marker in selected isolates is verified by PCR using primers designed to the IoAXR2 locus, SEQ ID NO: 5 AXR2 5' flank and SEQ ID NO: 6 AXR2 3' flank. A PCR verified ΔURA3 strain is transformed simultaneously with SEQ ID NO: 83 and SEQ ID NO: 67. Recombination of the two pieces during transformation results in integration of the following elements: i) four expression cassettes (each containing a promoter, a gene, and a terminator) for a xylose isomerase gene from *Sebaldella termitidis* encoding the amino acid sequence SEQ ID NO: 29 Seb XI flanked by *I. orientalis* ENO1, PDC, TDH3, or TEF2 promoter and terminator sequences, respectively; ii) an expression cassette for the selectable marker gene URA3 from *I. orientalis* consisting of a promoter, coding sequence and terminator, encoding the amino acid sequence SEQ ID NO: 17, flanked by loxP sequences; and iii) flanking DNA for targeted chromosomal integration into integration locus IoAXR2. Transformants are selected on SCD-URA plates and then are streaked for single colony isolation on SCD-URA plates. After single colony isolation, the correct integration of the expression cassettes is verified by PCR using primers designed to the IoAXR2 locus the IoAXR2 locus, SEQ ID NO: 5 AXR2 5' flank and SEQ ID NO: 6 AXR2 3' flank. A PCR verified isolate is designated as Strain 52.

A PCR verified isolate of strain 52 is transformed with SEQ ID: 13 to loop out the URA3 marker. SEQ ID NO: 13 contains: i) an expression cassette consisting of a promoter, coding sequence and terminator for the selectable marker gene invertase from *S. cerevisiae* (SEQ ID NO: 14); and ii) an expression cassette consisting of a promoter, coding sequence and terminator for CRE recombinase gen (Cre), encoding the amino acid sequence SEQ ID NO: 15. Transformants are selected on YNB plates containing 2% sucrose as the sole carbon source and 32 μg/ml x-alpha-gal. Selected transformants are streaked on SCD medium plates containing 1-2 g/L FOA as described previously. Isolates from the 5-FOA plates are streaked for single colony isolation on YPD plates containing 32 μg/ml x-alpha-gal. Isolates from the 5-FOA plates are streaked for single colony isolation on YPD plates containing 32 μg/ml x-alpha-gal. Loss of the URA3 marker in selected isolates is verified by PCR using primers designed to the IoAXR2 locus, SEQ ID NO: 5 AXR2 5' flank and SEQ ID NO: 6 AXR2 3' flank A PCR verified isolate is designated strain 53.

Strain 53 is transformed simultaneously with SEQ ID NO: 70 and SEQ ID NO: 71. Recombination of the two pieces during transformation results in integration of the following elements: i) four expression cassettes (each containing a promoter, a gene, and a terminator) for a xylose isomerase gene from *Sebaldella termitidis* encoding the amino acid sequence SEQ ID NO: 29 flanked by ENO1, PDC, TDH3, or TEF2 promoter and terminator sequences, respectively; ii) an expression cassette consisting of a promoter, coding sequence and terminator for the selectable marker gene URA3 from *I. orientalis*, encoding the amino acid sequence SEQ ID NO: 17, flanked by loxP sequences; and iii) flanking DNA for targeted chromosomal integration into integration locus IoXR. Transformants are selected on SCD-URA plates and then are streaked for single colony isolation on SCD-URA plates. After single colony isolation, the correct integration of the expression cassettes is verified by PCR using primers designed to the IoXR locus, SEQ ID NO: 22 XR 5' flank and SEQ ID NO: 23 XR 3' flank. A PCR verified isolate is designated as Strain 54.

Strain 54 is transformed simultaneously with SEQ ID NO: 85 and SEQ ID NO: 86. Recombination of the two pieces during transformation results in integration of the following elements: i) four expression cassettes for a xylose isomerase gene from *Sebaldella termitidis* encoding the amino acid sequence SEQ ID NO: 29 flanked by ENO1, PDC, TDH3, or TEF2 promoter and terminator sequences, respectively; ii) an expression cassette consisting of a promoter, coding sequence and terminator for the selectable marker gene MEL5 from *Saccharomyces cerevisiae* (MEL5), encoding the amino acid sequence SEQ ID NO: 10, flanked by loxP sequences; and iii) flanking DNA for targeted chromosomal integration into locus XR. Transformants are selected on Yeast Nitrogen Base (YNB) with amino acids and ammonium sulfate (BD #239210) plates containing 2% melibiose as the sole carbon source and 32 μg/ml x-alpha-gal which provides a colorimetric indication of the presence of the ScMEL5 marker gene. Colonies are streaked for single colony isolation on YPD (BD #24820) plates containing 32 μg/ml x-alpha-gal. After single colony isolation, the correct integration of the two plasmids is verified by PCR using primers designed to the IoXR locus, SEQ ID NO: 22 XR 5' flank and SEQ ID NO: 23 XR 3' flank. A PCR verified isolate is designated as Strain 55.

TABLE 10-1

Description of Example 10 strains which contain multiple codon variants of the xylose isomerase gene from *Sebaldella termitidis* and that produce no detectable glycerol

| Strain Number | Description | StXI gene sequences | Parent |
|---|---|---|---|
| 44 | Deletion of GPD genes and URA3 recycle | | 31 |
| 48 | GapN insertion at ADH9091 locus and URA3 recycle | | 44 |
| 50 | Deletion of XI genes from XR locus and URA3 recycle | | 48 |
| 51 | 4x StXI at first AXR2 allele and URA3 recycle (total of 4 XI genes) | SEQ ID NO: 88 (4 copies) | 50 |
| 53 | 4x StXI at second AXR2 allele and URA3 recycle (total of 8 XI genes) | SEQ ID NO: 88, 89, 90, 91 | 51 |
| 54 | 4x StXI at first XR allele (total of 12 XI genes) | SEQ ID NO: 88, 89, 90, 91 | 53 |
| 55 | 4x StXI at second XR allele (total of 16 XI genes) | SEQ ID NO: 88, 89, 90, 91 | 54 |

Example 11: Demonstration in Shake Flasks that Strains Containing Multiple Codon Variants of the *S. Termitidis* Xylose Isomerase Gene are Capable of Producing Ethanol from Xylose in Mixed Sugar Acetate Medium and in Medium Containing NREL Corn Stover Hydrolysate PCR verified strains are streaked out for single colonies on SCX-URA plates (Table 11-6) and incubated at 30° C. until single colonies are visible (overnight). A streak of colonies from each of the plates is used to inoculate Seed A 250-mL baffled flasks containing 30 mL of Glucose Medium with 130 g/L glucose (Table 11-1). Seed A flasks are incubated at 34° C. with shaking at 300 rpm for ~8 h. The $OD_{600}$ of each flask is measured and the Seed B flasks are inoculated from the Seed A flasks. The Seed B flasks containing either Mixed Sugar Acetate Medium (Table 11-2)

or NREL Corn Stover Hydrolysate Medium (Table 11-3) are inoculated to reach an initial $OD_{600}$ of 0.5. The Seed B flasks are incubated at 34° C. with shaking at 200 rpm overnight (12-16 h). Two production 125-mL flasks per strain, each containing 30 mL of the same medium used in the Seed B flasks, are inoculated using the Seed B cell suspensions to reach an initial $OD_{600}$ of ~0.5. The production flasks are incubated at 34° C. with shaking at 125 rpm for ~100 h. Samples are taken from the broth for analysis by high performance liquid chromatography as described in Example 15. The average values from the duplicate production flasks are presented in the graphs below.

The media compositions and the methods for preparing them are adapted from Verduyn, et. al, 1992, Yeast 8, 501-517. The solution compositions for the media and stocks used to prepare the media are listed in Tables 11-1 through 11-5, 9-8, and 9-9.

FIGS. 1A-1D show that strains 37 and 40 consume more than 65 g/L of xylose and produce about 70 g/L ethanol in less than 60 h, when grown in a Mixed Sugar Acetate Medium. The glucose is completely consumed between 24 and 30 h and the ethanol that is produced subsequent to that is clearly from the conversion of xylose. The ΔGPD strains 54 and 55 consume 34 and 55 g/L of xylose, respectively, in less than 60 h and produce 58 and 68 g/L ethanol in the same time period. The glucose is consumed between the 24 and 30 h and the ethanol that is produced subsequent to that is from the conversion of xylose. Additionally, no glycerol is generated by the ΔGPD strains 54 and 55.

FIGS. 2A-2D show that strains 37 and 40 consume more than 45 g/L of xylose and produce more than 50 g/L ethanol in less than 60 h when grown in a medium containing NREL corn stover hydrolysate. The glucose is consumed between the 24 and 30 h time points and the ethanol that is produced subsequent to that is clearly from the conversion of xylose. Strains 54 and 55 consume 19 and 34 g/L of xylose, respectively, in less than 60 h and produce 47 and 56 g/L ethanol in the same time period. The glucose is consumed by 24 h and the ethanol that is produced subsequent to that is from the conversion of xylose. Additionally, no glycerol is generated by the ΔGPD strains 54 and 55.

TABLE 11-1

| Glucose Medium For Seed A | |
|---|---|
| Pre-sterilization: | |
| DI water | Fill to 0.8 L |
| Glucose (anhydrous) | 130 g/L |
| MES (0.1M) | 19.5 g/L |
| 25X DMu3 Salts Solution (Table 11-5) | 40.0 ml/L |
| 15% Calcium Hydroxide | 1.3 mL/L |
| Post-sterilization (add aseptically): | |
| 1:100 aqueous dilution of Lubrizol antifoam (Lubrizol Corp, part number BCC-627) | 1.5 mL/L |
| 1000X DM3 Vitamin Solution (Table 9-8) | 1.0 mL/L |
| Fe, Cu, Zn Stock Solution (Table 11-4) | 9.0 mL/L |
| 1000X DM Trace Elements Solution (Table 9-9) | 1.0 mL/L |
| 50% w/v Glycerol | 0.2 mL/L |

Adjust final volume to 1 L

TABLE 11-2

| Mixed Sugar Acetate Medium For Seed B and Production flasks | |
|---|---|
| Pre-sterilization: | |
| DI water | Fill to 0.8 L |
| Glucose (anhydrous) | 130 g/L |
| Xylose | 70 g/L |
| MES (0.1M) | 19.5 g/L |
| 25X DMu3 Salts Solution (Table 11-5) | 40.0 mL/L |
| Acetic acid (glacial) | 8.0 mL/L |
| 15% Calcium Hydroxide | 1.3 mL/L |
| Post-sterilization (add aseptically): | |
| 1:100 aqueous dilution of Lubrizol antifoam (Lubrizol Corp, part number BCC-627) | 1.5 mL/L |
| 1000X DM3 Vitamin Solution (Table 9-8) | 1.0 mL/L |
| Fe, Cu, Zn Stock Solution (Table 11-4) | 9.0 mL/L |
| 1000X DM Trace Elements Solution (Table 9-9) | 1.0 mL/L |
| 50% w/v Glycerol | 0.2 mL/L |

Adjust final volume to 1 L

TABLE 11-3

| NREL Corn Stover Hydrolysate Medium For Seed B and Production flasks | |
|---|---|
| Use filtered NREL corn stover hydrolysate. Add pre-sterilization: | |
| Hydrolysate | Fill to 0.9 L |
| MES (0.1M) | 19.5 g/L |
| 25X DMu3 Salts Solution (Table 11-5) | 40.0 mL/L |
| 15% Calcium Hydroxide | 1.3 mL/L |
| Post-sterilization (add aseptically): | |
| 1:100 aqueous dilution of Lubrizol antifoam (Lubrizol Corp, part number BCC-627) | 1.5 mL/L |
| 1000X DM3 Vitamin Solution (Table 9-8) | 1.0 mL/L |
| Fe, Cu, Zn Stock Solution (Table 11-4) | 5.0 mL/L |
| 1000X DM Trace Elements Solution (Table 9-9) | 1.0 mL/L |
| 50% w/v Glycerol | 0.2 mL/L |

Adjust final volume with sterile hydrolysate to 1 L

TABLE 11-4

| Fe, Zn, Cu Stock Solution | |
|---|---|
| EDTA (Titriplex III ®) | 15.00 g/L |
| Zinc sulphate heptahydrate | 4.50 g/L |
| Copper(II)sulphate pentahydrate | 0.30 g/L |
| Iron sulphate heptahydrate | 3.00 g/L |
| Demineralized water | To 1000 mL |

Dissolve the EDTA and $ZnSO_4$•$7H_2O$ in 750 ml of demineralized water and set the pH to 6.0 with NaOH. While maintaining the pH at 6.0, dissolve the CuSO4•5H2O and FeSO4•7H2O one by one. When dissolved, adjust the pH to 4.0 with 1M HCl and adjust the volume to 1 liter. Filter through a 0.2 micron filter to sterilize.

TABLE 11-5

| 25X DMu3 Salts Solution | |
|---|---|
| Urea | 56.75 g/L |
| Potassium phosphate monobasic | 75.0 g/L |
| Magnesium sulphate heptahydrate | 25.0 g/L |
| Demineralized water | To 1000 mL |

TABLE 11-6

| SCX-URA plates | |
|---|---|
| Difco ™ Yeast Nitrogen Base without amino acids (BD #291940) | 6.7 g/L |
| Xylose | 20 g/L |
| Agar | 20 g/L |
| SC-URA Mixture (MP Biomedicals #4410-622) | 2 g/L |
| Distilled $H_2O$ | To 1000 mL |

Example 12: Demonstration in Shake Flasks that Strains Containing Multiple Codon Variants of the *S. Termitidis* Xylose Isomerase Gene are Capable of Producing Ethanol from Xylose in a Xylose Defined Medium PCR verified isolates of the strains are streaked out for single colonies on SCX-URA plates (Table 11-6) and incubated at 30° C. until single colonies are visible (1-2 days). A streak of colonies from the plate is used to inoculate Seed A 250-mL baffled flask containing 30 mL of Glucose Medium (Table 11-1). The Seed A flasks are incubated at 34° C. with shaking at 300 rpm for ~8 h. The $OD_{600}$ of the flask is measured and the Seed B 250-mL baffled flask containing 30 mL of Xylose Defined Medium (Table 12-1) is inoculated from the Seed A flasks to an initial $OD_{600}$ of 0.5. The Seed B flasks are incubated at 34° C. with shaking at 200 rpm overnight. Two production 125-mL baffled flasks, each containing 30 mL of the Xylose Defined Medium, are inoculated using the Seed B cell suspension to reach an initial $OD_{600}$ of 0.5. The production flasks are incubated at 34° C. with shaking at 125 rpm for 100 h. Samples are withdrawn from the broth for analysis by high performance liquid chromatography as described in Example 15. The average values from the duplicate production flasks are presented in the graphs and tables below.

The media compositions and the methods for preparing them are adapted from Verduyn, et. al, 1992, Yeast 8, 501-517. The solution compositions for the media are listed in Tables 11-1 and 12-1.

FIGS. 3A-4D show that strains 37 and 40 consume 95 g/L of xylose and produce more than 40 g/L ethanol in less than 33 h when grown in a Xylose Defined Medium containing 15 g/L glucose, 95 g/L xylose and ~8 g/L acetate. The glucose is consumed between the 7 and 24 h time points and the ethanol that is produced subsequent to that is clearly from the conversion of xylose. Strain 55 consumes all the xylose in less than 52 h and produces 34 g/L ethanol. The glucose is consumed between 7 and 24 h and the ethanol that is produced subsequent to that is from the conversion of xylose. Additionally, no glycerol is generated by the ΔGPD strain 55.

TABLE 12-1

| Xylose Defined Medium For Seed B and Production flasks | |
|---|---|
| **Pre-sterilization:** | |
| DI water | Fill to 0.8 L |
| Glucose (anhydrous) | 15 g/L |
| Xylose | 95 g/L |
| MES (0.1M) | 19.5 g/L |
| 25X DMu3 Salts Solution (Table 11-5) | 40.0 mL/L |
| Acetic acid (glacial) | 8.0 mL/L |
| 15% Calcium Hydroxide | 1.3 mL/L |
| **Post-sterilization (add aseptically):** | |
| 1:100 aqueous dilution of Lubrizol antifoam (Lubrizol Corp, part number BCC-627) | 1.5 mL/L |
| 1000X DM3 Vitamin Solution (Table 9-8) | 1.0 mL/L |
| Fe, Cu, Zn Stock Solution (Table 11-4) | 9.0 mL/L |
| 1000X DM Trace Elements Solution (Table 9-9) | 1.0 mL/L |
| 50% Glycerol | 0.2 mL/L |

Adjust final volume to 1 L

Example 13: Biomass Production for Enzyme Assays

Verified transformation isolates from xylose isomerase containing strains or control strains are streaked for single colonies on YPD or SCX-URA plates (Table 11-6) and incubated at 30° C. until single colonies are visible (overnight). A streak of colonies from each plate is used to inoculate seed A 250-mL baffled flasks containing 30 mL of Glucose Medium prepared with 170 g/L of glucose (Table 11-1). Seed A flasks are incubated at 34° C. with shaking at 250 rpm for ~16 h. The $OD_{600}$ of each flask is measured. Optionally, Seed B 250-mL flasks, containing 30 mL of Mixed Sugar Medium (Table 11-2 without acetic acid) are inoculated using Seed A cell suspensions to reach an initial $OD_{600}$ of ~0.15. Seed B flasks are incubated at 34° C. with shaking at 250 rpm for ~8 h. Production 125 mL flasks, containing 30 mL of Mixed Sugar Medium are inoculated using either Seed A or Seed B cell suspensions to reach an initial $OD_{600}$ of ~0.2. The production flasks are incubated at 34° C. with shaking at 125 rpm for ~12 h. The cells are harvested by centrifugation and the cell pellets are frozen at −80 C until use.

Example 14: Measurement of Xylose Isomerase Activity

Clarified cell lysates are prepared from cells grown to mid-log phase in shake flasks as described in Example 13. Cells are collected by centrifugation, washed once with cold 100 mM Sodium TES buffer, pH 7, and frozen as 0.2 to 0.4 g pellets at −80° C. until use. Each frozen pellet is suspended in an equal amount of cold 100 mM Sodium TES buffer, pH 7, containing 0.1 mM $MnCl_2$, 0.5 mM DL-dithiothreitol, and protease inhibitors (Complete, mini, EDTA-free protease inhibitor cocktail, Roche; Indianapolis, Ind., USA, 1 tablet per 20 mL buffer). Approximately 0.2 to 0.4 g of acid-washed glass beads (425-600 μm) are added to each tube and the mixture is lysed by vorteXIng in a bead beater: three cycles of 1-1.25 mM vortex, with samples placed on ice for 2-3 minutes between cycles. The samples are centrifuged immediately after the last vortex cycle at 13,200 rpm for 60 min at 4° C. After centrifugation the supernatants are transferred to fresh 1.5 mL tubes.

The protein concentrations of the cell lysates are determined with the Bio-Rad Coomassie Protein Reagent (catalog #500-0006) against a bovine serum albumin standard (Thermo Scientific catalog #23209) following the manufacturer's recommended directions. The assays are run in a 96-well plate and the absorbance is measured at 595 nm using a Molecular Devices SPECTRAmax PLUS UV-Visible spectrophotometer with plate reader (Sunnyvale, Calif., USA). Protein concentrations in cell free lysates are calculated based on standard curves generated from BSA standards.

Alternatively, protein concentrations of the cell free lysates are determined with the Pierce 660 nm Protein Assay Reagent (Thermo Scientific, catalog #PI-22660) against a bovine serum albumin standard. Dilutions of samples (10 μL, BSA standards or cell free lysates) are mixed with 150 μL reagent. After 10 min incubation at room temperature, absorbance is measured at 660 nm using a Molecular Devices SPECTRAmax PLUS UV-Visible spectrophotometer with plate reader (Sunnyvale, Calif., USA). Protein concentrations in cell free lysates are calculated based on standard curves generated from BSA standards.

The standard xylose isomerase activity assay contains 100 mM Na TES, pH 7.0, 0.3 mM $MnCl_2$, 2.5 units/ml SDH (Roche Diagnostics #10 109 339 001), 0.5 mM NADH, 100 mM xylose and an appropriate amount of cell lysate. Controls for each assay are run without the substrate xylose. Reactions are performed in 96-well UV transparent microtiter plates with a total volume of 0.2 mL per well at 25° C. The assays are started by the addition of substrates and are monitored by following the change in NADH absorbance at 340 nm. All assays are run in duplicate. The measured $\Delta A_{340}$ is converted to mM using an effective path length of 0.576 cm (determined by measuring the absorbance of a solution of NADH under these conditions versus that measured in a 1-cm cuvette, and applying Beer's law). One unit (U)=1 μmol xylulose produced in the coupled assay per minute. Specific activity is defined as μmoles/min/mg of protein or U/mg of protein. A Molecular Devices SPECTRAmax PLUS LW-Visible spectrophotometer with plate reader (Sunnyvale, Calif., USA), is used for spectral and kinetic determinations.

Xylose isomerase activity is also measured with the following changes to the standard assay (modified assay conditions): 100 mM Na TES, pH 7.4, 10 mM $MnCl_2$, 2.5 units/ml SDH (Roche Diagnostics #10 109 339 001), 0.5 mM NADH, 100 mM xylose and an appropriate amount of cell lysate.

Table 14-1 shows the xylose isomerase activities measured in cell lysates from strains 2 through 6. Three PCR confirmed sister isolate lysates are assayed per strain using the standard assay conditions. The order of activity for the xylose isomerases in cell lysates of strains 2 through 6 is 6>3~2~4>5.

TABLE 14-1

Specific Xylose Isomerase Activities of Cell Lysates from Strains 2 to 6 (assayed with 30 and 50 μg protein per cell lysate)

| Strain (XI source) | XI Gene Copy Number | Specific Activity (U/mg protein) | Std Dev |
|---|---|---|---|
| 2 (*Sebaldella termitidis*) | 2 | 0.046 | 0.007 |
| 3 (*Leptotrichia goodfellowii*) | 2 | 0.055 | 0.024 |
| 4 (*Proteiniphilum acetatigenes*) | 2 | 0.040 | 0.012 |
| 5 (*Paludibacter propionicigenes*) | 2 | 0.014 | 0.004 |
| 6 (*Bacteroides thetaiotaomicron*) | 2 | 0.069 | 0.001 |

Table 14-2 shows the xylose isomerase activities of cell lysates from strains containing one or two copies of codon variants of the *Sebaldella termitidis* xylose isomerase genes. The activities represent the averages for one or more PCR confirmed sister isolate cell lysates per strain measured using the standard assay conditions. This table shows that the activities of strain 9, 11, and 12 cell lysates, which contain the *Sebaldella termitidis* xylose isomerase gene sequences of SEQ ID NO: 89, SEQ ID NO: 91, and SEQ ID NO: 92, respectively, are significantly higher than those in strains 8 and 10 which contain the sequences of SEQ ID NO: 87 and SEQ ID NO: 90, respectively.

TABLE 14-2

Specific Activities of the Cell Lysates from *Sebaldella termitidis* Codon Variant XI containing strains (measured with 100 and/or 50 μg of protein per cell lysate)

| Strain | SEQ ID NO | XI Gene Copy Number | Specific Activity (U/mg protein) | Std Dev |
|---|---|---|---|---|
| 7 (ctrl) | | 0 | 0.001 | —* |
| 8 | 87 | 1 | 0.005 | —* |
| 9 | 89 | 1 | 0.027 | 0.005 |
| 10 | 90 | 1 | 0.010 | —* |
| 11 | 91 | 1 | 0.024 | 0.004 |
| 12 | 92 | 1 | 0.023 | 0.002 |
| 19 | 89 | 2 | 0.082 | 0.021 |
| 20 | 91 | 2 | 0.086 | 0.020 |

*Assays run with only one protein concentration

Table 14-3 shows the xylose isomerase activities of cell lysates from strains containing one copy of two different *Leptotrichia goodfellowii* xylose isomerase gene codon variants. The activities represent the averages for five PCR confirmed sister isolate cell lysates per strain measured using the standard assay conditions and 100 μg protein per cell lysate. The cell lysates of strain 14 (containing the xylose isomerase gene sequence of SEQ ID NO: 94) have 5 times more activity than the cell lysates of strain 13 (containing the xylose isomerase gene sequence of SEQ ID NO:93).

TABLE 14-3

Specific Activities of Cell Lysates from Two *Leptotrichia goodfellowii* XI Codon Variant Strains

| Strain | StXI gene sequence | XI Gene Copy Number | Specific Activity (U/mg protein) | Std Dev |
|---|---|---|---|---|
| 13 | SEQ ID NO: 93 | 1 | 0.0042 | 0.0006 |
| 14 | SEQ ID NO: 94 | 1 | 0.0278 | 0.0023 |

Table 14-4 shows the xylose isomerase activities of cell lysates from strains containing one copy of four different *L. goodfellowii* xylose isomerase gene codon variants. The activities represent the averages for two or three PCR confirmed sister isolate cell lysates per strain measured using the modified assay conditions. The order of XI activity of the strain cell lysates is 15>16~18>17.

TABLE 14-4

Specific Activities of Cell Lysates from Four *Leptotrichia goodfellowii* XI Variant Strains (activity measured using 25, 50 and 100 μg protein for each cell lysate in duplicate)

| Strain | StXI gene sequence | XI Gene Copy Number | Specific Activity (U/mg protein) | Std Dev |
|---|---|---|---|---|
| 15 | SEQ ID NO: 95 | 1 | 0.0253 | 0.0014 |
| 16 | SEQ ID NO: 96 | 1 | 0.0175 | 0.0071 |
| 17 | SEQ ID NO: 97 | 1 | 0.0156 | 0.0053 |
| 18 | SEQ ID NO: 98 | 1 | 0.0174 | 0.0024 |

Table 14-5 shows the xylose isomerase activities of cell lysates from strains containing two copies of *L. goodfellowii* xylose isomerase gene codon variants. In these strains one copy of the variant showing the highest activity as a one copy strain (strain 15) is combined with one copy of the same variant or other variants. The activities represent the averages for three PCR confirmed sister isolate cell lysates per strain measured using the modified assay conditions. The order of XI activity of the strain cell lysates is 21~24>22>23. Strain 21 has 2 copies of the XI codon variant of strain 15.

TABLE 14-5

Specific Activities of Four *Leptotrichia goodfellowii* XI Variant Strains (activity measured using 30, 61 and 122 μg protein per cell lysate)

| Strain | StXI gene sequences | XI Gene Copy Number | Specific Activity (U/mg protein) | Std Dev |
|---|---|---|---|---|
| 21 | SEQ ID NO: 95, SEQ ID NO: 95 | 2 | 0.0518 | 0.0024 |
| 22 | SEQ ID NO: 95, SEQ ID NO: 96 | 2 | 0.0492 | 0.0028 |
| 23 | SEQ ID NO: 95, SEQ ID NO: 97 | 2 | 0.0408 | 0.0067 |
| 24 | SEQ ID NO: 95, SEQ ID NO: 98 | 2 | 0.0517 | 0.0076 |

Table 14-6 shows the xylose isomerase activities of cell lysates from strains containing one copy of a *L. goodfellowii* xylose isomerase gene codon variant and one copy of a *S. termitidis* xylose isomerase gene codon variant. In these strains one copy of the *S. termitidis* XI codon variant with high activity as a one copy strain (strain 11; SEQ ID NO:48) is combined with one copy of either the *L. goodfellowii* XI variant from strain 15 (SEQ ID NO:52) or 18 (SEQ ID NO:55). The activities represent the averages for three PCR confirmed sister isolate cell lysates per strain measured using the modified assay conditions. Tables 14-4, 14-5 and 14-6 show that the *L. goodfellowii* XI codon variant of strain 15 consistently provides strains with higher enzyme activity than the other codon variants of this gene.

TABLE 14-6

Specific Activities of Cell Lysates from Strains Containing a *L. goodfellowii* XI Codon Variant and a *S. termitidis* XI Codon Variant (activity measured using 30, 61 and 122 μg protein per cell lysate)

| Strain | StXI gene sequences | XI Gene Copy Number | Specific Activity (U/mg protein) | Std Dev |
|---|---|---|---|---|
| 25 | SEQ ID NO: 95, SEQ ID NO: 91 | 2 | 0.0739 | 0.0005 |
| 26 | SEQ ID NO: 98, SEQ ID NO: 91 | 2 | 0.0566 | 0.0001 |

The results shown in Table 14-7 show the impact of acetate on the xylose isomerase activities of cell lysates from strains containing *S. termitidis* and/or *L. termitidis* xylose isomerase codon variants. The activities represent the activity for one PCR confirmed sister isolate cell lysate per strain measured using the modified assay conditions with acetate added to the reaction mixtures at the concentrations shown in Table 14-7. The pH of all reactions, with or without added acetate, is maintained at 7.4. XI activity in each cell lysate is calculated using duplicate levels of 12.5, 25, 50, and 100 μg cell lysate protein. XI activities are measured in 3 biological replicates for each strain and the average is shown.

These results demonstrate that when no acetate is present, the *S. termitidis* XI in cell lysates of strain 20 has a higher specific activity than the *L. goodfellowii* XI in cell lysates of strain 21. However, the *S. termitidis* XI cell lysates lose activity as the acetate concentration increases and at approximately 20.5 g/L acetate, the cell lysate activities of the two enzymes are almost identical. The activity profile of strain 25, with one copy of each gene, exhibits less acetate sensitivity than strain 20. However, when no acetate is present, the specific XI activity of strain 25 cell lysates is only 70% that of strain 20 cell lysates.

TABLE 14-7

Impact of Acetate on the Xylose Isomerase Activities in Cell Lysates from Strains Containing *S. termitidis* and/or *L. goodfellowii* Xylose Isomerase Codon Variants.

| Strain | StXI gene sequences | XI Gene Copy Number | [Acetate]; g/L | Specific Activity (U/mg protein) | Std Dev |
|---|---|---|---|---|---|
| 20 | SEQ ID NO: 91, SEQ ID NO: 91 | 2 | 0 | 0.113 | 0.003 |
| | | 2 | 5.1 | 0.101 | 0.004 |
| | | 2 | 10.3 | 0.094 | 0.007 |
| | | 2 | 20.5 | 0.075 | 0.003 |
| | | 2 | 41.1 | 0.060 | 0.005 |
| | | 2 | 82.1 | 0.040 | 0.007 |
| 21 | SEQ ID NO: 95, SEQ ID NO: 95 | 2 | 0 | 0.062 | 0.003 |
| | | 2 | 5.1 | 0.070 | 0.005 |
| | | 2 | 10.3 | 0.072 | 0.002 |
| | | 2 | 20.5 | 0.079 | 0.004 |
| | | 2 | 41.1 | 0.077 | 0.002 |
| | | 2 | 82.1 | 0.071 | 0.006 |
| 25 | SEQ ID NO: 95, SEQ ID NO: 91 | 2 | 0 | 0.077 | 0.003 |
| | | 2 | 5.1 | 0.076 | 0.006 |
| | | 2 | 10.3 | 0.074 | 0.005 |
| | | 2 | 20.5 | 0.066 | 0.002 |
| | | 2 | 41.1 | 0.059 | 0.001 |
| | | 2 | 82.1 | 0.046 | 0.006 |

Table 14-8 shows the xylose isomerase activities of cell lysates from strains 34, 36, 37, and 40 (strain construction described in Example 9). One or two PCR confirmed sister isolates are assayed per strain using the modified assay conditions with 10 μg protein per cell lysate. The specific activities in the table represent the averages of 2 or more assays of the PCR confirmed isolates.

TABLE 14-8

Measured Specific Xylose Isomerase Activities of cell lysates from control and multiple *Sebaldella termitidis* variant strains 34, 36, 37 and 40

| Strain Number | StXI Copy Number | StXI gene sequences | Specific Activity (U/mg protein) | Std Dev |
|---|---|---|---|---|
| 34 | 0 | | −0.03 | 0.002 |
| 36 | 4 | SEQ ID NO: 88, SEQ ID NO: 89, SEQ ID NO: 90, SEQ ID NO: 91 | 0.26 | 0.003 |
| 37 | 8 | SEQ ID NO: 88, SEQ ID NO: 89, SEQ ID NO: 90, SEQ ID NO: 91 | 1.03 | 0.053 |
| 40 | 16 | SEQ ID NO: 88, SEQ ID NO: 89, SEQ ID NO: 90, SEQ ID NO: 91 | 1.29 | 0.047 |

Example 15: Analytical Methods

Extracellular metabolites are measured using HPLC. For quantitation of the analytes in the shake flask and fermentation samples, 31.2 μL of standard or sample is aspirated using a Hamilton Microlab Autodiluter. The standard or sample and 472 μL of diluent are dispensed into a vial (1:16 dilution). The diluent contains approximately 1 g/L of the internal standard isobutyric acid as well as 50 mM $H_2SO_4$. The samples are filtered with a 0.45 μm Whatman filter and are analyzed using a Waters 2695 liquid chromatography system (Waters, Milford, Mass., USA) equipped with an automatic sampler, column heater, isocratic pump, refractive index or UV detector, and Empower 3 Software (Waters Corporation). Samples after dilution (20 μL) are injected onto in-line Fast Acid Analysis Column followed by a Bio-Rad 87H Column (Bio-Rad Laboratories, Inc.) and eluted with 10 mM sulfuric acid at 0.5 ml/min and 55° C. Glucose, xylose, arabinose, arabitol, pyruvate/xylulose, xylitol, lactic, glycerol, levulinate and ethanol are detected with the refractive index detector while acetate is detected with the UV detector.

Example 16: Demonstration in a Batch Fermentor that Strains 37 and 40, which Contain Multiple Codon Variants of the *S. termitidis* XI Gene, Produce Ethanol from Xylose in a Fermentor 15/95/8 Xylose Defined Medium The ethanol producing yeast strains 37 and 40 are run in fermentors to assess sugar consumption as well as ethanol production.

Cell concentration is obtained from an optical density measurement using an established conversion factor between dry cell mass and optical density. Optical density is measured at wavelength of 600 nm with a 1 cm pathlength using a model Genesys20 spectrophotometer (Thermo Scientific). Unless explicitly noted otherwise, an experimentally derived conversion factor of 1.88 $OD_{600}$ units per 1 g dry cell mass is used to estimate cell dry weight.

Oxygen uptake rate ("OUR") is calculated using methods known to those in the art as described above. For this example, Oxygen, $N_2$ and $CO_2$ values are measured by a mass spectrometer.

Fermentor 15/95/8 Xylose Defined Medium is adapted from Verduyn, et. al, 1992, Yeast 8, 501-517. Stock solutions compositions are described in Tables 9-8, 9-9, 11-4, and 16-2.

Fermentors are prepared as follows. Fermentors with a total volume of 2 L are operated with 1.5 kg of a fermentor medium. The pre-sterilization components of the Fermentor 15/95/8 Xylose Defined Medium of Table 16-3 are added to the fermentor. The fermentor is autoclaved. After autoclaving, sterile solutions of the post-sterilization components of the Fermentor 15/95/8 Xylose Defined Medium are added aseptically to the fermentor. Initial pH adjustment and inoculum volume bring the working mass to 1.5 kg.

PCR verified isolates of strains 37 and 40 are streaked out for single colonies on YPD or SCX-URA plates and incubated at 30° C. until single colonies are visible (1-2 days). A streak of colonies from each plate is used to inoculate Seed A 250-mL baffled flasks containing 30 mL of Glucose Medium (Table 11-1 of Example 11) with 130 g/L glucose. The Seed A flasks are incubated at 34° C. with shaking at 300 rpm for ~8 h. The $OD_{600}$ of the flask is measured and the Seed B 250-mL baffled flasks containing 30 mL of Xylose Defined Medium (Table 12-1 of Example 12) is inoculated from the Seed A flasks to an initial $OD_{600}$ of 0.005. The Seed B flasks are incubated at 34° C. with shaking at 200 rpm overnight. The $OD_{600}$ of the overnight Seed B cultures are measured.

One fermentor for each strain is inoculated with a sufficient quantity of the strain Seed B in order to achieve an initial cell density of 0.1 g/L (dry cell weight). The pH in the fermentors is maintained at 5.8 by controlled addition of a 15% ammonium hydroxide solution. The fermentors are sparged with 0.25 SLPM (standard liters per minute) air through a sparge ring at the base of the vessel. An average oxygen uptake rate of 1.0-1.6 mmol $O_2$/(L*h) is achieved by selecting an appropriate agitation speed. These fermentations are operated such that after the cells achieve a sufficient density, oxygen limitation is achieved and subsequently maintained throughout the rest of the fermentation (e.g., dissolved oxygen less than about 10% atmospheric air saturation). Dissolved oxygen is measured using Mettler Toledo INPRO® 6800 sensor (Mettler-Toledo GmbH, Urdorf, Switzerland), calibrated prior to inoculation. 0% is calibrated by unplugging the probe and measuring a null signal, 100% is calibrated using air sparging according to the run conditions in the vessel as detailed above (prior to inoculation).

Samples are taken immediately after inoculation, at the end of the batch, and periodically throughout the fermentation. Samples are analyzed for biomass growth via $OD_{600}$, ethanol, sugar concentrations by high performance liquid chromatography as described in Example 15.

The glucose, xylose and ethanol concentrations across the batch fermentations are shown in FIG. 4. In these fermentations, the glucose is depleted by 10 hours, and consequently, all subsequent ethanol production is derived from xylose. Both strains produce ethanol from xylose after the 10 hour timepoint.

Strains 37 and 40 each have xylose isomerase enzyme activities as measured in Example 14. In the fermentations of Example 16, these strains demonstrate the xylose consumption rates and ethanol production rates as shown in Table 16-1.

TABLE 16-1

Calculated rates from fermentations shown in FIG. 4. Rates for each fermentation are calculated using the initial and final time points for each fermentation as plotted in FIG. 4.

| Strain | Xylose consumption rate (g $L^{-1}$ $h^{-1}$) | Ethanol production rate (g $L^{-1}$ $h^{-1}$) |
|---|---|---|
| 37 | 2.97 | 1.34 |
| 40 | 3.61 | 1.71 |

TABLE 16-2

Fermentor 25X DMu3 Salts Solution

| Chemicals | MW | g | ml | Product code |
|---|---|---|---|---|
| Urea | 60.06 | 56.75 | | MP-821530 |
| Potassium phosphate monobasic | 136.09 | 75.0 | | Sigma P5379 |
| Magnesium sulphate heptahydrate | 246.47 | 25.0 | | Sigma M-7506 |
| Demineralized water | | | To 1000 mL | |

TABLE 16-3

Fermentor 15/95/8 Xylose Defined Medium
Recipe for 1.5 kg Fermentor media

| Pre-sterilization: | |
|---|---|
| DI water | 1281 g |
| Glucose (anhydrous) | 22.5 g |
| Xylose | 142.5 g |
| 1:100 aqueous dilution of Lubrizol antifoam (Lubrizol Corp, part number BCC-627) | 1.5 g |
| **Post-sterilization (add aseptically):** | |
| Acetic acid | 12.6 g |
| Fermentor 25X DMu3 Salts Solution (Table 16-2) | 60.0 g |
| 1000X DM3 Vitamin Solution (Table 9-8) | 1.5 g |
| 1000X DM Trace Elements Solution (Table 9-9) | 1.5 g |
| Fe, Cu, Zn Stock Solution (Table 11-4) | 7.5 g |
| 10% w/v glycerol | 1.5 g |

Example 17: Demonstration in a Batch Fermentor that Strains 36 and 40, Containing Multiple Codon Variants of the *S. termitidis* XI Gene, Produce Ethanol from Xylose in a Fermentor 130/70/8 Mixed Sugar Acetate Medium The ethanol producing yeast strains 36 and 40 are run in fermenters to assess sugar consumption as well as ethanol production. The fermentations are performed using the method of Example 16, with the following changes. Seed B flasks contain 30 mL of Mixed Sugar Acetate Medium as described in Table 11-2. When the fermenters are prepared, the fermentor medium used is the Fermentor Mixed Sugar Acetate Medium described in Table 17-2.

The glucose, xylose and ethanol concentrations across the batch fermentations are shown in FIG. 5. In these fermentations, the glucose is depleted at ~30 hours, and consequently, all subsequent ethanol production is derived from xylose. Strain 40 produces ethanol from xylose after the 30 hour time point.

Strains 1-36 and 40 each have xylose isomerase enzyme activities as measured in Example 14. In the fermentations of Example 17, these strains demonstrate the xylose consumption rates and ethanol production rates shown in Table 17-1.

TABLE 17-1

Calculated rates from fermentations shown in FIG. 5. Rates for each fermentation are calculated using the initial and final time points for each fermentation as plotted in FIG. 5.

| Strain | Xylose consumption rate (g $L^{-1}$ $h^{-1}$) | Ethanol production rate (g $L^{-1}$ $h^{-1}$) |
|---|---|---|
| 36 | 0.52 | 0.77 |
| 40 | 1.51 | 1.55 |

TABLE 17-2

Fermentor Mixed Sugar Acetate Medium
Recipe for 1.5 kg Fermentor media

| Pre-sterilization: | |
|---|---|
| DI water | 1146 g |
| Glucose (anhydrous) | 195 g |
| Xylose | 105 g |
| 1:100 aqueous dilution of Lubrizol antifoam (Lubrizol Corp, part number BCC-627) | 1.5 g |
| **Post-sterilization (add aseptically):** | |
| Acetic acid | 12.6 g |
| 25X Fermentor DMu3 Salts Solution (Table 16-2) | 60.0 g |
| 1000X DM3 Vitamin Solution (Table 9-8) | 1.5 g |
| 1000X Trace Elements Solution (Table 9-9) | 1.5 g |
| Fe, Cu, Zn Stock Solution (Table 11-4) | 7.5 g |
| 10% w/v glycerol | 1.5 g |

Example 18: Demonstration in a Batch Fermentor that the ΔGPD Strain 55, Containing Multiple Codon Variants of the *Sebaldella termitidis* Xylose Isomerase Gene, Produces Ethanol from Xylose but does not Produce Detectable Glycerol The ethanol producing yeast strains 40 (intact GPD) and 55 (ΔGPD) are run in fermenters to assess sugar consumption as well as ethanol and glycerol production. The fermentations are performed using the method of Example 17. Glycerol is measured by high performance chromatography as described in Example 15.

The time 0 and 65 h glucose, xylose, ethanol and glycerol concentrations for the fermentations of strains 40 and 55 are shown in Tables 18-1 and 18-2, respectively. Both strains produce more than 70 g/L of ethanol in 65 h. However, strain 40 produces a significant level of glycerol (11.6 g/L at 65 h) while strain 55 does not.

TABLE 18-1

| Strain 40 (intact GPD) Fermentation Results | | | | |
|---|---|---|---|---|
| Time (h) | [Glucose]; g/L | [Xylose]; g/L | [Ethanol]; g/L | [Glycerol]; g/L |
| 0 | 133.7 | 74.2 | 0.5 | 0.6 |
| 65 | 0.0 | 2.6 | 71.4 | 11.6 |

TABLE 18-2

| Strain 55 (ΔGPD) Fermentation Results | | | | |
|---|---|---|---|---|
| Time (h) | [Glucose]; g/L | [Xylose]; g/L | [Ethanol]; g/L | [Glycerol]; g/L |
| 0 | 133.0 | 72.1 | 0.0 | 0.0 |
| 65 | 0.0 | 15.7 | 72.8 | 0.0 |

What is claimed is:

1. A fermentation method for producing a bioproduct, the method comprising steps of:

(a) providing a fermentation medium comprising a carbohydrate composition comprising xylose, the medium having an acidic pH in the range of 3-7; and (b) fermenting the fermentation media using a genetically engineered yeast which is Crabtree negative, the yeast comprising an heterologous nucleic acid encoding a xylose isomerase having an amino acid sequence having 70% or greater identity to SEQ ID NO:29 or SEQ ID NO:33, wherein the engineered yeast produce at least 10 g/L of a bioproduct in a fermented medium, wherein the genetically engineered yeast can grow in the presence of an organic acid when the organic acid is at a concentration of 1 g/L or greater.

2. A fermentation method of claim 1 where in step (b) the yeast further comprises a heterologous nucleic acid encoding a transaldolase, and one or more heterologous genetic modification(s) selected from the group consisting of (a) a nucleic acid encoding a xylulokinase and (b) attenuation or elimination of xylose reductase expression.

3. The fermentation method of claim 1 where xylose is in an amount of at least 15 g/L in the fermentation medium.

4. The fermentation method of claim 1 where xylose is in an amount of less than 300 g/L in the fermentation medium.

5. The fermentation method of claim 1 where in the fermentation medium the carbohydrate composition comprises cellulose, hemicellulose, hydrolysates thereof, and combinations thereof.

6. The fermentation method of claim 1 wherein the consumption rate of xylose during step (b) is at a rate of 1 g $L^{-1}$ $hr^{-1}$ or greater.

7. The fermentation method of claim 1 wherein a final titer of the bioproduct is at least 20 g/L.

8. The fermentation method of claim 1, wherein the bioproduct is selected from the group consisting of amino acids, organic acids, hydroxyl-organic acids, alcohols, polyols, fatty acids, fatty acid methyl esters, monoacyl glycerides, diacyl glycerides, triacyl glycerides, and mixtures thereof.

9. The fermentation method of claim 1, wherein the bioproduct is a C3, C4, or C5 alcohol.

10. The fermentation process of claim 1, wherein the genetically modified Crabtree negative yeast is of the genus *Kluyveromyes* or *Issatchenkia*.

11. The fermentation method of claim 1, wherein the genetically engineered Crabtree negative yeast further comprises one or more heterologous modifications (a)-(c): (a) a nucleic acid encoding a xylulokinase, (b) attenuation or elimination of xylose reductase expression, and (c) a nucleic acid encoding a transaldolase.

12. The fermentation method of claim 1, wherein the genetically engineered Crabtree negative yeast further comprises one or more heterologous modifications (d)-(j): (d) a nucleic acid encoding a transketolase, (e) attenuation or elimination of auditor reductase expression, (f) attenuation or elimination of xylitol dehydrogenase expression, (g) a nucleic acid encoding a ribulose phosphate 3-epimerase, (h) a nucleic acid encoding a ribose 5-phosphate isomerase, (i) a nucleic acid encoding a xylose transporter, and (j) a nucleic acids encoding polypeptides promoting arabinose consumption.

13. The method of claim 1, wherein the heterologous nucleic acid encoding a xylose isomerase has an amino acid sequence having 75% or greater, 80% or greater, 85% or greater, 90% or greater, 95% or greater, 96% or greater, 97% or greater, 98% or greater, of 99% or greater, identity to SEQ ID NO:29 or SEQ ID NO:33.

14. The method of claim 1, wherein the heterologous nucleic acid encoding the xylose isomerase has an amino acid sequence having 70% or greater identity to SEQ ID NO:29 and comprises one or more of the following features relative to SEQ ID NO:29: (a) the sequence VXWGPGREGYSTA at positions 186-194, (b) the sequence LIVMEPKPXEQP at positions 231-238, (c) the amino acids H, D, K, and D at positions 101, 104, 234, and 339, respectively, (d) the amino acid E at position 232, (e) the amino acid E at position 268, (f) the amino acid H at position 271, (g) the amino acid D at position 296, (h) the amino acid D at position 307, (i) the amino acid E at position 309.

15. The method of claim 1, comprising one or more nucleic acid sequences encoding the St XI polypeptide selected from the group consisting of SEQ ID NO:88 to SEQ ID NO:92.

16. The method of claim 15, comprising nucleic acid sequences selected from the group consisting of (a) SEQ ID NO:89 and SEQ ID NO:91; (b) SEQ ID NO:89 and SEQ ID NO:92; (c) SEQ ID NO:91 and SEQ ID NO:92; (d) SEQ ID NO:89, SEQ ID NO:91, and SEQ ID NO:92; or (e) two or more copies of SEQ ID NO:89, SEQ ID NO:91, and/or SEQ ID NO:92 in any of (a)-(d).

17. The method of claim 1, comprising one or more nucleic acid sequences selected from the group consisting of SEQ ID NO:93 to SEQ ID NO:98.

18. The method of claim 15, comprising nucleic acid sequences selected from the group consisting of (a) SEQ ID NO:95 and SEQ ID NO:96; (b) SEQ ID NO:95 and SEQ ID NO:97; (c) SEQ ID NO:95 and SEQ ID NO:98; (d) SEQ ID NO:96 and SEQ ID NO:97; (e) SEQ ID NO:96 and SEQ ID NO:98; (f) SEQ ID NO:97 and SEQ ID NO:98; (g) SEQ ID NO:95, SEQ ID NO:96, and SEQ ID NO:97; (h) SEQ ID NO:95, SEQ ID NO:96, and SEQ ID NO:98; (i) SEQ ID NO:96, SEQ ID NO:97, and SEQ ID NO:98; (j) SEQ ID NO:95, SEQ ID NO:96, SEQ ID NO:97, and SEQ ID NO:98; or (k) two or more copies of SEQ ID NO:95, SEQ ID NO:96, SEQ ID NO:97, and SEQ ID NO:98 in any of (a)-(j).

* * * * *